US012590320B2

(12) United States Patent
Yang et al.

(10) Patent No.: US 12,590,320 B2
(45) Date of Patent: Mar. 31, 2026

(54) CELLULAR MODELS OF AND THERAPIES FOR OCULAR DISEASES

(71) Applicant: REFLECTION BIOTECHNOLOGIES LIMITED, Pak Shek Kok (HK)

(72) Inventors: Richard R. Yang, Pak Shek Kok (HK); Stephen H Tsang, New York, NY (US)

(73) Assignee: Reflection Biotechnologies Limited, Pak Shek Kok (HK)

( * ) Notice: Subject to any disclaimer, the term of this patent is extended or adjusted under 35 U.S.C. 154(b) by 515 days.

(21) Appl. No.: 16/635,863

(22) PCT Filed: Jul. 31, 2018

(86) PCT No.: PCT/IB2018/055755
§ 371 (c)(1),
(2) Date: Jan. 31, 2020

(87) PCT Pub. No.: WO2019/025984
PCT Pub. Date: Feb. 7, 2019

(65) Prior Publication Data
US 2020/0255859 A1      Aug. 13, 2020

Related U.S. Application Data

(60) Provisional application No. 62/539,473, filed on Jul. 31, 2017.

(51) Int. Cl.
| | |
|---|---|
| *C12N 15/86* | (2006.01) |
| *A61K 48/00* | (2006.01) |
| *A61P 27/02* | (2006.01) |
| *C07K 14/80* | (2006.01) |

(52) U.S. Cl.
CPC ............ *C12N 15/86* (2013.01); *A61K 48/005* (2013.01); *A61K 48/0075* (2013.01); *A61P 27/02* (2018.01); *C07K 14/80* (2013.01)

(58) Field of Classification Search
CPC ...................................................... C12N 15/86
See application file for complete search history.

(56) References Cited

U.S. PATENT DOCUMENTS

| | | | |
|---|---|---|---|
| 7,282,199 B2 | 10/2007 | Gao et al. | |
| 9,567,376 B2 | 2/2017 | Cronin et al. | |
| 12,065,663 B2 | 8/2024 | Yang et al. | |
| 2012/0108651 A1 | 5/2012 | Bare et al. | |
| 2012/0141422 A1 | 6/2012 | Barkats | |
| 2014/0010861 A1* | 1/2014 | Bancel .................... | A61P 19/10 536/23.4 |
| 2015/0376240 A1* | 12/2015 | Cronin ................. | C07K 14/705 435/235.1 |
| 2016/0244837 A1 | 8/2016 | Bare et al. | |
| 2016/0251648 A1 | 9/2016 | Wang et al. | |
| 2022/0025369 A1* | 1/2022 | Fotin-Mleczek et al. ................... A61K 31/7088 | |

FOREIGN PATENT DOCUMENTS

| | | | | |
|---|---|---|---|---|
| CN | 101812478 | A | | 8/2010 |
| CN | 101812479 | A | | 8/2010 |
| CN | 102618578 | A | | 8/2012 |
| CN | 102649968 | A | | 8/2012 |
| CN | 102676582 | A | | 9/2012 |
| CN | 102676583 | A | | 9/2012 |
| CN | 102994507 | A | | 3/2013 |
| CN | 102994536 | | | 3/2013 |
| CN | 103374574 | | | 10/2013 |
| CN | 103374575 | A | | 10/2013 |
| CN | 103374575 | B | * | 1/2015 |
| CN | 104450747 | A | | 3/2015 |
| CN | 103468820 | | | 6/2015 |
| CN | 104745591 | | | 7/2015 |
| CN | 104745592 | | | 7/2015 |
| CN | 104745594 | | | 7/2015 |
| CN | 111500635 | | | 8/2020 |
| CN | 111500635 | B | | 10/2020 |
| CN | 113015804 | A | | 6/2021 |
| CN | 113106124 | | | 7/2021 |
| CN | 113166763 | A | | 7/2021 |
| CN | 109136266 | B | | 2/2022 |
| CN | 114381465 | | | 4/2022 |
| CN | 113260704 | B | | 6/2022 |
| CN | 113106124 | B | | 9/2022 |
| CN | 114381465 | B | | 1/2024 |
| CN | 117916365 | B | | 3/2025 |
| EP | 2872183 | A1 | | 5/2015 |
| JP | 2010-035525 | | | 2/2010 |
| JP | 2017-500060 | | | 1/2017 |
| JP | 2025041881 | A | | 3/2025 |
| JP | 2025090820 | A | | 6/2025 |
| KR | 10-20170009812 | | | 1/2017 |

(Continued)

OTHER PUBLICATIONS

Schambach (Mol Ther, 15(6): 1167-73, 2007). (Year: 2007).*
Inazawa et al., 2010 (US 20100035758 A1).*
Li et al., 2013 (GeneSeq Accession No. BBC18586, computer printout, pp. 1-2) (Li 2013A).*
Li et al., 2013 (Geneseq Accession No. BBC18586, computer printout, pp. 1-6) (Li 2013B).*
Yang et al., 2013 (Geneseq Accession No. BAS77292, computer printout, pp. 1-3).*
GenBank Accession No. BC060857, "*Homo sapiens* cytochrome P450, family 4, subfamily V, polypeptide 2, mRNA (cDNA clone MGC:71790 IMAGE:30333559), complete cds," Jul. 17, 2006, 3 pages.

(Continued)

*Primary Examiner* — Mark L Shibuya
(74) *Attorney, Agent, or Firm* — Fish & Richardson P.C.

(57) ABSTRACT

Provided herein are methods for treating or preventing diseases of the eye such as Bietti's Crystalline Dystrophy (BCD) using, for example, vectors for delivering a gene encoding a CYP4V2 protein to the retina (for example, to the retinal pigment epithelial (RPE) cells) or using cells comprising such vectors.

34 Claims, 34 Drawing Sheets
Specification includes a Sequence Listing.

(56) References Cited

FOREIGN PATENT DOCUMENTS

| WO | WO-2004023973 A2 * | 3/2004 | ............ C07K 14/47 |
|---|---|---|---|
| WO | WO 2008125846 | 10/2008 | |
| WO | WO 2014011210 A1 | 1/2014 | |
| WO | WO 2014/020149 A1 * | 2/2014 | |
| WO | WO 2015048577 A2 | 4/2015 | |
| WO | WO 2015082690 A1 | 6/2015 | |
| WO | WO 2015168666 A2 | 11/2015 | |
| WO | WO 2016097183 | 6/2016 | |
| WO | WO 2017070632 A2 | 4/2017 | |
| WO | WO-2017072515 A1 * | 5/2017 | ......... A61K 38/1725 |
| WO | WO 2017197355 A2 | 11/2017 | |
| WO | WO2018199287 | 11/2018 | |

OTHER PUBLICATIONS

Igarashi et al., "New innovations for ocular gene therapy," Journal Medical Practitioners, 2017, 13(2):89-96 (English Abstract).

Nakano et al., "CYP4V2 in Bietti's crystalline dystrophy: ocular localization, metabolism of ω-3-polyunsaturated fatty acids, and functional deficit of the p.H331P variant," Mol. Pharmacol., Oct. 2012, 82(4):679-686.

Nakano et al., "Expression and characterization of CYP4V2 as a fatty acid omega—hydroxylase," Drug Metab. Dispos., Nov. 2009, 37(11):2119-2122.

Office Action in Japanese Appln. No. 2020-528530 dated Aug. 16, 2022, 23 pages (with English translation).

International Search Report mailed in International Application No. PCT/IB2018/055755 (Dec. 19, 2018).

Lai, Timothy Y.Y., et al., "Genotype-Phenotype Analysis of Bietti's Crystalline Dystrophy in Patients with CYP4V2 Mutations," Investigative Ophthalmology & Visual Science (IOVS) Nov. 30, 2007, vol. 48:11, 5212-5220.

Park YJ et al., "*Homo sapiens* cytochrome P450 family 4 subfamily V member 2 (CYP4V2), mRNA," NCBI Reference Sequence: NM_207352.3 May 21, 2017 https://www.ncbi.nlm.nih.gov/nuccore/NM_207352.3.

"Predicted: Colobus angolensis palliatus cytochrome P450 4V2 (LOC105524323), mRNA," NCBI Reference Sequence: XM_011959515.1 Mar. 30, 2015 https://www.ncbi.nlm.nih.gov/nuccore/XM_011959515.1.

Tashiro et al, "Unnamed Protein Product," Genbank accession No. BAC85487.1 Jan. 9, 2008 https://www.ncbi.nlm.nih.gov/protein/BAC85487.

Hata et al., "Reduction of lipid accumulation rescues Bietti's crystalline dystrophy phenotypes," PNAS, Mar. 26, 2018, 115(15):3936-3941.

Lockhart, "Function and Regulation of Cytochrome P450 4V2 and the Implications in Bietti's Crystalline Dystrophy," Thesis for the degree of Doctor of Philosophy, University of Washington, Department of Pharmaceutics, Jul. 14, 2016, 177 pages.

European Patent Office; Extended European Search Report mailed in corresponding European Patent Application No. 18842071.5 (May 21, 2021), 9 pages.

European Patent Office; Communication Pursuant to Article 94(3) EPC mailed in corresponding European Patent Application No. 18842071.5 (Apr. 13, 2022), 4 pages.

Office Action in Taiwanese Appln. No. 107126585, dated Dec. 15, 2022, 12 pages (with English translation).

Search Report in Taiwanese Appln. No. 107126585, mailed on Dec. 15, 2022, 2 pages (with English translation).

Office Action in Japanese Appln. No. 2020-528530 dated Apr. 12, 2023, 7 pages (with English translation).

Office Action in Korean Application No. 2020-7005930 dated Jun. 28, 2023, 17 pages (with English translation).

Office Action in New Zealand Application No. 761655 dated Aug. 7, 2023, 6 pages.

Office Action in Canadian Appln. No. 3071769, dated Oct. 16, 2023, 6 pages.

Office Action in Japanese Appln. No. 2020-528530, dated Jan. 23, 2024, 6 pages (with English translation).

Genbank Accession No. NP_997235.3, "cytochrome P450 4V2 [*Homo sapiens*]," Dec. 11, 2015, 3 pages.

Office Action in Chinese Appln. No 201880064626.5, dated Oct. 30, 2023, 14 pages (with English translation).

McClements et al., "Gene therapy for retinal disease," Translational Research, Apr. 2013, 161(4):241-254, 23 pages.

Office Action in Australian Application No. 2018311504, dated Oct. 5, 2023, 5 pages.

Agbandje-McKenna et al., "AAV capsid structure and cell interactions," Methods. Mol. Biol., Jan. 2011, 807:47-92.

Asokan et al., "Reengineering a receptor footprint of adeno-associated virus enables selective and systemic gene transfer to muscle," NAT Biotechnol. Jan. 2010, 28(1):79-82.

Balaggan et al., "Stable and efficient intraocular gene transfer using pseudotyped EIA V lentiviral vectors," J. Gene Med., Mar. 2006, 8(3):275-285.

Flannery et al., "Efficient photoreceptor-targeted gene expression in vivo by recombinant adeno-associated virus," Proc.Natl. Acad. Sci. U.S.A., Jun. 1997, 94(13):6916-6921.

Gao et al., "Novel adeno-associated viruses from rhesus monkeys as vectors for human gene therapy," PNAS, Sep. 2002, 99(18):11854-11859.

Gurda et al., "Mapping a Neutralizing Epitope onto the Capsid of Adeno-Associated Virus Serotype 8," J. Virol., Aug. 2012, 86(15):7739-7751.

Hameed et al., "A New Locus for Autosomal Recessive RP (RP29) Mapping to Chromosome 4q32-q34 in a Pakistani Family," Invest. Opthalmol. Vis. Sci., Jul. 2001, 42(7):1436-1438.

Kern et al., "Identification of a heparin-binding motif on adeno-associated virus type 2 capsids," J. Virol., Oct. 2003, 77(20):11072-11081.

Lebkowski et al., "Adeno-associated virus: a vector system for efficient introduction and integration of DNA into a variety of mammalian cell types," Oct. 1988, Mol. Cell Biol. 8(10):3988-3996.

Li et al., "Bietti crystalline corneoretinal dystrophy is caused by mutations in the novel gene CYP4V2," Am. J. Hum. Genet., May 2004, 74(5):817-826.

Michaelides et al., "An Early-Onset Autosomal Dominant Macular Dystrophy (MCDR3) Resembling North Carolina Macular Dystrophy Maps to Chromosome 5," Invest. Opthalmol. Vis. Sci., May 2003, 44(5):2178-2183.

Nam et al., "Structure of adeno-associated virus serotype 8, a gene therapy vector," J. Virol., Nov. 2007, 81(22):12260-12271.

Ng et al., "Genetics of Bietti Crystalline Dystrophy," Asia-Pacific Journal of Ophthalmology, Jul./Aug. 2016, 5(4):245-252.

Office Action in Australian Appln. No. 2018311504, dated May 23, 2024, 3 pages.

Office Action in Canadian Appln. No. 3,071,769, dated Jun. 12, 2024, 8 pages.

Office Action in Chinese Appln. No. 201880064626.5, mailed on Aug. 1, 2024, 25 pages (with English translation).

Office Action in European Appln. No. 18842071.5, dated May 10, 2024, 3 pages.

Office Action in Korean Appln. No. 10-2020-7005930, mailed on Jul. 31, 2024, 11 pages (with English translation).

Opie et al., "Identification of Amino Acid Residues in the Capsid Proteins of Adeno-Associated Virus Type 2 That Contribute to Heparan Sulfate Proteoglycan Binding," J. Virol., Jun. 2003, 77(12):6995-7006.

Opposition in Japanese Patent No. 7448953, dated Apr. 17, 2024, 136 pages (with English translation).

Padron et al., "Structure of Adeno-Associated Virus Type 4," J. Virol., Apr. 2005, 79(8):5047-5058.

Pang et al., "Efficiency of lentiviral transduction during development in normal and rd mice," Mol. Vis., Jul. 2006, 12:56-67.

Takahashi, "Delivery of genes to the eye using lentiviral vectors," Methods Mol. Biol., 2004, 246:439-449.

Thompson et al., "Mutations in the gene encoding lecithin retinol acyltransferase are associated with early-onset severe retinal dystrophy," Nat. Genet., Jun. 2001, 28(2):123-124.

(56)        References Cited

OTHER PUBLICATIONS

Vandenberghe et al., "Dosage thresholds for AAV2 and AAV8 photoreceptor gene therapy in monkey," Sci. Transl. Med., Jun. 2011, 3(88):88ra54.

Vardi et al., "mGluR6 Transcripts in Non-neuronal tissues," J. Histochem. Cytochem., Dec. 2011, 59(12):1076-1086.

Wang et al., "Sustained correction of bleeding disorder in hemophilia B mice by gene therapy," 1999 Proc. Natl. Acad. Sci., USA, Mar. 1999, 96(7):3906-3910.

Wobus et al., "Monoclonal antibodies against the adeno-associated virus type 2 (AAV-2) capsid: epitope mapping and identification of capsid domains involved in AAV-2-cell interaction and neutralization of AAV-2 infection," J. Virol., Oct. 2000, 74(19):9281-9293.

Wu et al., "Adeno-associated virus serotypes: vector toolkit for human gene therapy," Mol. Ther., Sep. 2006, 14(3):316-327.

Xie et al., "The atomic structure of adeno-associated virus (AAV-2), a vector for human gene therapy," PNAS, Aug. 2002, 99(16):10405-10410.

Yang, "A patient advocating for transparent science in rare disease research," Orphanet Journal of Rare Diseases, Jan. 19, 2023, 18(1):14.

Kuzmin et al., "The clinical landscape for AAV gene therapies," Nat. Rev. Drug. Discov., Mar. 2021, 20(3):173-174.

NCBI.gov [online], "CAG promoter," retrieved on May 2022, retrieved from URL<https://ncbi.nlm.nih.gov/nuccore/?term=CAG+promoter>, 3 pages.

NCBI.gov [online], "EFS promoter," retrieved on May 2022, retrieved from URL<https://ncbi.nlm.nih.gov/nuccore/?term=EFS+promoter>, 3 pages.

Nieuwenhuis et al., "Improving adeno-associated viral (AAV) vector-mediated transgene expression in retinal ganglion cells: comparison of five promoters," Gene Therapy, Jun. 2023, 30(6):503-519.

Third Party Observations in Chinese Appln. No. 201880064626.5, dated Oct. 16, 2024, 32 pages (with machine translation).

Zhang, "Retinitis Pigmentosa: Progress and Perspective," Asia-Pacific Journal of Ophthalmology, Jul./Aug. 2016, 5(4):265-271.

Office Action in Australian Appln. No. 2018311504, mailed on Sep. 26, 2024, 3 pages.

Third Party Observation for Chinese Appln. No. 201880064626.5, mailed on Jul. 1, 2024, 10 pages (with English translation).

Third Party Observation for Chinese Appln. No. 201880064626.5, mailed on Mar. 22, 2024, 33 pages (with English translation).

Notification of Decision to Grant Patent in Chinese Appln. No. 201880064626.5, dated Dec. 23, 2024, 2 pages (with English translation).

Decision on Opposition in Japanese Appln. No. 2020-528530, dated Nov. 20, 2024, 49 pages (with machine translation).

Extended European Search Report in European Appln No. 24179907.1, dated Dec. 5, 2024, 8 pages.

A Guide to Human Gene Therapy, Herzog and Zolotukhin (eds.), Jun. 2010, 415 pages.

Barnard et al., "Gene Therapy for Choroideremia Using an Adeno-Associated Viral (AAV) Vector," Cold Spring Harb Perspect Med., Oct. 2014, 5(3):a017293, 16 pages.

Cereso et al., "Proof of concept for AAV2/5-mediated gene therapy in iPSC-derived retinal pigment epithelium of a choroideremia patient," Mol. Ther. Methods Clin. Dev., Apr. 2014, 1:14011, 13 pages.

GenBank Accession No. AAR31180.1, "cytochrome p450 4V2 [*Homo sapiens*]," Oct. 1, 2004, 2 pages.

Li et al., "Utilization of fundus autofluorescence, spectral domain optical coherence tomography, and enhanced depth imaging in the characterization of Bietti Crystalline Dystrophy in Different Stages," Retina., Oct. 2015, 35(10):2074-2084.

Miyata et al., "Choroidal and retinal atrophy of Bietti Crystalline Dystrophy patients with CYP4V2 mutations compared to retinitis pigmentosa patients with EYS mutations," Retina, The Journal of Retinal and Vitreous Diseases, Jun. 2017, 37(6):1193-1202.

Naso et al., "Adeno-Associated Virus (AAV) as a Vector for Gene Therapy," BioDrugs., Jul. 2017, 31:317-334.

Office Action in Japanese Appln. No. 2024-025982, dated Apr. 1, 2025, 13 pages (with English translation).

Office Action in Korean Appln. No. 10-2020-7005930, dated Jan. 17, 2025, 8 pages (with English translation).

Opposition in European Patent No. EP3662066, dated Mar. 6, 2025, 51 pages.

Opposition in European Patent No. EP3662066, dated Mar. 7, 2025, 34 pages.

Schon et al., "Retinal gene delivery by adeno-associated virus (AAV) vectors: Strategies and applications," Eur. J. Pharm. Biopharm., Sep. 2015, 95(Part B):343-352.

Third Party Observation for Korean Appln. No. 10-2020-7005930, mailed on Jan. 9, 2025, 48 pages (with English translation).

Vasireddy et al., "AAV-Mediated Gene Therapy for Choroideremia: Preclinical Studies in Personalized Models," PLoS One, May 2013, 8(5):e61396, 13 pages.

Zhang et al., "Choroideremia is a systemic disease with lymphocyte crystals and plasma lipid and RBC membrane abnormalities," Invest Ophthalmol. Vis. Sci., Dec. 2015, 56(13):8158-8156.

Adeno-related Viruses: From Virus to Clinical, Xu (ed.), 1st ed., Nov. 2014, 228 pages (with English Abstract and Table of Contents).

GenBank Accession No. EF591488.1, "Gene-trap donor vector pZGI, complete sequence," Jun. 28, 2007, 5 pages.

Holehonnur et al., "The production of viral vectors designed to express large and difficult to express transgenes within neurons" Molecular Brain, Feb. 2015, 8:12, 20 pages.

Qu et al., "Progress in mechanism of CYP4V2 gene mutations for Bietti crystalline corneoretinal dystrophy," Chin. J. Exp. Opthalmol., Aug. 2014, 32(8):756-759 (with English abstract).

Request for Invalidation in Chinese Appln. No. 201880064626.5, issued on Apr. 3, 2025, 162 pages (with machine translation).

Song et al., "Current clinical trials and progress of gene therapy for the treatment of inherited retinal degenerations," Chin. J. Ocul. Fundus Dis., Nov. 2016, 32(6):650-654 (with English abstract).

Office Action in Taiwanese Appln. No. 112137422, issued on May 28, 2025, 31 pages (with machine translation).

Supplemental Request for Invalidation in Chinese Appln. No. 201880064626.5, issued on May 7, 2025, 35 pages (with machine translation).

Saatci et al., "Diagnostic and Management Strategies of Bietti Crystalline Dystrophy: Current Perspectives," Clinical Ophthalmology, Mar. 2023, 2023(17):953-967.

Statement of Opinion submitted by the Petitioner, related to the Request of Invalidation Examination for the patent of Chinese Appln. No. 201880064626.5, issued on Jun. 10, 2025, 29 pages (in Chinese with English machine translation).

Wu et al., "Photochemical Damage of the Retina," Survey of Ophthalmology, September-Oct. 2006, 51(5):461-480.

Statement of Opinion submitted by the Petitioner, related to the Request of Invalidation Examination for the Patent of Chinese Appln. No. 201880064626.5, issued on Jul. 10, 2025, 23 pages (with machine translation).

Amended Explanation of Evidence in the Invalidation Request for Japanese Patent No. 7448953, received on Oct. 27, 2025, 20 pages (with machine translation).

Amended Invalidation Request in Japanese Patent No. 7448953, received on Oct. 27, 2025, 261 pages (with machine translation).

Annex A as submitted on Aug. 22, 2022, Exhibit D37, Consolidated List in EP Appln. 18842071.5, 12 pages.

Annex B as submitted on Jan. 27, 2023, Exhibit D38, Consolidated List in EP Appln. 18842071.5, 2 pages.

Chang et al., "High-Fat Diet-Induced Retinal Dysfunction," Invest. Ophthalmol. Vis. Sci., Apr. 2015, 56(4):2367-2380.

Choi et al., "Crystalline Maculopathy Associated With High-Dose Lutein Supplementation," JAMA Ophthalmol., Dec. 2016, 134(12):1445-1448.

ClinicalTrialsArena.com [online], "Biogen's rare eye disease gene therapy falls short at Phase III," Mar. 2022, retrieved on Nov. 2025, retrieved from URL<https://www.clinicaltrialsarena.com/news/biogens-rare-eye-disease-gene-therapy-falls-short-at-phase-iii/>, 4 pages.

Decision on Invalidation Request in Chinese Appln. No. 201880064626.5, dated Nov. 6, 2025, 56 pages (with machine translation).

(56)                 References Cited

OTHER PUBLICATIONS

Dowling et al., "Inherited retinal dystrophy in the rat," J. Cell Biol, Jul. 1962, 14(1):73-109.

Explaination of Evidence in the Invalidation Request for Japanese Patent No. 7448953, received on Oct. 27, 2025, 12 pages (with machine translation).

GenBank Accession No. AY422002.1, "Homo sapiens cytochrome P450 4V2 (CYP4V2) mRNA, complete cds," dated Oct. 1, 2004, 3 pages.

GenBank Accession No. NP_997235.3, "cytochrome P450 4V2 [Homo sapiens]," Jun. 26, 2017, 3 pages.

GlobalGenes.org [online], "Biogen XLRP Gene Therapy Fails Late-Stage Study," May 2021, retrieved on Nov. 2025, retrieved from URL <https://globalgenes.org/raredaily/biogen-xlrp-gene-therapy-fails-late-stage-study/>, 3 pages.

Hata et al., "Reduction of lipid accumulation rescues Bietti's crystalline dystrophy phenotypes-Support Information," PNAS, Mar. 26, 2018, 115(15):3936-3941, 11 pages.

Invalidation Request in Chinese Appln. No. 201880064626.5, dated Sep. 2, 2025, 4 pages (with machine translation).

Invalidation Request in Japanese Patent No. 7448953, received on Oct. 27, 2025, 252 pages (with machine translation).

Jia et al., "Unravelling CYP4V2: Clinical features, genetic insight, pahtogenic mechanisms and therapeutic strategies in Bietti crystalline corneoretinal dystrophy," Progress in Retinal and Eye Research, Jun. 2025, 107(20250, 101377, 34 pages.

Kim et al., "The Effects of Metformin on Obesity-Induced Dysfunctional Retinas," Invest. Opthalmoll. Vis. Sci., Jan. 2017, 58(1):106-118.

Kovach et al., "Crystalline retinopathy: Unifying pathogenic pathways of disease," Survey of Ophthalmology, Jan.-Feb. 2019, 64(1):1-29, 84 pages.

Lockhart et al., "Generation and Characterization of a Murine Model of Bietti Crystalline Dystrophy," Invest. Ophthalmol. Vis. Sci., Aug. 2014, 55(9):5572-5581.

Ludwig, "Mammalian Expression Cassette Engineering for High-Level Protein Production," BioProcess International, May 2006, Supplement, 14-23, 9 pages.

Naash et al., "Light-induced acceleration of photreceptor degeneration in transgenic mice expressing mutant rhidispin," Invest Ophthalmol. Vis. Sci., Apr. 1996, 37(5):775-782.

Organisciak et al., "Susceptibility to retinal light damage in transgenic rats with rhodospin mutations," Invest. Ophthalmol. Vis. Sci., Feb. 2003, 44(2):486-492.

Patentee Reply in Response to the Communication pursuant to Rule 79(1) EPC dated Mar. 17, 2025, in Europepan Patent No. 3662066, submitted on Jul. 17, 2025, 218 pages.

Patentee Response to Request for Invalidation in Chinese Appln. No. 201880064626.5, dated Aug. 25, 2025, pages (with machine translation).

Patentee Response to Request for Invalidation in Chinese Appln. No. 201880064626.5, dated Jul. 10, 2025, 68 pages (with machine translation).

Patentee Response to Request for Invalidation in Chinese Appln. No. 201880064626.5, dated Jun. 9, 2025, 47 pages (with machine translation).

Patentee Response to Request for Invalidation in Chinese Appln. No. 201880064626.5, dated May 6, 2025, 115 pages (with machine translation).

Qu et al., "Trewating Bietti crystalline dystrophy in a high-fat diet exacerbated murine model using gene therapy," Gene Ther., Aug. 2020, 27(7-8):370-382.

Statement of Opinion by Petitioner in Chinese Invalidation Request in Appln. No. 201880064626.5, dated Sep. 2, 2025, 60 pages (with machine translation).

Statement of Opinion by Petitioner in Chinese Invalidation Request in Appln. No. 201880064626.5, dated Jul. 24, 2025, 43 pages (with machine translation).

Stern et al., "Retinal pigment epithelial cell proliferation," Exp. Biol. Med. (Maywood), Aug. 2015, 204(8):1079-1086.

Summons to Attend Oral Proceedings Pursuant to Rule 115(1) EPC in EP Appln. No. 18842071.5, dated Oct. 22, 2025, 39 pages.

Wang et al., "Expression of a mutant opsin gene increases the susceotibility of the retina to light damage," Vis. Neurosci., Jan.-Feb. 1997, 14(1):55-62.

Written Amendment submitted in Japanese Patent No. 7448953, dated Feb. 15, 2023, 51 pages (with English translation).

Wu et al., "Generation of a human induced pluripotent stem cell line from a Bietti crystalline corneoretinal dystrophy patient with CYP4V2 mutations," Stem Cell Research, May 2021, 53(2021):102330, 4 pages.

Yvon et al., "Using Stem Cells to Model Diseases of the Outer Retina," Computational and Structural Biotechnology Journal, May 2015, 13(2015):382-389.

Office Action in Japanese Appln. No. 2024025982, dated Nov. 11, 2025, 10 pages (with English translation).

Examination Report in Indian Appln. No. 202017008657, dated Jan. 27, 2026, 15 pages.

Genbank Accession No. AC110771.3, "Homo sapiens BAC clone RP11-173M11 from 4, complete sequence," Nov. 30, 2009, 40 pages.

Genbank Accession No. LT727128.1, "Mammalian expression vector pEF1-2FKBP-link-hFADD-DED, complete sequence," Feb. 6, 2017, 4 pages.

Genbank Accession No. NM_207352.4, "Homo Sapiens Cytochrome P450 Family 4 Subfamily V Member 2, mRNA," Nov. 22, 2018, 5 pages.

Stieger et al., "Adeno-associated virus mediated gene therapy for retinal degenerative disease," Methods Mol Biol., Jan. 2011, 807:179-218.

* cited by examiner

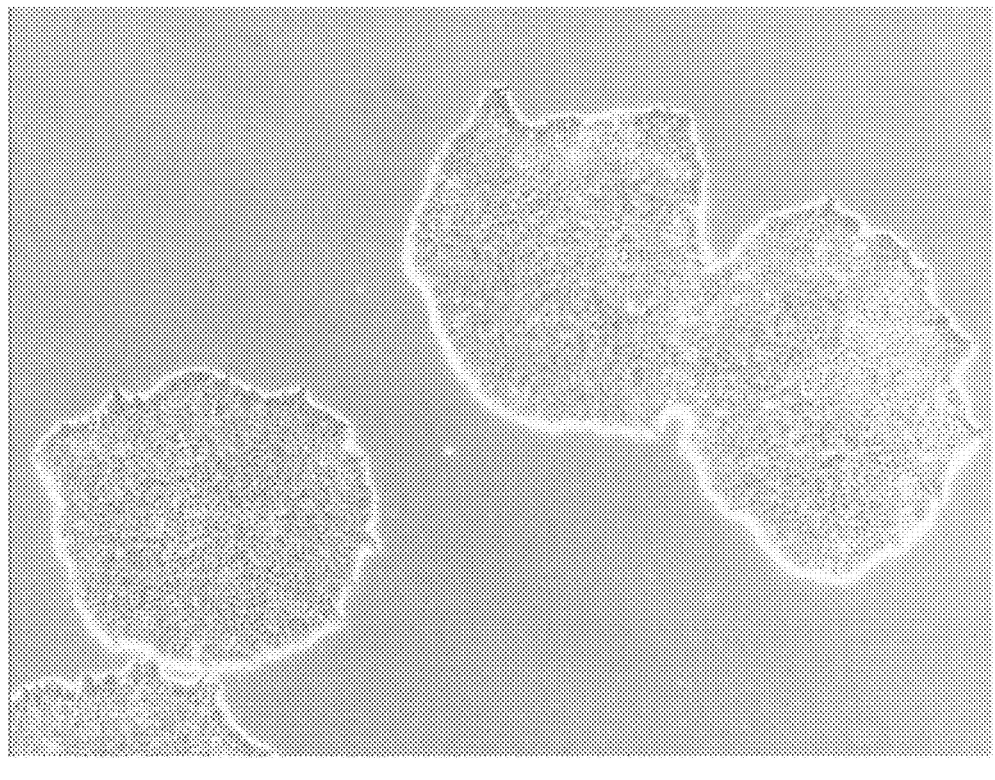
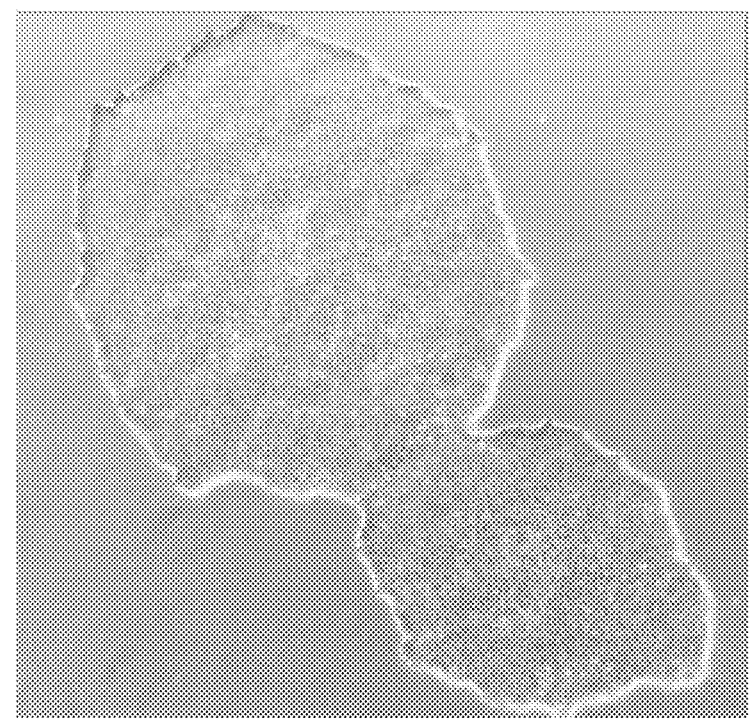
FIG. 1A(ii)

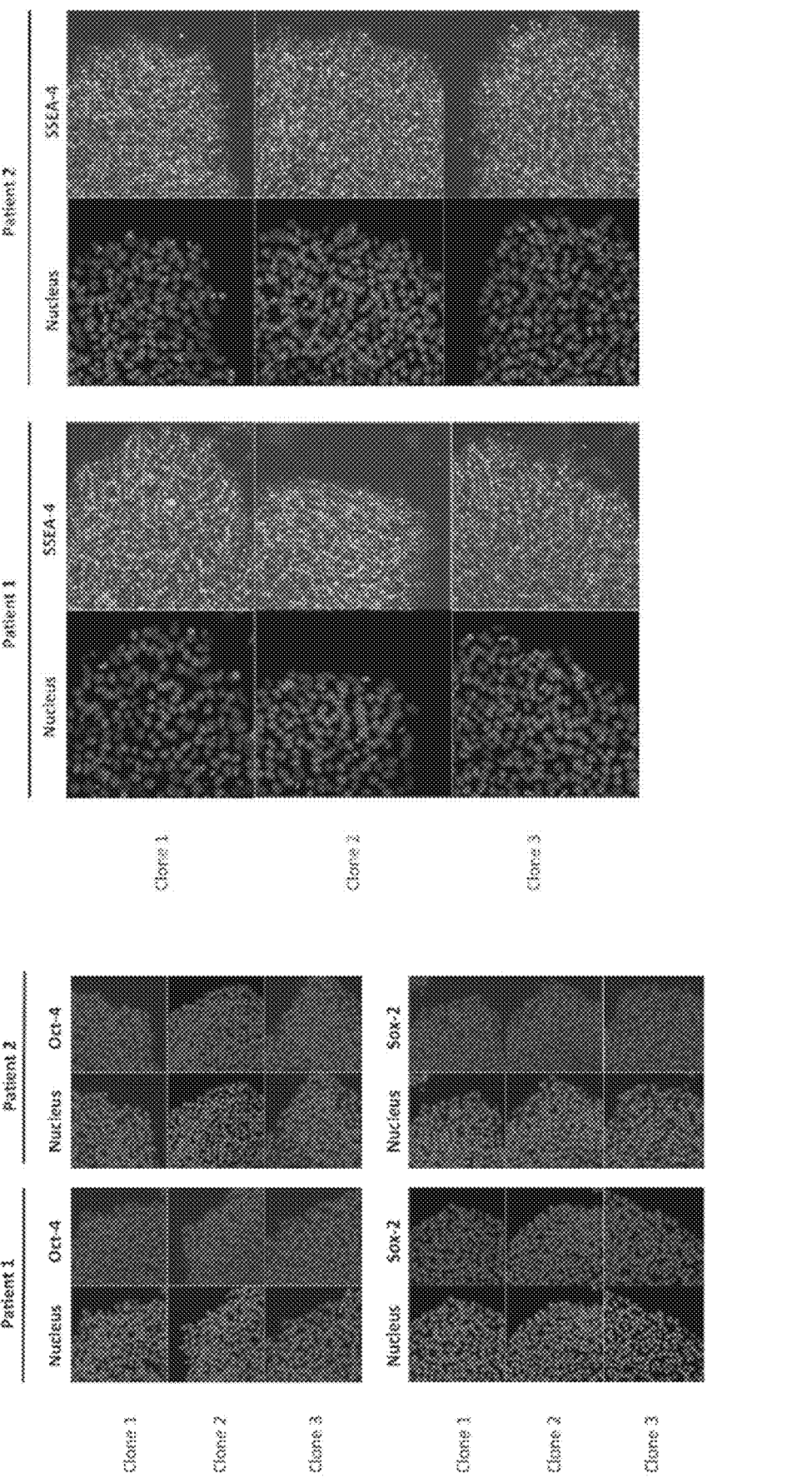
FIG. 1A(iii)

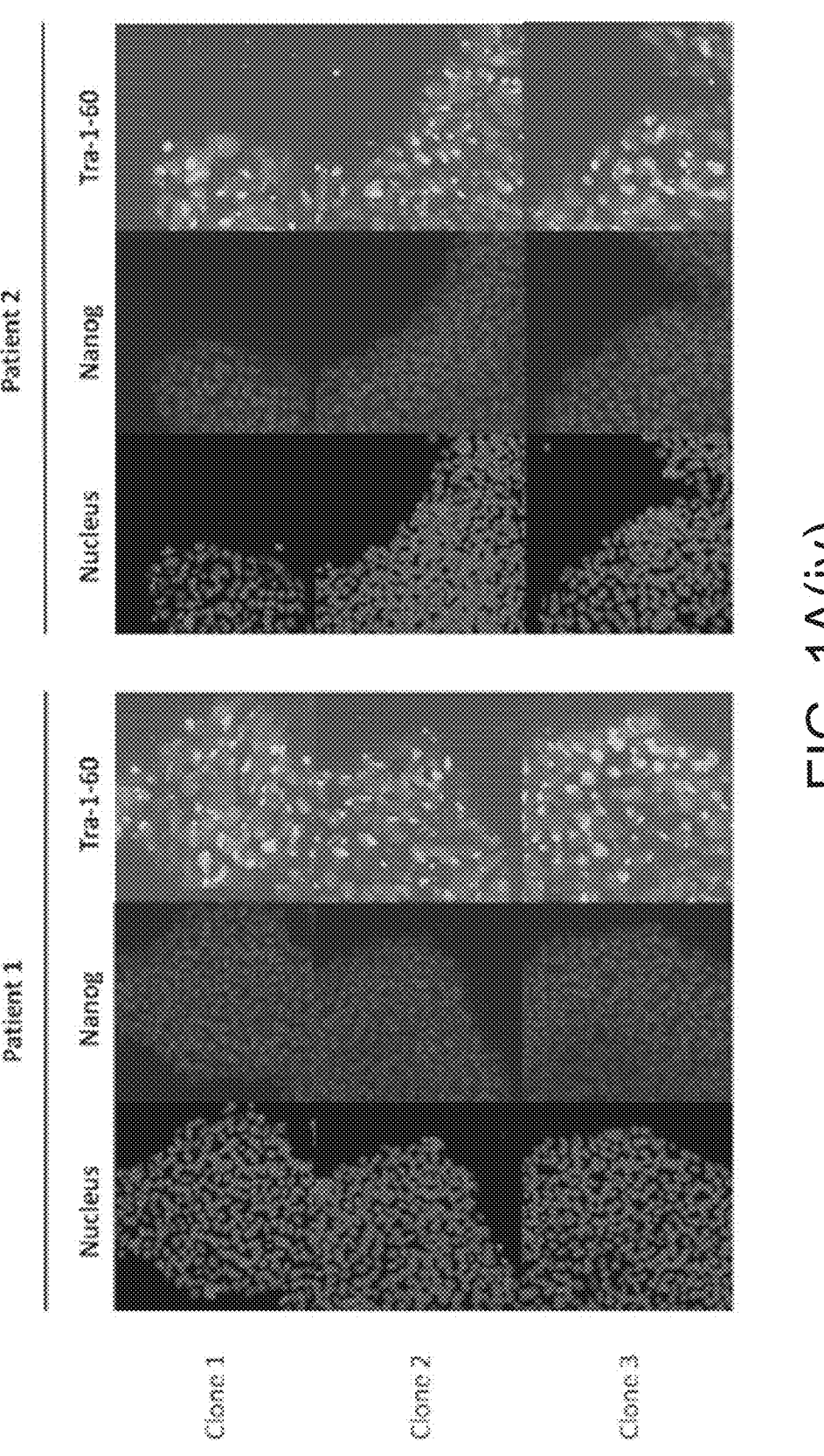
FIG. 1A(iv)

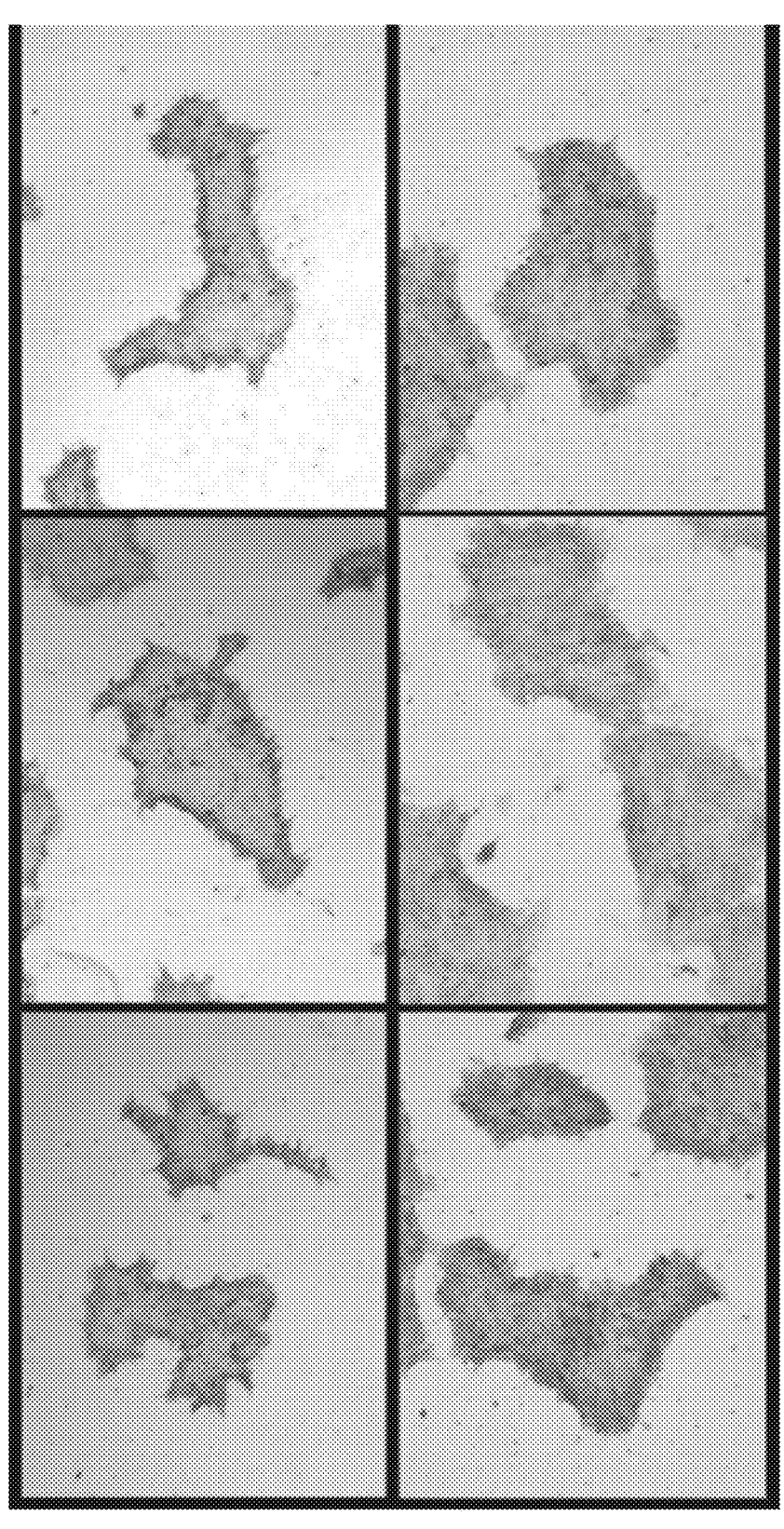
FIG. 1B(ii)

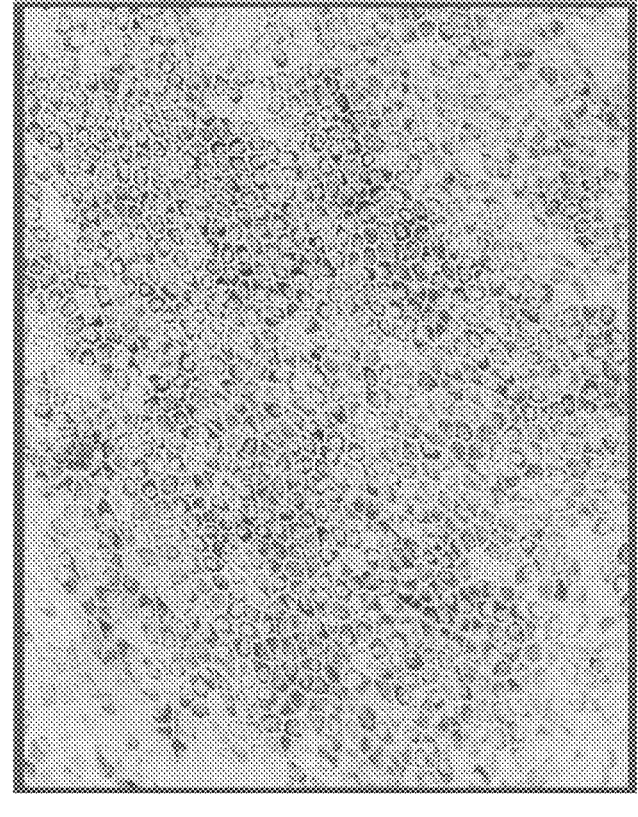
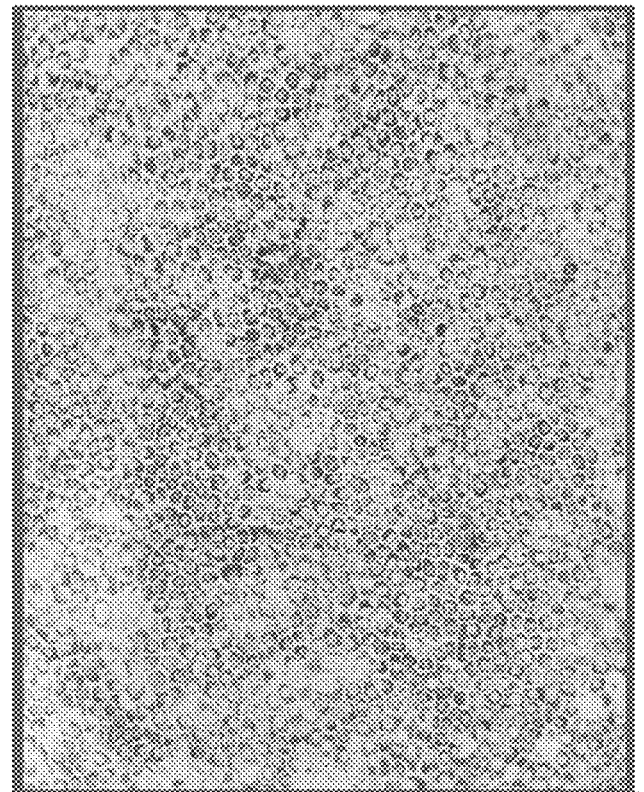
FIG. 2A(ii)

CYP4V2 Expression

CYP4V2op Expression

L1: amplicon + Cas9
L2: amplicon + g1 + Cas9
L3: amplicon + g2 + Cas9
L4: amplicon + g3 + Cas9
L5: amplicon + g4 + Cas9
L6: amplicon + g5 + Cas9
L7: amplicon only
M: 1kb DNA marker 1.5kb 500bp Human U6 Promoter trcrRNA g1 trcrRNA

IVT reverse primer

CBh

FIG. 17

SEQUENCE LISTING

```
<160> NUMBER OF SEQ ID NOS: 80

<210> SEQ ID NO 1
<211> LENGTH: 1578
<212> TYPE: DNA
<213> ORGANISM: Artificial
<220> FEATURE:
<223> OTHER INFORMATION: Synthetically generated coding sequence

<400> SEQUENCE: 1
atggcggggc tctggctggg gctcgtgtgg cagaagctgc tgctgtgggg cgcggcgagt        60
gccctttccc tggccggcgc cagtctggtc ctgagcctgc tgcagagggt ggcgagctac       120
gcgcggaaat ggcagcagat gcggcccatc cccacggtgg cccgcgccta cccactggtg       180
ggccacgcgc tgctgatgaa gccggacggg cgagaatttt ttcagcagat cattgagtac       240
acagaggaat accgccacat gccgctgctg aagctctggg tcgggccagt gcccatggtg       300
gccctttata atgcagaaaa tgtggaggta attttaacta gttcaaagca aattgacaaa       360
tcctctatgt acaagttttt agaaccatgg cttggcctag gacttcttac aagtactgga       420
aacaaatggc gctccaggag aaagatgtta acacccactt tccattttac cattctggaa       480
gatttcttag atatcatgaa tgaacaagca aatatattgg ttaagaaact tgaaaaacac       540
attaaccaag aagcatttaa ctgctttttt tacatcactc tttgtgcctt agatatcatc       600
tgtgaaacag ctatggggaa gaatattggt gctcaaagta atgatgattc cgagtatgtc       660
cgtgcagttt atagaatgag tgagatgata tttcgaagaa taaagatgcc ctggctttgg       720
cttgatctct ggtaccttat gtttaaagaa ggatgggaac acaaaaagag ccttcagatc       780
ctacatactt ttaccaacag tgtcatcgct gaacgggcca atgaaatgaa cgccaatgaa       840
gactgtagag gtgatggcag gggctctgcc ccctccaaaa ataaacgcag ggcctttctt       900
gacttgcttt taagtgtgac tgatgacgaa gggaacaggc taagtcatga agatattcga       960
gaagaagttg acaccttcat gtttgagggg cacgatacaa ctgcagctgc aataaactgg      1020
tccttatacc tgttgggttc taacccagaa gtccagaaaa aagtggatca tgaattggat      1080
gacgtgtttg ggaagtctga ccgtcccgct acagtagaag acctgaagaa acttcggtat      1140
ctggaatgtg ttattaagga gacccttcgc cttttttcctt ctgttccttt atttgcccgt      1200
agtgttagtg aagattgtga agtggcaggt tacagagttc taaaaggcac tgaagccgtc      1260
atcattccct atgcattgca cagagatccg agatacttcc ccaaccccga ggagttccag      1320
cctgagcggt tcttccccga gaatgcacaa gggcgccatc catatgccta cgtgcccttc      1380
tctgctggcc ccaggaactg tataggtcaa aagtttgctg tgatggaaga aaagaccatt      1440
ctttcgtgca tcctgaggca cttttggata gaatccaacc agaaaagaga agagcttggt      1500
ctagaaggac agttgattct tcgtccaagt aatggcatct ggatcaagtt gaagaggaga      1560
aatgcagatg aacgctaa                                                    1578
```

-continued

```
<210> SEQ ID NO 2
<211> LENGTH: 1578
<212> TYPE: DNA
<213> ORGANISM: Artificial
<220> FEATURE:
<223> OTHER INFORMATION: Synthetically generated coding sequence

<400> SEQUENCE: 2
atggctggac tgtggctggg actggtgtgg cagaaactgc tgctgtgggg ggccgcttcc      60
gcactgtcac tggctggggc ttcactggtg ctgagcctgc tgcagagggt ggcctcctac     120
gccagaaagt ggcagcagat gaggcccatc cctaccgtgg ccagagccta tccactggtg     180
ggacacgcac tgctgatgaa gcctgacggc agagagttct ttcagcagat catcgagtac     240
acagaggagt ataggcacat gccactgctg aagctgtggg tgggacccgt gcctatggtg     300
gccctgtaca cgccgagaa tgtggaagtg atcctgacca gcagcaagca gatcgataag     360
tctagcatgt ataagttcct ggagccttgg ctgggcctgg gcctgctgac ctctacaggc     420
aacaagtgga ggagccggag aaagatgctg accccaacat tccactttac aatcctggag     480
gacttcctgg acatcatgaa cgagcaggcc aatatcctgg tgaagaagct ggagaagcac     540
atcaaccagg aggcctttaa ttgcttcttt tacatcaccc tgtgcgccct ggacatcatc     600
tgtgagacag ctatgggcaa gaacatcggc gcccagtcta atgacgatag cgagtacgtg     660
cgggccgtgt atagaatgag cgagatgatc tttaggcgca tcaagatgcc ctggctgtgg     720
ctggatctgt ggtatctgat gttcaaggag ggctgggagc acaagaagtc cctgcagatc     780
ctgcacacct ttacaaactc tgtgatcgcc gagagagcca atgagatgaa cgccaatgag     840
gactgtaggg gcgatggaag gggcagcgcc ccttccaaga acaagcggag agccttcctg     900
gacctgctgc tgagcgtgac cgacgatgag ggcaatcgcc tgtcccacga ggacatccgg     960
gaggaggtgg atacattcat gtttgaggga cacgacacca cagccgccgc catcaactgg    1020
tccctgtacc tgctgggctc taatccagag gtgcagaaga aggtggatca cgagctggac    1080
gacgtgttcg gcaagtccga caggccagca accgtggagg atctgaagaa gctgagatac    1140
ctggagtgcg tgatcaagga gacactgcgc ctgttcccct ctgtgcctct gtttgcccgg    1200
tccgtgtctg aggactgtga ggtggccggc tatcgcgtgc tgaagggcac cgaggccgtg    1260
atcatccctt acgccctgca ccgggacccc aggtatttcc ctaacccaga ggagtttcag    1320
ccagagagat tctttcccga gaatgcccag ggcaggcacc cttacgccta tgtgccattc    1380
tccgccggac caaggaactg catcggacag aagtttgccg tgatggagga gaaaaccatc    1440
ctgtcttgta tcctgagaca cttctggatc gagagcaatc agaagaggga ggagctgggc    1500
ctggagggac agctgatcct gcggccaagc aacggcatct ggatcaaact gaaaagaagg    1560
aacgctgacg agaggtaa                                                  1578

<210> SEQ ID NO 3
<211> LENGTH: 1578
<212> TYPE: DNA
<213> ORGANISM: Artificial
<220> FEATURE:
<223> OTHER INFORMATION: Synthetically generated coding sequence

<400> SEQUENCE: 3
atggcggggc tctggctggg gctcgtgtgg cagaagctgc tgctgtgggg cgcggcgagt      60
gccctttccc tggccggcgc cagtctggtc ctgagcctgc tgcagagggt ggcgagctac     120
gcgcggaaat ggcagcagat gcggcccatc cccacggtgg cccgcgccta cccactggtg     180
```

-continued

```
ggccacgcgc tgctgatgaa gccggacggg cgagaatttt ttcagcagat cattgagtac    240
acagaggaat accgccacat gccgctgctg aagctctggg tcgggccagt gcccatggtg    300
gccctttata atgcagaaaa tgtggaggta attttaacta gttcaaagca aattgacaaa    360
tcctctatgt acaagttttt agaaccatgg cttggcctag gacttcttac aagtactgga    420
aacaaatggc gctccaggag aaagatgtta acacccactt tccattttac cattctggaa    480
gatttcttag atatcatgaa tgaacaagca aatatattgg ttaagaaact tgaaaaacac    540
attaaccaag aagcatttaa ctgctttttt tacatcactc tttgtgcctt agatatcatc    600
tgtgaaacag ctatggggaa gaatattggt gctcaaagta atgatgattc cgagtatgtc    660
cgtgcagttt atagaatgag tgagatgata tttcgaagaa taaagatgcc ctggctttgg    720
cttgatctct ggtaccttat gtttaaagaa ggatgggaac acaaaaagag ccttaagatc    780
ctacatactt ttaccaacag tgtcatcgcg gaacgggcca atgaaatgaa cgccaatgaa    840
gactgtagag gtgatggcag gggctctgcc ccctccaaaa ataaacgcag ggcctttctt    900
gacttgcttt taagtgtgac tgatgacgaa gggaacaggc taagtcatga agatattcga    960
gaagaagttg acaccttcat gtttgagggg cacgatacaa ctgcagctgc aataaactgg   1020
tccttatacc tgttgggttc taacccagaa gtccagaaaa aagtggatca tgaattggat   1080
gacgtgtttg ggaagtctga ccgtcccgct acagtagaag acctgaagaa acttcggtat   1140
ctggaatgtg ttattaagga gacccttcgc ctttttcctt ctgttccttt atttgcccgt   1200
agtgttagtg aagattgtga agtggcaggt tacagagttc taaaaggcac tgaagccgtc   1260
atcattccct atgcattgca cagagatccg agatacttcc ccaaccccga ggagttccag   1320
cctgagcggt tcttccccga gaatgcacaa gggcgccatc catatgccta cgtgcccttc   1380
tctgctggcc ccaggaactg tataggtcaa aagtttgctg tgatggaaga aaagaccatt   1440
ctttcgtgca tcctgaggca ctttttggata gaatccaacc agaaaagaga gagcttggt   1500 ctagaaggac agttgattct tcgtccaagt aatggcatct ggatcaagtt gaagaggaga   1560
aatgcagatg aacgctaa                                                  1578
```

```
<210> SEQ ID NO 4
<211> LENGTH: 525
<212> TYPE: PRT
<213> ORGANISM: Homo sapiens

<400> SEQUENCE: 4

Met Ala Gly Leu Trp Leu Gly Leu Val Trp Gln Lys Leu Leu Leu Trp
1               5                   10                  15

Gly Ala Ala Ser Ala Leu Ser Leu Ala Gly Ala Ser Leu Val Leu Ser
                20                  25                  30

Leu Leu Gln Arg Val Ala Ser Tyr Ala Arg Lys Trp Gln Gln Met Arg
            35                  40                  45

Pro Ile Pro Thr Val Ala Arg Ala Tyr Pro Leu Val Gly His Ala Leu
        50                  55                  60

Leu Met Lys Pro Asp Gly Arg Glu Phe Phe Gln Gln Ile Ile Glu Tyr
65                  70                  75                  80

Thr Glu Glu Tyr Arg His Met Pro Leu Leu Lys Leu Trp Val Gly Pro
                85                  90                  95

Val Pro Met Val Ala Leu Tyr Asn Ala Glu Asn Val Glu Val Ile Leu
            100                 105                 110

Thr Ser Ser Lys Gln Ile Asp Lys Ser Ser Met Tyr Lys Phe Leu Glu
            115                 120                 125
```

-continued

```
Pro Trp Leu Gly Leu Gly Leu Leu Thr Ser Thr Gly Asn Lys Trp Arg
    130             135             140
```

```
Ser Arg Arg Lys Met Leu Thr Pro Thr Phe His Phe Thr Ile Leu Glu
145             150             155             160
```

```
Asp Phe Leu Asp Ile Met Asn Glu Gln Ala Asn Ile Leu Val Lys Lys
            165             170             175
```

```
Leu Glu Lys His Ile Asn Gln Glu Ala Phe Asn Cys Phe Phe Tyr Ile
            180             185             190
```

```
Thr Leu Cys Ala Leu Asp Ile Ile Cys Glu Thr Ala Met Gly Lys Asn
            195             200             205
```

```
Ile Gly Ala Gln Ser Asn Asp Asp Ser Glu Tyr Val Arg Ala Val Tyr
    210             215             220
```

```
Arg Met Ser Glu Met Ile Phe Arg Arg Ile Lys Met Pro Trp Leu Trp
225             230             235             240
```

```
Leu Asp Leu Trp Tyr Leu Met Phe Lys Glu Gly Trp Glu His Lys Lys
            245             250             255
```

```
Ser Leu Gln Ile Leu His Thr Phe Thr Asn Ser Val Ile Ala Glu Arg
            260             265             270
```

```
Ala Asn Glu Met Asn Ala Asn Glu Asp Cys Arg Gly Asp Gly Arg Gly
            275             280             285
```

```
Ser Ala Pro Ser Lys Asn Lys Arg Arg Ala Phe Leu Asp Leu Leu Leu
    290             295             300
```

```
Ser Val Thr Asp Asp Glu Gly Asn Arg Leu Ser His Glu Asp Ile Arg
305             310             315             320
```

```
Glu Glu Val Asp Thr Phe Met Phe Glu Gly His Asp Thr Thr Ala Ala
            325             330             335
```

```
Ala Ile Asn Trp Ser Leu Tyr Leu Leu Gly Ser Asn Pro Glu Val Gln
            340             345             350
```

```
Lys Lys Val Asp His Glu Leu Asp Asp Val Phe Gly Lys Ser Asp Arg
            355             360             365
```

```
Pro Ala Thr Val Glu Asp Leu Lys Lys Leu Arg Tyr Leu Glu Cys Val
    370             375             380
```

```
Ile Lys Glu Thr Leu Arg Leu Phe Pro Ser Val Pro Leu Phe Ala Arg
385             390             395             400
```

```
Ser Val Ser Glu Asp Cys Glu Val Ala Gly Tyr Arg Val Leu Lys Gly
            405             410             415
```

```
Thr Glu Ala Val Ile Ile Pro Tyr Ala Leu His Arg Asp Pro Arg Tyr
            420             425             430
```

```
Phe Pro Asn Pro Glu Glu Phe Gln Pro Glu Arg Phe Phe Pro Glu Asn
    435             440             445
```

```
Ala Gln Gly Arg His Pro Tyr Ala Tyr Val Pro Phe Ser Ala Gly Pro
    450             455             460
```

```
Arg Asn Cys Ile Gly Gln Lys Phe Ala Val Met Glu Glu Lys Thr Ile
465             470             475             480
```

```
Leu Ser Cys Ile Leu Arg His Phe Trp Ile Glu Ser Asn Gln Lys Arg
            485             490             495
```

```
Glu Glu Leu Gly Leu Glu Gly Gln Leu Ile Leu Arg Pro Ser Asn Gly
            500             505             510
```

```
Ile Trp Ile Lys Leu Lys Arg Arg Asn Ala Asp Glu Arg
    515             520             525
```

<210> SEQ ID NO 5
<211> LENGTH: 525

<212> TYPE: PRT
<213> ORGANISM: Homo sapiens

<400> SEQUENCE: 5

```
Met Ala Gly Leu Trp Leu Gly Leu Val Trp Gln Lys Leu Leu Leu Trp
1               5                   10                  15

Gly Ala Ala Ser Ala Leu Ser Leu Ala Gly Ala Ser Leu Val Leu Ser
                20                  25                  30

Leu Leu Gln Arg Val Ala Ser Tyr Ala Arg Lys Trp Gln Gln Met Arg
            35                  40                  45

Pro Ile Pro Thr Val Ala Arg Ala Tyr Pro Leu Val Gly His Ala Leu
        50                  55                  60

Leu Met Lys Pro Asp Gly Arg Glu Phe Phe Gln Gln Ile Ile Glu Tyr
65                  70                  75                  80

Thr Glu Glu Tyr Arg His Met Pro Leu Leu Lys Leu Trp Val Gly Pro
                85                  90                  95

Val Pro Met Val Ala Leu Tyr Asn Ala Glu Asn Val Glu Val Ile Leu
            100                 105                 110

Thr Ser Ser Lys Gln Ile Asp Lys Ser Ser Met Tyr Lys Phe Leu Glu
        115                 120                 125

Pro Trp Leu Gly Leu Gly Leu Leu Thr Ser Thr Gly Asn Lys Trp Arg
        130                 135                 140

Ser Arg Arg Lys Met Leu Thr Pro Thr Phe His Phe Thr Ile Leu Glu
145                 150                 155                 160

Asp Phe Leu Asp Ile Met Asn Glu Gln Ala Asn Ile Leu Val Lys Lys
            165                 170                 175

Leu Glu Lys His Ile Asn Gln Glu Ala Phe Asn Cys Phe Phe Tyr Ile
            180                 185                 190

Thr Leu Cys Ala Leu Asp Ile Ile Cys Glu Thr Ala Met Gly Lys Asn
        195                 200                 205

Ile Gly Ala Gln Ser Asn Asp Asp Ser Glu Tyr Val Arg Ala Val Tyr
        210                 215                 220

Arg Met Ser Glu Met Ile Phe Arg Arg Ile Lys Met Pro Trp Leu Trp
225                 230                 235                 240

Leu Asp Leu Trp Tyr Leu Met Phe Lys Glu Gly Trp Glu His Lys Lys
            245                 250                 255

Ser Leu Lys Ile Leu His Thr Phe Thr Asn Ser Val Ile Ala Glu Arg
            260                 265                 270

Ala Asn Glu Met Asn Ala Asn Glu Asp Cys Arg Gly Asp Gly Arg Gly
        275                 280                 285

Ser Ala Pro Ser Lys Asn Lys Arg Arg Ala Phe Leu Asp Leu Leu Leu
        290                 295                 300

Ser Val Thr Asp Asp Glu Gly Asn Arg Leu Ser His Glu Asp Ile Arg
305                 310                 315                 320

Glu Glu Val Asp Thr Phe Met Phe Glu Gly His Asp Thr Thr Ala Ala
            325                 330                 335

Ala Ile Asn Trp Ser Leu Tyr Leu Leu Gly Ser Asn Pro Glu Val Gln
            340                 345                 350

Lys Lys Val Asp His Glu Leu Asp Asp Val Phe Gly Lys Ser Asp Arg
            355                 360                 365

Pro Ala Thr Val Glu Asp Leu Lys Lys Leu Arg Tyr Leu Glu Cys Val
        370                 375                 380

Ile Lys Glu Thr Leu Arg Leu Phe Pro Ser Val Pro Leu Phe Ala Arg
385                 390                 395                 400
```

Ser Val Ser Glu Asp Cys Glu Val Ala Gly Tyr Arg Val Leu Lys Gly
                405                 410                 415

Thr Glu Ala Val Ile Ile Pro Tyr Ala Leu His Arg Asp Pro Arg Tyr
                420                 425                 430

Phe Pro Asn Pro Glu Glu Phe Gln Pro Glu Arg Phe Phe Pro Glu Asn
                435                 440                 445

Ala Gln Gly Arg His Pro Tyr Ala Tyr Val Pro Phe Ser Ala Gly Pro
        450                 455                 460

Arg Asn Cys Ile Gly Gln Lys Phe Ala Val Met Glu Glu Lys Thr Ile
465                 470                 475                 480

Leu Ser Cys Ile Leu Arg His Phe Trp Ile Glu Ser Asn Gln Lys Arg
                485                 490                 495

Glu Glu Leu Gly Leu Glu Gly Gln Leu Ile Leu Arg Pro Ser Asn Gly
                500                 505                 510

Ile Trp Ile Lys Leu Lys Arg Arg Asn Ala Asp Glu Arg
        515                 520                 525

<210> SEQ ID NO 6
<211> LENGTH: 490
<212> TYPE: PRT
<213> ORGANISM: Homo sapiens

<400> SEQUENCE: 6

Arg Val Ala Ser Tyr Ala Arg Lys Trp Gln Gln Met Arg Pro Ile Pro
1               5                   10                  15

Thr Val Ala Arg Ala Tyr Pro Leu Val Gly His Ala Leu Leu Met Lys
                20                  25                  30

Pro Asp Gly Arg Glu Phe Phe Gln Gln Ile Ile Glu Tyr Thr Glu Glu
        35                  40                  45

Tyr Arg His Met Pro Leu Leu Lys Leu Trp Val Gly Pro Val Pro Met
        50                  55                  60

Val Ala Leu Tyr Asn Ala Glu Asn Val Glu Val Ile Leu Thr Ser Ser
65                  70                  75                  80

Lys Gln Ile Asp Lys Ser Ser Met Tyr Lys Phe Leu Glu Pro Trp Leu
                85                  90                  95

Gly Leu Gly Leu Leu Thr Ser Thr Gly Asn Lys Trp Arg Ser Arg Arg
                100                 105                 110

Lys Met Leu Thr Pro Thr Phe His Phe Thr Ile Leu Glu Asp Phe Leu
                115                 120                 125

Asp Ile Met Asn Glu Gln Ala Asn Ile Leu Val Lys Lys Leu Glu Lys
        130                 135                 140

His Ile Asn Gln Glu Ala Phe Asn Cys Phe Phe Tyr Ile Thr Leu Cys
145                 150                 155                 160

Ala Leu Asp Ile Ile Cys Glu Thr Ala Met Gly Lys Asn Ile Gly Ala
                165                 170                 175

Gln Ser Asn Asp Asp Ser Glu Tyr Val Arg Ala Val Tyr Arg Met Ser
                180                 185                 190

Glu Met Ile Phe Arg Arg Ile Lys Met Pro Trp Leu Trp Leu Asp Leu
                195                 200                 205

Trp Tyr Leu Met Phe Lys Glu Gly Trp Glu His Lys Lys Ser Leu Gln
        210                 215                 220

Ile Leu His Thr Phe Thr Asn Ser Val Ile Ala Glu Arg Ala Asn Glu
225                 230                 235                 240

Met Asn Ala Asn Glu Asp Cys Arg Gly Asp Gly Arg Gly Ser Ala Pro

-continued

```
                    245                 250                 255

Ser Lys Asn Lys Arg Arg Ala Phe Leu Asp Leu Leu Leu Ser Val Thr
                260                 265                 270

Asp Asp Glu Gly Asn Arg Leu Ser His Glu Asp Ile Arg Glu Glu Val
                275                 280                 285

Asp Thr Phe Met Phe Glu Gly His Asp Thr Thr Ala Ala Ala Ile Asn
                290                 295                 300

Trp Ser Leu Tyr Leu Leu Gly Ser Asn Pro Glu Val Gln Lys Lys Val
305                 310                 315                 320

Asp His Glu Leu Asp Asp Val Phe Gly Lys Ser Asp Arg Pro Ala Thr
                325                 330                 335

Val Glu Asp Leu Lys Lys Leu Arg Tyr Leu Glu Cys Val Ile Lys Glu
                340                 345                 350

Thr Leu Arg Leu Phe Pro Ser Val Pro Leu Phe Ala Arg Ser Val Ser
                355                 360                 365

Glu Asp Cys Glu Val Ala Gly Tyr Arg Val Leu Lys Gly Thr Glu Ala
                370                 375                 380

Val Ile Ile Pro Tyr Ala Leu His Arg Asp Pro Arg Tyr Phe Pro Asn
385                 390                 395                 400

Pro Glu Glu Phe Gln Pro Glu Arg Phe Phe Pro Glu Asn Ala Gln Gly
                405                 410                 415

Arg His Pro Tyr Ala Tyr Val Pro Phe Ser Ala Gly Pro Arg Asn Cys
                420                 425                 430

Ile Gly Gln Lys Phe Ala Val Met Glu Glu Lys Thr Ile Leu Ser Cys
                435                 440                 445

Ile Leu Arg His Phe Trp Ile Glu Ser Asn Gln Lys Arg Glu Glu Leu
                450                 455                 460

Gly Leu Glu Gly Gln Leu Ile Leu Arg Pro Ser Asn Gly Ile Trp Ile
465                 470                 475                 480

Lys Leu Lys Arg Arg Asn Ala Asp Glu Arg
                485                 490
```

<210> SEQ ID NO 7
<211> LENGTH: 500
<212> TYPE: PRT
<213> ORGANISM: Homo sapiens

<400> SEQUENCE: 7

```
Met Ser Pro Gly Leu Leu Leu Leu Gly Ser Ala Val Leu Leu Ala Phe
1                   5                   10                  15

Gly Leu Cys Cys Thr Phe Val His Arg Ala Arg Ser Arg Tyr Glu His
                20                  25                  30

Ile Pro Gly Pro Pro Arg Pro Ser Phe Leu Leu Gly His Leu Pro Cys
                35                  40                  45

Phe Trp Lys Lys Asp Glu Val Gly Gly Arg Val Leu Gln Asp Val Phe
                50                  55                  60

Leu Asp Trp Ala Lys Lys Tyr Gly Pro Val Val Arg Val Asn Val Phe
65                  70                  75                  80

His Lys Thr Ser Val Ile Val Thr Ser Pro Glu Ser Val Lys Lys Phe
                85                  90                  95

Leu Met Ser Thr Lys Tyr Asn Lys Asp Ser Lys Met Tyr Arg Ala Leu
                100                 105                 110

Gln Thr Val Phe Gly Glu Arg Leu Phe Gly Gln Gly Leu Val Ser Glu
                115                 120                 125
```

```
Cys Asn Tyr Glu Arg Trp His Lys Gln Arg Arg Val Ile Asp Leu Ala
130                 135                 140

Phe Ser Arg Ser Ser Leu Val Ser Leu Met Glu Thr Phe Asn Glu Lys
145                 150                 155                 160

Ala Glu Gln Leu Val Glu Ile Leu Glu Ala Lys Ala Asp Gly Gln Thr
                165                 170                 175

Pro Val Ser Met Gln Asp Met Leu Thr Tyr Thr Ala Met Asp Ile Leu
                180                 185                 190

Ala Lys Ala Ala Phe Gly Met Glu Thr Ser Met Leu Leu Gly Ala Gln
                195                 200                 205

Lys Pro Leu Ser Gln Ala Val Lys Leu Met Leu Glu Gly Ile Thr Ala
        210                 215                 220

Ser Arg Asn Thr Leu Ala Lys Phe Leu Pro Gly Lys Arg Lys Gln Leu
225                 230                 235                 240

Arg Glu Val Arg Glu Ser Ile Arg Phe Leu Arg Gln Val Gly Arg Asp
                245                 250                 255

Trp Val Gln Arg Arg Arg Glu Ala Leu Lys Arg Gly Glu Glu Val Pro
                260                 265                 270

Ala Asp Ile Leu Thr Gln Ile Leu Lys Ala Glu Glu Gly Ala Gln Asp
                275                 280                 285

Asp Glu Gly Leu Leu Asp Asn Phe Val Thr Phe Phe Ile Ala Gly His
        290                 295                 300

Glu Thr Ser Ala Asn His Leu Ala Phe Thr Val Met Glu Leu Ser Arg
305                 310                 315                 320

Gln Pro Glu Ile Val Ala Arg Leu Gln Ala Glu Val Asp Glu Val Ile
                325                 330                 335

Gly Ser Lys Arg Tyr Leu Asp Phe Glu Asp Leu Gly Arg Leu Gln Tyr
                340                 345                 350

Leu Ser Gln Val Leu Lys Glu Ser Leu Arg Leu Tyr Pro Pro Ala Trp
        355                 360                 365

Gly Thr Phe Arg Leu Leu Glu Glu Glu Thr Leu Ile Asp Gly Val Arg
        370                 375                 380

Val Pro Gly Asn Thr Pro Leu Leu Phe Ser Thr Tyr Val Met Gly Arg
385                 390                 395                 400

Met Asp Thr Tyr Phe Glu Asp Pro Leu Thr Phe Asn Pro Asp Arg Phe
                405                 410                 415

Gly Pro Gly Ala Pro Lys Pro Arg Phe Thr Tyr Phe Pro Phe Ser Leu
                420                 425                 430

Gly His Arg Ser Cys Ile Gly Gln Gln Phe Ala Gln Met Glu Val Lys
        435                 440                 445

Val Val Met Ala Lys Leu Leu Gln Arg Leu Glu Phe Arg Leu Val Pro
        450                 455                 460

Gly Gln Arg Phe Gly Leu Gln Glu Gln Ala Thr Leu Lys Pro Leu Asp
465                 470                 475                 480

Pro Val Leu Cys Thr Leu Arg Pro Arg Gly Trp Gln Pro Ala Pro Pro
                485                 490                 495

Pro Pro Pro Cys
                500
```

```
<210> SEQ ID NO 8
<211> LENGTH: 519
<212> TYPE: PRT
<213> ORGANISM: Homo sapiens

<400> SEQUENCE: 8
```

-continued

```
Met Ser Val Ser Val Leu Ser Pro Ser Arg Leu Leu Gly Asp Val Ser
1               5                   10                  15

Gly Ile Leu Gln Ala Ala Ser Leu Leu Ile Leu Leu Leu Leu Leu Ile
            20                  25                  30

Lys Ala Val Gln Leu Tyr Leu His Arg Gln Trp Leu Leu Lys Ala Leu
        35                  40                  45

Gln Gln Phe Pro Cys Pro Pro Ser His Trp Leu Phe Gly His Ile Gln
    50                  55                  60

Glu Leu Gln Gln Asp Gln Glu Leu Gln Arg Ile Gln Lys Trp Val Glu
65                  70                  75                  80

Thr Phe Pro Ser Ala Cys Pro His Trp Leu Trp Gly Gly Lys Val Arg
            85                  90                  95

Val Gln Leu Tyr Asp Pro Asp Tyr Met Lys Val Ile Leu Gly Arg Ser
            100                 105                 110

Asp Pro Lys Ser His Gly Ser Tyr Arg Phe Leu Ala Pro Trp Ile Gly
            115                 120                 125

Tyr Gly Leu Leu Leu Leu Asn Gly Gln Thr Trp Phe Gln His Arg Arg
            130                 135                 140

Met Leu Thr Pro Ala Phe His Tyr Asp Ile Leu Lys Pro Tyr Val Gly
145                 150                 155                 160

Leu Met Ala Asp Ser Val Arg Val Met Leu Asp Lys Trp Glu Glu Leu
            165                 170                 175

Leu Gly Gln Asp Ser Pro Leu Glu Val Phe Gln His Val Ser Leu Met
            180                 185                 190

Thr Leu Asp Thr Ile Met Lys Cys Ala Phe Ser His Gln Gly Ser Ile
            195                 200                 205

Gln Val Asp Arg Asn Ser Gln Ser Tyr Ile Gln Ala Ile Ser Asp Leu
    210                 215                 220

Asn Asn Leu Val Phe Ser Arg Val Arg Asn Ala Phe His Gln Asn Asp
225                 230                 235                 240

Thr Ile Tyr Ser Leu Thr Ser Ala Gly Arg Trp Thr His Arg Ala Cys
            245                 250                 255

Gln Leu Ala His Gln His Thr Asp Gln Val Ile Gln Leu Arg Lys Ala
            260                 265                 270

Gln Leu Gln Lys Glu Gly Glu Leu Glu Lys Ile Lys Arg Lys Arg His
            275                 280                 285

Leu Asp Phe Leu Asp Ile Leu Leu Leu Ala Lys Met Glu Asn Gly Ser
    290                 295                 300

Ile Leu Ser Asp Lys Asp Leu Arg Ala Glu Val Asp Thr Phe Met Phe
305                 310                 315                 320

Glu Gly His Asp Thr Thr Ala Ser Gly Ile Ser Trp Ile Leu Tyr Ala
            325                 330                 335

Leu Ala Thr His Pro Lys His Gln Glu Arg Cys Arg Glu Glu Ile His
            340                 345                 350

Ser Leu Leu Gly Asp Gly Ala Ser Ile Thr Trp Asn His Leu Asp Gln
            355                 360                 365

Met Pro Tyr Thr Thr Met Cys Ile Lys Glu Ala Leu Arg Leu Tyr Pro
    370                 375                 380

Pro Val Pro Gly Ile Gly Arg Glu Leu Ser Thr Pro Val Thr Phe Pro
385                 390                 395                 400

Asp Gly Arg Ser Leu Pro Lys Gly Ile Met Val Leu Leu Ser Ile Tyr
            405                 410                 415
```

-continued

```
Gly Leu His His Asn Pro Lys Val Trp Pro Asn Pro Glu Val Phe Asp
            420                 425                 430

Pro Phe Arg Phe Ala Pro Gly Ser Ala Gln His Ser His Ala Phe Leu
            435                 440                 445

Pro Phe Ser Gly Gly Ser Arg Asn Cys Ile Gly Lys Gln Phe Ala Met
    450                 455                 460

Asn Glu Leu Lys Val Ala Thr Ala Leu Thr Leu Leu Arg Phe Glu Leu
465                 470                 475                 480

Leu Pro Asp Pro Thr Arg Ile Pro Ile Pro Ile Ala Arg Leu Val Leu
                485                 490                 495

Lys Ser Lys Asn Gly Ile His Leu Arg Leu Arg Arg Leu Pro Asn Pro
            500                 505                 510

Cys Glu Asp Lys Asp Gln Leu
            515

<210> SEQ ID NO 9
<211> LENGTH: 519
<212> TYPE: PRT
<213> ORGANISM: Homo sapiens

<400> SEQUENCE: 9

Met Ser Val Ser Val Leu Ser Pro Ser Arg Arg Leu Gly Gly Val Ser
1               5                   10                  15

Gly Ile Leu Gln Val Thr Ser Leu Leu Ile Leu Leu Leu Leu Leu Ile
            20                  25                  30

Lys Ala Ala Gln Leu Tyr Leu His Arg Gln Trp Leu Leu Lys Ala Leu
            35                  40                  45

Gln Gln Phe Pro Cys Pro Pro Ser His Trp Leu Phe Gly His Ile Gln
    50                  55                  60

Glu Phe Gln His Asp Gln Glu Leu Gln Arg Ile Gln Glu Arg Val Lys
65                  70                  75                  80

Thr Phe Pro Ser Ala Cys Pro Tyr Trp Ile Trp Gly Gly Lys Val Arg
                85                  90                  95

Val Gln Leu Tyr Asp Pro Asp Tyr Met Lys Val Ile Leu Gly Arg Ser
            100                 105                 110

Asp Pro Lys Ser His Gly Ser Tyr Lys Phe Leu Ala Pro Arg Ile Gly
            115                 120                 125

Tyr Gly Leu Leu Leu Leu Asn Gly Gln Thr Trp Phe Gln His Arg Arg
    130                 135                 140

Met Leu Thr Pro Ala Phe His Asn Asp Ile Leu Lys Pro Tyr Val Gly
145                 150                 155                 160

Leu Met Ala Asp Ser Val Arg Val Met Leu Asp Lys Trp Glu Glu Leu
                165                 170                 175

Leu Gly Gln Asp Ser Pro Leu Glu Val Phe Gln His Val Ser Leu Met
            180                 185                 190

Thr Leu Asp Thr Ile Met Lys Ser Ala Phe Ser His Gln Gly Ser Ile
            195                 200                 205

Gln Val Asp Arg Asn Ser Gln Ser Tyr Ile Gln Ala Ile Ser Asp Leu
    210                 215                 220

Asn Ser Leu Val Phe Cys Cys Met Arg Asn Ala Phe His Glu Asn Asp
225                 230                 235                 240

Thr Ile Tyr Ser Leu Thr Ser Ala Gly Arg Trp Thr His Arg Ala Cys
                245                 250                 255

Gln Leu Ala His Gln His Thr Asp Gln Val Ile Gln Leu Arg Lys Ala
            260                 265                 270
```

```
Gln Leu Gln Lys Glu Gly Glu Leu Glu Lys Ile Lys Arg Lys Arg His
        275             280             285

Leu Asp Phe Leu Asp Ile Leu Leu Leu Ala Lys Met Glu Asn Gly Ser
        290             295             300

Ile Leu Ser Asp Lys Asp Leu Arg Ala Glu Val Asp Thr Phe Met Phe
305             310             315             320

Glu Gly His Asp Thr Thr Ala Ser Gly Ile Ser Trp Ile Leu Tyr Ala
                325             330             335

Leu Ala Thr His Pro Lys His Gln Glu Arg Cys Arg Glu Glu Ile His
            340             345             350

Gly Leu Leu Gly Asp Gly Ala Ser Ile Thr Trp Asn His Leu Asp Gln
        355             360             365

Met Pro Tyr Thr Thr Met Cys Ile Lys Glu Ala Leu Arg Leu Tyr Pro
    370             375             380

Pro Val Pro Gly Ile Gly Arg Glu Leu Ser Thr Pro Val Thr Phe Pro
385             390             395             400

Asp Gly Arg Ser Leu Pro Lys Gly Ile Met Val Leu Leu Ser Ile Tyr
                405             410             415

Gly Leu His His Asn Pro Lys Val Trp Pro Asn Leu Glu Val Phe Asp
            420             425             430

Pro Ser Arg Phe Ala Pro Gly Ser Ala Gln His Ser His Ala Phe Leu
        435             440             445

Pro Phe Ser Gly Gly Ser Arg Asn Cys Ile Gly Lys Gln Phe Ala Met
    450             455             460

Asn Gln Leu Lys Val Ala Arg Ala Leu Thr Leu Leu Arg Phe Glu Leu
465             470             475             480

Leu Pro Asp Pro Thr Arg Ile Pro Ile Pro Met Ala Arg Leu Val Leu
                485             490             495

Lys Ser Lys Asn Gly Ile His Leu Arg Leu Arg Arg Leu Pro Asn Pro
            500             505             510

Cys Glu Asp Lys Asp Gln Leu
            515
```

<210> SEQ ID NO 10
<211> LENGTH: 511
<212> TYPE: PRT
<213> ORGANISM: Homo sapiens

<400> SEQUENCE: 10

```
Met Val Pro Ser Phe Leu Ser Leu Ser Phe Ser Ser Leu Gly Leu Trp
1               5               10              15

Ala Ser Gly Leu Ile Leu Val Leu Gly Phe Leu Lys Leu Ile His Leu
                20              25              30

Leu Leu Arg Arg Gln Thr Leu Ala Lys Ala Met Asp Lys Phe Pro Gly
            35              40              45

Pro Pro Thr His Trp Leu Phe Gly His Ala Leu Glu Ile Gln Glu Thr
        50              55              60

Gly Ser Leu Asp Lys Val Val Ser Trp Ala His Gln Phe Pro Tyr Ala
65              70              75              80

His Pro Leu Trp Phe Gly Gln Phe Ile Gly Phe Leu Asn Ile Tyr Glu
                85              90              95

Pro Asp Tyr Ala Lys Ala Val Tyr Ser Arg Gly Asp Pro Lys Ala Pro
            100             105             110

Asp Val Tyr Asp Phe Phe Leu Gln Trp Ile Gly Arg Gly Leu Leu Val
```

-continued

```
            115                 120                 125

Leu Glu Gly Pro Lys Trp Leu Gln His Arg Lys Leu Leu Thr Pro Gly
    130                 135                 140

Phe His Tyr Asp Val Leu Lys Pro Tyr Val Ala Val Phe Thr Glu Ser
145                 150                 155                 160

Thr Arg Ile Met Leu Asp Lys Trp Glu Glu Lys Ala Arg Glu Gly Lys
                165                 170                 175

Ser Phe Asp Ile Phe Cys Asp Val Gly His Met Ala Leu Asn Thr Leu
            180                 185                 190

Met Lys Cys Thr Phe Gly Arg Gly Asp Thr Gly Leu Gly His Arg Asp
            195                 200                 205

Ser Ser Tyr Tyr Leu Ala Val Ser Asp Leu Thr Leu Leu Met Gln Gln
    210                 215                 220

Arg Leu Val Ser Phe Gln Tyr His Asn Asp Phe Ile Tyr Trp Leu Thr
225                 230                 235                 240

Pro His Gly Arg Arg Phe Leu Arg Ala Cys Gln Val Ala His Asp His
                245                 250                 255

Thr Asp Gln Val Ile Arg Glu Arg Lys Ala Ala Leu Gln Asp Glu Lys
            260                 265                 270

Val Arg Lys Lys Ile Gln Asn Arg Arg His Leu Asp Phe Leu Asp Ile
            275                 280                 285

Leu Leu Gly Ala Arg Asp Glu Asp Asp Ile Lys Leu Ser Asp Ala Asp
    290                 295                 300

Leu Arg Ala Glu Val Asp Thr Phe Met Phe Glu Gly His Asp Thr Thr
305                 310                 315                 320

Thr Ser Gly Ile Ser Trp Phe Leu Tyr Cys Met Ala Leu Tyr Pro Glu
            325                 330                 335

His Gln His Arg Cys Arg Glu Glu Val Arg Glu Ile Leu Gly Asp Gln
            340                 345                 350

Asp Phe Phe Gln Trp Asp Asp Leu Gly Lys Met Thr Tyr Leu Thr Met
            355                 360                 365

Cys Ile Lys Glu Ser Phe Arg Leu Tyr Pro Pro Val Pro Gln Val Tyr
    370                 375                 380

Arg Gln Leu Ser Lys Pro Val Thr Phe Val Asp Gly Arg Ser Leu Pro
385                 390                 395                 400

Ala Gly Ser Leu Ile Ser Met His Ile Tyr Ala Leu His Arg Asn Ser
                405                 410                 415

Ala Val Trp Pro Asp Pro Glu Val Phe Asp Ser Leu Arg Phe Ser Thr
            420                 425                 430

Glu Asn Ala Ser Lys Arg His Pro Phe Ala Phe Met Pro Phe Ser Ala
            435                 440                 445

Gly Pro Arg Asn Cys Ile Gly Gln Gln Phe Ala Met Ser Glu Met Lys
    450                 455                 460

Val Val Thr Ala Met Cys Leu Leu Arg Phe Glu Phe Ser Leu Asp Pro
465                 470                 475                 480

Ser Arg Leu Pro Ile Lys Met Pro Gln Leu Val Leu Arg Ser Lys Asn
                485                 490                 495

Gly Phe His Leu His Leu Lys Pro Leu Gly Pro Gly Ser Gly Lys
            500                 505                 510
```

<210> SEQ ID NO 11
<211> LENGTH: 520
<212> TYPE: PRT
<213> ORGANISM: Homo sapiens -continued

<400> SEQUENCE: 11

Met Ser Gln Leu Ser Leu Ser Trp Leu Gly Leu Trp Pro Val Ala Ala
1               5                   10                  15

Ser Pro Trp Leu Leu Leu Leu Leu Val Gly Ala Ser Trp Leu Leu Ala
            20                  25                  30

His Val Leu Ala Trp Thr Tyr Ala Phe Tyr Asp Asn Cys Arg Arg Leu
        35                  40                  45

Arg Cys Phe Pro Gln Pro Pro Arg Arg Asn Trp Phe Trp Gly His Gln
    50                  55                  60

Gly Met Val Asn Pro Thr Glu Glu Gly Met Arg Val Leu Thr Gln Leu
65                  70                  75                  80

Val Ala Thr Tyr Pro Gln Gly Phe Lys Val Trp Met Gly Pro Ile Ser
                85                  90                  95

Pro Leu Leu Ser Leu Cys His Pro Asp Ile Ile Arg Ser Val Ile Asn
                100                 105                 110

Ala Ser Ala Ala Ile Ala Pro Lys Asp Lys Phe Phe Tyr Ser Phe Leu
            115                 120                 125

Glu Pro Trp Leu Gly Asp Gly Leu Leu Leu Ser Ala Gly Asp Lys Trp
    130                 135                 140

Ser Arg His Arg Arg Met Leu Thr Pro Ala Phe His Phe Asn Ile Leu
145                 150                 155                 160

Lys Pro Tyr Met Lys Ile Phe Asn Glu Ser Val Asn Ile Met His Ala
                165                 170                 175

Lys Trp Gln Leu Leu Ala Ser Glu Gly Ser Ala Cys Leu Asp Met Phe
            180                 185                 190

Glu His Ile Ser Leu Met Thr Leu Asp Ser Leu Gln Lys Cys Val Phe
            195                 200                 205

Ser Phe Asp Ser His Cys Gln Glu Lys Pro Ser Glu Tyr Ile Ala Ala
    210                 215                 220

Ile Leu Glu Leu Ser Ala Leu Val Ser Lys Arg His His Glu Ile Leu
225                 230                 235                 240

Leu His Ile Asp Phe Leu Tyr Tyr Leu Thr Pro Asp Gly Gln Arg Phe
                245                 250                 255

Arg Arg Ala Cys Arg Leu Val His Asp Phe Thr Asp Ala Val Ile Gln
            260                 265                 270

Glu Arg Arg Arg Thr Leu Pro Ser Gln Gly Val Asp Asp Phe Leu Gln
        275                 280                 285

Ala Lys Ala Lys Ser Lys Thr Leu Asp Phe Ile Asp Val Leu Leu Leu
    290                 295                 300

Ser Lys Asp Glu Asp Gly Lys Lys Leu Ser Asp Glu Asp Ile Arg Ala
305                 310                 315                 320

Glu Ala Asp Thr Phe Met Phe Glu Gly His Asp Thr Thr Ala Ser Gly
                325                 330                 335

Leu Ser Trp Val Leu Tyr His Leu Ala Lys His Pro Glu Tyr Gln Glu
            340                 345                 350

Arg Cys Arg Gln Glu Val Gln Glu Leu Leu Lys Asp Arg Glu Pro Lys
        355                 360                 365

Glu Ile Glu Trp Asp Asp Leu Ala His Leu Pro Phe Leu Thr Met Cys
    370                 375                 380

Met Lys Glu Ser Leu Arg Leu His Pro Pro Val Pro Val Ile Ser Arg
385                 390                 395                 400

His Val Thr Gln Asp Ile Val Leu Pro Asp Gly Arg Val Ile Pro Lys

-continued

```
                    405               410               415

Gly Ile Ile Cys Leu Ile Ser Val Phe Gly Thr His His Asn Pro Ala
            420               425               430

Val Trp Pro Asp Pro Glu Val Tyr Asp Pro Phe Arg Phe Asp Pro Glu
            435               440               445

Asn Ile Lys Glu Arg Ser Pro Leu Ala Phe Ile Pro Phe Ser Ala Gly
        450               455               460

Pro Arg Asn Cys Ile Gly Gln Thr Phe Ala Met Ala Glu Met Lys Val
465               470               475               480

Val Leu Ala Leu Thr Leu Leu Arg Phe Arg Val Leu Pro Asp His Thr
                485               490               495

Glu Pro Arg Arg Lys Pro Glu Leu Val Leu Arg Ala Glu Gly Gly Leu
            500               505               510

Trp Leu Arg Val Glu Pro Leu Ser
            515               520

<210> SEQ ID NO 12
<211> LENGTH: 520
<212> TYPE: PRT
<213> ORGANISM: Homo sapiens

<400> SEQUENCE: 12

Met Pro Gln Leu Ser Leu Ser Ser Leu Gly Leu Trp Pro Met Ala Ala
1               5               10               15

Ser Pro Trp Leu Leu Leu Leu Leu Val Gly Ala Ser Trp Leu Leu Ala
            20               25               30

Arg Ile Leu Ala Trp Thr Tyr Thr Phe Tyr Asp Asn Cys Cys Arg Leu
            35               40               45

Arg Cys Phe Pro Gln Pro Pro Lys Arg Asn Trp Phe Leu Gly His Leu
        50               55               60

Gly Leu Ile His Ser Ser Glu Glu Gly Leu Leu Tyr Thr Gln Ser Leu
65               70               75               80

Ala Cys Thr Phe Gly Asp Met Cys Cys Trp Trp Val Gly Pro Trp His
                85               90               95

Ala Ile Val Arg Ile Phe His Pro Thr Tyr Ile Lys Pro Val Leu Phe
            100               105               110

Ala Pro Ala Ala Ile Val Pro Lys Asp Lys Val Phe Tyr Ser Phe Leu
            115               120               125

Lys Pro Trp Leu Gly Asp Gly Leu Leu Leu Ser Ala Gly Glu Lys Trp
        130               135               140

Ser Arg His Arg Arg Met Leu Thr Pro Ala Phe His Phe Asn Ile Leu
145               150               155               160

Lys Pro Tyr Met Lys Ile Phe Asn Glu Ser Val Asn Ile Met His Ala
                165               170               175

Lys Trp Gln Leu Leu Ala Ser Glu Gly Ser Ala Arg Leu Asp Met Phe
            180               185               190

Glu His Ile Ser Leu Met Thr Leu Asp Ser Leu Gln Lys Cys Val Phe
            195               200               205

Ser Phe Asp Ser His Cys Gln Glu Lys Pro Ser Glu Tyr Ile Ala Ala
        210               215               220

Ile Leu Glu Leu Ser Ala Leu Val Thr Lys Arg His Gln Gln Ile Leu
225               230               235               240

Leu Tyr Ile Asp Phe Leu Tyr Tyr Leu Thr Pro Asp Gly Gln Arg Phe
                245               250               255
```

-continued

```
Arg Arg Ala Cys Arg Leu Val His Asp Phe Thr Asp Ala Val Ile Gln
            260                 265                 270

Glu Arg Arg Arg Thr Leu Pro Ser Gln Gly Val Asp Asp Phe Leu Gln
            275                 280                 285

Ala Lys Ala Lys Ser Lys Thr Leu Asp Phe Ile Asp Val Leu Leu Leu
            290                 295                 300

Ser Lys Asp Glu Asp Gly Lys Lys Leu Ser Asp Glu Asp Ile Arg Ala
305                 310                 315                 320

Glu Ala Asp Thr Phe Met Phe Glu Gly His Asp Thr Thr Ala Ser Gly
                325                 330                 335

Leu Ser Trp Val Leu Tyr His Leu Ala Lys His Pro Glu Tyr Gln Glu
            340                 345                 350

Arg Cys Arg Gln Glu Val Gln Glu Leu Leu Lys Asp Arg Glu Pro Lys
            355                 360                 365

Glu Ile Glu Trp Asp Asp Leu Ala Gln Leu Pro Phe Leu Thr Met Cys
    370                 375                 380

Ile Lys Glu Ser Leu Arg Leu His Pro Pro Val Pro Ala Val Ser Arg
385                 390                 395                 400

Cys Cys Thr Gln Asp Ile Val Leu Pro Asp Gly Arg Val Ile Pro Lys
                405                 410                 415

Gly Ile Ile Cys Leu Ile Ser Val Phe Gly Thr His His Asn Pro Ala
                420                 425                 430

Val Trp Pro Asp Pro Glu Val Tyr Asp Pro Phe Arg Phe Asp Pro Lys
            435                 440                 445

Asn Ile Lys Glu Arg Ser Pro Leu Ala Phe Ile Pro Phe Ser Ala Gly
    450                 455                 460

Pro Arg Asn Cys Ile Gly Gln Ala Phe Ala Met Ala Glu Met Lys Val
465                 470                 475                 480

Val Leu Gly Leu Thr Leu Leu Arg Phe Arg Val Leu Pro Asp His Thr
                485                 490                 495

Glu Pro Arg Arg Lys Pro Glu Leu Val Leu Arg Ala Glu Gly Gly Leu
            500                 505                 510

Trp Leu Arg Val Glu Pro Leu Ser
            515                 520

<210> SEQ ID NO 13
<211> LENGTH: 520
<212> TYPE: PRT
<213> ORGANISM: Homo sapiens

<400> SEQUENCE: 13

Met Ser Leu Leu Ser Leu Ser Trp Leu Gly Leu Arg Pro Val Ala Ala
1               5                   10                  15

Ser Pro Trp Leu Leu Leu Leu Val Val Gly Ala Ser Trp Leu Leu Ala
            20                  25                  30

Arg Ile Leu Ala Trp Thr Tyr Ala Phe Tyr His Asn Gly Arg Arg Leu
        35                  40                  45

Arg Cys Phe Pro Gln Pro Arg Lys Gln Asn Trp Phe Leu Gly His Leu
    50                  55                  60

Gly Leu Val Thr Pro Thr Glu Glu Gly Leu Arg Val Leu Thr Gln Leu
65                  70                  75                  80

Val Ala Thr Tyr Pro Gln Gly Phe Val Arg Trp Leu Gly Pro Ile Thr
                85                  90                  95

Pro Ile Ile Asn Leu Cys His Pro Asp Ile Val Arg Ser Val Ile Asn
            100                 105                 110
```

-continued

```
Thr Ser Asp Ala Ile Thr Asp Lys Asp Ile Val Phe Tyr Lys Thr Leu
        115                 120                 125

Lys Pro Trp Leu Gly Asp Gly Leu Leu Leu Ser Val Gly Asp Lys Trp
        130                 135                 140

Arg His His Arg Arg Leu Leu Thr Pro Ala Phe His Phe Asn Ile Leu
145                 150                 155                 160

Lys Pro Tyr Ile Lys Ile Phe Ser Lys Ser Ala Asn Ile Met His Ala
                165                 170                 175

Lys Trp Gln Arg Leu Ala Met Glu Gly Ser Thr Cys Leu Asp Val Phe
        180                 185                 190

Glu His Ile Ser Leu Met Thr Leu Asp Ser Leu Gln Lys Cys Ile Phe
        195                 200                 205

Ser Phe Asp Ser Asn Cys Gln Glu Lys Pro Ser Glu Tyr Ile Thr Ala
        210                 215                 220

Ile Met Glu Leu Ser Ala Leu Val Val Lys Arg Asn Asn Gln Phe Phe
225                 230                 235                 240

Arg Tyr Lys Asp Phe Leu Tyr Phe Leu Thr Pro Cys Gly Arg Arg Phe
                245                 250                 255

His Arg Ala Cys Arg Leu Val His Asp Phe Thr Asp Ala Val Ile Gln
        260                 265                 270

Glu Arg Arg Arg Thr Leu Thr Ser Gln Gly Val Asp Asp Phe Leu Gln
        275                 280                 285

Ala Lys Ala Lys Ser Lys Thr Leu Asp Phe Ile Asp Val Leu Leu Leu
        290                 295                 300

Ser Glu Asp Lys Asn Gly Lys Glu Leu Ser Asp Glu Asp Ile Arg Ala
305                 310                 315                 320

Glu Ala Asp Thr Phe Met Phe Gly Gly His Asp Thr Thr Ala Ser Gly
                325                 330                 335

Leu Ser Trp Val Leu Tyr Asn Leu Ala Arg His Pro Glu Tyr Gln Glu
                340                 345                 350

Arg Cys Arg Gln Glu Val Gln Glu Leu Leu Lys Asp Arg Glu Pro Lys
        355                 360                 365

Glu Ile Glu Trp Asp Asp Leu Ala Gln Leu Pro Phe Leu Thr Met Cys
        370                 375                 380

Leu Lys Glu Ser Leu Arg Leu His Pro Pro Ile Pro Thr Phe Ala Arg
385                 390                 395                 400

Gly Cys Thr Gln Asp Val Val Leu Pro Asp Ser Arg Val Ile Pro Lys
                405                 410                 415

Gly Asn Val Cys Asn Ile Asn Ile Phe Ala Ile His His Asn Pro Ser
                420                 425                 430

Val Trp Pro Asp Pro Glu Val Tyr Asp Pro Phe Arg Phe Asp Pro Glu
        435                 440                 445

Asn Ala Gln Lys Arg Ser Pro Met Ala Phe Ile Pro Phe Ser Ala Gly
        450                 455                 460

Pro Arg Asn Cys Ile Gly Gln Lys Phe Ala Met Ala Glu Met Lys Val
465                 470                 475                 480

Val Leu Ala Leu Thr Leu Leu Arg Phe Arg Ile Leu Pro Asp His Arg
                485                 490                 495

Glu Pro Arg Arg Thr Pro Glu Ile Val Leu Arg Ala Glu Asp Gly Leu
        500                 505                 510

Trp Leu Arg Val Glu Pro Leu Gly
        515                 520
```

-continued

<210> SEQ ID NO 14
<211> LENGTH: 524
<212> TYPE: PRT
<213> ORGANISM: Homo sapiens

<400> SEQUENCE: 14

```
Met Pro Gln Leu Ser Leu Ser Trp Leu Gly Leu Gly Pro Val Ala Ala
1               5                   10                  15

Ser Pro Trp Leu Leu Leu Leu Leu Val Gly Gly Ser Trp Leu Leu Ala
            20                  25                  30

Arg Val Leu Ala Trp Thr Tyr Thr Phe Tyr Asp Asn Cys Arg Arg Leu
            35                  40                  45

Gln Cys Phe Pro Gln Pro Pro Lys Gln Asn Trp Phe Trp Gly His Gln
    50                  55                  60

Gly Leu Val Thr Pro Thr Glu Glu Gly Met Lys Thr Leu Thr Gln Leu
65                  70                  75                  80

Val Thr Thr Tyr Pro Gln Gly Phe Lys Leu Trp Leu Gly Pro Thr Phe
                85                  90                  95

Pro Leu Leu Ile Leu Cys His Pro Asp Ile Ile Arg Pro Ile Thr Ser
            100                 105                 110

Ala Ser Ala Ala Val Ala Pro Lys Asp Met Ile Phe Tyr Gly Phe Leu
            115                 120                 125

Lys Pro Trp Leu Gly Asp Gly Leu Leu Leu Ser Gly Gly Asp Lys Trp
    130                 135                 140

Ser Arg His Arg Arg Met Leu Thr Pro Ala Phe His Phe Asn Ile Leu
145                 150                 155                 160

Lys Pro Tyr Met Lys Ile Phe Asn Lys Ser Val Asn Ile Met His Asp
                165                 170                 175

Lys Trp Gln Arg Leu Ala Ser Glu Gly Ser Ala Arg Leu Asp Met Phe
            180                 185                 190

Glu His Ile Ser Leu Met Thr Leu Asp Ser Leu Gln Lys Cys Val Phe
            195                 200                 205

Ser Phe Glu Ser Asn Cys Gln Glu Lys Pro Ser Glu Tyr Ile Ala Ala
    210                 215                 220

Ile Leu Glu Leu Ser Ala Phe Val Glu Lys Arg Asn Gln Gln Ile Leu
225                 230                 235                 240

Leu His Thr Asp Phe Leu Tyr Tyr Leu Thr Pro Asp Gly Gln Arg Phe
                245                 250                 255

Arg Arg Ala Cys His Leu Val His Asp Phe Thr Asp Ala Val Ile Gln
            260                 265                 270

Glu Arg Arg Cys Thr Leu Pro Thr Gln Gly Ile Asp Asp Phe Leu Lys
            275                 280                 285

Asn Lys Ala Lys Ser Lys Thr Leu Asp Phe Ile Asp Val Leu Leu Leu
    290                 295                 300

Ser Lys Asp Glu Asp Gly Lys Glu Leu Ser Asp Glu Asp Ile Arg Ala
305                 310                 315                 320

Glu Ala Asp Thr Phe Met Phe Glu Gly His Asp Thr Thr Ala Ser Gly
                325                 330                 335

Leu Ser Trp Val Leu Tyr His Leu Ala Lys His Pro Glu Tyr Gln Glu
            340                 345                 350

Gln Cys Arg Gln Glu Val Gln Glu Leu Leu Lys Asp Arg Glu Pro Ile
            355                 360                 365

Glu Ile Glu Trp Asp Asp Leu Ala Gln Leu Pro Phe Leu Thr Met Cys
    370                 375                 380
```

```
Ile Lys Glu Ser Leu Arg Leu His Pro Pro Val Pro Val Ile Ser Arg
385             390             395             400

Cys Cys Thr Gln Asp Phe Val Leu Pro Asp Gly Arg Val Ile Pro Lys
                405             410             415

Gly Ile Val Cys Leu Ile Asn Ile Ile Gly Ile His Tyr Asn Pro Thr
            420             425             430

Val Trp Pro Asp Pro Glu Val Tyr Asp Pro Phe Arg Phe Asp Gln Glu
            435             440             445

Asn Ile Lys Glu Arg Ser Pro Leu Ala Phe Ile Pro Phe Ser Ala Gly
        450             455             460

Pro Arg Asn Cys Ile Gly Gln Ala Phe Ala Met Ala Glu Met Lys Val
465             470             475             480

Val Leu Ala Leu Thr Leu Leu His Phe Arg Ile Leu Pro Thr His Thr
                485             490             495

Glu Pro Arg Arg Lys Pro Glu Leu Ile Leu Arg Ala Glu Gly Gly Leu
            500             505             510

Trp Leu Arg Val Glu Pro Leu Gly Ala Asn Ser Gln
            515             520

<210> SEQ ID NO 15
<211> LENGTH: 524
<212> TYPE: PRT
<213> ORGANISM: Homo sapiens

<400> SEQUENCE: 15

Met Ser Leu Leu Ser Leu Pro Trp Leu Gly Leu Arg Pro Val Ala Thr
1               5               10              15

Ser Pro Trp Leu Leu Leu Leu Leu Val Val Gly Ser Trp Leu Leu Ala
                20              25              30

Arg Ile Leu Ala Trp Thr Tyr Ala Phe Tyr Asn Asn Cys Arg Arg Leu
            35              40              45

Gln Cys Phe Pro Gln Pro Pro Lys Arg Asn Trp Phe Trp Gly His Leu
        50              55              60

Gly Leu Ile Thr Pro Thr Glu Glu Gly Leu Lys Asn Ser Thr Gln Met
65              70              75              80

Ser Ala Thr Tyr Ser Gln Gly Phe Thr Val Trp Leu Gly Pro Ile Ile
                85              90              95

Pro Phe Ile Val Leu Cys His Pro Asp Thr Ile Arg Ser Ile Thr Asn
                100             105             110

Ala Ser Ala Ala Ile Ala Pro Lys Asp Asn Leu Phe Ile Arg Phe Leu
            115             120             125

Lys Pro Trp Leu Gly Glu Gly Ile Leu Leu Ser Gly Gly Asp Lys Trp
        130             135             140

Ser Arg His Arg Arg Met Leu Thr Pro Ala Phe His Phe Asn Ile Leu
145             150             155             160

Lys Ser Tyr Ile Thr Ile Phe Asn Lys Ser Ala Asn Ile Met Leu Asp
                165             170             175

Lys Trp Gln His Leu Ala Ser Glu Gly Ser Ser Arg Leu Asp Met Phe
                180             185             190

Glu His Ile Ser Leu Met Thr Leu Asp Ser Leu Gln Lys Cys Ile Phe
            195             200             205

Ser Phe Asp Ser His Cys Gln Glu Arg Pro Ser Glu Tyr Ile Ala Thr
    210             215             220

Ile Leu Glu Leu Ser Ala Leu Val Glu Lys Arg Ser Gln His Ile Leu
```

-continued

```
225                 230                 235                 240

Gln His Met Asp Phe Leu Tyr Tyr Leu Ser His Asp Gly Arg Arg Phe
                245                 250                 255

His Arg Ala Cys Arg Leu Val His Asp Phe Thr Asp Ala Val Ile Arg
                260                 265                 270

Glu Arg Arg Arg Thr Leu Pro Thr Gln Gly Ile Asp Asp Phe Phe Lys
                275                 280                 285

Asp Lys Ala Lys Ser Lys Thr Leu Asp Phe Ile Asp Val Leu Leu Leu
                290                 295                 300

Ser Lys Asp Glu Asp Gly Lys Ala Leu Ser Asp Glu Asp Ile Arg Ala
305                 310                 315                 320

Glu Ala Asp Thr Phe Met Phe Gly Gly His Asp Thr Thr Ala Ser Gly
                325                 330                 335

Leu Ser Trp Val Leu Tyr Asn Leu Ala Arg His Pro Glu Tyr Gln Glu
                340                 345                 350

Arg Cys Arg Gln Glu Val Gln Glu Leu Leu Lys Asp Arg Asp Pro Lys
                355                 360                 365

Glu Ile Glu Trp Asp Asp Leu Ala Gln Leu Pro Phe Leu Thr Met Cys
                370                 375                 380

Val Lys Glu Ser Leu Arg Leu His Pro Pro Ala Pro Phe Ile Ser Arg
385                 390                 395                 400

Cys Cys Thr Gln Asp Ile Val Leu Pro Asp Gly Arg Val Ile Pro Lys
                405                 410                 415

Gly Ile Thr Cys Leu Ile Asp Ile Ile Gly Val His His Asn Pro Thr
                420                 425                 430

Val Trp Pro Asp Pro Glu Val Tyr Asp Pro Phe Arg Phe Asp Pro Glu
                435                 440                 445

Asn Ser Lys Gly Arg Ser Pro Leu Ala Phe Ile Pro Phe Ser Ala Gly
                450                 455                 460

Pro Arg Asn Cys Ile Gly Gln Ala Phe Ala Met Ala Glu Met Lys Val
465                 470                 475                 480

Val Leu Ala Leu Met Leu Leu His Phe Arg Phe Leu Pro Asp His Thr
                485                 490                 495

Glu Pro Arg Arg Lys Leu Glu Leu Ile Met Arg Ala Glu Gly Gly Leu
                500                 505                 510

Trp Leu Arg Val Glu Pro Leu Asn Val Ser Leu Gln
                515                 520

<210> SEQ ID NO 16
<211> LENGTH: 531
<212> TYPE: PRT
<213> ORGANISM: Homo sapiens

<400> SEQUENCE: 16

Met Leu Pro Ile Thr Asp Arg Leu Leu His Leu Leu Gly Leu Glu Lys
1               5                   10                  15

Thr Ala Phe Arg Ile Tyr Ala Val Ser Thr Leu Leu Leu Phe Leu Leu
                20                  25                  30

Phe Phe Leu Phe Arg Leu Leu Leu Arg Phe Leu Arg Leu Cys Arg Ser
                35                  40                  45

Phe Tyr Ile Thr Cys Arg Arg Leu Arg Cys Phe Pro Gln Pro Pro Arg
                50                  55                  60

Arg Asn Trp Leu Leu Gly His Leu Gly Met Tyr Leu Pro Asn Glu Ala
65                  70                  75                  80
```

```
Gly Leu Gln Asp Glu Lys Lys Val Leu Asp Asn Met His His Val Leu
              85              90              95

Leu Val Trp Met Gly Pro Val Leu Pro Leu Leu Val Leu Val His Pro
              100             105             110

Asp Tyr Ile Lys Pro Leu Leu Gly Ala Ser Ala Ala Ile Ala Pro Lys
              115             120             125

Asp Asp Leu Phe Tyr Gly Phe Leu Lys Pro Trp Leu Gly Asp Gly Leu
  130             135             140

Leu Leu Ser Lys Gly Asp Lys Trp Ser Arg His Arg Arg Leu Leu Thr
145             150             155             160

Pro Ala Phe His Phe Asp Ile Leu Lys Pro Tyr Met Lys Ile Phe Asn
              165             170             175

Gln Ser Ala Asp Ile Met His Ala Lys Trp Arg His Leu Ala Glu Gly
              180             185             190

Ser Ala Val Ser Leu Asp Met Phe Glu His Ile Ser Leu Met Thr Leu
              195             200             205

Asp Ser Leu Gln Lys Cys Val Phe Ser Tyr Asn Ser Asn Cys Gln Glu
  210             215             220

Lys Met Ser Asp Tyr Ile Ser Ala Ile Ile Glu Leu Ser Ala Leu Ser
225             230             235             240

Val Arg Arg Gln Tyr Arg Leu His His Tyr Leu Asp Phe Ile Tyr Tyr
              245             250             255

Arg Ser Ala Asp Gly Arg Arg Phe Arg Gln Ala Cys Asp Met Val His
              260             265             270

His Phe Thr Thr Glu Val Ile Gln Glu Arg Arg Arg Ala Leu Arg Gln
              275             280             285

Gln Gly Ala Glu Ala Trp Leu Lys Ala Lys Gln Gly Lys Thr Leu Asp
  290             295             300

Phe Ile Asp Val Leu Leu Leu Ala Arg Asp Glu Asp Gly Lys Glu Leu
305             310             315             320

Ser Asp Glu Asp Ile Arg Ala Glu Ala Asp Thr Phe Met Phe Glu Gly
              325             330             335

His Asp Thr Thr Ser Ser Gly Ile Ser Trp Met Leu Phe Asn Leu Ala
              340             345             350

Lys Tyr Pro Glu Tyr Gln Glu Lys Cys Arg Glu Glu Ile Gln Glu Val
              355             360             365

Met Lys Gly Arg Glu Leu Glu Glu Leu Glu Trp Asp Asp Leu Thr Gln
  370             375             380

Leu Pro Phe Thr Thr Met Cys Ile Lys Glu Ser Leu Arg Gln Tyr Pro
385             390             395             400

Pro Val Thr Leu Val Ser Arg Gln Cys Thr Glu Asp Ile Lys Leu Pro
              405             410             415

Asp Gly Arg Ile Ile Pro Lys Gly Ile Ile Cys Leu Val Ser Ile Tyr
              420             425             430

Gly Thr His His Asn Pro Thr Val Trp Pro Asp Ser Lys Val Tyr Asn
              435             440             445

Pro Tyr Arg Phe Asp Pro Asp Asn Pro Gln Gln Arg Ser Pro Leu Ala
              450             455             460

Tyr Val Pro Phe Ser Ala Gly Pro Arg Asn Cys Ile Gly Gln Ser Phe
465             470             475             480

Ala Met Ala Glu Leu Arg Val Val Val Ala Leu Thr Leu Leu Arg Phe
              485             490             495

Arg Leu Ser Val Asp Arg Thr Arg Lys Val Arg Arg Lys Pro Glu Leu
```

-continued

```
                500                 505                 510
Ile Leu Arg Thr Glu Asn Gly Leu Trp Leu Lys Val Glu Pro Leu Pro
            515                 520                 525

Pro Arg Ala
    530

<210> SEQ ID NO 17
<211> LENGTH: 509
<212> TYPE: PRT
<213> ORGANISM: Homo sapiens

<400> SEQUENCE: 17

Met Glu Phe Ser Trp Leu Glu Thr Arg Trp Ala Arg Pro Phe Tyr Leu
1               5                   10                  15

Ala Phe Val Phe Cys Leu Ala Leu Gly Leu Leu Gln Ala Ile Lys Leu
            20                  25                  30

Tyr Leu Arg Arg Gln Arg Leu Leu Arg Asp Leu Arg Pro Phe Pro Ala
        35                  40                  45

Pro Pro Thr His Trp Phe Leu Gly His Gln Lys Phe Ile Gln Asp Asp
    50                  55                  60

Asn Met Glu Lys Leu Glu Glu Ile Ile Glu Lys Tyr Pro Arg Ala Phe
65                  70                  75                  80

Pro Phe Trp Ile Gly Pro Phe Gln Ala Phe Phe Cys Ile Tyr Asp Pro
                85                  90                  95

Asp Tyr Ala Lys Thr Leu Leu Ser Arg Thr Asp Pro Lys Ser Gln Tyr
                100                 105                 110

Leu Gln Lys Phe Ser Pro Pro Leu Leu Gly Lys Gly Leu Ala Ala Leu
        115                 120                 125

Asp Gly Pro Lys Trp Phe Gln His Arg Arg Leu Leu Thr Pro Gly Phe
    130                 135                 140

His Phe Asn Ile Leu Lys Ala Tyr Ile Glu Val Met Ala His Ser Val
145                 150                 155                 160

Lys Met Met Leu Asp Lys Trp Glu Lys Ile Cys Ser Thr Gln Asp Thr
                165                 170                 175

Ser Val Glu Val Tyr Glu His Ile Asn Ser Met Ser Leu Asp Ile Ile
            180                 185                 190

Met Lys Cys Ala Phe Ser Lys Glu Thr Asn Cys Gln Thr Asn Ser Thr
        195                 200                 205

His Asp Pro Tyr Ala Lys Ala Ile Phe Glu Leu Ser Lys Ile Ile Phe
    210                 215                 220

His Arg Leu Tyr Ser Leu Leu Tyr His Ser Asp Ile Ile Phe Lys Leu
225                 230                 235                 240

Ser Pro Gln Gly Tyr Arg Phe Gln Lys Leu Ser Arg Val Leu Asn Gln
                245                 250                 255

Tyr Thr Asp Thr Ile Ile Gln Glu Arg Lys Lys Ser Leu Gln Ala Gly
                260                 265                 270

Val Lys Gln Asp Asn Thr Pro Lys Arg Lys Tyr Gln Asp Phe Leu Asp
        275                 280                 285

Ile Val Leu Ser Ala Lys Asp Glu Ser Gly Ser Ser Phe Ser Asp Ile
    290                 295                 300

Asp Val His Ser Glu Val Ser Thr Phe Leu Leu Ala Gly His Asp Thr
305                 310                 315                 320

Leu Ala Ala Ser Ile Ser Trp Ile Leu Tyr Cys Leu Ala Leu Asn Pro
                325                 330                 335
```

```
Glu His Gln Glu Arg Cys Arg Glu Glu Val Arg Gly Ile Leu Gly Asp
            340                 345                 350

Gly Ser Ser Ile Thr Trp Asp Gln Leu Gly Glu Met Ser Tyr Thr Thr
            355                 360                 365

Met Cys Ile Lys Glu Thr Cys Arg Leu Ile Pro Ala Val Pro Ser Ile
    370                 375                 380

Ser Arg Asp Leu Ser Lys Pro Leu Thr Phe Pro Asp Gly Cys Thr Leu
385                 390                 395                 400

Pro Ala Gly Ile Thr Val Val Leu Ser Ile Trp Gly Leu His His Asn
                405                 410                 415

Pro Ala Val Trp Lys Asn Pro Lys Val Phe Asp Pro Leu Arg Phe Ser
                420                 425                 430

Gln Glu Asn Ser Asp Gln Arg His Pro Tyr Ala Tyr Leu Pro Phe Ser
            435                 440                 445

Ala Gly Ser Arg Asn Cys Ile Gly Gln Glu Phe Ala Met Ile Glu Leu
    450                 455                 460

Lys Val Thr Ile Ala Leu Ile Leu Leu His Phe Arg Val Thr Pro Asp
465                 470                 475                 480

Pro Thr Arg Pro Leu Thr Phe Pro Asn His Phe Ile Leu Lys Pro Lys
                485                 490                 495

Asn Gly Met Tyr Leu His Leu Lys Lys Leu Ser Glu Cys
                500                 505

<210> SEQ ID NO 18
<211> LENGTH: 505
<212> TYPE: PRT
<213> ORGANISM: Homo sapiens

<400> SEQUENCE: 18

Met Glu Pro Ser Trp Leu Gln Glu Leu Met Ala His Pro Phe Leu Leu
1               5                   10                  15

Leu Ile Leu Leu Cys Met Ser Leu Leu Leu Phe Gln Val Ile Arg Leu
            20                  25                  30

Tyr Gln Arg Arg Arg Trp Met Ile Arg Ala Leu His Leu Phe Pro Ala
            35                  40                  45

Pro Pro Ala His Trp Phe Tyr Gly His Lys Glu Phe Tyr Pro Val Lys
    50                  55                  60

Glu Phe Glu Val Tyr His Lys Leu Met Glu Lys Tyr Pro Cys Ala Val
65                  70                  75                  80

Pro Leu Trp Val Gly Pro Phe Thr Met Phe Phe Ser Val His Asp Pro
                85                  90                  95

Asp Tyr Ala Lys Ile Leu Leu Lys Arg Gln Asp Pro Lys Ser Ala Val
                100                 105                 110

Ser His Lys Ile Leu Glu Ser Trp Val Gly Arg Gly Leu Val Thr Leu
            115                 120                 125

Asp Gly Ser Lys Trp Lys Lys His Arg Gln Ile Val Lys Pro Gly Phe
            130                 135                 140

Asn Ile Ser Ile Leu Lys Ile Phe Ile Thr Met Met Ser Glu Ser Val
145                 150                 155                 160

Arg Met Met Leu Asn Lys Trp Glu Glu His Ile Ala Gln Asn Ser Arg
                165                 170                 175

Leu Glu Leu Phe Gln His Val Ser Leu Met Thr Leu Asp Ser Ile Met
            180                 185                 190

Lys Cys Ala Phe Ser His Gln Gly Ser Ile Gln Leu Asp Ser Thr Leu
            195                 200                 205
```

```
Asp Ser Tyr Leu Lys Ala Val Phe Asn Leu Ser Lys Ile Ser Asn Gln
    210             215                 220

Arg Met Asn Asn Phe Leu His His Asn Asp Leu Val Phe Lys Phe Ser
225             230                 235                 240

Ser Gln Gly Gln Ile Phe Ser Lys Phe Asn Gln Glu Leu His Gln Phe
            245                 250                 255

Thr Glu Lys Val Ile Gln Asp Arg Lys Glu Ser Leu Lys Asp Lys Leu
            260                 265                 270

Lys Gln Asp Thr Thr Gln Lys Arg Arg Trp Asp Phe Leu Asp Ile Leu
            275                 280                 285

Leu Ser Ala Lys Ser Glu Asn Thr Lys Asp Phe Ser Glu Ala Asp Leu
    290                 295                 300

Gln Ala Glu Val Lys Thr Phe Met Phe Ala Gly His Asp Thr Thr Ser
305                 310                 315                 320

Ser Ala Ile Ser Trp Ile Leu Tyr Cys Leu Ala Lys Tyr Pro Glu His
            325                 330                 335

Gln Gln Arg Cys Arg Asp Glu Ile Arg Glu Leu Leu Gly Asp Gly Ser
            340                 345                 350

Ser Ile Thr Trp Glu His Leu Ser Gln Met Pro Tyr Thr Thr Met Cys
            355                 360                 365

Ile Lys Glu Cys Leu Arg Leu Tyr Ala Pro Val Val Asn Ile Ser Arg
    370                 375                 380

Leu Leu Asp Lys Pro Ile Thr Phe Pro Asp Gly Arg Ser Leu Pro Ala
385                 390                 395                 400

Gly Ile Thr Val Phe Ile Asn Ile Trp Ala Leu His His Asn Pro Tyr
            405                 410                 415

Phe Trp Glu Asp Pro Gln Val Phe Asn Pro Leu Arg Phe Ser Arg Glu
            420                 425                 430

Asn Ser Glu Lys Ile His Pro Tyr Ala Phe Ile Pro Phe Ser Ala Gly
            435                 440                 445

Leu Arg Asn Cys Ile Gly Gln His Phe Ala Ile Ile Glu Cys Lys Val
    450                 455                 460

Ala Val Ala Leu Thr Leu Leu Arg Phe Lys Leu Ala Pro Asp His Ser
465                 470                 475                 480

Arg Pro Pro Gln Pro Val Arg Gln Val Val Leu Lys Ser Lys Asn Gly
            485                 490                 495

Ile His Val Phe Ala Lys Lys Val Cys
            500                 505
```

```
<210> SEQ ID NO 19
<211> LENGTH: 525
<212> TYPE: PRT
<213> ORGANISM: Pan troglodytes

<400> SEQUENCE: 19
```

```
Met Ala Gly Leu Trp Leu Gly Leu Val Trp Gln Lys Leu Leu Leu Trp
1               5                   10                  15

Gly Ala Ala Ser Ala Val Ser Leu Ala Gly Ala Ser Leu Val Leu Ser
            20                  25                  30

Leu Leu Gln Arg Val Ala Thr Tyr Ala Arg Lys Trp Gln Gln Met Arg
            35                  40                  45

Pro Ile Pro Thr Val Ala Arg Ala Tyr Pro Leu Val Gly His Ala Leu
    50                  55                  60

Leu Met Lys Pro Asp Gly Arg Glu Phe Phe Gln Gln Ile Ile Glu Tyr
```

-continued

```
65                    70                    75                    80

Thr Glu Glu Tyr Arg His Met Pro Leu Leu Lys Leu Trp Val Gly Pro
                85                    90                    95

Val Pro Met Val Ala Leu Tyr Asn Ala Glu Asn Val Glu Val Ile Leu
            100                   105                   110

Thr Ser Ser Lys Gln Ile Asp Lys Ser Ser Met Tyr Lys Phe Leu Glu
            115                   120                   125

Pro Trp Leu Gly Leu Gly Leu Leu Thr Ser Thr Gly Asn Lys Trp Arg
        130                   135                   140

Ser Arg Arg Lys Met Leu Thr Pro Thr Phe His Phe Thr Ile Leu Glu
145                   150                   155                   160

Asp Phe Leu Asp Ile Met Asn Glu Gln Ala Asn Thr Leu Val Lys Lys
                165                   170                   175

Leu Glu Lys His Ile Asn Gln Glu Ala Phe Asn Cys Phe Phe Tyr Ile
            180                   185                   190

Thr Leu Cys Ala Leu Asp Ile Ile Cys Glu Thr Ala Met Gly Lys Asn
            195                   200                   205

Ile Gly Ala Gln Ser Asn Asp Asp Ser Glu Tyr Val Arg Ala Val Tyr
    210                   215                   220

Arg Met Ser Glu Met Ile Phe Arg Arg Ile Lys Met Pro Trp Leu Trp
225                   230                   235                   240

Leu Asp Leu Trp Tyr Leu Met Phe Lys Glu Gly Trp Glu His Lys Lys
                245                   250                   255

Ser Leu Lys Ile Leu His Thr Phe Thr Asn Ser Val Ile Ala Glu Arg
            260                   265                   270

Ala Asn Glu Met Asn Ala Asn Glu Asp Cys Arg Gly Asp Gly Arg Gly
            275                   280                   285

Ser Ala Pro Ser Lys Asn Lys Arg Arg Ala Phe Leu Asp Leu Leu Leu
    290                   295                   300

Ser Val Thr Asp Asp Glu Gly Asn Arg Leu Ser His Glu Asp Ile Arg
305                   310                   315                   320

Glu Glu Val Asp Thr Phe Met Phe Glu Gly His Asp Thr Thr Ala Ala
                325                   330                   335

Ala Ile Asn Trp Ser Leu Tyr Leu Leu Gly Ser Asn Pro Glu Val Gln
            340                   345                   350

Lys Lys Val Asp His Glu Leu Asp Asp Val Phe Gly Lys Ser Asp Arg
            355                   360                   365

Pro Ala Thr Val Glu Asp Leu Lys Lys Leu Arg Tyr Leu Glu Cys Val
    370                   375                   380

Ile Lys Glu Thr Leu Arg Leu Phe Pro Ser Val Pro Leu Phe Ala Arg
385                   390                   395                   400

Ser Val Ser Glu Asp Cys Glu Val Ala Gly Tyr Arg Val Leu Lys Gly
                405                   410                   415

Thr Glu Ala Val Ile Ile Pro Tyr Ala Leu His Arg Asp Pro Arg Tyr
            420                   425                   430

Phe Pro Asn Pro Glu Glu Phe Gln Pro Glu Arg Phe Phe Pro Lys Asn
            435                   440                   445

Ala Gln Gly Arg His Pro Tyr Ala Tyr Val Pro Phe Ser Ala Gly Pro
    450                   455                   460

Arg Asn Cys Ile Gly Gln Lys Phe Ala Val Met Glu Glu Lys Thr Ile
465                   470                   475                   480

Leu Ser Cys Ile Leu Arg His Phe Trp Ile Glu Ser Asn Gln Lys Arg
                485                   490                   495
```

-continued

Glu Glu Leu Gly Leu Glu Gly Gln Leu Ile Leu Arg Pro Ser Asn Gly
                500                     505                     510

Ile Trp Ile Lys Leu Lys Arg Arg Asn Ala Asp Glu Arg
            515                     520                     525

<210> SEQ ID NO 20
<211> LENGTH: 525
<212> TYPE: PRT
<213> ORGANISM: Macaca mulatta

<400> SEQUENCE: 20

Met Ala Gly Ile Trp Leu Gly Leu Val Trp Gln Lys Leu Leu Leu Trp
1                   5                       10                      15

Gly Ala Ala Ser Ala Val Ser Leu Ala Gly Ala Ser Leu Val Leu Ser
                20                      25                      30

Leu Leu Gln Arg Val Ala Ser Tyr Val Arg Lys Trp Gln Gln Met Arg
            35                      40                      45

Pro Ile Pro Thr Val Ala Arg Ala Tyr Pro Leu Val Gly His Ala Leu
        50                      55                      60

Leu Met Lys Arg Asp Gly Arg Glu Phe Phe Gln Gln Ile Ile Glu Tyr
65                      70                      75                      80

Thr Glu Glu Tyr Arg His Met Pro Leu Leu Lys Leu Trp Val Gly Pro
                85                      90                      95

Val Pro Met Val Ala Leu Tyr Asn Ala Glu Asn Val Glu Val Ile Leu
                100                     105                     110

Thr Ser Ser Lys Gln Ile Asp Lys Ser Ser Met Tyr Lys Phe Leu Glu
            115                     120                     125

Pro Trp Leu Gly Leu Gly Leu Leu Thr Ser Thr Gly Asn Lys Trp Arg
        130                     135                     140

Ser Arg Arg Lys Met Leu Thr Pro Thr Phe His Phe Thr Ile Leu Glu
145                     150                     155                     160

Asp Phe Leu Asp Ile Met Asn Glu Gln Ala Asn Ile Leu Val Lys Lys
                165                     170                     175

Leu Glu Lys His Val Asn Gln Glu Ala Phe Asn Cys Phe Val Tyr Ile
            180                     185                     190

Thr Leu Cys Ala Leu Asp Ile Ile Cys Glu Thr Ala Met Gly Lys Asn
            195                     200                     205

Ile Gly Ala Gln Ser Asn Asp Asp Ser Glu Tyr Val Arg Ala Val Tyr
        210                     215                     220

Arg Met Ser Glu Met Ile Phe Arg Arg Ile Lys Met Pro Trp Leu Trp
225                     230                     235                     240

Leu Asp Leu Trp Tyr Leu Met Phe Lys Glu Gly Trp Glu His Lys Lys
                245                     250                     255

Ser Leu Lys Ile Leu His Ala Phe Thr Asn Asn Val Ile Ala Glu Arg
            260                     265                     270

Ala Asn Glu Met Asn Val Asp Glu Asp Cys Arg Gly Asp Gly Arg Asp
        275                     280                     285

Ser Ala Pro Ser Lys Asn Lys Arg Arg Ala Phe Leu Asp Leu Leu Leu
    290                     295                     300

Ser Val Thr Asp Asp Glu Gly Asn Arg Leu Ser His Glu Asp Ile Arg
305                     310                     315                     320

Glu Glu Val Asp Thr Phe Met Phe Glu Gly His Asp Thr Thr Ala Ala
                325                     330                     335

Ala Met Asn Trp Ser Leu Tyr Leu Leu Gly Ser Asn Pro Glu Val Gln

-continued

```
                340                 345                 350

Lys Lys Val Asp His Glu Leu Asp Asp Val Phe Gly Arg Ser Asp Arg
            355                 360                 365

Pro Ala Thr Val Glu Asp Leu Lys Lys Leu Arg Tyr Leu Glu Cys Val
        370                 375                 380

Ile Lys Glu Thr Leu Arg Leu Phe Pro Ser Val Pro Leu Phe Ala Arg
385                 390                 395                 400

Ser Val Ser Glu Asp Cys Glu Val Ala Gly Tyr Arg Val Leu Lys Gly
                405                 410                 415

Thr Glu Ala Val Ile Ile Pro Tyr Ala Leu His Arg Asp Pro Arg Tyr
            420                 425                 430

Phe Pro Asn Pro Glu Glu Phe Arg Pro Glu Arg Phe Phe Pro Glu Asn
        435                 440                 445

Ala Gln Gly Arg His Pro Tyr Ala Tyr Val Pro Phe Ser Ala Gly Pro
        450                 455                 460

Arg Asn Cys Ile Gly Gln Lys Phe Ala Val Met Glu Glu Lys Thr Ile
465                 470                 475                 480

Leu Ser Cys Ile Leu Arg His Phe Trp Ile Glu Ser Asn Gln Lys Arg
                485                 490                 495

Glu Glu Leu Gly Leu Glu Gly Gln Leu Ile Leu Arg Pro Thr Asn Gly
            500                 505                 510

Ile Trp Ile Lys Leu Lys Arg Arg Asn Ala Asp Glu Pro
        515                 520                 525

<210> SEQ ID NO 21
<211> LENGTH: 539
<212> TYPE: PRT
<213> ORGANISM: Canis lupus

<400> SEQUENCE: 21

Met Leu Lys Val Lys Trp Lys Glu Asn Val Phe Arg Glu Gly Asp Lys
1               5                   10                  15

Asp Ser Asn Met Leu Asp Ala Val Gln Leu Pro Ser Ile Lys Val Glu
            20                  25                  30

Ser Ala Leu Ser Asp Ala Glu Ala Gly Gly Ser Pro Gly Gly Arg Arg
        35                  40                  45

Pro Val Leu Thr Val Glu Arg Gly Arg Leu Ala Gln Gly Ser Met Ser
    50                  55                  60

Ser Leu Leu Lys Asn Pro Lys Asp Thr Thr Arg Asn Ser Leu Lys Ile
65                  70                  75                  80

Lys Tyr Phe Leu Pro Glu Phe Phe Gln Gln Val Ile Leu Tyr Ser Glu
                85                  90                  95

Glu Ser Arg His Leu Pro Leu Leu Lys Leu Trp Leu Gly Pro Ile Pro
            100                 105                 110

Ile Val Ala Ile Tyr Ser Ala Glu Asn Val Glu Val Ile Leu Thr Ser
        115                 120                 125

Ser Arg Gln Ile Asp Lys Ser Tyr Val Tyr Lys Phe Leu Glu Pro Trp
        130                 135                 140

Leu Gly Leu Gly Leu Leu Thr Ser Thr Gly Asn Lys Trp Arg Ser Arg
145                 150                 155                 160

Arg Lys Met Leu Thr Pro Thr Phe His Phe Thr Ile Leu Glu Asp Phe
                165                 170                 175

Leu Asp Val Met Asn Glu His Ala Asn Ile Leu Val Asn Lys Leu Glu
            180                 185                 190
```

-continued

```
Lys His Val Asn Gln Glu Ala Phe Asn Cys Phe Phe Tyr Ile Thr Leu
        195                 200                 205

Cys Ala Leu Asp Ile Ile Cys Glu Thr Ala Met Gly Lys Asn Ile Gly
        210                 215                 220

Ala Gln Asn Asn Glu Asp Ser Glu Tyr Val Arg Ala Ile Tyr Arg Met
225                 230                 235                 240

Ser Asp Thr Ile His Arg Arg Met Lys Met Pro Trp Leu Trp Leu Asp
                245                 250                 255

Phe Leu Phe Leu Met Phe Lys Glu Gly Arg Glu His Lys Arg Asn Leu
                260                 265                 270

Glu Ile Leu His Asn Phe Thr Asn Asn Val Ile Thr Glu Arg Ala Ser
                275                 280                 285

Glu Leu Lys Arg Asp Glu Glu His Gly Ser Ala Asp Lys Asp Cys Ser
        290                 295                 300

Pro Ser Lys Asn Lys Arg Arg Ala Phe Leu Asp Leu Leu Leu Asn Val
305                 310                 315                 320

Thr Asp Asp Glu Gly Asn Lys Leu Arg His Glu Asp Val Arg Glu Glu
                325                 330                 335

Val Asp Thr Phe Met Phe Glu Gly His Asp Thr Thr Ala Ala Ala Ile
                340                 345                 350

Asn Trp Ser Leu Tyr Leu Leu Gly Ser Tyr Pro Glu Val Gln Lys Gln
                355                 360                 365

Val Asp Ser Glu Leu Glu Asp Val Phe Gly Lys Ser Asp Arg Pro Ala
        370                 375                 380

Thr Leu Glu Asp Leu Lys Lys Leu Lys Tyr Leu Glu Cys Val Ile Lys
385                 390                 395                 400

Glu Ser Leu Arg Leu Phe Pro Ser Val Pro Leu Phe Ala Arg Asn Leu
                405                 410                 415

Asn Glu Asp Cys Val Val Ala Gly Tyr Lys Val Val Lys Gly Ser Gln
                420                 425                 430

Ala Ile Ile Ile Pro Tyr Ala Leu His Arg Asp Pro Arg Tyr Phe Pro
                435                 440                 445

Asn Pro Glu Glu Phe Gln Pro Glu Arg Phe Phe Pro Glu Asn Leu Gln
        450                 455                 460

Gly Arg His Pro Tyr Ala Tyr Ile Pro Phe Ser Ala Gly Pro Arg Asn
465                 470                 475                 480

Cys Ile Gly Gln Arg Phe Ala Ile Met Glu Glu Lys Thr Val Leu Ser
                485                 490                 495

Cys Val Leu Arg His Phe Trp Val Glu Ser Asn Gln Lys Arg Glu Glu
                500                 505                 510

Leu Gly Leu Ala Gly Glu Leu Ile Leu Arg Pro Thr Asn Gly Ile Trp
                515                 520                 525

Ile Lys Leu Lys Arg Arg Asn Ala Asp Glu Ser
        530                 535
```

```
<210> SEQ ID NO 22
<211> LENGTH: 527
<212> TYPE: PRT
<213> ORGANISM: Bos Taurus

<400> SEQUENCE: 22

Met Leu Ala Pro Trp Leu Leu Ser Val Gly Pro Lys Leu Leu Leu Trp
1               5                   10                  15

Ser Gly Leu Cys Ala Val Ser Leu Ala Gly Ala Thr Leu Thr Leu Asn
        20                  25                  30
```

```
Leu Leu Lys Met Val Ala Ser Tyr Ala Arg Lys Trp Arg Gln Met Arg
        35                  40                  45

Pro Val Pro Thr Ile Gly Asp Pro Tyr Pro Leu Val Gly His Ala Leu
        50                  55                  60

Met Met Lys Pro Asp Ala Arg Asp Phe Phe Gln Gln Ile Ile Asp Phe
65                  70                  75                  80

Thr Glu Glu Cys Arg His Leu Pro Leu Leu Lys Leu Trp Leu Gly Pro
                85                  90                  95

Val Pro Leu Val Ala Leu Tyr Asn Ala Glu Thr Val Glu Val Ile Leu
            100                 105                 110

Ser Ser Ser Lys His Ile Glu Lys Ser Tyr Met Tyr Lys Phe Leu Glu
            115                 120                 125

Pro Trp Leu Gly Leu Gly Leu Leu Thr Ser Thr Gly Asn Lys Trp Arg
        130                 135                 140

Ser Arg Arg Lys Met Leu Thr Pro Thr Phe His Phe Thr Ile Leu Glu
145                 150                 155                 160

Asp Phe Leu Asp Val Met Asn Glu Gln Ala Asn Ile Leu Val Thr Lys
                165                 170                 175

Leu Glu Lys His Val Asn Gln Glu Ala Phe Asn Cys Phe Phe Tyr Val
            180                 185                 190

Thr Leu Cys Thr Leu Asp Ile Ile Cys Glu Thr Ala Met Gly Lys Asn
            195                 200                 205

Ile Gly Ala Gln Arg Asn Asp Asp Ser Glu Tyr Val Arg Ala Val Tyr
        210                 215                 220

Arg Met Ser Asp Ser Ile His Gln Arg Met Lys Met Pro Trp Leu Trp
225                 230                 235                 240

Leu Asp Leu Ile Phe Tyr Met Phe Lys Asn Gly Arg Glu His Arg Arg
                245                 250                 255

Ser Leu Lys Ile Val His Asp Phe Thr Asn Asn Val Ile Thr Glu Arg
            260                 265                 270

Ala Asn Glu Met Lys Arg His Glu Glu Gly Thr Ser Asn Asp Lys Glu
            275                 280                 285

Lys Asp Phe Pro Pro Arg Lys Thr Lys Cys Arg Ala Phe Leu Asp Leu
        290                 295                 300

Leu Leu Asn Val Thr Asp Asp Gln Gly Asn Lys Leu Ser His Glu Asp
305                 310                 315                 320

Ile Arg Glu Glu Val Asp Thr Phe Met Phe Glu Gly His Asp Thr Thr
                325                 330                 335

Ala Ala Ala Ile Asn Trp Ser Leu Tyr Leu Leu Gly Trp Tyr Pro Glu
            340                 345                 350

Val Gln Gln Arg Val Asp Thr Glu Leu Glu Glu Val Phe Gly Lys Ser
            355                 360                 365

Asp Arg Pro Val Thr Leu Glu Asp Leu Lys Lys Leu Lys Tyr Leu Asp
        370                 375                 380

Cys Val Ile Lys Glu Ser Leu Arg Leu Phe Pro Ser Val Pro Phe Phe
385                 390                 395                 400

Ala Arg Asn Leu Thr Glu Asp Cys Glu Val Ala Gly His Lys Ile Val
                405                 410                 415

Gln Gly Cys Gln Val Ile Ile Val Pro Tyr Ala Leu His Arg Asp Pro
            420                 425                 430

Lys Tyr Phe Pro Asp Pro Glu Glu Phe Lys Pro Glu Arg Phe Phe Pro
        435                 440                 445
```

-continued

---

```
Glu Asn Leu Lys Gly Arg His Thr Tyr Ala Tyr Val Pro Phe Ser Ala
    450                 455                 460

Gly Pro Arg Asn Cys Ile Gly Gln Lys Phe Ala Ile Met Glu Glu Lys
465                 470                 475                 480

Thr Ile Leu Ser Cys Ile Leu Arg His Phe Trp Val Glu Ser Asn Gln
                485                 490                 495

Lys Arg Glu Glu Leu Gly Leu Ala Gly Glu Leu Ile Leu Arg Pro Ser
                500                 505                 510

Asn Gly Ile Trp Ile Lys Leu Lys Arg Arg Asn Thr Asp Glu Ser
            515                 520                 525

<210> SEQ ID NO 23
<211> LENGTH: 525
<212> TYPE: PRT
<213> ORGANISM: Mus musculus

<400> SEQUENCE: 23

Met Leu Trp Leu Trp Leu Gly Leu Ser Gly Gln Lys Leu Leu Leu Trp
1               5                   10                  15

Gly Ala Ala Ser Ala Val Ser Leu Ala Gly Ala Thr Ile Leu Ile Ser
                20                  25                  30

Ile Phe Pro Met Leu Val Ser Tyr Ala Arg Lys Trp Gln Gln Met Arg
            35                  40                  45

Ser Ile Pro Ser Val Ala Arg Ala Tyr Pro Leu Val Gly His Ala Leu
        50                  55                  60

Tyr Met Lys Pro Asn Asn Ala Glu Phe Phe Gln Gln Leu Ile Tyr Tyr
65                  70                  75                  80

Thr Glu Glu Phe Arg His Leu Pro Ile Ile Lys Leu Trp Ile Gly Pro
                85                  90                  95

Val Pro Leu Val Ala Leu Tyr Lys Ala Glu Asn Val Glu Val Ile Leu
            100                 105                 110

Thr Ser Ser Lys Gln Ile Asp Lys Ser Phe Leu Tyr Lys Phe Leu Gln
        115                 120                 125

Pro Trp Leu Gly Leu Gly Leu Leu Thr Ser Thr Gly Ser Lys Trp Arg
    130                 135                 140

Thr Arg Arg Lys Met Leu Thr Pro Thr Phe His Phe Thr Ile Leu Glu
145                 150                 155                 160

Asn Phe Leu Asp Val Met Asn Glu Gln Ala Asn Ile Leu Val Asn Lys
                165                 170                 175

Leu Glu Lys His Val Asn Gln Glu Ala Phe Asn Cys Phe Phe Tyr Ile
            180                 185                 190

Thr Leu Cys Ala Leu Asp Ile Ile Cys Glu Thr Ala Met Gly Lys Asn
        195                 200                 205

Ile Gly Ala Gln Ser Asn Asn Asp Ser Glu Tyr Val Arg Thr Val Tyr
    210                 215                 220

Arg Met Ser Asp Met Ile Tyr Arg Arg Met Lys Met Pro Trp Leu Trp
225                 230                 235                 240

Phe Asp Leu Trp Tyr Leu Val Phe Lys Glu Gly Arg Asp His Lys Arg
                245                 250                 255

Gly Leu Lys Cys Leu His Thr Phe Thr Asn Asn Val Ile Ala Glu Arg
            260                 265                 270

Val Lys Glu Arg Lys Ala Glu Glu Asp Trp Thr Gly Ala Gly Arg Gly
        275                 280                 285

Pro Ile Pro Ser Lys Asn Lys Arg Lys Ala Phe Leu Asp Leu Leu Leu
    290                 295                 300
```

-continued

```
Ser Val Thr Asp Glu Glu Gly Asn Arg Leu Ser Gln Glu Asp Ile Arg
305             310             315             320

Glu Glu Val Asp Thr Phe Met Phe Glu Gly His Asp Thr Thr Ala Ala
                325             330             335

Ala Ile Asn Trp Ser Leu Tyr Leu Leu Gly Thr Asn Pro Glu Val Gln
            340             345             350

Arg Lys Val Asp Gln Glu Leu Asp Glu Val Phe Gly Arg Ser His Arg
            355             360             365

Pro Val Thr Leu Glu Asp Leu Lys Lys Leu Lys Tyr Leu Asp Cys Val
        370             375             380

Ile Lys Glu Thr Leu Arg Val Phe Pro Ser Val Pro Leu Phe Ala Arg
385             390             395             400

Ser Leu Ser Glu Asp Cys Glu Val Gly Gly Tyr Lys Val Thr Lys Gly
            405             410             415

Thr Glu Ala Ile Ile Ile Pro Tyr Ala Leu His Arg Asp Pro Arg Tyr
            420             425             430

Phe Pro Asp Pro Glu Glu Phe Arg Pro Glu Arg Phe Phe Pro Glu Asn
            435             440             445

Ser Gln Gly Arg His Pro Tyr Ala Tyr Val Pro Phe Ser Ala Gly Pro
        450             455             460

Arg Asn Cys Ile Gly Gln Lys Phe Ala Val Met Glu Glu Lys Thr Ile
465             470             475             480

Leu Ala Cys Ile Leu Arg Gln Phe Trp Val Glu Ser Asn Gln Lys Arg
            485             490             495

Glu Glu Leu Gly Leu Ala Gly Asp Leu Ile Leu Arg Pro Asn Asn Gly
            500             505             510

Ile Trp Ile Lys Leu Lys Arg Arg His Glu Asp Asp Pro
            515             520             525

<210> SEQ ID NO 24
<211> LENGTH: 525
<212> TYPE: PRT
<213> ORGANISM: Rattus norvegicus

<400> SEQUENCE: 24

Met Leu Trp Leu Trp Leu Gly Leu Ser Gly Gln Lys Leu Leu Leu Trp
1               5               10              15

Gly Ala Ala Ser Ala Val Ser Val Ala Gly Ala Thr Val Leu Leu Asn
            20              25              30

Ile Leu Gln Met Leu Val Ser Tyr Ala Arg Lys Trp Gln Gln Met Arg
            35              40              45

Pro Ile Pro Ser Val Ala Arg Ala Tyr Pro Leu Val Gly His Ala Leu
        50              55              60

Phe Met Lys Pro Asn Asn Thr Glu Phe Phe Gln Gln Ile Ile Gln Tyr
65              70              75              80

Thr Glu Glu Phe Arg His Leu Pro Ile Ile Lys Leu Trp Ile Gly Pro
                85              90              95

Val Pro Leu Val Ala Leu Tyr Lys Ala Glu Asn Val Glu Val Ile Leu
            100             105             110

Thr Ser Ser Lys Gln Ile Asp Lys Ser Phe Met Tyr Lys Phe Leu Gln
            115             120             125

Pro Trp Leu Gly Leu Gly Leu Leu Thr Ser Thr Gly Ser Lys Trp Arg
        130             135             140

Ala Arg Arg Lys Met Leu Thr Pro Ser Phe His Phe Thr Ile Leu Glu
```

-continued

```
145                150                155                160

Asp Phe Leu Asp Val Met Asn Glu Gln Ala Asn Ile Leu Val Asn Lys
            165                170                175

Leu Glu Lys His Val Asn Gln Glu Ala Phe Asn Cys Phe Phe Pro Ile
            180                185                190

Thr Leu Cys Ala Leu Asp Ile Ile Cys Glu Thr Ala Met Gly Lys Asn
            195                200                205

Ile Gly Ala Gln Ser Asn Gly Asp Ser Glu Tyr Val Arg Thr Val Tyr
        210                215                220

Arg Met Ser Asp Met Ile Tyr Arg Arg Met Lys Met Pro Trp Phe Trp
225                230                235                240

Phe Asp Leu Trp Tyr Leu Met Phe Lys Glu Gly Arg Asp His Lys Lys
                245                250                255

Gly Leu Lys Ser Leu His Thr Phe Thr Asn Asn Val Ile Ala Glu Arg
            260                265                270

Val Asn Ala Arg Lys Ala Glu Gln Asp Cys Ile Gly Ala Gly Arg Gly
            275                280                285

Pro Leu Pro Ser Lys Thr Lys Arg Lys Ala Phe Leu Asp Leu Leu Leu
        290                295                300

Ser Val Thr Asp Glu Glu Gly Asn Lys Leu Ser His Glu Asp Ile Arg
305                310                315                320

Glu Glu Val Asp Thr Phe Met Phe Glu Gly His Asp Thr Thr Ala Ala
            325                330                335

Ala Ile Asn Trp Ser Leu Tyr Leu Leu Gly Ser Asn Pro Glu Val Gln
            340                345                350

Arg Lys Val Asp Lys Glu Leu Asp Asp Val Phe Gly Arg Ser His Arg
            355                360                365

Pro Val Thr Leu Glu Asp Leu Lys Lys Leu Lys Tyr Leu Asp Cys Val
        370                375                380

Ile Lys Glu Thr Leu Arg Val Phe Pro Ser Val Pro Leu Phe Ala Arg
385                390                395                400

Ser Leu Ser Glu Asp Cys Glu Val Ala Gly Tyr Lys Ile Ser Lys Gly
            405                410                415

Thr Glu Ala Val Ile Ile Pro Tyr Ala Leu His Arg Asp Pro Arg Tyr
            420                425                430

Phe Pro Asp Pro Glu Glu Phe Gln Pro Glu Arg Phe Phe Pro Glu Asn
            435                440                445

Ser Gln Gly Arg His Pro Tyr Ala Tyr Val Pro Phe Ser Ala Gly Pro
        450                455                460

Arg Asn Cys Ile Gly Gln Lys Phe Ala Val Met Glu Glu Lys Thr Ile
465                470                475                480

Leu Ala Cys Ile Leu Arg Glu Phe Trp Ile Glu Ser Asn Gln Lys Arg
            485                490                495

Glu Glu Leu Gly Leu Ala Gly Asp Leu Ile Leu Arg Pro Asn Asn Gly
        500                505                510

Ile Trp Ile Lys Leu Lys Arg Arg His Glu Asp Asp Pro
        515                520                525
```

<210> SEQ ID NO 25
<211> LENGTH: 530
<212> TYPE: PRT
<213> ORGANISM: Gallus gallus

<400> SEQUENCE: 25

```
Met Ala Met Glu Ile Thr Leu Gly Ser Met Glu Gly Thr Gln Leu Leu
1               5                   10                  15

Pro Trp Val Ala Gly Ala Ile Thr Leu Leu Leu Thr Val Val Thr Val
            20                  25                  30

His Phe Leu Pro Ser Leu Leu Asn Tyr Trp Trp Trp Trp Trp Val Met
        35                  40                  45

Lys Pro Ile Pro Gly Ile Arg Pro Cys Tyr Pro Phe Val Gly Asn Ala
    50                  55                  60

Leu Leu Leu Glu Arg Asn Gly Glu Gly Phe Phe Lys Gln Leu Gln Gln
65                  70                  75                  80

Tyr Ala Asp Glu Phe Arg Lys Met Pro Met Phe Lys Leu Trp Leu Gly
            85                  90                  95

Pro Leu Pro Val Thr Val Leu Phe His Pro Asp Ser Val Glu Val Ile
            100                 105                 110

Leu Ser Ser Ser Lys His Ile Lys Lys Ser Phe Leu Tyr Thr Phe Leu
        115                 120                 125

His Pro Trp Leu Gly Thr Gly Leu Leu Thr Ser Thr Gly Asp Lys Trp
    130                 135                 140

Arg Ser Arg Arg Lys Met Ile Thr Pro Thr Phe His Phe Ala Ile Leu
145                 150                 155                 160

Asn Asp Phe Leu Glu Val Met Asn Glu Gln Gly Gly Val Leu Leu Glu
            165                 170                 175

Lys Leu Glu Lys His Val Asp Lys Glu Pro Phe Asn Ile Phe Thr Asp
            180                 185                 190

Ile Thr Leu Cys Ala Leu Asp Ile Ile Cys Glu Thr Ala Met Gly Lys
            195                 200                 205

Asn Leu Gly Ala Gln Asp Asn Lys Asp Ser Glu Tyr Val Arg Ala Val
    210                 215                 220

Tyr Arg Met Ser Asp Leu Ile Gln Gln Arg Gln Lys Ser Pro Trp Leu
225                 230                 235                 240

Trp His Asp Leu Met Tyr Leu Leu Phe Lys Glu Gly Arg Glu His Glu
            245                 250                 255

Arg Asn Leu Lys Ile Leu His Gly Phe Thr Asp Thr Val Ile Ala Glu
            260                 265                 270

Lys Val Ala Glu Leu Glu Asn Thr Lys Leu Thr Lys His Asp Thr Asp
            275                 280                 285

Val Asn Thr Glu Glu Glu Ser Gly Ser Lys Lys Arg Glu Ala Phe Leu
    290                 295                 300

Asp Met Leu Leu Asn Ala Thr Asp Asp Glu Gly Lys Lys Leu Ser Tyr
305                 310                 315                 320

Lys Asp Ile Arg Glu Glu Val Asp Thr Phe Met Phe Glu Gly His Asp
            325                 330                 335

Thr Thr Ala Ala Ala Met Asn Trp Val Leu Tyr Leu Leu Gly His His
            340                 345                 350

Pro Glu Ala Gln Lys Lys Val His Gln Glu Leu Asp Glu Val Phe Gly
            355                 360                 365

Asn Thr Glu Arg Pro Val Thr Val Asp Asp Leu Lys Lys Leu Arg Tyr
    370                 375                 380

Leu Glu Cys Val Val Lys Glu Ala Leu Arg Leu Phe Pro Ser Val Pro
385                 390                 395                 400

Met Phe Ala Arg Ser Leu Gln Glu Asp Cys Tyr Ile Ser Gly Tyr Lys
            405                 410                 415

Leu Pro Lys Gly Thr Asn Val Leu Val Leu Thr Tyr Val Leu His Arg
```

-continued

```
                  420             425             430

Asp Pro Glu Ile Phe Pro Glu Pro Asp Glu Phe Arg Pro Glu Arg Phe
        435             440             445

Phe Pro Glu Asn Ser Lys Gly Arg His Pro Tyr Ala Tyr Val Pro Phe
        450             455             460

Ser Ala Gly Pro Arg Asn Cys Ile Gly Gln Arg Phe Ala Gln Met Glu
465             470             475             480

Glu Lys Thr Leu Leu Ala Leu Ile Leu Arg Arg Phe Trp Val Asp Cys
        485             490             495

Ser Gln Lys Pro Glu Glu Leu Gly Leu Ser Gly Glu Leu Ile Leu Arg
        500             505             510

Pro Asn Asn Gly Ile Trp Val Gln Leu Lys Arg Arg Pro Lys Thr Val
        515             520             525

Thr Glu
    530

<210> SEQ ID NO 26
<211> LENGTH: 523
<212> TYPE: PRT
<213> ORGANISM: Xenopus tropicalis

<400> SEQUENCE: 26

Met Glu Leu Gly Gly Glu Val His Leu Leu Val Trp Val Ala Ala Ala
1               5               10              15

Val Val Leu Leu Thr Leu Leu Ala Leu Ser Ile Leu Pro Ala Leu Gln
            20              25              30

Asp Tyr Val Arg Lys Arg Arg Ile Leu Lys Pro Ile Pro Gly Pro Gly
        35              40              45

Pro Asn Tyr Pro Leu Ile Gly Asp Ala Leu Phe Leu Lys Asn Asn Gly
    50              55              60

Gly Asp Phe Phe Leu Gln Ile Cys Glu Tyr Thr Glu Ser Tyr Arg Leu
65              70              75              80

Gln Pro Leu Leu Lys Val Trp Ile Gly Thr Ile Pro Phe Ile Val Val
            85              90              95

Tyr His Ala Asp Thr Val Glu Pro Val Leu Ser Ser Ser Lys His Met
            100             105             110

Asp Lys Ala Phe Leu Tyr Lys Phe Leu His Pro Trp Leu Gly Lys Gly
        115             120             125

Leu Leu Thr Ser Thr Gly Glu Lys Trp Arg Ser Arg Arg Lys Met Ile
    130             135             140

Thr Pro Thr Phe His Phe Ala Ile Leu Ser Glu Phe Leu Glu Val Met
145             150             155             160

Asn Glu Gln Ser Lys Ile Leu Val Glu Lys Leu Gln Thr His Val Asp
            165             170             175

Gly Glu Ser Phe Asp Cys Phe Met Asp Val Thr Leu Cys Ala Leu Asp
            180             185             190

Ile Ile Ser Glu Thr Ala Met Gly Arg Lys Ile Gln Ala Gln Ser Asn
        195             200             205

Arg Asp Ser Glu Tyr Val Gln Ala Ile Tyr Lys Met Ser Asp Ile Ile
    210             215             220

Gln Arg Arg Gln Lys Met Pro Trp Leu Trp Leu Asp Phe Leu Tyr Ala
225             230             235             240

His Leu Arg Asp Gly Lys Glu His Asp Lys Asn Leu Lys Ile Leu His
            245             250             255
```

```
Ser Phe Thr Asp Lys Ala Ile Leu Glu Arg Ala Glu Glu Leu Lys Lys
            260                 265                 270

Met Gly Glu Gln Lys Lys Glu His Cys Asp Ser Asp Pro Glu Ser Asp
            275                 280                 285

Lys Pro Lys Lys Arg Ser Ala Phe Leu Asp Met Leu Leu Met Ala Thr
            290                 295                 300

Asp Asp Ala Gly Asn Lys Met Ser Tyr Met Asp Ile Arg Glu Glu Val
305                 310                 315                 320

Asp Thr Phe Met Phe Glu Gly His Asp Thr Thr Ala Ala Ala Leu Asn
                325                 330                 335

Trp Ser Leu Phe Leu Leu Gly Ser His Pro Glu Ala Gln Arg Gln Val
            340                 345                 350

His Lys Glu Leu Asp Glu Val Phe Gly Lys Ser Asp Arg Pro Val Thr
            355                 360                 365

Met Asp Asp Leu Lys Lys Leu Arg Tyr Leu Glu Ala Val Ile Lys Glu
            370                 375                 380

Ser Leu Arg Ile Tyr Pro Ser Val Pro Leu Phe Gly Arg Thr Val Thr
385                 390                 395                 400

Glu Asp Cys Ser Ile Arg Gly Phe His Val Pro Lys Gly Val Asn Val
                405                 410                 415

Val Ile Ile Pro Tyr Ala Leu His Arg Asp Pro Glu Tyr Phe Pro Glu
                420                 425                 430

Pro Glu Glu Phe Arg Pro Glu Arg Phe Phe Pro Glu Asn Ala Ser Gly
            435                 440                 445

Arg Asn Pro Tyr Ala Tyr Ile Pro Phe Ser Ala Gly Leu Arg Asn Cys
            450                 455                 460

Ile Gly Gln Arg Phe Ala Leu Met Glu Glu Lys Val Val Leu Ser Ser
465                 470                 475                 480

Ile Leu Arg Asn Tyr Trp Val Glu Ala Ser Gln Lys Arg Glu Glu Leu
                485                 490                 495

Cys Leu Leu Gly Glu Leu Ile Leu Arg Pro Gln Asp Gly Met Trp Ile
            500                 505                 510

Lys Leu Lys Asn Arg Glu Thr Ala Pro Thr Ala
            515                 520
```

```
<210> SEQ ID NO 27
<211> LENGTH: 469
<212> TYPE: PRT
<213> ORGANISM: Equus caballus

<400> SEQUENCE: 27

Met Phe Val Leu Ile Glu Phe Lys Ile Lys Tyr Ser Leu Ser Asp Phe
1               5                   10                  15

Phe Gln Gln Leu Ile Tyr Tyr Thr Glu Glu Asn Arg His Leu Pro Leu
            20                  25                  30

Leu Lys Leu Trp Leu Gly Pro Val Pro Val Val Ile Phe Tyr Asn Ala
            35                  40                  45

Glu Asn Val Glu Val Ile Leu Thr Ser Ser Arg Gln Ile Asp Lys Ser
        50                  55                  60

Tyr Met Tyr Lys Phe Leu Lys Pro Trp Leu Gly Leu Gly Leu Leu Thr
65                  70                  75                  80

Ser Thr Gly Asn Lys Trp Arg Ser Arg Arg Lys Met Leu Thr Pro Thr
                85                  90                  95

Phe His Phe Thr Asn Leu Glu Asp Phe Leu Asp Val Met Asn Glu Gln
            100                 105                 110
```

```
Ala Asn Ile Leu Val Asn Lys Leu Glu Lys His Val Asn Gln Glu Ala
        115                 120                 125

Phe Asn Cys Phe Leu Tyr Ile Thr Leu Cys Ala Leu Asp Ile Ile Cys
    130                 135                 140

Glu Thr Ala Met Gly Lys Asn Ile Gly Ala Gln Arg Asn Asn Asp Ser
145                 150                 155                 160

Glu Tyr Val Arg Ala Val Tyr Arg Met Ser Asp Met Ile His Arg Arg
                165                 170                 175

Met Lys Met Pro Trp Leu Trp Leu Asp Ile Phe Phe Leu Met Phe Lys
                180                 185                 190

Glu Gly Arg Glu His Arg Arg Leu Leu Lys Ile Leu His Asn Phe Thr
                195                 200                 205

Asn Asn Val Ile Val Glu Arg Ala Ser Glu Met Lys Lys Asp Glu Glu
    210                 215                 220

Arg Ser Arg Ser Asp Asp Gly Gly Ser Ala Pro Ser Lys Asn Lys Arg
225                 230                 235                 240

Arg Ala Phe Leu Asp Leu Leu Leu Asn Val Thr Asp Asp Glu Gly Asn
                245                 250                 255

Lys Leu Ser His Glu Asp Ile Arg Gln Glu Val Asp Thr Phe Met Phe
                260                 265                 270

Glu Gly His Asp Thr Thr Ala Ala Ala Ile Asn Trp Ser Leu Tyr Leu
                275                 280                 285

Leu Gly Cys Tyr Pro Glu Val Gln Lys Lys Val Asp Ser Glu Leu Glu
    290                 295                 300

Glu Val Phe Gly Lys Ser Asp Arg Pro Ala Thr Leu Glu Asp Leu Lys
305                 310                 315                 320

Lys Leu Lys Tyr Leu Glu Cys Val Met Lys Glu Thr Leu Arg Leu Phe
                325                 330                 335

Pro Ser Val Pro Leu Phe Ala Arg Asn Leu Asn Glu Asp Cys Glu Val
                340                 345                 350

Ala Gly Tyr Lys Ile Val Lys Gly Ser Gln Ala Ile Ile Val Ser Tyr
                355                 360                 365

Ala Leu His Arg Asp Ser Arg Tyr Phe Pro Asn Pro Glu Glu Phe Lys
    370                 375                 380

Pro Glu Arg Phe Phe Pro Glu Asn Ser Gln Gly Arg His Pro Tyr Ala
385                 390                 395                 400

Tyr Val Pro Phe Ser Ala Gly Pro Arg Asn Cys Ile Gly Gln Lys Phe
                405                 410                 415

Ala Val Met Glu Glu Lys Ile Ile Leu Ser Cys Ile Leu Arg His Phe
                420                 425                 430

Trp Val Glu Ser Asn Gln Lys Arg Glu Glu Leu Gly Leu Ala Gly Glu
                435                 440                 445

Leu Ile Leu Arg Pro Ser Asn Gly Ile Trp Ile Lys Leu Lys Arg Arg
    450                 455                 460

Asn Thr Glu Glu Ser
465

<210> SEQ ID NO 28
<211> LENGTH: 524
<212> TYPE: PRT
<213> ORGANISM: Oryctolagus cuniculus

<400> SEQUENCE: 28

Met Trp Leu Trp Leu Gly Leu Val Gly Gln Lys Leu Leu Phe Trp Gly
```

-continued

```
1                    5                    10                   15

Ala Ala Ser Ala Val Ser Leu Ala Gly Ala Ser Leu Phe Leu Asn Leu
            20                   25                   30

Leu Gln Met Val Ala Ser Tyr Ala Arg Lys Trp Gln Gln Met Arg Pro
            35                   40                   45

Ile Pro Thr Ile Gly Arg Pro Tyr Pro Leu Val Gly His Ala Leu Tyr
        50                   55                   60

Met Lys Pro Ser Gly Lys Glu Phe Phe Gln Gln Leu Ile Gln Tyr Thr
65                   70                   75                   80

Glu Glu Tyr Arg His Leu Pro Leu Leu Lys Leu Trp Leu Gly Pro Leu
                85                   90                   95

Pro Ile Val Ala Leu Tyr Asn Ala Glu Asn Val Glu Val Ile Leu Asn
            100                  105                  110

Ser Ser Lys Gln Ile Asn Lys Ser Ser Met Tyr Gln Phe Leu Glu Pro
            115                  120                  125

Trp Leu Gly Leu Gly Leu Leu Thr Ser Thr Gly Tyr Lys Trp Arg Ser
        130                  135                  140

Arg Arg Lys Met Leu Thr Pro Thr Phe His Phe Thr Ile Leu Glu Asp
145                  150                  155                  160

Phe Leu Asp Ile Met Asn Glu Gln Ala Asn Ile Leu Val His Lys Leu
            165                  170                  175

Glu Lys His Val Asp Gln Glu Ala Phe Asn Cys Phe Phe Tyr Ile Thr
            180                  185                  190

Leu Cys Ala Leu Asp Ile Ile Cys Glu Thr Ala Met Gly Lys Asn Ile
        195                  200                  205

Gly Ala Gln Ser Asn Glu Asp Ser Glu Tyr Val Arg Ala Val Tyr Arg
        210                  215                  220

Met Ser Asp Val Ile Phe Arg Arg Met Lys Met Pro Trp Leu Trp Leu
225                  230                  235                  240

Asp Leu Trp Tyr Leu Met Phe Lys Glu Gly Trp Glu His Lys Arg Cys
            245                  250                  255

Leu Lys Ile Leu His Arg Phe Thr Asn Asn Val Ile Ala Glu Arg Val
            260                  265                  270

Ser Glu Met Lys Thr Asp Glu Glu His Arg Asp Ala Asp Ser Asn Cys
        275                  280                  285

Ala Pro Ser Thr Met Lys Arg Lys Ala Phe Leu Asp Leu Leu Leu Thr
        290                  295                  300

Val Thr Asp Glu Glu Gly Asn Lys Leu Ser His Glu Asp Ile Arg Glu
305                  310                  315                  320

Glu Val Asp Thr Phe Met Phe Glu Gly His Asp Thr Thr Ala Ala Ala
            325                  330                  335

Ile Asn Trp Ser Leu Tyr Leu Leu Gly Ser His Pro Glu Val Gln Arg
            340                  345                  350

Lys Val Asp Asp Glu Leu Asp Glu Val Phe Gly Lys Ser Asp Arg Pro
            355                  360                  365

Ala Thr Ser Glu Asp Leu Lys Lys Leu Lys Tyr Leu Glu Cys Val Ile
        370                  375                  380

Lys Glu Thr Leu Arg Leu Phe Pro Ser Val Pro Leu Phe Ala Arg Ser
385                  390                  395                  400

Leu Ser Asp Asp Cys Glu Val Ala Gly Phe Arg Val Val Lys Gly Thr
            405                  410                  415

Gln Ala Val Ile Val Pro Tyr Ala Leu His Arg Asp Pro Lys Tyr Phe
            420                  425                  430
```

-continued

```
Pro Asn Pro Glu Glu Phe Arg Pro Glu Arg Phe Phe Pro Glu Asn Ala
        435             440             445

Gln Gly Arg His Pro Tyr Ala Tyr Val Pro Phe Ser Ala Gly Pro Arg
    450             455             460

Asn Cys Ile Gly Gln Lys Phe Ala Ile Met Glu Glu Lys Thr Ile Leu
465             470             475             480

Ser Cys Ile Leu Arg Lys Leu Trp Val Glu Ser Asn Gln Lys Met Glu
            485             490             495

Glu Leu Gly Leu Ala Gly Glu Leu Ile Leu Arg Pro Thr Asn Gly Ile
            500             505             510

Trp Ile Lys Leu Lys Arg Arg Asn Ala Asp Lys Ala
        515             520

<210> SEQ ID NO 29
<211> LENGTH: 535
<212> TYPE: PRT
<213> ORGANISM: Drosophila melanogaster

<400> SEQUENCE: 29

Met Ser Ser Lys Val Ile Thr Ser Leu Met Ala Glu Ser Ile Leu Leu
1               5               10              15

Ser Lys Val Gly Gln Val Ile Ser Gly Tyr Ser Pro Ile Thr Val Phe
            20              25              30

Leu Leu Gly Ser Ile Leu Ile Phe Leu Val Val Tyr Asn Lys Arg Arg
        35              40              45

Ser Arg Leu Val Lys Tyr Ile Glu Lys Ile Pro Gly Pro Ala Ala Met
    50              55              60

Pro Phe Leu Gly Asn Ala Ile Glu Met Asn Val Asp His Asp Glu Leu
65              70              75              80

Phe Asn Arg Val Ile Gly Met Gln Lys Leu Trp Gly Thr Arg Ile Gly
            85              90              95

Ile Asn Arg Val Trp Gln Gly Thr Ala Pro Arg Val Leu Leu Phe Glu
            100             105             110

Pro Glu Thr Val Glu Pro Ile Leu Asn Ser Gln Lys Phe Val Asn Lys
        115             120             125

Ser His Asp Tyr Asp Tyr Leu His Pro Trp Leu Gly Glu Gly Leu Leu
    130             135             140

Thr Ser Thr Asp Arg Lys Trp His Ser Arg Arg Lys Ile Leu Thr Pro
145             150             155             160

Ala Phe His Phe Lys Ile Leu Asp Asp Phe Ile Asp Val Phe Asn Glu
            165             170             175

Gln Ser Ala Val Leu Ala Arg Lys Leu Ala Val Glu Val Gly Ser Glu
            180             185             190

Ala Phe Asn Leu Phe Pro Tyr Val Thr Leu Cys Thr Leu Asp Ile Val
        195             200             205

Cys Glu Thr Ala Met Gly Arg Arg Ile Tyr Ala Gln Ser Asn Ser Glu
    210             215             220

Ser Glu Tyr Val Lys Ala Val Tyr Gly Ile Gly Ser Ile Val Gln Ser
225             230             235             240

Arg Gln Ala Lys Ile Trp Leu Gln Ser Asp Phe Ile Phe Ser Leu Thr
            245             250             255

Ala Glu Tyr Lys Leu His Gln Ser Tyr Ile Asn Thr Leu His Gly Phe
            260             265             270

Ser Asn Met Val Ile Arg Glu Arg Lys Ala Glu Leu Ala Ile Leu Gln
```

-continued

```
                 275                 280                 285

Glu Asn Asn Asn Asn Asn Asn Asn Ala Pro Asp Ala Tyr Asp Asp
    290                 295                 300

Val Gly Lys Lys Lys Arg Leu Ala Phe Leu Asp Leu Leu Ile Asp Ala
305                 310                 315                 320

Ser Lys Glu Gly Thr Val Leu Ser Asn Glu Asp Ile Arg Glu Glu Val
                325                 330                 335

Asp Thr Phe Met Phe Glu Gly His Asp Thr Thr Ser Ala Ala Ile Ser
            340                 345                 350

Trp Thr Leu Phe Leu Leu Gly Cys His Pro Glu Tyr Gln Glu Arg Val
            355                 360                 365

Val Glu Glu Leu Asp Ser Ile Phe Gly Asp Asp Lys Glu Thr Pro Ala
    370                 375                 380

Thr Met Lys Asn Leu Met Asp Met Arg Tyr Leu Glu Cys Cys Ile Lys
385                 390                 395                 400

Asp Ser Leu Arg Leu Phe Pro Ser Val Pro Met Met Ala Arg Met Val
            405                 410                 415

Gly Glu Asp Val Asn Ile Gly Gly Lys Ile Val Pro Ala Gly Thr Gln
            420                 425                 430

Ala Ile Ile Met Thr Tyr Ala Leu His Arg Asn Pro Arg Val Phe Pro
            435                 440                 445

Lys Pro Glu Gln Phe Asn Pro Asp Asn Phe Leu Pro Glu Asn Cys Ala
    450                 455                 460

Gly Arg His Pro Phe Ala Tyr Ile Pro Phe Ser Ala Gly Pro Arg Asn
465                 470                 475                 480

Cys Ile Gly Gln Lys Phe Ala Ile Leu Glu Glu Lys Ala Val Ile Ser
            485                 490                 495

Thr Val Leu Arg Lys Tyr Lys Ile Glu Ala Val Asp Arg Arg Glu Asp
            500                 505                 510

Leu Thr Leu Leu Gly Glu Leu Ile Leu Arg Pro Lys Asp Gly Leu Arg
            515                 520                 525

Val Lys Ile Thr Pro Arg Asp
    530                 535
```

```
<210> SEQ ID NO 30
<211> LENGTH: 10
<212> TYPE: PRT
<213> ORGANISM: Artificial
<220> FEATURE:
<223> OTHER INFORMATION: Synthetically generated consensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 30
```

```
Phe Xaa Xaa Gly Xaa Xaa Xaa Cys Xaa Gly
1               5                   10
```

```
<210> SEQ ID NO 31
<211> LENGTH: 4
<212> TYPE: PRT
```

```
<213> ORGANISM: Artificial
<220> FEATURE:
<223> OTHER INFORMATION: Synthetically generated consensus sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 31

Glu Xaa Xaa Arg
1

<210> SEQ ID NO 32
<211> LENGTH: 1715
<212> TYPE: DNA
<213> ORGANISM: Artificial
<220> FEATURE:
<223> OTHER INFORMATION: Synthetically generated promoter sequence

<400> SEQUENCE: 32
gacattgatt attgactagt tattaatagt aatcaattac ggggtcatta gttcatagcc       60
catatatgga gttccgcgtt acataactta cggtaaatgg cccgcctggc tgaccgccca      120
acgacccccg cccattgacg tcaataatga cgtatgttcc catagtaacg ccaatagggd      180
ctttccattg acgtcaatgg gtggactatt tacggtaaac tgcccacttg gcagtacatc      240
aagtgtatca tatgccaagt acgccccct a ttgacgtcaa tgacggtaaa tggcccgcct      300
ggcattatgc ccagtacatg accttatggg actttcctac ttggcagtac atctacgtat      360
tagtcatcgc tattaccatg gtcgaggtg agccccacgt tctgcttcac tctccccatc      420 tccccccct ccccaccccc aattttgtat ttatttattt tttaattatt ttgtgcagcg      480 atggggcgg ggggggggg ggcgcgcgcc aggcggggcg gggcggggcg aggggcgggg      540
cggggcgagg cggagaggtg cggcggcagc caatcagagc ggcgcgctcc gaaagtttcc      600
ttttatggcg aggcggcggc ggcggcggcc ctataaaaag cgaagcgcgc ggcgggcggg      660
agtcgctgcg ttgccttcgc cccgtgcccc gctccgcgcc gcctcgcgcc gcccgccccg      720
gctctgactg accgcgttac tcccacaggt gagcgggcgg gacggccctt ctcctccggg      780
ctgtaattag cgcttggttt aatgacggct cgtttctttt ctgtggctgc gtgaaagcct      840
taaagggctc cgggagggcc ctttgtgcgg ggggagcgg ctcgggggg gcgtgcgtgt      900 gtgtgtgcgt ggggagcgcc gcgtgcggcc cgcgctgccc ggcggctgtg agcgctgcgg      960
gcgcggcgcg gggctttgtg cgctccgcgt gtgcgcgagg ggagcgcggc cggggggcggt     1020 gccccgcggt gcggggggc tgcgagggga acaaaggctg cgtgcggggt gtgtgcgtgg     1080
gggggtgagc aggggtgtg ggcgcggcgg tcgggctgta acccccccct gcacccccct     1140 cccgagttg ctgagcacgg cccggcttcg ggtgcggggc tccgtgcggg gcgtggcgcg     1200
gggctcgccg tgccgggcgg ggggtggcgg caggtggggg tgccgggcgg ggcgggggccg     1260 cctcgggccg gggagggctc gggggagggg cgcggcggcc ccgagcgcc ggcggctgtc     1320 gaggcgcggc gagccgcagc cattgccttt tatggtaatc gtgcgagagg gcgcagggac     1380
ttcctttgtc ccaaatctgg cggagccgaa atctgggagg cgccgccgca ccccctctag     1440
cgggcgcggg cgaagcggtg cggcgccggc aggaaggaaa tgggcgggga gggccttcgt     1500
gcgtcgccgc gccgccgtcc ccttctccat ctccagcctc ggggctgccg cagggggacg     1560
gctgccttcg gggggacgg ggcagggcgg ggttcggctt ctggcgtgtg accggcggct     1620
ctagagcctc tgctaaccat gttcatgcct tcttcttttt cctacagctc ctgggcaacg     1680
```

-continued

```
tgctggttat tgtgctgtct catcattttg gcaaa                         1715

<210> SEQ ID NO 33
<211> LENGTH: 589
<212> TYPE: DNA
<213> ORGANISM: Woodchuck hepatitis virus

<400> SEQUENCE: 33
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589

<210> SEQ ID NO 34
<211> LENGTH: 225
<212> TYPE: DNA
<213> ORGANISM: Bos Taurus

<400> SEQUENCE: 34
ctgtgccttc tagttgccag ccatctgttg tttgcccctc cccgtgcct tccttgaccc      60 tggaaggtgc cactcccact gtcctttcct aataaaatga ggaaattgca tcgcattgtc    120
tgagtaggtg tcattctatt ctggggggtg gggtggggca ggacagcaag ggggaggatt    180
gggaagacaa tagcaggcat gctggggatg cggtgggctc tatgg                    225

<210> SEQ ID NO 35
<211> LENGTH: 235
<212> TYPE: DNA
<213> ORGANISM: Artificial
<220> FEATURE:
<223> OTHER INFORMATION: Synthetically generated promoter sequence

<400> SEQUENCE: 35
gattggctcc ggtgcccgtc agtgggcaga gcgcacatcg cccacagtcc ccgagaagtt      60
ggggggaggg gtcggcaatt gaaccggtgc ctagagaagg tggcgcgggg taaactggga    120
aagtgatgtc gtgtactggc tccgcctttt tcccgaggqt gggggagaac cgtatataag    180
tgcagtagtc gccgtgaacg ttcttttttcg caacgggttt gccgccagaa cacag         235

<210> SEQ ID NO 36
<211> LENGTH: 54
<212> TYPE: DNA
<213> ORGANISM: Artificial
<220> FEATURE:
<223> OTHER INFORMATION: Synthetically generated signal sequence

<400> SEQUENCE: 36
gatccaataa aagatcttta ttttcattag atctgtgtgt tggttttttg tgtg           54

<210> SEQ ID NO 37
<211> LENGTH: 6
```

<212> TYPE: DNA
<213> ORGANISM: Artificial
<220> FEATURE:
<223> OTHER INFORMATION: Synthetically generated signal sequence

<400> SEQUENCE: 37 gccacc                                                                                        6

<210> SEQ ID NO 38
<211> LENGTH: 5
<212> TYPE: DNA
<213> ORGANISM: Artificial
<220> FEATURE:
<223> OTHER INFORMATION: Synthetically generated signal sequence

<400> SEQUENCE: 38 ccacc                                                                                         5

<210> SEQ ID NO 39
<211> LENGTH: 120
<212> TYPE: DNA
<213> ORGANISM: Simian virus 40

<400> SEQUENCE: 39
ttgtttattg cagcttataa tggttacaaa taaagcaata gcatcacaaa tttcacaaat        60
aaagcatttt tttcactgca ttctagttgt ggtttgtcca aactcatcaa tgtatcttat       120

<210> SEQ ID NO 40
<211> LENGTH: 576
<212> TYPE: DNA
<213> ORGANISM: Cytomegalovirus

<400> SEQUENCE: 40
tagtaatcaa ttacggggtc attagttcat agcccatata tggagttccg cgttacataa        60
cttacggtaa atggcccgcc tggctgaccg cccaacgacc cccgcccatt gacgtcaata       120
atgacgtatg ttcccatagt aacgccaata gggactttcc attgacgtca atgggtggag       180
tatttacggt aaactgccca cttggcagta catcaagtgt atcatatgcc aagtacgccc       240
cctattgacg tcaatgacgg taaatggccc gcctggcatt atgcccagta catgacctta       300
tgggactttc ctacttggca gtacatctac gtattagtca tcgctattac catggtgatg       360
cggttttggc agtacatcaa tgggcgtgga tagcggtttg actcacgggg atttccaagt       420
ctccacccca ttgacgtcaa tgggagtttg ttttggcacc aaaatcaacg ggactttcca       480
aaatgtcgta acaactccgc cccattgacg caaatgggcg gtaggcgtgt acggtgggag       540
gtctatataa gcagagctgg tttagtgaac cgtcag                                 576

<210> SEQ ID NO 41
<211> LENGTH: 1184
<212> TYPE: DNA
<213> ORGANISM: Homo sapiens

<400> SEQUENCE: 41
cgtgaggctc cggtgcccgt cagtgggcag agcgcacatc gcccacagtc cccgagaagt        60
tggggggagg ggtcggcaat tgaaccggtg cctagagaag gtggcgcggg gtaaactggg       120
aaagtgatgt cgtgtactgg ctccgccttt ttcccgaggg tgggggagaa ccgtatataa       180
gtgcagtagt cgccgtgaac gttctttttc gcaacgggtt tgccgccaga acacaggtaa       240
gtgccgtgtg tggttcccgc gggcctggcc tctttacggg ttatggccct tgcgtgcctt       300

```
gaattacttc cacctggctg cagtacgtga ttcttgatcc cgagcttcgg gttggaagtg        360
ggtgggagag ttcgaggcct tgcgcttaag gagcccttc gcctcgtgct tgagttgagg        420
cctggcctgg gcgctggggc cgccgcgtgc gaatctggtg gcaccttcgc gcctgtctcg        480
ctgctttcga taagtctcta gccatttaaa atttttgatg acctgctgcg acgctttttt        540
tctggcaaga tagtcttgta aatgcgggcc aagatctgca cactggtatt tcggttttttg       600 gggccgcggg cggcgacggg gcccgtgcgt cccagcgcac atgttcggcg aggcggggcc        660
tgcgagcgcg gccaccgaga atcggacggg ggtagtctca agctggccgg cctgctctgg        720
tgcctggcct cgcgccgccg tgtatcgccc cgccctgggc ggcaaggctg gcccggtcgg        780
caccagttgc gtgagcggaa agatggccgc ttccccggccc tgctgcaggg agctcaaaat      840
ggaggacgcg gcgctcggga gagcgggcgg gtgagtcacc cacacaaagg aaaagggcct       900
ttccgtcctc agccgtcgct tcatgtgact ccacggagta ccgggcgccg tccaggcacc       960
tcgattagtt ctcgagcttt tggagtacgt cgtctttagg ttgggggggag gggttttatg     1020 cgatggagtt tccccacact gagtgggtgg agactgaagt taggccagct tggcacttga      1080
tgtaattctc cttggaattt gccctttttg agtttggatc ttggttcatt ctcaagcctc      1140
agacagtggt tcaaagtttt tttcttccat ttcaggtgtc gtga                       1184
```

<210> SEQ ID NO 42
<211> LENGTH: 141
<212> TYPE: DNA
<213> ORGANISM: Adeno-associated virus

<400> SEQUENCE: 42

```
cctgcaggca gctgcgcgct cgctcgctca ctgaggccgc ccgggcaaag cccgggcgtc         60
gggcgacctt tggtcgcccg gcctcagtga gcgagcgagc gcgcagagag ggagtggcca        120
actccatcac tagggggttcc t                                                  141
```

<210> SEQ ID NO 43
<211> LENGTH: 141
<212> TYPE: DNA
<213> ORGANISM: Adeno-associated virus

<400> SEQUENCE: 43

```
aggaacccct agtgatggag ttggccactc cctctctgcg cgctcgctcg ctcactgagg         60
ccgggcgacc aaaggtcgcc cgacgcccgg gctttgcccg ggcggcctca gtgagcgagc        120
gagcgcgcag ctgcctgcag g                                                   141
```

<210> SEQ ID NO 44
<211> LENGTH: 117
<212> TYPE: DNA
<213> ORGANISM: Artificial
<220> FEATURE:
<223> OTHER INFORMATION: Synthetically generated mutant adeno-associated
      virus 2 inverted terminal repeat sequence

<400> SEQUENCE: 44

```
cctgcaggca gctgcgcgct cgctcgctca ctgaggccgc ccgggcaaag cccgggcgtc         60
gggcgacctt tggtcgcccg gcctcagtga gcgagcgagc gcgcagagag ggagtgg          117
```

<210> SEQ ID NO 45
<211> LENGTH: 141
<212> TYPE: DNA
<213> ORGANISM: Adeno-associated virus -continued

```
<400> SEQUENCE: 45
aggaacccct agtgatggag ttggccactc cctctctgcg cgctcgctcg ctcactgagg        60
ccgggcgacc aaaggtcgcc cgacgcccgg gctttgcccg ggcggcctca gtgagcgagc       120
gagcgcgcag ctgcctgcag g                                                 141

<210> SEQ ID NO 46
<211> LENGTH: 60
<212> TYPE: DNA
<213> ORGANISM: Homo sapiens

<400> SEQUENCE: 46
caaacagaag catgtgatta tcattcaaag cgaacgggcc aatgaaatga acgccaatga        60

<210> SEQ ID NO 47
<211> LENGTH: 75
<212> TYPE: DNA
<213> ORGANISM: Homo sapiens

<400> SEQUENCE: 47
caaacagaag catgtgatta tcattcaaat catacaggtc atcgctgaac gggccaatga        60
aatgaacgcc aatga                                                         75

<210> SEQ ID NO 48
<211> LENGTH: 20
<212> TYPE: RNA
<213> ORGANISM: Artificial
<220> FEATURE:
<223> OTHER INFORMATION: Synthetically generated oligonucleotide

<400> SEQUENCE: 48
ugauuaucau ucaaagcgaa                                                    20

<210> SEQ ID NO 49
<211> LENGTH: 20
<212> TYPE: RNA
<213> ORGANISM: Artificial
<220> FEATURE:
<223> OTHER INFORMATION: Synthetically generated oligonucleotide

<400> SEQUENCE: 49
gauuaucauu caaagcgaac                                                    20

<210> SEQ ID NO 50
<211> LENGTH: 20
<212> TYPE: RNA
<213> ORGANISM: Artificial
<220> FEATURE:
<223> OTHER INFORMATION: Synthetically generated oligonucleotide

<400> SEQUENCE: 50
gauaaucaca ugcuucuguu                                                    20

<210> SEQ ID NO 51
<211> LENGTH: 20
<212> TYPE: RNA
<213> ORGANISM: Artificial
<220> FEATURE:
<223> OTHER INFORMATION: Synthetically generated oligonucleotide

<400> SEQUENCE: 51
uucauuggcg uucauuucau                                                    20
```

-continued

```
<210> SEQ ID NO 52
<211> LENGTH: 20
<212> TYPE: RNA
<213> ORGANISM: Artificial
<220> FEATURE:
<223> OTHER INFORMATION: Synthetically generated oligonucleotide

<400> SEQUENCE: 52
cacaugcuuc uguuuggacu                                                 20

<210> SEQ ID NO 53
<211> LENGTH: 16
<212> TYPE: RNA
<213> ORGANISM: Artificial
<220> FEATURE:
<223> OTHER INFORMATION: Synthetically generated oligonucleotide

<400> SEQUENCE: 53
guuuuagagc uaugcu                                                     16

<210> SEQ ID NO 54
<211> LENGTH: 67
<212> TYPE: RNA
<213> ORGANISM: Artificial
<220> FEATURE:
<223> OTHER INFORMATION: Synthetically generated oligonucleotide

<400> SEQUENCE: 54
agcauagcaa guuaaaauaa ggcuaguccg uuaucaacuu gaaaaagugg caccgagucg      60
gugcuuu                                                               67

<210> SEQ ID NO 55
<211> LENGTH: 82
<212> TYPE: DNA
<213> ORGANISM: Artificial
<220> FEATURE:
<223> OTHER INFORMATION: Synthetically generated oligonucleotide

<400> SEQUENCE: 55
gttttagagc tagaaatagc aagttaaaat aaggctagtc cgttatcaac ttgaaaaagt      60
ggcaccgagt cggtgctttt tt                                              82

<210> SEQ ID NO 56
<211> LENGTH: 200
<212> TYPE: DNA
<213> ORGANISM: Artificial
<220> FEATURE:
<223> OTHER INFORMATION: Synthetically generated oligonucleotide

<400> SEQUENCE: 56
agaaaaataa atgaaagaaa ctagcatatt ttataagaaa atgtgttaac tagggtgcat      60
ccaagtccaa acagaagcat gtgattatca ttcaaatcat acaggtcatc gctgaacggg     120
ccaatgaaat gaacgccaat gaagactgta gaggtgatgg cagggctct gccccctcca     180 aaaataaacg cagggccttt                                                200

<210> SEQ ID NO 57
<211> LENGTH: 200
<212> TYPE: DNA
<213> ORGANISM: Artificial
<220> FEATURE:
<223> OTHER INFORMATION: Synthetically generated oligonucleotide

<400> SEQUENCE: 57
```

-continued

```
aaaggccctg cgtttatttt tggaggggggc agagcccctg ccatcacctc tacagtcttc        60
attggcgttc atttcattgg cccgttcagc gatgacctgt atgatttgaa tgataatcac       120
atgcttctgt ttggacttgg atgcacccta gttaacacat tttcttataa aatatgctag       180
tttctttcat ttattttttct                                                  200
```

<210> SEQ ID NO 58
<211> LENGTH: 1368
<212> TYPE: PRT
<213> ORGANISM: Streptococcus pyogenes

<400> SEQUENCE: 58

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335
```

-continued

Ala Leu Val Arg Gln Gln Leu Pro Glu Lys Tyr Lys Glu Ile Phe Phe
        340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
        370                 375             380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln

-continued

```
              755                    760                    765

Thr Thr Gln Lys Gly Gln Lys Asn Ser Arg Glu Arg Met Lys Arg Ile
    770                    775                    780

Glu Glu Gly Ile Lys Glu Leu Gly Ser Gln Ile Leu Lys Glu His Pro
785                    790                    795                    800

Val Glu Asn Thr Gln Leu Gln Asn Glu Lys Leu Tyr Leu Tyr Tyr Leu
                   805                    810                    815

Gln Asn Gly Arg Asp Met Tyr Val Asp Gln Glu Leu Asp Ile Asn Arg
                   820                    825                    830

Leu Ser Asp Tyr Asp Val Asp His Ile Val Pro Gln Ser Phe Leu Lys
                   835                    840                    845

Asp Asp Ser Ile Asp Asn Lys Val Leu Thr Arg Ser Asp Lys Asn Arg
    850                    855                    860

Gly Lys Ser Asp Asn Val Pro Ser Glu Glu Val Val Lys Lys Met Lys
865                    870                    875                    880

Asn Tyr Trp Arg Gln Leu Leu Asn Ala Lys Leu Ile Thr Gln Arg Lys
                   885                    890                    895

Phe Asp Asn Leu Thr Lys Ala Glu Arg Gly Gly Leu Ser Glu Leu Asp
                   900                    905                    910

Lys Ala Gly Phe Ile Lys Arg Gln Leu Val Glu Thr Arg Gln Ile Thr
                   915                    920                    925

Lys His Val Ala Gln Ile Leu Asp Ser Arg Met Asn Thr Lys Tyr Asp
    930                    935                    940

Glu Asn Asp Lys Leu Ile Arg Glu Val Lys Val Ile Thr Leu Lys Ser
945                    950                    955                    960

Lys Leu Val Ser Asp Phe Arg Lys Asp Phe Gln Phe Tyr Lys Val Arg
                   965                    970                    975

Glu Ile Asn Asn Tyr His His Ala His Asp Ala Tyr Leu Asn Ala Val
                   980                    985                    990

Val Gly Thr Ala Leu Ile Lys Lys Tyr Pro Lys Leu Glu Ser Glu Phe
                   995                    1000                   1005

Val Tyr Gly Asp Tyr Lys Val Tyr Asp Val Arg Lys Met Ile Ala
    1010                   1015                   1020

Lys Ser Glu Gln Glu Ile Gly Lys Ala Thr Ala Lys Tyr Phe Phe
    1025                   1030                   1035

Tyr Ser Asn Ile Met Asn Phe Phe Lys Thr Glu Ile Thr Leu Ala
    1040                   1045                   1050

Asn Gly Glu Ile Arg Lys Arg Pro Leu Ile Glu Thr Asn Gly Glu
    1055                   1060                   1065

Thr Gly Glu Ile Val Trp Asp Lys Gly Arg Asp Phe Ala Thr Val
    1070                   1075                   1080

Arg Lys Val Leu Ser Met Pro Gln Val Asn Ile Val Lys Lys Thr
    1085                   1090                   1095

Glu Val Gln Thr Gly Gly Phe Ser Lys Glu Ser Ile Leu Pro Lys
    1100                   1105                   1110

Arg Asn Ser Asp Lys Leu Ile Ala Arg Lys Lys Asp Trp Asp Pro
    1115                   1120                   1125

Lys Lys Tyr Gly Gly Phe Asp Ser Pro Thr Val Ala Tyr Ser Val
    1130                   1135                   1140

Leu Val Val Ala Lys Val Glu Lys Gly Lys Ser Lys Lys Leu Lys
    1145                   1150                   1155

Ser Val Lys Glu Leu Leu Gly Ile Thr Ile Met Glu Arg Ser Ser
    1160                   1165                   1170
```

-continued

```
Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365

<210> SEQ ID NO 59
<211> LENGTH: 1
<212> TYPE: DNA
<213> ORGANISM: Artificial
<220> FEATURE:
<223> OTHER INFORMATION: Synthetically generated spacer sequence

<400> SEQUENCE: 59 g                                                                        1

<210> SEQ ID NO 60
<211> LENGTH: 4799
<212> TYPE: DNA
<213> ORGANISM: Artificial
<220> FEATURE:
<223> OTHER INFORMATION: Synthetically generated expression construct

<400> SEQUENCE: 60
cctgcaggca gctgcgcgct cgctcgctca ctgaggccgc ccgggcaaag cccgggcgtc       60
gggcgacctt tggtcgcccg gcctcagtga gcgagcgagc gcgcagagag ggagtggcca      120
actccatcac taggggttcc tgcggccaat tcagtcgata actataacgg tcctaaggta      180
gcgatttaaa tacgcgctct cttaaggtag ccccgggacg cgtcaattga gatctcgaca      240
ttgattattg actagttatt aatagtaatc aattacgggg tcattagttc atagcccata      300
tatggagttc cgcgttacat aacttacggt aaatggcccg cctggctgac cgcccaacga      360 ccccccgccca ttgacgtcaa taatgacgta tgttcccata gtaacgccaa tagggacttt      420
ccattgacgt caatgggtgg actatttacg gtaaactgcc cacttggcag tacatcaagt      480
gtatcatatg ccaagtacgc ccccttattga cgtcaatgac ggtaaatggc ccgcctggca      540
```

-continued

```
ttatgcccag tacatgacct tatgggactt tcctacttgg cagtacatct acgtattagt      600
catcgctatt accatgggtc gaggtgagcc ccacgttctg cttcactctc cccatctccc      660
ccccctcccc accccaatt ttgtatttat ttatttttta attattttgt gcagcgatgg      720 gggcggggg gggggggcg cgcgccaggc ggggcggggc ggggcgaggg gcggggcggg      780
gcgaggcgga gaggtgcggc ggcagccaat cagagcggcg cgctccgaaa gtttcctttt      840
atggcgaggc ggcggcggcg gcggccctat aaaaagcgaa gcgcgcggcg ggcgggagtc      900
gctgcgttgc cttcgccccg tgccccgctc cgcgccgcct cgcgccgccc gccccggctc      960
tgactgaccg cgttactccc acaggtgagc gggcgggacg gcccttctcc tccgggctgt     1020
aattagcgct tggtttaatg acggctcgtt tcttttctgt ggctgcgtga aagccttaaa     1080
gggctccggg agggcccttt gtgcggggggg gagcggctcg gggggtgcgt gcgtgtgtgt     1140
gtgcgtgggg agcgccgcgt gcggcccgcg ctgcccggcg gctgtgagcg ctgcgggcgc     1200
ggcgcggggc tttgtgcgct ccgcgtgtgc gcgaggggag cgcggccggg ggcggtgccc     1260
cgcggtgcgg gggggctgcg aggggaacaa aggctgcgtg cggggtgtgt gcgtgggggg     1320
gtgagcaggg ggtgtgggcg cggcggtcgg gctgtaaccc cccctgcac ccccctcccc     1380 gagttgctga gcacggcccg gcttcgggtg cggggctccg tgcggggcgt ggcgcggggc     1440
tcgccgtgcc gggcgggggg tggcggcagg tgggggtgcc gggcggggcg gggccgcctc     1500 gggccggggga gggctcgggg gaggggcgcg gcggccccgg agcgccggcg gctgtcgagg     1560
cgcggcgagc cgcagccatt gccttttatg gtaatcgtgc gagagggcgc agggacttcc     1620
tttgtcccaa atctggcgga gccgaaatct gggaggcgcc gccgcacccc ctctagcggg     1680
cgcgggcgaa gcggtgcggc gccggcagga aggaaatggg cggggagggc cttcgtgcgt     1740
cgccgcgccg ccgtcccctt ctccatctcc agcctcgggg ctgccgcagg gggacggctg     1800
ccttcggggg ggacggggca gggcgggggtt cggcttctgg cgtgtgaccg gcggctctag     1860
agcctctgct aaccatgttc atgccttctt cttttttccta cagctcctgg gcaacgtgct     1920
ggttattgtg ctgtctcatc attttggcaa agaattctaa tacgactcac tatagggaga     1980
cccaagctgg ctagagccac catggctgga ctgtggctgg gactggtgtg gcagaaactg     2040
ctgctgtggg gggccgcttc cgcactgtca ctggctgggg cttcactggt gctgagcctg     2100
ctgcagaggg tggcctccta cgccagaaag tggcagcaga tgaggcccat ccctaccgtg     2160
gccagagcct atccactggt gggacacgca ctgctgatga agcctgacgg cagagagttc     2220
tttcagcaga tcatcgagta cacagaggag tataggcaca tgccactgct gaagctgtgg     2280
gtgggacccg tgcctatggt ggccctgtac aacgccgaga atgtggaagt gatcctgacc     2340
agcagcaagc agatcgataa gtctagcatg tataagttcc tggagccttg gctgggcctg     2400
ggcctgctga cctctacagg caacaagtgg aggagccgga gaaagatgct gaccccaaca     2460 ttccactttta caatcctgga ggacttcctg gacatcatga cgagcaggc caatatcctg     2520 gtgaagaagc tggagaagca catcaaccag gaggcctttta attgcttctt ttacatcacc     2580
ctgtgcgccc tggacatcat ctgtgagaca gctatgggca agaacatcgg cgcccagtct     2640
aatgacgata gcgagtacgt gcgggccgtg tatagaatga gcgagatgat ctttaggcgc     2700
atcaagatgc cctggctgtg gctggatctg tggtatctga tgttcaagga gggctgggag     2760
cacaagaagt ccctgcagat cctgcacacc tttacaaact ctgtgatcgc cgagagagcc     2820
aatgagatga acgccaatga ggactgtagg ggcgatggaa ggggcagcgc cccttccaag     2880
```

-continued

```
aacaagcgga gagccttcct ggacctgctg ctgagcgtga ccgacgatga gggcaatcgc    2940
ctgtcccacg aggacatccg ggaggaggtg gatacattca tgtttgaggg acacgacacc    3000
acagccgccg ccatcaactg gtccctgtac ctgctgggct ctaatccaga ggtgcagaag    3060
aaggtggatc acgagctgga cgacgtgttc ggcaagtccg acaggccagc aaccgtggag    3120
gatctgaaga agctgagata cctggagtgc gtgatcaagg agacactgcg cctgttcccc    3180
tctgtgcctc tgtttgcccg gtccgtgtct gaggactgtg aggtggccgg ctatcgcgtg    3240
ctgaagggca ccgaggccgt gatcatccct tacgccctgc accgggaccc caggtatttc    3300
cctaacccag aggagtttca gccagagaga ttctttcccg agaatgccca gggcaggcac    3360
ccttacgcct atgtgccatt ctccgccgga ccaaggaact gcatcggaca gaagtttgcc    3420
gtgatggagg agaaaaccat cctgtcttgt atcctgagac acttctggat cgagagcaat    3480
cagaagaggg aggagctggg cctggaggga cagctgatcc tgcggccaag caacggcatc    3540
tggatcaaac tgaaaagaag gaacgctgac gagaggtaaa agcttggtac cgatatcgcg    3600
gccgccctag ggagctcctc gaggcggccc gctcgagtct agagggccct tcgaaggtaa    3660
gcctatccct aaccctctcc tcggtctcga ttctacgcgt accggtcatc atcaccatca    3720
ccattgagtt tcgataatca acctctggat tacaaaattt gtgaaagatt gactggtatt    3780
cttaactatg ttgctccttt tacgctatgt ggatacgctg ctttaatgcc tttgtatcat    3840
gctattgctt cccgtatggc tttcattttc tcctccttgt ataaatcctg gttgctgtct    3900
ctttatgagg agttgtggcc cgttgtcagg caacgtggcg tggtgtgcac tgtgtttgct    3960
gacgcaaccc ccactggttg gggcattgcc accacctgtc agctcctttc cgggactttc    4020
gctttccccc tccctattgc cacggcggaa ctcatcgccg cctgccttgc ccgctgctgg    4080 acagggctc ggctgttggg cactgacaat tccgtggtgt tgtcgggaa atcatcgtcc     4140 tttccttggc tgctcgcctg tgttgccacc tggattctgc gcgggacgtc cttctgctac    4200 gtccccttcgg ccctcaatcc agcggacctt ccttcccgcg cctgctgccc ggctctgcgg    4260
cctcttccgc gtcttcgcct tcgccctcag acgagtcgga tctccctttg gccgcctcc     4320 ccgcatcgaa acccgctgat cagcctcgac tgtgccttct agttgccagc catctgttgt    4380
ttgcccctcc cccgtgcctt ccttgaccct ggaaggtgcc actcccactg tccttttccta   4440 ataaaatgag gaaattgcat cgcattgtct gagtaggtgt cattctattc tggggggtgg    4500
ggtggggcag gacagcaagg gggaggattg ggaagacaat agcaggcatg ctggggatgc    4560
ggtgggctct atggcttctg aggcggaaag aaccagatcc tctcttaagg tagcatcgag    4620
atttaaatta gggataacag ggtaatggcg cgggccgcag gaacccctag tgatggagtt    4680
ggccactccc tctctgcgcg ctcgctcgct cactgaggcc gggcgaccaa aggtcgcccg    4740
acgcccgggc tttgcccggg cggcctcagt gagcgagcga gcgcgcagct gcctgcagg     4799
```

<210> SEQ ID NO 61
<211> LENGTH: 4539
<212> TYPE: DNA
<213> ORGANISM: Artificial
<220> FEATURE:
<223> OTHER INFORMATION: Synthetically generated expression construct

<400> SEQUENCE: 61

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggcctaa ggcaattgag atctcgacat tgattattga    180
```

```
ctagttatta atagtaatca attacggggt cattagttca tagcccatat atggagttcc      240
gcgttacata acttacggta aatggcccgc ctggctgacc gcccaacgac ccccgcccat      300
tgacgtcaat aatgacgtat gttcccatag taacgccaat agggactttc cattgacgtc      360
aatgggtgga ctatttacgg taaactgccc acttggcagt acatcaagtg tatcatatgc      420
caagtacgcc ccctattgac gtcaatgacg gtaaatggcc cgcctggcat tatgcccagt      480
acatgacctt atgggacttt cctacttggc agtacatcta cgtattagtc atcgctatta      540
ccatgggtcg aggtgagccc cacgttctgc ttcactctcc ccatctcccc ccctccccca      600
cccccaattt tgtatttatt tattttttaa ttattttgtg cagcgatggg ggcggggggg      660
gggggggcgc gcgccaggcg gggcggggcg gggcgagggg cggggcgggg cgaggcggag      720
aggtgcggcg gcagccaatc agagcggcgc gctccgaaag tttccttttt a tggcgaggcg      780 gcggcggcgg cggccctata aaaagcgaag cgcgcggcgg gcgggagtcg ctgcgttgcc      840
ttcgccccgt gccccgctcc gcgccgcctc gcgccgcccg ccccggctct gactgaccgc      900
gttactccca caggtgagcg ggcgggacgg cccttctcct ccgggctgta attagcgctt      960
ggtttaatga cggctcgttt cttttctgtg gctgcgtgaa agccttaaag ggctccggga     1020
gggccctttg tgcggggggg agcggctcgg ggggtgcgtg cgtgtgtgtg tgcgtgggga     1080
gcgccgcgtg cggcccgcgc tgcccggcgg ctgtgagcgc tgcgggcgcg gcgcggggct     1140
ttgtgcgctc cgcgtgtgcg cgaggggagc gcggccgggg gcggtgcccc gcggtgcggg     1200
ggggctgcga ggggaacaaa ggctgcgtgc ggggtgtgtg cgtgggggggg tgagcagggg     1260 gtgtgggcgc ggcggtcggg ctgtaacccc ccctgcacc ccctcccg agttgctgag      1320 cacggcccgg cttcgggtgc ggggctccgt gcggggcgtg gcgcggggct cgccgtgccg     1380 ggcgggggt ggcggcaggt gggggtgccg ggcgggggcg ggccgcctcg ggccggggag     1440
ggctcggggg aggggcgcgg cggccccgga gcgccggcgg ctgtcgaggc gcggcgagcc     1500
gcagccattg cctttttatgg taatcgtgcg agagggcgca gggacttcct ttgtcccaaa     1560
tctggcggag ccgaaatctg ggaggcgccg ccgcaccccc tctagcgggc gcgggcgaag     1620
cggtgcggcg ccggcaggaa ggaaatgggc ggggagggcc ttcgtgcgtc gccgcgccgc     1680
cgtccccttc tccatctcca gcctcggggc tgccgcaggg ggacggctgc cttcgggggg     1740 gacgggcag ggcgggggttc ggcttctggc gtgtgaccgg cggctctaga gcctctgcta     1800
accatgttca tgccttcttc tttttcctac agctcctggg caacgtgctg gttattgtgc     1860
tgtctcatca ttttggcaaa gaattctaat acgactcact atagggagac ccaagctggc     1920
tagccaaagc ttccaccatg gcggggctct ggctggggct cgtgtggcag aagctgctgc     1980
tgtggggcgc ggcgagtgcc ctttccctgg ccggcgccag tctggtcctg agcctgctgc     2040 agaggggtggc gagctacgcg cggaaatggc agcagatgcg gcccatcccc acggtggccc     2100
gcgcctaccc actggtgggc cacgcgctgc tgatgaagcc ggacgggcga gaattttttc     2160
agcagatcat tgagtacaca gaggaatacc gccacatgcc gctgctgaag ctctgggtcg     2220
ggccagtgcc catggtggcc ctttataatg cagaaaatgt ggaggtaatt ttaactagtt     2280
caaagcaaat tgacaaatcc tctatgtaca agttttttaga accatggctt ggcctaggac     2340
ttcttacaag tactggaaac aaatggcgct ccaggagaaa gatgttaaca cccactttcc     2400
attttaccat tctggaagat ttcttagata tcatgaatga acaagcaaat atattggtta     2460
agaaacttga aaaacacatt aaccaagaag catttaactg cttttttttac atcactcttt     2520
```

-continued

```
gtgccttaga tatcatctgt gaaacagcta tggggaagaa tattggtgct caaagtaatg    2580
atgattccga gtatgtccgt gcagtttata gaatgagtga gatgatattt cgaagaataa    2640
agatgccctg gctttggctt gatctctggt accttatgtt taaagaagga tgggaacaca    2700
aaaagagcct tcagatccta catacttttta ccaacagtgt catcgctgaa cgggccaatg    2760
aaatgaacgc caatgaagac tgtagaggtg atggcagggg ctctgcccccc tccaaaaata    2820 aacgcagggc ctttcttgac ttgctttttaa gtgtgactga tgacgaaggg aacaggctaa    2880
gtcatgaaga tattcgagaa gaagttgaca ccttcatgtt tgaggggcac gatacaactg    2940
cagctgcaat aaactggtcc ttatacctgt tgggttctaa cccagaagtc cagaaaaaag    3000
tggatcatga attggatgac gtgtttggga agtctgaccg tcccgctaca gtagaagacc    3060
tgaagaaact tcggtatctg gaatgtgtta ttaaggagac ccttcgcctt tttccttctg    3120
ttcctttatt tgcccgtagt gttagtgaag attgtgaagt ggcaggttac agagttctaa    3180
aaggcactga agccgtcatc attccctatg cattgcacag agatccgaga tacttccccca    3240 accccgagga gttccagcct gagcggttct tccccgagaa tgcacaaggg cgccatccat    3300
atgcctacgt gcccttctct gctggcccca ggaactgtat aggtcaaaag tttgctgtga    3360
tggaagaaaa gaccattctt tcgtgcatcc tgaggcactt ttggatagaa tccaaccaga    3420
aaagagaaga gcttggtcta gaaggacagt tgattcttcg tccaagtaat ggcatctgga    3480
tcaagttgaa gaggagaaat gcagatgaac gctaagcggc cgcaactcga gactctagag    3540
gttaatcgat aatcaacctc tggattacaa aatttgtgaa agattgactg gtattcttaa    3600
ctatgttgct cctttttacgc tatgtggata cgctgcttta atgcctttgt atcatgctat    3660
tgcttcccgt atggctttca ttttctcctc cttgtataaa tcctggttgc tgtctcttta    3720
tgaggagttg tggcccgttg tcaggcaacg tggcgtggtg tgcactgtgt ttgctgacgc    3780
aacccccact ggttggggca ttgccaccac ctgtcagctc ctttccggga ctttcgcttt    3840
ccccctccct attgccacgg cggaactcat cgccgcctgc cttgcccgct gctggacagg    3900
ggctcggctg ttgggcactg acaattccgt ggtgttgtcg gggaaatcat cgtcctttcc    3960
ttggctgctc gcctgtgttg ccacctggat tctgcgcggg acgtccttct gctacgtccc    4020
ttcggccctc aatccagcgg accttccttc ccgcggcctg ctgccggctc tgcggcctct    4080
tccgcgtctt cgccttcgcc ctcagacgag tcggatctcc ctttgggccg cctccccgca    4140
tcgaaacccg ctgactagac gactgtgcct tctagttgcc agccatctgt tgtttgcccc    4200
tcccccgtgc cttccttgac cctggaaggt gccactccca ctgtcctttc ctaataaaat    4260
gaggaaattg catcgcattg tctgagtagg tgtcattcta ttctgggggg tggggtgggg    4320
caggacagca aggggggagga ttgggaagac aatagcaggc atgctgggga tgcggtgggc    4380
tctatggccg cgggccgcag gaaccccctag tgatggagtt ggccactccc tctctgcgcg    4440
ctcgctcgct cactgaggcc gggcgaccaa aggtcgcccg acgcccgggc tttgcccggg    4500
cggcctcagt gagcgagcga gcgcgcagct gcctgcagg                            4539
```

<210> SEQ ID NO 62
<211> LENGTH: 4539
<212> TYPE: DNA
<213> ORGANISM: Artificial
<220> FEATURE:
<223> OTHER INFORMATION: Synthetically generated expression construct

<400> SEQUENCE: 62

```
cctgcaggca gctgcgcgct cgctcgctca ctgaggccgc ccgggcaaag cccgggcgtc     60
```

```
gggcgacctt tggtcgcccg gcctcagtga gcgagcgagc gcgcagagag ggagtggcca      120
actccatcac taggggttcc tgcggcctaa ggcaattgag atctcgacat tgattattga      180
ctagttatta atagtaatca attacggggt cattagttca tagcccatat atggagttcc      240
gcgttacata acttacggta aatggcccgc ctggctgacc gcccaacgac ccccgcccat      300
tgacgtcaat aatgacgtat gttcccatag taacgccaat agggactttc cattgacgtc      360
aatgggtgga ctatttacgg taaactgccc acttggcagt acatcaagtg tatcatatgc      420
caagtacgcc ccctattgac gtcaatgacg gtaaatggcc cgcctggcat tatgcccagt      480
acatgacctt atgggacttt cctacttggc agtacatcta cgtattagtc atcgctatta      540
ccatgggtcg aggtgagccc cacgttctgc ttcactctcc ccatctcccc ccctccccca      600
cccccaattt tgtatttatt tatttttaa ttattttgtg cagcgatggg ggcggggggg      660 ggggggcgc gcgccaggcg gggcggggcg gggcgagggg cggggcgggg cgaggcggag      720
aggtgcggcg gcagccaatc agagcggcgc gctccgaaag tttccttta tggcgaggcg      780 gcggcggcgg cggccctata aaaagcgaag cgcgcggcgg gcgggagtcg ctgcgttgcc      840
ttcgccccgt gccccgctcc gcgccgcctc gcgccgcccg ccccggctct gactgaccgc      900
gttactccca caggtgagcg ggcgggacgg cccttctcct ccgggctgta attagcgctt      960
ggtttaatga cggctcgttt cttttctgtg gctgcgtgaa agccttaaag ggctccggga      1020
gggccctttg tgcggggggg agcggctcgg ggggtgcgtg cgtgtgtgtg tgcgtgggga      1080
gcgccgcgtg cggcccgcgc tgcccggcgg ctgtgagcgc tgcggcgcg gcgcggggct      1140 ttgtgcgctc cgcgtgtgcg cgagggagc gcggccgggg gcggtgcccc gcggtgcggg      1200
ggggctgcga ggggaacaaa ggctgcgtgc ggggtgtgtg cgtggggggg tgagcagggg      1260
gtgtgggcgc ggcggtcggg ctgtaacccc ccctgcacc cccctccccg agttgctgag      1320
cacggcccgg cttcgggtgc ggggctccgt gcggggcgtg gcgcggggct cgccgtgccg      1380
ggcggggggt ggcggcaggt ggggggtgccg ggcggggcgg ggccgcctcg ggccggggag      1440
ggctcggggg aggggcgcgg cggccccgga gcgccggcgg ctgtcgaggc gcggcgagcc      1500
gcagccattg cctttttatgg taatcgtgcg agagggcgca gggacttcct ttgtcccaaa      1560
tctggcggag ccgaaatctg ggaggcgccg ccgcacccc tctagcgggc gcgggcgaag      1620
cggtgcggcg ccggcaggaa ggaaatgggc ggggagggc ttcgtgcgtc gccgcgccgc      1680
cgtccccttc tccatctcca gcctcggggc tgccgcaggg ggacggctgc cttcgggggg      1740
gacggggcag ggcggggttc ggcttctggc gtgtgaccgg cggctctaga gcctctgcta      1800
accatgttca tgccttcttc tttttcctac agctcctggg caacgtgctg gttattgtgc      1860
tgtctcatca ttttggcaaa gaattctaat acgactcact ataggagac ccaagctggc      1920 tagccaaagc ttccaccatg gcggggctct ggctggggct cgtgtggcag aagctgctgc      1980
tgtggggcgc ggcgagtgcc ctttccctgg ccggcgccag tctggtcctg agcctgctgc      2040
agagggtggc gagctacgcg cggaaatggc agcagatgcg gcccatcccc acggtggccc      2100
gcgcctaccc actggtgggc cacgcgctg tgatgaagcc ggacgggcga gaatttttc      2160 agcagatcat tgagtacaca gaggaatacc gccacatgcc gctgctgaag ctctgggtcg      2220
ggccagtgcc catggtggcc ctttataatg cagaaaatgt ggaggtaatt ttaactagtt      2280
caaagcaaat tgacaaatcc tctatgtaca agttttttaga accatggctt ggcctaggac      2340
ttcttacaag tactggaaac aaatggcgct ccaggagaaa gatgttaaca cccactttcc      2400
```

-continued

```
attttaccat tctggaagat ttcttagata tcatgaatga acaagcaaat atattggtta    2460
agaaacttga aaaacacatt aaccaagaag catttaactg ctttttttac atcactcttt    2520
gtgccttaga tatcatctgt gaaacagcta tggggaagaa tattggtgct caaagtaatg    2580
atgattccga gtatgtccgt gcagtttata gaatgagtga gatgatattt cgaagaataa    2640
agatgccctg gctttggctt gatctctggt accttatgtt taaagaagga tgggaacaca    2700
aaaagagcct taagatccta catactttta ccaacagtgt catcgcggaa cgggccaatg    2760
aaatgaacgc caatgaagac tgtagaggtg atggcagggg ctctgccccc tccaaaaata    2820
aacgcagggc ctttcttgac ttgctttttaa gtgtgactga tgacgaaggg aacaggctaa    2880
gtcatgaaga tattcgagaa gaagttgaca ccttcatgtt tgaggggcac gatacaactg    2940
cagctgcaat aaactggtcc ttatacctgt tgggttctaa cccagaagtc cagaaaaaag    3000
tggatcatga attggatgac gtgtttggga agtctgaccg tcccgctaca gtagaagacc    3060
tgaagaaact tcggtatctg gaatgtgtta ttaaggagac ccttcgcctt tttccttctg    3120
ttcctttatt tgcccgtagt gttagtgaag attgtgaagt ggcaggttac agagttctaa    3180
aaggcactga agccgtcatc attccctatg cattgcacag agatccgaga tacttcccca    3240
accccgagga gttccagcct gagcggttct tccccgagaa tgcacaaggg cgccatccat    3300
atgcctacgt gcccttctct gctggcccca ggaactgtat aggtcaaaag tttgctgtga    3360
tggaagaaaa gaccattctt tcgtgcatcc tgaggcactt ttggatagaa tccaaccaga    3420
aaagagaaga gcttggtcta gaaggacagt tgattcttcg tccaagtaat ggcatctgga    3480
tcaagttgaa gaggagaaat gcagatgaac gctaagcggc cgcaactcga gactctagag    3540
gttaatcgat aatcaacctc tggattacaa aatttgtgaa agattgactg gtattcttaa    3600
ctatgttgct ccttttacgc tatgtggata cgctgcttta atgcctttgt atcatgctat    3660
tgcttcccgt atggctttca ttttctcctc cttgtataaa tcctggttgc tgtctcttta    3720
tgaggagttg tggcccgttg tcaggcaacg tggcgtggtg tgcactgtgt ttgctgacgc    3780
aacccccact ggttggggca ttgccaccac ctgtcagctc ctttccggga ctttcgcttt    3840 cccccctccct attgccacgg cggaactcat cgccgcctgc cttgcccgct gctggacagg    3900
ggctcggctg ttgggcactg acaattccgt ggtgttgtcg gggaaatcat cgtcctttcc    3960
ttggctgctc gcctgtgttg ccacctggat tctgcgcggg acgtccttct gctacgtccc    4020
ttcggccctc aatccagcgg accttccttc ccgcggcctg ctgccggctc tgcggcctct    4080
tccgcgtctt cgccttcgcc ctcagacgag tcggatctcc ctttgggccg cctccccgca    4140 tcgaacccg ctgactagac gactgtgcct tctagttgcc agccatctgt tgtttgcccc    4200
tcccccgtgc cttccttgac cctggaaggt gccactccca ctgtcctttc ctaataaaat    4260
gaggaaattg catcgcattg tctgagtagg tgtcattcta ttctgggggg tggggtgggg    4320
caggacagca aggggagga ttgggaagac aatagcaggc atgctgggga tgcggtgggc    4380
tctatggccg cgggccgcag gaacccctag tgatggagtt ggccactccc tctctgcgcg    4440
ctcgctcgct cactgaggcc gggcgaccaa aggtcgcccg acgcccgggc tttgcccggg    4500
cggcctcagt gagcgagcga gcgcgcagct gcctgcagg                           4539
```

<210> SEQ ID NO 63
<211> LENGTH: 4539
<212> TYPE: DNA
<213> ORGANISM: Artificial
<220> FEATURE:
<223> OTHER INFORMATION: Synthetically generated expression construct -continued

<400> SEQUENCE: 63

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggcctaa ggcaattgag atctcgacat tgattattga     180
ctagttatta atagtaatca attacggggt cattagttca tagcccatat atggagttcc     240
gcgttacata acttacggta aatggcccgc ctggctgacc gcccaacgac ccccgcccat     300
tgacgtcaat aatgacgtat gttcccatag taacgccaat agggactttc cattgacgtc     360
aatgggtgga ctatttacgg taaactgccc acttggcagt acatcaagtg tatcatatgc     420
caagtacgcc ccctattgac gtcaatgacg gtaaatggcc cgcctggcat tatgcccagt     480
acatgacctt atgggacttt cctacttggc agtacatcta cgtattagtc atcgctatta     540
ccatgggtcg aggtgagccc cacgttctgc ttcactctcc catctcccc ccctcccca     600 cccccaattt tgtatttatt tattttttaa ttattttgtg cagcgatggg ggcggggggg     660 ggggggggcgc gcgccaggcg gggcggggcg gggcgagggg cggggcgggg cgaggcggag     720
aggtgcggcg gcagccaatc agagcggcgc gctccgaaag tttcctttta tggcgaggcg     780
gcggcggcgg cggccctata aaaagcgaag cgcgcggcgg gcgggagtcg ctgcgttgcc     840
ttcgccccgt gccccgctcc gcgccgcctc gcgccgcccg ccccggctct gactgaccgc     900
gttactccca caggtgagcg ggcgggacgg cccttctcct ccgggctgta attagcgctt     960
ggtttaatga cggctcgttt cttttctgtg gctgcgtgaa agccttaaag ggctccggga    1020
gggccctttg tgcggggggg agcggctcgg ggggtgcgtg cgtgtgtgtg tgcgtgggga    1080
gcgccgcgtg cggcccgcgc tgcccggcgg ctgtgagcgc tgcgggcgcg gcgcggggct    1140
ttgtgcgctc cgcgtgtgcg cgagggggagc gcggccgggg gcggtgcccc gcggtgcggg    1200
ggggctgcga ggggaacaaa ggctgcgtgc ggggtgtgtg cgtgggggggg tgagcagggg    1260 gtgtgggcgc ggcggtcggg ctgtaacccc ccctgcacc cccctccccg agttgctgag    1320
cacggcccgg cttcgggtgc ggggctccgt gcggggcgtg gcgcggggct cgccgtgccg    1380
ggcggggggt ggcggcaggt gggggtgccg ggcgggggcg ggccgcctcg ggccggggag    1440
ggctcggggg aggggcgcgg cggccccgga gcgccggcgg ctgtcgaggc gcggcgagcc    1500
gcagccattg ccttttatgg taatcgtgcg agagggcgca gggacttcct ttgtcccaaa    1560
tctggcggag ccgaaatctg ggaggcgccg ccgcaccccc tctagcgggc gcgggcgaag    1620
cggtgcggcg ccggcaggaa ggaaatgggc ggggagggc ttcgtgcgtc gccgcgccgc    1680 cgtcccttc tccatctcca gcctcggggc tgccgcaggg ggacggctgc cttcgggggg    1740
gacggggcag ggcggggttc ggcttctggc gtgtgaccgg cggctctaga gcctctgcta    1800
accatgttca tgccttcttc tttttcctac agctcctggg caacgtgctg gttattgtgc    1860
tgtctcatca ttttggcaaa gaattctaat acgactcact ataggagac ccaagctggc    1920 tagccaaagc ttccaccatg gctggactgt ggctgggact ggtgtggcag aaactgctgc    1980
tgtggggggc cgcttccgca ctgtcactgg ctgggcttc actggtgctg agcctgctgc    2040
agagggtggc ctcctacgcc agaaagtggc agcagatgag gcccatccct accgtggcca    2100
gagcctatcc actggtggga cacgcactgc tgatgaagcc tgacggcaga gagttctttc    2160
agcagatcat cgagtacaca gaggagtata ggcacatgcc actgctgaag ctgtgggtgg    2220
gacccgtgcc tatggtggcc ctgtacaacg ccgagaatgt ggaagtgatc ctgaccagca    2280
```

```
gcaagcagat cgataagtct agcatgtata agttcctgga gccttggctg ggcctgggcc      2340
tgctgacctc tacaggcaac aagtggagga gccggagaaa gatgctgacc ccaacattcc      2400
actttacaat cctggaggac ttcctggaca tcatgaacga gcaggccaat atcctggtga      2460
agaagctgga gaagcacatc aaccaggagg cctttaattg cttcttttac atcaccctgt      2520
gcgccctgga catcatctgt gagacagcta tgggcaagaa catcggcgcc cagtctaatg      2580
acgatagcga gtacgtgcgg gccgtgtata gaatgagcga gatgatcttt aggcgcatca      2640
agatgccctg gctgtggctg gatctgtggt atctgatgtt caaggagggc tgggagcaca      2700
agaagtccct gcagatcctg cacacctta caaactctgt gatcgccgag agagccaatg      2760
agatgaacgc caatgaggac tgtaggggcg atggaagggg cagcgcccct tccaagaaca      2820
agcggagagc cttcctggac ctgctgctga gcgtgaccga cgatgagggc aatcgcctgt      2880
cccacgagga catccgggag gaggtggata cattcatgtt tgagggacac gacaccacag      2940
ccgccgccat caactggtcc ctgtacctgc tgggctctaa tccagaggtg cagaagaagg      3000
tggatcacga gctggacgac gtgttcggca agtccgacag gccagcaacc gtggaggatc      3060
tgaagaagct gagataccct gagtgcgtga tcaaggagac actgcgcctg ttcccctctg      3120
tgcctctgtt tgcccggtcc gtgtctgagg actgtgaggt ggccggctat cgcgtgctga      3180
agggcaccga ggccgtgatc atcccttacg ccctgcaccg ggaccccagg tatttcccta      3240
acccagagga gtttcagcca gagagattct ttcccgagaa tgcccagggc aggcaccctt      3300
acgcctatgt gccattctcc gccggaccaa ggaactgcat cggacagaag tttgccgtga      3360
tggaggagaa aaccatcctg tcttgtatcc tgagacactt ctggatcgag agcaatcaga      3420
agagggagga gctgggcctg gagggacagc tgatcctgcg gccaagcaac ggcatctgga      3480
tcaaactgaa aagaaggaac gctgacgaga ggtaagcggc cgcaactcga gactctagag      3540
gttaatcgat aatcaacctc tggattacaa aatttgtgaa agattgactg gtattcttaa      3600
ctatgttgct ccttttacgc tatgtggata cgctgcttta atgcctttgt atcatgctat      3660
tgcttcccgt atggctttca ttttctcctc cttgtataaa tcctggttgc tgtctcttta      3720
tgaggagttg tggcccgttg tcaggcaacg tggcgtggtg tgcactgtgt ttgctgacgc      3780
aacccccact ggttggggca ttgccaccac ctgtcagctc ctttccggga ctttcgcttt      3840 cccctccct attgccacgg cggaactcat cgccgcctgc cttgcccgct gctggacagg      3900
ggctcggctg ttgggcactg acaattccgt ggtgttgtcg gggaaatcat cgtcctttcc      3960
ttggctgctc gcctgtgttg ccacctggat tctgcgcggg acgtccttct gctacgtccc      4020
ttcggccctc aatccagcgg accttccttc ccgcggcctg ctgccggctc tgcggcctct      4080
tccgcgtctt cgccttcgcc ctcagacgag tcggatctcc ctttgggccg cctccccgca      4140
tcgaaacccg ctgactagac gactgtgcct tctagttgcc agccatctgt tgtttgcccc      4200
tcccccgtgc cttccttgac cctggaaggt gccactccca ctgtcctttc ctaataaaat      4260
gaggaaattg catcgcattg tctgagtagg tgtcattcta ttctgggggg tggggtgggg      4320
caggacagca aggggagga ttgggaagac aatagcaggc atgctgggga tgcggtgggc      4380
tctatggccg cgggccgcag gaaccccag tgatggagtt ggccactccc tctctgcgcg      4440
ctcgctcgct cactgaggcc gggcgaccaa aggtcgcccg acgcccgggc tttgcccggg      4500
cggcctcagt gagcgagcga gcgcgcagct gcctgcagg                            4539
```

<210> SEQ ID NO 64
<211> LENGTH: 2403

```
<212> TYPE: DNA
<213> ORGANISM: Artificial
<220> FEATURE:
<223> OTHER INFORMATION: Synthetically generated expression construct

<400> SEQUENCE: 64
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggacg     120
cgtaggcctg attggctccg gtgcccgtca gtgggcagag cgcacatcgc ccacagtccc     180
cgagaagttg gggggagggg tcggcaattg aaccggtgcc tagagaaggt ggcgcggggt     240
aaactgggaa agtgatgtcg tgtactggct ccgccttttt cccgagggtg ggggagaacc     300
gtatataagt gcagtagtcg ccgtgaacgt tcttttttcgc aacgggtttg ccgccagaac     360
acaggtgtcg tgacgcgacc aggtatgcat ctgcagctct aaggtaaata taaaattttt     420
aagtgtataa tgtgttaaac tactgattct aattgtttct ctcttttaga ttccaacctt     480
tggaactgac tgcagggatc caagctttct agagccacca tggctggact gtggctggga     540
ctggtgtggc agaaactgct gctgtggggg gccgcttccg cactgtcact ggctggggct     600
tcactggtgc tgagcctgct gcagagggtg gcctcctacg ccagaaagtg gcagcagatg     660
aggcccatcc ctaccgtggc cagagcctat ccactggtgg gacacgcact gctgatgaag     720
cctgacggca gagagttctt tcagcagatc atcgagtaca cagaggagta taggcacatg     780
ccactgctga agctgtgggt gggacccgtg cctatggtgg ccctgtacaa cgccgagaat     840
gtggaagtga tcctgaccag cagcaagcag atcgataagt ctagcatgta taagttcctg     900
gagccttggc tgggcctggg cctgctgacc tctacaggca acaagtggag gagccggaga     960
aagatgctga ccccaacatt ccactttaca atcctggagg acttcctgga catcatgaac    1020
gagcaggcca atatcctggt gaagaagctg gagaagcaca tcaaccagga ggcctttaat    1080
tgcttctttt acatcaccct gtgcgccctg gacatcatct gtgagacagc tatgggcaag    1140
aacatcggcg cccagtctaa tgacgatagc gagtacgtgc gggccgtgta tagaatgagc    1200
gagatgatct ttaggcgcat caagatgccc tggctgtggc tggatctgtg gtatctgatg    1260
ttcaaggagg gctgggagca caagaagtcc ctgcagatcc tgcacacctt tacaaactct    1320
gtgatcgccg agagagccaa tgagatgaac gccaatgagg actgtagggg cgatggaagg    1380
ggcagcgccc cttccaagaa caagcggaga gccttcctgg acctgctgct gagcgtgacc    1440
gacgatgagg gcaatcgcct gtcccacgag gacatccggg aggaggtgga tacattcatg    1500
tttgagggac acgacaccac agccgccgcc atcaactggt ccctgtacct gctgggctct    1560
aatccagagg tgcagaagaa ggtggatcac gagctggacg acgtgttcgg caagtccgac    1620
aggccagcaa ccgtggagga tctgaagaag ctgagatacc tggagtgcgt gatcaaggag    1680
acactgcgcc tgttccccct ctgtgcctct tttgcccggt ccgtgtctga ggactgtgag    1740
gtggccggct atcgcgtgct gaagggcacc gaggccgtga tcatccctta cgccctgcac    1800
cgggacccca ggtatttccc taacccagag gagtttcagc cagagagatt ctttcccgag    1860
aatgcccagg gcaggcaccc ttacgcctat gtgccattct ccgccggacc aaggaactgc    1920
atcggacaga agtttgccgt gatggaggag aaaaccatcc tgtcttgtat cctgagacac    1980
ttctggatcg agagcaatca aagagggagg gagctgggcc tggagggaca gctgatcctg    2040
cggccaagca acggcatctg gatcaaactg aaaagaagga acgctgacga gaggtaaaag    2100
cttgaattcc tcgaggatcc aataaaagat ctttatttttc attagatctg tgtgttggtt    2160
```

-continued

```
ttttgtgtgt ctagttgcca gccatctgtt gtttgcccct ccccccgtgcc ttccttgacc    2220 ctggaaggtg ccactcccag tttaaactta attaagggcc gcaggaaccc ctagtgatgg    2280
agttggccac tccctctctg cgcgctcgct cgctcactga ggccgggcga ccaaaggtcg    2340
cccgacgccc gggctttgcc cgggcggcct cagtgagcga gcgagcgcgc agctgcctgc    2400
agg                                                                 2403

<210> SEQ ID NO 65
<211> LENGTH: 1150
<212> TYPE: DNA
<213> ORGANISM: Artificial Sequence
<220> FEATURE:
<223> OTHER INFORMATION: Synthetic sequence

<400> SEQUENCE: 65
caatgagcag agatctggaa gaagggaggg ggcagccgtg caggcctctg aggaaagcat      60
ttcaggcagc agaaatcgta tctagtagac tatgattcta ttcttgtgtt ggaaagactg     120
caaaaatagc acttgaaaat taggaatttg cgtgacaact agggtgcatc caagtccaaa     180
cagaagcatg tgattatcat tcaaagcgaa cgggccaatg aaatgaacgc caatattgta     240
tattgttagg ttcagatatc attaaacaaa tttcagttat tgttagaatc tttagcatta     300
ttttttaaaa cacaagaaaa cctaagattt gtcagagttt tcccaagcag aagagcagcc     360
agagattgct ctcagttctc catgtggctt caagcataga gggtgaattc actaatctgc     420
ttgctgtttc ttttctcctc tacaacatgt aattaagtct ataattagat taaatttgtt     480
tttaaaagtt tcaccagata atccccaaaa tattaatgag gctttactgt attttcacaa     540
gagcctgaag actgtagagg tgatggcagg ggctctgccc cctccaaaaa taaacgcagg     600
gcctttcttg acttgctttt aagtatcaaa ttttaaagta gtttaactaa agaagattca     660
ttatatttta attagaaatt acaaaattta agaaactgat tacaggcttc cttctaacct     720
cccagacatg caagtccact tcctcaccac ctgctttctg aggttccagc agatgagcac     780
actgttgtat aatgattgca ttcactctac cacttaaact ttttctcatt agcgcaatcc     840
aatctctagg gtacatgttg tcgaaatgtt gaaataggct tagaaaaata aatgaaagaa     900
actagcatat tttataagaa aatgtgttgt gactgatgac gaagggaaca ggctaagtca     960
tgaagatatt cgagaagaag ttgacacctt catgtttgag gtagtaccag ctcaacttct    1020
tcagaaaacg attttgacta gtgctgggca cagcagtaga cacatttgtt tttcctttag    1080
ctgctgccat gagctactct acctagagga cagttaagag ccctccaaca gagaatcagc    1140
cagttcatga                                                          1150

<210> SEQ ID NO 66
<211> LENGTH: 72
<212> TYPE: DNA
<213> ORGANISM: Artificial Sequence
<220> FEATURE:
<223> OTHER INFORMATION: synthetic sequence

<400> SEQUENCE: 66
atctctaggg tactatctag tagactatga ttctattctt gtgttggaag gactgcaaaa      60
tagcacttga aa                                                        72

<210> SEQ ID NO 67
<211> LENGTH: 74
<212> TYPE: DNA
<213> ORGANISM: Artificial Sequence
```

<220> FEATURE:
<223> OTHER INFORMATION: Synthetic sequence
<220> FEATURE:
<221> NAME/KEY: misc_feature
<222> LOCATION: (22)..(22)
<223> OTHER INFORMATION: n=g,c,t or a
<220> FEATURE:
<221> NAME/KEY: misc_feature
<222> LOCATION: (62)..(62)
<223> OTHER INFORMATION: n=g,c,t or a

<400> SEQUENCE: 67
aaatctctag ggaactatct antagactat gattctattc ttgtgttgga acgactgcaa        60
antagcactt gaaa                                                          74

<210> SEQ ID NO 68
<211> LENGTH: 540
<212> TYPE: DNA
<213> ORGANISM: Artificial Sequence
<220> FEATURE:
<223> OTHER INFORMATION: Synthetic sequence

<400> SEQUENCE: 68
ttaagtctat aattagactg ttgtataatg attgcattca ctctaccact taaacttttt        60
ctcattagcg caatccaatc tctttaaaag tttcaccaga taatccccaa aatattaatg       120
aggctttact gtattttcac aagagcctat gttgtcgaaa tgtttcattc aaagcgaacg       180
ggccaatgaa atgaacgcca atgaagactg tagaggtgat ggcaggggct ctgccccctc       240
caaaaatagg gtactatcta gtagactatg attctattct tgtgttggaa agactgcaaa       300
aatagcactt gaaaattagg aatttgcgtg aaataggctt agaaaaataa atgaaagaaa       360
ctagcatatt ttataagaaa atgtgttaac tagggtgcat ccaagtccaa actaaacgca       420
gggcctttct tgacttgctt ttaagtgtga ctgatgacga agggaacagg ctaagtcatg       480
aagatattcg agaaggacat taaatttgtt agaagcatgt gattaaagtt gacaccttca       540

<210> SEQ ID NO 69
<211> LENGTH: 65
<212> TYPE: DNA
<213> ORGANISM: Artificial Sequence
<220> FEATURE:
<223> OTHER INFORMATION: Synthetic sequence

<400> SEQUENCE: 69
aaaggacgaa acaccgggtc ttcgagaaga cctgttttag agctagaaat agcaagttaa        60
aataa                                                                    65

<210> SEQ ID NO 70
<211> LENGTH: 26
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (6)..(26)
<223> OTHER INFORMATION: n=g,c,t or a

<400> SEQUENCE: 70
caccgnnnnn nnnnnnnnnn nnnnnn                                              26

<210> SEQ ID NO 71
<211> LENGTH: 26
<212> TYPE: DNA

-continued

```
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (5)..(25)
<223> OTHER INFORMATION: n=g,c,t or a

<400> SEQUENCE: 71
aaacnnnnnn nnnnnnnnnn nnnnnc                                           26

<210> SEQ ID NO 72
<211> LENGTH: 300
<212> TYPE: DNA
<213> ORGANISM: Artificial Sequence
<220> FEATURE:
<223> OTHER INFORMATION: Synthetic sequences

<400> SEQUENCE: 72
ttaaaattat gttttaaaat ggactatcat atgcttaccg taacttgaaa gtatttcgat     60
ttcttggctt tatatatctt gtggaaagga cgaaacaggg tgattatcat tcaaagcgaa    120
gttttagagc tagaaatagc aagttaaaat aaggctagtc cgttatcaac ttgaaaaagt    180
ggcaccgagt cggtgctttt ttgtttttaga gctagaaata gcaagttaaa ataaggctag    240
tccgttttta gcgcgtgcgc caattctgca gacaaatggc tctagaggta cccgttacat    300

<210> SEQ ID NO 73
<211> LENGTH: 23
<212> TYPE: DNA
<213> ORGANISM: Artificial Sequence
<220> FEATURE:
<223> OTHER INFORMATION: Synthetic sequence

<400> SEQUENCE: 73
tgattatcat tcaaagcgaa cgg                                             23

<210> SEQ ID NO 74
<211> LENGTH: 23
<212> TYPE: DNA
<213> ORGANISM: Artificial Sequence
<220> FEATURE:
<223> OTHER INFORMATION: Synthetic sequence

<400> SEQUENCE: 74
gattatcatt caaagcgaac ggg                                             23

<210> SEQ ID NO 75
<211> LENGTH: 23
<212> TYPE: DNA
<213> ORGANISM: Artificial Sequence
<220> FEATURE:
<223> OTHER INFORMATION: Synthetic sequence

<400> SEQUENCE: 75
gataatcaca tgcttctgtt tgg                                             23

<210> SEQ ID NO 76
<211> LENGTH: 23
<212> TYPE: DNA
<213> ORGANISM: Artificial Sequence
<220> FEATURE:
<223> OTHER INFORMATION: Synthetic sequence

<400> SEQUENCE: 76
ttcattggcg ttcatttcat tgg                                             23
```

-continued

```
<210> SEQ ID NO 77
<211> LENGTH: 23
<212> TYPE: DNA
<213> ORGANISM: Artificial Sequence
<220> FEATURE:
<223> OTHER INFORMATION: Synthetic sequence

<400> SEQUENCE: 77
cacatgcttc tgtttggact tgg                                              23

<210> SEQ ID NO 78
<211> LENGTH: 30
<212> TYPE: DNA
<213> ORGANISM: Artificial Sequence
<220> FEATURE:
<223> OTHER INFORMATION: Synthetic sequence

<400> SEQUENCE: 78
cagaaatcgc aagcatagag ggtgaattca                                       30

<210> SEQ ID NO 79
<211> LENGTH: 24
<212> TYPE: DNA
<213> ORGANISM: Artificial Sequence
<220> FEATURE:
<223> OTHER INFORMATION: Synthetic sequence

<400> SEQUENCE: 79
ctgttggagg gctcttaact gtcc                                             24

<210> SEQ ID NO 80
<211> LENGTH: 77
<212> TYPE: DNA
<213> ORGANISM: Artificial Sequence
<220> FEATURE:
<223> OTHER INFORMATION: Synthetic sequence

<400> SEQUENCE: 80
caaacagaag catgtgatta tcattcaaat catacaggtc atcgctgcga acgggccaat      60
gaaatgaacg ccaatga                                                     77
```

CELLULAR MODELS OF AND THERAPIES FOR OCULAR DISEASES

CROSS-REFERENCE TO RELATED APPLICATIONS

This application is a U.S. national phase filing under 35 U.S.C. § 371 of International Application No. PCT/IB2018/055755 titled "CELLULAR MODELS OF AND THERAPIES FOR OCULAR DISEASES", filed Jul. 31, 2018, which claims priority under 35 U.S.C. § 119 (e) to U.S. Application No. 62/539,473 titled "CELLULAR MODELS OF AND THERAPIES FOR OCULAR DISEASES" filed on Jul. 31, 2017. The entire contents of the foregoing are hereby incorporated by reference.

INCORPORATION BY REFERENCE

This application contains a Sequence Listing that has been submitted electronically as an ASCII text file named "43219-0003US1_UPDATEDSL_ST25.txt." The ASCII text file, created on Feb. 28, 2025, is 182,150 bytes in size. The material in the ASCII text file is hereby incorporated by reference in its entirety.

BACKGROUND

Bietti's Crystalline Dystrophy (BCD)

Bietti's Crystalline Dystrophy (BCD, a/k/a Bietti Crystalline Corneoretinal Dystrophy, Bietti Crystalline Retinopathy, Bietti's Retinal Dystrophy (OMIM 210370)) is a rare, autosomal recessive and blinding retinal dystrophy characterized by numerous tiny glistening yellow-white crystal-like deposits at the posterior pole of the retina, associated with atrophy of the retinal pigment epithelium (RPE), pigment clumps, and choroidal sclerosis. It was first identified by Dr. G. B. Bietti in 1937. The fundus photographs and SD-OCT images of BCD patients showed that the crystalline deposits were mainly located on the retinal side of the retinal pigment epithelium (RPE). (H. Kojima, A. Otani, K. Ogino et al., "Outer retinal circular structures in patients with Bietti crystalline retinopathy," British Journal of Ophthalmology, vol. 96, pp. 390-393, 2012.). Crystalline deposits in the corneal limbus have been estimated to occur in one quarter to one third of persons with BCD (Kaiser-Kupfer et al. Clinical biochemical and pathologic correlations in Bietti's crystalline dystrophy, Am J Ophthalmol., 1994, 118:569-82). In some cases, crystal deposits in the lens are also observed (Chung et al., J Ophthalmol. 57:447-450, 2013). In advanced stage, BCD patients have advanced choroidal sclerosis, decrease or absence of crystalline deposits, and attenuation of retinal vessels (Wada et al. Am J Ophthalmol 2005; 139:894-9). Abnormal ERG and retinal thinning are also present in BCD.

Clinically, BCD is progressive and associated with dystrophy and degeneration of RPE. Marked asymmetry between eyes of the same patient is common. Disease onset age and progression vary among BCD patients, even within the same family. Most patients develop night blindness, constricted visual field, poor color vision, macular degeneration and decreased visual acuity between the 2nd and 4th decade of life, and progress to legal blindness between the 3rd and 6th decade of life.

Located between vessels of the choriocapillaris and light-sensitive outer segments of the photoreceptors, the RPE is a monolayer of pigmented cells that closely interacts with photoreceptors (cones and rods) in the maintenance of visual function. A key function of RPE is to nurture, and remove waste products from the photoreceptors which is the neurosensory retina. Other functions of RPE include without limitation: light absorption, epithelial transport, spatial ion buffering, visual cycle, phagocytosis, secretion and immune modulation (Strauss, 2005, The retinal pigment epithelium in visual function. Physiol Rev 85:845-81). Therefore, dysfunction and degeneration of RPE cause photoreceptor dysfunction and degeneration which results in loss of vision. Given BCD is associated with progressive dystrophy and degeneration of RPE, the RPE is critical for purposes of both studying and treating BCD.

BCD is a rare disease. One source estimated BCD incidence rate to be 1:67,000 (ghr.nlm.nih.gov/condition/bietti-crystalline-dystrophy #statistics on the World Wide Web). Another source estimated that BCD prevalence is 2.5% of all RP patients (3 BCD index patients out of 121 RP index patients, see Mataftsi et al., Retina. 24:416-426, 2004). Based on this estimation and given RP incidence rate is estimated to be 1:4000 (Hartong et al., Lancet. 368:1795-1809, 2006), BCD incidence rate is estimated to be 1:160,000. Because BCD symptoms are similar to those of other eye disorders that progressively damage the retina, it is sometimes diagnosed generally as retinitis pigmentosa (RP) (Mataftsi A et al. Bietti's crystalline corneoretinal dystrophy: a cross-sectional study. Retina. 2004; 24:416-426). Although patients with BCD have been reported throughout different regions of the world, including Asia, Africa, Europe, the Middle East, North and South America, BCD has been reported to be more common in people with East Asia descent, especially in Chinese and Japanese populations (Hu 1983, Ophthalmic genetics in China. Ophthal Paed Genet 2:39-45; Li et al., Am J Hum Genet. 2004 May; 74 (5): 817-826).

Currently there is no approved treatment for BCD, and patients eventually become blind. There is a strong unmet medical need to develop life-changing treatment options for patients suffering from this rare disease.

CYP4V2

CYP4V2 (Cytochrome P450, Family 4, Subfamily V, Polypeptide 2, (OMIM 608614), synonym: CYP4AH1) is one of the proteins in the cytochrome P450 superfamily and a member of the heme thiolate cytochrome P450 subfamily 4 (CYP4). Cytochrome P450s (CYPs) are important heme-containing proteins, known for their monooxgenase reaction. They are involved in the metabolism of xenobiotics and endogenous compounds, such as steroids and fatty acids. Human CYPs are primarily membrane-associated proteins located either in the inner membrane of mitochondria or in the endoplasmic reticulum of cells. P450 proteins can be identified by their signature sequence element FxxGxxxCxG (SEQ ID NO:30), where the underlined cysteine serves as an axial ligand to the heme iron. Another signature sequence element for P450 protens is ExxR (SEQ ID NO: 31). The Human Genome Project has set the number of human P450 genes at 57. For reference, there are 103 mouse P450 genes and 89 rat P450 genes. (Guengerich & Cheng, Pharmacological Reviews, September 2011, 63 (3) 684-699).

Human CYP4 family consists of 12 genes and 10 pseudo genes. The human CYP4V2 gene (HGNC: 23198) is located at 4q35 and has 11 exons. Mutations in the CYP4V2 gene cause BCD (Li et al., Am J Hum Genet. 74:817-826, 2004). While CYP4V2 is expressed in almost all tissues, it is expressed at high levels in the retina and RPE and at somewhat lower levels in the cornea, tissues which show the major clinical findings of BCD (Li et al., Am J Hum Genet. 74:817-826, 2004; Nakano M, Kelly E J, Rettie A E: Expression and Characterization of CYP4V2 as a Fatty Acid omega-Hydroxylase. *Drug Metab Dispos* 2009; Nakano M, Kelly E J, Wiek C, Hanenberg H, Rettie A E: CYP4V2 in Bietti's crystalline dystrophy: ocular localization, metabolism of omega-3-polyunsaturated fatty acids, and functional deficit of the p.H331P variant. *Mol Pharmacol* 2012; 82:679-686).

Since CYP4V2 is a relatively new member of the P450 family and BCD is a rare disease, the function of CYP4V2 has not been extensively studied. Prior studies showed that CYP4V2 protein is predominantly active in fatty acid metabolism. Abnormalities in fatty acids and their metabolism have been demonstrated in serum, lymphocytes and skin fibroblasts of patients with BCD (Lee J, Jiao X, Hejtmancik J F et al: The metabolism of fatty acids in human Bietti crystalline dystrophy. Invest Ophthalmol Vis Sci 2001; 42:1707-1714; Lai T, Chu K O, Chan K P et al: Alterations in serum fatty acid concentrations and desaturase activities in Bietti crystalline dystrophy unaffected by CYP4V2 genotypes. *Invest Ophthalmol Vis Sci* 2010; 51:1092-1097). Another study showed that CYP4V2 is a omega-3-polyunsaturated fatty acids (PUFA) hydroxylase and a highly expressed P450 in the transformed human RPE cell line ARPE-19 (Nakano M, Kelly E J, Wiek C, Hanenberg H, Rettie A E: CYP4V2 in Bietti's crystalline dystrophy: ocular localization, metabolism of omega-3-polyunsaturated fatty acids, and functional deficit of the p.H331P variant. Molecular pharmacology 2012; 82:679-686).

Numerous mutations have been identified in the CYP4V2 gene and causing BCD, with at least one mutation in each of the gene's 11 exons. The most common CYP4V2 mutation among BCD patients is c. 802-8_810del17insGC (referring to a 17 base deletion with two bases (GC) inserted in the place starting 8 bases from the end of intron 6 of CYP4V2 gene, also referred to as IVS6-8 del/insGC, See SEQ ID NO: 46 showing sequence of the human CYP4V2 genomic DNA region comprising the c. 802-8_810del17insGC mutation and SEQ ID NO: 47 showing the corresponding wild-type sequence. The c. 802-8_810del17insGC mutation is illustrated in the following sequence which shows human CYP4V2 intron 6-exon 7 junction. Intron6 sequence is shown in lower case and exon 7 sequence in CAP letters. The 17 bps deletion and the insertion of GC are in brackets): caa aca gaa gca tgt gat tat cat tca aa (tca tac agG TCA TCG CT) (GC) GAA CGG GCC AAT GAA ATG AAC GCC AAT GA (SEQ ID NO:80)) resulting in the skipping of exon 7. (Xiao et al., Biochem Biophys Res Commun. 409:181-6, 2011; Meng et al., 2014, Mol. Vis., 20:1806-14; Wada et al., Am J Ophthalmol. 139:894-9, 2005; Jiao et al., European Journal of Human Genetics (2017) 25, 461-471). A recent study estimated that the age of the c. 802-8_810del17insGC mutation was to be 1,040-8,200 generations in the Chinese and 300-1100 generations in the Japanese populations. See Jiao et al., European Journal of Human Genetics (2017) 25, 461-471.

Various types of CYP4V2 mutations were found associated with BCD, including but not limited to, missense, duplicate, splice site, frameshift, deletion, insertion, indel, nonsense, polymorphisms (e.g., single nucleotide polymorphisms) and premature termination, as well as entire deletion of the CYP4V2 gene. A summary of select CYP4V2 mutations among human BCD patients is provided in Table 1 herein and can be found in various publications and online databases, e.g., LOVD (databases.lovd.nl/shared/genes/CYP4V2 on the World Wide Web), OMIM (omim.org/allelicVariant/608614 on the World Wide Web), and ClinVar (ncbi.nlm.nih.gov/clinvar?term=608614 [MIM] on the World Wide Web).

TABLE 1

| Select CYP4V2 Mutations among BCD Patients | | |
|---|---|---|
| Exon | Nucleotide Change | Predicted Protein Change |
| 1 | c.31C > T | p.Q11X |
| 1 | c.64C > G | p.L22V |
| 1 | c.71T > C | p.L24P |
| 1 | c.77G > A | p.G26D |
| 1 | c.130T > A | p.W44R |
| 1 | c.134A > C | p.Q45P |
| 1 | c.181G > A | p.G61S |
| 1 | c.197T > G | p.M66R |
| IVS1 | c.214 + 1G > A | Exon1del |
| IVS1 | c.214 + 25delT | Not available |
| IVS1 | c.215-2A > G | Exon2del |
| IVS1 | c.215-1G > A | Exon2del |
| 2 | c.219T > A | p.F73L |
| 2 | c.237G > T | p.E79D |
| 2 | c.253C > T | p.R85C |
| 2 | c.277T > C | p.W93R |
| 2 | c.283G > A | p.G95R |
| 2 | c.327G > A | Not available |
| IVS2 | c.327 + 1G > A | p.E72Gfs*5 |
| IVS2 | c.327 + 11G > C | Not available |
| 3 | c.332T > C | p.I111T |
| 3 | c.335T > G | p.L112* |
| 3 | c.367A > G | p.M123V |
| 3 | c.400G > T | p.G134* |
| 3 | c.413 + 2T > G | Splicing acceptor |
| 4 | c.518T > G | p.L173W |
| 5 | c.637_641delAGTAA | p.S213* |
| 5 | c.655T > C | p.Y219H |
| 6 | c.677T > A | p.M226K |
| 6 | c.694C > T | p.R232* |
| 6 | c.724delG | p.D242Ifs*35 |
| 6 | c.732G > A | p.W244* |
| 6 | c.761A > G | p.H254R |
| 6 | c.772C > T | pL258F |
| 6 | c.791delT | Deletion |
| 7 | c.802-8_806del13 | Exon7del |
| 7 | c.802-8_810del17insGC | Exon7del |
| 7 | c.810delT | p.(Glu271Argfs*34) |
| 7 | c.838G > T | p.E280* |
| 7 | c.958C > T | p.R320* |
| 7 | c.971A > T | p.D324V |
| 7 | c.974C > T | p.T325I |
| IVS7 | c.985 + 3A > G | Not available |
| 8 | c.992A > C | p.H331P |
| 8 | c.998C > A | p.T333K |
| 8 | c.1020G > A | p.W340* |
| 8 | c.1021T > C | p.S341P |
| 8 | c.1027 T > G | p.Y343D |
| 8 | c.1062dupA | p.V355Sfs*4 |
| IVS8 | c.1091-2A > G | Exon9del |
| 9 | c.1157A > C | p.K386T |
| 9 | c.1168C > T | p.R390C |
| 9 | c.1169G > A | p.R390H |
| 9 | c.1178C > T | p.P393L |
| 9 | c.1187C > T | p.P396L |
| 9 | c.1198C > T | p.R400C |
| 9 | c.1199G > A | p.R400H |
| 9 | c.1219G > T | p.E407* |
| 9 | c.1225 + 1 G > A | p.(G364_V408del) |
| 10 | C.1226-6_1235del16 | Exon10del |
| 10 | c.1328G > A | p.R443Q |
| 10 | c.1348C > T | p.Q450* |
| 10 | c.1355G > A | p.R452H |
| 10 | c.1372G > A | p.V458M |
| 10 | c.1393A > G | p.R465G |
| 10 | c.1396 A > CF | p.N466D |
| 10 | c.1399T > C | p.C467R |
| 10 | c.1441delT | p.(Ser481Argfs*4) |
| 10 | c.1445C > T | p.S482* |
| 11 | c.1523G > A | p.R508H |
| 11 | c.1526C > T | p.P509L |

TABLE 1-continued

| | Select CYP4V2 Mutations among BCD Patients | |
| --- | --- | --- |
| Exon | Nucleotide Change | Predicted Protein Change |
| | c.604G > A | p.(Glu202Lys) |
| | c.242C > G | p.(Thr81Arg) |
| | c.604 + 4A > G | p.(?) |
| | c.1249dup | p.(Thr417Asnfs*2) |
| | Entire CYP4V2 deletion | * |

This is a select list only and may not contain all pathologic CYP4V2 mutations/variants among BCD patients identified and reported to date. The mutations are relative to reference sequences (NM_207352.3) and (NP_997235.3). New CYP4V2 pathologic mutations among BCD patients are continuously being identified. All identified and future identified pathologic CYP4V2 mutations/variants associated with BCD are incorporated herein by reference.

Inherited Retinal Degenerations (IRDs)

Inherited Retinal Degenerations (IRDs) is a major cause of blindness. Currently more than 200 genes are known to be involved in IRDs and related disorders. Retinitis pigmentosa (RP) is the leading form of IRDs in humans. There are three general modes of inheritance for RP (autosomal dominant, autosomal recessive, and X-linked). Worldwide incidence rate of RP was estimated to be one in 4000, with autosomal recessive RP accounting for 50%-60% of RP (Hartong D T, Berson E L, Dryja T P. Retinitis pigmentosa. *Lancet.* 2006; 368:1795-809). A study in Europe has estimated that BCD prevalence is 2.5% of all RP patients and approximately 10% of persons with nonsyndromic autosomal recessive RP (Mataftsi A, Zografos L, Millá E, Secrétan M, Munier F L. Bietti's crystalline corneoretinal dystrophy: a cross-sectional study. Retina. 2004; 24:416-26). The same study also noted that BCD is often diagnosed generally as RP. Therefore, BCD may have been under-diagnosed. BCD is a worldwide disease but it is most common in East Asia especially in the Chinese and Japanese populations (Li et al., *Am J Hum Genet.* 2004 May; 74 (5): 817-826).

References for Table 1 Mutations

Li A, Jiao X, Munier F L, Schorderet D F, Yao W, et al. (2004) Bietti crystalline corneoretinal dystrophy is caused by mutations in the novel gene CYP4V2. Am J Hum Genet 74:817-826.

Xiao X, Mai G, Li S, Guo X, Zhang Q (2011) Identification of CYP4V2 mutation in 21 families and overview of mutation spectrum in Bietti crystalline corneoretinal dystrophy. Biochem Biophys Res Commun 409:181-186.

Shan M, Dong B, Zhao X, Wang J, Li G, et al. (2005) Novel mutations in the CYP4V2 gene associated with Bietti crystalline corneoretinal dystrophy. *Mol Vis* 11:738-743.

Rossi S, Testa F, Li A, Yaylacioglu F, Gesualdo C, et al. (2013) Clinical and genetic features in Italian Bietti crystalline dystrophy patients. Br J Ophthalmol 97:174-179.

Lin J, Nishiguchi K M, Nakamura M, Dryja T P, Berson E L, et al. (2005) Recessive mutations in the CYP4V2 gene in East Asian and Middle Eastern patients with Bietti crystalline corneoretinal dystrophy. J Med Genet 42: e38.

Manzouri B, Sergouniotis P I, Robson A G, Webster A R, Moore A (2012) Bietti crystalline retinopathy: report of retinal crystal deposition in male adolescent siblings. ARCH OPHTHALMOL 130:1470-1473.

Lai TY, Ng TK, Tam PO, Yam GH, Ngai JW, et al. (2007) Genotype phenotype analysis of Bietti's crystalline dystrophy in patients with CYP4V2 mutations. *Invest Ophthalmol Vis Sci* 48:5212-5220.

Parravano M, Sciamanna M, Giorno P, Boninfante A, Varano M (2012) Bietti crystalline dystrophy: a morphofunctional evaluation. Doc Ophthalmol 124:73-77.

Wada Y, Itabashi T, Sato H, Kawamura M, Tada A, et al. (2005) Screening for mutations in CYP4V2 gene in Japanese patients with Bietti's crystalline corneoretinal dystrophy. *Am J Ophthalmol* 139:894-899.

Zenteno J C, Ayala-Ramirez R, Graue-Wiechers F (2008) Novel CYP4V2 gene mutation in a Mexican patient with Bietti's crystalline corneoretinal dystrophy. Curr Eye Res 33:313-318.

Lee K Y, Koh A H, Aung T, Yong V H, Yeung K, et al. (2005) Characterization of Bietti crystalline dystrophy patients with CYP4V2 mutations. Invest Ophthalmol Vis Sci 46:3812-3816.

Yokoi Y, Sato K, Aoyagi H, Takahashi Y, Yamagami M, et al. (2011) A Novel Compound Heterozygous Mutation in the CYP4V2 Gene in a Japanese Patient with Bietti's Crystalline Corneoretinal Dystrophy. Case Rep Ophthalmol 2:296-301.

Haddad N M, Waked N, Bejjani R, Khoueir Z, Chouery E, et al. (2012) Clinical and molecular findings in three Lebanese families with Bietti crystalline dystrophy: report on a novel mutation. Mol Vis 18:1182-1188.

Fu Q, Wang F, Wang H, Xu F, Zaneveld J E, et al. (2013) Next-generation sequencing-based molecular diagnosis of a Chinese patient cohort with autosomal recessive retinitis pigmentosa. Invest Ophthalmol Vis Sci 54:4158-4166.

Song Y, Mo G, Yin G (2013) A novel mutation in the CYP4V2 gene in a Chinese patient with Bietti's crystalline dystrophy. Int Ophthalmol 33:269-276.

Jin Z B, Ito S, Saito Y, Inoue Y, Yanagi Y, et al. (2006) Clinical and molecular findings in three Japanese patients with crystalline retinopathy. Jpn J Ophthalmol 50:426-431.

Halford S, Liew G, Mackay D S, Sergouniotis P I, Holt R, Broadgate S, Volpi E V, Ocaka L, Robson A G, Holder G E, Moore A T, Michaelides M, Webster A R. Detailed phenotypic and genotypic characterization of bietti crystalline dystrophy. Ophthalmology. 2014; 121:1174-84

Houfa Yin, Chongfei Jin, Xiaoyun Fang, Qi Miao, Yingying Zhao, Zhiqing Chen, Zhaoan Su, Panpan Ye, Yao Wang and Jinfu Yin, Molecular Analysis and Phenotypic Study in 14 Chinese Families With Bietti Crystalline Dystrophy. PLOS One 9 (4), e94960. 2014 Apr. 16.

Xiao Hong Meng, Hong Guo, Hai Wei Xu, Qi You Li, Xin Jin, Yun Bai, Shi Ying Li, Zheng Qin Yin, Identification of novel CYP4V2 gene mutations in 92 Chinese families with Bietti's crystalline corneoretinal dystrophy, Molecular Vision (2014); 20:1806-1814

Galuh D N Astuti, Vincent Sun, Miriam Bauwens, Ditta Zobor, Bart P Leroy, Amer Omar, Bernhard Jurklies, Irma Lopez, Huanan Ren, Volkan Yazar, Christian Hamel, Ulrich Kellner, Bernd Wissinger, Susanne Kohl, Elfride De Baere, Rob W J Collin, and Robert K Koenekoop, Novel insights into the molecular pathogenesis of CYP4V2-associated Bietti's retinal dystrophy, Mol Genet Genomic Med. 2015 January; 3 (1): 14-29.

Xiaodong Jiao, Anren Li, Zi-Bing Jin, Xinjing Wang, Alessandro Iannaccone, Elias I Traboulsi, Michael B Gorin, Francesca Simonelli and J Fielding Hejtmancik, Identification and Population History of CYP4V2 mutations in

7

Patients with Bietti Crystalline Corneoretinal Dystrophy, European Journal of Human Genetics (2017) 25, 461-471.

SUMMARY

Cell Line Claims
Cell Line and Disease Model Claims
Cell Line Composition

In one aspect, a cellular disease model including a cell line is provided. Such a disease model includes (a) a stem cell provided from a subject or reprogrammed from a cell provided from a subject, or (2) a cell derived from a stem cell provided from a subject or reprogrammed from a cell provided from a subject, comprising one or more mutations in a target gene.

In some embodiments, the stem cell is an induced pluripotent stem (iPS) cell. In some embodiments, the stem cell is an embryonic stem (ES) cell, somatic (or adult) stem cell, or mesenchymal stem cell (MSC). In some embodiments, the cell provided from a subject is of any cell type and/or from any tissue of the subject. In some embodiments, the cell provided from a subject is a skin cell, a fibroblast or a blood cell. In some embodiments, wherein the cell provided from a subject is a skin fibroblast or a peripheral blood mononuclear cell (PBMC). In some embodiments, the cell provided from a subject is a urinary cell, a renal epithelial cell, a hair follicle, or a dermal papilla cell.

In some embodiments, the cell derived from a stem cell is an ocular cell. In some embodiments, the ocular cell is a retinal pigment epithelium (RPE) cell, photoreceptor cell (PRC, including rod cell, cone cell and photoreceptor progenitor cell), retinal cell, corneal cell, corneal epithelial cell (CEC), optic nerve cell, lens cell, choroidal endothelial (CE) cell, optic nerve cell or choroidal cell. In some embodiments, the cell derived from a stem cell is a neuron cell.

In some embodiments, the mutation is endogenous to the subject. In some embodiments, the mutation is exogenous to the subject. In some embodiments, the mutation is introduced artificially via genetic editing or genetic manipulation. In some embodiments, the cell line comprises a plurality of mutations that are endogenous and/or exogenous to the subject.

In some embodiments, the subject is a mammal. In some embodiments, the subject is a human.

In some embodiments, the target gene comprises a gene set forth in Table 4. In some embodiments, the target gene comprises a mutated or defective CYP4V2, CYP1B1, MYO7A, DFNB31, USHIC, USHIG, CDH23, PCDH15, CLRN1, ACO2, AFG3L2, ATXN2, AUH, C12orf65, CISD2, FOXC1, FOXF2, LTBP2, MTPAP, MYOC, NDUFS1, NR2F1, OPA1, OPA3, OPTN, PAX6, PDGF, PITX2, POLG, SPG7, TEK, TXNRD2, WFS1, ABCA4, REP-1, RPE65, CEP290, PDE6B, RPGR, MERTK, MT-ND4, FAM47E, GBA, GCH1, HTRA2, LRRK2, PARK2, PINK1, SNCA, SYNJI, NPC1, NPC2, CYP4A11, CYP4A22, CYP4B1, CYP4F2, CYP4F3, CYP4F8, CYP4F11, CYP4F12, CYP4F22, CYP4X1, CYP4Z1, or CYP46A gene or a CYP4V2, CYP1B1, MYO7A, DFNB31, USHIC, USHIG, CDH23, PCDH15, CLRN1, ACO2, AFG3L2, ATXN2, AUH, C12orf65, CISD2, FOXC1, FOXF2, LTBP2, MTPAP, MYOC, NDUFS1, NR2F1, OPA1, OPA3, OPTN, PAX6, PDGF, PITX2, POLG, SPG7, TEK, TXNRD2, WFS1, ABCA4, REP-1, RPE65, CEP290, PDE6B, RPGR, MERTK, MT-ND4, FAM47E, GBA, GCH1, HTRA2, LRRK2, PARK2, PINK1, SNCA, SYNJI, NPC1, NPC2, CYP4A11, CYP4A22, CYP4B1, CYP4F2, CYP4F3, CYP4F8, CYP4F11, CYP4F12, CYP4F22,

8

CYP4X1, CYP4Z1 or CYP46A gene that encodes a protein having defective or partial function or activity. In some embodiments, the target gene is CYP4V2.

In some embodiments, the cell line comprises an iPS cell. In some embodiments, the cell line comprises an iPS-RPE cell. In some embodiments, the cell line comprises an iPS-photoreceptor (iPS-PRC) cell, an iPS-corneal epithelial cell (iPS-CEC). an iPS-choroidal endothelial (CE) cell, an iPS-corneal cell, an iPS-choroidal cell, an iPS-optic nerve cell, an iPS-ocular cell or an iPS-neuron cell. In some embodiments, the CYP4V2 mutation in the cell line is endogenous to the subject. In some embodiments, the subject has a pathologic mutation in the CYP4V2 gene or in an ortholog of the CYP4V2 gene.

In some embodiments, the subject has at least one mutation set forth in Table 1. In some embodiments, the subject has inherited retinal degeneration (IRD) or retinitis pigmentosa (RP). In some embodiments, the subject has Bietti's Crystalline Dystrophy (BCD, a/k/a Bietti Crystalline Corneoretinal Dystrophy, Bietti Crystalline Retinopathy, Bietti's Retinal Dystrophy) or is at risk of developing BCD.

In some embodiments, the cell line comprises a CYP4V2 mutation that is exogenous to the subject and is introduced artificially via genetic editing or genetic manipulation.

In some embodiments, the cell line comprises an iPS cell, ES cell, MSC, or adult stem cell, or a RPE cell, photoreceptor cell, corneal epithelial cell. choroidal endothelial (CE) cell or choroidal cell derived from an iPS cell, ES cell, MSC, or adult stem cell. In some embodiments, the iPS cell or other type of stem cell is characterized by one or more of the following: a. the unique morphology of iPS, ES or MSC; b. one or more pluripotency markers, such as Oct-4, Sox-2, SSEA4, TRA-1-60, TRA-1-81, NANOG and AP; c. the ability to differentiate into the desired cell type (e.g., RPE), and/or d. a terotoma assay.

In some embodiments, the iPS-RPE cell or the RPE cell derived from other types of stem cell is characterized by: a. morphology: pigment and hexagonal shape, and/or b. one or more of the following biomarkers, retinaldehyde-binding protein 1 (RLBP1, alias: CRALBP), RPE65, BESTROPHIN-1, MITF, LRAT, RDH5, PAX6, MERTK, TYR, ZO-1 and/or VINCULIN.

In another aspect, a BCD human cellular model or a CYP4V2 function cellular model is provided. Such a model includes comprising an iPS cell or iPS cell line, or an iPS-RPE cell or iPS-RPE cell line derived from a cell or a cell line of a BCD patient, or derived from a cell or a cell line with artificially created CYP4V2 mutations.

In some embodiments, the cell line has an abnormal biochemical profile in one or more compounds of the following compound groups: (i) fatty acids, (ii) ceramides, (iii) sphingomyelins, (iv) sphingosine, (v) sphinganine, or (vi) hydroxy-fatty acids. as compared to a corresponding cell line of a healthy control. In some embodiments, the cell line has an abnormal biochemical profile in one or more compounds set forth in Table 2 as compared to the corresponding cell line of a healthy control.

Method of Making the Cellular Disease Model:

In another aspect, a method of making an iPS-derived BCD disease model is provided. Such a method includes obtaining cells from a subject having endogenous mutations in the CYP4V2 gene or cells with no endogenous mutations in the CYP4V2 gene but exogenous CYP4V2 mutation is introduced artificially via gene editing or gene manipulation at this stage or any of the following stages; inducing pluripotency in the cells or reprogramming the cells to produce iPSCs; culturing the iPSCs under conditions that result in differentiation of the iPSCs into desired ocular cells, thereby producing an iPS-derived ocular cell line.

In some embodiments, the cells obtained from the subject are somatic cells. In some embodiments, the cells obtained from the subject are skin cells, fibroblasts, blood cells, peripheral blood mononuclear cells (PBMC), or ocular cells. In some embodiments, the cells obtained from the subject are urinary cells, renal epithelial cells, a hair follicles, or dermal papilla cells. In some embodiments, the ocular cells are retinal pigment epithelial (RPE) cells, corneal epithelial cells (CECs), photoreceptor cells (PRCs), choroidal endothelial (CE) cells, optic nerve cells, retinal cells, corneal cells, or choroidal cells. In some embodiments, the pluripotency is induced or the cells are reprogrammed using one or more of the OCT4, SOX2, KLF4, and c-MYC transcription factors.

In some embodiments, the mutation is pathologic. In some embodiments, the cell line comprises one or more mutation among the mutations set forth in Table 1. In some embodiments, the cell line is heterozygous for the mutation. In some embodiments, the cell line is homozygous for the mutation.

In some embodiments, the cellular disease model exhibits abnormal levels in one or more compounds from the following compound groups as compared to that in a relevant cell line of a healthy control: (i) fatty acids, (ii) ceramides, (iii) sphingomyelins, (iv) sphingosine, (v) sphinganine, or (vi) hydroxy-fatty acids. In some embodiments, the cellular disease model exhibits abnormal levels as compared to that in a relevant cell line of a healthy control in one or more compounds set forth in Table 2.

Biochemical Assay Method:

In one aspect, a method of discovering abnormalities or phenotype in a disease cellular model is provided. Such a method typically includes evaluating and comparing the levels of one or more compounds between the cell line of a patient (or an genetically edited or manipulated cell line comprising an exogenous mutation in the gene causing such disease) and a healthy control, wherein the one or more compound is selected from the following groups: (i) fatty acids, (ii) ceramides, (iii) sphingomyelins, (iv) sphingosine, (v) sphinganine, and/or (vi) hydroxy-fatty acids.

In some embodiments, one or more of the compounds evaluated is set forth in Table 2. In some embodiments, the identification and/or evaluation of compound levels is performed using LC-MS, LC-MS/MS, GC-MS, GC-MS/MS, and/or FIA-MS/MS. In some embodiments, the disease cellular model comprises a mutated or defective gene set forth in Table 4. In some embodiments, the disease cellular model comprises a mutated or defective gene among the CYP4V2, CYP1B1, MYO7A, DFNB31, USHIC, USHIG, CDH23, PCDH15, CLRN1, ACO2, AFG3L2, ATXN2, AUH, C12orf65, CISD2, FOXC1, FOXF2, LTBP2, MTPAP, MYOC, NDUFS1, NR2F1, OPA1, OPA3, OPTN, PAX6, PDGF, PITX2, POLG, SPG7, TEK, TXNRD2, WFS1, ABCA4, REP-1, RPE65, CEP290, PDE6B, RPGR, MERTK, MT-ND4, FAM47E, GBA, GCH1, HTRA2, LRRK2, PARK2, PINK1, SNCA, SYNJI, NPC1, NPC2, CYP4A11, CYP4A22, CYP4B1, CYP4F2, CYP4F3, CYP4F8, CYP4F11, CYP4F12, CYP4F22, CYP4X1, CYP4Z1, or CYP46A gene.

Method of Use of the BCD Cellular Model (Drug, Dosage and Device Screening)

In another aspect, a method of screening a test agent for therapeutic efficacy against BCD is provided. Such a method typically includes contacting cells from an iPS-RPE cell line derived from a BCD patient or an iPS-RPE cell line comprising a mutated or defective CYP4V2 gene as a result of artificial genetic editing or manipulation with a test agent; and evaluating the cells for normalization in levels of one or more compounds set forth in Table 2; an increase in non-defective CYP4V2 nucleic acid sequence in the cells; an increase in the amount of CYP4V2 polypeptides in the cells; and/or improved cell structure, morphology or function, as compared to before contacting by such test agent; wherein normalization in levels of one or more compound set forth in Table 2; an increase in non-defective CYP4V2 nucleic acid sequence in the cells; an increase in the amount of CYP4V2 polypeptides in the cells; and/or improved cell structure, morphology or function, as compared to before treatment by such test agent, is indicative of a test agent that exhibits therapeutic efficacy against BCD.

In some embodiments, the test agents are selected from the group consisting of nucleic acids or analogs thereof, vectors containing nucleic acid sequence or encoding polypeptides, polypeptides or analogs thereof, antibodies, chemicals, small molecules, and/or any combination thereof. In some embodiments, the cells are evaluated using PCR techniques, immunoassays, sequencing, biochemical assay, function assay, microscopy or combination thereof.

In another aspect, a method of screening efficacy or efficiency of a formulation, vector or construct comprising a test agent for BCD is provided. Such a method typically includes contacting multiple cell samples from an iPS-RPE cell line derived from a BCD patient or an iPS-RPE cell line comprising a mutated or defective CYP4V2 gene as a result of artificial genetic editing or manipulation with a test agent formulated or packaged in various formulations, vectors or constructs; and evaluating the cell samples for normalization in levels of one or more compound set forth in table 2; an increase in non-defective CYP4V2 nucleic acid sequence in the cells; an increase in the amount of CYP4V2 polypeptides in the cells; improved cell structure, morphology or function; and/or cell tolerance or death, as compared to before treatment by such test agent and/or to cell samples treated by the same test agent but formulated or packaged in a different formulation, vector or construct, to determine and compare the efficiency or efficacy of such formulation, vector or construct; wherein the cells are evaluated using PCR techniques, immunoassays, sequencing, biochemical assay, cell viability assay, microscopy or combination thereof.

In one aspect, a method of screening effective and safe dosage range of a test agent for BCD is provided. Such a method typically includes contacting multiple cell samples from an iPS-RPE cell line derived from a BCD patient or an iPS-RPE cell line comprising a mutated or defective CYP4V2 gene as a result of artificial genetic editing or manipulation with a test agent in a different dose for each cell sample; evaluating the cell samples for normalization in levels of one or more compound set forth in table 2; an increase in non-defective CYP4V2 nucleic acid sequence in the cells; an increase in the amount of CYP4V2 polypeptides in the cells; improved cell structure, morphology or function, and/or cell tolerance or death, as compared to before treatment by such test agent and/or to cell samples treated by the same test agent but with a different dose, to determine and compare the effective and safety of different doses thereby determining a proper dosage range; wherein the cells are evaluated using PCR techniques, immunoassays, sequencing, biochemical assay, cell viability assay, function assay, microscopy or combination thereof.

In another aspect, a method of screening or evaluating efficacy or efficiency of a delivery device or method for delivering a therapeutic agent to the retina or retinal cells is provided. Such a method typically includes (i) contacting a cell sample from an iPS-RPE cell line derived from a BCD patient or an iPS-RPE cell line comprising a mutated or defective CYP4V2 gene as a result of artificial genetic editing or manipulation with a test agent without employing the delivery device or method; (ii) contacting another cell sample from an iPS-RPE cell line derived from a BCD patient or an iPS-RPE cell line comprising a mutated or defective CYP4V2 gene as a result of artificial genetic editing or manipulation with the test agent of the same dosage as in (i), employing the delivery device or method; (iii) evaluating and comparing the cell samples from (i) and (ii) for normalization in levels of one or more compound set forth in Table 2; an increase in non-defective CYP4V2 nucleic acid sequence in the cells; an increase in the amount of CYP4V2 polypeptides in the cells; improved cell structure, morphology or function; cell tolerance or death; and/or the levels of the test agent in the cells, as compared to before treatment by such test agent and/or treatment by the same test agent of the same dose but without employing the delivery device or method, to determine the efficacy or efficiency of such delivery device or technique; wherein the cells are evaluated using PCR techniques, immunoassays, sequencing, biochemical assay, function assay, microscopy or combination thereof.

In some embodiments, the retinal cells are RPE cells.

CRISPR Gene Editing Therapy

In one aspect, a composition is provided that includes: (a) a CRISPR guide RNA targeting a nucleic acid sequence (the "target sequence") of or within 100 bps to the CYP4V2 gene, and (b) a functional CRISPR-associated protein (Cas). In some embodiments, such a composition can further include (c) a donor nucleic acid sequence comprising all or a portion of a wild-type sequence or a functional sequence of the CYP4V2 gene for correction, disruption or replacement of CYP4V2 gene or a portion thereof.

In some embodiments, one or more components thereof is provided in the form of a DNA molecule encoding such component, an mRNA molecule encoding such component, a RNA molecule, a polypeptide, and/or a ribonucleoprotein (RNP) or protein-RNA complex. In some embodiments, two or more components thereof are in separate molecule or combined in one molecule or in one complex, are in separate vectors or combined in one vector, are in one or more nucleic acid complex, are in one or more RNP complex. In some embodiments, the donor nucleic acid sequence is provided in a single-stranded donor oligonucleotide (ssODN) or a vector. In some embodiments, the vector is a plasmid, a recombinant AAV vector, a recombinant lentivirus vector, and/or a combination thereof.

In some aspects, a composition including a cell with a pathologic CYP4V2 mutation that contains any of the compositions described herein is provided. In some embodiments, (a) the CRISPR guide RNA comprising (i) a CRISPR RNA (crRNA) which comprises a protospacer element sequence that is complementary to the target sequence of or within 100 bps to a target gene (the "target gene") and a sequence that corresponds to a complementary region of the trans-activating crRNA (tracrRNA), and (ii) a tracrRNA which comprises a region that is complementary to corresponding region of the crRNA and a sequence which interacts with a CRISPR-associated protein 9 (Cas9), and (b) the functional CRISPR-associated protein comprises Cas9.

In some embodiments, the protospacer element is about 20 bases, about 19 bases, about 21 bases, about 19-21 bases, about 18-22 bases, or about 16-24 bases. In some embodiments, the crRNA and the tracrRNA are in separate molecules. In some embodiments, the crRNA and the tracrRNA are combined into a single guide RNA (sgRNA). In some embodiments, the sgRNA is about 88-150 bps.

In some embodiments, the Cas9 comprises a Cas9 ortholog or a mutant Cas9 selected from: *Streptococcus pyogenes* (SpCas9), SpCas9 nickase (Cas9n D10A), SpCas9 (D1135E), eSpCas9, SpCas9-HF1, SpCas9 VRER, SpCas9 VQR, SpCas9EQR, *Staphylococcus aureus* (SaCas9), *Neisseria Meningitidis, Streptococcus thermophilus, Streptococcus pneumoniae, Campylobacter coli, Campylobacter jejuni, Streptococcus mutans, Pasteurella multocida, Bifidobacterium longum, Bacillus smithii, Treponema denticola, mycoplasma canis* and *Enterococcus faecalis*. In some embodiments, the CRISPR-associated protein, Cas9, or Cpf1, further includes one, two, three or more nuclear localization sequences (NLS) at the N-terminal and/or C-terminal, and/or a selection marker, including without limitation, GFP or EGFP.

In some embodiments, (a) the CRISPR guide RNA comprises a crRNA which comprises a protospacer element sequence that is complementary to the target sequence of or within 100 bps to a target gene, and (b) the functional CRISPR-associated protein comprises Cpf1. In some embodiments, the protospacer element is about 20 bases, about 21 bases, about 22 bases, about 23 bases, about 24 bases, about 19-25 bases, about 18-26 bases, or about 16-28 bases.

In some embodiments, the protospacer element sequence is selected from the group consisting of SEQ ID NOs: 48 to 52, or shares at least 85% sequence identity with one of SEQ ID NO: 48 to 52 for use with a Cas protein that has NGG as protospacer adjacent motif (PAM) to target the c. 802-8_810del17insGC mutation of the CYP4V2 gene. In some embodiments, the donor nucleic acid sequence is selected from SEQ ID NOs: 56 and 57, (this is the two donor template sequence) or shares at least 90% sequence identity with one of SEQ ID NO: 56 and 57, or a sequence that is complementary thereof, for use to correct, disrupt or replace the c. 802-8_810del17insGC mutation of the CYP4V2 gene.

CRISPR Gene Therapy Method Claims

In another aspect, a method of treating or preventing BCD in a subject or a cell with a mutated CYP4V2 gene is provided. Such a method includes (i) identify the pathologic mutation in the subject or the cell through sequencing; (ii) finding Cas related PAM sites within the region spanning from about 100 bps upstream from the first nucleotide involved in the mutation to about 100 bps downstream from the last nucleotide involved in the mutation; (iii) identity various protospacer element sequences targeting the CYP4V2 sequence relevant to each PAM site identified in (ii); (iv) assess activity level of each CRISPR guide RNA comprising a protospacer element sequence identified in (iii) and off-target editing profile based on the protospacer element sequence and PAM; (v) select one or more CRISPR guide RNA design based on (iv); (vi) design one or more donor nucleic acid sequence based on homology-based repair (HDR) for correcting, disrupting or replacing the targeted CYP4V2 mutation; (vii) construct the CRISPR guide RNA, Cas and donor nucleic acid sequence as provided herein; (viii) optionally validating and further selecting the components of (vii) in a cell isolated from the subject; or an iPS cell derived from the subject or a cell differentiated from a stem cell derived from the subject, or the genomic DNA isolated from the subject or a cell isolated or derived thereof to assess the activity level and/or off-target editing profile; and (ix) administering the components in (viii) to the subject or the cell via a delivery system selected from the group consisting of a ribonucleoprotein or protein-RNA complex, a vector, a protein, a nucleic acid molecule, a nanoparticle, a liposome, a micelle, a virosome, a nucleic acid complex, and/or a combination thereof, wherein the delivery is performed by electroporation or via lipid-mediated transfection, or nucleofection, or viral transduction or injection, or a combination thereof; (x) wherein for treatment in cells in vitro, a selection marker including without limitation GFP, EGFP or puromycin resistance is optionally added or incorporated into the components in (viii).

In one aspect, a gene editing composition is provided for correcting or replacing the c.802-8_810del17insGC mutation in a CYP4V2 gene in a subject in vivo or in a cell in vitro. Such a composition typically includes: (i) a CRISPR guide RNA comprising a protospacer element sequence selected from one of SEQ ID NO: 48 to 52 or sharing at least 80% sequence identity with one of the sequences in SEQ ID 48 to 52; (ii) a donor nucleic acid sequence selected from one of SEQ ID NOs: 56 and 57, or shares at least 90% sequence identity with one of SEQ ID NO: 56 and 57, or a sequence that is complementary thereof; and (iii) a Cas9 protein (exemplary sequence shown in SEQ ID NO: 58), optionally containing 1, 2, 3 or more NLS, and/or a selection marker including without limitation GFP or EGFP.

In some embodiments, an optional nucleotide G is added before the protospacer element sequence. In some embodiments, the CRISPR guide RNA includes a crRNA (exemplary sequence (excluding the 5' protospacer element sequence) shown in SEQ ID NO: 53) and a tracrRNA (exemplary sequence shown in SEQ ID NO: 54); and the protospacer element sequence is contained in the crRNA. In some embodiments, the CRISPR guide RNA includes a single guide RNA (sgRNA) comprising the protospacer element sequence (exemplary sgRNA sequence (excluding the 5' protospacer element sequence) shown in SEQ ID NO: 55).

In some embodiments, one or more components of (i), (ii) and (iii) is provided in in the form of a DNA molecule encoding such component, an mRNA molecule encoding such component, a nucleic acid molecule, a vector, a RNA molecule, a polypeptide, a ribonucleoprotein (RNP) or protein-RNA complex, and/or a combination thereof.

BCD Cell Therapy Ocular Disease Autologous Cell Therapy and Combination Treatment Claims BCD Cell Therapy Allogenic Cell Therapy or Autologous Cell Therapy without Genetic Repair for BCD In some aspects, a method of treating or preventing a disease of the eye in a subject is provided, wherein the disease is associated with a pathologic genetic or epigenetic alteration in the CYP4V2 gene. Such a method typically includes administering a cellular composition to the subject, wherein the cellular composition includes: retinal pigment epithelium (RPE) cells, photoreceptors or photoreceptor progenitors (PRCs), corneal epithelial cells (CECs), choroidal endothelial (CE) cells and/or other ocular cells derived from a stem cell.

In some embodiments, the stem cell is an embryonic stem (ES) cell, an iPC cell, an MSC, an adult stem cell or a tissue-specific stem cell. In some embodiments, the stem cell is from or derived from one or more subjects not having BCD or not having a pathologic CYP4V2 gene. In some embodiments, the stem cell is from or derived from one or more subjects with pathologic mutations in the CYP4V2 gene. In some embodiments, the subject is a human subject.

Genetically-repaired autologous cell therapy for BCD

In another aspect, a cellular composition is provided that includes (a) a stem cell reprogrammed from a cell isolated from or a stem cell isolated from a subject affected by BCD or having pathologic mutations in the CYP4V2 gene, or (b) a cell differentiated from a stem cell isolated from a subject or reprogrammed from a cell isolated from a subject affected by BCD or having pathologic mutations in the CYP4V2 gene.

In some embodiments, the stem cell reprogrammed from a cell isolated from the subject is an iPC cell. In some embodiments, the iPS cell is reprogrammed from any cell of any tissue from the subject. In some embodiments, the iPS cell is reprogrammed from a skin cell, a blood cell, a urinary cell, a hair cell, a fibroblast, a peripheral blood mononuclear cell (PBMC), a renal epithelial cell, a hair follicle, or a dermal papilla cell. In some embodiments, the stem cell isolated from the subject is an MSC, an adult stem cell or a tissue-specific stem cell. In some embodiments, the cell differentiated from a stem cell is an ocular cell. In some embodiments, the cell differentiated from a stem cell is an RPE cell, a PRC, a retinal cell, a corneal cell, a choroidal cell, a CEC or a CE cell. In some embodiments, the cell differentiated from a stem cell is an iPS-RPE, iPS-PRC, iPS-CEC or iPS-CE cell.

In some embodiments, (i) the cell isolated from a subject affected by BCD or having pathologic mutations in the CYP4V2 gene for use to reprogram into an iPSC, (ii) the stem cell isolated from a subject or iPS cell reprogrammed from a cell isolated from a subject affected by BCD or having pathologic mutations in the CYP4V2 gene, or (iii) the cell differentiated from a stem cell isolated from a subject or an iPS cell reprogrammed from a cell isolated from a subject affected by BCD or having pathologic mutations in the CYP4V2 gene, is genetically repaired to ameliorate the effect of the mutated CYP4V2 gene. In some embodiments, genetic repair is performed before reprogramming into an IPS cell. In some embodiments, genetic repair is performed after reprogramming to an iPS cell. In some embodiments, genetic repair is performed before differentiation of the stem cell or iPS cell. In some embodiments, genetic repair is performed after differentiation of the stem cell or iPS cell. In some embodiments, genetic repair is via gene transfer therapy. In some embodiments, genetic repair is via gene transfer therapy by using any composition or method of any one of the gene therapy claims. In some embodiments, genetic repair is via gene editing. In some embodiments, genetic repair is via gene editing by using any composition or method of any one of CRISPR gene therapy claims.

In another aspect, a method of treating or preventing a disease of the eye in a subject affected by BCD or having pathologic genetic or epigenetic alterations in the CYP4V2 gene is provided. Such a method typically includes administering any of the CYP4V2 autologous cellular compositions described herein to the subject, wherein the cellular composition includes: retinal pigment epithelium (RPE) cells, photoreceptors or photoreceptor progenitors (PRCs), corneal epithelial cells (CECs), choroidal endothelial (CE) cells, and/or other ocular cells derived from a stem cell of the subject.

In some embodiments, the stem cell is an iPC cell, an MSC, an adult stem cell or a tissue-specific stem cell. In some embodiments, the iPS cell is reprogrammed using one or more of the OCT4, SOX2, KLF4, and c-MYC transcription factors. In some embodiments, the genetically repaired cells demonstrate one or more of the following: normalization in levels of one or more compound set forth in Table 2;

an increase in non-defective CYP4V2 nucleic acid sequence in the cells; an increase in the amount of functional CYP4V2 polypeptides in the cells; and/or improved cell structure, morphology or function, as compared to before genetic repair is performed.

In some embodiments, the amount of cells administered is about 1,000 to about 100 million cells in a single administration. In some embodiments, the administration is via injection. In some embodiments, the administration is via sub-retinal injection. In some embodiments, the administration is via intravitreal injection. In some embodiments, the administration is via direct retinal injection. In some embodiments, the administration is via corneal injection. In some embodiments, the administration is by any other administration method that effectively delivers the cells to the sub-retinal place, the posterior segment, or the cornea of the eye of the subject. In some embodiments, the cells are administered via injection of cell suspension. In some embodiments, the cells are administered as part of a sheet, a matrix, a scaffold, or a tissue.

In some embodiments, the RPE cells are administered using natural and/or synthetic scaffolds to generate a functional RPE monolayer. In some embodiments, the subject is a human subject.

Genetically-Repaired Autologous Cell Therapy for Ocular Diseases

In another aspect, a cellular composition is provided that includes (a) a stem cell reprogrammed from a cell isolated from or a stem cell isolated from a subject affected by a disease caused by a mutated or defective gene or a gene encoding a protein having defective or partial function or activity, or (b) a cell differentiated from a stem cell isolated from a subject or reprogrammed from a cell isolated from a subject affected by a disease caused by a mutated or defective gene or a gene encoding a protein having defective or partial function or activity.

In some embodiments, the stem cell reprogrammed from a cell isolated from the subject is an iPS cell. In some embodiments, the iPS cell is reprogrammed from any cell of any tissue from the subject. In some embodiments, the iPS cell is reprogrammed from a skin cell, a blood cell, a urinary cell, a hair cell, a fibroblast, a peripheral blood mononuclear cell (PBMC), a renal epithelial cell, a hair follicle, or a dermal papilla cell. In some embodiments, the stem cell isolated from the subject is an MSC, an adult stem cell or a tissue-specific stem cell.

In some embodiments, the gene is involved in ocular development or function and/or mutation of which causes or is a risk factor to cause an ocular disease. In some embodiments, the gene is involved in neuronal development or function and/or mutation of which causes or is a risk factor to cause a neurodegenerative disease. In some embodiments, the gene is a cytochrome P450 gene. In some embodiments, the gene is one set forth in Table 4.

In some embodiments, the gene includes a mutated or defective CYP4V2, CYP1B1, MYO7A, DFNB31, USHIC, USHIG, CDH23, PCDH15, CLRN1, ACO2, AFG3L2, ATXN2, AUH, C12orf65, CISD2, FOXC1, FOXF2, LTBP2, MTPAP, MYOC, NDUFS1, NR2F1, OPA1, OPA3, OPTN, PAX6, PDGF, PITX2, POLG, SPG7, TEK, TXNRD2, WFS1, ABCA4, REP-1, RPE65, CEP290, PDE6B, RPGR, MERTK, MT-ND4, FAM47E, GBA, GCH1, HTRA2, LRRK2, PARK2, PINK1, SNCA, SYNJI, NPC1, NPC2, CYP4A11, CYP4A22, CYP4B1, CYP4F2, CYP4F3, CYP4F8, CYP4F11, CYP4F12, CYP4F22, CYP4X1, CYP4Z1, or CYP46A gene or a CYP4V2, CYP1B1, MYO7A, DFNB31, USHIC, USHIG, CDH23, PCDH15, CLRN1, ACO2, AFG3L2, ATXN2, AUH, C12orf65, CISD2, FOXC1, FOXF2, LTBP2, MTPAP, MYOC, NDUFS1, NR2F1, OPA1, OPA3, OPTN, PAX6, PDGF, PITX2, POLG, SPG7, TEK, TXNRD2, WFS1, ABCA4, REP-1, RPE65, CEP290, PDE6B, RPGR, MERTK, MT-ND4, FAM47E, GBA, GCH1, HTRA2, LRRK2, PARK2, PINK1, SNCA, SYNJI, NPC1, NPC2, CYP4A11, CYP4A22, CYP4B1, CYP4F2, CYP4F3, CYP4F8, CYP4F11, CYP4F12, CYP4F22, CYP4X1, CYP4Z1 or CYP46A gene that encodes a protein having defective or partial function or activity.

In some embodiments, the cell differentiated from a stem cell is any type of cell. In some embodiments, the cell differentiated from a stem cell is an ocular cell. In some embodiments, the cell differentiated from a stem cell is an RPE cell, a PRC, a retinal cell, a corneal cell, a choroidal cell, a CEC, a CE cell or an optic nerve cell. In some embodiments, the cell differentiated from a stem cell is an iPS-RPE, iPS-PRC, iPS-CEC or iPS-CE cell. In some embodiments, the cell differentiated from a stem cell is a neuron.

In some embodiments, (i) the cell isolated from a subject affected by a disease caused by a mutated or defective gene or a gene encoding a protein having defective or partial function or activity for use to reprogram into an iPSC, (ii) the stem cell isolated from a subject or iPS cell reprogrammed from a cell isolated from a subject affected by a disease caused by a mutated or defective gene or a gene encoding a protein having defective or partial function or activity, or (iii) the cell differentiated from a stem cell isolated from a subject or an iPS cell reprogrammed from a cell isolated from a subject affected by a disease caused by a mutated or defective gene or a gene encoding a protein having defective or partial function or activity, is genetically repaired to ameliorate the effect of the mutated or defective gene.

In some embodiments, genetic repair is performed before reprogramming into an IPS cell. In some embodiments, genetic repair is performed after reprogramming to an iPS cell. In some embodiments, genetic repair is performed before differentiation of the stem cell or iPS cell. In some embodiments, genetic repair is performed after differentiation of the stem cell or iPS cell. In some embodiments, genetic repair is via gene transfer therapy. In some embodiments, genetic repair is via gene transfer therapy by using any composition or method of any one of the claims related to gene therapy. In some embodiments, genetic repair is via gene editing therapy. In some embodiments, genetic repair is via gene editing therapy by using any composition or method of any one of the claims related to CRISPR gene therapy.

In another aspect, a method of treating or preventing a disease in a subject affected by a disease caused by a mutated or defective gene or a gene encoding a protein having defective or partial function or activity set forth in Table 4 is provided. Such a method typically includes administering an autologous cellular composition as described herein to the subject, wherein the cellular composition includes: retinal pigment epithelium (RPE) cells, photoreceptors or photoreceptor progenitors (PRCs), corneal epithelial cells (CECs), neurons, choroidal endothelial (CE) cells and/or other ocular cells derived from a stem cell of the subject, and wherein the mutated or defective gene in the cellular composition has been genetically repaired.

In still another aspect, a method of autologously treating a subject is provided. Such a method typically includes (i) providing cells from a subject having a disease of the eye;

(ii) inducing pluripotency in the cells from the subject to produce iPSCs; (iii) genetically repairing one or more mutations in a mutated or defective gene set forth in Table 4 in the iPSCs derived from the subject; (iv) differentiating the iPSCs into ocular cells; (v) alternative to step (iii), genetically repair the iPS-ocular cells via gene transfer therapy; and (vi) introducing the iPS-ocular cells into the subject, thereby autologously treating the subject having the disease of the eye.

In some embodiments, the stem cell is an iPC cell, an MSC, an adult stem cell or a tissue-specific stem cell. In some embodiments, the iPS cell is reprogrammed using one or more of the OCT4, SOX2, KLF4, and c-MYC transcription factors. In some embodiments, the genetically repaired cells demonstrate one or more of the following: an increase in non-defective target gene nucleic acid sequence in the cells; an increase in the amount of functional polypeptides encoded by the target gene in the cells; improved cell structure, morphology or function, and/or improved or normalized biochemical functions in the cells, as compared to before genetic repair is performed. In some embodiments, the amount of cells administered is about 1,000 to about 100 million cells in a single administration.

In some embodiments, the administration is via injection. In some embodiments, the administration is by sub-retinal injection. In some embodiments, the administration is by intravitreal injection. In some embodiments, the administration is by direct retinal injection. In some embodiments, the administration is by corneal injection. In some embodiments, the administration is by any other administration method that effectively delivers the cells to the sub-retinal place, the posterior segment, or the cornea of the eye of the subject. In some embodiments, the cells are administered via injection of cell suspension. In some embodiments, the cells are administered as part of a sheet, a matrix, a scaffold or a tissue. In some embodiments, the RPE cells are administered using natural and/or synthetic scaffolds to generate a functional RPE monolayer. In some embodiments, the subject is a human subject.

In some embodiments, the disease is associated with a genetic or epigenetic alteration or risk factor in the subject. In some embodiments, the disease is photoreceptor degeneration, retinal pigment epithelium cell degeneration, retinal degeneration, cornea degeneration, and/or choroidal disorders. In some embodiments, the disease is an inherited retinal degeneration (IRD). In some embodiments, the disease is retinitis pigmentosa (RP). In some embodiments, the disease is Bietti Crystalline Dystrophy (also known as Bietti Crystalline Corneoretinal Dystrophy; BCD). In some embodiments, the disease is related to neurological degeneration. In some embodiments, the disease is corneal dystrophy. In some embodiments, the subject has BCD or is at risk of developing BCD.

In some embodiments, the cells are fibroblasts, blood cells, or ocular cells. In some embodiments, the cells are obtained from urine or from hair or hair follicles. In some embodiments, the ocular cells are retinal pigment epithelial (RPE) cells, corneal epithelial cells (CECs), choroidal endothelial (CE) cells, or photoreceptor cells (PRCs).

In some embodiments, the genetic or epigenetic alteration is selected from the group consisting of a mutation, an insertion, a single nucleotide polymorphism, improper methylation, improper demethylation, and combinations thereof. In some embodiments, the genetic or epigenetic alteration is a mutation. In some embodiments, the genetic or epigenetic alteration in the iPS-ocular cells from the subject has been genetically repaired using gene editing. In some embodiments, the gene editing method utilizes a zinc-finger nuclease, TALEN technology, or CRISPR technology. In some embodiments, the genetic or epigenetic alteration in the iPSC-ocular cells from the subject has been genetically repaired using gene transfer. In some embodiments, the gene transfer method utilizes a recombinant AAV vector or another viral vector or non-viral vector to deliver a healthy copy of the target gene (e.g., cDNA) to the cells to be transplanted.

In some embodiments, the administering step takes place before the onset of disease symptoms or after the onset of disease symptoms. In some embodiments, the administration is to the eye or to another organ or tissue comprising neurons. In some embodiments, the administration is by injection. In some embodiments, the administration is by sub-retinal or intravitreal injection. In some embodiments, the administration is by direct retinal injection. In some embodiments, the administration is by corneal injection. In some embodiments, the administration is by any other administration method that effectively delivers the cells to the sub-retinal place, the posterior segment, or the cornea of the eye of the subject.

In some embodiments, the method further includes, prior to administering or transplanting, performing genotypic analysis on the cells to identify the presence or absence of the genetic or epigenetic alteration in one or more genes set forth in Table 4. In some embodiments, the genetic or epigenetic alteration is a mutation. In some embodiments, the mutation is in the CYP4V2 nucleic acid molecule. In some embodiments, the method further includes, prior to administering, evaluating the eye of the subject to identify the area(s) and extent of damaged or retained photoreceptors, retinal cells, or corneal cells.

In some embodiments, the method further includes, following administering, monitoring the subject. In some embodiments, the monitoring comprises performing non-invasive retinal imaging, corneal tests, perimetry, ERG, OCT, visual acuity tests, and/or functional studies. In some embodiments, the monitoring comprises evaluating the subject for an immune response. In some embodiments, the method further includes, following administering, evaluating the eye of the subject to identify the area(s) and extent of damaged or retained photoreceptors, retinal cells, or corneal cells.

Cell Therapy-RNP Claims

RNP Claims

In another aspect, a composition is provided that includes: (a) a CRISPR guide RNA targeting a nucleic acid sequence (the "target sequence") of or within 100 bps to a target gene (the "target gene"), and (b) a functional CRISPR-associated protein, in a ribonucleoprotein (RNP) or protein-RNA complex.

In some embodiments, the composition further includes (c) a donor nucleic acid sequence including all or a portion of a wild-type sequence or a functional sequence of the target gene for correction or replacement of such target gene or a portion thereof. In some embodiments, the target gene is involved in ocular development or function and/or mutation of which causes or is a risk factor to cause an ocular disease. In some embodiments, the target gene is involved in neuronal development or function and/or mutation of which causes or is a risk factor to cause a neurodegenerative disease.

In some embodiments, the target gene is a cytochrome P450 gene. In some embodiments, the target gene includes a gene set forth in Table 4 that is mutated or defective, or encodes a protein having defective or partial function or activity. In some embodiments, the donor nucleic acid sequence is provided in a single-stranded donor oligonucleotide (ssODN) or a vector.

In some embodiments, (a) the CRISPR guide RNA including (i) a CRISPR RNA (crRNA) which includes a protospacer element sequence that is complementary to the target sequence of or within 100 bps to a target gene and a sequence that corresponds to a complementary region of the trans-activating crRNA (tracrRNA), and (ii) a tracrRNA which includes a region that is complementary to corresponding region of the crRNA and a sequence which interacts with a CRISPR-associated protein 9 (Cas9), and (b) the functional CRISPR-associated protein comprises Cas9.

In some embodiments, the protospacer element is about 20 bases, about 19 bases, about 21 bases, about 19-21 bases, about 18-22 bases, or about 16-24 bases. In some embodiments, the crRNA and the tracrRNA are in different nucleic acid molecules. In some embodiments, the crRNA and the tracrRNA are combined into a single guide RNA (sgRNA). In some embodiments, the sgRNA is about 88-150 bps.

In some embodiments, the Cas9 comprises a Cas9 ortholog or a mutant Cas9 selected from: *Streptococcus pyogenes* (SpCas9), SpCas9 nickase (Cas9n D10A), SpCas9 (D1135E), eSpCas9, SpCas9-HF1, SpCas9 VRER, SpCas9 VQR, SpCas9EQR, *Staphylococcus aureus* (SaCas9), *Neisseria Meningitidis, Streptococcus thermophilus, Streptococcus pneumoniae, Campylobacter coli, Campylobacter jejuni, Streptococcus mutans, Pasteurella multocida, Bifidobacterium longum, Bacillus smithii, Treponema denticola, mycoplasma canis* and *Enterococcus faecalis*.

In some embodiments, (a) the CRISPR guide RNA comprises a crRNA which comprises a protospacer element sequence that is complementary to the target sequence of or within 100 bps to a target gene, and (b) the functional CRISPR-associated protein comprises Cpf1. In some embodiments, the protospacer element is about 20 bases, about 21 bases, about 22 bases, about 23 bases, about 24 bases, about 19-25 bases, about 18-26 bases, or about 16-28 bases. In some embodiments, the CRISPR-associated protein, Cas9, or Cpf1, further comprises one, two, three or more nuclear localization sequences (NLS) at the N-terminal and/or C-terminal, and/or a selection marker, including without limitation, GFP or EGFP.

In some embodiments, the protospacer element is 100% complementary to the target sequence or contains 1, 2, 3, 4, or 5 nucleotide mismatches corresponding to the target sequence. In some embodiments, the crRNA sequence further comprises a G nucleotide optionally added to the crRNA sequence immediately before the protospacer element. In some embodiments, the CRISPR guide RNA, crRNA and/or the tracrRNA, or the sgRNA, is chemically modified.

In some embodiments, the donor nucleic acid sequence is no more than about 1 kb, 800 bp, 600 bp, 500 bp, 400 bp, 300 bp, 280 bp, 260 bp, 240 bp, 220 bp, or 200 bp for a donor nucleic acid sequence provided in a ssODN and no more than about 30 kb, 25 kb, 20 kb, 15 kb, 10 kb, 9 kb, 8 kb, 7 kb, 6 kb, 5 kb, 4.5 kb, 4 kb, 3.5 kb, 3 kb, 2.5 kb, 2 kb, 1.5 kb, 1 kb, 0.5 kb, 0.2 kb, or 0.1 kb for a donor nucleic acid sequence provided in a vector. In some embodiments, the wild-type version of the target gene encodes an enzyme.

In some embodiments, the target gene includes a mutated or defective CYP4V2, CYP1B1, MYO7A, DFNB31, USHIC, USHIG, CDH23, PCDH15, CLRN1, ACO2, AFG3L2, ATXN2, AUH, C12orf65, CISD2, FOXC1, FOXF2, LTBP2, MTPAP, MYOC, NDUFS1, NR2F1, OPA1, OPA3, OPTN, PAX6, PDGF, PITX2, POLG, SPG7,

20

TEK, TXNRD2, WFS1, ABCA4, REP-1, RPE65, CEP290, PDE6B, RPGR, MERTK, MT-ND4, FAM47E, GBA, GCH1, HTRA2, LRRK2, PARK2, PINK1, SNCA, SYNJI, NPC1, NPC2, CYP4A11, CYP4A22, CYP4B1, CYP4F2, CYP4F3, CYP4F8, CYP4F11, CYP4F12, CYP4F22, CYP4X1, CYP4Z1, or CYP46A gene or a CYP4V2, CYP1B1, MYO7A, DFNB31, USHIC, USHIG, CDH23, PCDH15, CLRN1, ACO2, AFG3L2, ATXN2, AUH, C12orf65, CISD2, FOXC1, FOXF2, LTBP2, MTPAP, MYOC, NDUFS1, NR2F1, OPA1, OPA3, OPTN, PAX6, PDGF, PITX2, POLG, SPG7, TEK, TXNRD2, WFS1, ABCA4, REP-1, RPE65, CEP290, PDE6B, RPGR, MERTK, MT-ND4, FAM47E, GBA, GCH1, HTRA2, LRRK2, PARK2, PINK1, SNCA, SYNJI, NPC1, NPC2, CYP4A11, CYP4A22, CYP4B1, CYP4F2, CYP4F3, CYP4F8, CYP4F11, CYP4F12, CYP4F22, CYP4X1, CYP4Z1 or CYP46A gene that encodes a protein having defective or partial function or activity.

In some embodiments, any one or more components thereof including the CRISPR guide RNA, CRISPR-associated protein, and/or the donor nucleic acid sequence, is provided separately and/or additionally in a vector, a DNA and/or an mRNA which can transcribe and/or translate into such component. In one aspect, a pharmaceutical formulation including any of the compositions described herein are provided.

In another aspect, a method of treating a disease of a subject caused by a mutated or defective gene, or a gene encoding a protein having defective or partial function or activity is provided. Such a method includes disrupting, correcting or replacing such gene by administering to the subject any of the compositions described herein.

In another aspect, a method of treating an ocular disease or ameliorating a risk factor related thereto of a subject caused by a mutated or defective gene, or a gene encoding a protein having defective or partial function or activity is provided. Such a method includes disrupting, correcting or replacing such gene by administering to the subject any of the compositions described herein.

In another aspect, a method of treating a neurodegenerative disease or ameliorating a risk factor related thereto of a subject caused by a mutated or defective gene, or a gene encoding a protein having defective or partial function or activity is provided. Such a method includes disrupting, correcting or replacing such gene by administering to the subject any of the compositions described herein.

In another aspect, a method of treating a disease or ameliorating a risk factor related thereto of a subject caused by a mutated or defective cytochrome P450 gene, or a cytochrome P450 gene encoding a protein having defective or partial function or activity is provided. Such a method includes disrupting, correcting or replacing such gene by administering to the subject any of the compositions described herein.

In some embodiments, the mutated or defective gene, or gene encoding a protein having defective or partial function or activity, disrupted, corrected or replaced is a mutated or defective version of a gene set forth in Table 4, or a version of a gene set forth in Table 4 that encodes a protein having defective or partial function or activity. In some embodiments, the mutated or defective gene, or gene encoding a protein having defective or partial function or activity, is present in fibroblasts, blood, RPE, photoreceptor, retinal, corneal, choroidal, ocular, optic nerve, neuron, or stem cells, or any type of cells derived from a stem cell.

In some embodiments, the composition therein is delivered to fibroblasts, blood, RPE, photoreceptor, retinal, corneal, choroidal, ocular, optic nerve, neuron, or stem cells, or any type of cells derived from a stem cell. In some embodiments, delivery is performed by electroporation or via lipid-mediated transfection, or nucleofection, or viral transduction, or injection or a combination thereof. In some embodiments, any one or more components thereof including the CRISPR guide RNA, CRISPR-associated protein, and/or the donor nucleic acid sequence is administered to the subject or to the cells via a delivery system selected from the group consisting of a ribonucleoprotein or protein-RNA complex, a nanoparticle, a liposome, a micelle, a virosome, a nucleic acid complex, and/or a combination thereof.

In some embodiments, the treatment is performed to a subject in vivo. In some embodiments, the treatment is performed in vitro in fibroblasts, blood, RPE, photoreceptor, retinal, corneal, choroidal, ocular, optic nerve, neuron, or stem cells, or any type of cells derived from a stem cell. In some embodiments, the treated cells are transplanted to a subject in vivo, or if the treated cell is a stem cell, such stem cell is differentiated into the desired type of cells for transplantation and then the differentiated cells are transplanted into a subject in vivo . . . .

In some embodiments, the mutated or defective gene, or gene encoding a protein having defective or partial function or activity, is replaced. In some embodiments, the mutated or defective gene, or gene encoding a protein having defective or partial function or activity, has one or more mutations corrected or replaced. In some embodiments, the mutated or defective gene, or gene encoding a protein having defective or partial function or activity, is disrupted.

In some embodiments, the mutated or defective gene, or gene encoding a protein having defective or partial function or activity, has 1-20, 21-40, 41-60, 61-80, 81-100, 101-1000, 1001-10000 base pairs of nucleotides or mutations disrupted, corrected or replaced. In some embodiments, a region of the mutated or defective gene, or gene encoding a protein having defective or partial function or activity, is disrupted, corrected or replaced. In some embodiments, a region of less than about 10, 8, 6, 4, 2 or 1 kb of the mutated or defective gene, or gene encoding a protein having defective or partial function or activity, is disrupted, corrected or replaced.

In some embodiments, the mutated or defective gene, or gene encoding a protein having defective or partial function or activity, is disrupted, corrected or replaced via insertion and/or deletion of nucleotides. In some embodiments, the mutated or defective gene, or gene encoding a protein having defective or partial function or activity, is disrupted, corrected or replaced in one allele or both alleles. In some embodiments, two or more different CRISPR guide RNAs, CRISPR-associated proteins and/or donor nucleic acid sequences are used to disrupt, correct or replace one or more mutations or defects in the mutated or defective gene, or gene encoding a protein having defective or partial function.

In some embodiments, the subject is a mammal. In some embodiments, the subject is a human. In some embodiments, the method improves ocular development or function, or prevents ocular, retinal or corneal degeneration. In some embodiments, the method improves neurological development or function, or prevents neural degeneration. In some embodiments, the method improves expression or function of a P450 enzyme.

In some embodiments, a homology directed repair based on the donor nucleic acid sequence resulted in an intron and/or an exon of the target gene. In some embodiments, a homology directed repair based on the donor nucleic acid sequence resulted in a splice acceptor of the target gene.

Such a method can further include (c) a donor nucleic acid sequence comprising all or a portion of a target gene set forth in Table 4 with a mutation or alteration for generation of a mutated or altered target gene or a portion thereof.

In some aspects, a method of generating a cellular disease model of a disease caused by a mutated or defective gene, or a gene encoding a protein having defective or partial function or activity, by generating a mutation in such gene is provided. Such a method includes delivery to the cells of a healthy version of such gene via any of the compositions described herein. In some embodiments, delivery is performed by electroporation or via lipid-mediated transfection, or nucleofection, or viral transduction, or microinjection, or a combination thereof. In some embodiments, the cells are fibroblasts, blood, RPE, photoreceptor, retinal, corneal, choroidal, ocular, optic nerve, neuron, or stem cells, or any type of cells derived from a stem cell.

In still another aspect, a composition is provided that includes a cell with a mutated or defective gene set forth in Table 4.

In another aspect, a composition is provided that includes a cell with a mutated or defective CYP4V2, CYP1B1, MYO7A, DFNB31, USHIC, USHIG, CDH23, PCDH15, CLRN1, ACO2, AFG3L2, ATXN2, AUH, C12orf65, CISD2, FOXC1, FOXF2, LTBP2, MTPAP, MYOC, NDUFS1, NR2F1, OPA1, OPA3, OPTN, PAX6, PDGF, PITX2, POLG, SPG7, TEK, TXNRD2, WFS1, ABCA4, REP-1, RPE65, CEP290, PDE6B, RPGR, MERTK, MT-ND4, FAM47E, GBA, GCH1, HTRA2, LRRK2, PARK2, PINK1, SNCA, SYNJI, NPC1, NPC2, CYP4A11, CYP4A22, CYP4B1, CYP4F2, CYP4F3, CYP4F8, CYP4F11, CYP4F12, CYP4F22, CYP4X1, CYP4Z1, or CYP46A gene comprising a composition of any one of the claims herein In some embodiments, the vector is an AAV vector. In some embodiments, the protospacer element sequence is selected from the group consisting of SEQ ID NOs: 48 to 52, or shares at least 80% sequence identity with one of SEQ ID NO: 48 to 52 for use with a Cas protein that has NGG as protospacer adjacent motif (PAM) to target the c. 802-8_810del17insGC mutation of the CYP4V2 gene. In some embodiments, the donor nucleic acid sequence is selected from SEQ ID NOs: 56 and 57, or shares at least 90% sequence identity with one of SEQ ID NO: 56 and 57, or a sequence that is complementary thereof, for use to correct, disrupt or replace the c. 802-8_810del17insGC mutation of the CYP4V2 gene.

Gene Therapy Claims
Codon-Optimized Sequence Related Claims:

In one aspect, a nucleic acid molecule including the nucleic acid sequence of SEQ ID NO: 2 encoding a human CYP4V2 protein or a nucleic acid sequence sharing at least 90% sequence identity with the nucleic acid sequence of SEQ ID NO: 2 is provided.

In another aspect, an expression cassette including a nucleic acid molecule as described herein and one or more regulatory sequence operably linked to the nucleic acid sequence is provided. In still another aspect, a vector including a nucleic acid molecule as described herein or an expression cassette as described herein is provided.

In some embodiments, the vector is a viral vector. In some embodiments, the viral vector is selected from the group consisting of a recombinant adenovirus vector, a recombinant lentivirus vector, a recombinant herpes simplex virus vector, a recombinant sendai virus vector, and a recombinant retrovirus vector. In some embodiments, the vector is a recombinant adeno-associated virus (rAAV) vector or a plasmid. In some embodiments, the vector is a plasmid or a non-viral vector. In some embodiments, the non-viral vector is selected from the group consisting of naked nucleic acids, liposomes, dendrimers, and nanoparticles.

In some embodiments, a host cell including any of the nucleic acid molecules described herein and/or any of the compositions described herein. In some embodiments, the host cell is a bacteria cell, an *E. Coli* cell, a plant cell, an insect cell or a mammalian cell. In some embodiments, the host cell is a HEK293, HeLa, Vero, V27, A549, K562, B50, WI38, Hep G2 or BHK cell.

In another aspect, the use of any of the nucleic acid molecule described herein, of any of the expression cassettes described herein, or of any of the vectors described herein, to express the product encoded by such nucleic acid molecule, in a bacteria cell, an insect cell, a plant cell, a mammalian cell, an RPE cell, a photoreceptor or photoreceptor progenitor (PRC), a retinal cell, a corneal cell, an ocular cell, a neuron, a neuronal cell, a blood cell, an epithelial cell, a somatic cell, an iPS cell, a ES cell, an MSC, an adult stem cell, a stem cell, or any cell derived from a stem cell.

EFS and/or SPA Related Claims

In another aspect, a self-complementary adeno-associated virus (scAAV) vector including an elongation factor 1α short (EFS) promoter and/or a small polyadenylation (poly A) signal (SPA) operably linked to a nucleic acid molecule encoding a polypeptide, an interfering RNA molecule or an oligonucleotide is provided. In some embodiments, the EFS promoter consists of a nucleic acid sequence having at least 80% sequence identity of SEQ ID NO: 35 and the SPA consists of a nucleic acid sequence having at least 80% sequence identify of SEQ ID NO: 36.

In some embodiments, the scAAV vector is delivered to a cell such that the product encoded by the nucleic acid molecule is expressed in the cell. In some embodiments, the cell is a mammalian cell. In some embodiments, the cell is a retinal cell, a corneal cell, a choroidal cell, an ocular cell, a brain cell, a neuron, a neuronal cell, an iPS cell, a ES cell, an MSC, a stem cell, or any cell derived from a stem cell.

In one aspect, a method to reduce immune responses to viral vectors and preserve transduction efficiency in gene therapy and/or to maximize therapeutic effect to different patients of the same genetic disease is provided. Such a method includes (a) establishing a pool of more than one recombinant vrial vectors (e.g., rAAVs) with sufficient transduction efficiency in the target cell type for the gene therapy. The viral vector pool can be expanded by creating variants with antigenic region mutations or other mutations or variants on the capsids of said viral vectors and such mutations or variants confirmed with sufficient transduction efficiency in target cells relevant to the disease (e.g., in iPS-RPE cell lines for CYP4V2 gene therapy for BCD); (b) detecting pre-existing neutralizing anti-viral vector antibodies (NAbs) against different viral vecctor serotypes and/or capsid mutations or variants in the subject in need of the gene therapy, and/or testing and comparing different viral vectors in patient-specific cells (e.g., iPS-RPE cells) derived from such subject; (c) selecting a viral vector from the pool of viral vectors with sufficient transduction efficiency with lowest of cross-reactivity with the pre-existing NAbs in the subject and/or one viral vector with the best phenotype rescue result in the subject's patient-specific cells, such viral vector pool comprising different serotypes and capsid-modified viral vectors (e.g., including without limitation, capsid-mutant AAVs and/or capsid protein variant AAVs); (d) use the viral vector selected from (c) for administration to the subject;

and (e) repeat (b) through (d) (only the part relating to pre-existing NAbs) above each time the subject requires a gene therapy administration, including without limitation, a follow-up administration to the same eye or an administration to the contralateral eye, or to another organ.

In another aspect, a composition for treating or preventing a disease in a subject is provided, including an effective amount of a vector and a pharmaceutically acceptable carrier. Typically, the vector includes a nucleic acid molecule or a non-pathogenic variant thereof encoding a non-mutant or functional CYP4V2 protein operably linked to a regulatory sequence.

In some embodiments, the disease is Bietti Crystalline Dystrophy (also known as Bietti Crystalline Corneoretinal Dystrophy; BCD). In some embodiments, the disease is associated with a genetic or epigenetic alteration in the subject. In some embodiments, the disease is photoreceptor degeneration, retinal pigment epithelium cell degeneration, retinal degeneration, cornea degeneration, or choroidal degeneration. In some embodiments, the retinal degeneration is retinitis pigmentosa (RP). In some embodiments, the retinal degeneration is an inherited retinal degeneration (IRD). In some embodiments, the disease is BCD. In some embodiments, the disease is corneal dystrophy. In some embodiments, the subject has BCD or is at risk of developing BCD.

In one aspect, a vector including a nucleic acid molecule or a non-pathogenic variant thereof encoding a non-mutant or functional CYP4V2 protein operably linked to a regulatory sequence is provided.

In some embodiments, the vector is a viral vector. In some embodiments, the viral vector is selected from the group consisting of an adeno-associated virus (AAV) vector, an adenovirus vector, a lentivirus vector, a herpes simplex virus vector, a sendai virus vector, and a retrovirus vector. In some embodiments, the AAV is a recombinant AAV (rAAV). In some embodiments, the rAAV comprises an AAV genome or a derivative thereof, and/or an AAV capsid protein or a derivative thereof. In some embodiments, the rAAV is a chimeric AAV, a shuffled AAV, or a capsid-modified AAV.

In some embodiments, the AAV genome or AAV capsid protein is from any one of AAV1, AAV2, AAV3, AAV4, AAV5, AAV6, AAV7, AAV8, AAV9, AAV10, AAV11, AAV12, or another naturally derived serotype or isolate or Clade of AAV, or any derivative or hybrid thereof. In some embodiments, the rAAV is a pseudotyped AAV (e.g., AAV2/5, AAV2/8, AAV2/1, AAV2/4, AAV2/6, AAV2/7, AAV2/12, AAV2/10 and AAV2/9). In some embodiments, the rAAV is a hybrid AAV (e.g., AAV-DJ, AAV-DJ/8, or AAV-DJ/9). In some embodiments, the rAAV is developed through directed evolution and/or rational design (e.g., AAV 7m8 or AAV-PHP.B).

In some embodiments, the rAAV comprises one or more capsid mutations (e.g., Y-F, K-R, T-A, S-A and/or T-V mutations, (e.g., AAV2 with one or more capsid mutations among Y444F, Y500F, Y730F, Y252F, Y272F, Y700F, Y704F and T491V, or the corresponding mutation for a different AAV serotype, (e.g., AAV2/8 (Y733F), AAV2 (Y444F+Y500F+Y730F) and AAV2 (quadY-F+T-V))). In some embodiments, the serotype of the rAAV is selected from the group consisting of AAV1, AAV2, AAV3, AAV4, AAV5, AAV6, AAV7, AAV8, AAV9, AAV10, AAV11, AAV12, Anc80, rh10 and ShH10. In some embodiments, the rAAV vector is selected from the group consisting of AAV2/5, AAV2/8, AAV2/8 (Y733F), AAV2 (Y444F+Y500F+Y730F), AAV2/1, AAV2/4, AAV2/9, AAV2/6, AAV2/7, AAV1, AAV2, AAV4, AAV5, AAV6, AAV7, AAV8, AAV9, AAV12, Anc80, AAV 7m8, AAV-DJ, ShH10, AAV-PHP.B or a hybrid, a derivative or variant thereof.

In some embodiments, the rAAV vector is a single-stranded AAV vector or a self-complementary AAV (scAAV) vector. In some embodiments, the vector is a plasmid, or a non-viral vector (e.g., naked nucleic acids, liposomes, dendrimers, and nanoparticles).

In some embodiments, the non-mutant or functional CYP4V2 protein encoded by the nucleic acid sequence comprises: (i) the human CYP4V2 protein (SEQ ID NO: 4); (ii) a variant of (e.g., changing of the amino acids and/or a splice variant) of the human CYP4V2 protein or a functional CYP4V2 protein (e.g., SEQ ID NO: 5); (iii) one or more fragments of a functional CYP4V2 protein (e.g., SEQ ID NO: 6); (iv) all or part of sequences from one or more of the CYP4V2 ortholog of other species, (v) all or part of sequences from one or more other P450 proteins, including but not limited to, other CYP4 proteins and CYP46A1, (vi) a polypeptide which can ameliorate, treat, or arrest one or more biochemical abnormalities in one or more of the genes listed in Table 4 in a patient cell (e.g., the iPS-RPE cell of a BCD patient), and/or (vii) a combination of the above.

In some embodiments, the non-mutant or functional CYP4V2 protein encoded by the nucleic acid sequence comprises all or part of the amino acid sequence shown in SEQ ID NO: 4, 5 or 6. In some embodiments, the non-mutant or functional CYP4V2 protein encoded by the nucleic acid sequence comprises all or part of an amino acid sequence selected from the group consisting of CYP4V2, CYP4A11, CYP4A22, CYP4B1, CYP4F2, CYP4F3, CYP4F8, CYP4F11, CYP4F12, CYP4F22, CYP4X1, CYP4Z1 and CYP46A1 (SEQ ID NOs: 4-18), and derivatives, hybrids, variants and/or fragments thereof. In some embodiments, the non-mutant or functional CYP4V2 protein encoded by the nucleic acid sequence comprises all of part of the amino acid sequence selected from the group consisting of CYP4V2 (or orthologs of CYP4V2) of chimpanzee, Rhesus monkey, dog, cow, mouse, rat, chicken, frog, horse, rabbit and fruit fly (SEQ ID NOs: 19-29), and derivatives, hybrids, variants and/or fragments thereof.

In some embodiments, the non-mutant or functional CYP4V2 protein encoded by the nucleic acid sequence comprises a polypeptide having at least 80% amino acid sequence identity (e.g., at least 80%, 81%, 82%, 83%, 84%, 85%, 86%, 87%, 88%, 89%, 90%, 91%, 92%, 93%, 94%, 95%, 96%, 97%, 98%, or 99% sequence identity) to any of the sequences selected from the group consisting of SEQ ID NOs: 4-29. In some embodiments, the non-mutant or functional CYP4V2 protein encoded by the nucleic acid sequence comprises sequence elements of FxxGxxxCxG and ExxR (SEQ ID NOs: 30 and 31). In some embodiments, the non-mutant or functional CYP4V2 protein is a compound or agent which can ameliorate, treat, or arrest one or more biochemical abnormalities in one or more of the genes listed in Table 4 in a patient cell (e.g., the iPS-RPE cell of a BCD patient).

In some embodiments, the nucleic acid molecule encodes a non-mutant or functional CYP4V2 protein as described herein. In some embodiments, the nucleic acid molecule encodes a non-mutant or functional CYP4V2 protein comprising an amino acid sequence shown in SEQ ID NO: 4, 5 or 6 or having at least 80% sequence identity with any one of SEQ ID NO: 4, 5, or 6. In some embodiments, the nucleic acid molecule has at least 60% sequence identity to any of the sequences in SEQ ID NO: 1, 2 or 3. In some embodiments, the nucleic acid molecule has at least 70% sequence identity to any of the sequences in SEQ ID NO: 1, 2 or 3. In some embodiments, the nucleic acid molecule has at least 75% sequence identity to any of the sequences in SEQ ID NO: 1, 2 or 3. In some embodiments, the nucleic acid molecule has at least 76% sequence identity to any of the sequences in SEQ ID NO: 1, 2 or 3. In some embodiments, the nucleic acid molecule comprises a sequence shown in SEQ ID NO: 1, 2, or 3.

In some embodiments, the regulatory sequence comprises a promoter. In some embodiments, the promoter is an RPE cell-specific promoter, a retinal cell-specific promoter, a corneal cell-specific promoter, an ocular-cell specific promoter or a constitutive promoter. In some embodiments, the promoter is a mammalian beta actin promoter or a viral promoter.

In some embodiments, the promoter is selected from the group consisting of a CAG promoter (hybrid CMV early enhancer/Chicken beta actin promoter, also known as CAGGS promoter, CB promoter or CBA promoter), a chicken beta actin promoter, a small CBA (smCBA) promoter, a CB$^{SB}$ promoter, or a CBh promoter, another beta-actin promoter such as the human beta actin promoter, a elongation factor 1 alpha short (EFS) promoter, a elongation factor 1 alpha short (EF-1 alpha) promoter, a CMV promoter, a PGK promoter, a UBC promoter, a GUSB promoter, a UCOE promoter, a VMD2 (vitelliform macular dystrophy 2; also known as BEST1) promoter, a RPE65 promoter, or a hybrid or a derivative thereof.

In some embodiments, the promoter is a CAG promoter (hybrid CMV early enhancer/Chicken beta actin promoter, also known as CAGGS promoter, CB promoter or CBA promoter), a elongation factor 1 alpha short (EFS) promoter, a elongation factor 1 alpha short (EF-1 alpha) promoter or a CMV promoter, or a derivative or a hybrid thereof. In some embodiments, the regulatory sequence comprises an enhancer.

In some embodiments, the enhancer is a viral enhancer, including without limitation, a WPRE enhancer, an HPRE enhancer, a CTE enhancer or a derivative or hybrid thereof. In some embodiments, the regulatory sequence comprises a polyadenylation (polyA) signal. In some embodiments, the poly A signal is a bovine growth hormone polyadenylation signal (bGH polyA), a small poly A signal (SPA), a human growth hormone polyadenylation signal (hGH poly A), a SV40 poly A signal, a SV40 late poly A signal, or a derivative or hybrid thereof. In some embodiments, the regulatory sequence comprises a Kozak sequence (SEQ ID NO: 37 or 38)

In some embodiments, the composition is formulated with a carrier and additional components suitable for the specific route of administration.

In another aspect, a host cell including any of the vectors described herein are provided.

In another aspect, a method of treating or preventing a disease of the eye in a subject is provided, the method including administering a vector to the subject, wherein the vector comprises a nucleic acid molecule or a non-pathogenic variant thereof encoding a human CYP4V2 protein or a functional CYP4V2 protein operably linked to a regulatory sequence.

In one aspect, a method of preventing, arresting or slowing progression of, or ameliorating the dysfunction, dystrophy, disorder, degeneration and/or death of an ocular cell is provided, the method including delivering a vector to the ocular cell, wherein the vector comprises a nucleic acid molecule or a non-pathogenic variant thereof encoding a human CYP4V2 protein or a functional CYP4V2 protein operably linked to a regulatory sequence.

In some embodiments, the disease is Bietti Crystalline Dystrophy (also known as Bietti Crystalline Corneoretinal Dystrophy; Bietti Crystalline Retinopathy; Bietti's Retinal Dystrophy; BCD). In some embodiments, the subject is affected by other ophthalmological clinically-defined conditions (e.g., inherited retinal degeneration (IRD), retinitis pigmentosa (RP) or corneal dystrophy) caused by mutations in the CYP4V2 gene. In some embodiments, the disease of the eye is photoreceptor degeneration, retinal pigment epithelium cell degeneration, retinal degeneration, corneal dystrophy, or BCD.

In some embodiments, the vector is a viral vector. In some embodiments, the viral vector is selected from the group consisting of a recombinant adeno-associated virus (rAAV) vector, a recombinant adenovirus vector, a recombinant lentivirus vector, a recombinant herpes simplex virus vector, a recombinant sendai virus vector, and a recombinant retrovirus vector. In some embodiments, the viral vector is a rAAV vector. In some embodiments, the rAAV vector comprises a VP1, VP2, or VP3 capsid protein selected from any serotype of AAV1, AAV2, AAV3, AAV4, AAV5, AAV6, AAV7, AAV8, AAV9, AAV10, AAV11, AAV12, or another naturally derived serotype or isolate or Clade of AAV, or hybrids, variants or derivatives thereof.

In some embodiments, the rAAV vector 5' AAV ITR is selected from any one of AAV1, AAV2, AAV3, AAV4, AAV5, AAV6, AAV7, AAV8, AAV9, AAV10, AAV11, AAV12, or another naturally derived serotype or isolate or Clade of AAV, or mutations, chimeras, variants or fusions thereof. In some embodiments, the rAAV vector 3' AAV ITR is selected from any one of AAV1, AAV2, AAV3, AAV4, AAV5, AAV6, AAV7, AAV8, AAV9, AAV10, AAV11, AAV12, or another naturally derived serotype or isolate or Clade of AAV, or mutations, chimeras, variants or fusions thereof. In some embodiments, the rAAV is a chimeric AAV, a shuffled AAV, or a capsid-modified AAV. In some embodiments, the rAAV is a pseudotyped AAV (e.g., AAV2/5, AAV2/8, AAV2/1, AAV2/4, AAV2/6, AAV2/7, AAV2/12, AAV2/10 and AAV2/9). In some embodiments, the rAAV is a hybrid AAV (e.g., AAV-DJ, AAV-DJ/8, or AAV-DJ/9). In some embodiments, the rAAV is developed through directed evolution and/or rational design (e.g., AAV 7m8 or AAV-PHP.B).

In some embodiments, the rAAV comprises one or more capsid mutations (e.g., Y-F, K-R, T-A, S-A and/or T-V mutations (e.g., AAV2 with one or more capsid mutations among Y444F, Y500F, Y730F, Y252F, Y272F, Y700F, Y704F and T491V, or the corresponding mutation for a different AAV serotype, (e.g., AAV2/8 (Y733F), AAV2 (Y444F+Y500F+Y730F) and AAV2 (quadY-F+T-V))). In some embodiments, the serotype of the rAAV is selected from the group consisting of AAV1, AAV2, AAV3, AAV4, AAV5, AAV6, AAV7, AAV8, AAV9, AAV10, AAV11, AAV12, Anc80, rh10 and ShH10. In some embodiments, the rAAV vector is selected from the group consisting of AAV2/5, AAV2/8, AAV2/8 (Y733F), AAV2 (Y444F+Y500F+Y730F), AAV2/1, AAV2/4, AAV2/9, AAV2/6, AAV2/7, AAV1, AAV2, AAV4, AAV5, AAV6, AAV7, AAV8, AAV9, AAV12, Anc80, AAV 7m8, AAV-DJ, ShH10, AAV-PHP.B or a hybrid, a derivative or variant thereof.

In some embodiments, the rAAV vector is a single-stranded AAV vector or a self-complementary AAV (scAAV) vector. In some embodiments, the vector is a plasmid or a non-viral vector. In some embodiments, the non-viral vector is selected from the group consisting of naked nucleic acids, liposomes, dendrimers, and nanoparticles.

In some embodiments, the non-mutant or functional CYP4V2 protein encoded by the nucleic acid sequence comprises: (i) the human CYP4V2 protein (SEQ ID NO: 4); (ii) a variant of (e.g., changing of the amino acids and/or a splice variant) of the human CYP4V2 protein or a functional CYP4V2 protein (e.g., SEQ ID NO: 5); (iii) one or more fragments of a functional CYP4V2 protein (e.g., SEQ ID NO: 6); (iv) all or part of sequences from one or more of the CYP4V2 ortholog of other species; (v) all or part of sequences from one or more other P450 proteins, including but not limited to, other CYP4 proteins and CYP46A1; (vi) a polypeptide which can ameliorate, treat, or arrest one or more biochemical abnormalities in one or more genes listed in Table 4 in a patient cell (e.g., the iPS-RPE cell of a BCD patient), and/or (vii) a combination of the above.

In some embodiments, the non-mutant or functional CYP4V2 protein encoded by the nucleic acid sequence comprises all or part of the amino acid sequence shown in SEQ ID NO: 4, 5 or 6. In some embodiments, the non-mutant or functional CYP4V2 protein encoded by the nucleic acid sequence comprises all or part of an amino acid sequence selected from the group consisting of CYP4V2, CYP4A11, CYP4A22, CYP4B1, CYP4F2, CYP4F3, CYP4F8, CYP4F11, CYP4F12, CYP4F22, CYP4X1, CYP4Z1 and CYP46A1 (SEQ ID NOs: 4-18), and derivatives, hybrids, variants and/or fragments thereof.

In some embodiments, the non-mutant or functional CYP4V2 protein encoded by the nucleic acid sequence comprises all of part of the amino acid sequence selected from the group consisting of CYP4V2 (or orthologs of CYP4V2) of chimpanzee, Rhesus monkey, dog, cow, mouse, rat, chicken, frog, horse, rabbit and fruit fly (SEQ ID NOs: 19-29), and derivatives, hybrids, variants and/or fragments thereof. In some embodiments, the non-mutant or functional CYP4V2 protein encoded by the nucleic acid sequence comprises a polypeptide having at least 80% amino acid sequence identity (e.g., at least 80%, 81%, 82%, 83%, 84%, 85%, 86%, 87%, 88%, 89%, 90%, 91%, 92%, 93%, 94%, 95%, 96%, 97%, 98%, or 99% sequence identity) to any of the sequences selected from the group consisting of SEQ ID NOs: 4-29.

In some embodiments, the non-mutant or functional CYP4V2 protein encoded by the nucleic acid sequence comprises sequence elements of FxxGxxxCxG and ExxR (SEQ ID NOs: 30 and 31). In some embodiments, the non-mutant or functional CYP4V2 protein is a compound or agent which can ameliorate, treat, or arrest one or more biochemical abnormalities in one or more of the genes listed in Table 4 in a patient cell (e.g., the iPS-RPE cell of a BCD patient). In some embodiments, the nucleic acid molecule encodes a non-mutant or functional CYP4V2 protein as described herein. In some embodiments, the nucleic acid molecule encodes a non-mutant or functional CYP4V2 protein comprising an amino acid sequence shown in SEQ ID NO: 4, 5 or 6 or having at least 80% sequence identity with any one of SEQ ID NO: 4, 5, or 6. In some embodiments, the nucleic acid molecule encoding a functional CYP4V2 protein has a nucleic acid sequence shown in SEQ ID NO: 1, 2 or 3. In some embodiments, the nucleic acid molecule encoding a functional CYP4V2 protein has a sequence identity of at least 60% to any of SEQ ID NOs 1, 2 or 3.

In some embodiments, the regulatory sequence comprises a promoter. In some embodiments, the promoter is an RPE cell-specific promoter, a retinal cell-specific promoter, a corneal cell-specific promoter, or an ocular-cell specific promoter. In some embodiments, the promoter is a constitutive promoter. In some embodiments, the promoter is a mammalian beta actin promoter or a viral promoter.

In some embodiments, the promoter is selected from the group consisting of a CAG promoter (hybrid CMV early enhancer/Chicken beta actin promoter, also known as CAGGS promoter, CB promoter or CBA promoter), a chicken beta actin promoter, a small CBA (smCBA) promoter, a CB$^{SB}$ promoter, or a CBh promoter, another beta-actin promoter such as the human beta actin promoter, a elongation factor 1 alpha short (EFS) promoter, a elongation factor 1 alpha short (EF-1 alpha) promoter, a CMV promoter, a PGK promoter, a UBC promoter, a GUSB promoter, a UCOE promoter, a VMD2 (vitelliform macular dystrophy 2; also known as BEST1) promoter, a RPE65 promoter, or a hybrid or a derivative thereof. In some embodiments, the promoter is a CAG promoter (hybrid CMV early enhancer/Chicken beta actin promoter, also known as CAGGS promoter, CB promoter or CBA promoter), a elongation factor 1 alpha short (EFS) promoter, a elongation factor 1 alpha short (EF-1 alpha) promoter or a CMV promoter, or a derivative or a hybrid thereof.

In some embodiments, the regulatory sequence comprises an enhancer. In some embodiments, the enhancer is viral enhancer, including without limitation, a WPRE enhancer, an HPRE enhancer, a CTE enhancer or a derivative or hybrid thereof. In some embodiments, the regulatory sequence comprises a polyadenylation (poly A) signal. In some embodiments, the poly A signal is a bovine growth hormone polyadenylation signal (bGH poly A), a small poly A signal (SPA), a SV40 poly A signal, a human growth hormone polyadenylation signal (hGH poly A), a SV40 late poly A signal, or a derivative or hybrid thereof. In some embodiments, the regulatory sequence comprises a Kozak sequence (SEQ ID NO: 37 or 38)

In some embodiments, for in vitro treatment, the target cell is infected at a dose (MOI) of about 1×10^3 GC to about 1×10^6 GC per cell (GC: genomic copies, measuring genome containing AAV particles (a/k/a vector genome (vg) or genome particles (gp)). In some embodiments, for in vivo administration to a subject's eye, a single administration can be on the order of from about 1×10^6 to 2×10^13 GC (e.g., a high dose range of about 1×10^11 GC to about 1×10^12 GC, a medium dose range of about 1×10^10 GC to about 1×10^11 GC, a low dose range of about 1×10^9 GC to about 1×10^10 GC, a very low dose range of about 1×10^6 GC to about 1×10^9 GC, and a very high dose range of about 1×10^12 GC to about 2×10^13 GC), or any dose within these ranges that is sufficient to provide the desired effect.

In some embodiments, the administering step takes place before the onset of disease symptoms or after the onset of disease symptoms. In some embodiments, the administration is to the eye. In some embodiments, the administration is by sub-retinal injection. In some embodiments, the administration is by intravitreal injection. In some embodiments, the administration is by direct retinal injection. In some embodiments, the administration is by any other administration method that effectively delivers the vectors to the sub-retinal place, the posterior segment of the eye, the cornea or the RPE cells, the photorector cells or corneal epithelial cells of the subject.

In some embodiments, the administration is by corneal delivery. In some embodiments, the administration to the eye is achieved by delivery through the bloodstream. In some embodiments, the administration is via eye drops. In some embodiments, the administration is by delivery to the lens. In some embodiments, the administration is into the subretinal space, the cornea, the lens, or into the vitreus. In some embodiments, the ocular cells are selected from the group consisting of retinal pigment epithelium (RPE) cells, photoreceptor cells (PRCs), corneal epithelial cells (CECs), choroidal endothelial (CE) cells, retinal cells, corneal cells, lens cells, ganglion cells, optic nerve cells, and/or choroidal cells, as well as the said types of cells derived from a stem cell (including without limitation, an iPSC, a ES cell, an MSC, an adult stem cell and/or a tissue-specific stem cell).

In some embodiments, the methods described herein can further include identifying a subject having BCD or at risk of developing BCD.

Use of EFS and/or SPA in an rAAV vector comprising a nucleic acid sequence encoding Cas related Claims In one aspect, a composition including a recombinant adeno-associated virus (rAAV) vector comprising an elongation factor 1α short (EFS) promoter and/or a small polyadenylation (polyA) signal (SPA) operably linked to a nucleic acid molecule encoding a CRISPR associated protein (Cas) is provided.

In some embodiments, the EFS promoter consists of a nucleic acid sequence having at least 80% sequence identity of SEQ ID NO: 35 and the SPA consists of a nucleic acid sequence having at least 80% sequence identify of SEQ ID NO: 36. In some embodiments, the Cas encoded by the nucleic acid sequence operably linked to the EFS promoter and/or the SPA is a Cas9 or a Cpf1.

Host cells including a rAAV as described herein is provided. In some embodiments, the host cell is a bacteria cell, an *E. Coli* cell, a plant cell, an insect cell, or a mammalian cell. In some embodiments, the cell is a somatic cell or a stem cell. In some embodiments, the host cell is a retinal cell, a corneal cell, a choroidal cell, an ocular cell, a brain cell, a neuron, a neuronal cell, an iPS cell, a ES cell, an MSC, an adult stem cell, a tissue-specific cell, a stem cell, or any cell derived from a stem cell. In some embodiments, the rAAV vector is delivered to a host cell such that the Cas encoded by the nucleic acid molecule is expressed in the cell.

Other features and advantages of the inventions will be apparent from the Detailed Description, Description of Drawings, and Examples, and also from the claims. All publications, patent applications, patents, sequences, database entries, and other references mentioned herein are incorporated by reference in their entirety.

DESCRIPTION OF DRAWINGS

The inventions are further illustrated in the following figures and drawings, which do not limit the scope of the inventions described in the claims.

Cell Line Patent.

(i) Patient 1 (P1) iPS cells (ii) Patient 2 (P2) iPS cells (iii) characterization of P1 and P2 iPS cell lines by Oct-4, Sox-2 and SSEA-4 markers (iv) characterization of P1 and P2 iPS cell lines by Nanog and Tra-1-60 markers (b) iPS cells generated from a BCD patient and a healthy control from peripheral blood mononuclear cells (PBMC) of blood samples:

(i) phase contrast images of iPS cell lines (ii) AP staining results of iPS cell lines (c) BCD patient-derived iPS cell karyotype images showing apparently normal human karyotype.

FIG. 2: iPS-RPE cell lines derived from BCD patients:

(a) light-field pictures of iPS-RPE cell lines derived from BCD patients showing RPE unique morphology-hexagonal shape, pigmentation and monolayer:

(i) P1 iPS-RPE cells (ii) P2 iPS-RPE cells (b) RPE markers results of BCD patients' iPS-RPE cells, showing the presence of RPE-specific markers, RPE65, CRALBP and MITF.

Figure 1A:
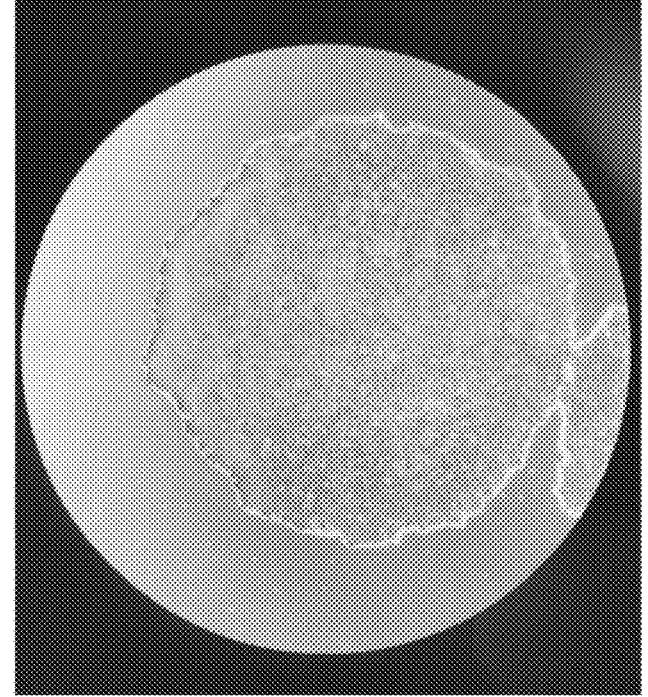
FIG. 1: iPS cell lines derived from BCD patients (a) iPS cells generated from fibroblasts of skin biopsy samples of BCD patients.
Figure 1A:
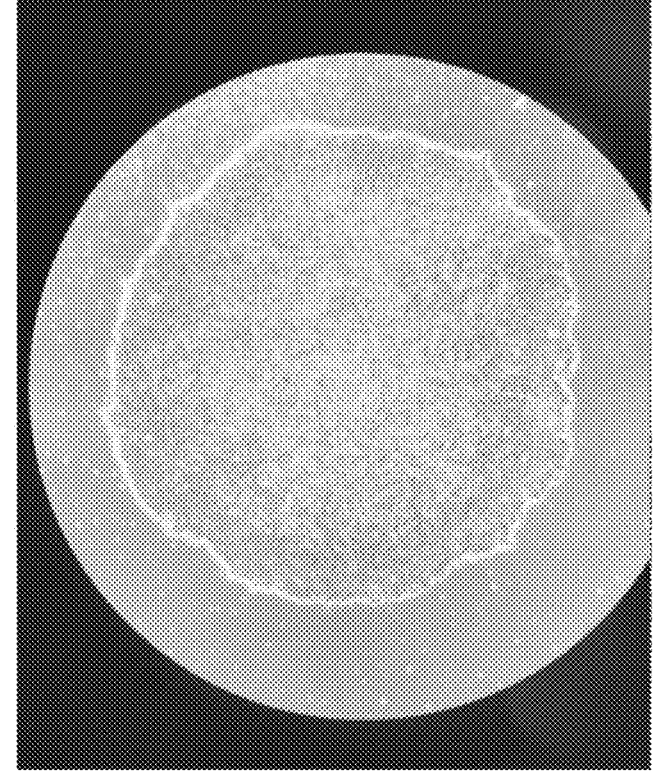
Figure 1B:
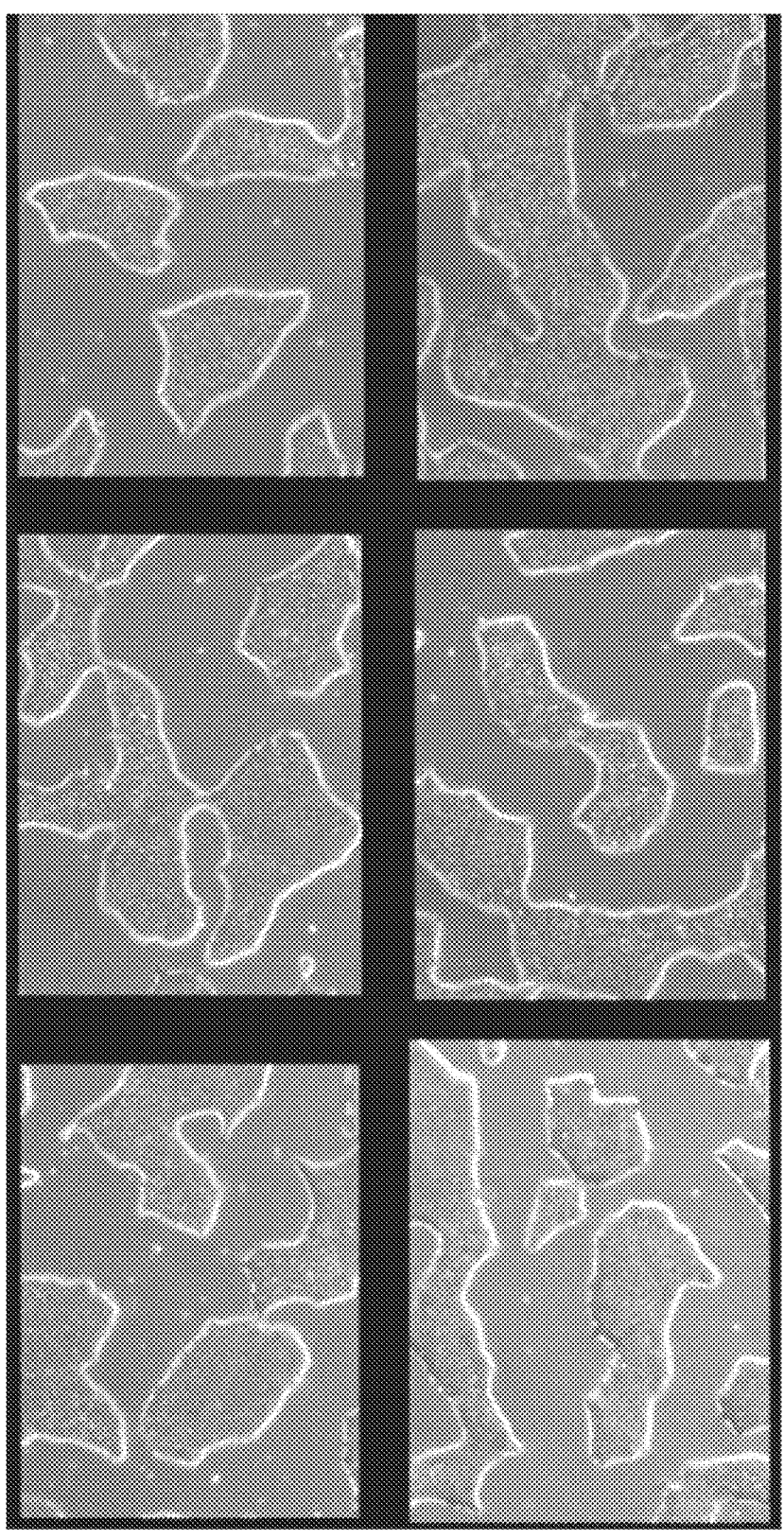
Figure 1C:
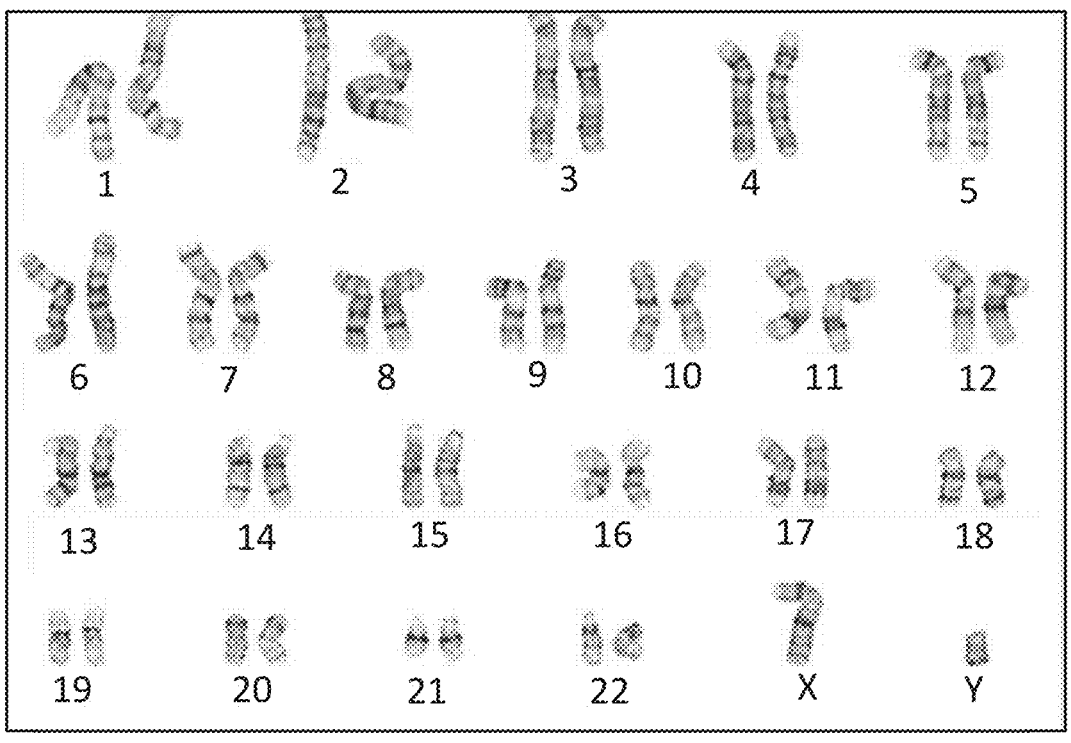
Figure 1C:
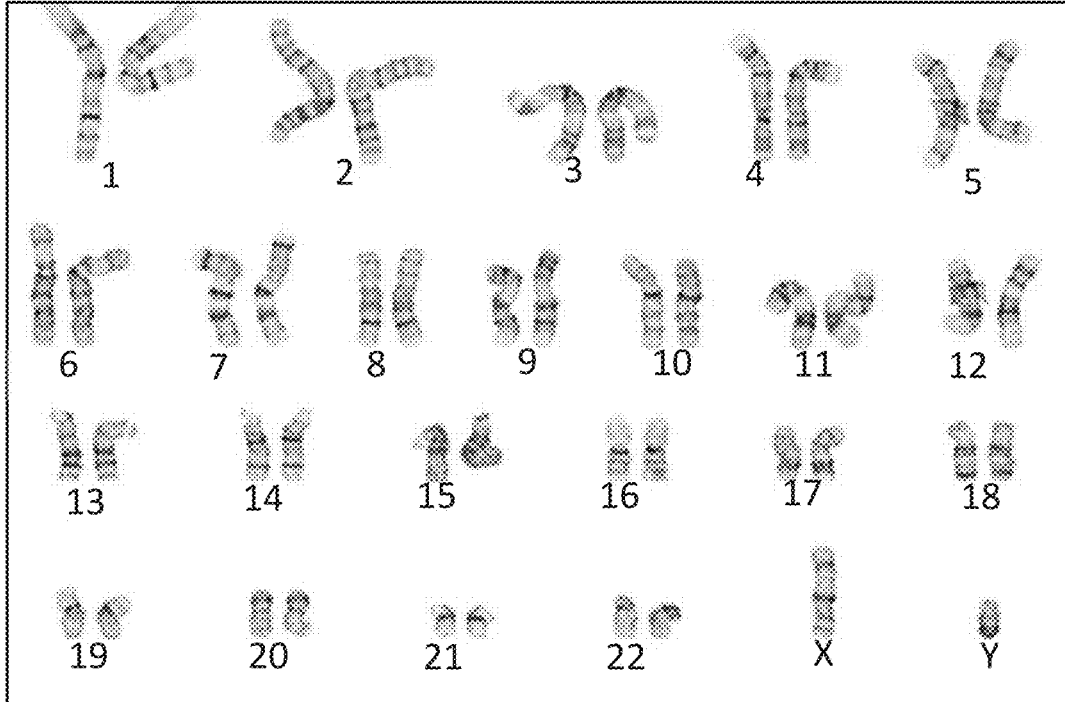
Figure 2A:
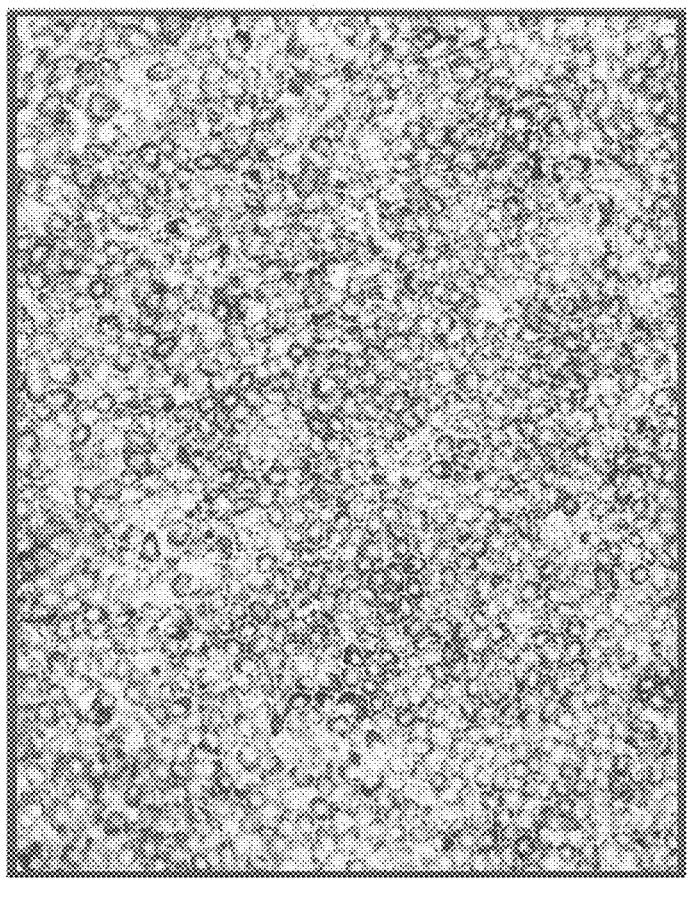
Figure 2A:
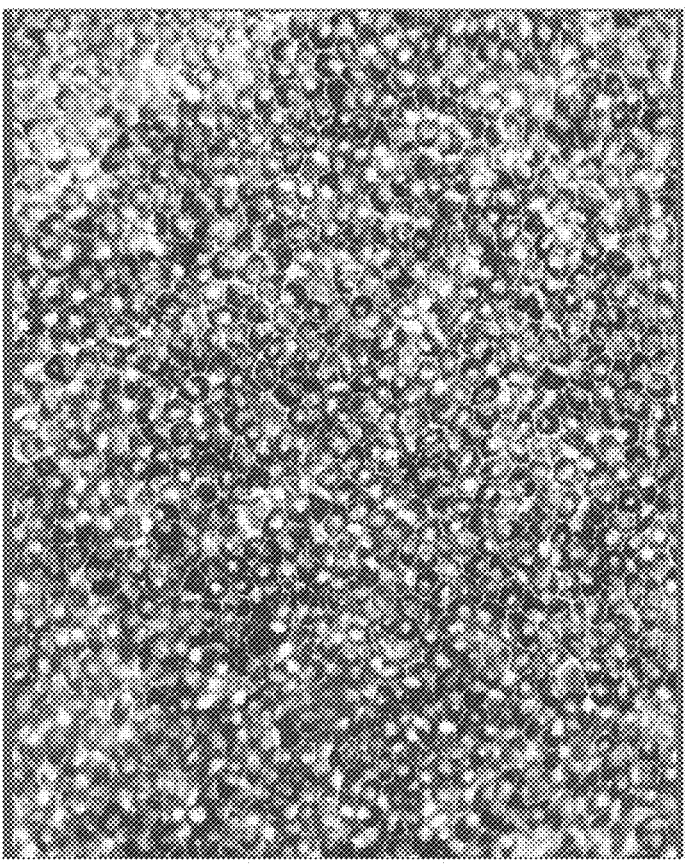
Figure 2A:
Figure 2B:
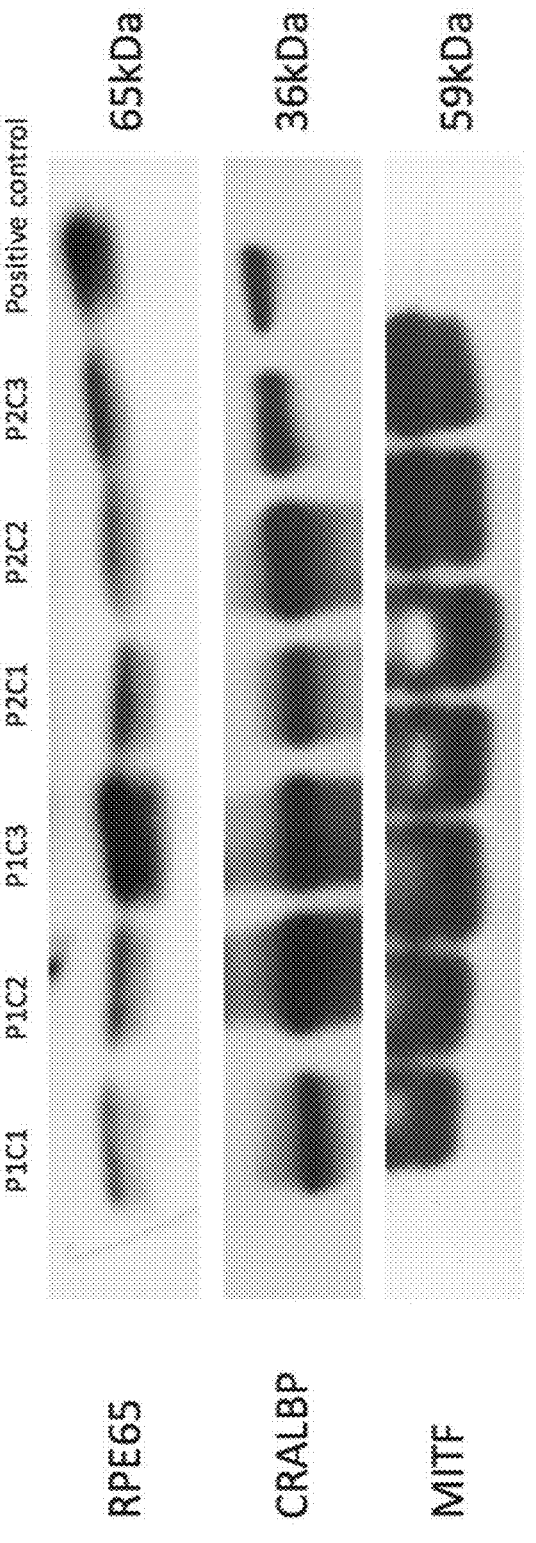
Figures 3, 4:
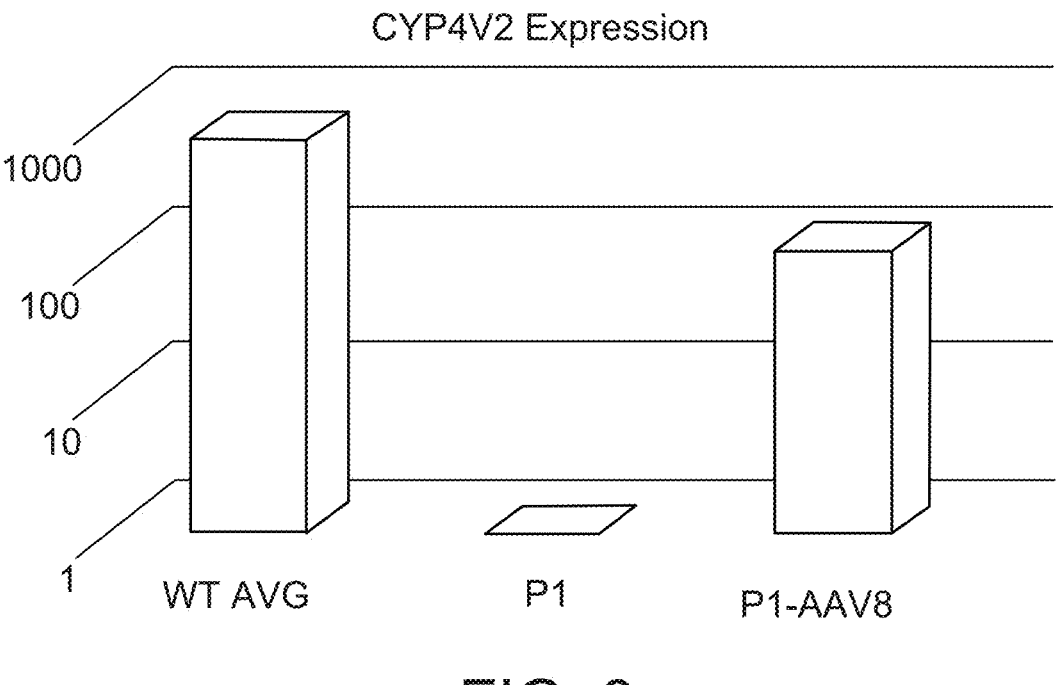

FIG. 3: qRT-PCR results of CYP4V2 expression in iPS-RPE samples. WT (controls). WT AVG (average of controls). P1 (BCD Patient 1). P1-AAV8 (P1 sample treated by AAV8.CYP4V2fv, MOI=1.5×10e4 GC/cell).

FIG. 4: qRT-PCR results of CYP4V2op expression in iPS-RPE samples. WT (controls). WT AVG (average of controls). P1 and P2 (BCD Patient 1 and Patient 2). P1-AAV2 (P1 sample treated by AAV2.CYP4V2op at MOI of 2×10e4 GC/cell). P2-AAV2 (P2 sample treated by AAV2.CYP4V2op at MOI of 2×10e4 GC/cell). P2-scAAV1 (P2 sample treated by scAAV1.CYP4V2op at MOI of 2×10e4 GC/cell).

Figure 5A:
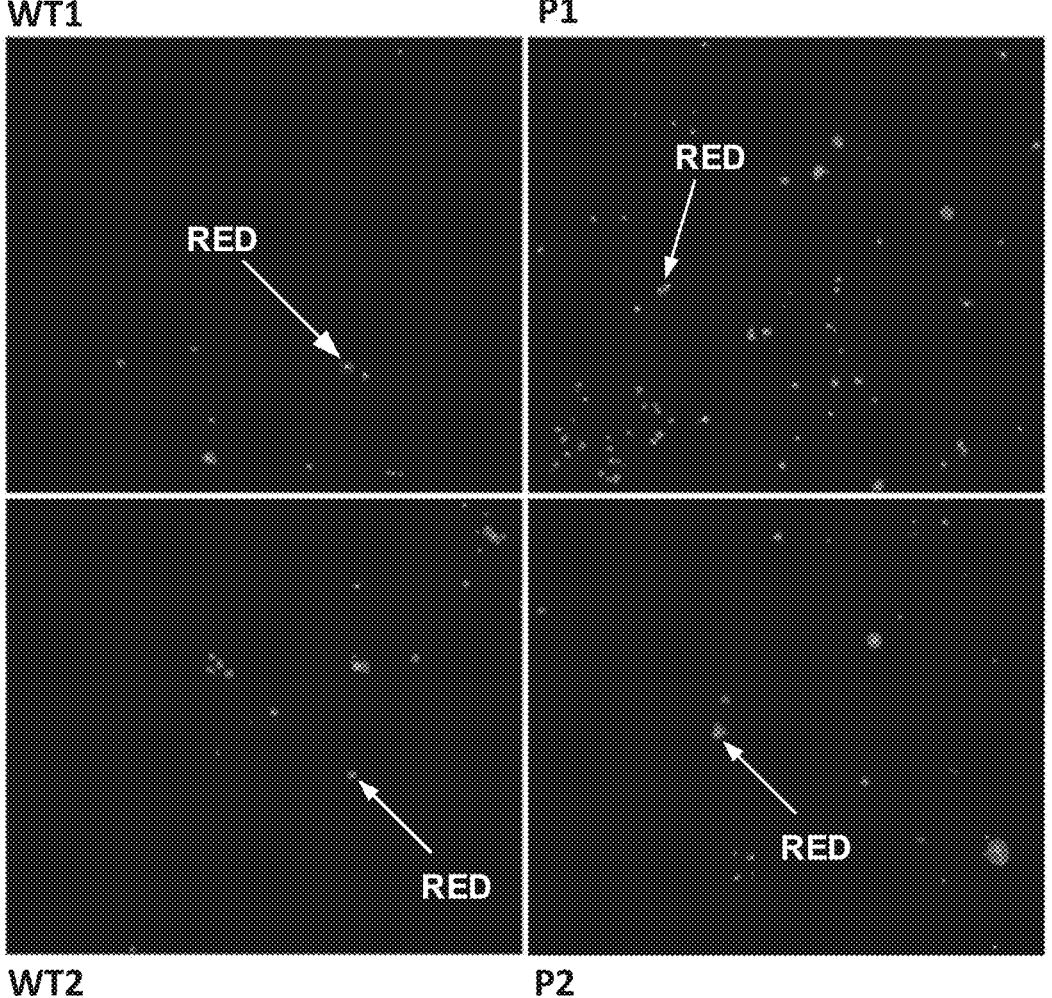
Figure 5B:
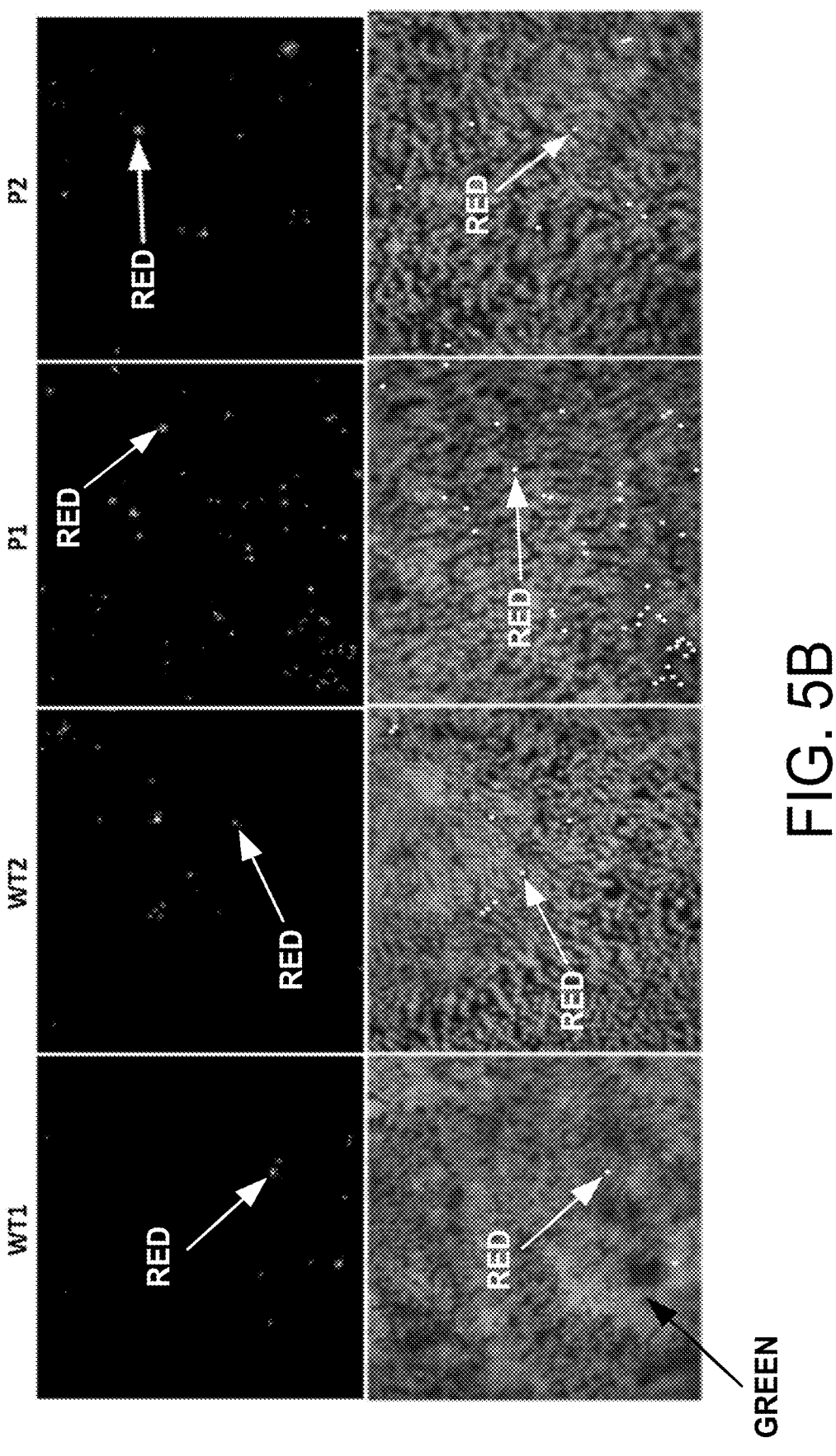

FIG. 5: Cell viability images of iPS-RPE samples without exposure to blue light. WT (controls). P1 and P2 (BCD Patient 1 and Patient 2). Red (dead/sick cells); Green (live/healthy cells). FIG. 5 (*a*): Red only. FIG. 5 (*b*): Red and green.

Figure 6A:
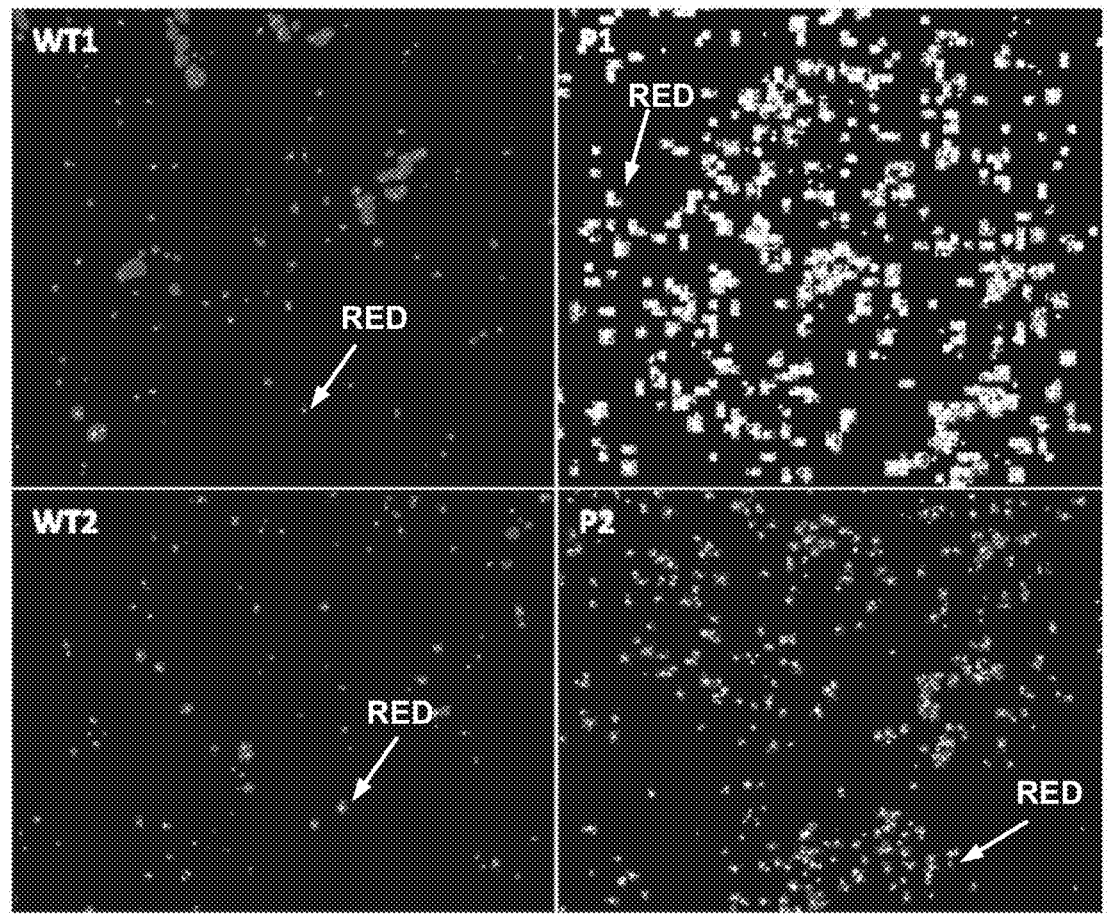
Figure 6B:
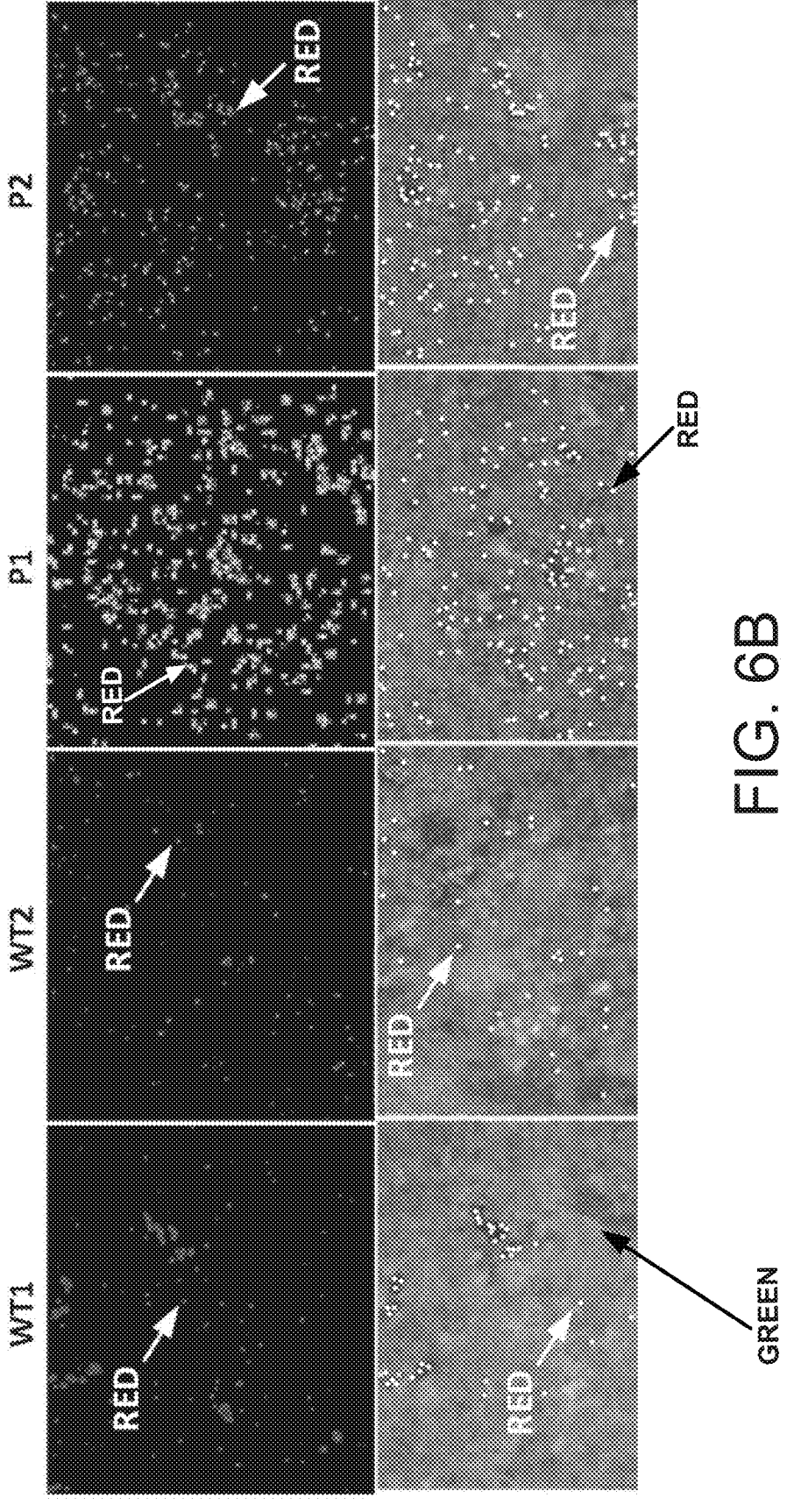

FIG. 6: Cell viability images of iPS-RPE samples after 1 hour exposure to blue light. WT (controls). P1 and P2 (BCD Patient 1 and Patient 2). Red (dead/sick cells); Green (live/healthy cells). FIG. 6 (*a*): Red only. FIG. 6 (*b*): Red and green.

Figure 7A:
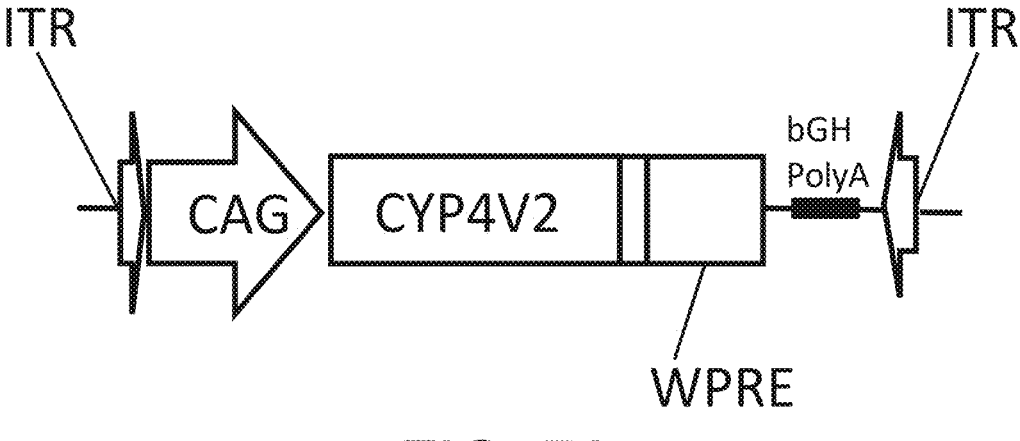
Figure 7B:
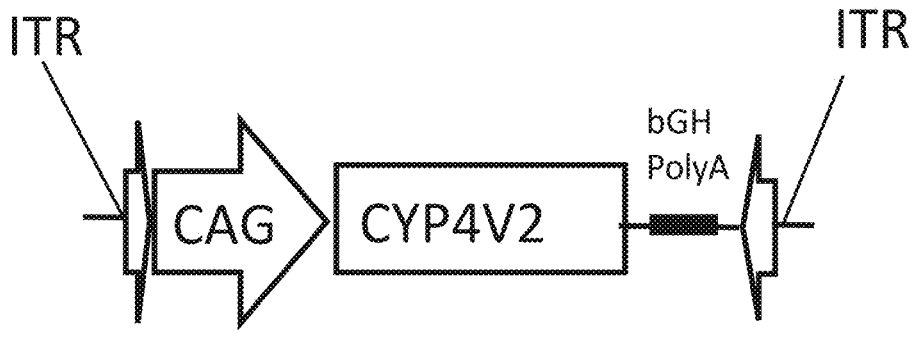

Gene Therapy:

FIG. 7: Schematics of and annotations to exemplary CYP4V2 expression cassettes and recombinant AAV (rAAV) vectors (a) CYP4V2 expression cassette (with an enhancer) packaged in single-stranded AAV (ssAAV) vectors (b) CYP4V2 expression cassette (without an enhancer) packaged in single-stranded AAV (ssAAV) vectors (c) CYP4V2 expression cassette packaged in self-complementary AAV (scAAV) or ssAAV vectors.

Annotations: An CYP4V2 expression cassette (as shown flanked by AAV ITRs) can be packaged in an rAAV vector with capsid from any AAV serotype or a hybrid or variant thereof. ITRs: Inverted terminal repeats (can be AAV2 ITRs or ITRs from other AAV serotypes). Exemplary AAV2 ITRs sequences shown in SEQ ID NOs: 42 and 43. CYP4V2: a cDNA encoding the human CYP4V2 protein or a functional variant thereof, e.g., CYP4V2st (SEQ ID NO: 1) or CYP4V2op (SEQ ID NO: 2) encoding the human CYP4V2 protein (SEQ ID NO: 4), or CYP4V2fv (SEQ ID NO: 3) encoding a functional CYP4V2 protein (SEQ ID NO: 5). A Kozak sequence (sequence shown in SEQ ID NO: 37 or 38) is inserted immediately before the CYP4V2 cDNA sequence. CAG: hybrid CAG promoter (exemplary sequence shown in SEQ ID NO: 32). Other promoters discussed herein can also be used, including without limitation, a CMV promoter (exemplary sequence shown in SEQ ID NO: 40) or a EF-1α promoter (exemplary sequence shown in SEQ ID NO: 41). WPRE: woodchuck hepatitis virus posttranscriptional regulatory element (exemplary sequence shown in SEQ ID NO: 33). bGH poly A: bovine growth hormone polyadenylation signal (exemplary sequence shown in SEQ ID NO: 34). Alternative polyA signals can be used, e.g., an SV40 late poly A signal (exemplary sequence shown in SEQ ID NO: 39). EFS: elongation factor 1α short (EFS) core promoter. Exemplary sequence shown in SEQ ID NO: 35. SPA: a small poly A signal. Exemplary sequence shown in SEQ ID NO: 36. Mutant/truncated ITR: One of the two ITRs used in an scAAV vector is a mutant/truncated ITR (shown as ITR*). Exemplary sequence shown in SEQ ID NO: 44. An enhancer is optional in CYP4V2 expression cassettes.

Figure 8A:
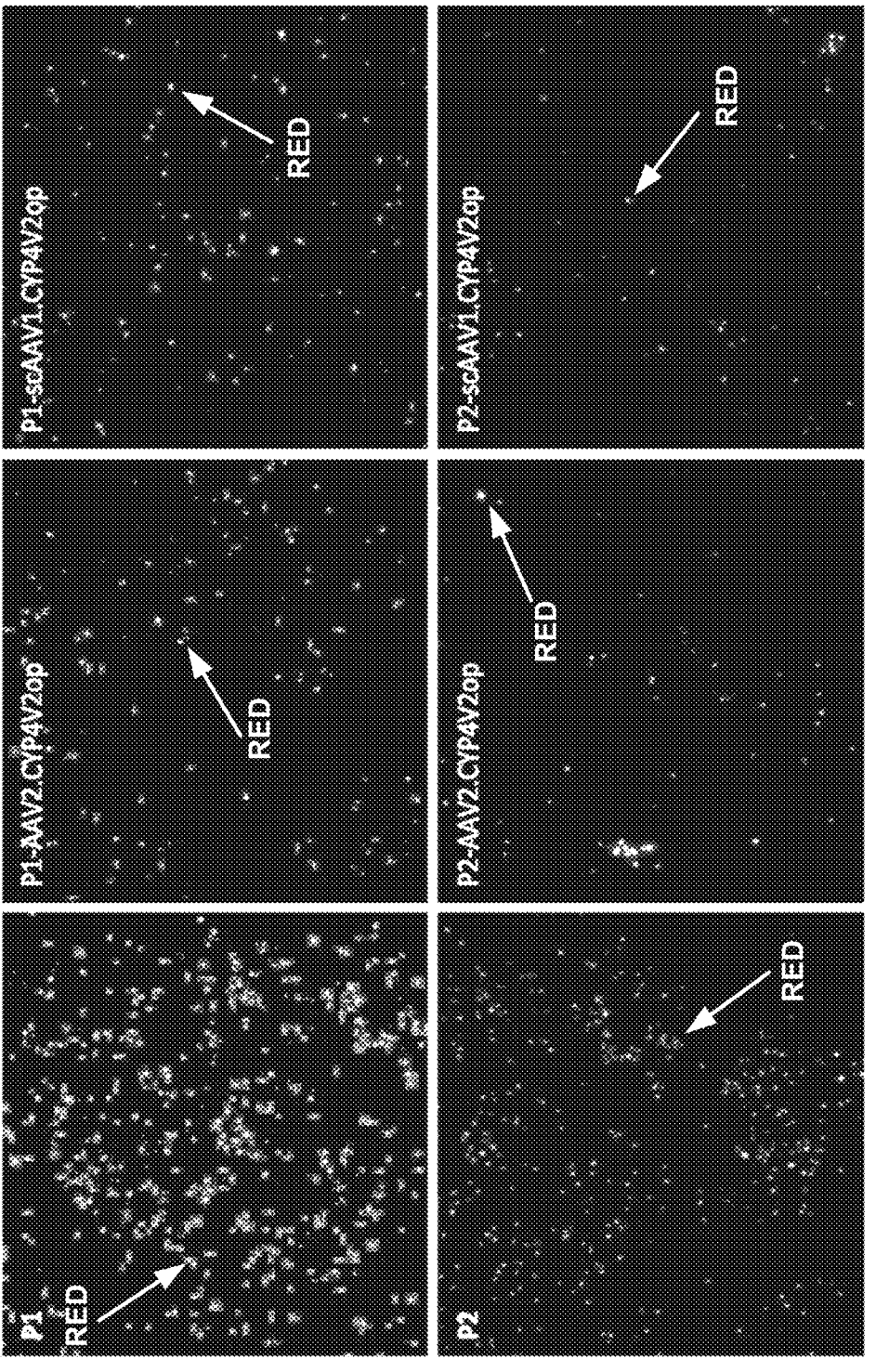
Figure 8B:
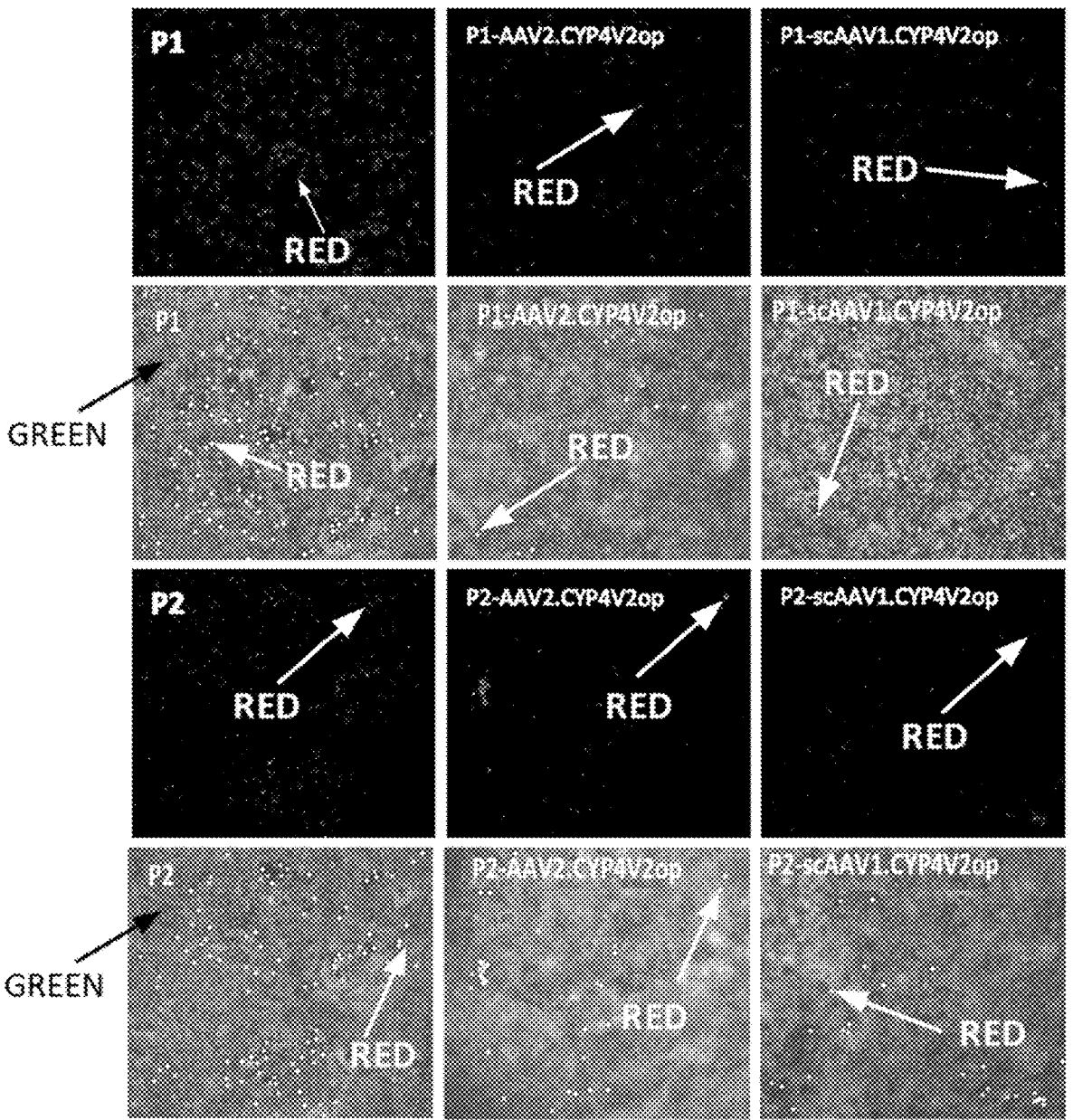

FIG. 8: Cell viability images of BCD patient-derived iPS-RPE samples after 1 hour exposure to blue light (without AAV.CYP4V2 treatment vs. treated by AAV2.CYP4V2op or scAAV1.CYP4V2op at MOI of 1×10e5 GC/cell). P1 and P2 (BCD Patient 1 and Patient 2). Red (dead/sick cells); Green (live/healthy cells). FIG. 8 (*a*): Red only. FIG. 8 (*b*): Red and green.

Figure 9A:
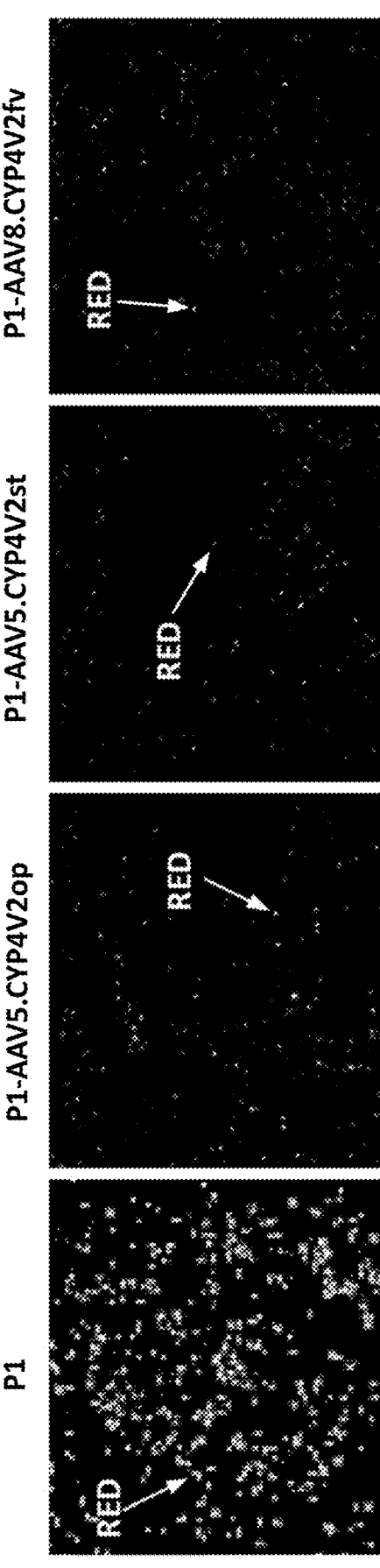
Figure 9B:
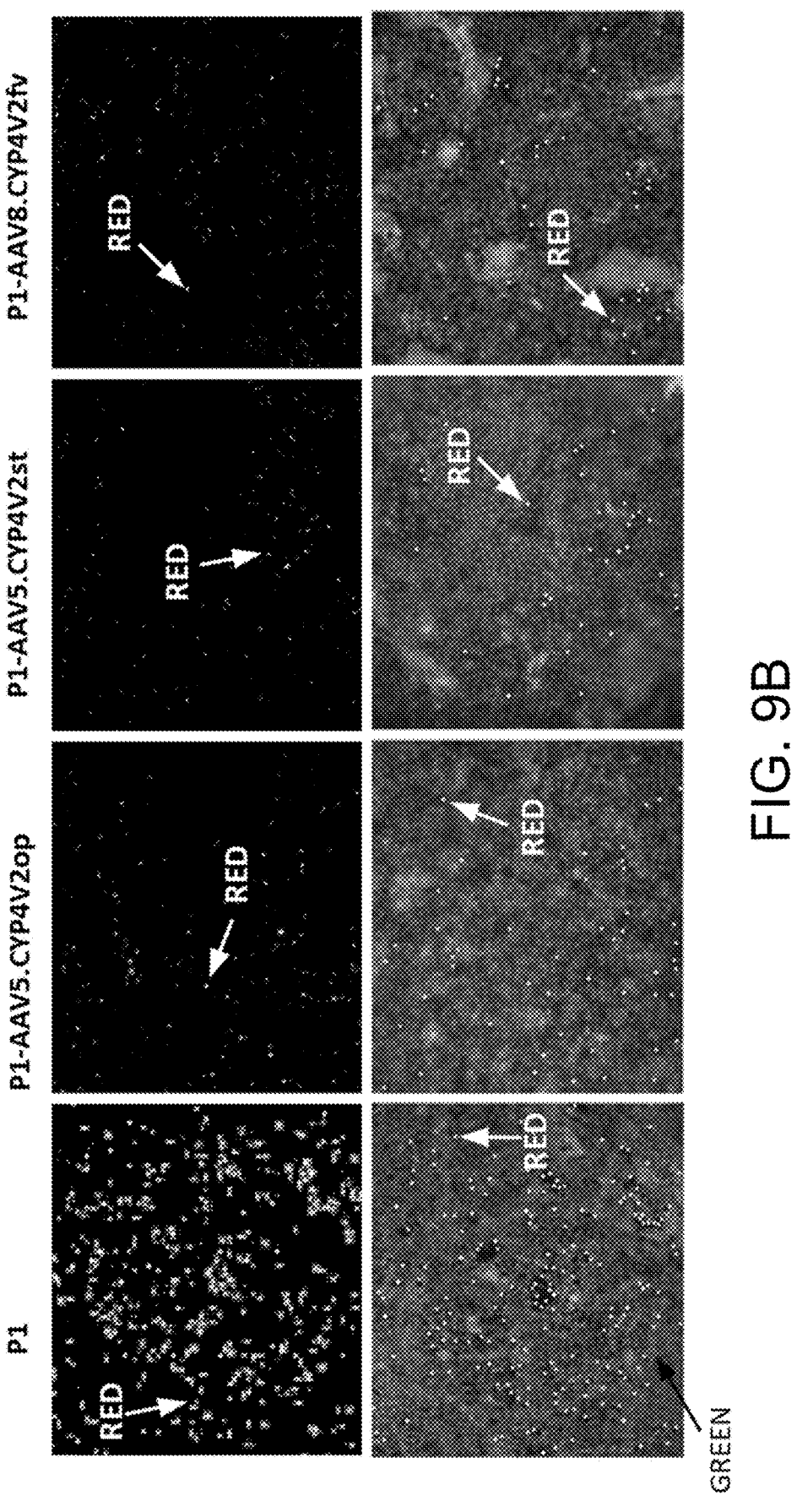

FIG. 9: Cell viability images of BCD patient-derived iPS-RPE samples after 1 hour exposure to blue light (without AAV.CYP4V2 treatment vs. treated by AAV5.CYP4V2op, AAV5.CYP4V2st, or AAV8.CYP4V2fv at MOI of 1×10e5 GC/cell). P1 (BCD Patient 1). Red (dead/sick cells); Green (live/healthy cells). FIG. 9 (*a*): Red only. FIG. 9 (*b*): Red and green.

Figure 10A:
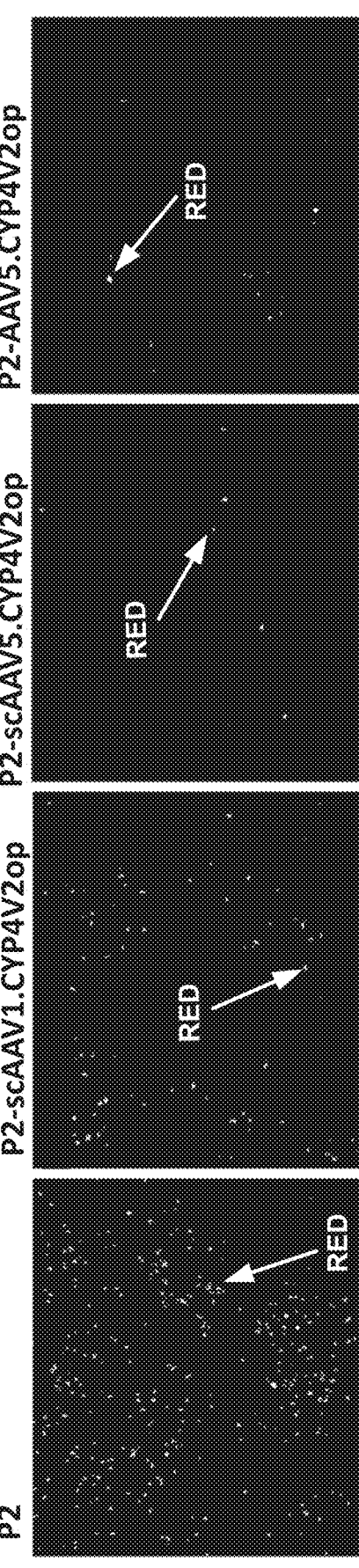
Figure 10B:
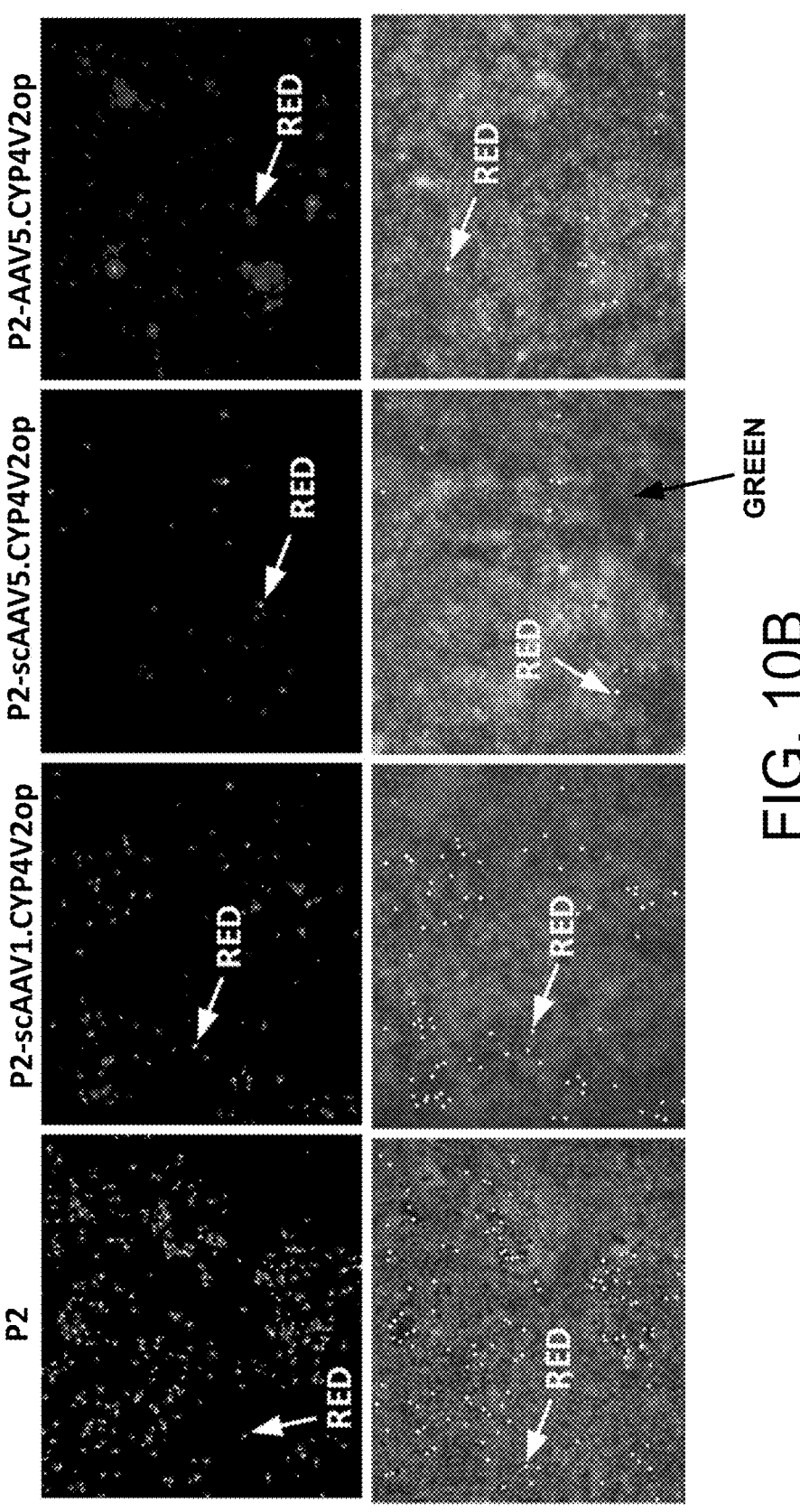

FIG. 10: Cell viability images of BCD patient-derived iPS-RPE samples after 1 hour exposure to blue light (without AAV.CYP4V2 treatment vs. treated by AAV5.CYP4V2op, scAAV1.CYP4V2op, or scAAV5.CYP4V2op at MOI of 1×10e4 GC/cell). P2 (BCD Patient 2). Red (dead/sick cells); Green (live/healthy cells). FIG. 10 (*a*): Red only. FIG. 10 (*b*): Red and green.

Figure 11A:
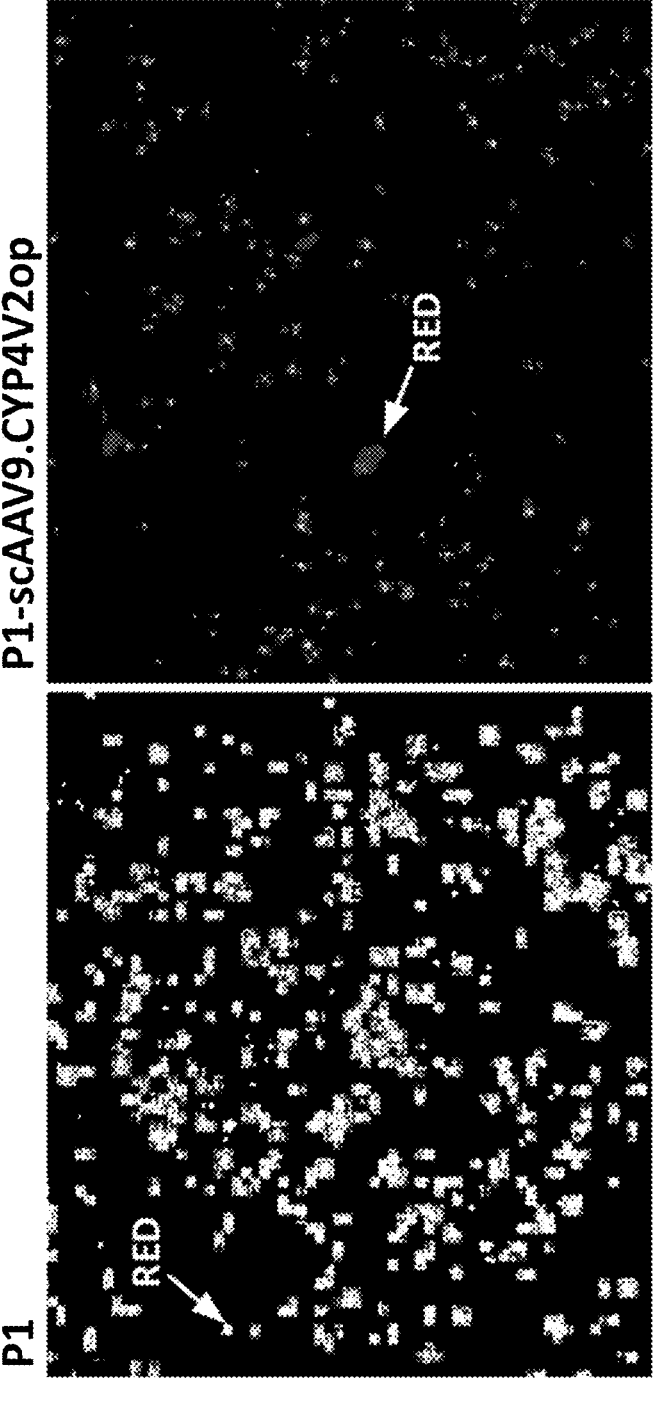
Figure 11B:
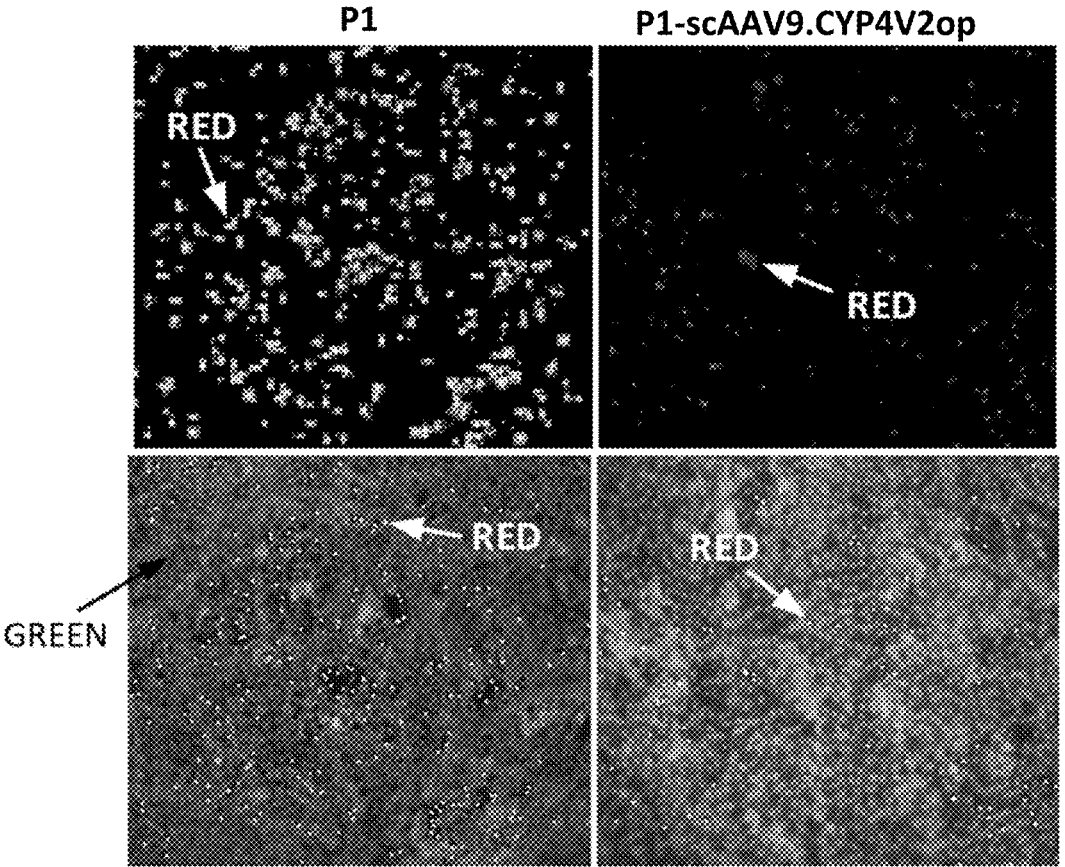

FIG. 11: Cell viability images of BCD patient-derived iPS-RPE samples after 1 hour exposure to blue light (without AAV.CYP4V2 treatment vs. treated by scAAV9.CYP4V2op at MOI of 1×10e5 GC/cell). P1 (BCD Patient 1). Red (dead/sick cells); Green (live/healthy cells). FIG. 11 (*a*): Red only. FIG. 11 (*b*): Red and green.

Figure 12:
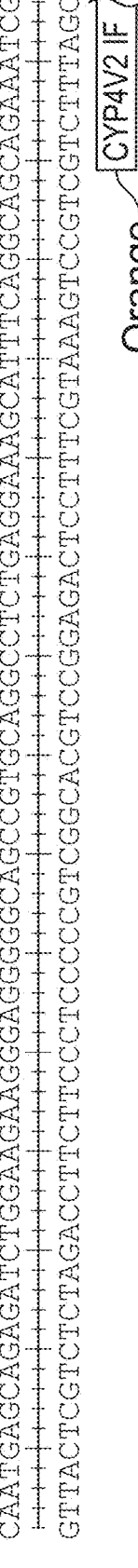
Figure 12:
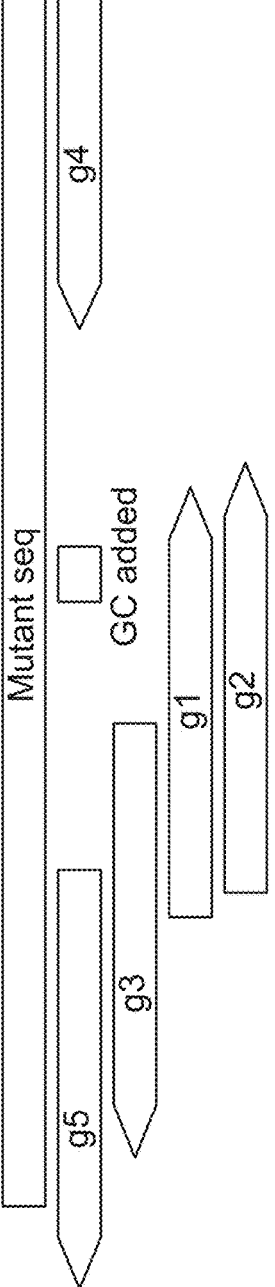
Figure 12:
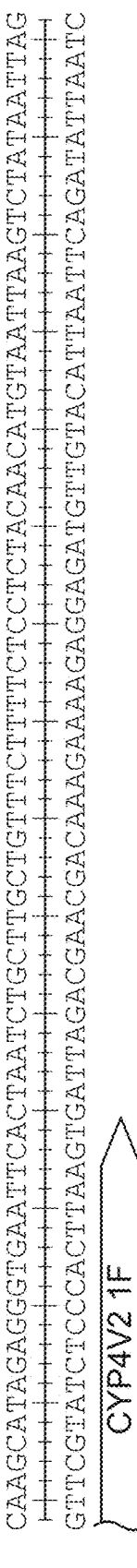
Figure 12:
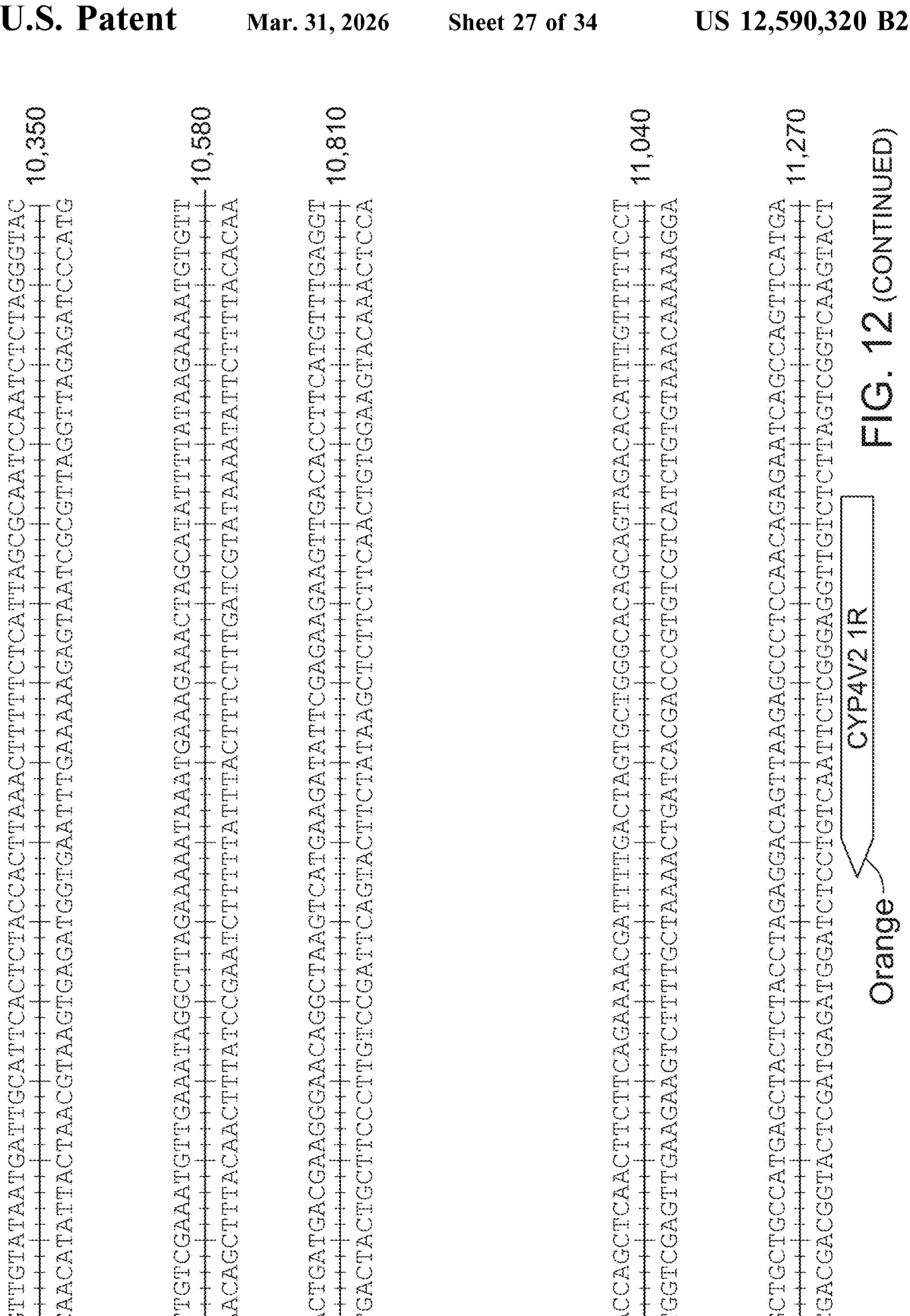

Cell Therapy:

FIG. 12 shows a region of the CYP4V2 sequence (SEQ ID NO:65) and the position of the guide RNAs (gRNAs) designed relative to the c.802-8_810del17insGC mutation and primers (orange arrows) for gRNA activity assay.

Figure 13:

FIG. 13 shows an in vitro surveyor assay. Lanes 1: amplicon+Cas9; 2: amplicon+g1+Cas9; 3: amplicon+g2+Cas9; 4: amplicon+g3+Cas9; 5: amplicon+g4+Cas9; 6: amplicon+g5+Cas9; 7: amplicon only; M: 1 kb DNA marker.

Figure 14:
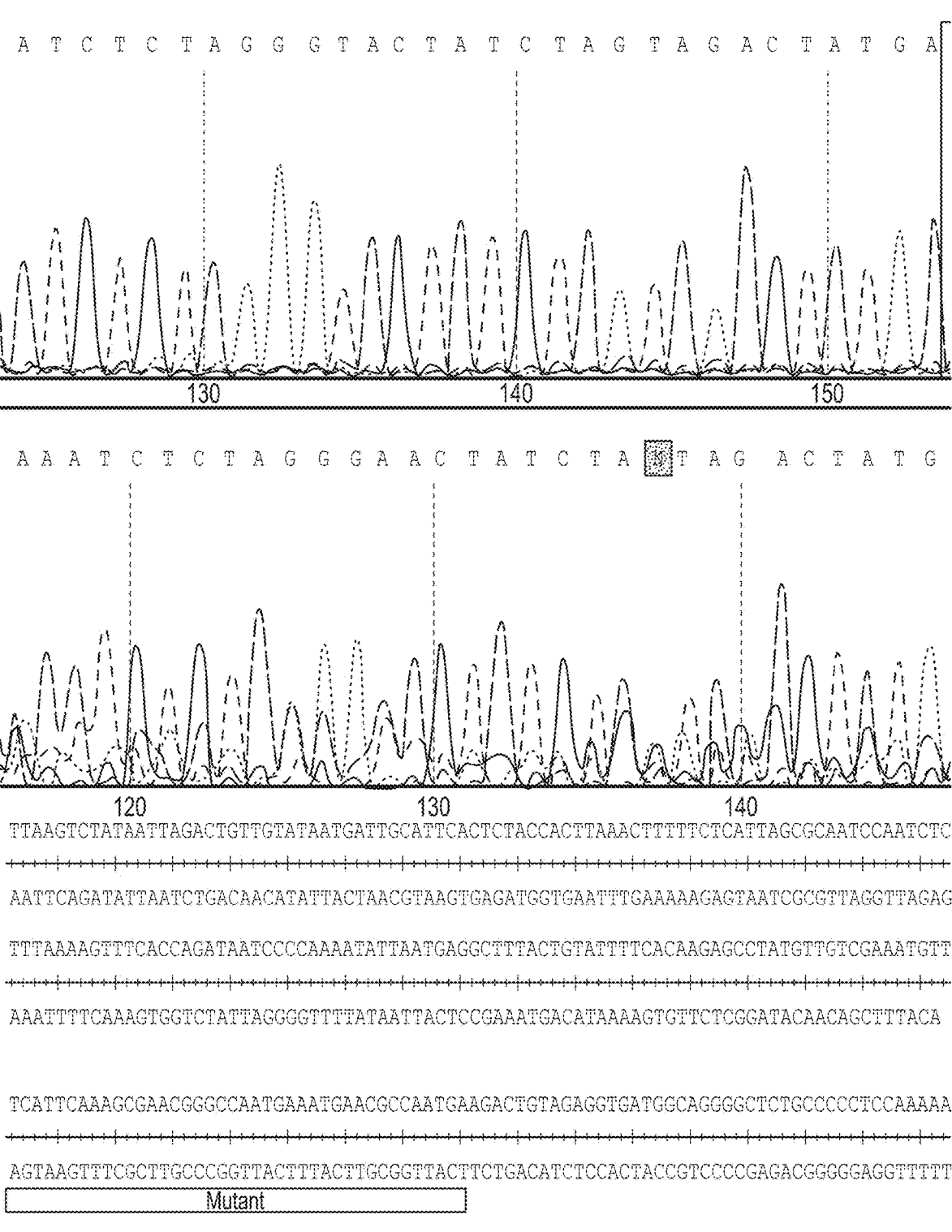
Figure 14:
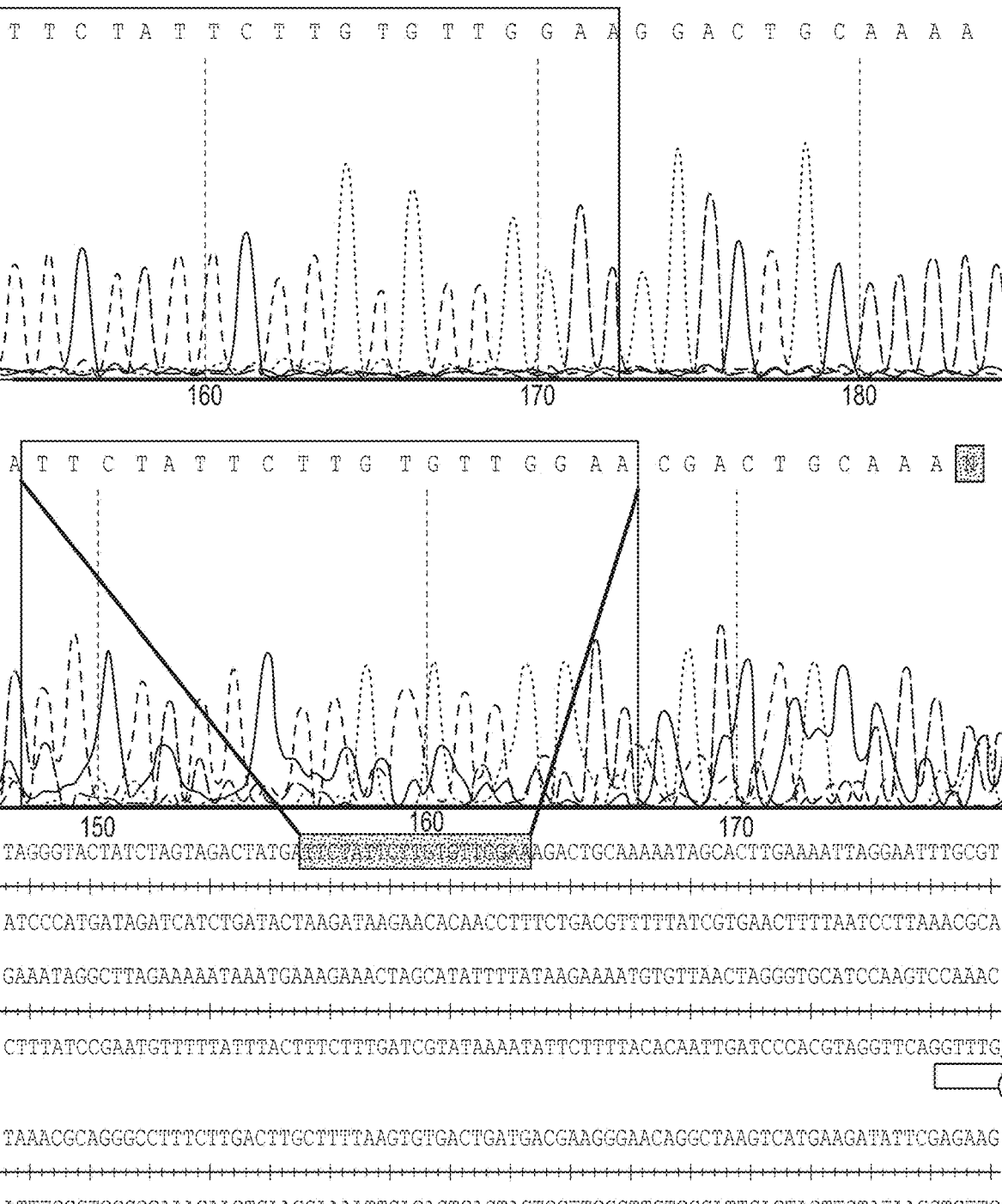
Figure 14:
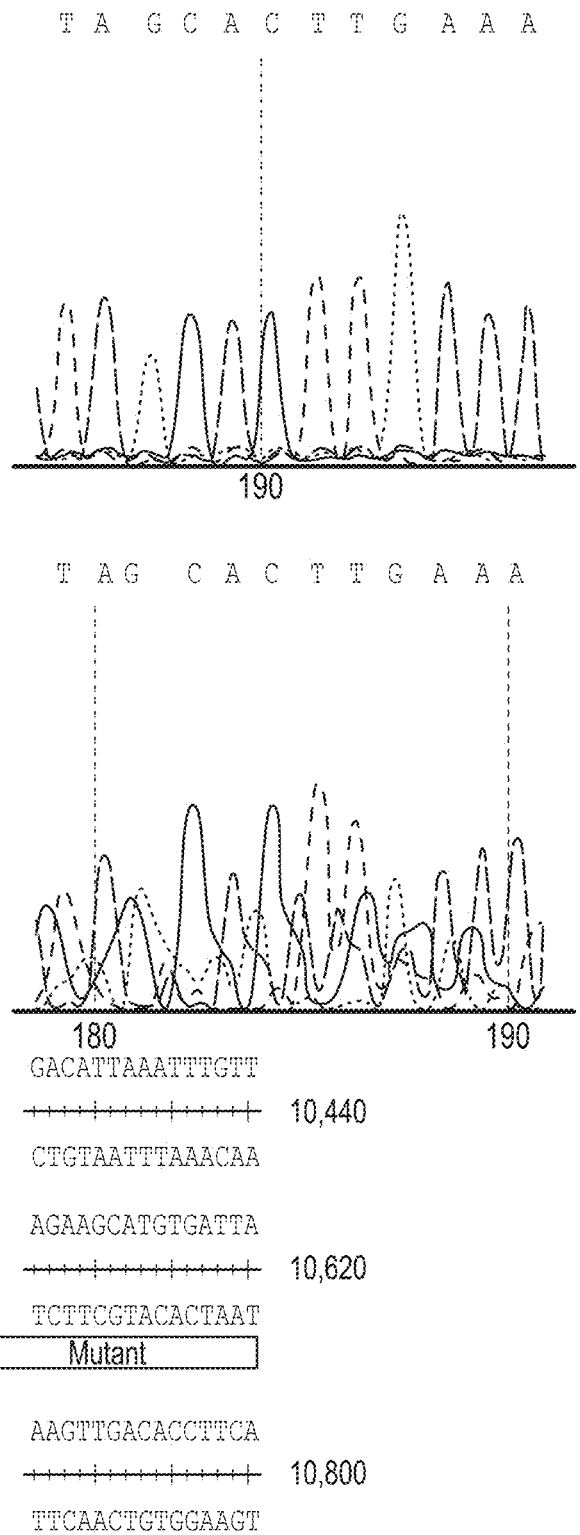

FIG. 14 is a sequence comparison confirming the DNA origin used in the surveyor assay. Top: untreated amplicon (SEQ ID NO:66); Middle: fragment from g2 treated amplicon (SEQ ID NO:67); Lower: CYP4V2 locus indicating mutation site (SEQ ID NO:68).

Figure 15:
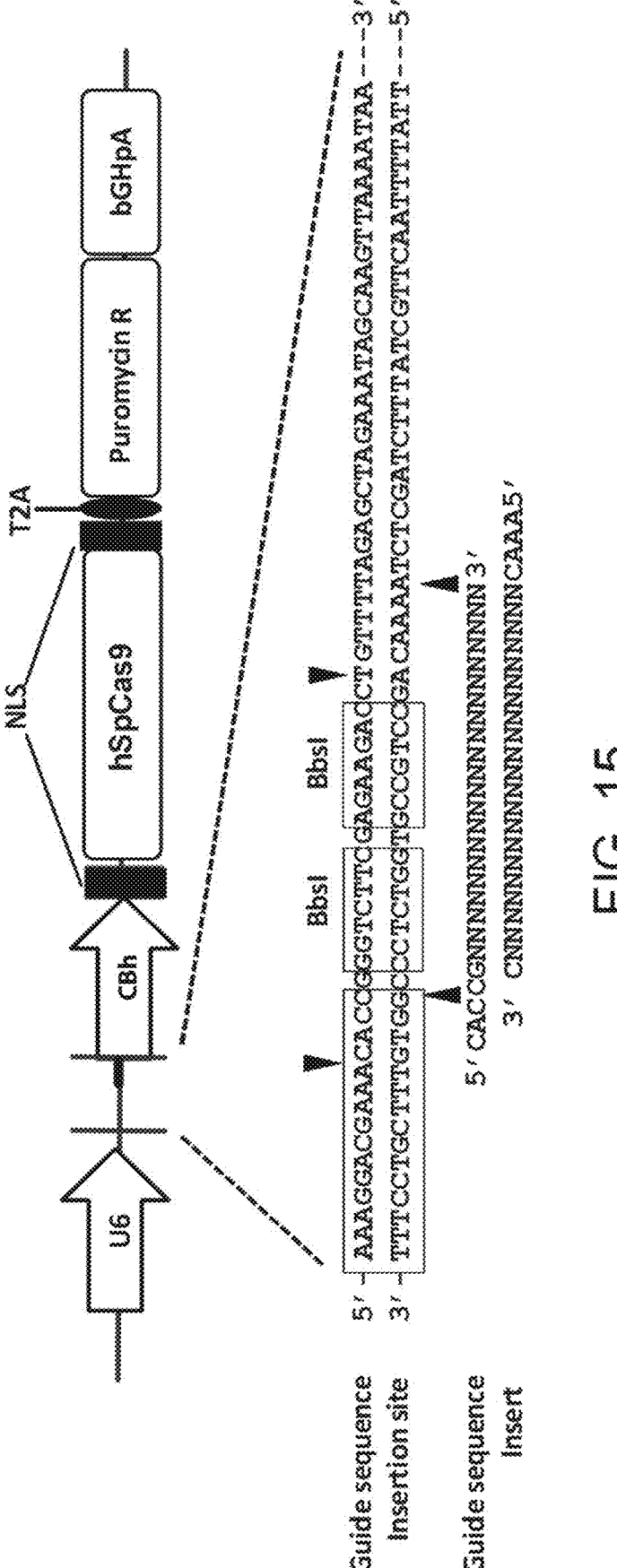

FIG. 15 is an illustration of gRNA vector construction. Guide sequence insertion site (SEQ ID NO:69); Guide sequence insert (SEQ ID NO:70 (top); SEQ ID NO:71 (bottom)).

Figure 16:
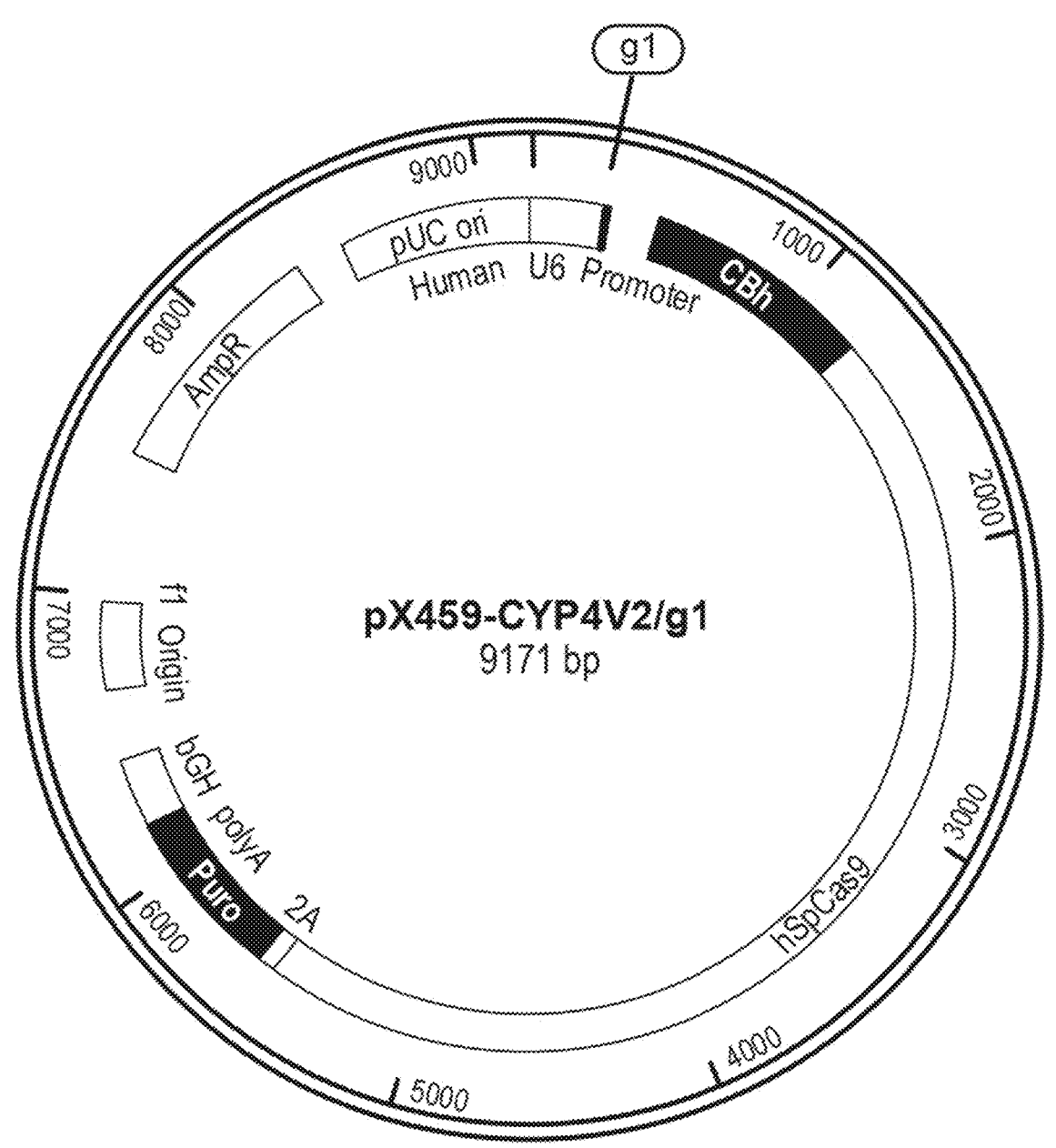

FIG. 16 is a vector map of gRNA (using g1 as example), Cas9 and PuroR co-expression plasmid pX459-hSpCas9-2A-Puro.

Figure 17:
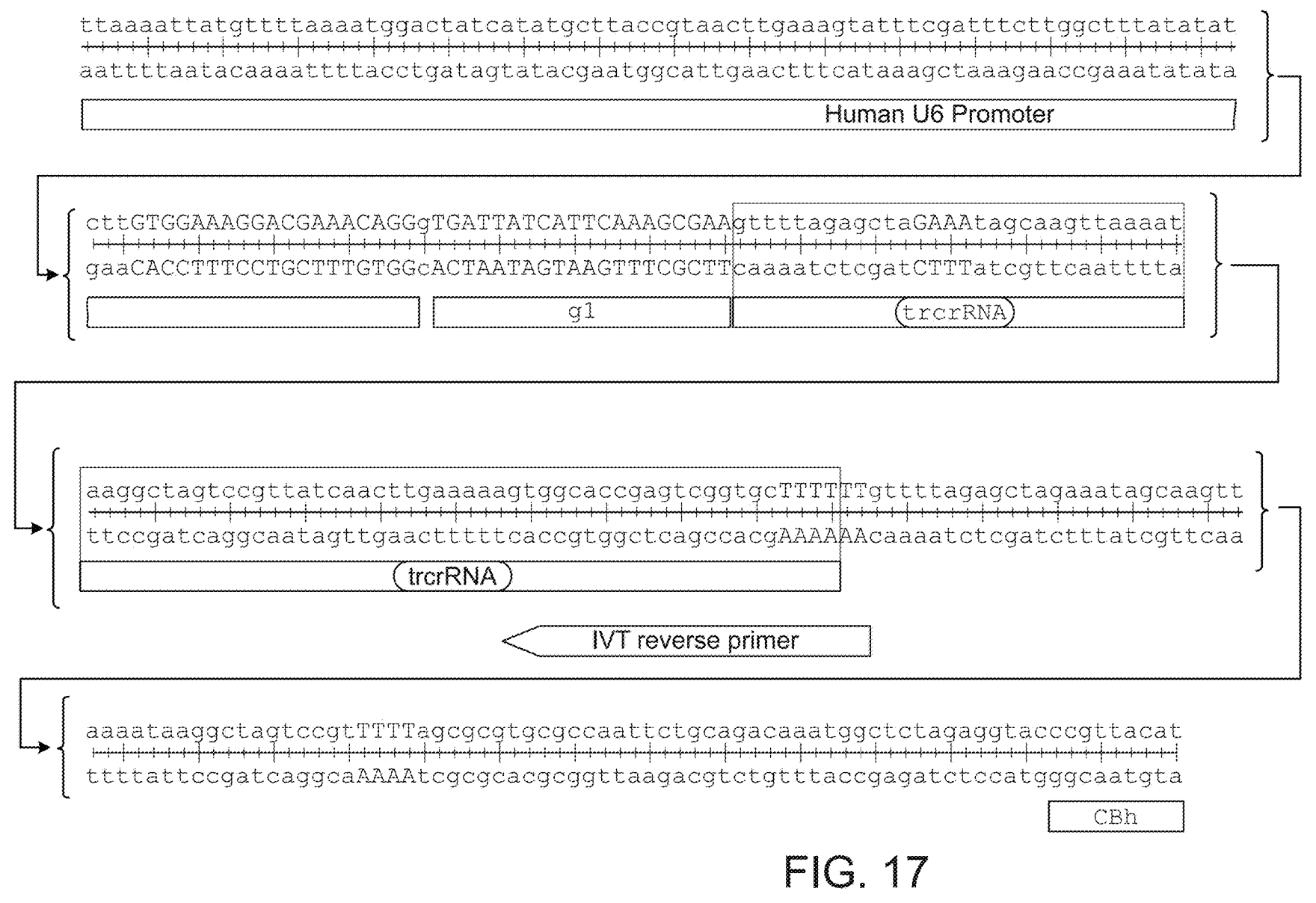

FIG. 17 shows the position of the gRNA (using g1 as an example) relative to the U6 promoter in the pX459-hSpCas9-2A-Puro.plasmid (SEQ ID NO:72). The "G" nucleotide in between the U6 promoter and the gRNA is to enhance transcription efficiency driven by the U6 promoter. It is optional and not necessary when a different promoter is used or when the gRNA starts with a "G" nucleotide.

DEFINITIONS

It is to be understood that as used in the specification and in the claims, "a" or "an" can mean one or more, depending upon the context in which it is used. Thus, for example, reference to "a cell" can mean "at least one cell" or "more than one cell".

The term "about" or "approximately" or the symbol "~" refers to within plus or minus 10% (inclusive) range of a given value or state. Unless otherwise clear from context, all numerical values provided herein can be modified by the term about.

The term "AAV.CYP4V2" refers to a recombinant adeno-associated virus (AAV) vector comprising a polynucleotide encoding a functional CYP4V2 protein.

The term "CYP4V2 gene therapy" refers to the introduction of a functional CYP4V2 protein or a polynucleotide encoding a functional CYP4V2 protein into a cell and/or a subject. See detailed discussion in the disclosure.

The term "effective amount" or "effective dosage" or "therapeutically effective dosage" refers to an amount of a compound (e.g., a vector) and/or cells sufficient and/or suitable to effect treatment when administered to a subject in need of such treatment. The effective amount will vary depending upon the specific activity of the therapeutic agent being used, the severity of the patient's disease state, and the age, physical condition, existence of other disease states, and nutritional status of the subject. Additionally, other medication and/or treatment the patient may be receiving will affect the determination of the effective amount of the therapeutic agent to administer. See description herein for more detailed discussion.

The term "treatment" or "treating" refers to administration of a composition as disclosed herein (e.g., an AAV comprising a transgene and/or cells) to a subject for purposes including 1) preventing or protecting against the disease or condition, that is, causing the clinical symptoms not to develop; 2) inhibiting the disease or condition, that is, arresting, slowing down, ameliorating or suppressing the development of clinical symptoms; 3) relieving the disease or condition, that is, causing the regression of clinical symptoms; and/or 4) replacing and/or restoring the function loss of the diseased cells, tissue and/or organ. In some embodiments, the term "treatment" or "treating" refers to relieving the disease or condition; that is, causing the regression of clinical symptoms. In some embodiments, the term "treatment" or "treating" alternately or additionally refers to the prophylactic treatment of a subject in need thereof. The prophylactic treatment can be accomplished by providing an appropriate dose of a therapeutic agent to a subject at risk of suffering from an ailment, thereby substantially averting onset of the ailment. It will be understood by those skilled in the art that it is not always possible to distinguish between "preventing" and "suppressing", since the ultimate inductive event or events may be unknown or latent, or the patient may not be ascertained until well after the occurrence of the event or events. Therefore, as used herein, the term "prophylaxis" is intended as an element of "treatment" to encompass both "preventing" and "suppressing" as defined herein.

The term "subject" refers to an animal, such as a mammal, e.g., a human. The methods described herein can be useful in human therapeutics, pre-clinical, and veterinary applications. In some embodiments, the subject is a mammal, and in some embodiments, the subject is human.

A "variant" is a protein with sequence homology to a reference biologically active protein that retains at least a portion of the therapeutic and/or biological activity of the biologically active protein. For example, a variant protein can have at least 70%, at least 75%, at least 80%, at least 85%, at least 90%, at least 95%, at least 96%, at least 97%, at least 98%, or at least 99% amino acid sequence identity compared with the reference biologically active protein. The term "biologically active protein" includes proteins modified deliberately, as for example, by site directed mutagenesis, insertions, or accidentally through mutations. A "variant" includes a "fragment", which is a truncated form of a native or non-native biologically active protein that retains at least a portion of the therapeutic and/or biological activity.

The term "nucleic acid" is used herein to refer to all forms of nucleic acid, polynucleotides and oligonucleotides, including deoxyribonucleic acid (DNA) and ribonucleic acid (RNA). Nucleic acids include genomic DNA, cDNA and RNA. Polynucleotides include naturally occurring, synthetic, and intentionally modified or altered polynucleotides. Polynucleotides can be single, double, or triplex, linear or circular, and can be of any length. A sequence or structure of a particular polynucleotide may be described herein according to the convention of providing the sequence in the 5' to 3' direction.

The term "sequence variant" means genes or polypeptides that have been modified compared to their native or original sequence by one or more nucleotide or amino acid insertions, deletions, and/or substitutions. Insertions can be located at either or both termini of the gene or protein, and/or can be positioned within internal regions of the nucleotide sequence or amino acid sequence. In deletion variants, one or more nucleotide or amino acid residues in a gene or polypeptide as described herein are removed. In substitution variants, one or more nucleotide or amino acid residues of a gene or polypeptide are removed and replaced with alternative residues. In one aspect, the substitutions are conservative in nature and conservative substitutions of this type are well known in the art.

As used herein, the term "therapy" or "treatment" can be applied either in vivo to a subject or in vitro in a cell.

As used herein, a plasmid is a type of a vector.

As used herein, the term "genetically repaired" or "genetic repair" refers to a cell which originally harbors a genetic defect (e.g., a mutation or a pathologic alteration) in a gene, its genetic defect having been repaired either through gene correction or disruption in the cell's genomic DNA or mRNA (herein defined as "gene editing", "gene editing therapy" or "gene correction"), or via gene transfer or supplementation of an exogenous nucleic acid molecule to the cell which expresses a functional protein corresponds the defective gene (herein defined as "gene transfer therapy" or "gene therapy").

As used herein, the term "percent sequence identity" or "sequence identity" shall be determined and calculated as follows. In calculating (percent) sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value (and rounded up to the next higher whole number (e.g., 65.01% shall be rounded up to 66% and deemed as 66% for purposes herein)). It will be appreciated that the length of the aligned region can be a portion of one or both sequences up to the full net length (without applying gap) size of the shorter sequence. To determine identical matches and calculate sequence identity between two protein encoding nucleotide sequences, any non-coding nucleotide sequence (e.g., without limitation, intron, UTR, Kozak sequence, promoter, enhancer or other regulatory sequences) shall be removed before submitting the two sequences for alignment and calculating the sequence identity. The alignment of two sequences to determine the number of identical matches of nucleotides or amino acid residues between the two sequences can be performed by using the Pairwise Sequence Alignment EMBOSS Needle which creates an optimal global alignment of two sequences using the Needleman-Wunsch algorithm (available at The European Bioinformatics Institute (EMBL-EBI) and on the World Wide Web: ebi.ac.uk/Tools/psa/emboss_needle/nucleotide.html for nucleotide alignment and ebi.ac.uk/Tools/psa/emboss_needle/for protein alignment) and using default parameters (For nucleotide sequence use: Matrix: EDNAFULL. Gap Open Penalty: 10. Gap Extend Penalty: 0.5. Output format: pair. End Gap Penalty: false. End Gap Open Penalty: 10. End Gap Extend Penalty: 0.5. For protein sequence use: Matrix: EBLOSUM62. Gap Open Penalty: 10. Gap Extend Penalty: 0.5. Output format: pair. End Gap Penalty: false. End Gap Open Penalty: 10. End Gap Extend Penalty: 0.5).

The term "adeno-associated virus vector" refers to a nucleic acid derived from any AAV serotype, e.g. AAV1, AAV2, AAV3, AAV4, AAV5, AAV6, AAV7, AAV8, AAV9, AAV10, AAV11, AAV12 serotype, or any other virus or serotype that shares homologous in its capsid protein sequence to the capsid protein of an AAV serotype. The term "recombinant adeno-associated virus" or "rAAV" refers to an infectious, replication-defective virus composed of an AAV protein shell encapsulating a nucleic acid molecule of interest, which is flanked on one or both sides by AAV ITRs. As used herein, the reference to a particular AAV serotype means an AAV having at least one capsid protein of that AAV serotype. For example, the term "AAV2" refers to an AAV having at least one AAV serotype 2 capsid protein.

The term "CYP4V2" refers to Cytochrome P450 4V2 or Cytochrome P450, family 4, subfamily V, polypeptide 2 (sometimes referred to as CYP4AH1), and its orthologues in other species. Mutations in CYP4V2 have been associated with BCD (see, for example, Li et al., *Am J Hum Genet.* 74:817-826, 2004) and retinitis pigmentosas (see, for example, Wang et al., *PLOS ONE* 7: e33673, 2012). The full-length genomic human CYP4V2 gene is about 22,053 bp in length and can be found at, e.g., genecards. org/cgi-bin/carddisp.pl?gene-CYP4V2&keywords=CYP4V2 on the World Wide Web. As used herein, the term "hCYP4V2" refers to a human CYP4V2 gene or protein. It would be understood that hCYP4V2 and CYP4V2 can refer to a gene or protein that contains a genetic or epigenetic alteration or a gene or protein that does not contain a genetic or epigenetic alteration.

As used herein, the term "functional CYP4V2" refers to a protein, or a nucleotide molecule that, when expressed, produces a protein that is effective to provide therapeutic benefits (e.g., to ameliorate or rescue abnormal fatty acid levels (e.g., DHA level) in target cells) to an individual (e.g., an individual with a genetic or epigenetic alteration in a CYP4V2 molecule). A functional CYP4V2 molecule can correspond to a wild-type hCYP4V2 sequence, or a naturally occurring variant thereof (e.g., a polymorphic variant; e.g., a variant that does not contain a pathologic alteration), or an optimized sequence. In some embodiments, a functional CYP4V2 molecule is a CYP4V2 molecule from another species (e.g., another mammal, such as a rodent, rabbit, dog, pig or a non-human primate) that shares a similar orthology as human CYP4V2. For example, an ortholog of a human CYP4V2 sequence is the murine mCyp4v3 sequence. In some embodiments, a functional CYP4V2 molecule is another P450 molecule (e.g., a CYP4 protein).

The term "ocular cell" refers to any cell in, or associated with the function of, the eye, including without limitation, a retina cell, a retina bipolar cell, a photoreceptor cell or a photorecptor progenitor cell (including rod and/or cone, altogether "PRCs"), a ganglion cell, a retinal pigment epithelium (RPE) cell, a choroidal epithelial (CE) cell, a corneal epithelium cell (CEC), a choroidal cell, or a corneal cell, or an optic-nerve cell.

The term "function loss" or "dysfunction" refers to a decrease in, or loss of, cellular function (e.g., photoreceptor function, photoreceptor cell function, retinal pigment epithelium cell function, lens function, choroid function or cornea function) as compared to a normal, non-diseased cell, or compared to the other eye or the same eye at an earlier time point. As used herein, "degeneration," "atrophy," "disorder," "disease," and/or "dystrophy" can be used synonymously with loss of function. The term "increased function" means to improve the function (e.g., the function of the photoreceptors, photoreceptors cells, retinal pigment epithelium cells, choroidal cells or corneal cells), or increase the number or percentage of functional photoreceptors or cells (e.g., photoreceptors cells, retinal pigment epithelium cells, choroidal cells or corneal cells) as compared to a diseased eye (having the same ocular disease), the same eye at an earlier time point, a non-treated portion of the same eye, or the contralateral eye of the same patient.

The term "transgene" refers to a donor nucleic acid that is intended or has been introduced into a cell or organism. Transgenes include any gene, such as a gene or cDNA set forth in Table 4.

The term "pharmaceutically acceptable formulation" and "physiologically acceptable formulation" and ""pharmaceutically acceptable carrier" mean a biologically acceptable formulation, gaseous, liquid or solid, or mixture thereof, which is suitable for one or more routes of administration, in vivo delivery, in vitro delivery or contact, and can include a formulation or carrier used in therapies for other diseases (for example, gene therapy or cell therapy for other ocular diseases). A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a protein, a polynucleotide, a plasmid, a viral vector or a nano-particle to a cell or a subject. Such compositions include, without limitation, solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo or in vitro contact or delivery. Aqueous and non-aqueous solvents, solutions and suspensions may include suspending agents, lubricating agent and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents, and immunosuppressant) can also be incorporated into the compositions. Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

The term "crRNA" refers to CRISPR RNA, which contains both the protospacer element and additional nucleotides which are complementary to the tracrRNA.

The term "tracrRNA" refers to transactivating crRNA, which hybridizes to the crRNA and binds to a Cas9 protein activating the complex to creating double-stranded breaks at specific sites within genomic sequence.

The term "sgRNA" refers to single-guide RNA, which combines the crRNA and tracrRNA, which are separate molecules in the native CRISPR/Cas9 system in *S. pyogenes*, into a single RNA construct.

The term "PAM" refers to "protospacer adjacent motif" which is a short sequence in either strand of the genome recognized by CRISPR nucleases as a cutting site. PAM varies with the nuclease (e.g., Cas9, Cpf1, etc.). The protospacer element sequence is usually directly upstream of the PAM site.

The term "protospacer element" (also referred to as "guide RNA" or "CRISPR gRNA" or "gRNA" or g1, g2, g3, g4, g5, etc.) refers to the portion of the crRNA (or sgRNA) that is complementary to the genomic DNA target sequence.

DHA: Docosahexaenoic Acid, a polyunsaturated omega-3 fatty acid, also known as 22:6 ($\omega$-3) or C22:6 n3.

AA: Arachidonic Acid, a polyunsaturated omega-6 fatty acid, also known as 20:4 ($\omega$-6) or C20:4 n6, or ARA.

PBS (+): phosphate buffered saline (PBS) with Calcium and Magnesium.

PBS (–): phosphate buffered saline (PBS) without Calcium or Magnesium.

DETAILED DESCRIPTION

Methods and Compositions for BCD Cellular Disease Models

Developing a proper BCD disease model and ascertaining the molecular level phenotype for BCD is critical BCD related research, development and testing of drugs and treatment options for BCD. It is also important for the study of CYP4V2 function. As outlined in the Background section herein, the clinical phenotype of BCD has been characterized, established and studied since 80 years ago, the genetic mutations causing BCD has been identified over a decade. However, there is still a gap between the clinical phenotype (e.g., crystal-like deposits in BCD patients' retina) and the underlying CYP4V2 mutations.

Prior studies on BCD have found abnormal fatty acid levels in BCD patients, including in fibroblasts, lymphocytes and serum. For example, in Lee et al., The Metabolism of Fatty Acids in Human Bietti Crystalline Dystrophy, *Invest Ophthalmol Vis Sci*. 2001 July; 42 (8): 1707-14, the researchers used a pulse-chase method to study abnormalities in BCD patients' fibroblast and lymphocytes. BCD patient and normal control's fibroblast and lymphocytes were incubated with [(14) C]18:3n-3 or [(14) C]18:2n-6. Fibroblasts from patients with BCD showed lower conversion of 18:3n-3, but not of 18:2n-6, into polyunsaturated fatty acids (PUFAs) than those of normal subjects. In another study (Lai et al., Alterations in Serum Fatty Acid Concentrations and Desaturase Activities in Bietti Crystalline Dystrophy Unaffected by CYP4V2 Genotypes, *Invest Ophthalmol Vis Sci* 2010; 51:1092-7), the researchers used GC-MS to analyze serum fatty acid concentrations in serum samples of BCD patients and control. The study found a higher concentration of octadecanoic acid (18:0) in BCD patients' serum than that in control subjects, as well as a lower concentration of octadecadienoic acid (18: In-9) than that in control subjects. In addition, the total monounsaturated fatty acid concentration was significantly lower in BCD than in the control. Yet in another study (Nakano et al., CYP4V2 in Bietti's Crystalline Dystrophy: Ocular Localization, Metabolism of omega-3-Polyunsaturated Fatty Acids, and Functional Deficit of the p.H331P Variant, Mol Pharmacol 82:679-686, 2012) which did not use BCD patient samples as study subject, the results suggested that the CYP4V2 enzyme possesses omega-hydroxylase activity toward omega-3-PUFAs.

It is important to confirm whether the abnormal fatty acid levels found in BCD patients' fibroblast and serum actually exist in BCD patients' RPE cells, which are the disease causing cells for BCD. Therefore, a BCD disease model allowing the direct investigation in BCD patients' RPE cells is desired to gain more understanding of BCD disease pathology and CYP4V2 functions, as well as to assess efficacy of potential treatment options. However, given RPE's location and rarity of BCD, it is not practical to obtain native RPE cells from BCD patients.

The present disclosure provides BCD cellular models and methods to generate BCD cellular models. BCD cellular models consist of BCD patient-specific stem cells (including without limitation, induced pluripotent stem cells (iPSCs), embryonic stem (ES) cells, somatic (or adult) stem cells, mesenchymal stem cells (MSC)) and ocular cells (including without limitation, RPE cells, photoreceptor (rod or cone) cells, photoreceptor progenitor cells, corneal epithelial cells, lens cells and/or choroid cells) derived from any stem cell of a BCD patient. In addition to patient-specific stem cells, BCD cellular model can also be generated by creating artificial CYP4V2 mutations in cells of individuals not having BCD and such cells can be ES cells, iPS cells or other stem cells, or any cells that can be reprogrammed into stem cells, or any ocular cells (whether derived from a stem cell or not).

Induced pluripotent stem cell technology provides an alternative for disease modeling to animal models. However, not all diseases have been successfully modeled using iPSC. (Urbach, A., Bar-Nur, O., Daley, G. Q. & Benvenisty, N. Differential Modeling of Fragile X Syndrome by Human Embryonic Stem Cells and Induced Pluripotent Stem Cells. Cell Stem Cell 6, 407-411 (2010)). In addition, given the reported fatty acid anabolism associated with BCD, it was unclear whether BCD patient-specific iPS or patient-specfic iPS-RPE cells can be generated by iPS technology.

A. Inducing Pluripotency

Methods of making induced pluripotent stem cells (iPSCs) are known in the art. Virtually all types of somatic cells can be used as the source cell for iPSC reprogramming. Briefly, iPSCs can be made by introducing a particular set of proteins (e.g., nucleic acids encoding a particular set of proteins or by direct delivery of proteins) into cells. It would be understood by the skilled artisan that one exemplary, non-limiting method is by introducing one or more transgenes encoding one or more of OCT4, SOX2, KLF4, and/or c-MYC (e.g., the "Yamanaka factors"). In some embodiment, the reprogramming uses all four transcription factors. In some embodiment, one, two or three transcription factors can be used. Li et al., *Stem Cells*, 2009; 27:2992-3000. Zhu et al., *Cell Stem Cell* 2010; 7:651-655. In some embodiments, iPSCs can be generated by direct delivery of the reprogramming proteins. Kim et al., *Cell Stem Cell*. 2009; 4 (6): 472-6. The Examples section provides methods for producing iPSCs using non-integrating methods, e.g., by Sendai virus (Example 1), or by episomal methods (Example 2). Any method of producing iPSCs, however, is contemplated within the scope of this disclosure.

Various methods (e.g., Sendai virus, episomal method, with or without small molecules) can be used to generate iPSCs, see Examples section, see also, for example, Hubbard et al., J. Vis. Exp., 2014, 92:52009. In addition, methods of making iPSCs from a number of different cell types are known in the art. See, for example, Hayashi et al., 2012, PLOS One, 7 (9): e45435; Poon et al. 2015, PLOS One, 10 (7): e0131288; Lamba et al. 2010, *PLOS One,* 5 (1): e8763. Typically, iPSCs express detectable levels of at least one marker including, without limitation, Oct-4, Sox-2, SSEA4, TRA-1-60, TRA-1-81, AP and/or NANOG.

Any type of stem cells can be used in generating the BCD cellular model described herein including without limitation, induced pluripotent stem cells (iPSCs), hematopoetic stem cells (HSCs), embryonic stem (ES) cells, mesenchymal stem cells, adult stem cells, or tissue-specific stem cells. Stem cells for use in the methods described herein can be pluripotent, multipotent, or totipotent stem cells.

As used herein, the term "pluripotent" refers to a cell capable of at least developing into one of ectodermal, endodermal and mesodermal cells. In one embodiment, the term "pluripotent" refers to cells that are totipotent and multipotent. As used herein, the term "totipotent" cell refers to a cell capable of developing into all lineages of cells. As used herein, the term "multipotent" refers to a cell that is not terminally differentiated. The pluripotent cells of the disclosure herein can be any stem cells or produced from non-pluripotent cells, such as fibroblasts, using induction, de-differentiation and nuclear transfer methods known in the art. The pluripotent cells described herein, whether stem cells or produced from non-pluripotent cells, can be from a subject having BCD or having CYP4V2 mutations, or from a healthy individual not having BCD for use as control or for use to create artificial CYP4V2 mutations.

Virtually any type of cells can be reprogrammed into iPS cells. See discussion in the sub-section entitled "Origination of Cells" herein.

B. Differentiation of iPSCs

BCD patient iPS cells were differentiated into iPS-RPE cells (or another type of ocular cells (e.g., iPS-CEC, iPS-CE cells or iPS-PRC). Methods for differentiating iPSCs into RPE cells or another type of ocular cell (e.g., CEC and PRC) are known. See, for example, the Examples section; Hayashi et al., 2012, PLOS One, 7 (9): e45435; Songstad, et al., Investigative Ophthalmology & Visual Science December 2015, Vol. 56, 8258-8267; and Lamba et al., PLOS One. 2010 Jan. 20; 5 (1): e8763. For example, induced pluripotent stem cells (iPSCs) reprogrammed from cells can be produced and further differentiated into, for example, RPE cells (referred to herein as "iPS-RPE"), corneal epithelial cells (referred to herein as "iPS-CEC"), photoreceptor cells (or photoreceptor progenitors; referred to herein as "iPS-PRC") or iPS-choroidal endothelial (CE) cells (referred to as "iPS-CE")

Differentiated cells, e.g., iPS-RPE cells, were tested for biochemical functions (as described herein and in the Examples section) to assess its biochemical defects/abnormalities as compared to iPS-RPE cells of healthy controls.

The iPS-RPE cell lines produced as described herein exhibit the morphology (e.g., pigmentation and hexagonal shape) and/or expresses one or more biomarkers that are indicative of RPE cells. Biomarkers for RPE cells (and iPS-RPE cells) are known and include, without limitation, one or more of RLBP1 (a/k/a CRALBP), RPE65, BESTROPHIN-1, MITF, VINCULIN, LRAT, RDH5, PAX6, MERTK, TYR, and/or ZO-1, and can be used to determine or confirm that RPE differentiation has taken place. Similarly, biomarkers for CECs (and iPS-CECs) and PRCs (and iPS-PRCs) are known and include, for example, cytokeratin 12 and cytokeratin 3 for corneal epithelial cells; and Crx for photoreceptors, recoverin for rods and cones, and Nrl for rods.

Through iPS reprogramming and RPE differentiation methods as described in Examples section, BCD patient-specific iPS and iPS-RPE cells were successfully generated.

C A Biochemical Assay to Identify Biochemical Defects/Abnormalities and Cell Viability Assay to Assess RPE Atrophy in BCD Patients' iPS-RPE Cells A set of biochemical assays were developed and used to assess and determine the phenotype in the BCD patient-specific iPS-RPE cells.

First, a more complete list of fatty acids was included in our biochemical assay. In a prior study has identified abnormal serum fatty acid levels in BCD patients, the samples were tested for the following fatty acids, 16:0, 16:1, 18:0, 18: In-9, 18:2n-6, 18:3n-3, 20:3n-6, 20:4n-6, 22:5n-3, 22:6n-3, 24:0 and 24:1. The study found a higher concentration of octadecanoic acid (18:0) in BCD patients' serum than that in control subjects, as well as a lower concentration of octadecadienoic acid (18: In-9) than that in control subjects. To determine whether the same fatty acids abnormalities exist in BCD patient-specific iPS-RPE cells and whether there are more abnormalities in other fatty acids, a biochemical assay encompassing more fatty acids was developed (See Table 2) using LC-MS.

Furthermore, to determine whether the BCD patient-specific iPS-RPE cells harbor other abnormalities in addition to fatty acids. other lipid species were included in the assay, including, ceramides (Cer), sphingomyelins (SM), and sphingosine and sphinganine (SOSA), to analyze the phenotype in BCD disease model and to determine the biochemical functions of the CYP4V2 protein. See Table 2 for a list of different species and compounds included in the biochemical assay used to test the BCD patient-specific iPS-RPE cells.

Surprisingly, the testing results (see Examples section) showed that BCD patient-specific iPS-RPE cells have a different fatty acids abnormality profile from those found in BCD patients' serum.

The eye is the light sensing organ of the human body. BCD begins with RPE atrophy, which in turn causes photoreceptor death and vision loss. A key function of the RPE is light absorption (Strauss, 2005, The retinal pigment epithelium in visual function. *Physiol Rev* 85:845-81). Environmental light exposure may affect the development and progression of human retinal degenerations such as age-related macular degeneration (AMD) and retinitis pigmentosa (RP). The use of light exposure in ocular disease models is a suitable model system to study retinal degenerations. Light exposure including blue light exposure have been widely used in retinal research (Dual roles of polyunsaturated fatty acids in retinal physiology and pathophysiology associated with retinal degeneration, Masaki Tanito & Robert Anderson (2009) Clinical Lipidology, 4:6, 821-827. Seko, et al., Graefes Arch Clin Exp Ophthalmol. 2001 January; 239 (1): 47-52. Blue light-induced apoptosis in cultured retinal pigment epithelium cells of the rat. Narimatsu, et al., Exp Eye Res. 2015 March; 132:48-51. Blue light-induced inflammatory marker expression in the retinal pigment epithelium-choroid of mice and the protective effect of a yellow intraocular lens material in vivo). Blue light exists in environmental light such as sunlight and artificial lighting (e.g., office lighting), as well as from electronic display devices such as TVs, monitors, smartphones, notebooks and tablets (Moon, et al., Blue light effect on retinal pigment epithelial cells by display devices, *Integr Biol* (Camb). 2017, 22;9 (5): 436-443. doi: 10.1039/c7ib00032d).

In this study, cell viability assay discovered RPE atrophy in BCD cellular model. Exposure to (blue) light caused significantly higher cell death in BCD patients' iPS-RPE samples than in controls' samples. Clinical phenotype of BCD (i.e., RPE atrophy) is evident in BCD cellular model. AAV.CYP4V2 demonstrated efficacy in rescuing RPE atrophy in BCD cellular model.

D. Applications of BCD Cellular Model

In addition to assessing cellular level phenotype associated with BCD, the BCD Cellular Model can be used for other applications of a disease model, including without limitation, drug screening, developing therapeutic agents or devices, determining dosage ranges, safety and toxicity testing, testing different formulations for BCD or other conditions related to CYP4V2, or the study of CYP4V2 functions and uses, including without limitation, developing and screening drugs comprising or expressing CYP4V2 protein, e.g., CYP4V2 gene therapy. Further, the BCD patient-specific iPS-RPE (and other BCD patient-specific stem cell derived ocular cells, including without limitation, iPS-photoreceptor cells, iPS-corneal cells) can be used as cell therapy, either in unmodified form or after genetic repair (e.g., by gene transfer or gene editing as described herein). The Examples section provides examples of non-limiting examples of applications of BCD Cellular Model.

E. Methods of Screening Compounds

Significantly, the iPSC-RPE cell lines described herein can provide human cellular disease models (e.g., BCD, retinitis pigmentosa, IRD). Such iPSC-RPE cells, iPSC-CEC cells or iPSC-PRC cells, which can be collectively referred to as "iPSC-ocular cells," can be used for diagnosing, prognosing, predicting the disease onset, severity and progression rate of a BCD patient or of a retinitis pigmentosa patient or of a patient having another type of inherited retinal disease. For example, such iPSC-ocular cell lines also can be used to screen test compounds for those that might have therapeutic efficacy for treating or preventing diseases associated with genetic or epigenetic alterations in a CYP4V2 nucleic acid (e.g., BCD).

The pluripotent cells described herein, particularly those produced from a subject having a genetic or epigenetic alteration in CYP4V2 or a subject that has an eye disease (e.g., BCD), can be used as a research tool in methods to identify compounds that are therapeutic candidates for treatment, diagnosis, prognosis or prevention of the eye disease (e.g., BCD). It would be understood that the test compounds can be any type of compounds. They may be of natural origin or may have been produced by chemical synthesis. They may be a library of structurally defined chemical compounds, of non-characterized compounds or substances, or a mixture of compounds. It would be appreciated by a skilled artisan that test compounds can be, without limitation, nucleic acids or analogs thereof, polypeptides or analogs thereof, antibodies, chemicals, and small molecules.

The cells described herein, in the presence or absence of a test compound, can be evaluated for their ability to grow and function in an animal model (e.g., in the eye of an animal model) and for their propensity, or lack of propensity, to form tumors. A number of methods can be used to evaluate the cells including, without limitation, PCR techniques, immunoassays, and/or lipid/fatty acid metabolism analyses.

42

Methods and Compositions for Cell Therapies

As discussed herein, CYP4V2 gene therapy demonstrated efficacy in correcting the biochemical abnormalities in BCD patient-specific iPS-RPE cells. However, a prerequisite for gene therapy to work in vivo is that the subject still has some RPE and photoreceptor cells remaining in the eye being treated. For late-stage BCD patients who have few or no RPE cells or photoreceptor cells left in the eye, cell therapy can be used as an alternative or in combination with gene therapy as a treatment option.

Cell therapy involves transplanting new cells to replace the dead or degenerated cells. For BCD, the new cells can be RPE cells, photoreceptor cells (cone and/or rod), photoreceptor progenitor cells, choroid cells, corneal epithelial cells, lens cells or other types of ocular cells, depending on which type of cells have shown degeneration and need a replacement in the subject. The following description and Examples herein used iPS-RPE cells to illustrate the methods and processes. They can be applied to other type of ocular cells.

Cell therapy for BCD and other types of ocular diseases including without limitation, inherited retinal diseases (IRD), retinitis pigmentosa (RP), macular degeneration (including age-related macular degeneration (AMD)), can be categorized as follows.

(1) Allogenic transplantation:

In one embodiment, RPE cells, PRCs, CECs, CE cells and other ocular cells derived from embryonic stem cells (ESC) or iPSCs from a healthy donor can be used in allogenic transplantation as cell therapy for BCD. It involves differentiating a healthy ESC or iPSC from a healthy individual (i.e., one without CYP4V2 mutations) into RPE cells and transplanting such ESC-RPE cell to a BCD patient's eye. Methods to reprogram iPSC and differentiate ESC or iPSC to RPE are provided herein the Examples section. In a prior study, embryonic stem cell (ESC) derived RPE cells have been used to treat age-related macular degeneration (AMD), see, Schwartz et al., *Investigative Ophthalmology & Visual Science* April 2016, Vol. 57, ORSFc1-ORSFc9. The pros of an allo-graft or allogenic transplantation is that it is less expensive than autologous transplantation because one common source can be used to treat multiple patients. However, it has significant downside such as immune rejection by the host subject may significantly affect its efficacy and duration. In addition, it requires long-term immunosuppressant which may lead to severe systemic side effects. Finally, the use of ESC can give rise to ethical concerns.

(2) Autologous Transplantation without Genetic Repair:

In one embodiment, autologous cells can be used in cell therapy for BCD. One such autologous source is iPS cells and iPS-RPE cells derived from a BCD patient, which can be transplanted to such BCD patient's eye. BCD is a relatively late onset disease. Symptom in BCD patients are usually developed in the 2nd, 3rd or even 4th decade of life. In addition, iPS reprogramming process have some degree of "reset the clock" effect on the iPS cells and cells derived from the iPS cells. Therefore, the iPS-RPE cells and other iPS-ocular cells derived a BCD patient can be used as a cell therapy for transplantation to the BCD patient even without any genetic repair of the CYP4V2 mutations in the iPS-RPE cells. iPS reprogramming and RPE differentiation methods are provided in the Examples section herein. As a precaution, whole genome sequencing can be performed to compare the genomic DNA in the iPS or iPS-RPE cells and the genomic DNA in the source cell (e.g., fibroblast or blood cell) whether there is any disease causing mutations was created during the iPS reprogramming and RPE differentiation process.

(3) Genetically Repaired Patient Autologous Cells for Cell Therapy for BCD and Other Types of IRDs and RPs The disclosure herein provides methods and compositions for generating genetically repaired autologous cells for cell therapy. As used herein, "genetically repaired" or "genetic repair" refers to correction of the CYP4V2 mutations through either gene editing of the patient's genome (e.g., directly on the chromosome using, e.g., CRISPR/Cas9, CRISPR/Cpf1, Zinc Finger, TALEN), or through gene transfer of a healthy copy of the CYP4V2 gene (cDNA, RNA or other form) into the patient cell, which typically does not integrate into the genome (e.g., the CYP4V2 gene therapy as described here) or correcting or compensating for the defective mRNA in the patient's cell.

As a disease caused by genetic mutations, the autologous cells for use in cell therapy for BCD or another IRD or RP ideally should have its genetic defects (i.e., the CYP4V2 mutations) and/or its dysfunctional CYP4V2 protein repaired before transplantation. In one embodiment, such genetic repair can be achieved by gene transfer therapy as discussed herein, including without limitation, an AAV-mediated gene therapy transfer of a nucleic acid sequencing encoding and expressing a functional CYP4V2 protein. Compositions and methods of CYP4V2 gene transfer therapy are provided here in, see detailed description herein and the Examples section. BCD patient-specific source cell, iPS or iPS-RPE cells can be treated by AAV.CYP4V2 (as provided herein), followed by iPS reprogramming and/or RPE differentiation (if applicable) and verification of improved biochemical functions (as provided herein), and then be transplanted to the same patient's eye. In another embodiment, such genetic repair can be achieved by gene editing, e.g., correcting the CYP4V2 mutation(s) in the genome or RNA in the cells of the BCD patient. In addition to being applied in vitro as a part of a cell therapy, such gene editing can also be applied directly in vivo as a gene therapy. Such gene editing can be performed on the patient's source cell (e.g., fibroblast or blood cell), iPS, iPS-RPE or other types of iPS-ocular cells. iPS reprogramming and RPE differentiation to generate the patient-specific iPS and iPS-RPE can be performed either before or after the genetic repair (e.g., gene transfer therapy or gene editing).

The disclosure herein provides compositions and methods to correct a CYP4V2 mutation through gene editing. The description in the Examples section herein illustrates the compositions and methods using a CRISPR/Cas9 construct to correct the c. 802-8_810del17insGC mutation, the most common mutation among BCD patients. it can also apply to other gene editing methods (e.g., CRISPR/Crp1, TALEN, Zinc finger) and other IRD mutations (e.g. without limitation, other CYP4V2 mutations in Table 1) in combination with methods known in the art.

The most common CYP4V2 mutation among BCD patients is c. 802-8_810del17insGC (referring to a 17 base deletion with two bases (GC) inserted in the place starting 8 bases from the end of intron 6 of CYP4V2 gene, also referred to as IVS6-8 del/insGC, See SEQ ID NO: 46 showing sequence of the human CYP4V2 genomic DNA region comprising the c.802-8_810del17insGC mutation and SEQ ID NO: 47 showing the corresponding wild-type sequence. The c. 802-8_810del17insGC mutation is illustrated in the following sequence which shows human CYP4V2 intron 6-exon 7 junction. Intron 6 sequence is shown in lower case and exon 7 sequence in CAP letters. The 17 bps deletion and the insertion of GC are in brackets): caa aca gaa gca tgt gat tat cat tca aa (tca tac agG TCA TCG CT) (GC) GAA CGG GCC AAT GAA ATG AAC GCC AAT GA) (SEQ ID NO: 46) resulting in the predicted skipping of exon 7. (Xiao et al., *Biochem Biophys Res Commun.* 409: 181-6, 2011; Meng et al., 2014, *Mol. Vis.,* 20:1806-14; Wada et al., *Am J Ophthalmol.* 139:894-9, 2005; Jiao et al., *European Journal of Human* Genetics (2017) 25, 461-471). A recent study estimated that the age of the c.802-8_810del17insGC mutation was to be 1,040-8,200 generations in the Chinese and 300-1100 generations in the Japanese populations. See Jiao et al., *European Journal of Human Genetics* (2017) 25, 461-471.

Cell therapy (also known as cellular therapy or cytotherapy) can be used as described herein to treat or prevent an eye disease in a subject. As described herein, BCD, certain RP, IRD and other eye diseases referred to herein are associated with a genetic or epigenetic alteration in a CYP4V2 nucleic acid sequence.

Cell therapy generally involves injecting, implanting, transplanting, or otherwise delivering a composition that includes cells to a subject (e.g., into a tissue or organ of a patient (e.g., an eye)). The methods described herein are unique because they allow genetically repaired autologous cell therapy of a subject having an eye disease.

Methods are described herein that include obtaining cells from a subject having an eye disease (e.g., associated with a genetic or epigenetic alteration in a CYP4V2 nucleic acid sequence) and repairing the mutation(s) within the CYP4V2 nucleic acid (e.g., DNA or RNA) using, for example, gene editing, or repairing via delivering a nucleic acid sequence encoding a functional CYP4V2 protein (e.g., gene transfer). The cells can be made pluripotent (e.g., by inducing pluripotency, e.g., to make iPSCs) and be differentiated into one or more ocular cells (e.g., iPS-RPE, iPS-CECs, iPS-PRCs) prior to administration back into the subject (e.g., into the eye of the subject). It would be appreciated that the cells can be genetically repaired prior to or after being made pluripotent, or after being differentiated into the ocular cells.

A. Origination of Cells

In some instances, autologous cells (e.g., subject (e.g., patient)-specific cells) can be used in the cell therapy methods described herein. For example, cells such as fibroblasts or peripheral blood mononuclear cells (PBMCs) can be obtained from a subject and used to produce iPSCs as described in the Examples section. Virtually all types of cells can be used to generate iPSCs and therefore can be used as source cells. In some instances, cells obtained from urine (see, e.g., Zhou et al., 2012, Nat. Protoc., 7:2080-9) or hair follicles or dermal papilla cells (see, e.g., Muchkaeva et al., 2014, Acta Naturae, 6:45-53) can be used to produce iPSCs.

B. Inducing Pluripotency

Methods of making induced pluripotent stem cells (iPSCs) are known in the art. Briefly, iPSCs can be made by introducing a particular set of proteins (e.g., nucleic acids encoding a particular set of proteins) into cells. It would be understood by the skilled artisan that one exemplary, non-limiting method is by introducing one or more transgenes encoding OCT4, SOX2, KLF4, c-MYC (e.g., the "Yamanaka factors"). In some embodiment, the reprogramming uses all four transcription factors. In some embodiment, one, two or three transcription factors can be used. Li et al., Stem Cells, 2009; 27:2992-3000. Zhu et al., Cell Stem Cell 2010; 7:651-655. In some embodiments, iPSCs can be generated by direct delivery of the reprogramming proteins. Kim et al., Cell Stem Cell. 2009; 4 (6): 472-6. The Examples section provides method for producing iPSCs using non-integrating methods, e.g., by Sendai virus (Example 1), or by episomal methods (Example 2). Any method of producing iPSCs, however, is contemplated within the scope of this disclosure.

Various methods (e.g., Sendai virus, episomal method, with or without small molecules) can be used to generate iPSCs, see Examples section, see also, for example, Hubbard et al., J. Vis. Exp., 2014, 92:52009. In addition, methods of making iPSCs from a number of different cell types are known in the art. See, for example, Hayashi et al., 2012, PLOS One, 7 (9): e45435; Poon et al. 2015, PLOS One, 10 (7): e0131288; Lamba et al. 2010, *PLOS One,* 5 (1): e8763. Typically, iPSCs express detectable levels of at least one marker including, without limitation, Oct-4, Sox-2, SSEA4, TRA-1-60, TRA-1-81, AP and/or NANOG.

Any type of stem cells can be used in the cell therapy methods described herein including without limitation, induced pluripotent stem cells (iPSCs), hematopoetic stem cells (HSCs), embryonic stem (ES) cells, mesenchymal stem cells, adult stem cells, or tissue-specific stem cells. Stem cells for use in the methods described herein can be pluripotent, multipotent, or totipotent stem cells.

As used herein, the term "pluripotent" refers to a cell capable of at least developing into one of ectodermal, endodermal and mesodermal cells. In one embodiment, the term "pluripotent" refers to cells that are totipotent and multipotent. As used herein, the term "totipotent" cell refers to a cell capable of developing into all lineages of cells. As used herein, the term "multipotent" refers to a cell that is not terminally differentiated. The pluripotent cells of the present invention can be any stem cells or produced from non-pluripotent cells, such as fibroblasts, using induction, de-differentiation and nuclear transfer methods known in the art. The pluripotent cells described herein, whether stem cells or produced from non-pluripotent cells, can be from a subject having BCD or having CYP4V2 mutations or a healthy individual.

iPSCs can be characterized by one or more of the following: a. the unique morphology of iPSC; b. one or more pluripotency markers, such as Oct-4, Sox-2, SSEA-4, TRA-1-60, TRA-1-81, Nanog and AP; c. the ability to differentiate into the desired cell type (e.g., RPE cells), and/or d. a terotoma assay. Not all of the above are necessary for characterizing iPSCs and validating pluripotency (e.g., teratoma; see, e.g., Buta et al., 2013, *Stem Cell Res.,* 11 (1): 552-562).

C. Gene Editing

A number of gene editing technologies can be used in the methods described herein to repair a genetic or epigenetic alteration present in the CYP4V2 nucleic acid of a subject. Gene editing can be performed using any number of technologies including clustered regularly interspaced short palindromic repeats (CRISPR) technology (see, for example, U.S. Pat. Nos. 8,697,359; 8,889,418; 8,999,641; and US 2014/0068797), transcription activator-like effector nucleases (TALEN) technology (see, for example, Li et al., 2011, Nucleic Acids Res., 39 (14): 6315-25) or zinc-finger nuclease technology (see, for example, Wright et al., 2005, The Plant J., 44:693-705).

To accomplish gene editing using CRISPR technology, nucleic acids encoding a nuclease (e.g., oftentimes a Cas9 nuclease but other nucleases (e.g., other Cas nucleases, e.g., Cpf1, or non-Cas nucleases) also can be used) can be incorporated into one or more vectors and administered to a subject as described herein. Simply by way of example, the cells described herein (e.g., subject cells prior to reprogramming to iPSCs, subject iPSCs prior to differentiation into RPE, corneal epithelial cells or photoreceptor cells, or after differentiation into RPE, corneal epithelial cells or photoreceptor cells (referred to herein as "iPSCs-RPE," "iPSC-CEC," or "iPSC-PRC")) can be transduced or transfected with one or more constructs (e.g., vectors, RNP, mRNAs) containing and/or encoding at least one guide RNA (gRNA), at least one CRISPR-associated protein (e.g., Cas9 or Cpf1), and at least one donor template nucleic acid. In some embodiments, the donor template nucleic acid is not required, e.g., when the genetic repair is achieved through knock out.

Similarly, to accomplish gene editing using TALEN technology, a nucleic acid encoding a TALEN (e.g., dimeric transcription factor/nuclease) can be incorporated into a vector and administered to a subject as described herein. Likewise, to accomplish gene editing using zinc-finger nuclease technology, a nucleic acid encoding a custom DNA endonuclease (e.g., a heterodimer in which each subunit contains a zinc finger domain and a FokI endonuclease domain) can be incorporated into one or more vectors and administered to a subject as described herein.

The components necessary to perform each of these technologies are available commercially and are customizable to the particular target sequence(s). See, for example, Caribou Biosciences; GenScript; CRISPR Therapeutics; Editas Medicine; Cellectis Bioresearch; Life Technologies; Sangamo BioSciences; or Sigma Aldrich Chemical Co.

Under the appropriate circumstances, gene editing can occur such that the genetic or epigenetic alteration in a subject's CYP4V2 nucleic acid is repaired and as a result a functional CYP4V2 protein is expressed. A CYP4V2 nucleic acid sequence has been repaired when the presence of the CYP4V2 nucleic acid (e.g., the CYP4V2 mRNA) is restored, the presence of the CYP4V2 protein is restored, or the function of the CYP4V2 protein is restored. Similarly, "repaired," or "corrected," can refer to a restoration of the affected sequence (e.g., the genetic or epigenetic alteration) to the wild type sequence or to another non-mutant sequence as described herein.

There may be some instances when it is desirable to introduce, using gene editing, one or more mutations into a cell (e.g., in the CYP4V2 nucleic acid). This is a way in which a cellular model of disease (e.g., BCD) can be created. For example, gene editing can be performed on embryonic stem cells (ES cells) to create cell lines with artificial CYP4V2 mutations, which then can be differentiated into RPE cells. Alternatively, gene editing can be performed on iPS cell lines from a healthy subject (e.g., a non-BCD subject) or on an RPE cell line (e.g., ARPE-19 cell line) to create CYP4V2 mutant iPS or RPE cell lines.

In some instances, it is desirable to screen the cells (e.g., using whole genome sequencing) after the gene editing steps are complete to confirm that the targeted mutation has been repaired and that no significant off-target editing occurred.

CRISPR and the CRISPR-associated protein 9 (Cas9), known as CRISPR-Cas9, consisting of an RNA-guided nuclease (Cas9) and a guide RNA, generates site-specific DNA breaks, which are repaired by endogenous cellular mechanisms. Possible outcomes of the approach include mutating a specific site through mutagenic non-homologous end-joining (NHEJ), creating insertions or deletions (indels) at the site of the break, and precise change of a genomic sequence through homologous recombination (HR) using an exogenously introduced donor template. The CRISPR guide RNA is composed of two RNAs termed CRISPR targeting RNA (crRNA, also referred to herein as CRISPR RNA) and trans-activating crRNA (tracrRNA). The crRNAs are typically about 20 nucleotides (nt) long. It hybridize to a target DNA sequence by Watson-Crick base pairing and guide the Cas endonuclease to cleave the target genomic DNA.

To genetically repair the most common CYP4V2 mutation via gene editing, various CYP4V2 mutation CRISPR correction constructs were developed (See the Example section). CRISPR was used because it is simpler to implement and edits at higher efficiency than other forms of gene editing, such as TALENs and zinc finger nucleases. The CRISPR constructs contain optimized and in vitro validated gRNA sequences and different construct options that can be readily used to correct the c.802-8_810del17insGC mutation in BCD patient cell lines, resulting in genetically repaired cells that can be used in cell therapy, including without limitation, autologous cell therapy, for BCD.

CRISPR gene editing therapy involves the use of a CRISPR associated protein (Cas) which is a nuclease and a CRISPR guide RNA. The role of the CRISPR guide RNA is to guide Cas to the sequence that is targeted by the CRISPR guide RNA via a protospacer element contained in the CRISPR guide RNA that is complementary (or specific to) the target sequence. For Cas (e.g., Cas9 or Crf1) to bind to and cleaves at or close to the target sequence, a protospacer adjacent motif (PAM) sequence also needs to be present. A PAM sequence is a short stretch of DNA (typically 2-6 nucleotides) that serves as a binding signal for Cas. Different Cas can have different PAM and cleavage pattern. For example, for *Streptococcus pyogenes* Cas9 (SpCas9), the canonical PAM sequence is NGG. For *Staphylococcus aureus* (SaCas9), PAM sequence is NGRRT or NGRRN. For *Neisseria meningitidis* (NM) and *Treponema denticola* (Td), the PAM sequence is NNNNGATT and NAAAAC, respectively. Engineered or mutated Cas can also result in altered PAM sequence. For example, SpCas9 VQR variant (D1135V, R1335Q and T1337R)'s PAM sequence is NGAN or NGNG. SpCas9 EQR variant (D1135E, R1335Q and T1337R)'s PAM sequence is NGAG. SpCas9 VRER variant (D1135V, G1218R, R1335E and T1337R)'s PAM sequence is NGCG. For Cpf1, the PAM sequence is TTTN. Typically Cas generates a double-stranded break (DSB) but altered Cas can result in a single-stranded break (e.g., SpCas9 Nickase (Cas9n D10A)) or no break (dCas9). Whereas Cas9 generates blunt ends 3 nt upstream of the PAM site, Cpf1 cleaves in a staggered fashion, creating a 5 nucleotide 5' overhang 18-23 bases away from the PAM.

The CRISPR guide RNA for Cas9 typically comprises a CRISPR RNA (crRNA) and a trans-activating crRNA (tracrRNA). The crRNA comprises a protospacer element sequence that is designed to be complementary (or specific) to a targeted sequence within to close to the gene targeted for correction, disruption or replacement, and a sequence that corresponds to a complementary region of the tracrRNA. The tracrRNA which comprises a region that is complementary to corresponding region of the crRNA and a sequence which interacts with the CRISPR-associated protein 9 (Cas9). No tracrRNA is required for Cpf1.

The length of protospacer element is typically about 20 nucleotides. Longer or shorter protospacer element sequence (about 16-24 nt) can also be used. The protospacer element can be 100% complementary to the target sequence or can contain mismatches to the target sequence. In some embodiments, a "G" nucleotide can be optionally added at the start the protospacer element sequence.

After a DNA molecule is cleaved by Cas, it can be repaired by one of two ways. An error-prone non-homologous end joining (NHEJ) repair can result in an indel mutation that can disrupt protein function encoded by the gene. NHEJ can be used to create artificial mutations in a cell line. In some embodiments, it can be used to create mutations in the CYP4V2 gene (e.g., an indel in an exon or a splice acceptor region) of a cell line (e.g., an ES cell, an iPS cell or an ARPE-19 cell line) with no endogenous CYP4V2 mutations and thereby generating a disease cellular model (e.g., a BCD cellular model). In addition, two more CRISPR guide RNAs can be used together to knock out a targeted region of a target gene or the entire target gene thereby generating a knockout model. In some embodiments, CRISPR based gene silencing is used to disrupt (or silence) or defective gene, e.g., in treating a dominant genetic disease. During gene silencing, the cell attempts to repair the broken DNA, but NHEJ often does so with errors that disrupt the gene hence effectively silencing it. In some embodiments, NHEJ may also result in correction of a mutation, e.g., especially when the mutation is a single nucleotide variation or of no more than about 10 nucleotides. Alternatively, if a donor nucleic acid sequence are available, the DNA break can be repaired by homology-directed repair (HDR) for correction or replacement of the target gene. A donor nucleic acid sequence can be provided in the form of a single-stranded DNA (ssDNA, or a single-stranded oligo DNA nucleotide (ssODN) or a vector. In some embodiments, the donor nucleic acid sequence is no more than about 1 kb, 800 bp, 600 bp, 500 bp, 400 bp, 300 bp, 280 bp, 260 bp, 240 bp, 220 bp, or 200 bp for a donor nucleic acid sequence provided in a ssODN. In some embodiments, the donor nucleic acid sequence is no more than about 25 kb, 20 kb, 15 kb, 10 kb, 9 kb, 8 kb, 7 kb, 6 kb, 5 kb, 4.5 kb, 4 kb, 3.5 kb, or 3 kb for a donor nucleic acid sequence provided in a vector. In some embodiments, a donor nucleic acid sequence is symmetrical. In some embodiments, a donor nucleic acid sequence is asymmetrical. In some embodiments, the length of a donor nucleic acid sequence can be adjusted for higher HRD rate. In some embodiments, if the PAM targeted by the Cas used in the CRISPR gene editing is also present in the donor nucleic acid sequence, it can be mutated (change to a different nucleotide) so that the PAM no longer exists in the donor nucleic acid sequence to avoid the donor template or the DNA sequence repaired by the donor template being cleaved and destroyed by Cas. In addition to correcting or replacing a mutated or defective gene or a portion thereof, HDR can also be used to create artificial mutation(s) in the CYP4V2 gene (e.g., inserting mutation in an exon or a splice acceptor region) of a cell line (e.g., an ES cell, an iPS cell or an ARPE-19 cell line) with no endogenous CYP4V2 mutations and thereby generating a disease cellular model (e.g., BCD cellular model).

The CRISPR guide RNA and Cas used in CRISPR gene editing therapy can be provided in a vector (e.g., a plasmid (e.g, pX330, pX458, pX459), a recombinant AAV vector or a recombinant lentivirus vector) or an mRNA encoding such component(s) and/or RNA and protein form.

The donor template can be provided in a ssDNA (e.g., ssODN) or cloned in a plasmid or other typess of vectors (e.g., an AAV vector (e.g., AAV2 or AAV6) for use in HDR.

Various compositions and methods can be used to improve the on-target editing or repair efficiencies and/or to lower the potential off-target. For example, different Cas (e.g., Cas9 or Cpf1) or Cas of different species (e.g., SpCas9, SaCas9, NMCas9) or variants (SpCas9, SpCas9 VQR) can be used to broaden the PAM selections available for a target sequence thereby enhancing specificity. If a target sequence region lacks the NGG PAM site for SpCas9 but is AT-rich, Cpf1 can be considered instead. Cas9 nickase (e.g., Cas9 D10A) only generates a single-strand break in the target DNA and therefore requires two pairing CRISPR guide RNAs to generate a double-strand break. This requirement dramatically increases target specificity, since it is unlikely that two off-target nicks will be generated within close enough proximity to cause a DSB. Furthermore, asymmetrical donor template may enhance HDR rate. Catalytically inactive dCas9 does not cut target DNA but can still attain a sequence replacement without any of the error-prone repair that normally accompanies Cas9 cutting. See, Richardson et al., Nature Biotechnology 34, 339-344 (2016).

Achieving targeted gene correction and in the meantime avoiding or minimizing off-target editing are the two objectives of gene editing. Prior research has revealed the off-target mutations caused by gene editing technologies, including without limitation, CRISPR and TALEN, see, e.g., Tsai et al, Nature Biotechnology 33, 187-197 (2015); Wang et al., Nature Biotechnology 33, 175-178 (2015); Wu, W. H. et al. CRISPR repair reveals causative mutation in a pre-clinical model of retinitis pigmentosa. Mol. Ther. 24, 1388-1394 (2016). For gene editing used in vivo, or in cell therapy (e.g., in vitro in cells first and then transplanting the cells in vivo), the second objective, avoiding or minimizing off-target editing is as important as achieving targeted gene correction because off-target editing may cause disease or induce tumor formation. It should be noted not all off-target editing can be predicted by computer software or algorithm.

Therefore, a careful design, validation and improvements were employed in developing and validating the CYP4V2 mutation CRISPR gene correction constructs:

(1) Multiple gRNA candidates were generated based on the mutant CYP4V2 nucleic acid sequence which contains the c.802-8_810del17insGC mutation (2) Top 5 gRNAs were selected using the following criteria (See SEQ ID NOs: 48-52, Table 5 and FIG. 12):
   a. The proximity of the gRNA cleavage site to the modification site, and
   b. The off-target profile of the gRNA;

(3) The activity of the top 5 gRNAs were validated in the genomic DNA of a BCD patient with homozygous c.802-8_810del17insGC mutations (See FIG. 13);

(4) Based on (2) and (3), three gRNAs were selected. Each of the 3 gRNAs was cloned into a pX459 plasmid together with nucleic acid sequences encoding Cas9 and puromycin resistance gene (Puro) for transfected cell selection using puromycin (See FIG. 15).

(5) Two donor templates (both forward and reverse complementary) providing HDR donor nucleic acid sequence were generated. The ssODNs contaning the donor template sequences were synthesized by IDT (See SEQ ID NO: 56 and 57).

(6) In addition to plasmid constructs, a CRISPR RNP construct was developed. A RNP construct offers certain advantages over other constructs. A detailed discussion is provided below and in the Examples section.

(7) The CYP4V2 CRISPR correction constructs are validated in iPS cells derived from a BCD patient with homozygous c. 802-8_810del17insGC mutations.

(8) Whole genome sequencing is performed in unmodified cells and iPS cells genetically repaired by the CYP4V2 mutation CRISPR correction constructs to confirm the correction of the c.802-8_810del17insGC mutation and to assess off-target edits.

Methods to determine the optimal conditions for transfection in iPSCs and to select for transfected cells are provided. See the Examples section for detailed description. It is contemplated that these constructs can be used in treating not only BCD patient-specific iPS cells in vitro, but also the source cells (e.g., fibroblasts or PBMCs) or iPS- RPE, iPS-PRC, iPS-CE cells or iPS-CEC cells or other ocular cells derived from BCD patient-specific iPS cells in vitro, as well as in vivo in patients with the c.802-8_810del17insGC mutation. In one embodiment, the components of the constructs can be used directly. In some embodiments, the components in the construct can be modified, or cloned into a different vector to achieve higher transduction efficiency in vivo or higher specificity to the target cell type or to achieve other purposes. For example, Cas9 can be modified to Cas9 nickase (Cas9n D10A), which contains a mutation allowing the endonuclease to create single-strand nicks, as opposed to double-stranded breaks. Pairing two opposite facing gRNA sequences with SpCas9 nickase is an efficient method of gene editing that prevents unwanted indels from forming. In addition to plasmids, other common vectors used to package CRISPR components include lentivirus vectors and adeno-associated virus (AAV) vectors. When using AAV vectors, the *Staphylococcus aureus* Cas9 orthologue (SaCas9) may be used as the endonuclease because SaCas9 is approximately 1 kb shorter than SpCas9, and offers additional flexibility around AAV packaging constraints.

Various improvements were made to the CRISPR RNP construct. Instead of IVT sgRNA or a crRNA: tracrRNA duplex, a synthetic sgRNA was used. Synthetic gRNAs have higher purity than IVT sgRNAs and therefore lower the risk of off-target editing caused by impurities in sgRNA. In addition, chemical modification is applied to the sgRNA to protect the sgRNA from intracellular degradation, which can increase editing efficiency. See Examples section for more details.

It is contemplated that, in addition to the plasmid constructs and CRISPR RNP constructs described herein, a mRNA construct comprising a Cas9-encoding mRNA and a guide RNA oligonucleotide also can be used.

After BCD patient-specific iPS cells are transfected with the CYP4V2 mutation CRISPR correction constructs the transfected cells are selected using puromycin. It should be understood that other markers, such as GFP, can be incorporated into the constructs and used as a marker in lieu of or in addition to puromycin. Following selection, single cell cloning is carried out, after which some cells from the single cell clone are harvested for sequencing. After sequencing results confirm successful on-target gene editing and no disease-causing gene edits are found, the remaining cells of the same clone are used for differentiation into the desired ocular cell type, e.g., iPS-RPE cells.

D. Differentiation of iPSCs

The genetically repaired BCD patient iPS cells are differentiated into iPS-RPE cells (or another type of ocular cells (e.g., iPS-CEC, iPS-CE cells or iPS-PRC). Methods for differentiating iPSCs into RPE cells or another type of ocular cell (e.g., CEC and PRC) are known. See, for example, Hayashi et al., 2012, *PLOS One,* 7 (9): e45435; Songstad, et al., *Investigative Ophthalmology & Visual Science* December 2015, Vol. 56, 8258-8267; and Lamba et al., *PLOS One.* 2010 Jan. 20;5 (1): e8763. For example, induced pluripotent stem cells (iPSCs) reprogrammed from cells can be produced and further differentiated into, for example, RPE cells (referred to herein as "iPS-RPE"), corneal epithelial cells (referred to herein as "iPS-CEC"), photoreceptor cells (or photoreceptor progenitors; referred to herein as "iPS-PRC"), or iPS-choroidal endothelial (CE) cells (referred to as "iPS-CE").

Differentiated cells, e.g., iPS-RPE cells, is tested for its biochemical functions (as described in the Examples section) to confirm it has improved biochemical functions as compared to iPS-RPE cells of the patient without genetic repair.

The iPSC-RPE cell lines produced as described herein exhibit the morphology (e.g., pigmentation and hexagonal shape) and/or expresses one or more biomarkers that are indicative of RPE cells. Biomarkers for RPE cells (and iPS-RPE cells) are known and include, without limitation, one or more of RLBP1 (a/k/a CRALBP), RPE65, BESTRO-PHIN-1, MITF, VINCULIN, LRAT, RDH5, PAX6, MERTK, TYR, and/or ZO-1, and can be used to determine or confirm that RPE differentiation has taken place. Similarly, biomarkers for CECs (and iPS-CECs) and PRCs (and iPS-PRCs) are known and include, for example, cytokeratin 12 and cytokeratin 3 for corneal epithelial cells; and Crx for photoreceptors, recoverin for rods and cones, and Nrl for rods.

E. Administration/Delivery

The genetically repaired iPS-RPE cells can be used in autologous transplantation to the patient from whom the iPS-RPE cells are derived. Patients with BCD or another ophthalmological condition due to CYP4V2 mutations can be treated by the cell therapy methods provided herein. Similarly, the method can be used to provide a genetically repaired autologous cell therapy for other ocular diseases caused by one or more genetic mutations.

Methods of administering or delivering cells are known, and methods of administering or delivering cells to the eye are known. see, e.g., Wert et al., *J Vis Exp.* 2012; (69): 4286; WO 2016/179496; Schwartz et al., *Investigative Ophthalmology & Visual Science* April 2016, Vol. 57, ORSFc1-ORSFc9. In one embodiment, the ocular cell can be transplanted via injection of cell suspension, e.g., suspension of RPE cells. In another embodiment, the cells can be transplanted as part of a sheet or scaffold, e.g., an in vitro tissue using natural and/or synthetic scaffolds to generate a polarized functional RPE monolayer.

The therapeutically effective amount of cells administered to the eye is known to those of skill in the art and will vary with the type of cells being transplanted, the maturity of the cells being transplanted and whether it is expected to divide post transplantation, the size of the area or number of cells targeted for replacement, and the subject being treated (e.g., the age, sex, weight, development stage of the disease and condition of the subject to be treated); the route of administration; and the required regimen. The therapeutically effective amount of cells used in ocular cell therapy can range from about $1*10^3$ to about $1*10^8$ cells in a single administration.

While iPSC cell lines can be generated for individual subjects, a cell bank of iPSCs having common HLA haplotypes (or in which the HLA haplotype has been genetically manipulated) can be generated, which would be designed to achieve immunologic matching with a large portion of the patient population. See, for example, Turner et al., *Cell Stem Cell*, 13:382-384, 2013. In addition, an iPSC cell line can be generated that is immunologically silent irrespective of the subject's genotype (see, for example, Riolobos et al., *Mol. Ther.*, 21:1232-41, 2013). When combined with these methods, the patient-specific iPS cells and iPS-ocular cells can be used not only in a strict autologous sense, but can also be used for transplantation to other patients.

Typically cell therapy administering step takes place after the onset of disease symptoms or after the subject has shown signs of retinal degeneration or corneal dystrophy, as applicable. In one embodiment, ocular cell therapy provided herein can be used independently in treating an ocular disease (e.g., BCD). In another embodiment, ocular cell therapy provided herein can be used in combination with one or more other treatment options, including without limitation, the CYP4V2 gene transfer therapy and/or CYP4V2 CRISPR gene editing therapy provided herein.

Similarly, administration can occur once, or a plurality of times (e.g., over several weeks, months, or years) and can be applied to the same eye or to the contralateral eye. Further, one or more types of cells can be administered in a single or separate administrations.

Post-treatment assessment can use methods described in the CYP4V2 Gene Therapy section herein, including without limitation, through eye exams such as visual function, e.g., as measured by visual acuity, visual field, dark adaptation, visual function and/or Optical Coherence Tomography (OCT, e.g., Spectral Domain-OCT (SD-OCT)) and ERG.

Methods of Using CRISPR RNP in Ocular Cell Therapy and Gene Therapy

CRISPR RNP is a gene-editing ribonucleoprotein (RNP) complex that includes a guide RNA complexed with a Cas protein (e.g., Cas9 protein). The guide RNA is made up of two RNAs termed CRISPR RNA (crRNA) and trans-activating crRNA (tracrRNA). In one embodiment, the crRNA and the tracrRNA are provided as two separate nucleic acid molecules. In another embodiment, the crRNA and tracrRNA can be combined in a chimeric single guide RNA (sgRNA). The sgRNAs can be about 100 nucleotides (nt) in length, or shorter or longer as desired or necessary. Twenty nt at the 5' end (crRNA) hybridize to a target DNA sequence by Watson-Crick base pairing and guide the Cas endonuclease to cleave the target genomic DNA, with the remaining double-stranded structure at the 3' side for Cas9 recognition.

CRISPR RNPs have pros and cons as compared to traditional Cas9/gRNA constructs (e.g., plasmid constructs which incorporate nucleic acid sequences the CRISPR guide RNA and Cas9 protein). For example, the guide RNA (crRNA and tracrRNA) and Cas9 protein can be delivered into target cells as intact complexes, overcoming the need for the cell's own transcription machinery to express the CRISPR components. As a result, CRISPR RNPs can edit quickly after transfection. In addition, the CRISPR components deplete quicker from cells, which can reduce the chance of off-target editing. Furthermore, it may reduce the chance of integrational mutagenesis caused by plasmids. Given these advantages, RNP can also be advantageous in in vivo gene editing. On the other hand, however, as RNP clears quickly from cells through protein degradation, it may have lower on-target editing efficiency than the plasmid constructs whose expression last longer in cells.

To evaluate the above hypothesis and to prove whether CRISPR RNP constructs can achieve both objectives of the gene editing desired in ocular cell therapy and gene therapy, two sets of constructs were designed. One construct is a plasmid construct and the other is a RNP construct. Both constructs use the same BCD patient's iPS cells for transfection, which are subsequently sequenced to analyze on-target genetic repair and off-target editing of each construct. Off-target editing are determined by comparing against genomic DNA from unmodified fibroblasts of the same patient. Results from both plasmid construct and RNP construct can be compared.

Detailed description of RNP, methods to form RNP and to use the RNP construct to generate genetically repaired cells (iPS and iPS-RPE cells) for a BCD patient, is provided in the Examples section.

It should be noted that a similar CRISPR RNP construct can be used to correct or inactivate other mutations of BCD and mutations of other RP and IRDs. In one aspect, the crRNA sequence used herein is changed to another crRNA sequence specifically targeting a different target mutation sequence. In another aspect, a guide RNA or a sgRNA in a RNP construct can be modified to enhance gene editing efficiency. See, Hendel et al, *Nat Biotechnol.* 2015 September; 33 (9): 985-989. In some embodiments, the CRISPR RNP constructs can be transfected using electroporation. In some embodiments, the CRISPR RNP construct can be transfected using lipofection or nucleofection. In some embodiments, the CRISPR RNP construct can be delivered via microinjection.

In addition to genetically repairing and treating patients' cells in vitro, CRISPR RNP constructs can also be used to treat an ocular disease caused by genetic mutations in vivo and have advantages over other types of CRISPR constructs (e.g., plasmids and/or mRNAs encoding the CRISPR components) for in vivo applications. For example, CRISPR RNP constructs have higher potency, lower off-target risk, and/or lower toxicity or innate immune response activation as compared to in vitro transcribed Cas9 mRNA and sgR-NAs. In one embodiments, CRISPR RNP constructs comprised of a Cas9 protein complexed with a guide RNA targeting the region of the mutant DNA sequence can be injected directly into the subject's eye (e.g., sub-retinal injection, intravitreal injection or to the cornea). In another embodiment, engineered variants of Cas9 with multiple SV40 nuclear localization sequences (NLS) which have shown increased editing efficiency in brain cells in vivo (Staahl et al., *Nat Biotechnol.* 2017 May; 35 (5): 431-434) can be used to achieve higher editing efficiency in ocular cells. Cas9 protein with one or multiple NLSs (at N-terminal and/or C-terminal) are commercially available at various CROs, such as IDT and Feldan. In some embodiments, the CRISPR RNP construct is delivered "as is." In some embodiments, the CRISPR RNP construct is formulated with a pharmaceutically acceptable carrier when delivered. In some embodiments, the CRISPR RNP construct is delivered in a packaged form, e.g., in a nanoparticle.

It would be understood that the ratio between the CRISPR RNP components, e.g., the guide RNA and Cas9 protein can be adjusted and optimized by testing different ratios in patient cell lines in vitro (e.g., BCD patient-specific iPS cells or iPS-RPE cells) before treatment in vitro or in vivo. The CRISPR RNP construct can be used independently or in combination with another CRISPR construct, including without limitation, a plasmid or vector encoding a CRISPR guide RNA or crRNA, or a Cas protein or a combination thereof; a Cas9-encoding mRNA; a guide RNA oligonucleotide; another CRISPR RNP construct; or a combination or hybrid thereof. In addition, the CRISPR RNP constructs can be used to correct or inactivate one or more than one mutations related to one or more than one ocular diseases.

Gene Therapy and Cell Therapy Combination Treatment

The disclosure herein provides multiple treatment options for BCD and other ocular diseases caused by CYP4V2 mutations, including without limitation, CYP4V2 gene transfer therapy and CYP4V2 CRISPR gene editing therapy. Both CYP4V2 gene transfer therapy and CYP4V2 gene editing therapy can be used either in vivo or in vitro or both in vivo and in vitro. When applied in vivo, CYP4V2 gene transfer therapy and/or CYP4V2 CRISPR gene editing therapy can treat remaining ocular cells affected by BCD as gene therapy. When applied in vitro in patient cells or patient derived cells, the cells treated by CYP4V2 gene transfer therapy and/or by CYP4V2 CRISPR gene editing therapy can be transplanted to the patient to replace died or degenerated ocular cells as cell therapy. Significantly, gene therapy and cell therapy compositions and methods provided herein can be combined to provide additional benefits to patients which cannot be achieved by using gene therapy or cell therapy alone. The "combination treatment" can also broaden the eligible patient base. For example, for late-stage patients who have no or little photoreceptor or RPE cells left, gene therapy is not as effective as for early-stage patients. In this case, cell therapy can benefit by providing new cells (e.g., RPE or photoreceptor cells), whereas gene therapy can improve the effect of cell therapy by rescuing the remaining RPE or photoreceptor cells and/or by improving the conditions of choroid cells whose healthy affects the conditions of ocular cells. The combination of the "rescue" and "replacement" effect of gene therapy and cell therapy, respectively, makes the combination treatment an improvement from either gene therapy or cell therapy. This combination treatment method can be applied to other ocular diseases caused by one or more genetic mutations.

Methods and Compositions for CYP4V2 Gene Therapy

The present disclosure relates to various compositions comprising a nucleic acid molecule encoding a functional CYP4V2 protein and various methods utilizing the same for treating an ocular cell and/or ocular disease. In one embodiment, a functional CYP4V2 protein can be used directly for treatment purpose. In some embodiments, a nucleic acid molecule encoding a functional CYP4V2 protein is used. In some embodiments, an expression cassette comprising such nucleic acid molecule encoding a functional CYP4V2 protein operably linked with one or more regulatory sequences is used to direct and control expression of the product of the nucleic acid molecule. In some embodiments, a vector is used to package such CYP4V2 expression cassette comprising a nucleic acid molecule encoding a functional CYP4V2 protein and one or more regulatory sequences for enhanced delivery to the target cell and to achieve the desired expression of the product of such CYP4V2 encoding nucleic acid molecule and expression cassette.

In some embodiments, the vector is a recombinant adeno-associated virus (rAAV) vector. In some embodiments, the vector is a plasmid. In some embodiments, the vector is another type of viral or non-viral vector. The treatment methods comprise administering or delivering an effective amount (or an effective concentration) of said vectors to the subject's eye and/or the target cells. In one embodiment, the treatment is directly applied in vivo. In another embodiment, the treatment comprises treatment ex vivo in target cells (e.g., an ocular cell) and transplanting the treated target cells into the subject (e.g., to the subject's eye). The treatment methods are directed to ocular diseases and other conditions associated with CYP4V2 mutations. In one embodiment, the ocular disease is Bietti's Crystalline Dystrophy (BCD).

A. Functional CYP4V2 Protein and Nucleic Acids encoding a Functional CYP4V2 Protein CYP4V2 (Cytochrome P450, Family 4, Subfamily V, Polypeptide 2, (MIM 608614), synonym: CYP4AH1) is one of the proteins in the cytochrome P450 superfamily (P450) and a member of the cytochrome P450 subfamily 4 (CYP4). Cytochrome P450s (CYPs) are important heme-containing proteins, known for their roles as oxidase enzymes. The term P450 is derived from the spectrophotometric peak at the wavelength of the absorption maximum of the enzyme (450 nm) when it is in the reduced state and complexed with carbon monoxide. They are involved in the metabolism of xenobiotics and endogenous compounds, such as steroids and fatty acids. CYP enzymes have been identified in all kingdoms of life: animals, plants, fungi, protists, bacteria, archaea, and even in viruses. However, they are not omnipresent; for example, they have not been found in *Escherichia coli.*

P450 proteins share key elements in structure. For example, P450 proteins can be identified by their signature sequence element FXXGXXXCXG (SEQ ID NO: 30), where the cysteine serves as an axial ligand to the heme iron. Sequence identity is relatively low among P450 proteins but their general topography and structural fold are highly conserved. The conserved core is composed of a coil termed the 'meander', a four-helix bundle, helices J and K, and two sets of beta-sheets. These constitute the haem-binding loop (with an absolutely conserved cysteine that serves as the 5th ligand for the haem iron), the proton-transfer groove and the conserved EXXR motif (SEQ ID NO: 31) in helix K. P450 proteins are primarily membrane-associated proteins located either in the inner membrane of mitochondria or in the endoplasmic reticulum of cells.

In addition to structural similarities, P450 proteins also share functional similarities. The most common reaction catalyzed by P450 enzymes is a monooxygenase reaction, e.g., insertion of one atom of oxygen into the aliphatic position of an organic substrate (RH) while the other oxygen atom is reduced to water:

$$RH + O_2 + NADPH + H^+ \rightarrow ROH + H_2O + NADP^+$$

Many hydroxylation reactions (insertion of hydroxyl groups) use P450 enzymes. Many P450 enzymes have steroids and/or fatty acids as substrates.

The human CYP4V2 protein (NCBI RefSeq: NP_997235.3) has 525 amino acids (amino acid sequence shown in SEQ ID NO: 4). There are variants of human CYP4V2 protein, including pathologic variants (i.e., mutations) (See Table 1 herein for a select list of CYP4V2 mutations among BCD patients) and non-pathologic (i.e., functional) variants.

In one aspect, a functional CYP4V2 protein is the human CYP4V2 protein (SEQ ID NO: 4). In other aspects, a functional CYP4V2 protein is a functional variant or fragment of the human CYP4V2 protein, including without limitation, one with an amino acid sequence as shown in SEQ ID NO: 5).

A functional CYP4V2 protein can also be a variant of another functional CYP4V2 protein. The following is a discussion based upon changing of the amino acids of a polypeptide described herein to create an equivalent, or even an improved, second-generation molecule. For example, certain amino acids may be substituted for other amino acids in a protein structure without appreciable loss of interactive binding capacity with structures such as, for example, binding sites on substrate molecules. e.g., binding site for fatty acids. Since it is the interactive capacity and nature of a protein that defines that protein's biological functional activity, certain amino acid substitutions can be made in a protein sequence, and in its underlying DNA or RNA coding sequence, and nevertheless produce a protein with like properties. It is thus contemplated that various changes can be made in the amino acid sequence of a functional CYP4V2 protein or the DNA or RNA sequences of genes or coding regions thereof without appreciable loss of their biological utility or activity, as discussed herein. For example, SEQ ID NO: 5 is the amino acid sequence of a CYP4V2 protein variant which has one amino acid change from the human CYP4V2 protein sequence shown in SEQ ID NO: 4.

Various techniques, algorithms, software and tools can be used to design or engineer functional derivatives, variants and/or fragments of a functional CYP4V2 protein, e.g., the human CYP4V2 protein. For example, the structure and functions of the various polypeptides or changes can be modeled, resolved or predicted by NMR, x-ray crystallography, or computer modeling, e.g., ClustalW, SWISS-MODEL server, Swiss-Pdb Viewer, Polyphen-2, PROVEAN, SIFT, Condel, MutationAssessor and FatHMM.

A functional CYP4V2 protein can also be a fragment or derived from a fragment of a functional CYP4V2 protein. For example, the human CYP4V2 protein (SEQ ID NO: 4) and its variant (SEQ ID NO: 5) both have a transmembrane domain between about the 13th amino acid residue and about the 35th residue from the N-terminus. The backbone of human CYP4V2 protein (SEQ ID NO: 4) is located between about 36-525aa. Thus, a functional CYP4V2 can be derived from deletion of the first about 35 amino acids from the human CYP4V2 protein (SEQ ID NO: 6) and replacing it with an alternative transmembrane domain sequence. Another source of a functional CYP4V2 protein is a splice variant of a functional CYP4V2 protein.

The predicted transmembrane segment of CYP4V2 resides near the N terminus, followed by a globular structural domain typical of the CYP450 family. The globular domain of CYP4V2 includes 18 helices and beta structural segments. The heme group is located close to the surface of the protein, coordinated by the I helix toward the protein interior and the L helix superficially. Li et al., *Am J Hum Genet.* 74:817-826, 2004. CYP4V2 protein is predominantly active in fatty acid metabolism. Many other P450 enzymes are also involved in fatty acid metabolism. CYP4V2 is ubiquitously expressed in almost all tissues and organs. Expression of CYP4V2 was found in heart, brain, placenta, lung, liver, skeletal muscle, kidney, pancreas, retina, retinal pigment epithelium, cornea and lymphocytes (Li et al., *Am J Hum Genet.* 74:817-826, 2004). However, most other P450 enzymes are not present in ocular cells. For example, CYP4V2 and CYP1B1 were the only P450 enzymes expressed at high levels in ARPE-19 cell line; CYP2E1, CYP2J2, and CYP3A4 were transcribed at only low levels (5% of CYP4V2 mRNA expression), and transcripts for CYP4A11, CYP4B1, CYP4F2, CYP4F3, and CYP4F12 were not detectable (Nakano, et al., Mol Pharmacol 2012; 82:679-686). The fact that symptoms of CYP4V2 mutations is restricted to the eye, where CYP4V2 is the only major P450 enzymes expressed besides CYP1B1 and the only P450 sub-family 4 (CYP4) enzymes expressed, but not shown in organs where CYP4V2 is present with other P450 enzymes, suggest that other P450 enzymes, particularly CYP4 enzymes, can be used to substitute all or part of the functions of CYP4V2. Indeed, the CYP4 sub-family has been found to share common roles in fatty acid metabolism, including without limitation, as hydroxylase for PUFAs. See, Hardwick, *Biochem. Pharmacol.,* 75 (12): 2263-75; Fer et al., *J. Lipid Res.,* 49 (11): 2379-89; Nakano et al., *Mol. Pharmacol.,* 2012, 82:679-686). Protein sequences of human CYP4 proteins are shown in SEQ ID NOs: 8-18.

In addition to shared substrates and functions with the other proteins of the CYP4 sub-family, computational analysis revealed that CYP4V2 was formed from the duplication of the ancestors of CYP46A (SEQ ID NO: 7), which was then duplicated to generate the whole CYP4 family. Pan et al., *Int. J. Mol. Sci.,* 2016, 17 (7) pii: E1020. doi: 10.3390/ijms17071020.

Furthermore, the CYP4V2 gene (or orthologs of the CYP4V2 gene, e.g., Cyp4v3 for mouse) is conserved in many species, including without limitation, human, chimpanzee, Rhesus monkey, dog, cow, mouse, rat, chicken, frog, horse, rabbit and fruit fly (SEQ ID NOs: 19-29). Orthologs with human gene CYP4V2 have been found in 196 organisms.

A functional CYP4V2 protein can comprise or be designed, engineered, or derived from, including without limitation, the following:

(i) the human CYP4V2 protein (SEQ ID NO: 4)

(ii) a variant of (e.g., changing of the amino acids and/or a splice variant) of the human CYP4V2 protein or a functional CYP4V2 protein (e.g., SEQ ID NO: 5), (iii) one or more fragments of a functional CYP4V2 protein (e.g., SEQ ID NO: 6), (iv) a CYP4V2 (or ortholog) protein of other species, (v) another CYP4 protein or CYP46A1, (vi) a polypeptide which can ameliorate, treat, or arrest one or more biochemical abnormalities in one or more compounds listed in Table 2 in a patient cell (e.g., the iPS-RPE cell of a BCD patient), and/or (vii) a derivative, hybrid or variant of any one or more of (i) to (vi) above.

It is contemplated that the compositions and methods disclosed herein may be utilized to express any functional CYP4V2 protein as described above. In one embodiment, a functional CYP4V2 protein is a polypeptide comprising all or part of the amino acid sequence shown in SEQ ID NO: 4, 5 or 6. In some embodiments, a functional CYP4V2 protein is a polypeptide comprising all or part of an amino acid sequence selected from the group consisting of CYP4V2, CYP4A11, CYP4A22, CYP4B1, CYP4F2, CYP4F3, CYP4F8, CYP4F11, CYP4F12, CYP4F22, CYP4X1, CYP4Z1 and CYP46A (SEQ ID NOs: 4-18), and CYP4V2 of chimpanzee, Rhesus monkey, dog, cow, mouse, rat, chicken, frog, horse, rabbit and fruit fly (SEQ ID NOs: 19-29), and derivatives, hybrids, variants and/or fragments thereof. In some embodiments, a functional CYP4V2 protein can have at least 80% amino acid sequence identity (e.g., at least 80%, 81%, 82%, 83%, 84%, 85%, 86%, 87%, 88%, 89%, 90%, 91%, 92%, 93%, 94%, 95%, 96%, 97%, 98%, or 99% sequence identity) to any of the sequences selected from the group consisting of SEQ ID NOs: 4-29. In one embodiment, a functional CYP4V2 protein is a polypeptide comprising sequence elements of FxxGxxxCxG and ExxR (SEQ ID NOs: 30 and 31).

In some embodiments, a functional CYP4V2 protein is a compound or agent which can ameliorate, treat, or arrest one or more biochemical abnormalities in a patient cell (e.g., the iPS-RPE cell of a BCD patient).

In one embodiment, a functional CYP4V2 protein can be used directly to treat BCD, similar to protein-based drugs for other diseases. In another embodiment, a nucleic acid molecule encoding a functional CYP4V2 protein is used to express the functional CYP4V2 protein in the targeted cells. In one embodiment, the nucleic acid molecule is a RNA. In another embodiment, the nucleic acid molecule is a DNA, including without limitation, a complementary DNA (cDNA), for long-term expression. The cDNA can be positive- or negative-sense, single- or double-stranded. In some embodiments, the nucleic acid encoding a functional CYP4V2 protein is operably linked with one or more regulatory sequences to form a CYP4V2 expression cassette. In some embodiments, such an expression cassette is packaged in a vector for enhanced delivery and/or expression efficiency.

A codon consists of a set of three nucleotides and encodes a specific amino acid or results in the termination of translation (i.e. stop codons). The vast majority of amino acids (usually everything but methionine) are encoded by multiple codons. Therefore, different nucleic acid sequences can be used to express the same protein. The sequence identity between two nucleic acid molecules encoding the same protein sequence can range from 0% to over 99%. For example, a nucleic acid sequence (SEQ ID NO: 1) and another nucleic acid sequence (SEQ ID NO: 2), both encoding the human CYP4V2 protein (SEQ ID NO: 4), only share a sequence identity of 77%.

Codon-optimization of nucleic acid sequences may improve and/or stabilize protein expression without changing the encoded amino acid sequence. Codon optimization replaces codons present in a nucleic acid sequence with preferred codons encoding the same amino acid, for example, codons preferred for mammalian expression. Various strategies and parameters can be used in codon-optimization, including without limitation, codon usage bias, GC content, CpG dinucleotides content, mRNA secondary structure, cryptic splicing sites, premature Poly A sites, internal chi sites and ribosomal binding sites, negative CpG islands, RNA instability motif (ARE), repeat sequences (direct repeat, reverse repeat, and Dyad repeat) and restriction sites that may interfere with cloning. Methods of codon optimization are known in the art, e.g., U.S. Pat. No. 6,114,148 and US20110081708. A codon optimized nucleic acid sequence of a given amino acid sequence or a nucleic acid sequence encoding a polypeptide can be generated by the methods described herein and/or by using various codon optimization software, including through online software.

It would be appreciated that, depending on the codon-optimization methods, configuration, algorithms or software being used, different codon-optimized nucleic acid sequences encoding the same protein can be generated. However, codon optimization does not always lead to improved expression compared to a wild-type, unmodified nucleic acid sequence. See Alexeyev M F, Winkler H H: Gene synthesis, bacterial expression and purification of the *Rickettsia prowazekii* ATP/ADP translocase. *Biochim Biophys Acta*. 1999, 1419:299-306. 10.1016/S0005-2736 (99) 00078-4; Curran K A, Leavitt J M, Karim A S, Alper H S: Metabolic engineering of muconic acid production in *Saccharomyces cerevisiae*. *Metab Eng*. 2013, 15:55-66; Agashe D, Martinez-Gomez N C, Drummond D A, Marx C J: Good codons, Bad transcript: large reductions in gene expression and fitness arising from synonymous mutations in a Key enzyme. *Mol Biol* Evol. 2013, 30 (3): 549-560. 10.1093/molbev/mss273. doi: 10.1093/molbev/mss273.

A codon optimized nucleic acid sequence (SEQ ID NO: 2) encoding the human CYP4V2 protein (SEQ ID NO: 4) is provided herein. Both SEQ ID NO: 1 and SEQ ID NO: 2 encode the same human CYP4V2 protein (SEQ ID NO: 4). The codon-optimized nucleic acid sequence (SEQ ID NO: 2) has an improved codon adaptation index (CAI) of 0.95 over a CAI of 0.94 for the nucleic acid sequence shown in SEQ ID NO: 1. A CAI of 1.0 is considered to be perfect in the desired expression organism. It would be understood that the present disclosure covers all forms and types of the codon-optimized nucleic acid sequence as represented by the cDNA sequence shown in SEQ ID NO: 2, including any RNA sequence or DNA sequence or other nucleic acid sequence corresponding to such cDNA sequence or derived therefrom, and it can be in single-stranded or double-stranded form of, and/or positive-, negative-, anti-, or complementary-sense to the sequence provided herein.

In addition to codon-optimization, other methods can be used to improve translational performance. For example, Kozak sequence or Shine-Dalgarno Sequence can be used to increase the efficiency of translational initiation. A different stop codon (e.g., TGA) can be used to increase the efficiency of translational termination. In addition to ORF sequence, a nucleic acid sequence encoding a functional CYP4V2 protein may also include one or more non-coding sequences such as UTR(s) and/or one or more introns to improve protein expression. A Kozak sequence (exemplary sequence shown in SEQ ID NO: 36) can be inserted immediately before a CYP4V2 encoding cDNA to enhance expression.

As discussed herein, it is contemplated that functional variants and/or fragments of the human CYP4V2 protein can be utilized. A nucleic acid sequence encoding a functional variant (SEQ ID NO: 5) of the human CYP4V2 protein (SEQ ID NO: 4) is provided in SEQ ID NO: 3.

In some embodiments, a CYP4V2 nucleic acid molecule is a polynucleotide molecule that encodes any functional CYP4V2 protein, including without limitation, SEQ ID NOs: 4-30 or encoding a polypeptide with at least 80% amino acid sequence identity to any of the sequences shown in SEQ ID NOs: 4-30. In some embodiments, a CYP4V2 nucleic acid molecule is a polynucleotide sharing at least 60% sequence identity to any of SEQ ID NO: 1, 2 or 3.

A vector (e.g., a viral or non-viral vector) and a CYP4V2 expression cassette as described herein typically contains one or more CYP4V2 nucleic acid molecules or a fragment thereof. It would be understood that a nucleic acid molecule can take many forms including, without limitation, DNA or RNA, single-stranded nucleic acids (e.g., ssDNA, ssRNA), double-stranded nucleic acids (e.g., dsDNA, dsRNA), plus-strand or minus-strand nucleic acids, complementary DNAs (cDNAs), genomic DNA, messenger RNA (mRNA), small interfering RNA (siRNA), and/or DNA directed RNA interference (ddRNAi)). Nucleic acid molecules also can include one or more nucleotide analogs or backbone modifications. In addition, it would be understood that a cDNA can be synthesized from an mRNA template in a reaction catalyzed by a reverse transcriptase enzyme, or can be designed and synthesized based on the protein it intends to encode, including without limitation, a codon-optimized cDNA, or can be synthesized from another nucleic acid molecule through mutagenesis. It also would be understood that a cDNA can contain only exons, or can contain exons plus other sequences, e.g., untranslated regions (UTR) and/or introns. In some instances, a vector and a CYP4V2 expression cassette described herein can include a nucleic acid molecule that has a sequence encoding the human CYP4V2 protein, or a functional variant or a fragment thereof.

A suitable nucleic acid sequence can be any nucleic acid sequence that encodes a functional CYP4V2 protein. Such nucleic acid sequence may or may not contain non-coding elements, such as UTRs, introns or a Kozak sequence. It may include a wild type sequence or a synthetic or modified sequence (e.g., a codon-optimized sequence). A nucleic acid sequence encoding a functional CYP4V2 protein can be generated as described herein or by other methods known in the art.

A nucleic acid molecule with the sequence as shown in SEQ ID NO: 1 encoding the human CYP4V2 protein is herein referred to as "CYP4V2st." A nucleic acid molecule with a codon-optimized sequence as shown in SEQ ID NO: 2 encoding the human CYP4V2 protein is herein referred to as "CYP4V2op." A nucleic acid molecule with the sequence shown in SEQ ID NO: 3 encoding a functional variant of the human CYP4V2 protein is herein referred to as "CYP4V2fv." In some embodiments, a nucleic acid sequence encoding a functional CYP4V2 protein has a sequence identity of at least 60% with one of SEQ ID NOs 1, 2 or 3.

A functional CYP4V2 protein and a nucleic acid molecule encoding such functional CYP4V2 protein can be synthesized or isolated, purified and detected by methods known in the art. In addition, protein synthesis or isolation, purification and detection are also commercially available through CROs including Wuxi Apptec (Shanghai, China) and GenScript (Piscataway, New Jersey). Nucleic acid molecule synthesis or isolation, purification cloning, and detection are commercially available through CROs including GenScript (Piscataway, New Jersey) and Integrated DNA Technologies (Coralville, Iowa).

A polypeptide can be synthesized (e.g., through recombinant protein expression or chemical synthesis) or isolated. As used herein, a "purified" polypeptide is a polypeptide that has been separated or purified from cellular components that naturally accompany it. Typically, a polypeptide is considered "purified" when it is at least 70% (e.g., at least 75%, 80%, 85%, 90%, 95%, or 99%), by dry weight, free from the polypeptides and naturally occurring molecules with which it is naturally associated. Since a polypeptide that is chemically synthesized is, by nature, separated from the components that naturally accompany it, a synthetic polypeptide is "purified."

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Polypeptides typically are detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide or a portion of a polypeptide can be generated using methods well known in the art. The antibody can be attached to a solid support such as a microtiter plate using methods known in the art. In the presence of a polypeptide, an antibody-polypeptide complex is formed.

An "isolated" nucleic acid molecule typically refers to a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a construct (e.g., a cloning construct, or an expression construct for use in gene therapy), usually for convenience of manipulation, to express a protein, to generate a fusion protein, or for other purposes, including without limitation, for packaging into a vector (e.g., a viral or non-viral vector).

Nucleic acids can be isolated using techniques routine in the art. For example, nucleic acids can be isolated using any method including, without limitation, recombinant nucleic acid technology, site-specific mutagenesis, the polymerase chain reaction (PCR) and/or other genetic engineering methods. General PCR techniques are described, for example, in *PCR Primer: A Laboratory Manual*, Dieffenbach &

Dveksler, Eds., Cold Spring Harbor Laboratory Press, 1995. Recombinant nucleic acid techniques include, for example, restriction enzyme digestion and ligation, which can be used to isolate a nucleic acid. Mutagenesis protocols are described, for example, in *In Vitro Mutagenesis Protocols*, Braman, ed., Humana Press, 2002.

Isolated nucleic acids also can be chemically synthesized, either as a single nucleic acid molecule or as a series of oligonucleotides.

Constructs containing a nucleic acid are known in the art. Constructs, including cloning constructs and expression constructs, can be custom made commercially or can be produced by recombinant DNA techniques routine in the art. A construct can have regulatory sequences operably linked to a nucleic acid to be expressed, and further can include sequences such as those encoding a selectable marker (e.g., an antibiotic resistance gene). Regulatory sequences are discussed herein. A construct containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification or detection of the encoded polypeptide (e.g., 6xHis tag, glutathione S-transferase (GST), CFP, Fc, FLAG, HA, Myc, RFP, Strep, VSV, GFP, and YFP).

Constructs carrying a nucleic acid sequence can be introduced into a host cell. As used herein, "host cell" refers to the particular cell into which the nucleic acid is introduced and also includes the progeny of such a cell that carry the construct. A host cell can be any prokaryotic or eukaryotic cell. For example, host cells can be bacterial cells such as *E. coli*, or in insect cells, yeast or mammalian cells (such as Chinese hamster ovary cells (CHO), COS cells, HEK293 cells, HeLa, Vero, V27, A549, K562, B50, WI38 and BHK cells). Other host cells include without limitation iPS cells, ES cells, RPE cells, iPS-RPE cells, iPS-photoreceptor cells, ES-RPE cells, ARPE-19 cells, cornea cells, photoreceptor cells, choroid cells, optic nerve cells, any other type of ocular cells discussed herein, neuronal cells, epithelial cells, blood cells, fibroblasts, lymphocytes, and stem cell derived cells. Many methods for introducing nucleic acids or a vector or an expression cassette carrying a nucleic acid transgene into host cells, both in vivo and in vitro, are well known to those skilled in the art and include, without limitation, electroporation, sonoporation, calcium phosphate precipitation, polyethylene glycol (PEG) transformation, heat shock, lipofection, microinjection, and viral-mediated nucleic acid transfer.

Nucleic acids can be detected using any number of amplification techniques (see, e.g., PCR Primer: A Laboratory Manual, 1995, Dieffenbach & *Dveksler, Eds.*, Cold Spring Harbor Laboratory Press, Cold Spring Harbor, NY; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid. Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46) and Southern blot conditions for oligonucleotide probes greater than about 100 nucleotides (see Sections 9.47-9.54).

B. Vectors

In some embodiments, the nucleic acid molecule encoding a functional CYP4V2 protein or fragment thereof is delivered to the ocular cells in need of treatment by means of a vector. For delivery to the ocular cells, the therapeutic vector is desirably non-toxic and efficient in delivering a nucleic acid molecule (e.g., DNA, RNA) into the target cells. Gene therapy vectors are known in the art and can be viral vectors or non-viral vectors.

One approach for in vivo introduction of nucleic acid into a cell is by use of a viral vector containing nucleic acid molecule, e.g., a cDNA. Infection of cells with a viral vector has the advantage that a large proportion of the targeted cells can receive the nucleic acid molecule. Additionally, molecules encoded within the viral vector, e.g., by a cDNA contained in the viral vector, are expressed efficiently in cells that have taken up viral vectors containing the nucleic acid molecule.

Examples of viral vectors that can be used include, without limitation, adenovirus vectors, adeno-associated virus vectors (AAV), lentivirus vectors, herpes virus (HV) vectors such as herpes simplex virus (HSV) vectors, papillomavirus vectors, poxvirus vectors, human foamy virus (HFV) vectors, Epstein Barr virus (EBV) vectors, vaccinia virus vectors, Sendai virus vectors and retrovirus vectors. Plasmids can also be used to deliver a nucleic acid molecule into the target cell. In some instances, the viral vector is a recombinant viral vector such as a recombinant AAV (rAAV) vector. It would be understood by a skilled artisan that certain vectors will integrate, or are more prone to integrate, into the genome of the host cell (e.g., the subject's cells), while other vectors will not integrate, or are less prone to integrate, into the genome of the host cell (e.g., extrachromosomal expression).

Recombinant AAV (rAAV) vectors are commonly used in gene therapy approaches. AAVs belong to the parvovirus family and each contains a single strand DNA. rAAV vectors are currently considered to be the safest and most efficient platform for gene transfer in mammalian cells (Salganik et al, 2015, Microbiol. Spectr., 3 (4): doi: 10.1128/microbiolspec.MDNA3-0052-2014). To date, 12 AAV serotypes (AAV1 to AAV12) and more than 100 variants have been isolated from human and nonhuman primate tissue samples (see, e.g., Gao et al., 2005, Curr. Gene Ther., 5:285-97) and from other species. Both naturally occurring and modified AAV types can be used in the methods described herein.

Wild-type AAVs contain a linear single-stranded DNA genome enclosed within a capsid composed of three proteins VP1, VP2, and VP3. In recombinant AAVs (rAAVs), the rep and cap genes from the wild-type AAV genome are typically replaced by a transgene expression cassette, flanked by the AAV inverted terminal repeats (ITRs) required for packaging. As used herein, "rAAV vector" refers to a recombinant AAV vector containing one or more capsid elements of or derived from one or more AAV virus.

Despite the advantages of AAV and other viral vector-mediated gene therapy, not all viral vectors and not all AAV types are suitable for treating a particular disease. Two major challenges faced by gene therapy using viral vectors (e.g., AAV vectors). First, sufficient transduction efficiency by the AAV vector in the cell type targeted for treatment is desirable. Second, potential immune reactions triggered by the viral vector need to be considered. See Madsen et al., Adeno-associated virus serotype 2 induces cell-mediated immune responses directed against multiple epitopes of the capsid protein VP1. J Gen Virol 90, 2622-2633 (2009); Mingozzi et al., CD8 (+) T-cell responses to adeno-associated virus capsid in humans. *Nat Med* 13, 419-422 (2007). Although as compared to most other organs and tissues, the eye is considered as an immune-privileged organ relative to many other organs and immune responses in AAV-mediated gene therapy in the eye can be controlled by the use of immunosuppressant, the role of immune responses such as neutralizing antibodies (NABs) in AAV transduction of the eye, is unclear in large animals. In addition, intravitreal AAV administration is more susceptible to interactions with the immune system than subretinal administration. Therefore, the viral vector used in ocular gene therapy will trigger minimal or no immune response, so to avoid potential side effects and ensure the transduction/expression efficiency of the viral vectors are not substantially reduced by immune reactions, e.g., pre-existing NABs in the subject, and/or to lower the dose of rAAV vectors.

Various compositions and methods relating to AAV vector design and selection can be used to address these challenges. For use of CYP4V2 gene therapy to treat BCD, a vector with sufficient transduction efficiency in RPE cells is desired when the cells targeted for treatment are primarily RPE cells. When treating the corneal cells of a BCD patient, a vector with sufficient transduction efficiency in corneal cells is desired. In some embodiments, a vector with sufficient transduction efficiency in RPE cells is used. In some embodiments, a vector with sufficient transduction efficiency in corneal cells is used. In some embodiments, a vector with sufficient transduction efficiency in RPE and photoreceptor cells is used. In some embodiments, a vector with sufficient transduction efficiency in RPE, photoreceptor and choroid cells is used. In some embodiments, a vector with sufficient transduction efficiency in retinal cells is used. In some embodiments, a vector with sufficient transduction efficiency in ocular cells is used. In some embodiments, a vector with sufficient transduction efficiency in ocular cells and/or blood cells is used. To address the potential immune response (e.g., NABs and cell-based immune responses against the gene therapy vectors), different AAV serotypes and variants, modified AAV vectors and/or immuno-suppression protocols can be used.

An rAAV vector used herein can be based on or derived from either a wild type AAV (e.g., from one of AAV1 to AAV12 or other wild-type AAV variants isolated from human or other species, including without limitation, AAV1, AAV2, AAV4, AAV5, AAV6, AAV8, AAV9, AAV10, AAV11 and AAV12) or a modified AAV. A modified AAV can be generated in many different ways, including without limitation, a pseudotyped AAV (e.g., AAV2/5, AAV2/8, AAV2/1, AAV2/4, AAV2/6, AAV2/7, AAV2/9, AAV2/12, AAV8/2), a chimeric AAV (e.g., AAV-DJ), a capsid modified AAV (e.g., a capsid mutant AAV (e.g., AAV with Y-F, K-R, T-A, S-A and/or T-V mutations, and AAV-DJ/8 or AAV-DJ/9 which are capsid mutant AAVs from AAV-DJ), a capsid variant AAV (e.g., AAV 7m8 and derivatives), an ancestral AAV (e.g., Anc80). a recombinant AAV involving any change to the genome and/or capsid of a naturally occurring AAV or variant, and any combination thereof. It would be understood that there are different ways to refer to a modified AAV, including without limitation, artificial, modified, synthesized, reconstructed, engineered, evolved, designed, derived or enhanced AAV, or AAV generated through rational designed and/or directed evolution and/or DNA shuffling, or an AAV variant. The use of a modified AAV can have certain advantages over an unmodified AAV, including without limitation, higher transduction efficiency, higher tissue- or cell-specificity, less immune reactions, and/or more suitable for certain type of administration (e.g., intravitreal injection, or delivery through the blood stream).

In some embodiments, a modified AAV vector used herein is a pseudotyped AAV. AAV pseudotyping refers to the mixing of a capsid and genome from different viral serotypes. These serotypes are denoted using a slash, so that AAV2/5 indicates a virus containing the genome (e.g., ITRs) of serotype 2 packaged in the capsid from serotype 5. In some embodiments, an AAV vector is an AAV2/1, AAV2/2, AAV2/5, AAV2/8, AAV2/6, AAV2/9, AAV2/4, AAV2/7, AAV2/10 or AAV2/12 vector.

In some embodiments, a modified AAV vector used herein is a chimeric (sometimes also referred to as hybrid or shuffled) AAV which is derived from different AAV serotypes, including from different AAV serotypes isolated from different species. In some embodiments, an AAV vector is AAV-DJ, AAV-DJ/8 or AAV-DJ/9. AAV-DJ is an AAV variant generated from the libraries of AAV hybrids of eight serotypes by DNA shuffling method. Grimm, D. et al. (2008). J. Virol. 82:5887-5911. It is able to efficiently transduce a broad range of cell types including ocular cells. Moreover, chimeric AAVs possess more ability to evade immune neutralization than naturally occurring AAVs and thus can efficiently deliver higher quantities of therapeutic transgene. A hybrid AAV can be further modified. For example, AAV-DJ/8 and AAV-DJ/9 were created by making point mutations in the heparin binding domain (HBD) of AAV-DJ. Grimm, D. et al. (2008). J. Virol. 82:5887-5911.

In some embodiments, a modified AAV used herein is a capsid mutant AAV. It involves creating one or more mutations (e.g., point mutations) in AAV capsid protein. Capsid mutant AAVs can have advantages over unmodified AAVs. For example, point mutation of surface exposed tyrosine (Y) residues of AAV capsid protein was reported as a simple and effective method for evading phosphorylation and subsequent ubiquitination, leading to higher transduction efficiency both in vitro and in vivo (Zhong et al., Proc Natl Acad Sci USA. 2008;105 (22): 7827-32: Markusic et al., Mol Ther. 2010; 18 (12): 2048-56; Li et al., Hum Gene Ther. 2010 November; 21 (11): 1527-1543). For example, site-directed mutagenesis of each of the seven AAV2 capsid tyrosine residues (Y252, Y272, Y444, Y500, Y700, Y704, and Y730) by phenylalanine residue substitution leads to increased vector transduction and transgene expression by circumventing EGFR-PTK phosphorylation and the ubiquitin-proteasome pathway in human cells in vitro and murine hepatocytes in vivo (Zhong et al., *Virology.* 2008 Nov. 25; 381 (2): 194-202). It has also been reported that point mutations on the AAV capsid at specific tyrosine (Y), serine(S), threonine (T) and lysine (K) residues could lead to significant transduction improvement both in vitro and in vivo (Gabriel et al., Hum Gene Ther Methods. 2013; 24 (2): 80-93; Sen et al., Hum Gene Ther Methods. 2013; 24 (2): 104-16; Sen et al., Sci Rep. 2013; 3:1832; Wu et al., *J Virol.* 2006;80 (22): 11393-7). Capsid mutations can also be made to a modified AAV to generate another modified AAV. For example, AAV-DJ/8 and AAV-DJ/9 were created by making point mutations in the heparin binding domain (HBD) of AAV-DJ, a hybrid AAV. Grimm, D. et al. (2008). *J. Virol.* 82:5887-5911. Capsid mutations can also make an AAV evade NABs and generate less immune response. Furthermore, certain capsid mutations can make an AAV more suitable for intravitreal delivery. Kay et al., *PLOS One,* 8: e62097, 2013. In some embodiments, an AAV vector used herein is a modified AAV with one or more capsid mutations, include without limitation, Tyrosine to Phenylalanine (Y-F), Threonine to Valine (T-V), Lysine to Arginine (K-R), Threonine to Alanine (T-A), Serine to Alanine (S-A) and/or affecting the AAV's heparin binding domain (HBD), and/or in its antigenic regions, including without limitations at positions 459, 493 and 551. In some embodiments, an AAV vector is an AAV2 with one or more capsid mutations among Y444F, Y500F, Y730F, Y252F, Y272F, Y700F, Y704F and T491V, wherein the number (e.g., 444) indicates the location of a point mutation of the AAV capsid. In some embodiments, an AAV vector is an AAV5 with one or more capsid mutations among Y263F and Y719F. In some embodiments, an AAV vector is an AAV8 with one or more capsid mutations among Y447F, Y733F, and T494V, In some embodiment, an AAV vector is an AAV1 with a capsid mutant of Y731F. In some embodiments, an AAV vector is an AAV6 with one or more capsid mutations among Y445F and Y731F. In some embodiments, an AAV vector is an AAV9 with a capsid mutation of Y731F. In some embodiments, an AAV vector is an AAV-DJ, AAV-DJ/8 or AAV-DJ/9 with one or more capsid mutations among K137R, T251A and S503A.

In some embodiments, a modified AAV vector is an AAV with variant AAV capsid proteins. Variant AAV capsid proteins are known in the art. In some embodiments, a non-naturally occurring capsid protein can include a selected AAV sequence (e.g., a fragment of a vp1 capsid protein) in combination with heterologous sequences (e.g., sequences obtained from a different selected AAV serotype, non-contiguous portions of the same AAV serotype, from a non-AAV viral source, or from a non-viral source). In some embodiments, a modified AAV vector includes one or more insertions of amino acids (e.g., from about 5 amino acids to about 11 amino acids) in the capsid protein GH loop. Variant AAV capsid proteins can confer increased infectivity of a retinal cell compared to the infectivity of the retinal cell by a non-variant AAV (e.g., wild type AAVs). In some embodiments, a modified AAV is one that can deliver the transgene across the blood-ocular barrier (BOB) which makes it suitable for delivery through the bloodstream, offering an alternative route of administration/delivery from the conventional administrations (e.g., sub-retinal injection or intravitreal injection) used in ocular gene therapy. In some embodiments, an AAV with variant AAV capsid proteins is an AAV 7m8, or its derivatives or variants (Dalkara et al., *Science Translation Medicine*, 5: 189ra76, 2013; PCT Application No. PCT/US2012/034413, PCT Application No. PCT/US2014/039015, U.S. application Ser. No. 14/214,011 and U.S. application Ser. No. 13/899,481). In some embodiments, an AAV with variant AAV capsid proteins is an AAV-PHP.B.

In some embodiments, an AAV vector can be reconstructed or synthesized through reconstruction of the viral revolutionary lineage. Such reconstruction can yield ancestral, ancient or parental AAVs. In one embodiment, an AAV vector is an Anc80 (an ancestor of AAV1, 2, 8 and 9) or its derivative. Zinn et al., *Cell Rep.* 2015 Aug. 11;12 (6): 1056-68.

In some embodiments, one or more AAVs and/or other viral vectors can be modified (e.g., optimized for intravitreal delivery, for enhanced transduction in target cell type (e.g., RPE cells), or for delivery through the bloodstream) by means of techniques known in the art including, e.g., "directed evolution" and/or "rational design". See, e.g., Asuri et al., *Mol Ther.* 20:329-338, 2012 and Yang et al., *Methods Mol Biol.* 709:127-139, 2011. Modified AAVs or other viral vectors can be described as, e.g., "engineered", "hybrid", "evolved", "enhanced" or "designed" vectors. Such modifications can, e.g., improve vector targeting (e.g., improving suitability for intravitreal delivery or for delivery through the bloodstream), transduction efficiency and/or lower immune reaction, resulting in, e.g., a lower dose being required. In some embodiments, an rAAV vector is an AAV serotype rh10 (EP 20100178940) or ShH10. In some embodiments, an rAAV vector is an AAV-PHP.B (US20150079038).

In some embodiments, an AAV vector can be generated and/or selected from a combination of more than one strategies stated herein. For example, AAV-DJ/8 and AAV-DJ/9 were created by making point mutations in the heparin binding domain (HBD) of AAV-DJ, a hybrid AAV.

It is known in the art that certain AAVs can be more suitable for intravitreal delivery than some other AAVs. Many such AAVs for intravitreal delivery involve modifying the AAV capsid protein via mutations (e.g., AAV2 (quadY-F+T-V) (Kay et al., *PLOS One.* 2013 Apr. 26;8 (4)). or variant AAV capsid proteins (e.g., AAV 7m8). In addition, there are AAVs suitable for delivery through the bloodstream, e.g., AAV-PHP.B. Their use, however, are not limited to intravitreal delivery or delivery through the bloodstream, e.g., they can also be used as AAV vectors for sub-retinal and other routes of administration.

In some embodiments, a self-complementary AAV vector (scAAV) is used. Wild type AAVs have a single-stranded DNA genome. One downside of AAV is its single-stranded DNA genome. Because the single-stranded AAV genome depends on the cell's DNA replication machinery to synthesize the complementary strand, transgene expression is delayed and is not as robust as double-stranded DNA. For CYP4V2 gene therapy, we developed an scAAV design (see FIG. 7) to circumvent rate-limiting second-strand synthesis in conventional single-stranded AAV vectors and to facilitate robust transgene expression. The scAAV.CYP4V2 comprises an intra-molecular self-complementary CYP4V2 DNA structure which eliminates the requirement for host cell DNA synthesis and results in faster and more robust expression upon transduction. The self-complementary structure of an scAAV, however, reduces the scAAV vector's packaging limit from about 4.7-5.0 kb for ssAAV to about 2.4-2.5 kb for scAAV. Therefore, shorter length regulatory sequences (e.g., promoter, enhancer and/or poly A signal) are required in an scAAV design. To ensure the expression cassette does not exceed the vector packaging limit and depending on the length of the cDNA and other regulatory sequences used, certain optional regulatory sequence may need to be excluded from the scAAV construct, such as an enhancer. One of the two ITRs in an scAAV design is a truncated ITR and has a mutation in the terminal resolution site (TRS). For a detailed discussion on scAAV structure, purification and production, see McCarthy, Molecular Therapy, Volume 16, Issue 10, p1648-1656 Oct. 2008.

A number of other vector designs can be utilized. For example, a dual vector system (e.g., an AAV-based dual vector system, e.g., trans-splicing or hybrid dual AAV vectors) can be used to express a nucleic acid sequence (e.g., a CYP4V2 nucleic acid sequence). See, e.g., Colella, et al., Gene Ther. 21, 450-456, 2014. For example, a dual vector system can include (i) a first AAV vector polynucleotide having an inverted terminal repeat at each end (5' and 3' end) of the polynucleotide, and between the inverted terminal repeats, a suitable promoter operably linked to a partial coding sequence that encodes an N-terminal part of the protein encoded by the nucleic acid sequence of interest; and ii) a second AAV vector polynucleotide having an inverted terminal repeat at each end (5' and 3' end) of the polynucleotide, and between the inverted terminal repeats, a partial coding sequence that encodes a C-terminal part of the protein encoded by the nucleic acid sequence of interest, followed by a polyadenylation (pA) signal sequence.

Various rAAVs vectors were designed and generated for our study, including scAAV2/1, AAV2/2, AAV2/5, scAAV2/5, AAV2/8, scAAV2/9 and AAV2/2 (Y444F+Y500F+Y730F) (see schematic drawings and annotations in FIG. 7 herein). They demonstrate that rAAV vectors of various vector designs can be used in CYP4V2 gene therapy. In addition, inclusion of multiple rAAV vectors as options can help to reduce potential immune response in CYP4V2 gene therapy given the pre-existing neutralizing antibodies and other individual immune response against certain AAV types among the patient population. It would also provide more options if a subsequent administration to the same eye or an administration to the contralateral eye of the same subject is desired.

Methods to produce viral delivery vectors, including production using helper-free system, are known in the art. See, e.g., PCT/US2007/010055; Patent No: 6458587, Patent No: U.S. Pat. No. 6,428,988 B1). Production of various vectors used in gene therapy, including without limitation, AAV, adenovirus, lentivirus and retrovirus vectors, is also commercially available through contract research organizations (CROs) and contract manufacturing organizations (CMOs), e.g., Vector Biolabs (Malvern, PA) and Cell Biolabs, Inc., (San Diego, CA).

In some embodiments, a recombinant AAV vector useful in the methods described herein can be generated by culturing a host cell (e.g., a HEK293 cell) which contains a nucleic acid molecule encoding an AAV serotype capsid protein, or fragment thereof; a rep gene; a minigene comprising, at a minimum, AAV inverted terminal repeats (ITRs) and a nucleic acid molecule of interest (e.g., having a CYP4V2 nucleic acid sequence); and sufficient helper functions to permit packaging of the nucleic acid of interest into the AAV capsid protein. The components required to be cultured in the host cell to package a nucleic acid in an AAV capsid can be provided to the host cell in cis or trans. Alternatively, any one or more of the required components (e.g., nucleic acid molecule of interest, rep sequences, cap sequences, and/or helper functions) can be provided by a stable host cell which has been engineered to contain one or more of the required components. Any of these components can be selected from among any suitable serotype. For example, rAAV vectors are generated by co-transfecting producer cells (e.g., HEK 293 cells) with (a) a plasmid (AAV cis-plasmid) containing a cloned recombinant AAV genome composed of the gene of interest (e.g., a cDNA encoding CYP4V2) and other desired regulatory sequences flanked by the two AAV ITRs, (b) a separate construct expressing in trans the AAV viral Rep and Cap genes. (c) the adenovirus helper factors, which are provided by either adenovirus infection or transfecting into producer cells a third plasmid that provides these adenovirus helper factors. In addition to HEK293 cells, other cell lines can be used in the production of rAAV vectors, including without limitation, HeLa, Vero, A549, B50, WI38 and BHK cells.

In some embodiments, the viral delivery vector is a rAAV2 virus, a rAAV2/5 virus, a rAAV2/8 virus, a rAAV2/1 virus, a rAAV2/4 virus, a rAAV2/6 virus, a rAAV2/9 virus, a rAAV2/12 virus or a rAAV virus with capsid elements from one or more of AAV1, AAV2, AAV5, AAV8, AAV9 and/or AAV12 virus. In one embodiment, the viral delivery vector is a rAAV virus with one or more Y-F mutations, including without limitation, AAV2 (Y444F+Y500F+Y730F), or AAV8 (Y733F).

In some embodiments, the viral delivery vector is a single-stranded rAAV (ssAAV) virus. In some embodiments, the viral delivery vector is a self-complementary rAAV (scAAV) virus.

In addition to AAV vectors, other viral vectors can be used in CYP4V2 gene therapy. For example, adenoviral vectors have also been demonstrated to be useful for gene delivery. For example, Mori et al., 2002. IOVS, 43:1610-1615 discloses the use of an adenoviral vector that is an E-1 deleted, partially E-3 deleted type 5 Ad in which the transgene (green fluorescent protein) is driven by a CMV promoter. Peak expression levels were demonstrated upon injection of 10^7 to 10^8 viral particles, with subretinal injection providing higher levels of expression than intravitreal injection.

In some embodiments, the delivery vector is a plasmid containing a nucleic acid molecule encoding the human CYP4V2 protein or a functional variant or fragment thereof.

Non-viral vectors also can be used in CYP4V2 gene therapy. Examples of non-viral vectors include, without limitation, naked nucleic acids, dendrimers, liposomes (e.g., cationic or anionic liposomes), polymers (e.g., polyplexes), lipid-polymer systems, and nanoparticles (e.g., inorganic or synthesized nanoparticles). For example, efficient non-viral ocular gene transfer was demonstrated by Farjo et al., 2006, *PLOS* 1: e38, who used compacted DNA nanoparticles as a system for non-viral gene transfer to ocular tissues. As a proof of concept, the pZEEGFP5.1 (5,147 bp) expression construct that encodes the enhanced green fluorescent protein (GFP) cDNA transcriptionally-controlled by the CMV immediate-early promoter and enhancer was used. DNA nanoparticles were formulated by mixing plasmid DNA with CK3OPEG10K, a 30-mer lysine peptide with an N-terminal cysteine that is conjugated via a maleimide linkage to 10 kDa polyethylene glycol using known methods. Nanoparticles were concentrated up to 4 mg/ml of DNA in saline. The compacted DNA was delivered at a 0.6 µg dose to the vitreal cavity. GFP expression was observed in the lens, retina, and pigment epithelium/choroid/sclera by PCR and microscopy.

Further, a number of patents have been issued for methods of ocular gene transfer including, but not limited to, U.S. Pat. No. 7,144,870 which provides methods of hyaluronic acid mediated adenoviral transduction; U.S. Pat. Nos. 7,122,181 and 6,555,107 which provide lentiviral vectors and their use to mediate ocular gene delivery; U.S. Pat. No. 6,106,826 which provides herpes simplex viral vectors and their use to mediate ocular gene delivery; and U.S. Pat. No. 5,770,580 which provides DNA expression vectors and their use to mediate ocular gene delivery.

A method of screening and selecting suitable vectors for use in CYP4V2 gene therapy from different vectors is provided in the Examples section herein. The Examples used different AAV vectors to illustrate the method. It would be understood that such method can also be used by the skilled in the art to compare and select among different types of vectors, e.g., viral-vs. non-viral vectors, adenovirus vs. AAV, lentivirus vs. AAV, HSV vs. AAV, etc.

C. CYP4V2 Expression Cassettes and Regulatory Sequences

The disclosure also provides an expression cassette comprising a nucleic acid sequence encoding a functional CYP4V2 protein (e.g., a nucleic acid sequence of SEQ ID NO: 1, 2 or 3) and an expression control sequence operably linked to the CYP4V2 encoding nucleic acid sequence. In addition to the nucleic acid molecule encoding a functional CYP4V2 protein, the other key elements of an expression cassette used in CYP4V2 gene therapy include one or more regulatory sequences to control the expression of said nucleic acid molecule. In some embodiments, the expression cassette is packaged in a delivery vector (e.g., in a rAAV vector flanked by the AAV ITRs) for enhanced delivery, transduction and/or expression efficiency. Any AAV ITRs can be used in the methods described herein. The ssAAV vectors described in the Examples herein contain two AAV2 ITRs of about 141 bp each (exemplary sequences shown in SEQ ID NO 42 and 43). The scAAV vector described in the Examples contains two AAV2 ITRs, one of which is truncated (exemplary sequences shown in SEQ ID NO 44 and 45). An AAV2 ITR usually has a length of about 132 to about 167 bp depending on the parental vector being used.

As used herein, the term "regulatory sequence" refers to any genetic element (e.g., polynucleotide sequence) that can exert a regulatory effect on the replication or expression (transcription or translation) of the nucleic acid sequence, or otherwise direct, influence and/or regulate expression of the nucleic acid sequence. Common expression control sequences include promoters, polyadenylation (poly A) signals, enhancers, upstream regulatory domains, introns, 5'-UTRs, response elements, or inducible elements, origins of replication, internal ribosome entry sites (IRES), transcription initiation sequences, termination sequences, RNA processing sequences such as splicing and polyadenylation (polyA) sequences, sequences that stabilize cytoplasmic mRNA, sequences that enhance translation efficiency (i.e., Kozak consensus sequence), sequences that enhance protein stability, or sequences that enhance secretion of the encoded protein. Regulatory sequences can be of bacterial, yeast, insect, mammalian, or viral origin or can be derivatives, hybrids or variants thereof, or can be synthetic, and vectors can contain a combination of regulatory sequences from different origins. For example, regulatory sequences can be heterologous (e.g., of a different origin or from a different gene; e.g., from a non-CYP4V2 gene) or homologous (e.g., from the same gene; e.g., from a CYP4V2 gene) relative to the coding sequence whose expression they are regulating (e.g., a CYP4V2 gene). As used herein, "operably linked" means that a promoter and/or other regulatory sequence(s) are positioned relative to a nucleic acid coding sequence in such a way as to direct, influence or regulate expression of the nucleic acid coding sequence. A regulatory sequence can be "operably linked" with a nucleic acid coding sequence in the same vector or in a different vector. One or more regulatory sequences operably linked to a nucleic acid coding sequence can be contiguous and/or can act in trans or at a distance to direct, influence or regulate expression of the nucleic acid coding sequence. Among the regulatory sequences, a promoter is essential, while other regulatory sequences such enhancers, introns and terminators can be beneficial but are optional.

Various promoter sequences can be used to drive expression of a nucleic acid coding sequence. Some promoters are constitutive promoters, which direct expression in virtually all tissues and most cell types. while other promoters are more controlled. Regulated promoters might act only in certain tissues or cells (i.e., tissue- or cell-specific promoters) or at certain times in development (i.e., development-stage specific promoters) and/or may be conditioned to environmental conditions or external stimuli such as a chemical, oxygen levels, heat, or light (i.e., inducible promoters).

In some instances, it may be desirable to use a constitutive (or ubiquitous) promoter. Exemplary constitutive promoters include without limitation, the cytomegalovirus (CMV) promoter (Gray et al., Hum Gene Ther. 2011 September; 22 (9): 1143-1153; Norman et al., PLOS ONE 5 (8): e12413, August 2010), the chicken β-actin promoter, the hybrid CAG (a/k/a CAGGS, CBA or CB) promoter derived from CMV/Chicken beta actin/rabbit beta-globin (Miyazaki J, Takaki S, Araki K, Tashiro F, Tominaga A, Takatsu K, Yamamura K. 1989. Expression vector system based on the chicken β-actin promoter directs efficient production of interleukin-5. Gene 79:269-277; Acland, G. M. et al. Mol Then, 2005, 12:1072-1082), the small CBA (smCBA) promoter (~953 bps, see, Mah, et al. 2003, Hum. Gene Ther. 14:143-152; Haire, et al. 2006 IOVS, 2006, 47:3745-3753), the CBh promoter (~800 bps, see, Gray et al., Hum Gene Ther. 2011 September; 22 (9): 1143-1153), the human β-actin promoter (ACTB) (Norman et al., PLOS ONE 5 (8): e12413, August 2010), the elongation factor 1 alpha (EF-1 alpha) promoter (see, Gill et al., Gene Ther. 2001;8 (20): 1539-1546; Norman et al., *PLOS ONE* 5 (8): e12413, August 2010), the phosphoglycerate kinase (PGK, human or mouse) promoter (Norman et al., *PLOS ONE* 5 (8): e12413, August 2010), the Ubiquitin C (UBC) promoter (Norman et al., *PLOS ONE* 5 (8): e12413, August 2010), the GUSB (Glucuronidase Beta) promoter, the GUSB minimal promoter (hGBp) (Husain, Gene Therapy (2009) 16, 927-932), the UCOE promoter, the elongation factor 1α short (EFS) promoter, the Simian virus 40 (SV40) promoter. the Rous sarcoma virus (RSV) promoter, See, e.g., Powell, Discov Med. 2015 January; 19 (102): 49-57, for a general comparison and discussion of various promoters. It should be understood that in some cases "constitutive" or "ubiquitous" promoters can be prone to silencing or promote differential expression strength in selected cell types, see, e.g., Mccown et al., Brain Res. 1996; 713 (1-2): 99-107; Gray et al., Hum Gene Ther. 2011; 22:1143-1153.

In some instances, it is desirable to use a cell-specific or tissue-specific promoter, which directs expression of a nucleic acid coding sequence in a particular type of cell or tissue. Based on the disclosure herein, it would be appreciated that a cell-specific or a tissue-specific promoter can be specific for an ocular cell or tissue, or for lymphocytes. Ocular cell types include, without limitation, retina cells, retina bipolar cells, photoreceptor cells, rod cells and cone cells, ganglion cells, retinal pigment epithelium (RPE) cells, choroid cells or corneal epithelium cells. Thus, a cell-specific promoter as described herein can be a retina-specific promoter (e.g., RPE-specific, photoreceptor-specific (e.g., cone-specific and/or rod-specific) and/or choroid-specific) or a cornea-specific promoter. Exemplary ocular cell-specific promoters include, without limitation, the human G-protein-coupled receptor protein kinase 1 a/k/a rhodopsin kinase 1 (GRK1) promoter (Genbank Accession number AY327580), a 292 nt fragment (positions 1793-2087) of the GRK1 promoter (see, Beltran et al., Gene Therapy 17:1162-74, 2010), the human interphotoreceptor retinoid-binding protein proximal (IRBP) promoter, a 235 nt fragment of the hIRBP promoter, the RPGR proximal promoter, the red opsin promoter, the red-green opsin promoter, the blue opsin promoter, the mouse opsin promoter (both long and short versions, Le et al., Molecular Vision 2006; 12:389-398; Beltran et al., Gene Therapy 17:1 162-74, 2010), the rhodopsin (Rho) promoter (Mussolino et al., Gene Therapy, 18:637-45, 2011); the alpha-subunit of cone transducin (Morrissey et al., BMC Dev, Biol, 11:3, 2011); beta phosphodiesterase (PDE) promoter; the retinitis pigmentosa (RP1) promoter (Nicord et al., J. Gene Vied. 9:1015-23, 2007), the NXNL2/NXNL1 promoter (Lambard et al., PLOS One, 5: el3025, 2010), the RPE65 promoter (Li et al., Investigative Ophthalmology & Visual Science, December 2002, Vol. 43, 3640); the retinal degeneration slow/periph-erin 2 (Rds/perphZ) promoter (Cai et al., Exp Eye Res, 91:186-94, 2010), the VMD2 promoter (vitelliform macular dystrophy 2; a/k/a BEST1, Kachi et al., Human Gene Therapy, 20:31-9, 2009), the IRBP/GNAT2 promoter (hIRBP enhancer fused to cone transducin alpha promoter), the Rds (retinal degeneration slow) promoter, the hPDE6b promoter, or the VEcad promoter (VE-cadherin/Cadherin 5 (CDH5)/CD144 promoter). It would be appreciated that other promoters are known in the art can be used in lieu of, or in addition to, any of the exemplary promoters provided herein based on the rationale and discussions provided herein.

Exemplary inducible promoters include without limita-tion, a calcium-sensitive promoter (e.g., the NFAT promoter, see, Gene Ther. 2013 March; 20 (3): 248-54), the zinc-inducible sheep metalioihionine (MX) promoter, the dex-amethasone (Dex)-inducible mouse mammary tumor virus (MMTV) promoter, the T7 polymerase promoter system; the ecdysone insect promoter, the tetracycline-repressible sys-tem, the tetracycline-inducible system, the RU486-inducible system, the rapamycin-inducible system, a number of com-mercial available inducible promoters, and inducible pro-moters regulated by a specific physiological state, e.g., temperature, acute phase, a particular differentiation state of the cell, or in replicating cells only. In some embodiments, the inducible promoter is one that is tightly regulated and specific for a particular ocular cell type.

A promoter can be a hybrid of, or truncated/shortened or modified version of or otherwise derived from another promoter and/or another regulatory sequence, e.g., the CAG promoter is a hybrid of CMV immediate early enhancer, chicken beta actin promoter and rabbit beta-globin gene, the smCBA promoter is a truncated version of the CBA pro-moter. A promoter can contain other elements, e.g., an intron, exon and/or an enhancer, e.g., the CAG promoter. More than one promoters can be used together in an expres-sion cassette.

In some instances, it may be desirable to use an enhancer sequence in order to increase and/or stabilize expression above that which occurs due to the promoter. Representative enhancer sequences include, without limitation, a post-transcriptional regulatory element (e.g., a woodchuck hepa-titis virus post-transcriptional regulatory element (a/k/a WPRE), or a Hepatitis B Virus post-transcriptional regula-tory element (a/k/a HPRE or HBVPRE, Donello et al., J Virol. 1998 June; 72 (6): 5085-92; Sun et al., DNA Cell Biol. 2009 May; 28 (5): 233-240), or various shortened, mutant or modified WPREs, e.g., a ~247 bps shortened WPRE con-taining minimal gamma and alpha elements of the WPRE (Choi et al., Mol Brain. 2014; 7:17; Donello et al., J Virol. 1998 June; 72 (6): 5085-5092; Zanta-Boussif et al., *Gene Therapy* (2009) 16, 605-619), or the 1RBP enhancer (Nicord et al., *J. Gene Vied.* 9:1015-23, 2007), a constitutive trans-port element (CTE) enhancer (e.g., the Mason-Pfizer Mon-key Virus CTE or Avian Leukemia Virus CTE), the cyto-megalovirus (CMV) immediate early enhancer, one derived from an immunoglobulin gene or SV40 enhancer, or the cis-acting element identified in the mouse proximal pro-moter, an intron regulatory sequence, e.g., a mini-intron splice donor/splice acceptor referred to as SD-SA derived from SV-40, an internal ribosome entry site (IRES), which can be used to produce more than one polypeptide from a single gene transcript, e.g., a protein that contains more than one polypeptide chain, or two different proteins, can be a poliovirus internal ribosome entry sequence, which supports transgene expression in RPE, photoreceptors and ganglion cells.

The polyadenylation of a transcript is important for nuclear export, translation, and mRNA stability. Therefore, the efficiency of transcript polyadenylation is important for transgene expression. Representative Poly A signal sequences include, without limitation, an SV40 poly A signal, an SV40 late polyA signal, an SV40 early poly A signal, a bovine growth hormone polyadenylation (bGH polyA) signal, a small poly A, or a human growth hormone polyadenylation signal (hGH polyA). In some instances, an upstream enhancer (USE) sequence can be used to increase the efficiency of a poly A signal, e.g., SV40 late 2xUSE, HIV-1 USE (Human immunodeficiency virus 1), GHV USE (Ground squirrel hepatitis virus), Adenovirus (L3) USE (Adenovirus), hTHGB USE (Human prothrombin), or hC2 USE (Human C2 complement gene) (Schambach A, Galla M, Maetzig T, Loew R, Baum C. Improving transcriptional termination of self-inactivating gamma-retroviral and lenti-viral vectors. *Mol Ther.* 2007; 15 (6): 1167-1173).

Like promoter sequences, the other regulatory sequences used in an expression cassette can be a hybrid of, shortened/truncated, modified or otherwise derived versions of a regulatory sequence. For example, the shortened WPRE, the SV40 late 2xUSE, the SV40 late poly A. In addition to the elements described herein, an expression cassette can also contain other regulatory sequences, e.g., introns, UTRs, and linker sequences. The inclusion of a splice site (i.e., exon flanked by two introns) has been demonstrated to be useful to increase gene expression of proteins from expression cassettes.

It is known in the art that it is common for a regulatory sequence or a hybrid regulatory sequences to have multiple versions and have more than one names. For example, various promoters, enhancers and poly A signals have mul-tiple versions, including without limitation, the CMV pro-moter, EF1α promoter, the WPRE enhancer, and the SV40 poly A signal. The CAG promoter has multiple alternative names including without limitation, the CBA promoter, CB promoter or CAGGS promoter. In addition, it is also known the in art that a regulatory sequence can be shortened, modified or combined with other sequences to generate a derivative or variant, e.g., the CAG (a/k/a CBA, CB or CAGGS) promoter is a hybrid of CMV immediate early enhancer, chicken beta actin promoter and rabbit beta-globin gene, the smCBA promoter is a truncated CAG promoter. the $CB^{SB}$ promoter is a shortened CAG promoter, differing by about 152 bp at the 5' end of the CMV immediate early enhancer. Furthermore, a regulatory sequence can be termed differently, e.g., a post-transcriptional regulatory element such as HPRE or WPRE can also be referred to as an enhancer. Any regulatory sequences described herein con-template all variations, derivatives and/or hybrids of such regulatory sequence. Any exemplary sequence provided herein relating to a regulatory sequence is exemplary in nature and does not limit the definition or scope of such regulatory sequence to the one shown in the exemplary sequence.

In some embodiments, microRNA (miRNA) technique can be used in the expression cassette design to achieve targeted expression specificity, e.g., via repress off-target transgene expression Simply by way of example and without limitation, a target sequence for miR181 (an miRNA shown to be expressed exclusively in ganglion cells and inner retina) can be added immediately downstream of CYP4V2 cDNA to inhibit synthesis of expression cassette-mediated CYP4V2 protein in ganglion cells and inner retinal cells. Similarly, a target sequence for an miRNA that is exclusively expressed in certain cell types can be used to repress expression cassette-mediated CYP4V2 protein expression in these types of cells to achieve targeted tissue- or cell-specific expression.

D. Designing Efficient Expression Cassettes and Delivery Vectors for CYP4V2 Gene Therapy A detailed discussion on the CYP4V2 expression cassette and delivery vector design method and various designs for these studies are provided in the Examples section herein. Use of EFS Promoter and/or Small PolyA Signal (SPA) in Treating an Ocular Disease As discussed herein, a gene delivery vector has a packaging size limit. For example, single-stranded AAV vectors have a packaging limit of about 4.7-5.0 kb, exceeding which the transduction and expression efficiency would drop significantly. For self-complementary AAVs (scAAVs), the packaging limit is halved to about 2.4-2.5 kb. Therefore, size does matter for vector-mediated gene delivery and gene therapy. For double stranded self-complementary vectors, it is desirable and sometimes critical to use small size regulatory sequences to make enough room for the transgene (e.g., cDNA). Because of this size limitation, large promoters also are not suitable for use with scAAV. For CYP4V2 gene therapy, given the size of the cDNA is about 1578 bp and the AAV ITRs (with mutation) are about 258 bp, there is only about 500-600 bp left for the regulatory sequences. Because CYP4V2 is almost ubiquitously expressed, in some embodiments, it is desirable to use a constitutive promoter to drive the CYP4V2 transgene expression. However, there is no room for the constitutive CAG promoter we used in the single-stranded AAV design which is about 1.7 kb, or for a shortened CBA promoter (smCBA) which is about 953 bp or for CBh promoter which is about 800 bp, nor for many other constitutive promoters such as the CMV promoter which is about 600 bp. Instead, a short length EFS promoter can be used (exemplary sequence shown in SEQ ID NO: 34) for the scAAV design. The same size limitation applies other regulatory sequences, e.g., poly A signal. A bGH Poly A is about 225 bp, an SV40 poly A is about 240 bp and an SV40 late polyA is about 120 bp. Any one of them would take up a large portion of the ~500 bp length left for regulatory sequences including the promoter. Therefore, a small poly A signal (SPA) was used, which is only about 54 bp (exemplary sequence shown in SEQ ID NO: 35) for the scAAV design.

The design using a EFS promoter and a SPA only occupy about 300 bps and together with the AAV ITRs occupy a total of about 600 bps, thus leaving about 1.8-1.9 kb remaining packaging space for the nucleic acid sequencing encoding the desired protein and any other sequences in an expression cassette designed for a scAAV, and leaving about 4.1-4.4 kb remaining packaging space for the nucleic acid sequencing encoding the desired protein and any other sequences in an expression cassette designed for a ssAAV. As a result, larger size cDNAs and/or other sequences can be packaged in a rAAV vector with the EFS promoter and the SPA, as compared to the use of larger promoters and poly A signal sequences, including without limitation, CMV promoter, CAG promoter, smCBA promoter, CBh promoter, EF1 alpha promoter, bGH polyA, SV40 poly A and SV40 late poly A.

Figure 7C:
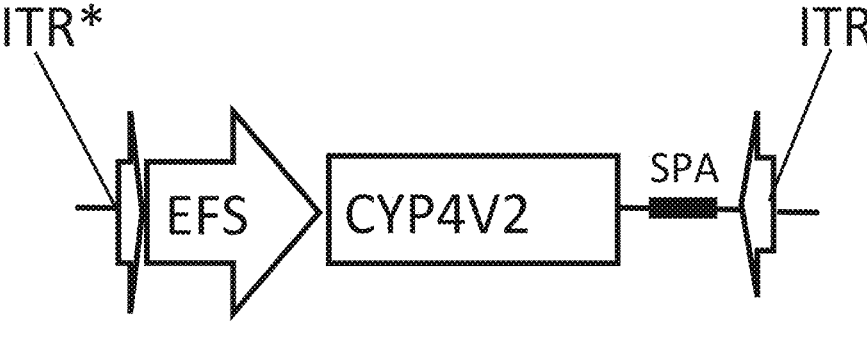

A schematic of the expression cassette comprising the EFS promoter and the SPA are provided in FIG. 7c. The construct shown in FIG. 7b includes a CYP4V2 cDNA. The CYP4V2 cDNA can be replaced by another gene of interest for the expression cassette to be used for other transgene expression.

The use of the EFS promoter and the SPA in an expression cassette and a delivery vector to drive a nucleic acid coding sequence to treat an ocular disease was tested in this study. An scAAV2/1 vector containing the EFS promoter, a CYP4V2 cDNA and the SPA, termed the scAAV1.EFS.CYP4V2op.SPA, was generated. The scAAV1-EFS-CYP4V2op-SPA was applied in the iPS-RPE cells of BCD patient. The scAAV1-EFS-CYP4V2op-SPA showed fast and robust action in iPS-RPE cells of BCD patient in just 4 days despite the short lengths of the EFS promoter and the SPA (See Table 3). It demonstrates that the EFS promoter and/or SPA are small size regulatory sequences that are very useful in an scAAV system for ocular gene therapy. In addition, the robust expression of scAAV vectors make the scAAV design also suitable for other routes of administration (e.g., intravitreal delivery) in addition to sub-retinal delivery.

The use of the EFS promoter and/or SPA is not limited to CYP4V2 gene therapy or in a scAAV construct. They can be used for gene therapy involving other genes, where the transgene size and/or an scAAV design requires the use of short length promoter and poly A signal to drive fast and sufficient protein expression.

E. Treatment Options, Subject Selection and Administration

CYP4V2 gene therapy can be applied in multiple ways. In some instances, the treatment can be applied in vivo to a subject (e.g., a BCD patient) through an effective delivery of the delivery vectors containing the CYP4V2 expression cassette to the cells, tissue or organ targeted for treatment, e.g., RPE, photoreceptors, choroid, cornea, lymphocytes, the retina or the eye, of the subject. In some instances, the treatment can be applied in vitro in the targeted cells (e.g., patient iPS-RPE cells, patient iPS-photoreceptor cells, iPS-photoreceptor progenitor cells, iPS-CEC, lymphocytes). Then the treated cells can be transplanted to a subject in need (e.g., a BCD patient). In some instances, the treatment can be applied through combining both the in vivo and in vitro approaches. In some instances, CYP4V2 gene therapy can be used independently. In some instances, CYP4V2 gene therapy can be used with another treatment option.

Subjects who are candidates for the present methods of treatment include those who are diagnosed of BCD. Subjects suffering from other ophthalmological clinically-defined conditions (e.g., inherited retinal degeneration (IRD), retinitis pigmentosa (RP) or corneal dystrophy) caused by mutations in the CYP4V2 gene can also be treated using the methods described herein. A diagnosis of BCD, IRD, RP, corneal dystrophy or another ophthalmological condition caused by mutations in the CYP4V2 gene can be made using methods known in the art. The methods described herein can include identifying a subject, e.g., a child, adolescent, or adult subject, who has BCD or another ophthalmological condition caused by mutations in the CYP4V2 gene, or who is suspected of having BCD or another ophthalmological condition caused by mutations in the CYP4V2 gene (e.g., based on the presence of symptoms of the condition and no other obvious cause), and obtaining a sample comprising genomic DNA from the subject, detecting the presence of mutations in the CYP4V2 gene using known molecular biological methods.

Numerous mutations have been identified in the CYP4V2 gene and causing BCD, with at least one mutation in each of the gene's 11 exons. Genotype analysis has shown that the most common CYP4V2 mutation among BCD patients is c.802-8_810del17insGC (referring to a 17 base deletion with two bases (GC) inserted in the place starting 8 bases from the end of intron 6 of CYP4V2 gene, also referred to as IVS6-8 del/insGC; this insertion-deletion mutation is at intron 6-exon 7 junction and the 17 bp deletion includes the exon 7 splice-acceptor site, leading to an in-frame deletion of 62 amino acid-encoding exon 7) resulting in the skipping of exon 7. (Xiao et al., Biochem Biophys Res Commun. 409:181-6, 2011; Meng et al., 2014, Mol. Vis., 20:1806-14; Wada et al., Am J Ophthalmol. 139:894-9, 2005; Jiao et al., European Journal of Human Genetics (2017) 25, 461-471). Various types of mutations were found in CYP4V2 mutations associated with BCD, including but not limited to, missense, splice site, frameshift, deletion, insertion, indel, nonsense, polymorphisms (e.g., single nucleotide polymorphisms) and premature termination. A summary of select CYP4V2 mutations among human BCD patients is provided in Table 1 and can be found in various publications and online databases, e.g., LOVD (databases.lovd.nl/shared/genes/CYP4V2 on the World Wide Web), OMIM (omim.org/allelicVariant/608614 on the World Wide Web), and ClinVar (ncbi.nlm.nih.gov/clinvar?term=608614 [MIM] on the World Wide Web).

It should be noted that the human CYP4V2 mutations in Table 1 are not exhaustive. More CYP4V2 mutations may be identified in the future. It would be understood that not all variations to the reference sequence are mutations. Some variations are non-pathologic. Methods to confirm whether a genetic variation is pathologic, i.e., a mutation, is known in the art, including but not limited to, comparing the variation to previously clinically identified known mutations, and/or determining whether a corresponding alteration in function exists. For example, one method to ascertain whether a genetic variation is a pathologic variation (i.e., a mutation) is to test the biochemical functions of the iPS-RPE cell line derived from the subject as described herein and assess whether any abnormalities exist as compared to those of healthy control's iPS-RPE cell line.

Patients with BCD or another ophthalmological condition due to CYP4V2 mutations that can be treated using a method described herein preferably retain some photoreceptors and visual function, e.g., as measured by visual acuity, visual field, visual function and/or Optical Coherence Tomography (OCT, e.g., Spectral Domain-OCT (SD-OCT)).

Before administration, the final product will undergo a series of steps (e.g., ultrapurification) to meet clinical grade criteria. Clinical grade productions are commercially available through various GMP facilities, including without limitation, the facilities in the NIH Gene Therapy Resource Program (GTRP) and contract manufacturing organizations (CMOs).

Prior to administration, the subject can test for pre-existing neutralizing antibodies (NAb) against the type of AAV vector which the subject is going to receive administration of. In one embodiment, if the subject has pre-existing NAb against such AAV type, an alternate AAV vector with low cross-reactivity to the subject's pre-existing NAb or an AAV vector with modified capsid structure can be used for administration to such subject to lower immune reactions and retain sufficient transduction efficiency by AAV vector. Other methods to minimize immune response are known in the art, including without limitation, applying immunosuppression agents and protocols before, during and/or post-treatment.

Viral or non-viral vectors, or combinations thereof (e.g., hybrid vectors), can be delivered into ocular cells of a subject using one or more physical means. Ocular cells as used herein refers to, without limitation, retinal pigment epithelium (RPE) cells, photoreceptor cells, corneal epithelial cells, retina cells, retina bipolar cells, rod cells, cone cells, ganglion cells, choroid cells and/or lens cells. In addition to, or alternatively, vectors can be delivered into nearby or neighboring cells or cells which can in contact with the targeted cells, including, without limitation, cells in the brain or cells in the optic nerve or blood cells.

Treatment in vitro can use any method or a combination of methods and/or agents that effectively delivers a vector to the cell targeted for treatment (e.g., an iPS-RPE cell from a BCD patient). Treatment in vitro can be done through one or more than one rounds of infections. In some instances, the vectors are applied in cultured cells directly to transfect or transduce the cells. In some instances, other methods of delivery and/or enhancing transfection/transduction efficiency in cells can be used, including without limitation, multiple transfections/transductions, electroporation, magnetofection, or sonoporation. Methods and agents used in infecting/transfecting a cell with a vector or an expression cassette is known in the art, including without limitation, as described in the Examples section herein.

The cells treated in vitro can then be transplanted to the eye of the subject. For example, the genetically repaired iPS-RPE cells from a BCD patient can be transplanted to the patient via sub-retinal injection. Methods, agents and devices used in cell transplantation to the eye are known in the art, see, e.g., Wert et al., J Vis Exp. 2012; (69): 4286; WO 2016/179496; Schwartz et al., Investigative Ophthalmology & Visual Science April 2016, Vol. 57, ORSFc1-ORSFc9.

For in vivo treatment, the vector and/or expression cassette can be delivered to the cells targeted for treatment in vivo (e.g., through administration to the eye of a subject in need of treatment for delivery to the cells targeted for treatment). Delivery methods of a nucleic acid molecule, an expression cassette, a vector to a target ocular cell in vivo in known in the art. For example, administration to the eye can use any method (or a combination of methods and/or agents) that effectively delivers a vector to the retina, the sub-retinal space, the choroid, or generally to the posterior segment of the eye, the cornea, the lens, or the vitreous, depending on the cells targeted for treatment. Administration can be via any suitable means including, without limitation, injection (e.g., sub-retinal injection, intravitreal injection, direct retinal injection, direct injection into the eye's posterior suprachoroidal space), eye drops, and can be applied in combination with other delivery techniques (e.g., electrically assisted delivery to the corneal epithelium). A CYP4V2 nucleic acid, expression cassette and/or delivery vector can also be introduced into cells using, for example, DNA particle bombardment (e.g., by a gene gun), hydrodynamic gene transfer, eye drops, electroporation, magnetofection, or sonoporation. Administration and delivery methods and techniques to the eye are known in the art. Simply by way of example, see, without limitation, Wert et al., J Vis Exp. 2012; (69): 4286; WO 2016/179496; Mohan et al., Prog Retin Eye Res. 2012 January; 31 (1): 43-64.

In addition to conventional delivery to RPE cells using sub-retinal injection, one aspect of the methods discussed herein is intravitreal delivery of the nucleic acid molecule (e.g., having a non-mutant CYP4V2 nucleic acid sequence) for treatment or prevention of an eye disease. Some vectors (e.g., AAV2 (quadY-F+T-V) and AAV 7m8) show particular promise for efficient transduction in the retina through intravitreal administration. In addition, AAVs or other viral vectors can be modified by means of techniques known in the art including, e.g., "directed evolution" and "rational design" to improve or optimize their suitability as vectors for gene delivery to one or more types of cells or tissues (e.g., intravitreal injection) other than through the conventional sub-retinal injection. scAAV vectors can also be used in intravitreal delivery in addition to sub-retinal delivery because of its prompt and robust expression profile. Because CYP4V2 is almost ubiquitously distributed with particularly high expression in the retina, genetic and epigenetic alterations of CYP4V2 are particularly suitable for repair via intravitreal administration of one or more vectors. Current gene therapy methods generally require sub-retinal administration of the vector. Therefore, one of the technical advances achieved by the materials and methods disclosed herein is the intravitreal delivery of a nucleic acid sequence (e.g., a wild type or non-mutant nucleic acid sequence, or a nucleic acid sequences encoding gene editing polypeptides) and/or a polypeptide for treating and preventing diseases of the eye associated with genetic or epigenetic alterations in the nucleic acid sequence of CYP4V2.

Certain techniques and agents may be used to facilitate the administration or delivery process. Non-limiting examples including the use of a lubricating agent such that adherence of the vector to the delivery vehicle (e.g., a needle) is avoided. In addition, the use of immunosuppressive drugs before, during and/or after the administration or delivery process can increase the infection or transduction efficiency.

A vector can be formulated for delivery into ocular cells of a subject using various pharmaceutically and/or physiologically acceptable vehicle excipients, diluents, and/or carriers. Examples of vehicle excipients, diluents, and/or carriers suitable for administration to the eye, which can be referred to as pharmaceutically acceptable carriers, include sterile, pyrogen-free water and sterile, pyrogen-free, buffered saline (e.g., saline buffered using phosphate or other buffers such as HEPES to maintain pH at appropriate physiological levels), isotonic sodium chloride solution, balanced salt solution, emulsions (e.g., oil/water emulsions), and various types of wetting agents. In some instances, the formulation can include other medicinal agents, pharmaceutical agents, stabilizing agents, buffers, carriers, adjuvants, and diluents. In some instances, the formulation can include DBPS, glycerol or Tween20 for long-term storage.

Methods of determining the most effective means of administration and therapeutically effective dosages are known to those of skill in the art and will vary with the vector, its capsid structure, the vector design (e.g., ssAAV vs. scAAV), the composition of the expression cassette, the expression levels of the vector, the promoter, other regulatory sequences or the nucleic acid molecule, the vector titer, the target cell type, the target expression levels, the size of the area or number of cells targeted, and the subject being treated (e.g., the age, sex, weight, development stage of the disease and condition of the subject to be treated, and potential immnue reactions); the route of administration; the location of the cells targeted for treatment (e.g., retina vs. cornea); the nature and expression level of the relevant gene in wild-type cells and/or tissue; and the required regimen. Therapeutically effective doses can be determined and evaluated in disease models (e.g., BCD cellular model (e.g., iPS-RPE cell line from BCD patients) or an animal model, and confirmed or refined by clinical trials. For treatment of cells in vitro, the dose is usually expressed as MOI and then multiple the MOI by the number of cells being treated. The MOI generally ranges between about $1 \times 10^3$ GC to about $1 \times 10^6$ GC per cell or an infectious MOI of about 100 to about 10,000 GC per cell (GC: genomic copies, measuring genome containing AAV particles (a/k/a vector genome (vg) or genome particles (gp)). For in vivo treatment, in addition to the factors described above, the actual dose administered may also be affected by individual situations specific to each patient during the administration, e.g., a reduced dose during the sub-retinal administration for patient 6 in the Choroideremia case described below. Therefore, the therapeutically effective dose for a single administration in vivo can be on the order of from about $1 \times 10^6$ to $2 \times 10^{13}$ GC, inclusive (e.g., a high dose range of about $1 \times 10^{11}$ GC to about $1 \times 10^{12}$ GC, a medium dose range of about $1 \times 10^{10}$ GC to about $1 \times 10^{11}$ GC, a low dose range of about $1 \times 10^9$ GC to about $1 \times 10^{10}$ GC, a very low dose range of about $1 \times 10^6$ GC to about $1 \times 10^9$ GC, and a very high dose range of about $1 \times 10^{12}$ GC to about $2 \times 10^{13}$ GC), or any dose within these ranges that is sufficient to provide the desired effect. In one embodiment, the composition is administered at a dose of about $1 \times 10^6$ to $2 \times 10^{13}$ GC. In another embodiment, the in vivo administered dose is determined by multiplying the number of cells targeted for treatment by the target MOI (e.g., $1 \times 10^3$ GC to about $1 \times 10^6$ GC per cell). The volume of the agent containing the rAAV vectors in any single administration to the eye can range from about 1 μL (0.001 mL) to about 1000 μL (1 mL).

The compositions as described herein can be formulated as a single dose or a plurality of doses. Similarly, administration can occur once, or a plurality of times (e.g., over several weeks, months, or years) and can be applied to the same eye or to the contralateral eye. Under circumstances of multiple administrations, the same or different AAV serotypes and/or route(s) of administration can be considered. Administration can also be applied to treat different tissues and cells, e.g., one administration targeting the RPE and another administration targeting the cornea.

Methods of viral vector generation, GMP production, purification, formulation and doses for use in gene therapy (including ocular gene therapy) are known to those of skill in the art, and methods of preparation of viral vectors can be performed by any of a number of companies and methods as demonstrated in various groups' gene therapy studies for LCA-2 below. Expression cassettes provided herein can be inserted into any of the exemplary viral vectors listed below. Alternatively, viral vectors can be generated based on the examples provided below. See, Bainbridge et al., 2008. N Engl J Med. 358:2231-9; Maguire et al., 2008. N Engl J Med. 358:2240-8; Hauswirth et al., Hum Gene Ther. 2008 October; 19 (10): 979-990.

For example, in the Bainbridge study, the tgAAG76 vector, a recombinant adeno-associated virus vector of serotype 2 was used for gene delivery. The vector contains the human RPE65 coding sequence driven by a human RPE65 promoter and terminated by the bovine growth hormone polyadenylation site, as described elsewhere. The vector was produced by Targeted Genetics Corporation according to Good Manufacturing Practice guidelines with the use of a B50 packaging cell line, an adenovirus-adeno-associated virus hybrid shuttle vector containing the tgAAG76 vector genome, and an adenovirus 5 helper virus. The vector was filled in a buffered saline solution at a titer of $1 \times 10^{11}$ vector particles per milliliter and frozen in 1-ml aliquots at −70° C.

Maguire used the recombinant AAV2.hRPE65v2 viral vector which is a replication-deficient AAV vector containing RPE65 cDNA that has been documented to provide long-term, sustained (>7.5 years, with ongoing observation) restoration of visual function in a canine model of LCA2 after a single sub-retinal injection of AAV2.RPE65. The cis plasmid used to generate AAV2.RPE65 contains the kanamycin-resistance gene. The virus was manufactured by The Center for Cellular and Molecular Therapeutics after triple transfection of HEK293 cells and was isolated and purified by microfluidization, filtration, cation exchange chromatography (POROS 50HS; GE Healthcare, Piscataway, N.J.), density gradient ultracentrifugation and diafiltration in PBS. This combination provides optimal purity of the AAV vector product, including efficient removal of empty capsids and residual cesium chloride. A portion of the product was supplemented with PF68 NF Prill Poloxamer 188 (PF68; BASF, Ludwigshafen, Germany) to prevent subsequent losses of vector to product contact surfaces. The purified virus, with or without PF68, was then passed through a 0.22-μm filter using a sterile 60-ml syringe and syringe filter, and stored frozen (−80° C.) in sterile tubes until use. An injection of 1.5×10^10 vector genome of AAV2.hRPE65v2 in a volume of 150 μl of phosphate-buffered saline supplemented with Pluronic F-68 NF Prill Poloxamer 188 was administered into the subretinal space.

The viral vector used by Hauswirth was a recombinant adeno-associated virus serotype 2 (rAAV2) vector, altered to carry the human RPE65 gene (rAAV2-CB$^{SB}$-hRPE65), that had been previously demonstrated to restore vision in animal models with RPE65 deficiency. The RPE65-LCA viral vector was delivered by subretinal injection (5.96×10^10 vector genomes in 150 μl).

Methods and protocols of administration of therapeutic agents (e.g., protein, nucleic acid molecule, expression cassettes, gene therapy vectors, cells), including without limitation, to the eye, and other procedures and protocols (including without limitation, immunology tests, eye examinations and immunosuppressant) are known in the art. For example, the following is an example of sub-retinal injection of AAV vectors used by MacLaren in treating choroideremia. Surgery was first undertaken to detach the retina through a 41G Teflon cannula (DORC International BV, Zuidland, Netherlands) using balanced salt solution (Alcon Laboratories, Fort Worth, TX, USA). Once the retinal target area had been detached from the underlying retinal pigment epithelium, a fixed volume (0.1 mL) containing 1×10^10 genome particles of AAV2.REP1 was injected through a fresh syringe into the sub-retinal space that had been created in the first five patients. In patient 6, a reduced dose of up to 6×10^9 genome particles was injected. The vector was injected slowly through the same retinotomy, causing the detachment to extend further. Surgery was uncomplicated in the first five patients, but in patient 6, difficulty in detachment of the retina from the peripheral macula necessitated the induction of detachment from a point close to the fovea, which caused visible stretching of the papillomacular bundle. Because of concerns about stretch-related damage of this vital structure in a patient with 6/7.5 vision, a smaller volume of vector (maximum 0.06 mL) was injected in the second step. In all patients, the surplus vector remaining in the syringe was expelled through the cannula into a polypropylene vial and then frozen. This surplus vector was later tested for potency with Western blot after transduction of the human-derived HT1080 cell line. Patients were treated with a 10-day oral course of prednisolone, starting 2 days before surgery at 1 mg/kg (70-100 mg) for 7 days and then reduced to 40 mg for 1 day, 20 mg for 1 day, and 10 mg for 1 day. Blood samples were taken for immunological tests before, and 1 week and 5-6 weeks after surgery. See MacLaren et al., Lancet. 2014 Mar. 29; 383 (9923): 1129-1137.

In the Hauswirth study, administration was performed as follows. After mild intravenous sedation, the surgical eye received retrobulbar anesthesia and was then prepped and draped in a standard sterile fashion. A standard three-port 23-gauge core and peripheral vitrectomy was performed. The conjunctiva over the right-sided sclerotomy was dissected with Westcott scissors and 0.3 forceps. Hemostasis was maintained by eraser-tipped cautery. The sclerotomy was enlarged with a 20-gauge MVR blade so that the sub-retinal cannula could easily be inserted into the eye. The vector was drawn into a 39-gauge injection cannula (Synergetics, O'Fallon, MO) and was introduced into the sub-retinal space. At the end of the procedure, the sclerotomy sites were secured with 7.0 Vicryl sutures and the conjunctiva was closed with interrupted sutures. Sub-conjunctival antibiotics and steroids were administered. Topical antibiotics and steroids were used for 20 days after surgery. See, Hauswirth et al., Hum Gene Ther. 2008 October; 19 (10): 979-990.

For CYP4V2 gene therapy treatment in vitro, post-treatment assessment can compare cell morphology and/or biochemical dysfunctions of patient's cells, e.g., comparing the levels of the compounds showed abnormalities in BCD patient's iPS-RPE cells (or iPS-PRC or iPS-CEC cells, if applicable) before and post-treatment, to assess whether the morphology and/or the biochemical function of the cells has improved post treatment.

For CYP4V2 gene therapy treatment in vivo, post-treatment assessment can use eye and retinal (and corneal tests, if applicable) examinations known in the art for retinal and corneal diseases, including without limitation, dark adaptation, contrast sensitivity, visual field test, visual acuity test, color vision test, ERG, OCT, fundus imaging, cornea examination, functional tests such as mobility, etc. Efficacy can be verified by one of the following: improved vision, stop of disease progression, or slower than expected rate of retinal degeneration or loss of vision.

One challenge of viral vector-mediated gene therapy is immune responses from the subject receiving the gene therapy. In addition to conventionally associated risks to the subject, the immune responses can significantly reduce the transduction efficiency of the viral vectors and/or result in a failure to establish long-term transgene expression. Mingozzi F, Meulenberg J J, Hui D J, Basner-Tschakarjan E, Hasbrouck N C, Edmonson S A, Hutnick N A, Betts M R, Kastelein J J, Stroes E S, High K A, AAV-1-mediated gene transfer to skeletal muscle in humans results in dose-dependent activation of capsid-specific T cells. Blood. 2009 Sep. 3; 114 (10): 2077-86.

Perhaps, in part because of the unique immunological environment of the eye, the immunological effects of various recombinant viral vectors (e.g., AAV, lentivirus, adenovirus) in ocular gene therapy appear to be fairly benign. Nevertheless, a significant cell-mediated immune response can develop after intraocular administration of adenovirus. Neither AAV nor lentivirus, however, elicit a cell-mediated response and are thus promising vectors for treatment of chronic ocular (retinal) diseases. J Bennett, Immune response following intraocular delivery of recombinant viral vectors, Gene Therapy (2003) 10, 977-982. doi: 10.1038/sj.gt.3302030. On the other hand, however, previous study showed that intravitreal administration of AAV vectors resulted in an increase in anti-AAV antibodies levels in both vitreal fluid as well as serum of non-human primates. Moreover, the presence of pre-existing neutralizing antibody titers in the serum of monkeys correlated strongly with weak, decaying, or no transgene expression following intravitreal administration of AAV. Kotterman et al., Antibody Neutralization Poses a Barrier to Intravitreal Adeno-Associated Viral Vector Gene Delivery to Non-Human Primates, Gene Ther. 2015 February; 22 (2): 116-126. Therefore, it is desirable to reduce immune responses in ocular gene therapy, especially those of neutralizing antibodies (NAbs), to preserve desired transduction efficiency and/or long-term transgene expression.

Historically a common practice for companies in the gene therapy field has been using AAV vector of one serotype. It typically uses a vector type with good transduction efficiency and large amount of safety data in animal studies and/or clinical trials of other gene therapy. For example, AAV2 is the most commonly used AAV serotype for ocular gene therapy in clinical trials. However, the best serotype for one patient is not always the best for another patient due to the individual differences in the immune system, e.g., pre-existing anti-AAV antibodies. For example, prevalence of pre-existing anti-AAV neutralizing antibodies against specific AAV serotypes are different among countries and populations. In addition, immune reactions can significantly reduce the transduction efficiency which can reduce efficacy of the gene therapy being applied and/or require a higher dose being administered.

A method is provided herein to reduce immune responses to viral vectors, preserve transduction efficiency, to lower viral vector and/or immunosuppressant dose, and/or to maximize therapeutic effect to different patients of the same genetic disease, in viral vector mediated gene therapy, comprising:

(a) establishing a pool of more than one recombinant viral vectors (e.g., rAAVs) with sufficient transduction efficiency in the target cell type for the gene therapy. The viral vector pool can be expanded by creating variants with antigenic region mutations or other mutations or variants on the capsids of said viral vectors after such mutations or variants are confirmed with sufficient transduction efficiency in target cells relevant to the disease (e.g., in iPS-RPE or RPE cell lines for CYP4V2 gene therapy for BCD).

(b) detecting pre-existing neutralizing anti-viral vector antibodies (NAbs) against different viral vector serotypes and/or capsid mutations or variants in the subject in need of the gene therapy, and/or testing and comparing different viral vectors in patient-specific disease target cells (e.g., iPS-RPE cells) derived from such subject.

(c) selecting a viral vector from said pool of viral vectors with (i) sufficient transduction efficiency in the disease target cells and (ii) low cross-reactivity with the pre-existing NAbs in the subject, and/or (iii) good phenotype rescue result in the subject's patient-specific disease target cells (e.g., patient-specific iPS-RPE or RPE cell lines for CYP4V2 gene therapy for BCD), wherein such viral vector pool comprising different serotypes and/or capsid-modified viral vectors (e.g., including without limitation, capsid-mutant AAVs and/or capsid protein variant AAVs).

(d) use the viral vector selected from (c) for administration to the subject.

(e) repeat (b) through (d) (only the part relating to pre-existing NAbs) above each time the subject requires a gene therapy administration, including without limitation, a follow-up administration to the same organ (e.g., an eye or a contralateral eye), or to another organ.

Potential benefits of this method include reduced use of immnosupressants, lower dose of rAAV vectors, higher transduction efficiency and longer-term transgene expression, and/or higher percentage of patients eligible for the gene therapy.

It would be appreciated that this method can be used in connection with other viral vectors. In addition, this method can be used in all types of ocular gene therapy and non-ocular gene therapy, whether it is relates to the CYP4V2 gene or another gene(s).

Methods of detecting pre-existing anti-AAV antibodies are known in the art. It is worth noting that the anti-AAV antibodies include both neutralizing antibodies and non-neutralizing antibodies. Methods to detect pre-exiting anti-AAV neutralizing antibodies and other immune response to AAVs are known in the art. Melvin Y Rincon et al., JMIR Res Protoc. 2016 April-June; 5 (2): e102; Hauswirth et al., Hum Gene Ther. 2008 October; 19 (10): 979-990. Although the effect is most significant with neutralizing antibodies, even non-neutralizing antibodies can trigger vector clearance by the immune system. The non-neutralizing antibodies can be detected by ELISA. Boutin S, Monteilhet V, Veron P, Leborgne C, Benveniste O, Montus M F, Masurier C, Prevalence of serum IgG and neutralizing factors against adeno-associated virus (AAV) types 1, 2, 5, 6, 8, and 9 in the healthy population: implications for gene therapy using AAV vectors. Hum Gene Ther. 2010 June; 21 (6): 704-12.

Unless otherwise defined, all technical and scientific terms used herein have the same meaning as commonly understood by one of ordinary skill in the art to which the methods and compositions of matter belong. In addition to the definitions of terms provided herein, definitions of common terms in molecular biology may also be found in Glossary of Genetics: Classical and Molecular, Rieger et al., 1991, 5th Ed, Springer-Verlag; in *Current Protocols in Molecular Biology*, Ausubel et al., Eds., 1998 Supplement, Greene Publishing Associates, Inc. and John Wiley & Sons, Inc.; in *Current Protocols in Cell Biology*, Bonifacino et al., Eds., 1999 Supplement, John Wiley & Sons, Inc.; and in *Current Protocols in Neuroscience*, Crawley et al., Eds., 1999 Supplement, John Wiley & Sons, Inc.

Representative methods and materials are described herein; other suitable methods and materials known in the art also can be used. The methods and materials are illustrative only and not intended to be limiting.

EXAMPLES

The inventions are further described in the following examples, which do not limit the scope of the inventions nor the claims.

The studies were initiated, designed, organized and sponsored by Reflection Biotechnologies Limited ("ReflectionBio"), a biotechnology company founded and driven by a patient and family living with a rare retinal disease. Rare disease patients shoulder the inevitable odds of genetic mutations for mankind, but are often ignored by society and under-supported by public resources. As a patient-driven biotechnology company, ReflectionBio applies a '*By Patients, For Patients*' approach for the patients to join forces and to play a more active role in driving scientific and medical R&D on rare diseases and other challenging diseases.

Patients diagnosed with BCD and having different bi-allelic CYP4V2 mutations (including homozygous CYP4V2 mutation or compound heterozygous CYP4V2 mutations) were included in this study. Particularly, one patient (herein referred to as Patient 1, P1 or RB001) has homozygous c.802-8_810del17insGC mutation. The c.802-

8_810del17insGC mutation results in an in-frame deletion of 62 amino acid-encoding exon 7. The c. 802-8_810del17insGC mutation is the most common mutation among BCD patients. Patient 2 (P2 or RB002) has compound heterozygous CYP4V2 mutations, each of the mutations is a single nucleotide change that results in only one amino acid change in the 525-amino acid long CYP4V2 protein.

Informed consents were obtained. Procedures followed the Declaration of Helsinki guidelines and were approved by an Institutional Review Board.
BCD Human Cellular Disease Model Examples
Clinically, BCD is associated with RPE atrophy, which in turn causes photoreceptor death and vision loss. Therefore, it is critical to create and use a human RPE model to study BCD and to develop treatment for BCD.

Example 1-Generation and Characterization of Induced Pluripotent Stem Cells (iPSCs) Derived from BCD Patients In the study, integration-free methods were used to generate iPSCs from BCD patients. Traditional technologies used for iPSC reprogramming (e.g., lentivirus, retrovirus) integrate into the genome of the target cells. The resulting iPSCs and cells differentiated from those iPSCs will contain foreign DNA and could be unsafe and problematic for use in cell therapy and drug discovery applications. Furthermore, the integration could occur in a critical region of the genome, causing problems with unrelated developmental processes. Comparing to traditional reprogramming methods, integration-free reprogramming methods generate iPSCs that do not contain detectable vectors or transgenes, thus making them more suitable for cell therapy and drug discovery applications.

In the study, two different integration-free reprogramming methods were used to generate iPSCs from BCD patients, one employing Sendai virus, the other employing episomal vectors. Two different types of samples were used, one is skin sample (skin fibroblasts) and the other is blood sample (peripheral blood mononuclear cells (PBMCs)). Either method can be used to generate BCD patient-specific iPSCs from skin, blood or other samples, such as urine and hair samples.
A. iPSC Reprogramming from Skin Sample
Skin biopsy was performed on BCD patients, and human fibroblast cells were obtained from the biopsy. BCD patient-specific fibroblast cells were then reprogrammed into iPS cell lines using Sendai virus, a footprint-free RNA virus that carries no risk of altering the host genome. Other vectors, including without limitation, lentivirus, also can be used in iPS reprogramming, but with a risk of integrating into the genome of the host cell. See FIG. 1 for photos of iPS cells derived from BCD patients. Fibroblast cells from healthy individuals also were reprogrammed in the same way to generate wild-type (or control) iPS cell lines.

To generate iPSCs, $5 \times 10^4$ fibroblasts were plated and cultured in 12-well plate until the cells became adherent (for about 12 hours) and were around 70%-80% confluent. The culture medium was removed, and the cells were transfected with a Sendai virus expressing Oct3/4, Sox2, Klf4 and c-Myc (CytoTune™-iPS 2.0 Sendai Reprogramming Kit, A16517, Life Technologies) at a MOI of 5:5:3:5 in 500 μl of fibroblast culture medium. The cells were incubated at 37° C. and 5% CO2 overnight, after which the virus-containing medium was removed and replaced with KO-DMEM medium (KnockOut DMEM, 15% KnockOut serum replacement, 1 L-glutamine, 1 nonessential amino acids, 1 penicillin-streptomycin, 0.1 mM β-Mercaptoethanol, basic fibroblast growth factor (bFGF) 10 ng/ml.). The transfected cells were incubated for about 7 days, with the medium changed every day.

The transfected cells were washed in PBS, exposed to trypsin (e.g., TrypLE Express at 37° C. for 4 mins) and resuspended in 2 ml KO-DMEM medium containing 10 μM ROCK inhibitor. The cells were then plated on a mitomycin-C-treated MEF feeder layer and returned to 37° C. and 5% CO2. After 24 hours and every day following, the medium was removed and replaced with KO-DMEM medium (without ROCK inhibitor). Colonies were visible 7-14 days after passage. Each iPS colony was microdissected into chunks of about 100-150 cells, following a brief treatment with KO-DMEM medium with 10 μM ROCK inhibitor, and then cultured again in KO-DMEM medium at 37° C. and 5% CO2 for another week.

iPSC characterization was performed using rimary antibodies of pluripotent markers: OCT4 Santa Cruz sc-9081 Rabbit poly, SOX2 R&D Systems 245610 Mouse IgG, TRA-1-60 Millipore (Chemicon) MAB4381, Mouse, IgM, SSEA4 Millipore (Chemicon) MAB4304 Mouse IgG, Nanog R&D Systems AF1997 Goat poly. Typically for characterization using markers, cells were washed, blocked (e.g., with 3% serum and 0.1% Triton X), exposed to a primary antibody (1:200) and incubated at room temperature for 2-3 hours. The cells were washed again, exposed to a secondary antibody and incubated at room temperature for 60 mins. Cells were then nuclear counterstained (e.g., using 1:10000 Dapi in PBST).

See FIG. 1 (a) for iPSCs generated from fibroblasts of BCD patients, and characterization by Oct-4, Sox-2, SSEA-4, Nanog and Tra-1-60 markers,
B. iPSC Reprogramming from Blood Sample
In addition to skin biopsy samples, iPSCs also were generated from blood samples of BCD patient and healthy control. The iPSCs were generated from peripheral blood mononuclear cells (PBMCs) using an episomal method. The protocol is described as below.
T cells activation:
a) Frozen PBMCs were thawed and about 0.5 million viable cells were subjected to T cell activation using Dynabeads (Human T activator, CD3/CD28, Thermo Fisher, Cat #11132D) according to the manufacturer's protocol.
b) Activated T cells were then expanded in blood cell culture medium for 10-14 days.
Reprogramming:
a) To generate iPSC lines, activated T cells were dissociated from dynabeads and electroporated with Episomal iPSC Reprogramming Vectors (Cat. No. A14703, Invitrogen, Carlsbad, CA, USA) using the Neon Transfection System (Cat. No. MPK10096, Invitrogen) according to the manufacturer's instructions.
b) The two sets of electroporated cells were plated on two sets of 35 mm dishes pre-cultured with CF1 MEF feeders (Cat #: (ASF-1213, Applied StemCell, Milpitas, CA, USA). The cells were fed daily with human iPSC growth medium.
c) After 2-3 weeks, human ESC-like iPSC colonies were picked and transferred to matri-gel coated 24-well plates for expansion.
d) Patient-specific human iPSC lines were then grown and passaged on Matrigel (Corning Cat #354277) in Human iPSC Feeder-Free Growth Medium (mTeSR™1, Catalog #05850, StemCell Technologies Inc., Vancouver, Canada) for 2-3 more passages until enough cell number obtained before cryopreservation.

Alkaline phosphatase:

a) For alkaline phosphatase (AP) staining, iPSCs were fixed and then stained with alkaline phosphatase staining solution (Naphthol/fast red violet, Sigma).

b) Cell images are captured using an Olympus microscope (IX51, Olympus, Tokyo, Japan).

See FIG. 1 (b) for phase contrast Images of iPSCs generated from peripheral blood mononuclear cells (PBMC) of blood samples of a BCD patient and a healthy control, and AP staining results.

See FIG. 1 (c) for BCD patient-derived iPSC karyotype images showing apparently normal human karyotype.

Example 2-Differentiation of iPSCs of BCD Patients Into Retinal Pigment Epithelium (RPE) Cells iPSC differentiation started at passage 3 to 6 for all iPSC lines of BCD patients and healthy controls. For differentiation, iPS colonies were cultured to confluence in 6-well culture dishes (Costar, Corning, Corning, NY) pre-treated with 1:50 diluted Matrigel (CORNING, 356230) in differentiation medium consisting of Knock-Out (KO) DMEM (Thermo Fisher Scientific, 10829018), 15% KO serum replacement (Thermo Fisher Scientific, 10829028), 1% non-essential amino acids (Thermo Fisher Scientific, 11140050), 2 mmol/L glutamine (Thermo Fisher Scientific, 35050061), 50 U/ml penicillin-streptomycin (Thermo Fisher Scientific, 10378016), and 10 mmol/L nicotinamide (Sigma-Aldrich, N0636) for the first 14 days. During the 15th to 28th days of differentiation, differentiation medium was supplemented with 100 ng/ml human Activin-A (PeproTech, 120-14). From day 29, Activin-A was removed until differentiation was completed. After 8-10 weeks, pigmented clusters formed and were manually picked and plated on Matrigel-coated dishes. Those cells were maintained in MEM (alpha modification, Sigma-Aldrich, M-4526)-based RPE medium, which contains N1 supplement (5 ml per 500 ml medium), Taurine (125 mg per 500 ml medium), Hydrocortisone (10 μg per 500 ml medium), Triiodo-thyronin (0.0065 μg per 500 ml medium) (all from Sigma-Aldrich), 2 mmol/L glutamine, 50 U/ml penicillin-streptomycin, 1% non-essential amino acids and 5% fetal bovine serum (all from GIBCO-BRL). Cells were cultured for another 6-8 weeks to allow them to form a functional monolayer for functional assays.

The RPE cells differentiated from BCD patients' iPSCs were observed under light microscopy and distinct RPE pigment and hexagonal cell shapes were seen (See FIG. 2). In addition to morphological distinctions, iPS-derived RPE cells from BCD patients were also validated by the presence of RPE-specific markers, RPE65, CRALBP and MITF. See FIG. 2 (b) for RPE markers results of BCD patients' iPS-RPE cells, showing the presence of RPE-specific markers, RPE65, CRALBP and MITF.

Multiple protocols can be used to differentiate iPSCs into RPE cells. The RPE differentiation protocol described herein is an extended protocol which usually takes more than 3 months. Other protocols take less time, e.g., less than 2 months. While both shorter and extended protocols can differentiate iPSCs into RPE cells, there can be differences in terms of the risk of tumorigenesis among iPSC-RPE cells generated by different protocols. The risk of tumorigenesis associated with iPSC differentiation is attributed to a portion of the iPS cells remaining undifferentiated or not fully differentiated at the end of the protocol, and the extended protocol likely contributes to the lack of tumor formation because the iPSCs are fully differentiated into mature RPE cells. The longer-term protocol was used to ensure the purity of the iPS-RPE cell lines generated for biochemical and other assays and functional studies, and to support the safety of iPSC-RPE cells for cell therapy, including without limitation, autologous transplantation.

Example 3-Biochemical. Cell Viability and other Assays for BCD Cellular Model and CYP4V2 Functional Studies Lipid Assays:

Previous studies on BCD and function of the CYP4V2 enzyme have focused on fatty acids. In this study, more lipidassays including not only fatty acids but also ceramides (Cer), sphingomyelins (SM), and sphingosine and sphinganine (SOSA), were used to analyze the biochemical abnormalities/phenotype in BCD disease model and to analyze the biochemical functions of the CYP4V2 protein.

Biochemical assays in free fatty acids (FFA), ceramides (Cer), sphingomyelins (SM), and sphingosine and sphinganine (SOSA) were conducted at the Biomarkers Core Laboratory of Columbia University (New York, NY, USA) based on its relevant assays and protocols.

Free fatty acids (FFA), ceramide, sphingosine and sphinganine were extracted by using chloroform:methanol. Briefly, about 1 million of iPS-RPE cells were homogenized in 150 μL water. 100 μL of homogenate was mixed with 3 mL of chloroform:methanol (v: v=2:1) containing internal standards (Palmitic acid-D31, C12 ceramide, C25 ceramide, C17 sphingosine, C17 sphinganine). The sample was vortexed well and 0.5 mL of water was added to allow for phase separation. The mixture was vortexed again and centrifuged at 3,000 g for 10 minutes at 4° C. The lower organic phase was transferred to a second clean glass tube using a Pasteur pipette. Two ml of chloroform was added to the residual aqueous phase, followed by vortex mixing and centrifugation again to extract any remaining lipids. The lower organic phases were pooled and evaporated under nitrogen at 37° C. The extracted lipids were reconstituted in 50 μl of methanol: acetonitrile (v: v=1:1) and transferred to LC autosampler vials for injection. Sphingomyelin was also extracted by chloroform:methanol like other lipids, but only 2 μL cell homogenate was placed for sample preparation for sphingomyelin. All assays were performed on a Waters Xevo TQ MS ACQUITY UPLC system (Waters, Milford, MA, USA). FFA was eluted by a 100 mm Waters ACQUITY UPLC HSS C18 column. Ceramide, sphingosine, sphinganine, sphingomyelin were separated on a 100 mm Waters ACQUITY UPLC BEH Phenyl column. FFA was monitored by using negative SIR method and others by positive MRM acquisition.

A list of compounds tested in the biochemical assays is provided in Table 2 below. Certain chemical compounds were purchased for use as standards in this study (as annotated in Table 2. Nu-Chek: Nu-Chek Prep, Inc., Elysian, MN, USA; Cayman: Cayman Chemical Company, Ann Arbor, MI, USA). Other compounds used existing standards available at the Biomarkers Core Laboratory of the Columbia University (New York, NY, USA). All FFAs were detected by single MS, whereas other types of compounds were detected by MS/MS.

TABLE 2

TEST COMPOUND LIST

| Fatty Acids (FFA) | Description | Vendor | Cat # | Ceramides (Cer) | Description |
|---|---|---|---|---|---|
| C12 | C12:0 (LAURIC ACID) | Nu-Chek | N-12-A | C14 | C14 Ceramide (d18:1/14:0) |
| C13 | C13:0 (TRIDECANOIC ACID) | Nu-Chek | N-13-A | C16:1 | C16:1 Ceramide (d13:1/16:1) |
| C14:1 Isomer 1 | | | | C16 | C16 Ceramide (d18:1/16:0) |
| C14:1 Isomer 2 | | | | C18:1 | C18:1 Ceramide (d18:1/18:1) |
| C14 Myristic Acid | C14:0 (MYRISTIC ACID) | | | C18 | C18 Ceramide (d18:1/18:0) |
| C15 | C15:0 (PENTADECANOIC ACID) | Nu-Chek | N-15-A | C20:5 | C20:5 Ceramide (d18:1/20:5) |
| C16:1 n7 cis | Δ 9 cis (PALMITOLEIC ACID) | Nu-Chek | U-40-A | C20:4 | C20:4 Ceramide (d18:1/20:4) |
| C16:1 n9 cis | cis-7-Hexadecencic Acid | Cayman | 10007290 | C20:1 | C20:1 Ceramide (d18:1/20:1) |
| C16:1 n7 trans | Δ 9 trans (PALMITELAIDIC ACID) | Nu-Chek | U-41-A | C20 | C20 Ceramide (d18:1/20:0) |
| C16 Palmitic Acid | C16:0 (PALMITIC ACID) | | | C22:6 | C22:6 Ceramide (d18:1/22:6) |
| C17 | C17:0 (MARGARIC ACID) | Nu-Chek | N-17-A | C22:5 | C22:5 Ceramide (d18:1/22:5) |
| C18:3 n3 Alpha | C18:3n-3:(ALPHA LINOLENIC ACID) | Nu-Chek | U-62-A | C22:1 | C22:1 Ceramide (d18:1/22:1) |
| C18:3 n6 Gamma | C18:3n-6 (GAMMA LINOLENIC ACID) | Nu-Chek | U-63-A | C22 | C22 Ceramide (d18:1/22:0) |
| C18:2 n6 9, 12 cis | Δ 9 cis,12 cis (LINOLEIC ACID) | Nu-Chek | U-59-A | C24:1 | C24:1 Ceramide (d18:1/24:1) |
| C18:2 n6 9, 12 trans | Δ 9 trans 12 trans (LINOELAIDIC ACID) | Nu-Chek | U-60-A | C24 | C24 Ceramide (d18:1/24:0) |
| C18:1 Oleic Acid | C18:1n-9 (OLEIC ACID) | | | C26:1 | C26:1 Ceramide (d18:1/26:1) |
| C18 Stearic Acid | C18:0 (STEARIC ACID) | | | C26 | C26 Ceramide (d18:1/26:0) |
| C19 | C19:0 (NONADECANOIC ACID) | Nu-Chek | N-19-A | C28:1 | C28:1 Ceramide (d18:1/28:1) |
| C20:5 n3 EPA | EICOSAPENTAENOIC ACID (EPA) | Nu-Chek | U-99-A | C28 | C28 Ceramide (d18:1/28:0) |
| C20:4 n6 AA | ARACHIDONIC ACID (AA) | Nu-Chek | U-71-A | | |
| C20:4 Isomer | | | | Sphingomyelins (SM) | |
| C20:3 n6 | HOMOGAMMA LINOLENIC ACID | Nu-Chek | U-69-A | C14:1 | C14:1 Sphingomyelin (d18:1/14:1) |
| C20:3 Isomer 1 | | | | C14 | C14 Sphingomyelin (d18:1/14:0) |
| C20:3 Isomer 2 | | | | C16:1 | C16:1 Sphingomyelin (d18:1/16:1) |
| C20:2 n6 | 11-14 EICOSADIENOIC ACID | Nu-Chek | U-68-A | C16 | C16 Sphingomyelin (d18:1/16:0) |
| C20:2 Isomer | | | | C18:1 | C18:1 Sphingomyelin (d18:1/18:1) |
| C20:1 n9 | 11-EICOSENOIC ACID | Nu-Chek | U-66-A | C18 | C18 Sphingomyelin (d18:1/18:0) |
| C20 Arachidic Acid | C20:0 (ARACHIDIC ACID) | | | C20:5 | C20:5 Sphingomyelin (d18:1/20:5) |
| C21 | HENEICOSANOIC ACID | Nu-Chek | N-21-A | C20:4 | C20:4 Sphingomyelin (d18:1/20:4) |
| C22:6 n3 DHA | DOCOSAHEXAENOIC ACID (DHA) | Nu-Chek | U-84-A | C20:1 | C20:1 Sphingomyelin (d18:1/20:1) |
| C22:5 n3 DPA | 7-10-13-16-19 DOCOSAPENTAENOIC ACID | Nu-Chek | U-101-A | C20 | C20 Sphingomyelin (d18:1/20:0) |
| C22:5 n6 | 4-7-10-13-16 DOCOSAPENTAENOIC ACID | Nu-Chek | U-102-A | C22:6 | C22:6 Sphingomyelin (d18:1/22:6) |
| C22:4 n6 | 7-10-13-16 DOCOSATETRAENOIC | Nu-Chek | U-83-A | C22:5 | C22:5 Sphingomyelin (d18:1/22:5) |
| C22:1 n9 | 13-DOCOSENOIC (ERUCIC) | | | C22:1 | C221 Sphingomyelin (d18:1/22:1) |
| C22 | BEHENIC ACID | Nu-Chek | N-22-A | C22 | C22 Sphingomyelin (d18:1/22:0) |
| C23 | TRICOSANOIC ACID | Nu-Chek | N-23-A | C24:1 | C24:1 Sphingomyelin (d18:1/24:1) |
| C24:1 n9 | NERVONIC ACID | Nu-Chek | U-88-A | C24 | C24 Sphingomyelin (d18:1/24:0) |
| C24 | LIGNOCERIC ACID | Nu-Chek | N-24-A | C26:1 | C26:1 Sphingomyelin (d18:1/26:1) |
| C25 | PANTACOSANOIC ACID | Cayman | 15197 | C26 | C26 Sphingomyelin (d18:1/26:0) |
| C26:1 | C26:1 n9 (Hexaccsaenoic acid) | | | C28:1 | C28:1 Sphingomyelin (d18:1/28:1) |
| C26 | HEXACOSANOIC ACID | Cayman | 13354 | C28 | C28 Sphingomyelin (d18:1/28:0) |
| SOSA | | | | | |
| SO | Sphingosine (c18:1) | | | | |
| SA | Sphinganine (d18:0) | | | | |
| SO-1P | Sphingosine-1-Phosphate (d18:1) | | | | |
| SA-1P | Sp0inganine-1-Phosphate (d18:0) | | | | |

Hydroxy-fatty acid Assays:

In addition, LC-MS/MS was used to detect hydroxy-fatty acids in iPS-RPE cells, including 16-HEPE, 17-HEPE, 18-HEPE, 19-HEPE, 20-HEPE, 17-HDHA, 18-HDHA, 19-HDHA, 20-HDHA, 21-HDHA, 22-HDHA, 19 (20)-EpDPA (formal name: (+) 19,20-epoxy-4Z,7Z,10Z,13Z,16Z-docosapentaenoic acid, a/k/a (+) 19,20 EDP, (+) 19,20-epoxy Docosapentaenoic Acid, (+) 19,20-epoxy DPA, (+) 19,20-EpDPE), and 19 (20)-DiHDPA (formal name: (+) 19,20-dihydroxy-4Z,7Z,10Z,13Z, 16Z-docosapentaenoic acid, a/k/a: (+) 19,20-DiHDoPE). The HDHA compounds are hydroxy-metabolites of DHA and the HEPE compounds are hydroxy-metabolites of EPA, respectively. 19 (20)-EpDPA is a DHA epoxygenase metabolite, derived via epoxidation of the ω-3 double bond of DHA. 19 (20)-DiHDPA is also a metabolite of DHA. DHA is an important fatty acid and the most abundant @-3 fatty acid for the brain and retina. A previous research indicated that CYP4V2 is a hydroxylase for ω-3 fatty acids, particularly DHA.

Materials: Hydroxy-fatty acid standards (+) 18-HEPE (Item No. 32840), (+) 20-HDHA (Item No. 33750), (+) 19 (20)-EpDPA (Item No. 10175) and (+) 19 (20)-DiHDPA (Item No. 10007001) were purchased from Cayman Chemical Company (Ann Arbor, MI, USA). Internal standard deuterated palmitic acid (C16-D31 fatty acid) was purchased from C/D/N Isotopes Inc. (#D-2002, Quebec, Canada).

It should be understood that in addition to LC-MS or LC-MS/MS methods described above, the chemical species and compounds tested in the study can also be detected and/or quantified by using other methods. For example, there are GC-MS or GC-MS/MS methods for FFA with methylation pre-treatment. For Cer and SM, FIA-MS/MS or GC-MS/MS can be used.

Cell Viability Assay:

Blue light exposure: iPS-RPE cells were seeded in 3.5 cm dishes and 4-well chamber dishes. After 2 months, they were exposed to 430±20 nm (blue) light at 1.5 mW/cm² for 1 hour in PBS (+) containing 10 μg/ml glucose. The same seeding density was used for all cell lines. After blue light exposure, treated cells were fed with fresh RPE medium and recovered in incubator of 5% $CO_2$ and 37° C. overnight.

In addition to 1 hour, shorter or longer light exposure durations can be used, e.g., no exposure, 30 minutes, 45 minutes, 75 minutes, 90 minutes or 120 minutes, etc. Similarly, exposure to light of a different wavelength or a broader spectrum can also be used. Moreover, iPS-RPE samples of different culture days (e.g., 2 months, 3 months, 4 months, 5 months or 6 months in RPE culture) can be used, e.g., to study the effect of aging.

Cell viability assay: Live/healthy cells were labeled by cell-permeant dye Calcein AM (Thermo Fisher Scientific, catalog no.: C3099, USA) at a final concentration of 3 µmol/ml PBS (+) (1 ml for each 3.5 cm dish or 200 µl for each chamber) and dead/sick cells were labeled by Pro- pidium Iodide (PI) (Thermo Fisher Scientific, catalog no.: P3566, USA) at a final concentration of 2 µg/ml PBS (+) (1 ml for each 3.5 cm dish or 200 µl for each chamber) at room temperature for 1 hour. Since PI is DNA-binding and is not permeant to live cells, it is commonly used to detect dead cells in a population. Then after washing with PBS (−), cellular fluorescent levels were observed and photos were taken by inverted fluorescent microscope (Nikon Eclipse Ts2R) at 20 times magnification. Dead/live cell ratios were calculated after photos were processed by ImageJ (Fiji).

In addition to biochemical assays and cell viability test, RPE function tests can be performed in BCD patient iPS- RPE cells such as phagocytic activity, transepithelial resis- tance.

CYP4V2 Expression:

Experiments were performed to detect and compare CYP4V2 expression levels in control and BCD patient- specific iPS-RPE cells. CYP4V2 expression in cell lines can be assessed by either anti-CYP4V2 antibody (Western Blot) or by quantitative PCR.

CYP4V2 Western Blot: 45 µg whole cell protein from each iPS-RPE sample was run on a 7.5% SDS page gel, then wet transfer to a membrane. The membrane was blocked with 5% BSA in PBST for 1 hour at room temperature then incubated with primary antibody (Anti-CYP4V2 produced in rabbit, Sigma Aldrich catalog #: SAB 1410565, USA) at a concentration of 1:1000 in 5% BSA overnight at 4° C. Wash was done for 3×10 minutes with PBST. The membrane then was incubated with secondary antibody goat anti-rabbit IgG HRP (Santa Cruz catalog #: sc-2004, USA) at a con- centration of 1:3000 in 5% BSA for 4 hours at 4° C. Final wash was done for 3×10 minutes with PBST. GAPDH was used as loading control.

CYP4V2 western blot detected CYP4V2 protein expres- sion in controls' iPS-RPE samples but not in BCD patient iPS-RPE sample. After treatment by AAV.CYP4V2, CYP4V2 protein was detected in BCD patient-specific iPS- RPE samples.

Real-time PCR and relative mRNA quantification: Healthy controls' (WT), BCD patient's, BCD patient's AAV.CYP4V2 treated iPS-RPE samples were harvested and lysed with TRIZOL reagent (Invitrogen). Total RNA was isolated according to the manufacturer's instructions. DNase I (Invitrogen) treatment was then performed to prevent genomic DNA contamination. The reverse transcription reaction was conducted by Superscript III Reverse Tran- scription kit, and a random hexamer (Invitrogen) was used to generate cDNA. Real-time PCR method was performed using Maxima SYBR Green/ROX qPCR Master Mix (Fisher Scientific) with StepOne Real-time PCR System (Invitrogen) to quantify gene expression levels (38 cycles). Primers specific to CYP4V2 exon 7 region and CYP4V2op, respectively, were used. Actin was used as the housekeeping gene.

Results: Quantitative PCR was performed to test the expres- sion of CYP4V2 and CYP4V2op in iPS-RPE cell samples. The transcript levels of CYP4V2 and CYP4V2op were normalized by a patient sample and a control sample, respectively. For CYP4V2, all non-patient control samples expressed similar levels of CYP4V2, several hundred folds higher than the CYP4V2 expression level in the patient sample. After AAV.CYP4V2 treatment, the patient sample CYP4V2 expression level increased more than a hundred folds to a level comparable to the non-patient control samples (FIG. 3). For CYP4V2op, all the AAV-treated samples expressed much higher levels compared with non- treated samples (FIG. 4). These results demonstrated that AAV vectors were able to deliver the CYP4V2 cDNA' into BCD patients' iPS-RPE cells and the expression cassettes were able to express the gene.

Example 4-Phenotype in BCD Cellular Model and Findings on CYP4V2 Functions

Lipid Testing results:

To determine whether and which biochemical defects/ abnormalities (i.e., phenotype) exist in the BCD cellular model (e.g., BCD patient iPS-RPE cells), the biochemical assays described in Example 3 was used to detect and quantify fatty acids, ceramides, sphingomyelins, sphingo- sina, sphinganine, and hydroxy-fatty acids in the iPS-RPE cells derived from BCD patients as compared to those of the iPS-RPE cells derived from healthy controls.

Before testing, the cells were harvested as follows. Approximately 1 million iPS-RPE cells derived from a BCD patient were washed twice with PBS, then detached from dish by a plastic cell lifter and transferred to a 1.5 ml Eppendorf tube using a 1 ml pipette. The Eppendorf tube was placed in a −80° C. freezer before testing. Health control iPS-RPE cells were harvested in the same way. Biochemical assay results are shown in Table 3 below:

TABLE 3

| mol % of total fatty acids | WT | P1 | P1 AAV2.op | P2 | P2 AAV2tri.op | P2 AAV2.op | P2 AAV8.fv | P2 scAAV1.op |
|---|---|---|---|---|---|---|---|---|
| C12 | 0.2% | 0.1% | 0.1% | 0.1% | 0.1% | 0.0% | 0.0% | 0.1% |
| C13 | 0.0% | 0.0% | 0.0% | 0.0% | 0.0% | 0.0% | 0.0% | 0.0% |
| C14:1 Isomer 1 | 0.1% | 0.1% | 0.1% | 0.0% | 0.0% | 0.0% | 0.1% | 0.1% |
| C14:1 Isomer 2 | 0.0% | 0.1% | 0.0% | 0.1% | 0.0% | 0.0% | 0.0% | 0.1% |
| C14 Myristic Acid | 1.0% | 0.6% | 0.6% | 0.7% | 0.3% | 0.8% | 0.8% | 1.1% |
| C15 | 1.3% | 0.5% | 0.7% | 0.5% | 0.5% | 0.6% | 0.5% | 0.7% |
| C16:1 n7 cis | 2.7% | 2.4% | 1.7% | 2.3% | 2.9% | 2.9% | 2.8% | 3.8% |
| C16:1 n9 cis | 0.9% | 0.9% | 0.8% | 1.0% | 1.0% | 1.1% | 1.2% | 1.6% |
| C16:1 n7 trans | 0.4% | 0.5% | 0.4% | 0.5% | 0.5% | 0.4% | 0.5% | 0.4% |
| C16 Palmitic Acid | 20.3% | 14.2% | 12.7% | 14.8% | 17.0% | 17.2% | 17.9% | 17.4% |
| C17 | 1.1% | 0.5% | 0.8% | 0.5% | 0.4% | 0.5% | 0.5% | 0.4% |

Fatty Acid Test Results

TABLE 3-continued

Fatty Acid Test Results

| mol % of total fatty acids | WT | P1 | P1 AAV2.op | P2 | P2 AAV2tri.op | P2 AAV2.op | P2 AAV8.fv | P2 scAAV1.op |
|---|---|---|---|---|---|---|---|---|
| C18:3 n3 Alpha | 0.0% | 0.0% | 0.0% | 0.0% | 0.0% | 0.0% | 0.0% | 0.0% |
| C18:3 n6 Gamma | 0.1% | 0.1% | 0.1% | 0.1% | 0.1% | 0.1% | 0.1% | 0.1% |
| C18:2 n6 9, 12 cis | 1.5% | 1.1% | 0.9% | 0.9% | 0.9% | 1.0% | 1.0% | 1.3% |
| C18:2 n6 9, 12 trans | 0.1% | 0.1% | 0.1% | 0.1% | 0.1% | 0.0% | 0.1% | 0.1% |
| C18:1 n9 Oleic Acid | 22.2% | 20.9% | 19.0% | 18.5% | 19.4% | 20.8% | 19.7% | 28.6% |
| C18 Stearic Acid | 26.3% | 17.9% | 24.2% | 19.4% | 16.5% | 16.6% | 17.7% | 14.4% |
| C19 | 0.2% | 0.2% | 0.2% | 0.2% | 0.2% | 0.2% | 0.2% | 0.2% |
| C20:5 n3 EPA | 0.8% | 1.9% | 1.3% | 1.9% | 1.6% | 1.7% | 1.4% | 1.6% |
| C20:4 n6 AA | 5.4% | 15.2% | 13.3% | 14.7% | 14.2% | 13.2% | 13.0% | 7.9% |
| C20:4 Isomer | 0.0% | 0.0% | 0.0% | 0.0% | 0.0% | 0.0% | 0.0% | 0.0% |
| C20:3 n6 | 0.5% | 0.8% | 0.8% | 0.9% | 0.3% | 0.9% | 0.8% | 0.6% |
| C20:3 Isomer 1 | 0.1% | 0.3% | 0.3% | 0.4% | 0.3% | 0.3% | 0.3% | 0.1% |
| C20:3 Isomer 2 | 3.8% | 6.0% | 5.5% | 5.1% | 5.5% | 4.1% | 4.2% | 3.0% |
| C20:2 n6 | 0.4% | 0.4% | 0.5% | 0.3% | 0.4% | 0.3% | 0.4% | 0.6% |
| C20:2 Isomer | 0.5% | 0.6% | 0.8% | 0.7% | 0.3% | 0.7% | 0.7% | 0.9% |
| C20:1 n9 | 3.7% | 2.9% | 2.7% | 2.7% | 3.6% | 3.4% | 3.3% | 6.1% |
| C20 Arachidic Acid | 0.8% | 0.5% | 0.5% | 0.5% | 0.6% | 0.6% | 0.5% | 0.5% |
| C21 | 0.0% | 0.0% | 0.0% | 0.0% | 0.0% | 0.0% | 0.0% | 0.0% |
| C22:6 n3 DHA | 2.2% | 6.1% | 5.6% | 7.2% | 6.2% | 6.5% | 6.5% | 4.1% |
| C22:5 n3 DPA | 1.0% | 2.0% | 2.4% | 2.8% | 2.1% | 2.6% | 2.1% | 1.7% |
| C22:5 n6 | 0.1% | 0.4% | 0.5% | 0.4% | 0.3% | 0.3% | 0.4% | 0.2% |
| C22:4 n6 | 0.7% | 1.3% | 1.7% | 1.4% | 1.4% | 1.3% | 1.3% | 1.0% |
| C22:1 n9 | 0.5% | 0.6% | 0.6% | 0.6% | 0.7% | 0.7% | 0.7% | 0.9% |
| C22 | 0.2% | 0.2% | 0.2% | 0.1% | 0.2% | 0.2% | 0.2% | 0.1% |
| C23 | 0.0% | 0.0% | 0.0% | 0.0% | 0.0% | 0.0% | 0.0% | 0.0% |
| C24:1 n9 | 0.3% | 0.4% | 0.4% | 0.4% | 0.4% | 0.4% | 0.5% | 0.3% |
| C24 | 0.1% | 0.2% | 0.2% | 0.2% | 0.2% | 0.2% | 0.2% | 0.1% |
| C25 | 0.0% | 0.0% | 0.0% | 0.0% | 0.0% | 0.0% | 0.0% | 0.0% |
| C26:1 | 0.0% | 0.1% | 0.1% | 0.1% | 0.1% | 0.1% | 0.1% | 0.0% |
| C26 | 0.0% | 0.0% | 0.0% | 0.0% | 0.0% | 0.0% | 0.0% | 0.0% |
| Sum | 100.0% | 100.0% | 100.0% | 100.0% | 100.0% | 100.0% | 100.0% | 100.0% |
| Total of n-3 Fatty acids | 4.0% | 10.0% | 9.4% | 11.9% | 9.9% | 10.8% | 10.1% | 7.4% |

Footnote to Table 3:
WT: Wild-type control iPS-RPE.
P1: Patient 1 iPS-RPE.
P2: Patient 2 iPS-RPE.
Patient untreated and AAV treated samples were culture day and clone line matched.
P1 AAV2.op and P2 AAV2.op samples were treated by AAV2.CYP4V2op ( 1 day. MOI: $5 \times 10^4$ GC/cell) and harvested 10 days post treatment.
P2 AAV2trip.op sample was treated by AAV2tri(Y-F).CAP4V2op (1 day. MOI: $5 \times 10^4$ GC/cell) and harvested 10 days post treatment.
P2 AAV8.fv sample was treated by AAV8.CYP4V2fv (1 day. MOI: $2 \times 10^5$ GC/cell) and harvested 10 days post treatment.
P2 scAAV1.op sample was treated by scAAV1.CYP4V2op (1 day. MOI: $2 \times 10^5$ GC/cell) and harvested 4 days post treatment.

The results showed that BCD patient iPS-RPE cell samples have a different fatty acid profile from that of the control. In particular, BCD patient samples have much higher levels of DHA (22:6 n3) and total of omega-3 (ω-3, or n3) fatty acids (sum of C18:3 n3 Alpha, C20:5 n3 EPA, C22:6 n3 DHA and C22:5 n3 DPA) than those of control. This confirmed suggestions from a previous study that CYP4V2 affects omega-3 fatty acid metabolism.

Surprisingly, in addition to abnormalities in n3 fatty acid levels, BCD patient iPS-RPE cells also showed higher level of C20:4 n6 (Arachidonic Acid, or AA). Abnormal level of AA has not been reported in prior studies relating to BCD.

Interestingly, abnormalities in n3 fatty acids (including DHA) and n6 fatty acids (including AA) was not found in a prior research which tested fatty acid levels in BCD patients' serum. The different fatty acid profiles of BCD patient iPS-RPE cells and serum supports the hypothesis that the function of CYP4V2 is substituted by other CYP4 enzymes in non-retinal or non-RPE cells, many of which are expressed in other organs and tissues together with CYP4V2 except that CYP4V2 is the only CYP4 enzyme with relatively high expression level in RPE cells.

In addition to fatty acids, BCD patient iPS-RPE cells may have phenotype in other compounds or compound classes. Experiments are conducted to screen for phenotype in other compound classes, including without limitation, corticoster-oid, sphingolipids and phospholipids including sphingomy-elin, ceramide, sphingosine and sphinganine, and in lipid signaling. Furthermore, isotopic tracing experiment and proteomic analysis (e.g., mass spectrometry-based proteomic analysis) is performed in BCD patients' iPS-RPE cells.

Further, a prior research found that CYP4V2 is a ω-3 fatty acid (DHA and EPA) hydroxylase. Interestingly, hydroxy-DHAs or hydroxy-EPAs described in Example 3 were not detected in either healthy control or BCD patient's iPS-RPE cells using LC-MS/MS. It is possible that the CYP4V2 enzymatic functions are different in live cells vs. in a chemical reaction outside live cells which was conducted in the prior research, or the hydroxy-fatty acids are intermediates that are fast converted into other compounds or forms in live cells, or the hydroxy-fatty acids are at trace level which can be detected only when a sample contains a very large amount of cells.

Cell Viability Assay Results:

Clinically, BCD is associated with RPE atrophy, which in turn causes photoreceptor death and vision loss. Cell viability assay (as described in Example 3 above) revealed RPE atrophy in BCD patients' iPS-RPE cell samples. See FIGS. 5 and 6 for cell viability comparison between iPS-RPE samples of controls and BCD patients (FIG. 5-without exposure to blue light; FIG. 6—after 1 hour exposure to blue light).

Significantly, these images revealed that:

(1) After exposure to light, significant levels of cell death were shown in iPS-RPE samples derived from BCD patients (P1 and P2), much higher than those of controls (WT1 and WT2) (See FIG. 6). For example, the dead/live cell ratio of P1 iPS-RPE was 20.87%, as compared to 3.0% for WT2 iPS-RPE. The clinical phenotype of BCD, RPE atrophy, was evident in the BCD Cellular Model.

(2) Different levels of RPE atrophy was observed between BCD P1 and P2 iPS-RPE samples. P1 iPS-RPE showed a higher cell death level than P2 iPS-RPE.

(3) Even without blue light exposure, BCD patient iPS-RPE sample (P1) showed RPE atrophy (FIG. 5).

BCD patients differ widely in disease onset age and progression. BCD onset ranges from early teenage to the $3^{rd}$ decade of life or even beyond the $3^{rd}$ decade; leading to legal blindness during the $3^{rd}$ decade to 6th decade of life. In addition, BCD sibling patients with the same CYP4V2 mutation can have material difference in disease onset age and progression. Previously there was no explanation to these differences. The difference in RPE atrophy levels between different BCD patient's iPS-RPE samples provides a guidance at the cellular level as to the difference in disease onset and progression among BCD patients.

Multiple phenotypes (both molecule-level phenotype such as biochemical (e.g., lipid) abnormalities and cellular-level phenotype such as cell viability) have been found in the BCD Cellular Model in this study, including the clinical phenotype of BCD (i.e., RPE atrophy).

Example 5-Use of iPS and iPS-RPE Cells from a BCD Subject to Screen Drug Candidates and Dosage Range, Study BCD and CYP4V2 Function and in Cell Therapy, and to Assess Patient-Specific Responses As the BCD disease human cellular model, iPS and iPS-RPE cells from BCD patients have a broad range of applications, including without limitation, to study BCD and CYP4V2 function (see Examples 3 and 4 above, for example); to screen drug candidates and dosage range for BCD and related diseases (see the Examples herein).

Methods and examples to use the BCD cellular model (e.g., BCD patient-specific iPS-RPE cell line or iPS-RPE cell lines with artificially generated CYP4V2 mutations) is described in detail in the Examples herein, which are related to the use of the BCD cellular model in gene therapy and cell therapy. In addition to testing gene therapy and as cellular base for cell therapy, such BCD cellular model can be used to screen and test efficacy and/or safety of other therapeutic agents (e.g., drug candidates) and dosage, formulation and vector (viral or non-viral vectors) thereof or devices or delivery mechanisms for treating BCD, IRD or RP, in the same or similar way as described in detail in the Examples herein.

In using the BCD cellular model, the efficacy of a therapeutic agent can be assessed by comparing the levels of compounds in the various species and RPE atrophy described in Examples 3 and 4 above and other Examples herein before treatment and post treatment by such therapeutic agent and assess whether the abnormalities in the levels of these compounds and whether RPE atrophy in the BCD cellular model improve post treatment. Similarly, different doses, formulations (e.g., formulation for chemical compounds, active pharmaceutical ingredients, or vector type and/or capsid for gene therapy, or vector type for gene editing) or key constructs (e.g., a promoter or other regulatory sequence in a gene therapy expression cassette) of a therapeutic agent can be compared using the BCD cellular model. In addition, BCD cellular model can be used to test the efficacy of a medical device or method, including without limitation, in delivering therapeutic agents to the ocular cells or in improving transduction or transfection efficiency. It would be understood that the treated cells can be compared to untreated cells or to the same cells prior to exposure to the compound. Different dosages can be used to determine the effective dosage range (measured by per cell, per 1 million cells or per 0.5 million cells, etc.). Data relating to the levels of different compounds of fatty acids and other compounds and RPE atrophy stated in Examples 3 and 4 above, in BCD patient's iPS-RPE cells (post treatment vs. without treatment) as compared to those in RPE or iPS-RPE cells of healthy control can be used to assess therapeutic effect and effective dosage range.

Furthermore, BCD patient-specific iPS cell lines, iPS-RPE cell lines and other iPS-derived cell lines can be used to assess such patient's individual responses to a therapeutic agent, dose, or device. The patient-specific iPS cells, iPS-RPE cells and other iPS-derived cells possess traits specific to each patient, including without limitation, immune response (e.g., intracellular immunity, RPE immunity), genotype (e.g., different mutations between patients which may result in a different response). Such application can be used to develop and screen individualized therapeutic agent (e.g., different AAV vector serotypes or capsid mutations) or personalized optimal dosage for different patients of the same disease. This approach can be used for other diseases, including without limitation, other ocular diseases.

Since BCD patient-specific iPS-RPE revealed individual differences in BCD patients, it can be used to assess individualized optimal dosage and develop personalized medicine. For example, as seen in the gene therapy Examples below, at the same dosage of 1×10e5 MOI, AAV2.CYP4V2op achieved different rescue levels (i.e., different efficacy levels) of RPE atrophy between P1 and P2's iPS-RPE. This is an advantage BCD cellular model has over animal models.

BCD patient-specific iPS-RPE cells (i.e., BCD cellular model) can be used to assess and suggest therapeutic effective dosage for treatment in vivo by multiply the optimal dose level (e.g., indicated as MOI for gene therapy in vitro) determined in BCD cellular model in vitro by the estimated number of ocular cells (e.g., RPE cells) targeted for treatment in vivo to arrive the dose level of gene therapy vectors for use in vivo (e.g., GC or gp). Such vector dose level is adjusted by a multiplier (e.g., 1 to 10 (e.g., 1 to 5 for sub-retinal injection or 5 to 10 for intravitreal injection; the other factors affecting the multiplier to be applied include the size of the area targeted, and the subject being treated (e.g., the age, weight, development stage of the disease and condition of the subject to be treated, and potential immune reactions (i.e., pre-exisiting NAbs); the location and density of the cells targeted for treatment) to suggest the therapeutic effective dose range for treatment in vivo, which can be confirmed or further refined by clinical trials. This method can also be used to assess or suggest personalized optimal dose for treatment in vivo for individual patient.

Example 6-BCD Cellular Model with Artificially Created CYP4V2 Mutations

Because BCD is a rare disease, patient samples can be difficult to obtain. To overcome this difficulty, a BCD cellular model can be generated by using gene editing technologies such as CRISPR to create artificial mutations in the CYP4V2 gene in non-BCD patient cells such as embryonic stem (ES) cell lines or iPS cells from a subject without BCD.

For example, as demonstrated in the Examples herein, sgRNA 1, sgRNA 2, sgRNA 3, sgRNA 4 or sgRNA 5 (See SEQ ID NOs: 48 to 52 for the protospacer element sequence in each of sg$NA1, sgRNA2, sgRNA3, sgRNA4 and sgRNA5, respectively; See SEQ ID NO: 55 and 59 for additional sequence for the IVT sgRNAs) were used in combination with SpCas9 protein to create cleavage in a region of the CYP4V2 gene in a BCD patient's genomic DNA containing the c.802-8_810del17insGC mutation, the most common CYP4V2 mutation among BCD patient. Amongst them, sgRNA 3, sgRNA 4, and sgRNA 5 are not specific to the c.802-8_810del 17insGC mutation sequence and therefore can create double stranded DNA break (DSB) in the CYP4V2 gene of a healthy cell (e.g., an ES or iPSC without a CYP4V2 mutation). In particular, after transfection, sgRNA 4 and Cas9 can create a DSB in exon 7 of CYP4V2 gene, which can result in a mutation in exon 7 (in one or both alleles) when the DNA is repaired through non-homologous end joining (NHEJ) in cells, e.g., an indel error created by NHEJ can result in a frameshift mutation. As a result, some cells can have artificially created CYP4V2 mutations and can be used as a BCD cellular disease model or used to generate BCD cellular model (e.g, differentiate the ES or iPS cells into RPE cells to generate CYP4V2 mutation containing ES-RPE or iPS-RPE cells). Similarly, two sets of gRNAs designed to create DSB at different regions of the CYP4V2 gene can be used to generate a large deletion or a knockout mutation within the CYP4V2 gene or to knockout the entire CYP4V2 gene in cells, thereby generating a BCD cellular model containing a CYP4V2 mutation(s). More detailed discussion on how to use CRISPR system to cut and/or correct a target sequence, and how to validate the results are provided in the Examples and disclosure herein.

These BCD cellular model with artificially created CYP4V2 mutations can be used to mimic BCD patient-specific cellular model in studying BCD and CYP4V2 functions, as well as in related applications as discussed herein, including but not limited to, testing and comparing drug candidates, determining dosage range and testing medical devide or delivery method.

The same method can be used to generate cellular disease models with artificially created mutations for an ocular or other disease, including the ones associated with a mutation or genetic defect in one or more gene(s) set forth in Table 4.

Example 7-Generation and Use of Isogenic Control for Ocular Diseases

A mutation-corrected isogenic patient-specific iPS cell line and/or other cell lines derived from thereof (e.g., iPS-RPE cells, iPS-RPCs, iPS-CECs, iPS-CE cells or other iPS-ocular cells) can be used as an isogenic control in studying a disease and/or the implications of the specific mutation or defective gene. A conventional control (e.g., a cell line, e.g., an ES-RPR or iPS-RPE cell line) derived from ES or another individual possesses individual differences including genetic differences from a patient in addition to differences in the disease related gene. This Example provides a method to eliminate individual differences between controls and the "background noise" resulted therefrom. It comprises generating and using a mutation-corrected isogenic control from a patient to compare to the same patient's cell line harboring the mutation. Since a patient-specific disease model and an mutation-corrected isogenic control derived from the same patient do not have any individual differences, they can be analyzed and compared to precisely identify the phenotype, biochemical abnormalities, and other structural and functional defects associated with the mutation or defective gene of the patient, A mutation-corrected isogenic control can be generated by using gene-editing technologies including without limitation CRISPR, ZFN and TALEN. A specific example on how to use CRISPR gene editing to correct the c.802-8_810del 17insGC mutation, the most common mutation among BCD patients, thereby generating an isogenic control from a BCD patient is provided in the Examples herein. The same approach can be used to create isogenic control for other ocular diseases. Isogenic controls have significant advantages over conventional controls and can be indispensable in studying ocular diseases with a subtle phenotype (e.g., age-related macular degeneration (AMD). In addition, isogenic controls can be used to compare and identity the impact differences of multiple genetic risk factors, mutations and/or multiple genes in an ocular disease by creating isogenic control with each one of the genetic risk factor, mutation or gene corrected and compare such isogenic control to the disease model to determine the impact of related risk factor, mutation or gene in the ocular and other disease, including the ones associated with the a mutation or genetic defect in one or more gene(s) set forth in Table 4.

An isogenic control can be compared to a patient-specific cellular disease model to identify phenotype, biochemical abnormalities, and other structural and functional defects associated with the genetic mutation and/or the related defective protein, A specific non-limiting Example and discussions on how to use bio-assays to identity biochemical abnormalities/phenotype between patient cell lines and controls are provided herein in Examples 3 and 4 above, including without limitation, lipidomics, proteomics and isotopic tracing.

Discussion on BCD Human Cellular Disease Model

Given that BCD is a rare disease, it is impracticable to obtain the disease manifesting human RPE cells from BCD patients through biopsy. The lack of a viable BCD human disease model has limited prior research on BCD to using non-BCD disease causing cells (e.g., fibroblasts and lymphocytes, which are not part of the eye) and serum from BCD patients as study subjects. The results from these studies were centered around fatty acid anabolism. In the study described herein, iPS cell lines derived from BCD patients were successfully generated and utilized to generate patient-specific BCD disease RPE cells, which carry BCD disease phenotype in vitro. The BCD phenotype was directly identified in BCD patient-specific iPS-RPE cells, the primary cell type affected in BCD. Before the present study, it was not known whether iPS cell lines and iPS-RPE cell lines could be successfully generated due, in part, to the fatty acid anabolism associated with BCD.

Biochemical testing showed that iPS-RPE cells from BCD patients have abnormal levels of fatty acids as compared to those of healthy control's iPS-RPE cells, including ones which have not been reported in prior BCD studies. The in vitro phenotype of BCD disease-specific iPS-RPE cells provide more insights to the pathways regulated by CYP4V2 and pathogenesis of BCD, and provided invaluable insights into the pathogenesis of BCD and function of CYP4V2 protein, and further supports the use of iPS-RPE cell lines from BCD patients as a viable and robust BCD human disease model.

The iPS cell lines, iPS-RPE cell lines and other iPS-ocular cell lines from BCD patients have further applications, such as use for drug screening, developing novel therapeutic agents or determining dosage ranges, as well as use in cell therapy.

In addition to BCD patient-specific iPS, iPS-RPE and other iPS-ocular cell lines, a BCD human disease cellular model can be developed via gene editing to create pathologic CYP4V2 mutations artificially in other cell lines derived from ES cells or iPS cells of non-BCD individuals, including without limitation, ES cell lines, iPS cell lines and RPE cell lines.

Furthermore, methods to generate isogenic controls for ocular diseases are provided. Isogenic controls do not possess individual differences from a patient-specific disease model. Hence an isogenic control has its advantages in studying ocular diseases over conventional controls.
CYP4V2 Gene Therapy Example 8-cDNAs Encoding the human CYP4V2 Protein and a Functional CYP4V2 Protein Three cDNAs were used in the study. The cDNA with sequence shown in SEQ ID NO: 1 (herein referred to as CYP4V2st) and the cDNA with sequence shown in SEQ ID NO: 2 (herein referred to as CYP4V2op) both encode the human CYP4V2 protein (amino acid sequence shown in SEQ ID NO: 4. NP_997235.3). The cDNA with sequence shown in SEQ ID NO: 3 (herein referred to as CYP4V2fv) encodes a functional variant of the human CYP4V2 protein (amino acid sequence shown in SEQ ID NO: 5).

SEQ ID NO: 5 is the amino acid sequence of a functional variant of the human CYP4V2 protein (SEQ ID NO: 4). Both proteins (SEQ ID NO: 4 and SEQ ID NO: 5) are functional CYP4V2 proteins as defined herein. The functional CYP4V2 protein shown in SEQ ID NO: 5 has one amino acid change from the human CYP4V2 protein shown in SEQ ID NO: 4. The cDNA shown in SEQ ID NO: 3 encoding the functional CYP4V2 protein (SEQ ID NO; 5) has two nucleotide differences from the cDNA shown in SEQ ID NO: 1 which encodes the human CYP4V2 protein (SEQ ID NO: 4). Both of the codon-optimized cDNA shown in SEQ ID NO: 2 and cDNA shown in SEQ ID NO: 1 encode the human CYP4V2 protein (SEQ ID NO: 4) and share a sequence identity of 77%.

A codon-optimized cDNA (CYP4V2fv-op) encoding the functional CYP4V2 protein of SEQ ID NO: 5 is provided herein which comprises the cDNA sequence of CYP4V2op (SEQ ID NO: 2), except that the CYP4V2 fv-op sequence retains the one or two nucleotide differences between SEQ ID NO: 1 and 3.

In addition to CYP4V2op and CYP4V2fv-op, other codon-optimized cDNAs or nucleic acid sequences encoding the human CYP4V2 protein or a functional CYP4V2 protein (e.g., any of SEQ ID NOs: 4 to 29) can be generated by methods described in the disclosure herein. A codon-optimized nucleic acid molecule encoding the human CYP4V2 protein (SEQ ID NO: 4) or a functional CYP4V2 protein (SEQ ID NO: 5 or any of SEQ ID Nos: 6 to 29) can be tested in BCD patient-specific iPS-RPE cells lines (or RPE cells with artificially created CYP4V2 mutations) to determine and/or confirm its expression efficiency and rescue function for treating BCD. Such tests includes without limitation, protein expression (e.g., western blot specific to the functional CYP4V2 protein it encodes), PCR to detect the related gene expression, and/or efficacy in rescuing the biochemical abnormalities and RPE atrophy in BCD patient-specific iPS-RPE cell lines by compositions (e.g., in an expression cassette and/or a vector) and methods provided herein.

```
(CYP4V2st cDNA, 1578 bp)
                                                        SEQ ID NO: 1
ATGGCGGGGCTCTGGCTGGGGCTCGTGTGGCAGAAGCTGCTGCTGTGGGGCGCGGCGAGTGCCCT

TTCCCTGGCCGGCGCCAGTCTGGTCCTGAGCCTGCTGCAGAGGGTGGCGAGCTACGCGCGGAAAT

GGCAGCAGATGCGGCCCATCCCCACGGTGGCCCGCGCCTACCCACTGGTGGGCCACGCGCTGCTG

ATGAAGCCGGACGGGCGAGAATTTTTTCAGCAGATCATTGAGTACACAGAGGAATACCGCCACAT

GCCGCTGCTGAAGCTCTGGGTCGGGCCAGTGCCCATGGTGGCCCTTTATAATGCAGAAAATGTGG

AGGTAATTTTAACTAGTTCAAAGCAAATTGACAAATCCTCTATGTACAAGTTTTTAGAACCATGG

CTTGGCCTAGGACTTCTTACAAGTACTGGAAACAAATGGCGCTCCAGGAGAAAGATGTTAACACC

CACTTTCCATTTTACCATTCTGGAAGATTTCTTAGATATCATGAATGAACAAGCAAATATATTGG

TTAAGAAACTTGAAAAACACATTAACCAAGAAGCATTTAACTGCTTTTTTTACATCACTCTTTGT

GCCTTAGATATCATCTGTGAAACAGCTATGGGGAAGAATATTGGTGCTCAAAGTAATGATGATTC

CGAGTATGTCCGTGCAGTTTATAGAATGAGTGAGATGATATTTCGAAGAATAAAGATGCCCTGGC

TTTGGCTTGATCTCTGGTACCTTATGTTTAAAGAAGGATGGGAACACAAAAAGAGCCTTCAGATC

CTACATACTTTTACCAACAGTGTCATCGCTGAACGGGCCAATGAAATGAACGCCAATGAAGACTG

TAGAGGTGATGGCAGGGGCTCTGCCCCCTCCAAAAATAAACGCAGGGCCTTTCTTGACTTGCTTT

TAAGTGTGACTGATGACGAAGGGAACAGGCTAAGTCATGAAGATATTCGAGAAGAAGTTGACACC

TTCATGTTTGAGGGGCACGATACAACTGCAGCTGCAATAAACTGGTCCTTATACCTGTTGGGTTC

TAACCCAGAAGTCCAGAAAAAAGTGGATCATGAATTGGATGACGTGTTTGGGAAGTCTGACCGTC
```

-continued

CCGCTACAGTAGAAGACCTGAAGAAACTTCGGTATCTGGAATGTGTTATTAAGGAGACCCTTCGC

CTTTTTCCTTCTGTTCCTTTATTTGCCCGTAGTGTTAGTGAAGATTGTGAAGTGGCAGGTTACAG

AGTTCTAAAAGGCACTGAAGCCGTCATCATTCCCTATGCATTGCACAGAGATCCGAGATACTTCC

CCAACCCCGAGGAGTTCCAGCCTGAGCGGTTCTTCCCCGAGAATGCACAAGGGCGCCATCCATAT

GCCTACGTGCCCTTCTCTGCTGGCCCCAGGAACTGTATAGGTCAAAAGTTTGCTGTGATGGAAGA

AAAGACCATTCTTTCGTGCATCCTGAGGCACTTTTGGATAGAATCCAACCAGAAAAGAGAAGAGC

TTGGTCTAGAAGGACAGTTGATTCTTCGTCCAAGTAATGGCATCTGGATCAAGTTGAAGAGGAGA

AATGCAGATGAACGCTAA (CYP4V2op cDNA, 1578 bp)

SEQ ID NO: 2

ATGGCTGGACTGTGGCTGGGACTGGTGTGGCAGAAACTGCTGCTGTGGGGGGCCGCTTCCGCACT

GTCACTGGCTGGGGCTTCACTGGTGCTGAGCCTGCTGCAGAGGGTGGCCTCCTACGCCAGAAAGT

GGCAGCAGATGAGGCCCATCCCTACCGTGGCCAGAGCCTATCCACTGGTGGGACACGCACTGCTG

ATGAAGCCTGACGGCAGAGAGTTCTTTCAGCAGATCATCGAGTACACAGAGGAGTATAGGCACAT

GCCACTGCTGAAGCTGTGGGTGGGACCCGTGCCTATGGTGGCCCTGTACAACGCCGAGAATGTGG

AAGTGATCCTGACCAGCAGCAAGCAGATCGATAAGTCTAGCATGTATAAGTTCCTGGAGCCTTGG

CTGGGCCTGGGCCTGCTGACCTCTACAGGCAACAAGTGGAGGAGCCGGAGAAAGATGCTGACCCC

AACATTCCACTTTACAATCCTGGAGGACTTCCTGGACATCATGAACGAGCAGGCCAATATCCTGG

TGAAGAAGCTGGAGAAGCACATCAACCAGGAGGCCTTTAATTGCTTCTTTTACATCACCCTGTGC

GCCCTGGACATCATCTGTGAGACAGCTATGGGCAAGAACATCGGCGCCCAGTCTAATGACGATAG

CGAGTACGTGCGGGCCGTGTATAGAATGAGCGAGATGATCTTTAGGCGCATCAAGATGCCCTGGC

TGTGGCTGGATCTGTGGTATCTGATGTTCAAGGAGGGCTGGGAGCACAAGAAGTCCCTGCAGATC

CTGCACACCTTTACAAACTCTGTGATCGCCGAGAGAGCCAATGAGATGAACGCCAATGAGGACTG

TAGGGGCGATGGAAGGGGCAGCGCCCCTTCCAAGAACAAGCGGAGAGCCTTCCTGGACCTGCTGC

TGAGCGTGACCGACGATGAGGGCAATCGCCTGTCCCACGAGGACATCCGGGAGGAGGTGGATACA

TTCATGTTTGAGGGACACGACACCACAGCCGCCGCCATCAACTGGTCCCTGTACCTGCTGGGCTC

TAATCCAGAGGTGCAGAAGAAGGTGGATCACGAGCTGGACGACGTGTTCGGCAAGTCCGACAGGC

CAGCAACCGTGGAGGATCTGAAGAAGCTGAGATACCTGGAGTGCGTGATCAAGGAGACACTGCGC

CTGTTCCCCTCTGTGCCTCTGTTTGCCCGGTCCGTGTCTGAGGACTGTGAGGTGGCCGGCTATCG

CGTGCTGAAGGGCACCGAGGCCGTGATCATCCCTTACGCCCTGCACCGGGACCCCAGGTATTTCC

CTAACCCAGAGGAGTTTCAGCCAGAGAGATTCTTTCCCGAGAATGCCCAGGGCAGGCAGCCTTAC

GCCTATGTGCCATTCTCCGCCGGACCAAGGAACTGCATCGGACAGAAGTTTGCCGTGATGGAGGA

GAAAACCATCCTGTCTTGTATCCTGAGACACTTCTGGATCGAGAGCAATCAGAAGAGGGAGGAGC

TGGGCCTGGAGGGACAGCTGATCCTGCGGCCAAGCAACGGCATCTGGATCAAACTGAAAAGAAGG

AACGCTGACGAGAGGTAA (CYP4V2fv cDNA, 1578 bp)

SEQ ID NO: 3

ATGGCGGGGCTCTGGCTGGGGCTCGTGTGGCAGAAGCTGCTGCTGTGGGGCGCGGCGAGTGCCCT

TTCCCTGGCCGGCGCCAGTCTGGTCCTGAGCCTGCTGCAGAGGGTGGCGAGCTACGCGCGGAAAT

GGCAGCAGATGCGGGCCATCCCCACGGTGGCCCGCGCCTACCCACTGGTGGGCCACGCGCTGCTG

ATGAAGCCGGACGGCGAGAATTTTTTTCAGCAGATCATTGAGTACACAGAGGAATACCGCCACAT

GCCGCTGCTGAAGCTCTGGGTCGGGCCAGTGCCCATGGTGGCCCTTTATAATGCAGAAAATGTGG

AGGTAATTTTAACTAGTTCAAAGCAAATTGACAAATCCTCTATGTACAAGTTTTTAGAACCATGG

-continued

CTTGGCCTAGGACTTCTTACAAGTACTGGAAACAAATGGCGCTCCAGGAGAAAGATGTTAACACC

CACTTTCCATTTTACCATTCTGGAAGATTTCTTAGATATCATGAATGAACAAGCAAATATATTGG

TTAAGAAACTTGAAAAACACATTAACCAAGAAGCATTTAACTGCTTTTTTTTACATCACTCTTTGT

GCCTTAGATATCATCTGTGAAACAGCTATGGGGAAGAATATTGGTGCTCAAAGTAATGATGATTC

CGAGTATGTCCGTGCAGTTTATAGAATGAGTGAGATGATATTTCGAAGAATAAAGATGCCCTGGC

TTTGGCTTGATCTCTGGTACCTTATGTTTAAAGAAGGATGGGAACACAAAAAGAGCCTTAAGATC

CTACATACTTTTACCAACAGTGTCATCGCGGAACGGGCCAATGAAATGAACGCCAATGAAGACTG

TAGAGGTGATGGCAGGGGGTCTGCCCCCTCCAAAAATAAACGCAGGGCCTTTCTTGACTTGCTTT

TAAGTGTGACTGATGACGAAGGGAACAGGCTAAGTCATGAAGATATTCGAGAAGAAGTTGACACC

TTCATGTTTGAGGGGCACGATACAACTGCAGCTGCAATAAACTGGTCCTTATACCTGTTGGGTTC

TAACCCAGAAGTCCAGAAAAAAGTGGATCATGAATTGGATGACGTGTTTGGGAAGTCTGACCGTC

CCGCTACAGTAGAAGACCTGAAGAAACTTCGGTATCTGGAATGTGTTATTAAGGAGACCCTTCGC

CTTTTTCCTTCTGTTCCTTTATTTGCCCGTAGTGTTAGTGAAGATTGTGAAGTGGCAGGTTACAG

AGTTCTAAAAGGCACTGAAGCCGTCATCATTCCCTATGCATTGCACAGAGATCCGAGATACTTCC

CCAACCCCGAGGAGTTCCAGCCTGAGCGGTTCTTCCCCGAGAATGCACAAGGGCGCCATCCATAT

GCCTACGTGCCCTTCTCTGCTGGCCCCAGGAACTGTATAGGTCAAAGTTTGCTGTGATGGAAGA

AAAGACCATTCTTTCGTGCATCCTGAGGCACTTTTGGATAGAATCCAACCAGAAAAGAGAAGAGC

TTGGTCTAGAAGGACAGTTGATTCTTCGTCCAAGTAATGGCATCTGGATCAAGTTGAAGAGGAGA

AATGCAGATGAACGCTAA (human CYP4V2 protein, NP_997235.3, 525 aa)

SEQ ID NO: 4

MAGLWLGLVWQKLLLWGAASALSLAGASLVLSLLQRVASYARKWQQMRPIPTVARAYPLVGHALL

MKPDGREFFQQIIEYTEEYRHMPLLKLWVGPVPMVALYNAENVEVILTSSKQIDKSSMYKFLEPW

LGLGLLTSTGNKWRSRRKMLTPTFHFTILEDFLDIMNEQANILVKKLEKHINQEAFNCFFYITLC

ALDIICETAMGKNIGAQSNDDSEYVRAVYRMSEMIFRRIKMPWLWLDLWYLMFKEGNEHKKSLQI

LHTFTNSVIAERANEMNANEDCRGDGRGSAPSKNKRRAFLDLLLSVTDDEGNRLSHEDIREEVDT

FMFEGHDTTAAAINWSLYLLGSNPEVQKKVDHELDDVFGKSDRPATVEDLKKLRYLECVIKETLR

LFPSVPLFARSVSEDCEVAGYRVLKGTEAVIIPYAIHRDPRYFPNPEEFQPERFFPENAQGRHPY

AYVPFSAGPRNCIGQKFAVMEEKTILSCILRHFWIESNQKREELGLEGQLILRPSNGIWIKLKRR

NADER (functional variant of human CYP4V2 protein; 525 aa)

SEQ ID NO: 5

MAGEWLGLVWQKLLLWGAASALSLAGASLVLSLLQRVASYARKWQQMRPIPTVARAYPLVGHALL

MKPDGREFFQQIIEYTEEYRHMPLLKLWVGPVPMVALYNAENVEVILTSSKQIDKSSMYKFLEPW

LGLGLLTSIGNKWRSRRKMLTPTFHFTILEDFLDIMNEQANILVKKLEKHINQEAFNCFFYITLC

ALDIICETAMGKNIGAQSNDDSEYVRAVYRMSEMIFRRIKMPWLWLDLWYLMFKEGWEHKKSLKI

LHTFTNSVIAERANEMNANEDCRGDGRGSAPSKNKRRAFLDLLLSVTDDEGNRLSHEDIREEVDT

FMFEGHDTTAAAINWSLYLLGSNPEVQKKVDHELDDVFGKSDRPATVEDLKKLRYLECVIKETLR

LFPSVPLFARSVSEDCEVAGYRVLKGTEAVIIPYALHRDPRYFPNPEEFQPERFFPENAQGRHPY

AYVPFSAGPRNCIGQKFAVMEEKTILSCILRHFWIESNQKREELGLEGQLILRPSNGIWIKLKRR

NADER

-continued (fragment of CYP4V2 without transmembrane domain; 490 aa)

SEQ ID NO: 6

RVASYARKWQQMRPIPTVARAYPLVGHALLMKPDGREFFQQIIEYTEEYRHMPLLKLWVGPVPMV

ALYNAENVEVILTSSKQIDKSSMYKFLEPWLGLGLLTSTGNKWRSRRKMLIPTFHFTILEDFLDI

MNEQANILVKKLEKHINQEAFNCFFYITLCALDIICETAMGKNIGAQSNDDSEYVRAVYRMSEMI

FRRIKMPWLWLDLWYLMFKEGWEHKKSLQILHTFTNSVIAERANEMNANEDCRGDGRGSAPSKNK

RRAFLDLILSVTDDEGNRLSHEDIREEVDTFMFEGHDTTAAAINWSLYILGSNPEVQKKVDHELD

DVFGKSDRPATVEDLKKLRYLECVIKETLRLFPSVPLFARSVSEDCEVAGYRVLKGTEAVIIPYA

LHRDPRYFPNPEEFQPERFFPENAQGRHPYAYVPFSAGPRNCIGQKFAVMEEKTILSCILRHFWI

ESNQKREELGLEGQLILRPSNGIWIKIKRRNADER

Example 9-Designing Efficient Expression Cassettes and Delivery Vectors for CYP4V2 Gene Therapy As described herein, an expression cassette and a delivery vector comprise various elements. Results can vary significantly based on different designs. Given the large amount of options in each of the important elements including but not limited to the ones listed below and numerous combinations thereof, a thoughtful design of efficient expression cassettes and delivery vectors is required for the success of CYP4V2 gene therapy. In addition, the design process need to take into consideration the disease phenotype and characteristics (e.g., types of cells/tissues targeted for treatment) and safety (e.g., toxicity, immune response). Finally, a design needs to be tested and verified in a sound disease model.

(a) Type of delivery vector;
(b) Vector serotype and capsid design/selection;
(c) Additional vector design, e.g., ssAAV vs. scAAV;
(d) cDNA design;
(e) promoter design/selection;
(f) polyA signal design/selection; and
(g) any other regulatory sequences, e.g., an enhancer, or junction/linker sequence.

For (a), a viral vector was chosen to achieve high transduction efficiency in target cells (e.g., human RPE). Among various types of viral vectors, AAV vectors were chosen because of its safety profile and the size of the CYP4V2 encoding nucleic acid (e.g., a CYP4V2 cDNA) fits in the packaging limit of AAV vectors. Vectors with larger packaging limit, e.g., a HSV vector, a lentivirus vector, a Baculovirus or adenovirus vectors, can also be used for CYP4V2 gene therapy. In addition to viral vectors, non-viral vectors, e.g., nanoparticles, including but not limited to, liposome nanoparticles, solid lipid nanoparticles, liposome protamine/DNA lipoplex (LPD), can also be used for CYP4V2 gene therapy.

For (b), because RPE cells are the primary cell type targeted for treatment in CYP4V2 gene therapy for BCD, an AAV serotypes with sufficient transduction efficiency in RPE cells is preferred. In addition, the following factors were considered. Because expression of CYP4V2 was observed broadly in various human tissues and organs, e.g., heart, brain, placenta, lung, liver, skeletal muscle, kidney, pancreas, retina, RPE, cornea and lymphocytes, and in addition to RPE, BCD also affects choroid, photoreceptors and, in some patients, the cornea, and that abnormalities have been previously reported in BCD patients' skin fibroblast, lymphocytes and serum, AAV serotypes and capsid structures that do not restrict AAV transduction only in RPE cells, but also can transduce other cells/tissues, e.g., photoreceptors, choroid, and/or cornea, can be designed and/or selected, in addition to AAV serotypes and capsid structures with good transduction efficiency in RPE cells. As a result, a wide range of AAV serotypes and capsid structures are suitable and can be used. AAV2, AAV5, AAV8, AAV1, AAV9 and a capsid mutant AAV vector (AAV2 (Y444F+Y500F+Y730F) were selected for the study. In addition to transduction efficiency, another factor that was considered is the pre-existing NABs against different AAV serotypes in the general population and other potential individual differences among patients (including without limitation other types of immune responses (e.g., intracellular immunity or RPE immunity) or due to difference in genotype (e.g., different mutations)). In this design, multiple AAV types were used and tested including ones sharing low cross-reactivity to NABs to lower potential immune responses and to maximize therapeutic effect to different patients.

For (c), because the full-length CYP4V2 cDNA is 1578 bp (including start and stop codons), both ssAAV and scAAV designs can be used in CYP4V2 gene therapy. ssAAV and scAAV designs each has its own pros and cons as described herein. Compared to ssAAV, a scAAV design offers rapid expression and higher DNA stability. However, its packaging limit (about 2.4-2.5 kb) restricts the use of larger size and potentially more active regulatory sequences (e.g., promoter, PolyA signal). In addition, depending on the size of the promoter used, a scAAV design may need to shorten or go without some optional regulatory sequences (e.g., an enhancer). Both ssAAV and scAAV vectors were designed and generated for use in CYP4V2 gene therapy. Various pseudotyped AAVs containing AAV2 genome (e.g., the AAV2 ITRs (SEQ ID NOs: 42 and 43) and a capsid from each of the AAV types described in (b) above were generated. For the scAAV, one of the two AAV2 ITRs was truncated/mutated (SEQ ID NO: 44).

For (d), as discussed herein, there are multiple functional CYP4V2 proteins. Further, numerous nucleic acid sequences can encode the same protein. Three (3) cDNAs were generated in the study; the first one (SEQ ID NO: 1) referred to as CYP4V2st) encoding the human CYP4V2 protein (SEQ ID NO: 4), the second one is a codon-optimized cDNA (SEQ ID NO: 2, referred to as CYP4V2op) encoding the human CYP4V2 protein (SEQ ID NO: 4), and the third one (SEQ ID NO: 3, referred to as CYP4V2fv) encoding a functional variant of the human CYP4V2 protein (SEQ ID NO: 5). A Kozak sequence (exemplary sequences shown in SEQ ID NO: 37 or 38) was inserted before the cDNA start codon.

For (e), similar to the rationale in (b), the promoter needs to work well to drive expression in target cells (e.g., RPE cells when the target cell type for treatment is RPE, cornea cells when the target cell type is cornea cells). The promoter is a major element in the expression cassette of gene therapy vectors. Optimal promoter selection can enhance target specificity and gene expression. Depending on the cell or tissue type(s) targeted for treatment, the promoter used in CYP4V2 gene therapy can be either a constitutive promoter or a cell-specific promoter (e.g., a promoter specific to RPE cells, a promoter specific to both RPE and photoreceptors, a promoter specific to RPE cells and choroid cells, a promoter specific to RPE, photoreceptor and choroid cells, a promoter specific to cornea cells, a promoter specific to RPE, photoreceptor, choroid, and cornea cells, or a promoter specific to ocular cells). Because CYP4V2 is almost ubiquitously expressed and multiple cell types are affected in BCD (the primary one being RPE, other cell types include, e.g., cornea, retina, lymphocytes), constitutive promoters were chosen in this design to broaden the effect of the expression cassette and delivery vector in multiple tissue and cell types. For the expression cassette used in ssAAV vectors, a strong constitutive promoter was used, the CAG promoter which is ~1.7 kb in length (exemplary sequence shown in SEQ ID NO: 32). The CAG promoter (also known as CBA, CAGGS or CB promoter) is a strong synthetic promoter. The CAG promoter is composed of the following regulatory elements: (C) cytomegalovirus (CMV) early enhancer element; (A) the promoter region and the first exon of the chicken beta-Actin gene, and a chimeric intron from chicken beta-actin gene and the rabbit beta-globin gene, and (G) the splice acceptor of the rabbit beta-Globin gene. The CAG promoter was used because it has both stronger and longer-lasting activity than the CMV promoter (exemplary sequence shown in SEQ ID NO: 40), which is the most commonly used constitutive promoter to drive expression in mammalian cells. For the expression cassette used in scAAV vectors, due to the packaging size limitation of scAAV, a much shorter constitutive promoter was used, the elongation factor 1 alpha short (EFS) promoter (exemplary sequence shown in SEQ ID NO: 35). The EFS promoter is the miniaturized version of the EF-1 alpha promoter (~1.2 Kb, exemplary sequence shown in SEQ ID NO: 41). The EF-1 alpha promoter is a constitutive promoter derived from human elongation factor-1 alpha (EF-la). The EFS promoter also can be used in the expression cassette design for ssAAVs. In addition to the CAG promoter, CMV promoter, EF1 alpha promoter and EFS promoter, other constitutive promoters can be used, including without limitation, another viral promoter such as the CMV promoter, a derivative or variant of the CAG (a/k/a CBA, CAGGS or CB promoter) such as the smCBA promoter, CB$^{SB}$ promoter, or the CBh promoter, another beta-actin promoter such as the human beta actin promoter, a derivative or variant of the EF-1 alpha promoter, PGK promoter, the UBC promoter, the GUSB promoter, the UCOE promoter or other promoters described herein. Further, a cell-specific promoter can be used, including without limitation, the ocular cell-specific promoters described herein, e.g., a VMD2 (a/k/a BEST1) promoter or a RPE65 promoter to drive expression in RPE.

For (f), a bGH polyA was used (exemplary sequence shown in SEQ ID NO: 34) for the expression cassette design used in ssAAVs and a shorter polyA signal, a small polyA (SPA) (exemplary sequence shown in SEQ ID NO: 36) for the expression cassette design used in scAAVs. The SPA also can be used in expression cassette for ssAAVs. Other polyA signals (including derivatives or variants) also can be used instead, including without limitation, a SV40 polyA signal, a SV40 late polyA signal (exemplary sequence shown in SEQ ID NO: 39) or other polyA signals as described herein, including without limitation, a polyA signal used in combination with an upstream enhancer (USE).

For (g), a WPRE enhancer was used (exemplary sequence shown in SEQ ID NO: 33) for the expression cassette used in ssAAVs. For expression cassette design used in scAAVs, given the size limit, an enhancer was not included. It should be noted that an enhancer is optional in both ssAAV and scAAV CYP4V2 expression cassettes. It should also be noted, however, that it is possible to include short-length enhancer sequences, e.g., a shortened WPRE containing minimal gamma and alpha elements of the WPRE, in combination with small-sized promoter and polyA signal in the scAAV CYP4V2 expression cassette. Besides WPRE, other enhancers as described herein, such as an HPRE enhancer or a CTE enhancer can be used.

In some instances, the CYP4V2 expression cassette includes a promoter (e.g., a CAG (a/k/a CBA, CAGGS, CB) promoter, a EF-1 alpha promoter, a smCBA promoter, a CBh promoter, a EFS promoter, a human beta-actin promoter, a CMV promoter, a VMD2 promoter, or a RPE65 promoter), a nucleic acid sequence encoding a functional CYP4V2 protein (e.g., a cDNA encoding the human CYP4V2 protein or a functional variant or fragment thereof), optionally linked with an enhancer sequence (e.g., a WPRE enhancer, a HPRE enhancer or a shortened WPRE or HPRE enhancer), and a polyA signal (e.g., a bGH polyA, a SPA, or an SV40 PolyA, or a fragment or derivative thereof, e.g., an SV40 late polyA), and other regulatory sequences (e.g., a Kozak sequence). See SEQ ID NOs: 1-41 for exemplary sequences.

It would be understood that (i) the exemplary sequences of various regulatory sequences provided in the SEQ section are exemplary in nature and there are different versions of these regulatory sequences that can achieve the same or similar function, and (ii) there are different variants, fragments and/or derivatives of these sequences that can also be used, e.g., a truncated CAG promoter, a shortened WPRE enhancer, a SV40 late polyA.

Based on the design approach described above, multiple CYP4V2 cDNAs, CYP4V2 expression cassettes and rAAV vectors for use in CYP4V2 gene therapy were generated, including:

(1) Three CYP4V2 cDNAs as shown in SEQ ID NO: 1, 2 and 3, respectively. CYP4V2st (SEQ ID NO: 1) and CYP4V2op (SEQ ID NOs 2) both encode the human CYP4V2 protein (SEQ ID NO: 4). CYP4V2fv (SEQ ID NO: 3) encodes a functional variant of the human CYP4V2 protein (SEQ ID NO: 5);

(2) Two CYP4V2 expression cassettes (CYP4V2 denotes a nucleic acid sequence encoding the human CYP4V2 protein or a functional CYP4V2 protein. See FIG. 7 for a schematic drawing):
 (i) CAG-CYP4V2-WPRE-bGH polyA
 (ii) EFS-CYP4V2-SPA (3) The above mentioned CYP4V2 cDNAs and CYP4V2 expression cassettes were packaged in six different AAV vectors (AAV2, AAV5, AAV8, AAV1, AAV2 (Y444F+Y500F+Y730F) and AAV9) to create the following rAAV vectors containing a CYP4V2 cDNA and expression cassette, including both ssAAV and scAAV vector constructs:
 (i) recombinant AAV2/2-CAG-CYP4V2op-WPRE-bGH polyA (herein referred to as AAV2.CYP4V2op), (ii) recombinant AAV2/2 (Y444F+Y500F+Y730F)-CAG-CYP4V2op-WPRE-bGH PolyA (herein referred to as AAV2tri (Y-F).CYP4V2op or AAV2tri.CYP4V2op), (iii) recombinant AAV2/5-CAG-CYP4V2op-WPRE-bGH PolyA (herein referred to as AAV5.CYP4V2op).

(iv) recombinant AAV2/5-CAG-CYP4V2st-WPRE-bGH polyA (herein referred to as AAV5.CYP4V2st), (v) recombinant AAV2/8-CAG-CYP4V2fv-WPRE-bGH polyA (herein referred to as AAV8.CYP4V2fv), (vi) recombinant self-complementary AAV2/1-EFS-CYP4V2op-SPA (herein referred to as scAAV1.CYP4V2op), (vii) recombinant self-complementary AAV2/5-EFS-CYP4V2op-SPA (herein referred to as scAAV5.CYP4V2op), and (viii) recombinant self-complementary AAV2/9-EFS-CYP4V2op-SPA (herein referred to as scAAV9.CYP4V2op).

When packaged in an rAAV vector, the expression cassette was flanked by two AAV2 ITRs (SEQ ID NOs: 42 and 43). For scAAV, one of the AAV2 ITRs was truncated/mutated (SEQ ID NO: 44). It would be understood that non-AAV2 genome, including non-AAV2 ITRs can also be used to package the expression cassette. A Kozak sequence (SEQ ID NO: 37 or 38) was inserted immediately before the CYP4V2 cDNAs. See FIG. 7 for schematic drawings showing the design of these expression cassettes. It would be appreciated that a CYP4V2 cDNA can be packaged in different expression cassettes and that a CYP4V2 expression cassette can be packaged in different AAV vectors. For example, the CYP4V2op cDNA can be used in both CAG-CYP4V2-WPRE-bGH PolyA expression cassette and EFS-CYP4V2-SPA expression cassette. Either CAG-CYP4V2-WPRE-bGH Poly A expression cassette or EFS-CYP4V2-SPA expression cassette can be packaged in any suitable AAV vector, including but not limited to, AAV1, AAV2, AAV2 (Y444F+Y500F+Y730F), AAV5, AAV8, AAV8 (Y733F), AAV9, AAV6, AAV7, AAV4, AAV12, AAV-PHP.B and other vectors. An scAAV design can be used in any suitable AAV vector to create a recombinant scAAV vector, e.g., scAAV1, scAAV2, SCAAV2 (Y444F+Y500F+Y730F), scAAV5, scAAV8, scAAV8 (Y733F), scAAV3, scAAV4, scAAV6, scAAV7, scAAV9, scAAV12, etc.

It would be understood that similar design process can be used in designing other vectors (e.g., a lentivirus vector or a plasmid) for the CYP4V2 gene therapy. Depending on the type of the vector, certain elements described above may not be necessary or may need to be adjusted accordingly, e.g., a promoter sequence.

In addition to the cDNAs, regulatory sequences and AAV types and designs specified herein, other design options for each key element of the CYP4V2 expression cassette and delivery vector can also be used. An example on how to compare transduction efficiency of various AAV types and the strength of different promoters in a targeted cell type is provided herein in the Examples section. Similar methods can be used to assess and compare the design options for other key elements of the expression cassette and delivery vector, e.g., cDNA, enhancer, polyA signal, ssAAV vs. scAAV, AAV vs. HSV etc. Further, as provided herein, the efficiency of a CYP4V2 expression cassette and delivery vector can be assessed and compared through testing in BCD cellular model, e.g., iPS-RPE cells of BCD patients, with methods described herein and/or other methods to assess biochemical abnormalities, RPE function or atrophy.

The CYP4V2 cDNAs, expression cassettes and delivery vectors described above were tested in BCD patient-specific human iPS-RPE cell lines, and the results are shown and discussed in the following Examples.

In addition, the junction/linker sequences between various regulator sequences (including without limitation, between ITR and a promoter, between an enhancer and a polyA signal, or between a polyA signal and ITR), or between a regulatory sequence and a cDNA (including without limitation, between a promoter and a cDNA, between a cDNA and an enhancer, or between a cDNA and a polyA signal) may also play a role in regulating the expression of the target gene (e.g., CYP4V2). Sequences of different CYP4V2 expression cassettes (inclusive of ITRs and junction/linker sequences) used in the study are listed in Example 11 below.

Exemplary sequences of certain regulatory sequences and ITR sequences discussed in this Example are provided as follows:

(CAG promoter, 1715 bp)

SEQ ID NO: 32

GACATTGATTATTGACTAGTTATTAATAGTAATCAATTACGGGGTCATTAGTTCATAGCC

CATATATGGAGTTCCGCGTTACATAACTTACGGTAAATGGCCCGCCTGGCTGACCGCCCAACGAC

CCCCGCCCATTGACGTCAATAATGACGTATGTTCCCATAGTAACGCCAATAGGGACTTTCCATTG

ACGTCAATGGGTGGACTATTTACGGTAAACTGCCCACTTGGCAGTACATCAAGTGTATCATATGC

CAAGTACGCCCCCTATTGACGTCAATGACGGTAAATGGCCCGCCTGGCATTATGCCCAGTACATG

ACCTTATGGGACTTTCCTACTTGGCAGTACATCTACGTATTAGTCATCGCTATTACCATGGGTCG

AGGTGAGCCCCACGTTCTGCTTCACTCTCCCCATCTCCCCCCCCTCCCCACCCCCAATTTTGTAT

TTATTTATTTTTTAATTATTTTGTGCAGCGATGGGGGCGGGGGGGGGGGGGCGCGCGCCAGGCG

GGGCGGGGCGGGGCGAGGGGCGGGGCGGGGCGAGGCGGAGAGGTGCGGCGGCAGCCAATCAGAGC

GGCGCGCTCCGAAAGTTTCCTTTTATGGCGAGGCGGCGGCGGCGGCGGCCCTATAAAAAGCGAAG

CGCGCGGCGGGCGGGAGTCGCTGCGTTGCCTTCGCCCCGTGCCCCGCTCCGCGCCGCCTCGCGCC

GCCCGCCCCGGCTCTGACTCACCGCGTTACTCCCACAGGTGAGCGGGCGGGACGGCCCTTCTCCT

-continued

CCGGGCTGTAATTAGCGCTTGGTTTAATGACGGCTCGTTTCTTTTCTGTGGCTGCGTGAAAGCCT

TAAAGGGCTCCGGGAGGGCCCTTTGTGCGGGGGGGAGCGGCTCGGGGGGTGCGTGCGTGTGTGTG

TGCGTGGGGAGCGCCGCGTGCGGCCCGCGCTGCCCGGCGGCTGTGAGCGCTGCGGGCGCGGCGCG

GGGCTTTGTGCGCTCCGCGTGTGCGCGAGGGGAGCGCGGCCGGGGGCGGTGCCCCGCGGTGCGGG

GGGGCTGCGAGGGGAACAAAGGCTGCGTGCGGGGTGTGTGCGTGGGGGGGTGAGCAGGGGGTGTG

GGCGCGGCGGTCGGGCTGTAACCCCCCCCTGCACCCCCCTCCCCGAGTTGCTGAGCACGGCCCGG

CTTCGGGTGCGGGGCTCCGTGCGGGGCGTGGCGCGGGGCTCGCCGTGCCGGGCGGGGGGTGGCGG

CAGGTGGGGGTGCCGGGCGGGGCGGGGCCGCCTCGGGCCGGGGAGGGGCTCGGGGGAGGGGCGCGG

CGGCCCCGGAGCGCCGGCGGCTGTCGAGGCGCGGCGAGCCGCAGCCATTGCCTTTTATGGTAATC

GTGCGAGAGGGCGCAGGGACTTCCTTTGTCCCAAATCTGGCGGAGCCaAAATCTGGGAGGCGCCG

CCGCACCCCCTCTAGCGGGCGCGGGCGAAGCGGTGCGGCGCCGGCAGGAAGGAAATGGGCGGGGA

GGGCCTTCGTGCGTCGCCGCGCCGCCGTCCCCTTCTCCATCTCCAGCCTCGGGGCTGCCGCAGGG

GGACGGCTGCCTTCGGGGGGGACGGGGCAGGGCGGGGTTCGGCTTCTGGCGTGTGACCGGCGGCT

CTAGAGCCTCTGCTAACCATGTTCATGCCTTCTTCTTTTTCCTACAGCTCCTGGGCAACGTGCTG

GTTATTGTGCTGTCTCATCATTTTGGCAAA (WPRE enhancer, 589 bp)

SEQ ID NO: 33
AATCAACCTCTGGATTACAAAATTTGTGAAAGATTGACTGGTATTCTTAACTATGTTGCT

CCTTTTACGCTATGTGGATACGCTGCTTTAATGCCTTTGTATCATGCTATTGCTTCCCGTATGGC

TTTCATTTTCTCCTCCTTGTATAAATCCTGGTTGCTGTCTCTTTATGAGGAGTTGTGGCCCGTTG

TCAGGCAACGTGGCGTGGTGTGCACTGTGTTTGCTGACGCAACCCCCACTGGTTGGGGCATTGCC

ACCACCTGTCAGCTCCTTTCCGGGACTTTCGCTTTCCCCCTCCCTATTGCCACGGCGGAACTCAT

CGCCGCCTGCCTTGCCCGCTGCTGGACAGGGGCTCGGCTGTTGGGCACTGACAATTCCGTGGTGT

TGTCGGGGAAATCATCGTCCTTTCCTTGGCTGCTCGCCTGTGTTGCCACCTGGATTCTGCGCGGG

ACGTCCTTCTGCTACGTCCCTTCCGCCCTCAATCCAGCGGACCTTCCTTCCCGCGGCCTGCTGCC

GGCTCTGCGGCCTCTTCCGCGTCTTCGCCTTCGCCCTCAGACGAGTCGGATCTCCCTTTGGGCCG

CCTCCCCGC (bGH polyA, 225 bp)

SEQ ID NO: 34
CTGTGCCTTCTAGTTGCCAGCCATCTGTTGTTTGCCCCTCCCCCGTGCCTTCCTTGACCC

TGGAAGGTGCCACTCCCACTGTCCTTTCCTAATAAAATGAGGAAATTGCATCGCATTGTCTGAGT

AGGTGTCATTCTATTCTGGGGGGTGGGGTGGGGCAGGACAGCAAGGGGGAGGATTGGGAAGACAA

TAGCAGGCATGCTGGGGATGCGGTGGGCTCTATGG (EFS promoter, 235 bp)

SEQ ID NO: 35
g attggctccg gtgcccgtca gtgggcagag cgcacatcgc ccacagtccc cgagaagttg gggggagggg tcggcaattg aaccggtgcc tagagaaggt ggcgcggggt aaactgggaa agtgatgtcg tgtactggct ccgccttttt cccgagggtg ggggagaacc gtatataagt gcagtagtcg ccgtgaacgt tctttttcgc aacgggtttg ccgccagaac acag (SPA, 54 bp)

SEQ ID NO: 36
GATCCAATAAAAGATCTTTATTTTCATTAGATCTGTGTGTTGGTTTTTTGTGTG (Kozak sequence, 6 bp)

SEQ ID NO: 37

GCCACC

-continued (Kozak sequence, 5 bp)

SEQ ID NO: 38

CCACC (SV40 late PolyA, 120 bp)

SEQ ID NO: 39

TTGTTTATTGCAGCTTATAATGGTTACAAATAAAGCAATAGCATCACAAATTTCACAAAT

AAAGCATTTTTTTCACTGCATTCTAGTTGTGGTTTGTCCAAACTCATCAATGTATCTTAT (CMV promoter, 576 bp)

SEQ ID NO: 40

TAGTAATCAATTACGGGGTCATTAGTTCATAGCCCATATATGGAGTTCCGCGTTACATAA

CTTACGGTAAATGGCCCGCCTGGCTGACCGCCCAACGACCCCCGCCCATTGACGTCAATAATGAC

GTATGTTCCCATAGTAACGCCAATAGGGACTTTCCATTGACGTCAATGGGTGGAGTATTTACGGT

AAACTGCCCACTTGGCAGTACATCAAGTGTATCATATGCCAAGTACGCCCCCTATTGACGTCAAT

GACGGTAAATGGCCCGCCTGGCATTATGCCCAGTACATGACCTTATGGGACTTTCCTACTTGGCA

GTACATCTACGTATTAGTCATCGCTATTACCATGGTGATGCGGTTTTGGCAGTACATCAATGGGC

GTGGATAGCGGTTTGACTCACGGGGATTTCCAAGTCTCCACCCCATTGACGTCAATGGGAGTTTG

TTTTGGCACCAAAATCAACGGGACTTTCCAAAATGTCGTAACAACTCCGCCCCATTGACGCAAAT

GGGCGGTAGGCGTGTACGGTGGGAGGTCTATATAAGCAGAGCTGGTTTAGTGAACCGTCAG (EF-1 alpha promoter, 1184 bp)

SEQ ID NO: 41 cgtgaggctccggtgcccgtcagtgggcagagcgcacatcgcccacagtccccgagaagt tggggggagggggtcggcaattgaaccggtgcctagagaaggtggcgcggggtaaactgggaaagt gatgtcgtgtactggctccgcctttttcccgagggtgggggagaaccgtatataagtgcagtagt cgccgtgaacgttctttttcgcaacgggtttgccgccagaacacaggtaagtgccgtgtgtggtt cccgcgggcctggcctctttacgggttatggcccttgcgtgccttgaattacttccacctggctg cagtacgtgattcttgatcccgagcttcggggttggaagtgggtgggagagttcgaggccttgcgc ttaaggagccccttcgcctcgtgcttgagttgaggcctggcctgggcgctggggccgccgcgtgc gaatctggtggcaccttcgcgcctgtctcgctgctttcgataagtctctagccatttaaaattttt tgatgacctgctgcgacgctttttttctggcaagatagtcttgtaaatgcgggccaagatctgca cactggtatttcggtttttggggccgcgggcggcgacggggcccgtgcgtcccagcgcacatgtt cggcgaggcggggcctgcgagcgcggccaccgagaatcggacgggggtagtctcaagctggccgg cctgctctggtgcctggcctcgcgccgccgtgtatcgccccgccctgggcggcaaggctggcccg gtcggcaccagttgcgtgagcggaaagatggccgcttcccggccctgctgcagggagctcaaaat ggaggacgcggcgctcgggagagcgggcgggtgagtcacccacacaaaggaaaagggcctttccg tcctcagccgtcgcttcatgtgactccacggagtaccgggcgccgtccaggcacctcgattagtt ctcgagcttttggagtacgtcgtctttaggttggggggaggggtttttatgcgatggagtttcccc acactgagtgggtggagactgaagttaggccagcttggcacttgatgtaattctccttggaatttt gccctttttgagtttggatcttggttcattctcaagcctcagacagtggttcaaagtttttttct tccatttcaggtgtcgtga (AAV2 5' Left-ITR, 141 bp)

SEQ ID NO: 42 cctgcaggca gctgcgcgct cgctcgctca ctgaggccgc ccgggcaaag cccgggcgtc gggcgacctt tggtcgcccg gcctcagtga gcgagcgagc gcgcagagag ggagtggcca actccatcac tagggggttcc -continued

```
(AAV2 3' Right-ITR, 141 bp)
                                                    SEQ ID NO: 43
ag gaacccctag tgatggagtt ggccactccc tctctgcgcg ctcgctcgct cactgaggcc gggcgaccaa aggtcgcccg acgcccgggc tttgcccggg cggcctcagt gagcgagcga gcgcgcagct gcctgcagg (mutant AAV2 5' ITR in scAAV construct, 117 bp)
                                                    SEQ ID NO: 44
cctgcaggca gctgcgcgct cgctcgctca ctgaggccgc ccgggcaaag cccgggcgtc gggcgacctt tggtcgcccg gcctcagtga gcgagcgagc gcgcagagag ggagtgg (AAV2 3' ITR in scAAV construct, 141 bp)
                                                    SEQ ID NO: 45
aggaaccc ctagtgatgg agttggccac tccctctctg cgcgctcgct cgctcactga ggccgggcga ccaaaggtcg cccgacgccc gggctttgcc cgggcggcct cagtgagcga gcgagcgcgc agctgcctgc agg
```

Example 10-Methods of Using BCD Cellular Model to Test, Compare and Screen AAV Serotypes and Capsid Structure, Promoter and Other Regulatory Sequence Activity and cDNA Expression Levels, as well as a Vector's Overall Efficacy and Dosage Levels in CYP4V2 Gene Therapy and to Assess Personalized Optimal Vector and Dosage for Different Patients The BCD cellular model (e.g., BCD patient-specific iPS-RPE cell lines, or ES-RPE, iPS-RPE or RPE cell lines with artificially generated CYP4V2 mutations) can be used in drug and dosage screening. BCD patient-specific iPS-RPE samples were used to test, compare and screen various components and dosage for CYP4V2 gene therapy, including vector type (e.g., AAV serotypes and capsid structure), promoter, enhancer, polyA signal and other sequences in the CYP4V2 expression cassette and CYP4V2 cDNA, as well as a vector's overall efficacy and dosage levels. Phenotype rescue was used to test and compare efficacy.

Vectors of different serotype (e.g., AAV1, AAV2, AAV5, AAV8, AAV9) or capsid (e.g., AAV with capid mutation(s), e.g., AAV2 vs AAV2tri (Y-F)) or structure (e.g., scAAV vs. ssAAV) can be tested, compared by using different vectors with the same expression cassette. For example, AAV2.CYP4V2op, AAV2tri (Y-F).CYP4V2op and AAV5.CYP4V2op all have the same expression cassette but are different in AAV serotype/capsid. scAAV1.CYP4V2op, scAAV5.CYP4V2op and scAAV9.CYP4V2op all share the same expression cassette but are different in AAV serotype. Results from phenotype rescue can be used to test and compare AAV serotype/capsid (e.g., AAV2 vs AAV2tri (Y-F) vs AAV5) and structure (e.g., scAAV5 vs ssAAV5) efficiency difference in transducting and delivering the CYP4V2 cDNA to BCD patient RPE cells.

The same method can be used to test and compare activity level of different expression cassette, cDNA, or regulatory sequences or other sequences (e.g., junction/linker sequences) by testing phenotype rescue efficacy of rAAV vectors of the same construct (except for the element being tested and compared).

Furthermore, as described in the Examples herein, different dosages (e.g., 1×10e4 and 1×10e5) of the same vector (e.g., rAAV vector, e.g., scAAV1.CYP4V2op) can be applied to iPS-RPE samples of the same patient to assess therapeutic effective dosage range (measured by MOI per cell).

In addition, given BCD cellular model exhibited individual differences, it can also be used to assess and discover the personalized optimal dosage and vector construct for each patient individually.

See related Examples and disclosure herein for more related discussion.

Example 11-Generation of Various Recombinant Adeno-Associated Virus (rAAV) Vectors Carrying a Functional CYP4V2-encoding Nucleic Acid Sequence and Expression Cassette Various AAV.CYP4V2 vectors designed for this study (See Examples herein), including AAV2.CYP4V2op, AAV2tri (Y-F).CYP4V2op, AAV5.CYP4V2st, AAV5.CYP4V2op, AAV8.CYP4V2fv and scAAV1.CYP4V2op, were custom made by Vector BioLabs (Malvern, PA, USA). Recombinant AAV vectors from Vector BioLabs are helper-free. The production process involves: (1) cloning a pAAV cis-plasmid, which is an AAV2 ITR-containing plasmid that includes the relevant CYP4V2 cDNA (i.e., CYP4V2st, CYP4V2op or CYP4V2fv) and regulatory sequences of a CYP4V2 expression cassette, (2) large-scale preparation of pAAV cis-plasmid and complimentary plasmids (a plasmid that carries the relevant AAV Rep-Cap genes and a plasmid that provides the helper genes isolated from adenovirus) by using Qiagen Endo-free Mega Prep kit, (3) large-scale co-transfection of the three plasmids described above into plates of HEK293 cells. (4) Two days after transfections, cell pellets were harvested, and viruses were released using three cycles of freeze/thaw. AAV viruses were purified using CsCl-gradient ultra-centrifugation, followed by desalting. and (5) viral titer (genome copies (GC)/ml) were determined using real-time PCR. The purified rAAV vectors were stored at −80° C. until use.

Sequences of different CYP4V2 expression cassettes (inclusive of ITRs and junction/linker sequences) packaged in various AAV.CYP4V2 vectors for the study are listed as follows.

SEQ ID NO: 60 - Sequence of CYP4V2 expression cassette
in AAV2.CYP4V2op, AAV2tri(Y-F).CYP4V2op, and AAV5.CYP4V2op.:
Left-ITR: 1-141
CAG promoter: 237-1951
CYP4V2op cDNA: 2002-3579
WPRE enhancer: 3736-4324
bGH polyA: 4350-4574
Right-ITR 4659-4799

```
   1 CCTGCAGGCA GCTGCGCGCT CGCTCGCTCA CTGAGGCCGC CCGGGCAAAG

51 CCCGGGCGTC GGGCGACCTT TGGTCGCCCG GCCTCAGTGA GCGAGCGAGC

101 GCGCAGAGAG GGAGTGGCCA ACTCCATCAC TAGGGGTTCC TGCGGCCAAT

151 TCAGTCGATA ACTATAACGG TCCTAAGGTA GCGATTTAAA TACGCGCTCT

201 CTTAAGGTAG CCCCGGGACG CGTCAATTGA GATCTCGACA TTGATTATTG

251 ACTAGTTATT AATAGTAATC AATTACGGGG TCATTAGTTC ATAGCCCATA

301 TATGGAGTTC CGCGTTACAT AACTTACGGT AAATGGCCCG CCTGGCTGAC

351 CGCCCAACGA CCCCCGCCCA TTGACGTCAA TAATGACGTA TGTTCCCATA

401 GTAACGCCAA TAGGGACTTT CCATTGACGT CAATGGGTGG ACTATTTACG

451 GTAAACTGCC CACTTGGCAG TACATCAAGT GTATCATATG CCAAGTACGC

501 CCCCTATTGA CGTCAATGAC GGTAAATGGC CCGCCTGGCA TTATGCCCAG

551 TACATGACCT TATGGGACTT TCCTACTTGG CAGTACATCT ACGTATTAGT

601 CATCGCTATT ACCATGGGTC GAGGTGAGCC CCACGTTCTG CTTCACTCTC

651 CCCATCTCCC CCCCCTCCCC ACCCCCAATT TTGTATTTAT TTATTTTTTA

701 ATTATTTTGT GCAGCGATGG GGGCGGGGGG GGGGGGGGCG CGCGCCAGGC

751 GGGGCGGGGC GGGGCGAGGG GCGGGGCGGG GCGAGGCGGA GAGGTGCGGC

801 GGCAGCCAAT CAGAGCGGCG CGCTCCGAAA GTTTCCTTTT ATGGCGAGGC

851 GGCGGCGGCG GCGGCCCTAT AAAAAGCGAA GCGCGCGGCG GCGGGAGTC

901 GCTGCGTTGC CTTCGCCCCG TGCCCCGCTC CGCGCCGCCT CGCGCCGCCC

951 GCCCCGGCTC TGACTGACCG CGTTACTCCC ACAGGTGAGC GGGCGGGACG

1001 GCCCTTCTCC TCCGGGCTGT AATTAGCGCT TGGTTTAATG ACGGCTCGTT

1051 TCTTTTCTGT GGCTGCGTGA AAGCCTTAAA GGGCTCCGGG AGGGCCCTTT

1101 GTGCGGGGGG GAGCGGCTCG GGGGGTGCGT GCGTGTGTGT GTGCGTGGGG

1151 AGCGCCGCGT GCGGCCCGCG CTGCCCGGCG GCTGTGAGCG CTGCGGGCGC

1201 GGCGCGGGGC TTTGTGCGCT CCGCGTGTGC GCGAGGGGAG CGCGGCCGGG

1251 GGCGGTGCCC CGCGGTGCGG GGGGGCTGCG AGGGGAACAA AGGCTGCGTG

1301 CGGGGTGTGT GCGTGGGGGG GTGAGCAGGG GGTGTGGGCG CGGCGGTCGG

1351 GCTGTAACCC CCCCCTGCAC CCCCCTCCCC GAGTTGCTGA GCACGGCCCG

1401 GCTTCGGGTG CGGGGCTCCG TGCGGGGCGT GGCGCGGGGC TCGCCGTGCC

1451 GGGCGGGGGG TGGCGGCAGG TGGGGGTGCC GGGCGGGGGC GGGCCGCCTC

1501 GGGCCGGGGA GGGCTCGGGG GAGGGGCGCG GCGGCCCCGG AGCGCCGGCG

1551 GCTGTCGAGG CGCGGCGAGC CGCAGCCATT GCCTTTTATG GTAATCGTGC

1601 GAGAGGGCGC AGGGACTTCC TTTGTCCCAA ATCTGGCGGA GCCGAAATCT

1651 GGGAGGCGCC GCCGCACCCC CTCTAGCGGG CGCGGGCGAA GCGGTGCGGC

1701 GCCGGCAGGA AGGAAATGGG CGGGGAGGGC CTTCGTGCGT CGCCGCGCCG

1751 CCGTCCCCTT CTCCATCTCC AGCCTCGGGG CTGCCGCAGG GGGACGGCTG

1801 CCTTCGGGGG GACGGGGCA GGGCGGGGTT CGGCTTCTGG CGTGTGACCG
```

-continued

```
1851 GCGGCTCTAG AGCCTCTGCT AACCATGTTC ATGCCTTCTT CTTTTTCCTA

1901 CAGCTCCTGG GCAACGTGCT GGTTATTGTG CTGTCTCATC ATTTTGGCAA

1951 AGAATTCTAA TACGACTCAC TATAGGGAGA CCCAAGCTGG CTAGAGCCAC

2001 CATGGCTGGA CTGTGGCTGG GACTGGTGTG GCAGAAACTG CTGCTGTGGG

2051 GGGCCGCTTC CGCACTGTCA CTGGCTGGGG CTTCACTGGT GCTGAGCCTG

2101 CTGCAGAGGG TGGCCTCCTA CGCCAGAAAG TGGCAGCAGA TGAGGCCCAT

2151 CCCTACCGTG GCCAGAGCCT ATCCACTGGT GGGACACGCA CTGCTGATGA

2201 AGCCTGACGG CAGAGAGTTC TTTCAGCAGA TCATCGAGTA CACAGAGGAG

2251 TATAGGCACA TGCCACTGCT GAAGCTGTGG GTGGGACCCG TGCCTATGGT

2301 GGCCCTGTAC AACGCCGAGA ATGTGGAAGT GATCCTGACC AGCAGCAAGC

2351 AGATCGATAA GTCTAGCATG TATAAGTTCC TGGAGCCTTG GCTGGGCCTG

2401 GGCCTGCTGA CCTCTACAGG CAACAAGTGG AGGAGCCGGA GAAAGATGCT

2451 GACCCCAACA TTCCACTTTA CAATCCTGGA GGACTTCCTG GACATCATGA

2501 ACGAGCAGGC CAATATCCTG GTGAAGAAGC TGGAGAAGCA CATCAACCAG

2551 GAGGCCTTTA ATTGCTTCTT TTACATCACC CTGTGCGCCC TGGACATCAT

2601 CTGTGAGACA GCTATGGGCA AGAACATCGG CGCCCAGTCT AATGACGATA

2651 GCGAGTACGT GCGGGCCGTG TATAGAATGA GCGAGATGAT CTTTAGGCGC

2701 ATCAAGATGC CCTGGCTGTG GCTGGATCTG TGGTATCTGA TGTTCAAGGA

2751 GGGCTGGGAG CACAAGAAGT CCCTGCAGAT CCTGCACACC TTTACAAACT

2801 CTGTGATCGC CGAGAGAGCC AATGAGATGA ACGCCAATGA GGACTGTAGG

2851 GGCGATGGAA GGGGCAGCGC CCCTTCCAAG AACAAGCGGA GAGCCTTCCT

2901 GGACCTGCTG CTGAGCGTGA CCGACGATGA GGGCAATCGC CTGTCCCACG

2951 AGGACATCCG GGAGGAGGTG GATACATTCA TGTTTGAGGG ACACGACACC

3001 ACAGCCGCCG CCATCAACTG GTCCCTGTAC CTGCTGGGCT CTAATCCAGA

3051 GGTGCAGAAG AAGGTGGATC ACGAGCTGGA CGACGTGTTC GGCAAGTCCG

3101 ACAGGCCAGC AACCGTGGAG GATCTGAAGA AGCTGAGATA CCTGGAGTGC

3151 GTGATCAAGG AGACACTGCG CCTGTTCCCC TCTGTGCCTC TGTTTGCCCG

3201 GTCCGTGTCT GAGGACTGTG AGGTGGCCGG CTATCGCGTG CTGAAGGGCA

3251 CCGAGGCCGT GATCATCCCT TACGCCCTGC ACCGGGACCC CAGGTATTTC

3301 CCTAACCCAG AGGAGTTTCA GCCAGAGAGA TTCTTTCCCG AGAATGCCCA

3351 GGGCAGGCAC CCTTACGCCT ATGTGCCATT CTCCGCCGGA CCAAGGAACT

3401 GCATCGGACA GAAGTTTGCC GTGATGGAGG AGAAAACCAT CCTGTCTTGT

3451 ATCCTGAGAC ACTTCTGGAT CGAGAGCAAT CAGAAGAGGG AGGAGCTGGG

3501 CCTGGAGGGA CAGCTGATCC TGCGGCCAAG CAACGGCATC TGGATCAAAC

3551 TGAAAAGAAG GAACGCTGAC GAGAGGTAAA AGCTTGGTAC CGATATCGCG

3601 GCCGCCCTAG GGAGCTCCTC GAGGCGGCCC GCTCGAGTCT AGAGGGCCCT

3651 TCGAAGGTAA GCCTATCCCT AACCCTCTCC TCGGTCTCGA TTCTACGCGT

3701 ACCGGTCATC ATCACCATCA CCATTGAGTT TCGATAATCA ACCTCTGGAT

3751 TACAAAATTT GTGAAAGATT GACTGGTATT CTTAACTATG TTGCTCCTTT

3801 TACGCTATGT GGATACGCTG CTTTAATGCC TTTGTATCAT GCTATTGCTT
```

```
3851 CCCGTATGGC TTTCATTTTC TCCTCCTTGT ATAAATCCTG GTTGCTGTCT

3901 CTTTATGAGG AGTTGTGGCC CGTTGTCAGG CAACGTGGCG TGGTGTGCAC

3951 TGTGTTTGCT GACGCAACCC CCACTGGTTG GGGCATTGCC ACCACCTGTC

4001 AGCTCCTTTC CGGGACTTTC GCTTTCCCCC TCCCTATTGC CACGGCGGAA

4051 CTCATCGCCG CCTGCCTTGC CCGCTGCTGG ACAGGGGCTC GGCTGTTGGG

4101 CACTGACAAT TCCGTGGTGT TGTCGGGGAA ATCATCGTCC TTTCCTTGGC

4151 TGCTCGCCTG TGTTGCCACC TGGATTCTGC GCGGGACGTC CTTCTGCTAC

4201 GTCCCTTCGG CCCTCAATCC AGCGGACCTT CCTTCCCGCG CCTGCTGCC

4251 GGCTCTGCGG CCTCTTCCGC GTCTTCGCCT TCGCCCTCAG ACGAGTCGGA

4301 TCTCCCTTTG GGCCGCCTCC CCGCATCGAA ACCCGCTGAT CAGCCTCGAC

4351 TGTGCCTTCT AGTTGCCAGC CATCTGTTGT TTGCCCCTCC CCCGTGCCTT

4401 CCTTGACCCT GGAAGGTGCC ACTCCCACTG TCCTTTCCTA ATAAAATGAG

4451 GAAATTGCAT CGCATTGTCT GAGTAGGTGT CATTCTATTC TGGGGGGTGG

4501 GGTGGGGCAG GACAGCAAGG GGGAGGATTG GGAAGACAAT AGCAGGCATG

4551 CTGGGGATGC GGTGGGCTCT ATGGCTTCTG AGGGGGAAAA AACCAGATCC

4601 TCTCTTAAGG TAGGATCGAG ATTTAAATTA GGGATAACAG GGTAATGGCG

4651 CGGGCCGCAG GAACCCCTAG TGATGGAGTT GGCCACTCCC TCTCTGCGCG

4701 CTCGCTCGCT CACTGAGGCC GGGCGACGAA AGGTCGCCCG ACGCCCGGGC

4751 TTTGCCCGGG CGGCCTCAGT GAGCGAGCGA GCGCGCAGCT GCCTGCAGG
```

SEQ ID NO: 61 - Sequence of CYP4V2 expression cassette in
A2V5.CYP4V2st. AAV5.CYP4V2st has the same promoter (CAG),
enhancer (WPRE) and polyA (bGH-polyA) as AAV2.CYP4V2op,
AAV2tri(Y-F).CYP4V2op and AAV5.CYP4V2op (SEQ ID NO: 60)
but different CYP4V2 cDNA and junction/linker sequences:
Left-ITR: 1-141
CAG promoter: 166-1880
CYP4V2st cDNA: 1938-3515
WPRE enhancer: 3551-4139
bGH polyA: 4163-4387
Right-ITR: 4399-4539

```
   1 CCTGCAGGCA GCTGCGCGCT CGCTCGCTCA CTGAGGCCGC CCGGGCAAAG

51 CCCGGGCGTC GGGCGACCTT TGGTCGCCCG GCCTCAGTGA GCGAGCGAGC

101 GCGCAGAGAG GGAGTGGCCA ACTCCATCAC TAGGGGTTCC TGCGGCCTAA

151 GGCAATTGAG ATCTCGACAT TGATTATTGA CTAGTTATTA ATAGTAATCA

201 ATTACGGGGT CATTAGTTCA TAGCCCATAT ATGGAGTTCC GCGTTACATA

251 ACTTACGGTA AATGGCCCGC CTGGCTGACC GCCCAACGAC CCCCGCCCAT

301 TGACGTCAAT AATGACGTAT GTTCCCATAG TAACGCCAAT AGGGACTTTC

351 CATTGACGTC AATGGGTGGA CTATTTACGG TAAACTGGCC ACTTGGCAGT

401 ACATCAAGTG TATCATATGC GAAGTACGCC CCCTATTGAC GTCAATGACG

451 GTAAATGGGC CGCCTGGCAT TATGCCCAGT ACATGACCTT ATGGGACTTT

501 CCTACTTGGC AGTACATCTA CGTATTAGTC ATCGCTATTA CCATGGGTCG

551 AGGTGAGCCC CACGTTCTGC TTCACTCTCC CCATCTCCCC CCCCTCCCCA

601 CCCCCAATTT TGTATTTATT TATTTTTTAA TTATTTTGTG CAGCGATGGG

651 GGCGGGGGGG GGGGGGGCGG CGCGCCAGGCG GGGGGGGGCG GGGCGAGGGG

701 CGGGGCGGGG CGAGGCGGAG AGGTGCGGCG GCAGGCAATC AGAGCGGCGC

751 GCTCCGAAAG TTTCCTTTTA TGGCGAGGCG GCGGCGGCGG CGGCCCTATA
```

-continued

```
 801 AAAAGCGAAG CGCGCGGCGG GCGGGAGTCG CTGCGTTGCC TTCGCCCCGT

851 GCCCCGCTCC GCGCCGCCTC GCGCCGCCCG CCCCGGCTCT GACTGACCGC

901 GTTACTCCCA CAGGTGAGCG GGGGGGACGG CCCTTCTCCT CCGGGCTGTA

951 ATTAGCGCTT GGTTTAATGA CGGCTCGTTT CTTTTCTGTG GCTGCGTGAA

1001 AGCCTTAAAG GGCTCCGGGA GGGCCCTTTG TGCGGGGGGG AGCGGCTCGG

1051 GGGGTGCGTG CGTGTGTGTG TGCGTGGGGA GCGCCGCGTG CGGCCCGCGC

1101 TGCCCGGCGG CTGTGAGCGC TGCGGGCGCG GCGCGGGGCT TTGTGCGCTC

1151 CGCGTGTGCG CGAGGGGAGC GCGGCCGGGG GCGGTGCCCC GCGGTGCGGG

1201 GGGGCTGCGA GGGGAACAAA GGCTGCGTGC GGGGTGTGTG CGTGGGGGGG

1251 TGAGCAGGGG GTGTGGGCGC GGCGGTCGGG CTGTAACCCC CCCCTGCACC

1301 CCCCTCCCCG AGTTGCTGAG CACGGCCCGG CTTCGGGTGC GGGGCTCCGT

1351 GCGGGGCGTG GCGCGGGGCT CGCCGTGCCG GGCGGGGGGT GGCGGCAGGT

1401 GGGGGTGCCG GGCGGGGCGG GGGCGCCTCG GCCGGGGAG GGCTCGGGGG

1451 AGGGGCGCGG CGGCCCCGGA GCGCCGGCGG CTGTCGAGGC GCGGCGAGCC

1501 GCAGCCATTG CCTTTTATGG TAATCGTGCG AGAGGGCGCA GGGACTTCCT

1551 TTGTCCCAAA TCTGGCGGAG CCGAAATCTG GGAGGCGCCG CCGCACCCCC

1601 TCTAGCGGGC GCGGGCGAAG CGGTGCGGCG CCGGCAGGAA GGAAATGGGC

1651 GGGGAGGGCC TTCGTGCGTC GCCGCGGCGC CGTCCCCTTC TCCATCTCCA

1701 GCCTCGGGGC TGGCGCAGGG GGACGGGTGC CTTCGGGGGG GACGGGGCAG

1751 GGCGGGGTTC GGCTTCTGGC GTGTGACCGG CGGCTCTAGA GCCTCTGCTA

1801 ACCATGTTCA TGCCTTCTTC TTTTTCCTAC AGCTCCTGGG CAACGTGCTG

1851 GTTATTGTGC TGTCTCATCA TTTTGGCAAA GAATTCTAAT ACGACTCACT

1901 ATAGGGAGAC CCAAGCTGGC TAGCCAAAGC TTCCACCATG GCGGGGCTCT

1951 GGCTGGGGCT CGTGTGGCAG AAGCTGCTGC TGTGGGGCGC GGCGAGTGCC

2001 CTTTCCCTGG CCGGCGCCAG TCTGGTCCTG AGCCTGCTGC AGAGGGTGGC

2051 GAGCTACGCG CGGAAATGGC AGCAGATGCG GCCCATCCCC ACGGTGGCCC

2101 GCGCCTACCC ACTGGTGGGC CACGCGCTGC TGATGAAGCC GGACGGGCGA

2151 GAATTTTTTC AGCAGATCAT TGAGTACACA GAGGAATACC GCCACATGCC

2201 GCTGCTGAAG CTCTGGGTCG GGCCAGTGCC CATGGTGGCC CTTTATAATG

2251 CAGAAAATGT GGAGGTAATT TTAACTAGTT CAAAGCAAAT TGACAAATCC

2301 TCTATGTACA AGTTTTTAGA ACCATGGCTT GGCCTAGGAC TTCTTACAAG

2351 TACTGGAAAC AAATGGCGCT CCAGGAGAAA GATGTTAACA CCCACTTTCC

2401 ATTTTACCAT TCTGGAAGAT TTCTTAGATA TCATGAATGA ACAAGCAAAT

2451 ATATTGGTTA AGAAACTTGA AAAACACATT AACCAAGAAG CATTTAACTG

2501 CTTTTTTTAC ATCACTCTTT GTGCCTTAGA TATCATCTGT GAAACAGCTA

2551 TGGGGAAGAA TATTGGTGCT CAAAGTAATG ATGATTCCGA GTATGTCCGT

2601 GCAGTTTATA GAATGAGTGA GATGATATTT CGAAGAATAA AGATGCCCTG

2651 GCTTTGGCTT GATCTCTGGT ACCTTATGTT TAAAGAAGGA TGGGAACACA

2701 AAAAGAGCCT TCAGATCCTA CATACTTTTA CCAACAGTGT CATCGCTGAA

2751 CGGGCCAATG AAATGAACGC CAATGAAGAC TGTAGAGGTG ATGGCAGGGG

2801 CTCTGCCCCC TCCAAAAATA AACGCAGGGC CTTTCTTGAC TTGCTTTTAA
```

-continued

```
2851 GTGTGACTGA TGACGAAGGG AACAGGCTAA GTCATGAAGA TATTCGAGAA

2901 GAAGTTGACA CCTTCATGTT TGAGGGGCAC GATACAACTG CAGCTGCAAT

2951 AAACTGGTCC TTATACCTGT TGGGTTCTAA CCCAGAAGTC CAGAAAAAAG

3001 TGGATCATGA ATTGGATGAC GTGTTTGGGA AGTCTGACCG TCCCGCTACA

3051 GTAGAAGACC TGAAGAAACT TCGGTATCTG GAATGTGTTA TTAAGGAGAC

3101 CCTTCGCCTT TTTCCTTCTG TTCCTTTATT TGCCCGTAGT GTTAGTGAAG

3151 ATTGTGAAGT GGCAGGTTAC AGAGTTCTAA AAGGCACTGA AGCCGTCATC

3201 ATTCCCTATG CATTGCACAG AGATCCGAGA TACTTCCCCA ACCCCGAGGA

3251 GTTCCAGCCT GAGCGGTTCT TCCCCGAGAA TGCACAAGGG CGCCATCCAT

3301 ATGCCTACGT GCCCTTCTCT GCTGGCCCCA GGAACTGTAT AGGTCAAAAG

3351 TTTGCTGTGA TGGAAGAAAA GACCATTCTT TCGTGCATCC TGAGGCACTT

3401 TTGGATAGAA TCCAACCAGA AAGAGAAGA GCTTGGTCTA GAAGGACAGT

3451 TGATTCTTCG TCCAAGTAAT GGCATCTGGA TCAAGTTGAA GAGGAGAAAT

3501 GCAGATGAAC GCTAAGCGGC CGCAACTCGA GACTCTAGAG GTTAATCGAT

3551 AATCAACCTC TGGATTACAA AATTTGTGAA AGATTGACTG GTATTCTTAA

3601 CTATGTTGCT CCTTTTACGC TATGTGGATA CGCTGCTTTA ATGCCTTTGT

3651 ATCATGCTAT TGCTTCCCGT ATGGCTTTCA TTTTCTCCTC CTTGTATAAA

3701 TCCTGGTTGC TGTCTCTTTA TGAGGAGTTG TGGCCCGTTG TCAGGCAACG

3751 TGGCGTGGTG TGCACTGTGT TTGCTGACGC AACCCCCACT GGTTGGGGCA

3801 TTGCCACCAC CTGTCAGCTC CTTTCCGGGA CTTTCGCTTT CCCCCTCCCT

3851 ATTGCCACGG CGGAACTCAT CGCCGCCTGC CTTGCCCGCT GCTGGACAGG

3901 GGCTCGGCTG TTGGGCACTG ACAATTCCGT GGTGTTGTCG GGGAAATCAT

3951 CGTCCTTTCC TTGGCTGCTC GCCTGTGTTG CCACCTGGAT TCTGCGCGGG

4001 ACGTCCTTCT GCTACGTCCC TTCGGCCCTC AATCCAGCGG ACCTTCCTTC

4051 CCGCGGCCTG CTGCCGGCTC TGCGGCCTCT TCCGCGTCTT CGCCTTCGCC

4101 CTCAGACGAG TCGGATCTCC CTTTGGGCCG CCTCCCCGCA TCGAAACCCG

4151 CTGACTAGAC GACTGTGCCT TCTAGTTGCC AGCCATCTGT TGTTTGCCCC

4201 TCCCCCGTGC CTTCCTTGAC CCTGGAAGGT GCCACTCCCA CTGTCCTTTC

4251 CTAATAAAAT GAGGAAATTG CATCGCATTG TCTGAGTAGG TGTCATTCTA

4301 TTCTGGGGGG TGGGGTGGGG CAGGACAGCA AGGGGGAGGA TTGGGAAGAC

4351 AATAGCAGGC ATGCTGGGGA TGCGGTGGGC TCTATGGCCG CGGGCCGCAG

4401 GAACCCCTAG TGATGGAGTT GGCCACTCCC TCTCTGCGCG CTCGCTCGCT

4451 CACTGAGGCC GGGCGACCAA AGGTCGCCCG ACGCCCGGGC TTTGCCCGGG

4501 CGGCCTCAGT GAGCGAGCGA GCGCGCAGCT GCCTGCAGG
```

-continued

SEQ ID NO: 62 - Sequence of CYP4V2 expression cassette in
AAV8.CYP4V2fv, AAV8.CYP4V2fv has the same promoter (CAG),
enhancer (WPRE) and polyA (bGH-polyA) and junction/linker
sequences as AAV5.CYP4V2st (SEQ ID NO: 61) and differs
only in CYP4V2 cDNA sequence:
Left-ITR: 1-141
CAG promoter: 166-1880
CYP4V2fv cDNA: 1938-3515
WPRE enhancer: 3551-4139
bGH polyA: 4163-4387
Right-ITR: 4399-4539

```
   1 CCTGCAGGCA GCTGCGCGCT CGCTCGCTCA CTGAGGCCGC CCGGGCAAAG

51 CCCGGGCGTC GGGCGACCTT TGGTCGCCCG GCCTCAGTGA GCGAGCGAGC

101 GCGCAGAGAG GGAGTGGCCA ACTCCATCAC TAGGGGTTCC TGCGGCCTAA

151 GGCAATTGAG ATCTCGACAT TGATTATTGA CTAGTTATTA ATAGTAATCA

201 ATTACGGGGT CATTAGTTCA TAGCCCATAT ATGGAGTTCC GCGTTACATA

251 ACTTACGGTA AATGGCCCGC CTGGCTGACC GCCCAACGAC CCCCGCCCAT

301 TGACGTCAAT AATGACGTAT GTTCCCATAG TAACGCCAAT AGGGACTTTC

351 CATTGACGTC AATGGGTGGA CTATTTACGG TAAACTGCCC ACTTGGCAGT

401 ACATCAAGTG TATCATATGC CAAGTACGCC CCCTATTGAC GTCAATGACG

451 GTAAATGGCC CGCCTGGCAT TATGCCCAGT ACATGACCTT ATGGGACTTT

501 CCTACTTGGC AGTACATCTA CGTATTAGTC ATCGCTATTA CCATGGGTCG

551 AGGTGAGCCC CACGTTCTGC TTCACTCTCC CCATCTCCCC CCCCTCCCCA

601 CCCCCAATTT TGTATTTATT TATTTTTTAA TTATTTTGTG CAGCGATGGG

651 GGCGGGGGGG GGGGGGGCGC GCGCCAGGCG GGGCGGGGCG GGGCGAGGGG

701 CGGGGCGGGG CGAGGCGGAG AGGTGCGGCG GCAGCCAATC AGAGCGGCGC

751 GCTCCGAAAG TTTCCTTTTA TGGCGAGGCG GCGGCGGCGG CGGCCCTATA

801 AAAAGCGAAG CGCGCGGCGG GCGGGAGTCG CTGCGTTGCC TTCGCCCCGT

851 GCCCCGCTCC GCGCCGCCTC GCGCCGCCCG CCCCGGCTCT GACTGACCGC

901 GTTACTCCCA CAGGTGAGCG GGCGGGACGG CCCTTCTCCT CCGGGCTGTA

951 ATTAGCGCTT GGTTTAATGA CGGCTCGTTT CTTTTCTGTG GCTGCGTGAA

1001 AGCCTTAAAG GGCTCCGGGA GGGCCCTTTG TGCGGGGGGG AGCGGCTCGG

1051 GGGGTGCGTG CGTGTGTGTG TGCGTGGGGA GCGCCGCGTG CGGCCCGCGC

1101 TGCCCGGCGG CTGTGAGCGC TGCGGGCGCG GCGCGGGGCT TTGTGCGCTC

1151 CGCGTGTGCG CGAGGGGAGC GCGGCCGGGG GCGGTGCCCC GCGGTGCGGG

1201 GGGGCTGCGA GGGGAACAAA GGCTGCGTGC GGGGTGTGTG CGTGGGGGGG

1251 TGAGCAGGGG GTGTGGGCGC GGCGGTCGGG CTGTAACCCC CCCCTGCACC

1301 CCCCTCCCCG AGTTGCTGAG CACGGCCCGG CTTCGGGTGC GGGGCTCCGT

1351 GCGGGGCGTG GCGCGGGGCT CGCCGTGCCG GCGGGGGGGT GGCGGCAGGT

1401 GGGGGTGCCG GCGGGGGCGG GGCCGCCTCG GCCGGGGGAG GGCTCGGGGG

1451 AGGGGCGCGG CGGCCCCGGA GCGCCGGCGG CTGTCGAGGC GCGGCGAGCC

1501 GCAGCCATTG CCTTTTATGG TAATCGTGCG AGAGGGCGCA GGGACTTCCT

1551 TTGTCCCAAA TCTGGCGGAG CCGAAATCTG GGAGGCGCCG CCGCACCCCC

1601 TCTAGCGGGC GCGGGCGAAG CGGTGCGGCG CCGGCAGGAA GGAAATGGGC

1651 GGGGAGGGCC TTCGTGCGTC GCCGCGCCGC CGTCCCCTTC TCCATCTCCA

1701 GCCTCGGGGC TGCCGCAGGG GGACGGCTGC CTTCGGGGGG GACGGGGCAG
```

-continued

```
1751 GGCGGGGTTC GGCTTCTGGC GTGTGACCGG CGGCTCTAGA GCCTCTGCTA

1801 ACCATGTTCA TGCCTTCTTC TTTTTCCTAC AGCTCCTGGG CAACGTGCTG

1851 GTTATTGTGC TGTCTCATCA TTTTGGCAAA GAATTCTAAT ACGACTCACT

1901 ATAGGGAGAC CCAAGCTGGC TAGCCAAAGC TTCCACCATG GCGGGGCTCT

1951 GGCTGGGGCT CGTGTGGCAG AAGCTGCTGC TGTGGGGCGC GGCGAGTGCC

2001 CTTTCCCTGG CCGGCGCCAG TCTGGTCCTG AGCCTGCTGC AGAGGGTGGC

2051 GAGCTACGCG CGCAAATGGC AGCAGATGCG GCCCATCCCC ACGGTGGCCC

2101 GCGCCTACCC ACTGGTGGGC CACGCGCTGC TGATGAAGCC GGACGGGCGA

2151 GAATTTTTTC AGCAGATCAT TGAGTAGACA GAGGAATACC GCCACATGCC

2201 GCTGCTGAAG CTCTGGGTCG GCCAGTGCC CATGGTGGCC CTTTATAATG

2251 CAGAAAATGT GGAGGTAATT TTAACTAGTT CAAAGCAAAT TGACAAATCC

2301 TCTATGTACA AGTTTTTAGA ACCATGGCTT GGCCTAGGAC TTCTTACAAG

2351 TACTGGAAAC AAATGGGGCT CCAGGAGAAA GATGTTAACA CCCACTTTCC

2401 ATTTTAGGAT TCTGGAAGAT TTCTTAGATA TCATGAATGA ACAAGCAAAT

2451 ATATTGGTTA AGAAACTTGA AAAACACATT AACCAAGAAG CATTTAACTG

2501 CTTTTTTTAC ATCACTCTTT GTGCCTTAGA TATCATCTGT GAAACAGCTA

2551 TGGGGAAGAA TATTGGTGCT CAAAGTAATG ATGATTCCGA GTATGTCCGT

2601 GCAGTTTATA GAATGAGTGA GATGATATTT CGAAGAATAA AGATGCCCTG

2651 GCTTTGGCTT GATCTCTGGT ACCTTATGTT TAAAGAAGGA TGGGAACACA

2701 AAAAGAGCCT TAAGATCCTA CATACTTTTA CCAACAGTGT CATCGCGGAA

2751 CGGGCCAATG AAATGAACGC CAATGAAGAC TGTAGAGGTG ATGGCAGGGG

2801 CTCTGCCCCC TCCAAAAATA AAGGCAGGGC CTTTCTTGAC TTGCTTTTAA

2851 GTGTGACTGA TGACGAAGGG AACAGGCTAA GTCATGAAGA TATTCGAGAA

2901 CAAGTTGAGA CCTTCATGTT TGAGGGGCAC GATACAAGTG CAGCTGCAAT

2951 AAACTGGTCC TTATACCTGT TGGGTTCTAA CCCAGAAGTC CAGAAAAAAG

3001 TGGATCATGA ATTGGATGAC GTGTTTGGGA AGTCTGACCG TCCCGCTACA

3051 GTAGAAGACC TGAAGAAACT TCGGTATCTG GAATGTGTTA TTAAGGAGAC

3101 CCTTCGCCTT TTTCCTTCTG TTCCTTTATT TGCCCGTAGT GTTAGTGAAG

3151 ATTGTGAAGT GGCAGGTTAG AGAGTTCTAA AAGGCACTGA AGCCGTCATC

3201 ATTCCCTATG CATTGCACAG AGATCCGAGA TACTTCCCCA ACCCCGAGGA

3251 GTTCCAGCCT GAGCGGTTCT TCCCCGAGAA TGCACAAGGG CGCCATCCAT

3301 ATGCCTACGT GCCCTTCTCT GCTGGCCCCA GGAACTGTAT AGGTCAAAAG

3351 TTTGCTGTGA TGGAAGAAAA GACCATTCTT TCGTGCATCC TGAGGCACTT

3401 TTGGATAGAA TCCAAGCAGA AAAGAGAAGA GCTTGGTCTA GAAGGACAGT

3451 TGATTCTTCG TCCAAGTAAT GGCATCTGGA TCAAGTTGAA GAGGAGAAAT

3501 GCAGATGAAC GCTAAGCGGC CGCAACTCGA GACTCTAGAG GTTAATCGAT

3551 AATCAACCTC TGGATTACAA AATTTGTGAA AGATTGACTG GTATTCTTAA

3601 CTATGTTGCT CCTTTTACGC TATGTGGATA CGCTGCTTTA ATGCCTTTGT

3651 ATCATGCTAT TGGTTCCCGT ATGGCTTTCA TTTTCTCCTC CTTGTATAAA

3701 TCCTGGTTGC TGTCTCTTTA TGAGGAGTTG TGGCCCGTTG TCAGGCAACG
```

-continued

```
3751 TGGCGTGGTG TGCACTGTGT TTGCTGACGC AACCCCCACT GGTTGGGGCA

3801 TTGCCACCAC CTGTCAGCTC CTTTCCGGGA CTTTCGCTTT CCCCCTCCCT

3851 ATTGCCACGG CGGAACTCAT CGGCGCCTGC CTTGCCCGCT GCTGGACAGG

3901 GGCTCGGCTG TTGGGGACTG ACAATTCCGT GGTGTTGTCG GGGAAATCAT

3951 CGTCCTTTCC TTGGCTGCTC GCCTGTGTTG CCACGTGGAT TCTGCGCGGG

4001 ACGTCCTTCT GCTACGTCCC TTCGGCCCTC AATCCAGCGG ACCTTCCTTC

4051 CCGCGGCCTG CTGCCGGCTC TGCGGCCTCT TCCGCGTCTT CGCCTTCGGC

4101 CTCAGACGAG TCGGATCTCC CTTTGGGCCG CCTCCCCGCA TCGAAACCCG

4151 CTGAGTAGAC GACTGTGCCT TCTAGTTGCC AGCCATCTGT TGTTTGCCCC

4201 TCCCCCGTGC CTTCCTTGAC CCTGGAAGGT GCCACTCCCA CTGTCCTTTC

4251 CTAATAAAAT GAGGAAATTG CATCGCATTG TCTGAGTAGG TGTCATTCTA

4301 TTCTGGGGGG TGGGGTGGGG CAGGACAGCA AGGGGGAGGA TTGGGAAGAC

4351 AATAGCAGGC ATGCTGGGGA TGGGGTGGGC TCTATGGCCG CGGGCCGCAG

4401 GAACCCCTAG TGATGGAGTT GGCCACTCCC TCTCTGCGCG CTCGCTCGCT

4451 CACTGAGGCC GGGCGACCAA AGGTCGCCCG ACGCCCGGGC TTTGCCCGGG

4501 CGGCCTCAGT GAGCGAGCGA GCGCGCAGCT GCCTGCAGG
```

SEQ ID NO: 63 - Sequence of CYP4V2 expression cassette in
AAV5.CYP4V2op (new), AAV5.CYP4V2op (new) has the same
promoter (CAG), enhancer (WPRE) and polyA (bGH-polyA) and
the same junction/linker sequences as AAV5.CYP4V2st (SEQ ID
NO: 61) and AAV8.CYP4V2fv (SEQ ID NO: 62) but different
CYP4V2 cDNA sequences:
Left-ITR: 1-141
CAG promoter: 166-1880
CYP4V2op cDNA: 1938-3515
WPRE enhancer: 3551-4139
bGH polyA: 4163-4387
Right-ITR: 4399-4539

```
CCTGCAGGCA GCTGCGCGCT CGCTCGCTCA CTGAGGCCGC CCGGGCAAAG

CCCGGGCGTC GGGCGACCTT TGGTCGCCCG GCCTCAGTGA GCGAGCGAGC

GCGCAGAGAG GGAGTGGCCA ACTCCATCAC TAGGGGTTCC TGCGGCCTAA

GGCAATTGAG ATCTCGACAT TGATTATTGA CTAGTTATTA ATAGTAATCA

ATTACGGGGT CATTAGTTCA TAGCCCATAT ATGGAGTTCC GCGTTACATA

ACTTACGGTA AATGGCCCGC CTGGCTGACC GCCCAACGAC CCCCGCCCAT

TGACGTCAAT AATGACGTAT GTTCCCATAG TAACGCCAAT AGGGACTTTC

CATTGACGTC AATGGGTGGA CTATTTACGG TAAACTGCCC ACTTGGCAGT

ACATCAAGTG TATCATATGC CAAGTACGCC CCCTATTGAC GTCAATGACG

GTAAATGGCC CGCCTGGCAT TATGCCCAGT ACATGACCTT ATGGGACTTT

CCTACTTGGC AGTACATCTA CGTATTAGTC ATCGCTATTA CCATGGGTCG

AGGTGAGCCC CACGTTCTGC TTCACTCTCC CCATCTCCCC CCCCTCCCCA

CCCCCAATTT TGTATTTATT TATTTTTTAA TTATTTTGTG CAGCGATGGG

GGCGGGGGGG GGGGGGGCGC GCGCCAGGCG GGGCGGGGCG GGGCGAGGGG

CGGGGCGGGG CGAGGCGGAG AGGTGCGGCG GCAGCCAATC AGAGCGGCGC

GCTCCGAAAG TTTCCTTTTA TGGCGAGGCG GCGGCGGCGG CGGCCCTATA

AAAAGCGAAG CGCGCGGCGG GCGGGAGTCG CTGCGTTGCC TTCGCCCCGT

GCCCCGCTCC GCGCCGCCTC GCGCCGCCCG CCCCGGCTCT GACTGACCGC

GTTACTCCCA CAGGTGAGCG GGCGGGACGG CCCTTCTCCT CCGGGCTGTA
```

-continued

```
ATTAGCGCTT GGTTTAATGA CGGCTCGTTT CTTTTCTGTG GCTGCGTGAA

AGCCTTAAAG GGCTCCGGGA GGGCCCTTTG TGCGGGGGGG AGCGGCTCGG

GGGGTGCGTG CGTGTGTGTG TGCGTGGGGA GCGCCGCGTG CGGCCCGCGC

TGCCCGGCGG CTGTGAGCGC TGCGGGCGCG GCGCGGGGCT TTGTGCGCTC

CGCGTGTGCG CGAGGGGAGC GCGGCCGGGG GCGGTGCCCC GCGGTGCGGG

GGGGCTGCGA GGGGAACAAA GGCTGCGTGC GGGGTGTGTG CGTGGGGGGG

TGAGCAGGGG GTGTGGGCGC GGCGGTCGGG CTGTAACCCC CCCCTGCACC

CCCCTCCCCG AGTTGCTGAG CACGGCCCGG CTTCGGGTGC GGGGCTCCGT

GCGGGGCGTG GCGCGGGGCT CGCCGTGCCG GGCGGGGGGT GGCGGCAGGT

GGGGGTGCCG GGCGGGGCGG GGCCGCCTCG GGCCGGGGAG GGCTCGGGGG

AGGGGCGCGG CGGCCCCGGA GCGCCGGCGG CTGTCGAGGC GCGGCGAGCC

GCAGCCATTG CCTTTTATGG TAATCGTGCG AGAGGGCGCA GGGACTTCCT

TTGTCCCAAA TCTGGCGGAG CCGAAATCTG GGAGGCGCCG CCGCACCCCC

TCTAGCGGGC GCGGGCGAAG CGGTGCGGCG CCGGCAGGAA GGAAATGGGC

GGGGAGGGCC TTCGTGCGTC GCCGCGCCGC CGTCCCCTTC TCCATCTCCA

GCCTCGGGGC TGCCGCAGGG GGACGGCTGC CTTCGGGGGG GACGGGGCAG

GGCGGGGTTC GGCTTCTGGC GTGTGACCGG CGGCTCTAGA GCCTCTGCTA

ACCATGTTCA TGCCTTCTTC TTTTTCCTAC AGCTCCTGGG CAACGTGCTG

GTTATTGTGC TGTCTCATCA TTTTGGCAAA GAATTCTAAT ACGACTCACT

ATAGGGAGAC CCAAGCTGGC TAGCCAAAGC TTCCACC

ATGGCTGGACTGTGGCTGGGACTGGTGTGGCAGAAACTGCTGCTGTGGGGGGCCGCTTCCGCACTGTCACTGGCTGGG

GCTTCACTGGTGCTGAGCCTGCTGCAGAGGGTGGCCTCCTACGCCAGAAAGTGGCAGCAGATGAGGCCCATCCCTACC

GTGGCCAGAGCCTATCCACTGGTGGGACACGCACTGCTGATGAAGCCTGACGGCAGAGAGTTCTTTCAGCAGATCATC

GAGTACACAGAGGAGTATAGGCACATGCCACTGCTGAAGCTGTGGGTGGGACCCGTGCCTATGGTGGCCCTGTACAAC

GCCGAGAATGTGGAAGTGATCCTGACCAGCAGCAAGCAGATCGATAAGTCTAGCATGTATAAGTTCCTGGAGCCTTGG

CTGGGCCTGGGCCTGCTGACCTCTACAGGCAACAAGTGGAGGAGCCGGAGAAAGATGCTGACCCCAACATTCCACTTT

ACAATCCTGGAGGACTTCCTGGACATCATGAACGAGCAGGCCAATATCCTGGTGAAGAAGCTGGAGAAGCACATCAAC

CAGGAGGCCTTTAATTGCTTCTTTTACATCACCCTGTGCGCCCTGGACATCATCTGTGAGACAGCTATGGGCAAGAAC

ATCGGCGCCCAGTCTAATGACGATAGCGAGTACGTGCGGGCCGTGTATAGAATGAGCGAGATGATCTTTAGGCGCATC

AAGATGCCCTGGCTGTGGCTGGATCTGTGGTATCTGATGTTCAAGGAGGGCTGGGAGGAGAAGAAGTCCCTGCAGATC

CTGCACACCTTTACAAACTCTGTGATCGCCGAGAGAGCCAATGATGATGAACGCCAATGAGGACTGTAGGGGCGATGGA

AGGGGCAGCGCCCCTTCCAAGAACAAGCGGAGAGCCTTCCTGGACCTGCTGCTGAGCGTGACCGACGATGAGGGCAAT

CGCCTGTCCCACGAGGACATCCGGGAGGAGGTGGATACATTCATGTTTGAGGGACACGACACCACAGCCGCCGCCATC

AACTGGTCCCTGTACCTGCTGGGCTCTAATCCAGAGGTGCAGAAGAAGGTGGATCACGAGCTGGACGACGTGTTCGGC

AAGTCCGACAGGCCAGCAACCGTGGAGGATCTGAAGAAGCTGAGATACCTGGAGTGCGTGATCAAGGAGACACTGCGC

CTGTTCCCCTCTGTGCCTCTGTTTGCCCGGTCCGTGTCTGAGGACTGTGAGGTGGCCGGCTATCGCGTGCTGAAGGGC

ACCGAGGCCGTGATCATCCCTTACGCCCTGCACCGGGACCCCAGGTATTTCCCTAACCCAGAGGAGTTTCAGCCAGAG

AGATTCTTTCCCGAGAATGCCCAGGGCAGGCACCCTTACGCCTATGTGCCATTCTCCGCCGGACGAAGGAACTGCATC

GGACAGAAGTTTGCCGTGATGGAGGAGAAAACCATCCTGTCTTGTATCCTGAGACACTTCTGGATCGAGAGCAATCAG

AAGAGGGAGGAGCTGGGCCTGGAGGGACAGCTGATCCTGCGGCCAAGCAACGGCATCTGGATCAAACTGAAAAGAAGG
```

-continued

```
AACGCTGACGAGAGGTAAGCGGC CGCAACTCGA GACTCTAGAG GTTAATCGAT

AATCAACCTC TGGATTACAA AATTTGTGAA AGATTGACTG GTATTCTTAA

CTATGTTGCT CCTTTTACGC TATGTGGATA CGCTGCTTTA ATGCCTTTGT

ATCATGCTAT TGCTTCCCGT ATGGCTTTCA TTTTCTCCTC CTTGTATAAA

TCCTGGTTGC TGTCTCTTTA TGAGGAGTTG TGGCCCGTTG TCAGGCAACG

TGGCGTGGTG TGCACTGTGT TTGCTGACGC AACCCCCACT GGTTGGGGCA

TTGCCACCAC CTGTCAGCTC CTTTCCGGGA CTTTCGCTTT CCCCCTCCCT

ATTGCCACGG CGGAACTCAT CGCCGCCTGC CTTGCCCGCT GCTGGACAGG

GGCTCGGCTG TTGGGCACTG ACAATTCCGT GGTGTTGTCG GGGAAATCAT

CGTCCTTTCC TTGGCTGCTC GCCTGTGTTG CCACCTGGAT TCTGCGCGGG

ACGTCCTTCT GCTACGTCCC TTCGGCCCTC AATCCAGCGG ACCTTCCTTC

CCGCGGCCTG CTGCCGGCTC TGCGGCCTCT TCCGCGTCTT CGCCTTCGCC

CTCAGACGAG TCGGATCTCC CTTTGGGCCG CCTCCCCGCA TCGAAACCCG

CTGACTAGAC GACTGTGCCT TCTAGTTGCC AGCCATCTGT TGTTTGCCCC

TCCCCCGTGC CTTCCTTGAC CCTGGAAGGT GCCACTCCCA CTGTCCTTTC

CTAATAAAAT GAGGAAATTG CATCGCATTG TCTGAGTAGG TGTCATTCTA

TTCTGGGGGG TGGGGTGGGG CAGGACAGCA AGGGGGAGGA TTGGGAAGAC

AATAGCAGGC ATGCTGGGGA TGCGGTGGGC TCTATGGCCG CGGGCCGCAG

GAACCCCTAG TGATGGAGTT GGCCACTCCC TCTCTGCGCG CTCGCTCGCT

CACTGAGGCC GGGCGACCAA AGGTCGCCCG ACGCCCGGGC TTTGCCCGGG

CGGCCTCAGT GAGCGAGCGA GCGCGCAGCT GCCTGCAGG
```

SEQ ID NO: 64 - Sequence of CYP4V2 expression cassette in
scAAV1.CYP4V2op, scAAV5.CYP4V2op, and scAAV9.CYP4V2op.
Left-ITR (truncated): 1-117
EFS promoter: 130-364
CYP4V2op cDNA: 520-2097
SPA: 2116-2169
Right-1TR: 2263-2403

```
   1 cctgcaggca gctgcgcgct cgctcgctca ctgaggccgc ccgggcaaag cccgggcgtc 61 gggcgacctt tggtcgcccg gcctcagtga gcgagcgagc gcgcagagag ggagtggacg 121 cgtaggcctg attggctccg gtgcccgtca gtgggcagag cgcacatcgc ccacagtccc 181 cgagaagttg gggggagggg tcggcaattg aaccggtgcc tagagaaggt ggcgcggggt 241 aaactgggaa agtgatgtcg tgtactggct ccgccttttt cccgagggtg ggggagaacc 301 gtatataagt gcagtagtcg ccgtgaacgt tcttttttcgc aacgggtttg ccgccagaac 361 acaggtgtcg tgacgcgacc aggtatgcat ctgcagctct aaggtaaata taaattttt 421 aagtgtataa tgtgttaaac tactgattct aattgtttct ctcttttaga ttccaacctt 481 tggaactgac tgcagggatc caagctttct agagccacca tggctggact gtggctggga 541 ctggtgtggc agaaactgct gctgtggggg gccgcttccg cactgtcact ggctggggct 601 tcactggtgc tgagcctgct gcagagggtg gcctcctacg ccagaaagtg gcagcagatg 661 aggcccatcc ctaccgtggc cagagcctat ccactggtgg acacgcact gctgatgaag 721 cctgacggca gagagttctt tcagcagatc atcgagtaca cagaggagta taggcacatg 781 ccactgctga agctgtgggt gggacccgtg cctatggtgg ccctgtacaa cgccgagaat 841 gtggaagtga tcctgaccag cagcaagcag atcgataagt ctagcatgta taagttcctg 901 gagccttggc tgggcctggg cctgctgacc tctacaggca caagtggag gagccggaga
```

```
                          -continued
 961 aagatgctga ccccaacatt ccactttaca atcctggagg acttcctgga catcatgaac 1021 gagcaggcca atatcctggt gaacaagctg gagaagcaca tcaaccagga ggcctttaat 1081 tgcttctttt acatcaccct gtgcgccctg gacatcatct gtgagacagc tatgggcaag 1141 aacatcggcg cccagtctaa tgacgatagc gagtacgtgc gggccgtgta tagaatgagc 1201 gagatgatct ttaggcgcat caagatgccc tggctgtggc tggatctgtg gtatctgatg 1261 ttcaaggagg gctgggagca caagaagtcc ctgcagatcc tgcacacctt tacaaactct 1321 gtgatcgccg agagagccaa tgagatgaac gccaatgagg actgtagggg cgatggaagg 1381 ggcagcgccc cttccaagaa caagcggaga gccttcctgg acctgctgct gagcgtgacc 1441 gacgatgagg gcaatcgcct gtcccacgag gacatccggg aggaggtgga tacattcatg 1501 tttgagggac acgacaccac agccgccgcc atcaactggt ccctgtacct gctgggctct 1561 aatccagagg tgcagaagaa ggtggatcac gagctggacg acgtgttcgg caagtccgac 1621 aggccagcaa ccgtggagga tctgaagaag ctgagatacc tggagtgcgt gatcaaggag 1661 acactgcgcc tgttcccctc tgtgcctctg tttgcccggt ccgtgtctga ggactgtgag 1741 gtggccggct atcgcgtgct gaagggcacc gaggccgtga tcatccctta cgccctgcac 1801 cgggacccca ggtatttccc taacccagag gagtttcagc cagagagatt ctttcccgag 1861 aatgcccagg gcaggcaccc ttacgcctat gtgccattct ccgccggacc aaggaactgc 1921 atcggacaga agtttgccgt gatggaggag aaaaccatcc tgtcttgtat cctgagacac 1981 ttctggatcg agagcaatca gaagagggag gagctgggcc tggagggaca gctgatcctg 2041 cggccaagca acggcatctg gatcaaactg aaaagaagga acgctgacga gaggtaaaag 2101 cttgaattcc tcgaggatcc aataaaagat ctttattttc attagatctg tgtgttggtt 2161 ttttgtgtgt ctagttgcca gccatctgtt gtttgcccct ccccgtgcc ttccttgacc 2221 ctggaaggtg ccactcccag tttaaactta attaagggcc gcaggaaccc ctagtgatgg 2281 agttggccac tccctctctg cgcgctcgct cgctcactga ggccgggcga ccaaaggtcg 2341 cccgacgccc gggctttgcc cgggcggcct cagtgagcga gcgagcgcgc agctgcctgc 2401 agg
```

To assess the difference in efficacy between CYP4V2st and CYP4V2op cDNAs in CYP4V2 gene therapy, two AAV5 vectors with the same promoter (CAG), enhancer (WPRE) and polyA (bGH-polyA) and the same junction/linker sequences, one carrying the CYP4V2st CDNA (AAV5.CYP4V2st (SEQ ID NO: 61)) and the other carrying the CYP4V2op cDNA (AAV5.CYP4V2op (new) (SEQ ID NO: 63)) are compared for efficacy in rescuing RPE atrophy in BCD patient-derived iPS-RPE using cell viability assay described herein.

To assess whether different junction/linker sequences used in SEQ ID NO: 60 and SEQ ID NO: 63 affect the expression of CYP4V2 cDNA or expression cassette, two AAV5 vectors (AAV5.CYP4V2op (SEQ ID NO: 60) and AAV5.CYP4V2op (new) (SEQ ID NO: 63)) with the same promoter (CAG), enhancer (WPRE) and polyA (bGH-polyA) and the same CYP4V2 CDNA (CYP4V2op (SEQ ID NO: 2)) but different junction/linker sequences are compared for efficacy in rescuing RPE atrophy in BCD patient-derived iPS-RPE using cell viability assay described herein.

It should be understood that different CYP4V2 cDNAs (SEQ ID Nos: 1, 2, 3, or others) can be used in any CYP4V2 expression cassette described herein in lieu of the CYP4V2 cDNA contained in the expression cassette sequences provided herein for use in CYP4V2 gene therapy. It should also be understood that each CYP4V2 expression cassette described herein can be packaged in rAAV vectors of various serotypes/capsids for use in CYP4V2 gene therapy, including those different from the ones used in this study (e.g., AAV1, AAV2, AAV2 (Y444F+Y500F+Y730F), AAV5, AAV8 and AAV9). In addition, the CYP4V2 expression cassette packaged in scAAV vectors used in this study can also be packaged in ssAAV vectors for use in CYP4V2 gene therapy, after changing the mutant AAV ITR used in scAAV construct to non-mutant AAV ITR used in ssAAV construct. Moreover, the CYP4V2 cDNAs or expression cassettes (with or without the AAV ITRs) described herein can be packaged in other viral vectors (i.e., non-AAV vectors, such as retroviruses, lentiviruses, adenoviruses and herpes simplex viruses or other viral vectors) or non-viral vectors (e.g., plasmids, nanoparticles, or lipid-based nanoparticles (e.g., liposome-protamine-DNA complex (LPD)) for use in CYP4V2 gene therapy.

Example 12-Treating BCD Patient-Derived iPS-RPE Cells by AAV.CYP4V2 iPS-RPE cells derived from BCD patients were infected with various AAV.CYP4V2 vectors described above in serum-free RPE medium. After 1 day, the virus-containing medium was replaced with fresh serum-containing RPE medium to continue RPE culture. To assess therapeutic effects of different dosage, different multiplicity of infection (MOI, genomic copies (GC)/cell) was tested.

Example 13-Assays to Assess the Effect of AAV.CYP4V2 Gene Therapy

After AAV.CYP4V2 infection, the iPS-RPE cells of BCD patients were cultured in RPE medium for at least 4 days for scAAV or at least 10 days for ssAAV before the cells were harvested for testing. Cell harvesting protocols and sample preparation protocols were followed as previously described.

The biochemical tests described in the Examples herein for detecting fatty acids, ceramides (Cer), sphingomyelins (SM), and sphingosine and sphinganine (SOSA), were performed on AAV.CYP4V2-treated BCD patient iPS-RPE cells and the same biochemical testing protocol using LC-MS was followed. Table 3 above shows the results in healthy control iPS-RPE cells, BCD patient iPS-RPE cells without AAV.CYP4V2 treatment and post-AAV.CYP4V2 treatment.

The results demonstrated that phenotype in BCD patient iPS-RPE cells (e.g., abnormal fatty acids levels (e.g., DHA, AA and total of n3 fatty acids) as compared to control) were ameliorated or corrected by AAV.CYP4V2 gene therapy. This established the efficacy of AAV.CYP4V2 gene therapy in BCD patient-derived iPS-RPE cell lines. Because BCD is primarily caused by RPE degeneration, the efficacy of AAV.CYP4V2 gene therapy in BCD patient-specific iPS-RPE cell lines established the efficacy of AAV.CYP4V2 gene therapy for BCD patients.

Significantly, the scAAV1.CYP4V2op treatment achieved most significant improvement in a very short time (just 4 days post treatment). This proved that scAAV is fast acting because it does not require the cell machinery to synthesize a complementary DNA strand. For the same reason, it is expected that longer time window between AAV.CYP4V2 treatment and cell harvesting for testing can generate more significant improvements in results, particularly for CYP4V2 gene therapy packaged in ssAAV vectors.

The fast and robust results achieved by scAAV vector in human RPE cells established that scAAV vectors can be particularly useful in rescuing early onset diseases and/or late stage human patient of RPE or retinal degenerations. In addition, the robust expression profile of scAAV vectors make it also suitable for intravitreal administration for delivery to the retina.

Rescue of RPE Atrophy by AAV.CYP4V2

BCD patient-derived iPS-RPE samples were exposed to blue light for 1 hour, then cell viability assay was performed on the samples the next day as previously described herein.

Cell viability images comparing patient iPS-RPE samples without vs. with AAV.CYP4V2 treatment are shown in Figures herein.

Each of AAV2.CYP4V2op and scAAV1.CYP4V2op treatment showed rescue of RPE atrophy in BCD patient-derived iPS-RPE samples as compared to untreated patient samples (FIG. 8. MOI=1×10e5 GC/cell). Interestingly, rescue efficacy by AAV2.CYP4V2op and scAAV1.CYP4V2op at 1×10e5 MOI is higher in P2 iPS-RPE than in P1 iPS-RPE. This suggests that the optimal dosage for use of AAV.CYP4V2 gene therapy to treat BCD can vary based on individual differences among patients and that BCD patient-specific iPS-RPE is a useful tool in assessing personalized optimal dose for different patients.

Each of AAV5.CYP4V2op, AAV5.CYP4V2st and AAV8.CYP4V2fv treatment rescued RPE atrophy in BCD patient-derived iPS-RPE sample as compared to untreated patient sample (FIG. 9. MOI=1×10e5).

Each of AAV5.CYP4V2op, scAAV1.CYP4V2op and scAAV5.CYP4V2op treatment rescued RPE atrophy in BCD patient-derived iPS-RPE sample as compared to untreated patient sample (FIG. 10. MOI=1×10e4).

scAAV9.CYP4V2op treatment rescued RPE atrophy in BCD patient-derived iPS-RPE sample as compared to untreated patient sample (FIG. 11. MOI=1×10e5. 2 weeks post treatment).

Significantly, AAV.CYP4V2 treatment at a lower dose (MOI=1×10e4) in P2 samples achieved similar or better results than a higher dose (MOI=1×10e5 GC/cell) of treatment by the same vector in P1 samples. This demonstrated at the cellular level that to achieve the same or similar efficacy in rescuing RPE atrophy, different patients may need different dosage. In other words, one vector and one similar dose level for all patients of the same disease may not be the most medically or economically efficient approaching for gene therapy. BCD cellular model and similar cellular models for other ocular diseases can provide a guidance on personalized optimal dose.

Other AAV.CYP4V2 vectors are also tested and show improved RPE atrophy in BCD patient iPS-RPE sample, including AAV2tri (Y-F).CYP4V2op treatment (MOI of 1×10e4) and AAV5.CYP4V2op (new) (SEQ ID NO: 63) at different MOI levels (1×10e4 and 1×10e5 GC/cell). Additionally, the cell viability images were processed by ImageJ (Fiji) to count the number of dead and live cells in the iPS-RPE samples. Four different areas/images from each sample were used to count and the dead/live cell ratios from multiple images of the same sample were averaged. Dead/live cell ratios demonstrated AAV.CYP4V2 treatment rescued RPE cell atrophy in BCD patient-derived iPS-RPE. For example, the dead/live cell ratio of WT2 is 3.0%, P1 (no AAV.CYP4V2 treatment) is 20.87%, and P1 treated by AAV5.CYP4V2st is 9.69%. Treatment by other AAV.CYP42 vectors also reduced the dead/live cell ratio in BCD patient iPS-RPE samples.

These results demonstrated that:
(1) various AAV.CYP4V2 vectors, expression cassettes and CYP4V2 cDNAs rescued RPE atrophy in BCD;
(2) Self-complementary AAV vector (scAAV) is fast in achieving rescue efficacy;
(3) Efficacy can be achieved at different dosage levels.

Example 14-Safety of AAV.CYP4V2 Vectors and GMP Manufacturing for Clinical Use

Prior studies demonstrated that CYP4V2 is almost ubiquitously expressed in human organs and expression level within the eye in high in retina. In addition, the safety of AAV vectors have been established in gene therapy studies and clinical trials for other diseases. Therefore, it is reasonable to expect that AAV.CYP4V2 vectors are safe to use in gene therapy.

In this study, various AAV.CYP4V2 vectors were used to treat human iPS-RPE samples at a high dose (e.g., 1×10e5 MOI). No material difference in cell death between untreated and AAV.CYP4V2 treated samples was observed, except that AAV.CYP4V2 rescued RPE atrophy in BCD patient-derived iPS-RPE samples as described in the Example above. This established the safety of AAV.CYP4V2 vectors and demonstrates that high levels of expression of the transduced CYP4V2-encoding gene can be achieved without significant evidence of toxicity.

In addition to testing in cell lines, the safety of AAV.CYP4V2 gene therapy can also be tested in animals, e.g., in mice, rats or non-human primates, and/or via human clinical trials. Various manufacturing methods and platforms are available to produce recombinant AAV vectors for human clinical use. For example, and without limitation, GMP manufacturing of rAAV vectors can use a 2-plasmid transfection method or a 3-plasmid transfection method, can use mammalian cell lines such as HEK293, A459 or 293T, or insect cell line such as the baculovirus/Sf9 cell platform, can use adherent or suspension cell culture. Further, various methods, processes and/or platforms, including without limitation, herpes simplex virus (HSV)-based production system, single-use bioreactors (e.g., iCELLis), HYPER-Stacks, roller bottles, and column chromatography, can be used to increase yield or titer, or improve purity, and/or to avoid potential contamination. These rAAV vector clinical production methods, processes, techniques and platforms are known in the art and are commercially available via contract manufacturing organizations (CMOs) or academic GMP facilities, e.g., Lonza (USA), Cobra Biologics (UK), Nationwide Children's Hospital (NCH. Ohio, USA), Children's Hospital of Philadelphia (CHOP. USA), WuXi Biologics (China and USA). AAV.CYP4V2 vectors for human clinical use can be manufactured using any one or more of the methods, processes, techniques, platforms and GMP facilities mentioned herein and/or others known in the art or to be developed in the future.

Example 15-Subject Selection and Administration of AAV.CYP4V2 in vivo to Treat BCD An exemplary subject eligibility criteria for AAV.CYP4V2 human clinical trial is listed as follows:

Inclusion Criteria

Subjects are eligible for study participation if they meet all of the following inclusion criteria.

1. Are willing and able to provide informed consent for participation in the study.
2. ≥18 years of age.
3. Have a genetically-confirmed diagnosis of bi-allelic CYP4V2 mutation.
4. Have active disease clinically visible within the macular region in the study eye.
5. Have a best corrected visual acuity (BCVA) of 34-73 ETDRS letters (equivalent to worse than or equal to 20/40 Snellen acuity, but better than or equal to 20/200 Snellen acuity) in the study eye.

Exclusion Criteria

Subjects are not eligible for study participation if they meet any of the following exclusion criteria.

1. Have a history of amblyopia in the eligible eye.
2. Are unwilling to use barrier contraception methods, for a period of 3 months, if treated with AAV.
3. Previous intraocular surgery performed in the study eye within 3 months of first visit.
4. Have any other significant ocular or non-ocular disease/disorder which, in the opinion of the investigator, may either put the subjects at risk because of participation in the study, or may influence the results of the study, or the subject's ability to participate in the study. This includes but is not limited to, a subject:
   with a contraindication to oral corticosteroid (eg prednisolone/prednisone)
   with a clinically significant cataract who, in the clinical opinion of the study investigator, is not an appropriate candidate for the surgical procedure (e.g., sub-retinal surgery).
5. Have participated in another research study involving an investigational product in the past 12 weeks or received a gene/cell-based therapy at any time previously.

For use of AAV.CYP4V2 to treat BCD, the patient should have genetic or molecular confirmed diagnosis of BCD, i.e., confirmation of bi-allelic CYP4V2 mutation via genetic testing (single gene test or multi gene panel test if medically necessary). Because BCD is sometimes diagnosed as inherited retinal disorder (IRD), retinal degeneration (RD), or retinitis pigmentosa (RP), AAV.CYP4V2 can also be used to treat a patient of IRD, RD or RP with genetically confirmed bi-allelic CYP4V2 mutation.

For AAV.CYP4V2 treatment in vivo, the patient should have viable retinal cells as determined by optical coherence tomography (OCT) and/or ophthalmoscopy. Preferably, the patient should have some vision left (e.g., best corrected visual acuity (BCVA) better than or equal to 20/200 (Decimal 0.1 in the to-be-treated eye.

Various means/route of administration can be used to deliver AAV.CYP4V2 vectors to the target cells (e.g., retinal or corneal cells) in vivo, including without limitation, administration to the retina can be performed via sub-retinal injection, intravitreal injection (using AAV vectors suitable for intravitreal delivery, e.g., AAV2 (Y444F+Y500+Y730F), AAV 7m8 or their derivatives), or delivery through the bloodstream (using AAV vectors that can penetrate the blood-retinal barrier, e.g., AAV9 or AAV-PHP.B). In addition, AAV.CYP4V2 vectors can also be encapsulated in a device to be implanted intravitreally as a way of administration.

Surgical/administration methods related to gene therapy, as well as certain techniques to improve delivery/transduction efficiency (e.g., internal limiting membrane (ILM) peeling and vitrectomy (VIT)), are known in the art. Immunosuppressants, e.g., corticosteroids may be used before, during and/or after AAV administration to minimize immune responses.

In addition to treating patients in vivo, CYP4V2 gene therapy (including AAV.CYP4V2 gene therapy) can be used to treat the target cells (e.g., BCD patient's iPS derived RPE cells, retinal cells corneal epithelium cells, or corneal cells) in vitro and then transplant such cells to the patient as a cell therapy. Methods of using AAV.CYP4V2 vectors to treat BCD patient iPS-RPE cells are provided in the Examples and disclosure herein. Methods of cell implantation/transplantation, e.g., to the retina and cornea, are known in the art. For example, the same or similar methods and surgical techniques to transplant ES-RPE cells to the retina can be used to transplant BCD patient's iPS-RPE cells.

Therapeutically effective doses can be determined and evaluated in disease models (e.g., BCD cellular model (e.g., iPS-RPE cell line derived from BCD patients) or an animal model, and confirmed or refined by clinical trials. For treatment of cells in vitro, the dose is usually expressed as MOI and then multiply the MOI by the number of cells being treated. The MOI generally ranges between about $1 \times 10^3$ GC to about $1 \times 10^6$ GC per cell or an infectious MOI of about 100 to about 10,000 GC per cell (GC: genomic copies, measuring genome containing AAV particles (a/k/a vector genome (vg) or genome particles (gp)). For in vivo treatment, typical clinical factors should be considered to determine the dose, such as route of administration, the size of the area or number of cells targeted, and the subject being treated (e.g., the age, weight, development stage of the disease and condition of the subject to be treated, and potential immune reactions); the location of the cells targeted for treatment (e.g., retina vs. cornea). In addition, the transduction efficiency and rescue efficacy of the AAV.CYP4V2 vector being used should also be considered. Finally, if possible, individual differences in optimal dose at the cellular level among patients should also be considered, which can be assessed in the patient-specific iPS-RPE cells. Therefore, the therapeutically effective dose for a single local administration to the eye in vivo can be on the order of from about $1\times10^{6}$ to about $2\times10^{13}$ GC, inclusive (e.g., a high dose range of about $1\times10^{11}$ GC to about $1\times10^{12}$ GC, a medium dose range of about $1\times10^{10}$ GC to about $1\times10^{11}$ GC, a low dose range of about $1\times10^{9}$ GC to about $1\times10^{10}$ GC, a very low dose range of about $1\times10^{6}$ GC to about $1\times10^{9}$ GC, and a very high dose range of about $1\times10^{12}$ GC to about $2\times10^{13}$ GC), or any dose within these ranges that is sufficient to provide the desired effect. In one embodiment, the composition is administered at a dose of about $1\times10^{6}$ to about $2\times10^{13}$ GC. In another embodiment, the in vivo administered dose is determined by multiplying the number of cells targeted for treatment by the target MOI (e.g., about $1\times10^{3}$ GC to about $1\times10^{6}$ GC per cell). The volume of the agent containing the rAAV vectors in any single local administration to the eye can range from about 1 μL (0.001 mL) to about 1000 μL (1 mL). Treatment by delivery via bloodstream requires a much higher dose and can be in the range of about $1\times10^{6}$ to about $2\times10^{14}$ GC per kg of body weight.

See "E. Treatment Options, Subject Selection and Administration" and other disclosure herein for more description.

Example 16-Post-Treatment Evaluation

Since the clinical symptoms of BCD are similar to those of many other types of IRDs, RDs and RP, e.g., loss in visual acuity, restricted visual fields, night blindness, reduced dark adaptation, contrast sensitivity and color vision, changes in the retina (and in cornea for some patients) and diminished responses on electroretinogram (ERG), related measures can be used to assess a BCD patient's disease state and progression pre- and post-treatment, thereby evaluating treatment outcome. These measures and related examinations and tests are known in the art for retinal and corneal diseases. For example, and without limitation, best corrected visual acuity (using visual acuity chart) can be used as the primary outcome measure for BCD gene therapy, with one or more of the following as secondary outcome measures: microperimetry (change in sensitivity), fundus autofluorescence (AF) (change in AF), optical coherence tomography (OCT) (ellipsoid zone and retinal thickness), contrast sensitivity (Pelli-Robson chart), color vision (Farnsworth-Munsell 100 hue test) and ERG (changes in ERG). In addition, functional tests such as mobility test can also be used as a primary or secondary outcome measure. Evaluations can be performed at different time points post treatment, e.g., 2 weeks, 1 month, 2 months, 3 months, 6 months and 12 months. Results can be used to evaluate treatment outcome. Efficacy can be shown as one of the following: improvement in one or more of the primary or secondary outcome measures, stop of disease progression, or slower than expected rate of retinal degeneration or loss of vision (by using data from a natural history study if necessary).

Example 17: Method to Reduce Immune Responses and to Address Individual Differences in Gene Therapy Viral vector-mediated gene therapy may trigger cellular, local or systemic immune responses, which may pose safety risks. Immune reactions also may decrease transduction efficiency and thereby diminish the treatment effect of viral vector-mediated gene therapy. Immune responses may occur in the form of the humoral response (or antibody-mediated response) recognizing antigens or pathogens that in the lymph or blood, and/or cell-mediated immunity. To minimize immune responses, immunosuppressants such as corticosteroids are often used in connection with a gene therapy administration. Immunosuppressant drugs have effects, e.g., may cause increased intraocular pressure, cataracts, and other adverse events (e.g., prolonged use of immunosuppressant may increase risk of cancer). In addition to immune response, other individual differences exist among patients, e.g., in response to different types (e.g., different serotype or different capsid mutation/structure) of vectors, or in response to the same vector at the same dose.

A method to reduce immune responses to viral vectors, preserve transduction efficiency, to lower viral vector and/or immunosuppressant dose, and/or to maximize therapeutic effect to different patients of the same genetic disease, in viral vector mediated gene therapy, comprising:

(a) establishing a pool of more than one recombinant viral vectors (e.g., rAAVs) with sufficient transduction efficiency in the target cell type for the gene therapy. The viral vector pool can be expanded by creating variants with antigenic region mutations or other mutations or variants on the capsids of said viral vectors after such mutations or variants are confirmed with sufficient transduction efficiency in target cells relevant to the disease (e.g., in iPS-RPE or RPE cell lines for CYP4V2 gene therapy for BCD).

(b) detecting pre-existing neutralizing anti-viral vector antibodies (NAbs) against different viral vector serotypes and/or capsid mutations or variants in the subject in need of the gene therapy, and/or testing and comparing different viral vectors in patient-specific disease target cells (e.g., iPS-RPE cells) derived from such subject.

(c) selecting a viral vector from said pool of viral vectors with (i) sufficient transduction efficiency in the disease target cells and (ii) low cross-reactivity with the pre-existing NAbs in the subject, and/or (iii) good phenotype rescue result in the subject's patient-specific disease target cells (e.g., patient-specific iPS-RPE or RPE cell lines for CYP4V2 gene therapy for BCD), wherein such viral vector pool comprising different serotypes and/or capsid-modified viral vectors (e.g., including without limitation, capsid-mutant AAVs and/or capsid protein variant AAVs).

(d) use the viral vector selected from (c) for administration to the subject.

(e) repeat (b) through (d) (only the part relating to pre-existing NAbs) above each time the subject requires a gene therapy administration, including without limitation, a follow-up administration to the same organ (e.g., an eye or a contralateral eye), or to another organ.

Specifically, various rAAV vectors including five different AAV (AAV1, AAV2, AAV5, AAV8 and AAV9) serotypes and a capsid mutation AAV (AAV2.tri (Y-F)) were generated and tested to assess differences among different patients' cell lines in this study.

Example 18: Use of scAAV in Rapid Rescue of Retinal Diseases and Use of EFS and/or SPA in an scAAV or an AAV Vector in Treating Ocular Diseases As demonstrated in Example 13 above, scAAV.CYP4V2 treatment achieved robust rescue of biochemical phenotype in BCD patient iPS-RPE cells in a very short time (just 4 days). In addition, scAAV.CYP4V2 showed rescue of RPE atrophy in BCD patient iPS-RPE cell line two weeks post AAV treatment (See FIG. 11). The fast and robust expression in human iPS-RPE cells driven by the EFS promoter (exemplary sequence shown in SEQ ID NO: 35) and SPA (exemplary sequence shown in SEQ ID NO: 36) in an scAAV vector demonstrated the suitability of EFS promoter and/or SPA in driving a transgene expression in human ocular cells and treating human ocular diseases. The fast rescue achieved by scAAV vectors with the EFS promoter and SPA make them particularly useful in treating fast progressing diseases or patients of advanced disease stage.

In addition, the study proved the fast and robust expression of an scAAV design in human retinal cells. The makes scAAV-mediated gene therapy particularly helpful in treating early onset retinal disease patient or in treating a late stage patient who requires a rapid rescue.

Discussion on CYP4V2 Gene Therapy

BCD is a rare blinding eye disease for which currently there is no approved treatment available. In a clinical research involving the use the BCD patient-specific iPS-RPE cell lines, the efficacy of various AAV.CYP4V2 vector and expression cassette designs in rescuing the phenotype in BCD patient-specific iPS-RPE cells were proved in this study as assessed through fatty acid and lipid assays. In addition, different doses (MOI) were tested which can serve as a guidance for determining the dose range for treatment in vivo. Finally, there is no significant evidence of toxicity associated with AAV.CYP4V2 gene therapy.

Cell Therapy and CRISPR Gene-editing Therapy Examples

Example 19-Use of iPSCs, iPS-RPE or iPS-ocular Cells from a BCD Subject in Cell Therapy BCD is a relatively late onset disease. Symptom in BCD patients are usually developed in the 2nd, $3^{rd}$ or even 4th decade of life. In addition, iPS reprogramming process can have some "reset the clock" effect. Therefore, the iPS-RPE cells and other iPS-ocular cells derived a BCD patient can be used as a cell therapy for transplantation to the BCD patient even without any genetic repair of the CYP4V2 mutations in the iPS-RPE cells.

Alternatively, the iPSCs, iPS-RPE cells, iPS-PRCs, iPS-CE cells, iPS-CECs and/or other iPS-ocular cells derived from a BCD patient can be genetically repaired before cell therapy transplantation. Genetic repair can be achieved by either CYP4V2 gene therapy as described in Examples above or by gene editing. See the Examples herein for more detailed description on gene editing.

Example 20-Genetically Repaired Patient Autologous Cells for Ocular Cell Therapy Patient-specific iPSC derived cells (e.g., iPS-RPE cells, iPS-CECs, iPS-CE cells, iPS-PRCs, or iPS-ocular cells) can be used as a source of autologous cells for transplantation in cell therapy for ocular diseases, including without limitation, retinal and corneal diseases. Compared to cells generated from allogenic sources, such as ES cells (e.g., ES-RPE cells, ES-CEC or ES-PRC, and tissues made up of such ES-derived cells) or iPS cells of another individual, such patient-specific iPS-derived autologous cells and tissues made from such cells usually requires little to no immuno-suppression of the patient and do not have ethical issues related to the use of ES and ES-derived cells.

However, iPSCs generated from a patient source cells (e.g., fibroblasts or blood cells) and cells and tissues derived from such patient-specific iPSCs (e.g., patient-specific iPS-RPE cells, iPS-PRCs, iPS-CECs, iPS-CE cells and iPS-ocular cells) still possess disease-causing mutations and related phenotype. To generate healthy patient-derived cells and/or tissues, pathologic mutations can be genetically repaired or corrected with gene-editing technology, including without limitation, the clustered regularly interspersed short palindromic repeats (CRISPR), which can be designed to correct a target mutation in a patient's cell. These genetically repaired healthy iPSCs then can be used to generate various cell types (e.g., iPS-RPE cells, iPS-CECs, iPS-CE cells, iPS-PRCs or other iPS-ocular cells) that no longer harbor the pathologic mutations of the patient.

Furthermore, this proof-of-concept study demonstrates these gene-corrected iPSCs and/or gene-corrected iPS-derived cells (e.g., iPS-RPE cells) no longer have the phenotype (e.g., abnormal biochemical profile as assessed by bioassays, e.g., lipidomics and/or proteomics) as seen in (uncorrected) iPS-derived cells from the patient. Therefore, these gene-corrected cells serve as a source of regenerative, genetically-repaired autologous cells that can be used as replacement cells in cell therapy. Compositions and methods relating to gene-corrected patient autologous cells are described in detail herein and in Examples below.

Another type of genetically repaired patient cells are patient iPSCs or iPS-derived cells (e.g., iPS-RPE cells, iPS-PRCs, iPS-CE cells, iPS-CECs and iPS-ocular cells, iPS-neuron cells) treated by gene supplementation therapy (e.g., CYP4V2 gene therapy) as described herein above. Post gene therapy treatment, the patient-specific cells possess a healthy copy of the mutated gene (e.g., a cDNA) and/or express a functional protein encoded by the healthy transgene. Furthermore, the gene therapy treated patient-specific cells demonstrate improved or normalized biochemical profile or other phentotype seen in untreated patient cells. Therefore, they also can be used as a source of genetically repaired autologous cells for use as replacement cells in cell therapy, e.g., CYP4V2 gene therapy treated BCD patient-specfic iPS-RPE cells, iPS-PRCs, iPS-CECs, iPS-CE cells and iPS-ocular cells as genetically-repaired patient autologous cells for use in cell therapy for BCD. Compositions and methods relating to CYP4V2 gene therapy treated BCD patient-specific cells are described in detail in Examples herein above. The discussion herein below focuses on the type of genetic repair by correcting the mutation in genomic DNA.

Autologous cell replacement for ocular and retinal degenerative diseases associated with genetic mutations depends on the ability to repair a patient's pathogenic mutation by genetically correcting the mutation via gene editing or to repair or mitigate the consequence of the mutation (e.g., via delivery of a healthy copy of a transgene relative to the disease gene, e.g., CYP4V2 gene therapy) before transplantation. Here, patient-specific iPSCs from a BCD patient with the most common CYP4V2 mutation (c.802-

8_810del17insGC) were generated and the CRISPR gene-editing components (CRISPR guide RNA and donor template) and various constructs (plasmid and RNP) to correct this mutation were developed. Although CRISPR/Cas9 is used herein as the means for gene editing, it is anticipated that other CRISPR system (e.g., Cpf1) and other gene gous cells from a patient with a different mutation in CYP4V2, or a patient with a mutation in another gene associated with an ocular disease, or a patient with a mutation in a gene associated with other types of diseases, including without limitation, in any gene contained in Table 4.

TABLE 4

| Target Gene List |
| --- |
| ABCA4, ABCC6, ABHD12,ADAM9, AHI1, AFPL1, ALMS1, ARL13B, ARL6, ARMS2, ATXN7, BBS1, BBS10, BBS12, BBS2, BBS4, BBS5, BBS7, BBS9, BEST1, C1QTNF5, C2, C2orf71, C3, C5orf42, C8orf37, CA4, CABP4, CACNA1F, CACNA2D4, CAPN5, CC2D2A CDH23, CDH3, CDHR1, CEP164, CEP290, CEP41, CERKL, CFB, CFH, CHM, CHR2, CIB2, CLN3, CLN5, CLN6, CLN8, CLRN1, CNGA1, CNGA3, CNGB1, CNGB3, CNNM4, COL11A1, COL2A1, COL9A1, CRB1, CRX, CYP4V2, DFNB31, DHDDS, EFEMP1, ELOVL4, ERCC6, EYS, FAM161A, FBLN5, FLVCR1, FSCN2, FZD4, GNAT1, GNAT2, GNPTG, GPR143, GPR179, GPR98, GRK1, GRM6, GRN, GUCA1A, GUCA1B, GUCY2D, HARS, HMCN1, HTRA1, IDH3B, IFT140, IFT80, IMPDH1, IMPG2, INPP5E, INVS, IQCB1, ITM2B, JAG1, KCNJ13, KCNNV2, KCTD7, KIF11, KLHL7, LCA5, LRAT, LRIT3, LRP5, LZTFL1, MAK, MERTK, MFN2, MFRP, MFSD8, MKKS, MKS1, MT-ND4, MTTP, MYO7A NDP, NEK4, NEK8, NMNAT1, NPHP1, NPHP3, NPHP4, NR2E3, NRL, NUB1, NYX, OA1, OAT, OCA1, OCA2, OFD1, OPA1, OPA3, OPN1LW, OPN1MW, OPN1SW, OTX2, PANK2, PAX2, PCDH15, PDE6A, PDE6B, PDE6C, PDE6G, PDE6H, PDGF, PDZD7, PEX1, PEX10, PEX14, PEX16, PEX19, PEX2, PEX5, PEX6, PEX7, PGK1, PHYH, PITPNM3, PLA2G5, PPT1, PRCD, PROM1, PRPF3, PRPF31, PRPF6, PRPF8, PRPH2, RAB28, RAX2, RBP3, RBP4, RD3, RDH12, RGH5, RDS, RGR, RGS9, RGS9BP, RHO, RIMS1, RLBP1, ROM1, RP1, RP1L1, RP2, RP9, RPE65, RPGR, RPGRIP1, RPGRIP1L, RS1, SAG, SDCCAG8, SEMA4A, SLC24A1, SLC45A2, SNRNP200, SPATA7, TEAD1, TIMM8A, TIMP3, TLR3, TLR4, TMEM126A, TMEM231, TMEM237, TMEM67, TOPORS, TPP1, TREX1 , TRIM32, TRPM1, TSPAN12, TTC21B, TTC8, TTPA, TULP1, TYR, TYRP1, UNC119, USH1C, USH1G, USH2A, VCAN, VPS13B, WDPCP, WDR19, WFS1, WHRN, ZNF423, ZNF513, ACO2, AFG3L2, AUH, C12orf65, CISD2, CYP1B1, FOXC1, FOXF2, LTBP2, MTPAP, MYOC, NDUFS1, NR2F1, OPTN, PAX6, PITX2, POLG, SPG7, TEK, TXNRD2, ATXN2, ROBO3, PHOX2A, HOXA1, SALL4, CHN1, TUBB3, KIF21A, HOXB1, FAM47E, GBA, GCH1, HTRA2, LRRK2, PARK2, PINK1, SNCA, SYNJ1, NPC1, NPC2, CYP4A11, CYP4A22, CYP4B1, CYP4F2, CYP4F3, CYP4F8, CYP4F11, CYP4F12, CYP4F22, CYP4X1, CYP4Z1, CYP46A1 | editing techniques including but not limited to TALEN as well as emerging and future gene editing techniques such as CRISPR/Cpf1 can be used to achieve same or similar results. It is also expected that gene editing can be applied not only to iPSCs, but also to the original source cells that will be used to generate the iPSCs, as well as to the cells generated from the iPSCs, to correct the pathogenic mutation(s) in such cells.

While the iPS-derived cell lines are generated on a patient-specific basis, its application in cell therapy does not have to be. A key factor limiting the wide use of iPSC-based cell therapy is immunologic differences among human individuals. There are multiple approaches to solve this problem. For example, one approach is to develop a number of cell banks that contain a limited number of lines with common HLA haplotypes, designed to achieve immunologic matching with a large portion of the patient population. Such a cell bank can be created by generating iPSCs from patients with selected haplotypes or by genetic manipulation of HLA genotypes. Another approach is to produce a cell type that would be immunologically silent regardless of the patient's genotype.

The following describes the methods on how to generate genetically repaired patient-specific autologous cells, how to assess the effect of the genetic repair in the cells, and how to use them in cell therapy. The examples provided herein are related to generating genetically-repaired patient autologous cells from a BCD patient with the c.802-8_810del17insGC mutation in the CYP4V2 gene, the most common mutation among BCD patients. The same methods can be used to generate genetically-repaired patient autolo- Using BCD, a disease with CYP4V2 mutations, as an example, iPSCs were generated from patient-specific cells carrying the BCD patient's specific mutation. The patient-specific iPSCs are transfected with CRISPR guide RNAs (gRNA), Cas9 endonuclease, and a donor homology template. CYP4V2 gene copies show mutation correction and conversion to the wild-type allele. The corrected iPSCs then are used to generate gene-corrected iPS-RPE cells. The gene-corrected iPS-RPE cells are then tested to confirm they no longer have phenotype (e.g., abnormal biochemical profile (e.g., fatty acids profile)). These genetically-repaired patient autologous cells can be transplanted (either directly (e.g., cell suspension) or in other forms, such as part of a layer, a sheet, a matrix, a scaffold or a tissue) to the same patient as an autologous cell therapy for BCD.

(i) Generation of BCD Patient-Specific iPSC Lines:

iPSCs were generated from patient-specific cells from a BCD patient carrying homozygous c.802-8_810del17insGC mutation in the CYP4V2 gene as described herein. See Example 1 for methods to generate patient-specific iPSCs. The BCD patient's mutation was identified by sequencing (ii) Designing, Screening and Selection of CRISPR gene editing components and constructs targeting the mutation:

See the Examples herein on CRISPR gene editing therapy for a detailed description.

(CRISPR gRNAs were selected to minimize the off-target editing and to maximize specificity with a target sequence directly centered on the mutation site. Multiple gRNAs with high specificity to the region containing the patient-specific CYP4V2 mutation were screened. The candidate gRNAs were separately inserted into an expression vector also containing the Cas9 endonuclease responsible for mediating target DNA cleavage and transfected into a 293 cell line. Genomic DNA from the patient was amplified by PCR using primers for the CYP4V2 region, and the PCR products were analyzed for DNA cleavage activity. A survey assay was used to assess which gRNA candidate has relatively high activity for the mutation site. The gRNA with the highest cutting efficiency is used for gene editing.)

(iii) Gene Editing in iPSCs:

See Examples below on CRISPR gene editing therapy for a detailed description.

For genetic recessive diseases like BCD, gene correction in one allele or mutation is sufficient. Multiple CRISPR constructs targeting different mutations can be used to correct multiple mutations harbored by a cell.

(iv) Generation of iPS-RPE Cells or other iPS-ocular cells from Gene Corrected iPSC:

After confirming precise correction of the pathogenic mutation with no or minimal off-target editing via sequencing, the iPSC corrected by gene editing is used to differentiate into and generate iPS-RPE cells or the other type of iPS-ocular cells (e.g., iPS-PRCs, iPS-CECs, or iPS-CE cells) affected by the relevant disease as described herein. The corrected iPS-RPE cells derived from BCD patient then go through the same RPE fate confirmation (e.g., distinct RPE morphology (e.g., pigment and/or hexagonal shape) and.or RPE-specific markers).

(v) Bioassays to Confirm Phenotype-Free

Bioassays are used to confirm these gene-corrected iPSCs and/or gene-corrected iPS-derived cells (e.g., iPS-RPE cells) no longer have the phenotype as seen in (uncorrected) iPS-derived cells from the patient. The bioassays can be any type of biological assay which can identify and assess the cellular and/or molecular level phenotype in patient cells as it relates to a specific disease. For example, they can include without limitation, lipidomics, proteomics, protein expression and/or other biochemical tests. For BCD, the bioassay includes fatty acids and ceramides tests as described in the Examples herein. Results indicate that these gene corrected iPS-RPE cells derived from the BCD patient no longer have the relevant biochemical defect/dysfunction as seen in uncorrected iPS-RPE cells derived from BCD patients. This proves that gene-corrected, iPS-RPE cells are phenotype-free and therefore is a source of replacement cells suitable for cell therapy.

(vi) Transplantation:

These genetically-repaired patient autologous cells (e.g., iPS-RPE cells, iPS-PRCs, iPS-CE cells, iPS-CECs and other iPS-ocular cells) can be transplanted (either directly or as part of a layer, a sheet, a matrix, a scaffold or a tissue) to the same patient as a cell therapy for BCD.

Example 21-Specific Example of CRISPR Gene Editing Therapy for an Ocular Disease CRISPR/Cas9 is highly specific when gRNAs are designed correctly, but specificity and off-target editing is still a major concern, particularly as CRISPR is being developed for clinical use. The following Example describes in detail methods to develop CRISPR gene editing therapy constructs with high on-target specificity and low off-target editing risk for use in treating on ocular disease. In addition, the c.802-8_810del17insGC mutation represents one of the most challenging mutations to correct among all known CYP4V2 mutations and other genetic ocular diseases. Most CYP4V2 mutations are single nucleotide change, insertion or deletion (See Table 1: Select CYP4V2 Mutations among BCD Patients), whereas the c.802-8_810del17insGC mutation involves a 17 bp deletion and a 2 bp insertion, and both an intron and an exon.

Several sets of CRISPR gene editing therapy constructs to correct the most common pathologic CYP4V2 mutation (c.802-8_810del17insGC mutation) were designed and constructed. The following is a detailed description on the design, compositions and methods of use of these CRISPR CYP4V2 Gene Editing constructs to correct the mutation and treat BCD.

(a) Analyzing the Mutation

The c.802-8_810del17insGC mutation involves both an intron and an exon, and both a deletion and an insertion, and it affects a splice acceptor site.

The c.802-8_810del17insGC mutation refers to a 17 base deletion with two bases (GC) inserted in the place starting 8 bases from the end of intron 6 of CYP4V2 gene, also referred to as IVS6-8 del/insGC; See SEQ ID NO: 46 showing sequence of the human CYP4V2 genomic DNA region comprising the c.802-8_810del17insGC mutation and SEQ ID NO: 47 showing the corresponding wild-type sequence. The c.802-8_810del17insGC mutation is illustrated in the following sequence which shows human CYP4V2 intron 6-exon 7 junction. Intron6 sequence is shown in lower case and exon 7 sequence in CAP letters. The 17 bps deletion and the insertion of GC are in brackets): caa aca gaa gca tgt gat tat cat tca aa (tca tac agG TCA TCG CT) (GC) GAA CGG GCC AAT GAA ATG AAC GCC AAT GA) is predicted to result in the skipping of exon 7. The wild type CYP4V2 has the following sequence: CAA ACA GAA GCA TGT GAT TAT CAT TCA AA (T CAT ACA GGT CAT CGC T) GA ACG GGC CAA TGA AAT GAA CGC CAA TGA (SEQ ID NO:47), while the c.802-8_810del17insGC mutant CYP4V2 has the following sequence: CAA ACA GAA GCA TGT GAT TAT CAT TCA AA (G C) GA ACG GGC CAA TGA AAT GAA CGC CAA TGA (SEQ ID NO:46). The bracketed nucleotides in the wild type sequence are the 17 nucleotides that are deleted and the bracketed nucleotides in the mutant sequence are the 2 nucleotides that are inserted following the 17 base pair deletion.

To achieve good repair rate using CRISPR, a Cas generated cleavage as close as possible to the mutated sequence is desired. The region of the CYP4V2 genomic DNA containing the c.802-8_810del17insGC mutation has multiple SpCas9 PAM sites (NGG). Therefore, regular SpCas9 can used to correct this mutation. Alternatively, Cas9 of other species, a mutated Cas9 or other CRISPR nuclease (e.g., Cpf1) with a different PAM (e.g., TTTN for Cpf1 which is present in the mutated sequence) can be used to correct the c.802-8_810del17insGC mutation and/or other mutations.

(b) CRISPR gRNA design and selection

Based on the various PAM sites present in the c.802-8_810del 17insGC mutation region of the CYP4V2 gene, multiple related protospeacer element sequences (herein referred to as gRNA, typically is 20 nt in length but can be in different length, e.g., 17-22nt for use with Cas9) were screened using DeskGen software. Five (5) gRNA candidates were selected using the following criteria: a) the proximity of the gRNA/Cas9 cleavage site to the target correction site; and b) the predicted off-target profiles of the gRNA (See Table 5 and FIG. 12; See SEQ ID NOs: 48 to 52 for gRNA sequences).

TABLE 5

Sequences of gRNA candidates

| gRNA | Off-target score | Sequence | SEQ ID NO |
|------|------|----------|-----------|
| CYP4V2 g1 | 87 | 5'-TGA TTA TCA TTC AAA GCG AA CGG-3' | 73 |
| CYP4V2 g2 | 98 | 5'-GAT TAT CAT TCA AAG CGA AC GGG-3' | 74 |
| CYP4V2 g3 | 73 | 5'-GAT AAT CAC ATG CTT CTG TT TGG-3' | 75 |
| CYP4V2 g4 | 70 | 5'-TTC ATT GGC GTT CAT TTC AT TGG-3' | 76 |
| CYP4V2 g5 | 32 | 5'-CAC ATG CTT CTG TTT GGA CT TGG-3' | 77 |

The PAM site corresponding to each gRNA candidate is highlighted in bold. To avoid confusion, PAM sequence is not part of the gRNA (protospacer element) sequence.

(c) gRNA Validation Using Patient Genomic DNA

Genomic DNA of a BCD patient (P1) with homozygous c.802-8_810del17insGC mutations was used to select and validate the gRNAs. DNA amplicons flanking a region of CYP4V2 containing the mutation site and various target sites were prepared using primers (See Table 6 and FIG. 12). DNA amplicons, single guide RNA (sgRNA) prepared by in vitro transcription (IVT) (each comprising one of the gRNA1, gRNA2, gRNA3, gRNA4, or gRNA5) and SpCas9 protein were mixed and incubated at 37° C. for 1 hr. Active sgRNA mediated Cas9 protein to create double stranded breaks in the amplicons and display various fragment patterns (Table 7). The reactions were loaded and DNA fragments were resolved on 1.5% agarose gel (FIG. 13).

TABLE 6

Primers used in gRNA validation

| | Sequences | Amplicon (bp) |
|------|-----------|---------------|
| CYP4V2 1F | 5'-CAG AAA TCG CAA GCA TAG AGG GTG AAT TCA-3' (SEQ ID NO: 78) | 1062 bp |
| CYP4V2 1R | 5'-CTG TTG GAG GGC TCT AAA CTG TCC-3' (SEQ ID NO: 79) | |

TABLE 7

Predicted DNA fragments created by active gRNAs

| gRNA | DNA amplicon size (bp) | Fragment sizes (bp) | |
|------|------|------|------|
| g1 | 1062 bp | 442 | 620 |
| g2 | | 443 | 619 |
| g3 | | 416 | 646 |
| g4 | | 455 | 607 |
| g5 | | 410 | 652 |

To confirm the fragments are indeed originated from the amplicon, DNA samples of untreated amplicon (FIG. 16, top panel) and the smallest fragment of g2-treated (FIG. 16, middle panel) were subjected to Sanger sequencing (FIG. 14). All 5 gRNAs showed predicted cleavage activities.

In addition to or in lieu of validation in patient genomic DNA harboring the mutation, gRNAs activities can also be validated in patient cells, including without limitation, somatic cells, stem cells, iPSCs, or cells derived from a stem cell.

(d) Construction of gRNA Expressing Vectors

Three gRNAs (g1, g2 and g3) with highest activities and highest off-target scores were cloned into pX-U6-CBh-Cas9-Puro gRNA expression vector by inserting a double-stranded oligo cassette of each active gRNA. Each cassette was synthesized based on one of the gRNA sequences of g1, g2 and g3. Schematic illustrations showing the construct of the expression vector and the insertion site of the gRNA is provided in FIG. 15 and FIG. 16. See FIG. 17 for a more detailed illustration (using g1 as example) showing the entire IVT sgRNA sequence (SEQ ID NO: 55 (not including the protospacer element sequence or the optional "G")) following the U6 promoter. The "G" nucleotide (SEQ ID NO: 59) inserted at the start of each protospacer element (gRNA) sequence is optional. It is mainly to enhance the transcription efficiency of the U6 promoter. It is not needed if the protospacer element sequence starts with a "G" residue or if a non-UT promoter is used (e.g., H1 promoter). All gRNA constructs were verified by both restriction enzyme digestion and sequencing.

Three plasmids each expressing a top gRNA (g1, 92 or g3) and co-expressing hSpCas9 and Puromycin resistance genes, namely pX459-hSpCas9-2A-Puro, were developed (FIGS. 15 and 16) and included as one of the constructs (see Table 8 below) for gene correction of the c.802-8_810del17insGC mutation.

It would be understood that the guide RNA, Cas protein and/or selection marker (e.g., puromycin resistence gene and/or GFP, EGFP or RFP) can be packaged in one plasmid or in separate plasmid. Furthermore, when more than one gRNA is used (either to correct multiple mutations or to correct the same mutation, e.g., a pairing gRNAs for use with Cas9 Nickase), they can be packaged in the same vector or in separate vectors.

In addition to the plasmid vector described herein, various other vector(s).can be used to package CRISPR gene editing components (guide RNA and/or Cas protein), and/or selection marker, including without limitation, pX458 plasmid vector, adeno-associated virus (AAV) vectors, and/or lentivirus vectors . . . . In addition to DNA constructs encoding the CRISPR components, guide RNA, Cas protein and/or selection markers can be used directly or in an mRNA construct or RNP construct.

(e) Construction and Validation of CRISPR RNP

In addition to a DNA construct in a vector (e.g., a pX459 plasmid as described above), a CRISPR ribonucleoprotein (RNP) construct was developed for each of g1, g2, g3, g4 and g5 (See Tables 5 and 8). Each RNP construct comprises (i) a chimeric single guide RNA (sgRNA) comprising the relevant protospacer element (See Tables 5 and 8 and detailed description herein); and (ii) a SpCas9 protein forming a ribonucleoprotein (RNP) complex. The cleavage activities of various RNP constructs (sgRNA1: Cas9, sgRNA2: Cas9, sgRNA3: Cas9, sgRNA4: Cas9, sgRNA5: Cas9) at the target site of the CYP4V2 gene were validated in patient genomic DNA (See FIGS. 12, 13 and 14) as described in paragraph (c) above.

A sgRNA typically is about 100nt in length but can vary in lengths comprising a 17nt-22nt protospacer element sequence. A sgRNA can be IVT derived or synthetic. IVT sgRNAs corresponding to g1, g2, g3, g4, and g5 were generated and validated as described above. Synthetic sgR- NAs corresponding to g1 and g2 were custom ordered from Synthego (Silicon Valley, CA, USA) as described below.

In lieu of a sgRNA, a crRNA (exemplary sequence in SEQ ID NO: 53) and tracrRNA (exemplary sequence in SEQ ID NO: 54) duplex can be used together with a Cas protein (e.g., Cas9) to form a CRISPR RNP complex (crRNA: tracrRNA: Cas9). When using a Cpf1 protein, no tracrRNA is required.

A sgRNA or crRNA: tracrRNA can be chemically modified to protect against intracellular RNA degradation. For example, a chemically modified synthetic RNA can contain 2'-O-methyl analogs and 3' phosphorothioate internucleotide linkages at the 5' and 3' terminal three bases of the gRNA (Synthego (Silicon Valley, CA, USA). Synthetic sgRNA or crRNA and tracrRNA based on a given protospacer element sequence (e.g., CRISPR g1, g2, 93, g4 or g5 (See SEQ ID NOs: 48 to 52) are commercially available, e.g., from Synthego Corporation (Silicon Valley, CA, USA) or IDT, with chemically modification available as an option.

(f) Construction of Donor Template

In a homology-directed repair (HDR), a donor template is used to provide the donor nucleic acid sequence required to correct the mutated sequence of the target gene. Two separate donor templates for HDR were generated in the form of single-stranded Oligo DeoxyNucleotide (ssODN). The first one, referred to as CPY4V2 donor template 1 or CYP4V2 ssODN 1 (SEQ ID NO: 56), contains the 17 bp correction and has the sequence as follows:

```
5'-AGA AAA ATA AAT GAA AGA AAC TAG CAT ATT TTA TAA

GAA AAT GTG TTA ACT AGG GTG CAT CCA AGT CCA AAC

AGA AGC ATG TGA TTA TCA TTC AAA TCA TAC AGG TCA

TCG CTG AAC GGG CCA ATG AAA TGA ACG CCA ATG AAG

ACT GTA GAG GTG ATG GCA GGG GCT CTG CCC CCT CCA

AAA ATA AAC GCA GGG CCT TT-3';
``` while the second donor template, referred to as CYP4V2 donor template 2 or CYP4V2 ssODN 2 (SEQ ID NO: 57) is the reverse complement of CYP4V2.donor template 1.

Either one of the donor templates can be used with any gRNA or sgRNA (g1, g2, g3, g4 or g5) described above, and a Cas9 protein to generate homology-directed repair (HDR) to correct the target CYP4V2 (c.802-8_810del17insGC) mutation.

The donor templates provided herein are 200 nt in length. Donor templates of various lengths can be used. A donor template can be symmetrical or asymmetrical relative to the target site. A donor template can be provided by an ssDNA, ssODN or a vector (e.g., a plsmid or an AAV vector) containing or encoding the donor nucleic acid sequence. If the donor template has an intact sequence complementary to the protospacer element in the CRISPR guide RNA and the PAM sequence targeted by the Cas protein, to avoid this donor template being degraded by the Cas protein (e.g., Cas9) in cells, mutations can be made to the donor template, e.g., to mutate the Cas9 PAM "NGG" in the donor template and change it to "NGT" or another non-PAM sequence. However, if the intended PAM mutation to be introduced by the donor template is within coding region, cautions need to be made to ensure it would be a silent mutation.

Donor templates can be synthetically made and are commercially available. For example, DNA oligos of a given sequence can be custom ordered (Ultramer® DNA Oligonucleotides, Integrated DNA Technologies (IDT), Coralville, Iowa, USA)

(g) Cas Protein and Selection Marker

CRISPR-associated proteins/nucleases (Cas) (e.g., Cas9 or Cpf1) are commercially available, including without limitation, encoded by a plasmid or as recombinant protein for use in a RNP construct. A Cas protein can also include one, two or more nuclear localization sequences (NLS) (e.g., Catalog #: 1074182, Integrated DNA Technologies (IDT), Coralville, Iowa, USA; Catalog #: A034a-a-1000, Feldan (Quebec, Canada); Cpf1: Catalog #: 1076158 (IDT)) and may also be fused with a selection marker (e.g., a SpCas9 protein fused with EGFP, Catalog #: PR-137211-E (Novatein Biosciences, Woburn, MA, USA).

When transfecting a CRISPR gene editing construct in vitro in cells, a selection marker can be used to evaluate the rate of transfection and/or to assist in picking the cells for next step processing. Various selection markers including without limitation fluorescence (e.g., GFP, EGFP, RFP) and/or puromycin) can be used in the process. A selection marker can be integrated with any component of a CRISPR construct or can be provided separately in a transfection process. For example, a fluorescence labeling can be combined with the tracrRNA (IDT) or the Cas9 protein (Novatein Biosciences, Catalogue #: PR-137211-E) for convenient imaging and manual or FACS sorting of transfected cells. A puromycin resistance gene can be provided in a vector that is co-transfected with the CRISPR construct for selection using puromycin. Selection using puromycin is illustrated in the Examples. Selection markers of various types such as antibiotics selection marker (e.g., puromycin) or fluorescence labeling are commercially available and can be integrated into a CRISPR component (e.g., the Cas9 protein or the CRISPR guide RNA) or provided separately (e.g., an expression plasmid expressing the puromycin resistance gene), including without limitation: IDT, Sigma Aldrich, Novatein Biosciences, Clonetech Laboratories, and InvivoGen.

(h) Consructs and Recommended Protocol

The following table (Table 8) shows the CRISPR gene editing constructs (plasmid and RNP) generated for each one of the 3 gRNAs (gRNA1, gRNA2 and gRNA3). They contain three gRNA plasmid constructs or respective sgRNA, two donor templates (forward and reverse complimentary) and SpCas9 protein.

TABLE 8

Plasmid and RNP Constructs for CYP4V2
mutation (c.802-8_810del17insGC) CRISPR
Gene Correction Therapy[1]

| Item # | Type | Name |
|---|---|---|
| 1 | DNA construct/plasmid[2] | CYP4V2-g1 (See Table 1 and SEQ ID NO: 48 for sequence) |
| 2 | DNA construct/plasmid[2] | CYP4V2-g2 (See Table 1 and SEQ ID NO: 49 for sequence) |
| 3 | DNA construct/plasmid[2] | CYP4V2-g3 (See Table 1 and SEQ ID NO: 50 for sequence) |
| 4 | sgRNA[3] | CYP4V2-g1 (See Table 1 and SEQ ID NO: 48 for sequence) |
| 5 | sgRNA[3] | CYP4V2-g2 (See Table 1 and SEQ ID NO: 49 for sequence) |
| 6 | sgRNA[3] | CYP4V2-g3 (See Table 1 and SEQ ID NO: 50 for sequence) |

TABLE 8-continued

Plasmid and RNP Constructs for CYP4V2
mutation (c.802-8_810del17insGC) CRISPR
Gene Correction Therapy[1]

| Item # | Type | Name |
|---|---|---|
| 7 | Donor template[4] | CYP4V2 donor template 1 (See para (f) and SEQ ID NO: 56) |
| 8 | Donor template[4] | CYP4V2 donor template 2 (See para (f) and SEQ ID NO: 57) |
| 9 | Protein | SpCas9 (See SEQ ID NO: 58 for exemplary sequence) |

[1]The constructs for correcting the c.802-8_810del17insGC mutation, the most common CYP4V2 mutation among BCD patients. CRISPR gRNAs and constructs for correcting other CYP4V2 mutations can be designed and validated by using the methods as described herein. In addition to plasmid and RNP constructs, other constructs including without limitation, mRNA and viral vector, can also be used to provide/express one or more CRISPR components.
[2]A pX459 plasmid encoding the CRISPR components (sgRNA and SpCas9 protein), and puromycin (Puro) resistance gene as selection marker. See FIG. 17 showing DNA construct and sequence encoding the sgRNA (using g1 as example, and FIG. 15 and 16 for vector construct and map). Each sgRNA sequence contains (a) a 20 nt protospacer element (SEQ ID NO: 48, 49, or 50 for g1, g2 and g3, respectively), and (b) a 82 nt sequence (SEQ ID NO: 55 (sequence shown in DNA format as included in the plasmid DNA; for RNA sequence, use "U" to replace "T" in the DNA sequence). The pX459 vector contains a "G" nucleotide (SEQ ID NO: 59 and FIG. 17) immediately after the human U6 promoter sequence and before the protospacer element sequence to enhance transcription efficiency driven by the U6 promoter, which is also included in the IVT derived sgRNA. The CRISPR components (gRNA and Cas protein) can also be cloned in other vectors, including without limitation, viral vectors such as lentivirus vectors or AAV vectors. CRISPR gRNA and Cas protein (e.g., Cas9 protein) can be cloned in separate vectors or in one vector.
[3]sgRNA based on various protospacer elements (CYP4V2 g1, CYP4V2 g2, or CYP4V2 g3, see Table 5 and SEQ ID NO: 48, 49 or 50, respectively). See description above for the IVT sgRNAs. In addition to IVT sgRNAs, synthetic sgRNAs with chemical modifications were ordered from Synthego Corporation (Silicon Valley, CA, USA). Instead of sgRNA, a crRNA (comprising the 20 nt protospacer sequence of CYP4V2 g1, g2 or g3, and remaining sequence of the crRNA (exemplary sequence shown in SEQ ID NO: 53)) and a tracrRNA (exemplary sequence shown in SEQ ID NO: 54) duplex can be used.
[4]A donor template for homology-directed repair (HDR). Donor templates of different lengths can also be used, and can be constructed in different forms, including without limitation, as ssODN or in a vector (e.g., in an adeno-associated virus (AAV) vector (e.g., AAV2 or AAV6). Concentration of each reagent is at about 1000 (ng/µL.).

The following protocols are for delivering CYP4V2 mutation CRISPR gene repair constructs to the patient iPSCs via electroporation and nucleofection. Other methods, including without limitation, lipofection, viral vector transduction (e.g., lentivirus or AAV vectors (e.g., use AAV6 to deliver the donor template), or microjection can also be used. P1 iPSCs of passages 11 to 14 are used.

Protocol No. 1 (Electroporation using plasmids):
1. Following Neon® transfection system (Life Technologies) instructions, use mixture containing 2.5 µg (2.5 µl of stock) pX459.gRNA (Item #1, or 2 or 3. Do not combine gRNAs) and 2.5 µg (2.5 µl of stock) ssODN (Either item #7 or 8) for about 1 million cells.
2. Apply electroporation (EP) conditions: a) 1100V, 30 ms, 1 pulse; or b) 1200V, 30 ms, 1 pulse.
3. After EP, evenly split cells into 3 wells of a 6-well plate with Rock inhibitor (10 µM).
4. Two days after plating, add puromycin as indicated in Table 9.
5. Two days after adding Puromycin, replace the spent media with fresh puromycin-free media.
6. Maintain the cultures for 2 weeks before picking colonies.

TABLE 9

Conditions and puromycin
concentration level
for diseased iPSCs

| | Puromycin concentration (µg/ml) | | |
|---|---|---|---|
| 1100 V 30 ms 1 p | 0.1 | 0.15 | 0.2 |

TABLE 9-continued

Conditions and puromycin
concentration level
for diseased iPSCs

| | Puromycin concentration (µg/ml) | | |
|---|---|---|---|
| 1200 V 30 ms 1 p | 0.1 | 0.15 | 0.2 |

Protocol No. 2 (Electroporation using RNP):
1. Use ice bucket. Thaw one sgRNA (Itesm #4, or 5, or 6; do not combine gRNAs), one ssODN donor template (either item #7 or 8) and SpCas9 protein (Item #9), as well as the Cas9-Puro expression vector onice. The Cas9-Puro expression vector is used as a selection marker. It is a pX459-hSpCas9-2A-Puro plasmid and has a structure shown in FIG. 15 except that it did not clone in a gRNA.
2. Label 1.7 ml Eppendorf tubes and 6-well-plates clearly. For each sample, prepare one Eppendorf tube and 1 well. Add 3 ml culture medium (TeSR-E8 from StemCell Technologies (Cat #05940)) into each well.
3. Prepare one 10 cm dish with 25 ml PBS to wash Neon® tip.
4. Prepare 6-well-plate for plating the electroporated cells. Add 3 ml of culture medium into each well.
5. In each Eppendorf tube, add 4 µg (4 µl of stock) sgRNA (Item 4, 5 or 6. Do not combine sgRNAs) and 10 µg (10 µl of stock) SpCas9 protein (Item #9), leave the tube at room temperature for at least 10 min.
6. Add 5 µg (5 µl of stock) ssODN (either item #7 or 8) and 2.5 µg (2.5 µl of stock)
Cas9-Puro expression vector in each tube.
7. Resuspend the cells in appropriate Neon® EP buffer R to final density $1 \times 10^7$ cells/ml.
8. Aliquot 105 µL cell suspension and add into each Eppendorf tube with CRISPR RNP mixture.
9. Add 3 ml Buffer E2 to Neon® pipette and sit the Neon® pipette on Neon® pipette station.
10. Use 100 µL Neon® tip. Aspirate 100 µL EP mixture from each Eppendorf tube and insertinto the Neon® pipette.
11. Apply one of the EP conditions in Table 9 above and follow steps 3 to 6 of Protocol No. 1 above.

Note: If iPSCs do not grow well, condition media is recommended. Collect spent medium (without Puromycin) and filter it to get rid of cell debris. Mix at 1:1 ratio of spent medium and fresh medium. The use of Matrigel (Corning Cat #354277) and the media TeSR-E8 from StemCell Technologies (Cat #05940) is recommended for culturing human iPSCs in feeder free conditions throughout the gene editing process. The addition of Rock Inhibitor (final concentration 10 µM) to the media for 48 hours when plating the cells after EP will help preserve cell viability.

Protocol No. 3 (Nucleofection using RNP):
1. Lonza 4D-nucleofector, parameter set up: Lonza program, DS-150
2. Prepare RNP (cas9+gRNA) and ssODN separately (bring the volume to a maximum of 10 µL), mix it before use. See Table 10.
(1) gRNA1+CYP4V2 Forward ssODN (2) gRNA2+ CYP4V2 Forward ssODN

155

(3) gRNA1+CYP4V2 Reverse ssODN (4) gRNA2+ CYP4V2 Reverse ssODN

TABLE 10

| Each group reaction | gRNA 30 µM (µL) | Cas9 20 µM (µL) | ssODN 30 µM (µL) | PBS (µL) |
|---|---|---|---|---|
| P1 iPS cells | 4 | 1 | 4 | 1 |
| kit buffer/ each group | Volume (µL)/sample | | 4 sample (µL) 10 | |
| Solution | 16.4 | | 65.6 | |
| Supplement | 3.6 | | 14.4 | |

3. Harvest and count cells: 5*105 iPS cells
4. Suspend cell with RNP+ssODN (10 µL) by gently pipetting up and down 3-5 times
5. Add Lonza kit buffer 20 µL into cell suspension, minimize the incubation time before nucleofection.
6. Load the mixture (30 µL) into the Lonza kit well. Check impedance.
7. Electroporate the cells using the setting parameter (DS150).
8. Gently resuspend the electroporated cells by adding 70 µL of mTeSR (w/Rock inhibitor) directly into the kit well.
9. Plate cells in passage medium at one well of 6 well plate.
10. Observe cell viability 24 hours after electroporation and replace the medium with culture medium.

Note: No selection marker is used for this protocol. Cells survived nucleofection are picked for single cell expansion. In addition to Lonza DS-150 program, other parameters such as CB-150 can also be used.

Example 22-Generating Genetically-repaired Patient Cell Line and Use of RNP in Generating Genetically-repaired Patient Cell Line and in Ocular Cell Therapy Each of expression plasmid construct containing CRISPR g1 or g2 (Item #1 or 2) and CRISPR RNP construct containing sgRNA1 or sgRNA2 (Item #4 or 5, Synthego, Silicon Valley, CA, USA) and SpCas9 (Item #9, Catalog #: A034a-a-1000 from Feldan (Quebec, Canada), or from Synthego (e.g., Cas9 nuclease 2NLS, S. pyogenes), alongside a CYP4V2 donor template (Item #7 or #8, ssODN, Ultramer DNA Oligonucleotides, Integrated DNA Technologies (IDT), Coralville, Iowa, USA), is used to transfect patient iPSCs harboring the c.802-8_810del17insGC mutation.

Assessing Gene Correction by Homology-directed Repair (HDR):

After transfection, picked cells are collected for PCR followed by targeted amplicon sequencing to assess for gene correction in the CYP4V2 region containing the c.802-8_810del17insGC mutation. Deep sequencing of transfected cells shows that the reads contained precise correction of the mutation, with insertion of the 17 bp "TCATACAGGTCATCGCT" and deletion of "GC", resulting in correcting the mutation to the wild-type sequence (SEQ ID NO: 47). Correction of mutation is not seen in any untransfected control iPSCs. The results also serve as an indication of HDR frequency among transfected cells.

Obtaining iPS Clones with Minimal or No Off-Target Editing:

156

After assessing HDR, the transfection is performed again in patient iPSCs harboring the c.802-8_810del17insGC mutation. Transfected cells go through single-cell cloning and expansion. Clonal cell lines with confirmed on-target HDR are then assessed for off-target editing through sequencing. For clinical application, whole-genome sequencing (60× coverage) is used to compare the edited and untransfected cell lines of the same patient. An edited clonal iPS cell line with no off-target editing or minimal off-target editing with no known material adverse consequence in the genome is selected.

Differentiate of Genetically Corrected iPS into the Desired Type of Cells

The selected iPS clonal cell line is then differentiated into iPS-RPE cells (See the Examples herein). The selected iPS clonal cell line can be differentiated into other types of cells that are desired for use in cell therapy (e.g., iPS-RPE cells, iPS-PRCs, iPS-CE cells, iPS-CECs or other iPS-ocular cells).

Bio-Assay to Confirm Genetically-Repaired iPS or iPS-Derived Cells No Longer have Phenotype The genetically-corrected (or genetically-repaired) iPS-RPE cells are tested for biochemical function (See the Examples herein) and confirmed that they no longer have phenotype as seen in untreated patient iPS-RPE cells. CYP4V2 expression is detected in genetically repaired patient iPS-RPE cells.

Unlike a plasmid or other vector constructs (e.g., AAV, lentivirus) which results in sustained expression of CRISPR components it encodes (e.g., gRNA, the Cas nuclease, and/or the donor template), a CRISPR RNP construct is fast on and fast off. Components of a RNP construct are degraded relatively quickly in the transfected cells. Therefore, the use of RNP constructs lowers the risk of off-target editing as compared to plasmid and other constructs. This makes RNP construct particularly suitable for clinical application, such as in generating genticcally-reparied patient cells suitable for transplantation, as well as for in vivo treatment (e.g., injecting the RNP constructs to a subject's eye for in vivo gene correction). In addition to treating BCD, the CRISPR RNP constructs and methods provided herein can be use in treating other diseases, including diseases associated with a mutated or defective gene set forth in Table 4.

Example 23: Use of Genetically Repaired Cells in Ocular Cell Therapy

The genetically-repaired iPS-RPE cells, iPS-PRCs, iPS-CECs, iPS-CE cells or other iPS-ocular cells can be transplanted to the patient's eye as an ocular cell therapy. For example, they can be used as autologous replacement cells for dead or degenerated RPE cells, photoreceptors or other ocular cells in a BCD patient. The genetically repaired cells can be transplanted either directly (e.g., cell suspension) or in other forms, including without limitation, as part of a layer, a sheet, a matrix, a scaffold or a tissue. The amount of genetically repaired cells used in a transplanted depends on the cell type targeted for replacement, the size of the area needing replacement cells, and the subject being treated (e.g., the age, sex, weight, development stage of the disease and condition of the subject to be treated); the route of administration; the location of the transplantation (e.g., retina vs. cornea); the form of the transplantation (e.g., cell suspension vs. as part of a layer, a sheet, a matrix, a scaffold or a tissue); and the required regimen. The amount of cells in a single transplantation to one eye of a given cell type (e.g, RPE cells, photoreceptors, CECs, or CE cells) can range from about 1,000 cells to 10 million cells.

If required, cells can be manufactured in a GMP facility for clinical use. GMP facilities for cell therapy products are commercially available via research institutes, contract manufacturing organizations (CMOs) and contract research organizations (CROs), e.g., Cellular Therapy Integrated Services at Case Western Reserve University, Center for Cell and Gene Therapy at Baylor College of Medicine, CELLforCURE, New York Stem Cell Foundation and Lonza.

Patient-specific autologous administration can use the same administration/delivery methods as used in allogenic ocular cell therapy (e.g., embryonic stem cell derived RPE (ES-RPE) transplant) for retinal degeneration diseases, including those affected by RPE degeneration, such as age-related macular degeneration (AMD). Such administration/surgical methods are known in the art.

Example 24-Gene Therapy and Cell Therapy Combination Treatment for Ocular Diseases The disclosures herein described compositions and methods for use in gene therapy and cell therapy for BCD. For ocular diseases, gene therapy and cell therapy each has its own pros and cons. On the one hand, gene therapy works better in early- to mid-disease stage when the patient still has plenty of retinal (or ocular) cells remaining to receive and get rescued by the gene therapy treatment. However, gene therapy does not work well or may not work at all for late-stage patients who have no the relevant ocular cells left (e.g., RPE or PRC). Cell therapy, on the other hand, provides replacement cells to replace the dead or degenerated cells in the patient's eye and has its advantages over gene therapy particularly for late-stage patients and dominantly inherited diseases. However, cell therapy cannot rescue the remaining "original" cells in the patient's eye, whose survival not only preserves the patient's remaining vision, but also benefits the integration of the replacement cells.

To overcome the limitations of gene therapy and cell therapy and bring maximum benefits to patients, a gene therapy and cell therapy combination treatment method was developed for BCD, which can also be used for other ocular diseases. Such method comprising:
(a) apply gene therapy (e.g., AAV.CYP4V2 gene therapy or CRISPR gene correcction therapy) in the patient's eye in vivo; and
(b) in vitro generation of genetically-repaired patient-specific autologous iPS-ocular cells (e.g., iPS-RPE cells, iPS-PRCs, iPS-CE cells, iPS-CECs or other types of ocular cells which is affected by the disease) and transplant these cells into the patient's eye.
wherein (a) and (b) can be applied sequentially (first (a) then (b), or first (b) then (a)) or simultaneously (e.g., injecting gene therapy vectors and cells in one administration). Each of (a) or (b) can be applied one or more times to the same eye. Depending on the disease, disease-stage and patient's individual situation, (a) and (b) can target the same types or different types of ocular cells. For example, in the case of BCD, gene therapy vectors driven by a ubiquitous promoter can result in CYP4V2 expression in RPE cells, photoreceptors and other retinal cells, whereas cell therapy may focus on providing regenerated RPE cells and/or photoreceptors. In this case, cell therapy can benefit by providing new cells (e.g., RPE or photoreceptor cells), whereas gene therapy can improve the effect of cell therapy by rescuing the remaining RPE or photoreceptor cells and/or by improving the conditions of choroid cells whose healthy affects the conditions of ocular cells. The combination of the "rescue" and "replacement" effect of gene therapy and cell therapy, respectively, makes the combination treatment an improvement from either gene therapy or cell therapy. This combination treatment method can be applied to ocular and other diseases caused by one or more genetic mutations, including without limitation, diseases associated with a mutated or defective gene set forth in Table 4.

SEQUENCES

LIST OF SEQUENCES

All reference numbers used in the sequences are NCBI reference numbers unless otherwise annotated.
Part I: Gene Therapy Sequences
A. cDNA and functional CYP4V2 protein sequences
SEQ ID NO:1—a cDNA sequence (1578 bp) encoding the human CYP4V2protein (SEQ ID NO: 4), referred to as CYP4V2st herein.
SEQ ID NO:2—a codon-optimized cDNA sequence (1578 bp) encoding the human CYP4V2 protein (SEQ ID NO: 4), referred to as CYP4V2op herein.
SEQ ID NO:3—a cDNA sequence (1578 bp) encoding a functional CYP4V2 protein (SEQ ID NO: 5), referred to as CYP4V2fv herein. SEQ ID NO: 4—amino acid sequence (525 aa) of the human CYP4V2protein (NP 997235.3)
SEQ ID NO: 5—amino acid sequence (525 aa) of a functional variant of the human CYP4V2 protein SEQ ID NO: 6—fragment of human CYP4V2 protein without transmembrane domain (490 aa)
SEQ ID NO: 7—amino acid sequence of human CYP46A1
SEQ ID NO: 8—amino acid sequence of human CYP4A11
SEQ ID NO: 9—amino acid sequence of human CYP4A22
SEQ ID NO: 10—amino acid sequence of human CYP4B1
SEQ ID NO: 11—amino acid sequence of human CYP4F2
SEQ ID NO: 12—amino acid sequence of human CYP4F3
SEQ ID NO: 13—amino acid sequence of human CYP4F8
SEQ ID NO: 14—amino acid sequence of human CYP4F11
SEQ ID NO: 15—amino acid sequence of human CYP4F12
SEQ ID NO: 16—amino acid sequence of human CYP4F22
SEQ ID NO: 17—amino acid sequence of human CYP4X1
SEQ ID NO: 18—amino acid sequence f human CYP4Z1
SEQ ID NO: 19—amino acid sequence of CYP4V2 chimpanzee
SEQ ID NO: 20—amino acid sequence of CYP4V2 Rhesus Monkey
SEQ ID NO: 21—amino acid sequence of CYP4V2 dog
SEQ ID NO: 22—amino acid sequence of CYP4V2 cattle
SEQ ID NO: 23—amino acid sequence of CYP4V2 house mouse
SEQ ID NO: 24—amino acid sequence of CYP4V2 Norway rat SEQ ID NO: 25—amino acid sequence of CYP4V2 chicken SEQ ID NO: 26—amino acid sequence of CYP4V2 tropical clawed frog SEQ ID NO: 27—amino acid sequence of CYP4V2 horse SEQ ID NO: 28—amino acid sequence of CYP4V2 rabbit SEQ ID NO: 29—amino acid sequence of CYP4V2 fruit fly SEQ ID NO: 30—P450 signature element sequence SEQ ID NO: 31—P450 signature element sequence B. Exemplary regulatory sequences and ITR sequences SEQ ID NO: 32—CAG promoter sequence SEQ ID NO: 33—WPRE enhance sequence SEQ ID NO: 34—bGH PolyA sequence SEQ ID NO: 35—EFS promoter sequence SEQ ID NO: 36—small polyA (SPA) sequence SEQ ID NO: 37—Kozak sequence SEQ ID NO: 38—Kozak sequence SEQ ID NO: 39—SV40 late PolyA sequence SEQ ID NO: 40—CMV promoter sequence SEQ ID NO: 41—EF-1 alpha promoter sequence SEQ ID NO: 42—AAV5' Left-ITR sequence SEQ ID NO: 43—AAV3' Right-ITR sequence SEQ ID NO: 44—mutant AAV5' ITR sequence used in scAAV SEQ ID NO: 45—AAV3' ITR sequence used in scAAV Part II. Cell Therapy Sequences SEQ ID NO:46—region of human CYP4V2 gene containing c.802- 8 810del17insGC mutation SEQ ID NO: 47—region of wild-type human CYP4V2 gene without the c.802-8 810del17insGC mutation SEQ ID NO: 48—gRNA 1

SEQ ID NO: 49—gRNA 2

SEQ ID NO: 50—gRNA 3

SEQ ID NO: 51—gRNA 4

SEQ ID NO: 52—gRNA 5

SEQ ID NO: 53—crRNA exemplary sequence

SEQ ID NO: 54—tracrRNA exemplary sequence

SEQ ID NO: 55—sgRNA exemplary sequence

SEQ ID NO: 56—donor template 1 sequence

SEQ ID NO: 57—donor template 2 sequence

SEQ ID NO: 58—SpCas9 amino acid sequence

SEQ ID NO: 59—additional nucleotide inserted immediately after the U6 promoter sequence and before the protospacer element sequence in a plasmid construct and in an IVT sgRNA Part III: CYP4V2 Expression Cassette Sequences (inclusive of AAV ITRs and junction/linker sequences).

SEQ ID NO: 60—Sequence of CYP4V2 expression cassette in AAV2.CYP4V2op, AAV2tri (Y-F). CYP4V2op, and AAV5. CYP4V2op.

SEQ ID NO: 61—Sequence of CYP4V2 expression cassette in AAV5.CYP4V2st. AAV5. CYP4V2st has the same promoter (CAG), enhancer (WPRE) and polyA (bGH-polyA) as AAV2. CYP4V2op, AAV2tri (Y-F). CYP4V2op and AAV5.CYP4V2op (SEQ ID NO: 60) but different CYP4V2 cDNA and junction/linker sequences.

SEQ ID NO: 62—Sequence of CYP4V2 expression cassette in AAV8.CYP4V2fv. AAV8. CYP4V2fv has the same promoter (CAG), enhancer (WPRE) and polyA (bGH-polyA) and junction/linker sequences as AAV5. CYP4V2st (SEQ ID NO: 61) and differs only in CYP4V2 cDNA sequence.

SEQ ID NO: 63—Sequence of CYP4V2 expression cassette in AAV5. CYP4V2op (new). AAV5. CYP4V2op (new) has the same promoter (CAG), enhancer (WPRE) and polyA (bGH-polyA) and the same junction/linker sequences as AAV5. CYP4V2st (SEQ ID NO: 61) and AAV8. CYP4V2fv (SEQ ID NO: 62) but different CYP4V2 cDNA sequences.

SEQ ID NO: 64-Sequence of CYP4V2 expression cassette in SCAAV1. CYP4V2op, scAAV5. CYP4V2op, and scAAV9. CYP4V2op. SEQUENCES

```
(CYP4V2st cDNA, 1578 bp)
                                                      SEQ ID NO: 1
ATGGCGGGGCTCTGGCTGGGGCTCGTGTGGCAGAAGCTGCTGCTGTGGGGCGCGGCGAGTGCCCTTTCCC
TGGCCGGCGCCAGTCTGGTCCTGAGCCTGCTGCAGAGGGTGGCGAGCTACGCGCGGAAATGGCAGCAGAT
GCGGCCCATCCCCACGGTGGCCCGCGCCTACCCACTGGTGGGCCACGCGCTGCTGATGAAGCCGGACGGG
CGAGAATTTTTTCAGCAGATCATTGAGTACACAGAGGAATACCGCCACATGCCGCTGCTGAAGCTCTGGG
TCGGGCCAGTGCCCATGGTGGCCCTTTATAATGCAGAAAATGTGGAGGTAATTTTAACTAGTTCAAAGCA
AATTGACAAATCCTCTATGTACAAGTTTTTAGAACCATGGCTTGGCCTAGGACTTCTTACAAGTACTGGA
AACAAATGGCGCTCCAGGAGAAAGATGTTAACACCCACTTTCCATTTTACCATTCTGGAAGATTTCTTAG
ATATCATGAATGAACAAGCAAATATATTGGTTAAGAAACTTGAAAAACACATTAACCAAGAAGCATTTAA
CTGCTTTTTTTACATCACTCTTTGTGCCTTAGATATCATCTGTGAAACAGCTATGGGGAAGAATATTGGT
GCTCAAAGTAATGATGATTCCGAGTATGTCCGTGCAGTTTATAGAAGTGAGATGATATTTCGAAGAA
TAAAGATGCCCTGGCTTTGGCTTGATCTCTGGTACCTTATGTTTAAAGAAGGATGGGAACACAAAAAGAG
CCTTCAGATCCTACATACTTTTACCAACAGTGTCATCGCTGAACGGGCAATGAAATGAACGCCAATGAA
GACTGTAGAGGTGATGGCAGGGGCTCTGCCCCCTCCAAAAATAAACGCAGGGCCTTTCTTGACTTGCTTT
TAAGTGTGACTGATGACGAAGGGAACAGGCTAAGTCATGAAGATATTCGAGAAGAAGTTGACACCTTCAT
GTTTGAGGGGCACGATACAACTGCAGCTGCAATAAACTGGTCCTTATACCTGTTGGGTTCTAACCCAGAA
GTCCAGAAAAAAGTGGATCATGAATTGGATGACGTGTTTGGGAAGTCTGACCGTCCCGCTACAGTAGAAG
ACCTGAAGAAACTTCGGTATCTGGAATGTGTTATTAAGGAGACCCTTCGCCTTTTTCCTTCTGTTCCTTT
ATTTGCCCGTAGTGTTAGTGAAGATTGTGAAGTGGCAGGTTACAGAGTTCTAAAAGGCACTGAAGCCGTC
ATCATTCCCTATGCATTGCACAGAGATCCGAGATACTTCCCCAACCCCGAGGAGTTCAGCCTGAGCGGT
TCTTCCCCGAGAATGCACAAGGGCGCCATCCATATGCCTACGTGCCCTTCTCTGCTGGCCCCAGGAACTG
TATAGGTCAAAAGTTTGCTGTGATGGAAGAAAAGACCATTCTTTCGTGCATCCTGAGGCACTTTTGGATA
GAATCCAACCAGAAAAGAGAAGAGCTTGGTCTAGAAGGACAGTTGATTCTTCGTCCAAGTAATGGCATCT
GGATCAAGTTGAAGAGGAGAAATGCAGATGAACGCTAA (CYP4V2op cDNA, 1578 bp)
                                                      SEQ ID NO: 2
ATGGCTGGACTGTGGCTGGGACTGGTGTGGCAGAAACTGCTGCTGTGGGGGGCCGCTTCCGCACTGTCAC
TGGCTGGGGCTTCACTGGTGCTGAGCCTGCTGCAGAGGGTGGCCTCCTACGCCAGAAAGTGGCAGCAGAT
GAGGCCCATCCCTACCGTGGCCAGAGCCTATCCACTGGTGGGACACGCACTGCTGATGAAGCCTGACGGC
AGAGAGTTCTTTCAGCAGATCATCGAGTACACAGAGGAGTATAGGCACATGCCACTGCTGAAGCTGTGGG
TGGGACCCGTGCCTATGGTGGCCCTGTACAACGCCGAGAATGTGGAAGTGATCCTGACCAGCAGCAAGCA
GATCGATAAGTCTAGCATGTATAAGTTCCTGGAGCCTTGGCTGGGCCTGGGCCTGCTGACCTCTACAGGC
AACAAGTGGAGGAGCCGGAGAAAGATGCTGACCCCAACATTCCACTTTACAATCCTGGAGGACTTCCTGG
```

-continued

```
ACATCATGAACGAGCAGGCCAATATCCTGGTGAAGAAGCTGGAGAAGCACATCAACCAGGAGGCCTTTAA
TTGCTTCTTTTACATCACCCTGTGCGCCCTGGACATCATCTGTGAGACAGCTATGGGCAAGAACATCGGC
GCCCAGTCTAATGACGATAGCGAGTACGTGCGGGCCGTGTATAGAATGAGCGAGATGATCTTTAGGCGCA
TCAAGATGCCCTGGCTGTGGCTGGATCTGTGGTATCTGATGTTCAAGGAGGGCTGGGAGCACAAGAAGTC
CCTGCAGATCCTGCACACCTTTACAAACTCTGTGATCGCCGAGAGAGCCAATGAGATGAACGCCAATGAG
GACTGTAGGGGCGATGGAAGGGGCAGCGCCCCTTCCAAGAACAAGCGGAGAGCCTTCCTGGACCTGCTGC
TGAGCGTGACCGACGATGAGGGCAATCGCCTGTCCCACGAGGACATCCGGGAGGAGGTGGATACATTCAT
GTTTGAGGGACACGACACCACAGCCGCCGCCATCAACTGGTCCCTGTACCTGCTGGGCTCTAATCCAGAG
GTGCAGAAGAAGGTGGATCACGAGCTGGACGACGTGTTCGGCAAGTCCGACAGGCCAGCAACCGTGGAGG
ATCTGAAGAAGCTGAGATACCTGGAGTGCGTGATCAAGGAGACACTGCGCCTGTTCCCCTCTGTGCCTCT
GTTTGCCCGGTCCGTGTCTGAGGACTGTGAGGTGGCCGGCTATCGCGTGCTGAAGGGCACCGAGGCCGTG
ATCATCCCTTACGCCCTGCACCGGGACCCCAGGTATTTCCCTAACCCAGAGGAGTTTCAGCCAGAGAGAT
TCTTTCCCGAGAATGCCCAGGGCAGGCACCCTTACGCCTATGTGCCATTCTCCGCCGGACCAAGGAACTG
CATCGGACAGAAGTTTGCCGTGATGGAGGAGAAAACCATCCTGTCTTGTATCCTGAGACACTTCTGGATC
GAGAGCAATCAGAAGAGGGAGGAGCTGGGCCTGGAGGGACAGCTGATCCTGCGGCCAAGCAACGGCATCT
GGATCAAACTGAAAAGAAGGAACGCTGACGAGAGGTAA (CYP4V2fv cDNA, 1578 bp)
                                                           SEQ ID NO: 3
ATGGCGGGGCTCTGGCTGGGGCTCGTGTGGCAGAAGCTGCTGCTGTGGGGCGCGGCGAGTGCCCTTTCCC
TGGCCGGCGCCAGTCTGGTCCTGAGCCTGCTGCAGAGGGTGGCGAGCTACGCGCGGAAATGGCAGCAGAT
GCGGCCCATCCCCACGGTGGCCGCGCCTACCCACTGGTGGGCCACGCCTGCTGATGAAGCCGGACGGGG
CGAGAATTTTTTCAGCAGATCATTGAGTACACAGAGGAATACCGCCACATGCCGCTGCTGAAGCTCTGGG
TCGGGCCAGTGCCCATGGTGGCCCTTTATAATGCAGAAATGTGGAGGTAATTTTAACTAGTTCAAAGCA
AATTGACAAATCCTCTATGTACAAGTTTTTAGAACCATGGCTTGGCCTAGGACTTCTTACAAGTACTGGA
AACAAATGGCGCTCCAGGAGAAAGATGTTAACACCCACTTTCCATTTTACCATTCTGGAAGATTTCTTAG
ATATCATGAATGAACAAGCAAATATATTGGTTAAGAAACTTGAAAAACACATTAACCAAGAAGCATTTAA
CTGCTTTTTTTACATCACTCTTTGTGCCTTAGATATCATCTGTGAAACAGCTATGGGGAAGAATATTGGT
GCTCAAAGTAATGATGATTCCGAGTATGTCCGTGCAGTTTATAGAATGAGTGAGATGATATTTCGAAGAA
TAAAGATGCCCTGGCTTTGGCTTGATCTCTGGTACCTTATGTTTAAAGAAGGATGGGAACACAAAAAGAG
CCTTAAGATCCTACATACTTTTACCAACAGTGTCATCGCGGAACGGGCCAATGAAATGAACGCCAATGAA
GACTGTAGAGGTGATGGCAGGGGTCTGCCCCCTCCAAAAATAAACGCAGGGCCTTTCTTGACTTGCTTT
TAAGTGTGACTGATGACGAAGGGAACAGGCTAAGTCATGAAGATATTCGAGAAGAAGTTGACACCTTCAT
GTTTGAGGGGCACGATACAACTGCAGCTGCAATAAACTGGTCCTTATACCTGTTGGGTTCTAACCCAGAA
GTCCAGAAAAAAGTGGATCATGAATTGGATGACGTGTTTGGGAAGTCTGACCGTCCCGCTACAGTAGAAG
ACCTGAAGAAACTTCGGTATCTGGAATGTGTTATTAAGGAGACCCTTCGCCTTTTTCCTTCTGTTCCTTT
ATTTGCCCGTAGTGTTAGTGAAGATTGTGAAGTGGCAGGTTACAGAGTTCTAAAAGGCACTGAAGCCGTC
ATCATTCCCTATGCATTGCACAGAGATCCGAGATACTTCCCCAACCCCGAGGAGTTCCAGCCTGAGCGGT
TCTTCCCCGAGAATGCACAAGGGCGCCATCCATATGCCTACGTGCCTTCTCTGCTGGCCCCAGGAACTG
TATAGGTCAAAAGTTTGCTGTGATGGAAGAAAAGACCATTCTTTCGTGCATCCTGAGGCACTTTTGGATA
GAATCCAACCAGAAAGAGAAGAGCTTGGTCTAGAAGGACAGTTGATTCTTCGTCCAAGTAATGGCATCT
GGATCAAGTTGAAGAGGAGAAATGCAGATGAACGCTAA (human CYP4V2 protein, NP_997235.3, 525 aa)
                                                           SEQ ID NO: 4
MAGLWLGLVWQKLLLWGAASALSLAGASLVLSLLQRVASYARKWQQMRPIPTVARAYPLVGHALLMKPDG
REFFQQIIEYTEEYRHMPLLKLWVGPVPMVALYNAENVEVILTSSKQIDKSSMYKFLEPWLGLGLLTSTG
NKWRSRRKMLTPTFHFTILEDFLDIMNEQANILVKKLEKHINQEAFNCFFYITLCALDIICETAMGKNIG
AQSNDDSEYVRAVYRMSEMIFRRIKMPWLWLDLWYLMFKEGWEHKKSLQILHTFTNSVIAERANEMNANE
DCRGDGRGSAPSKNKRRAFLDLLLSVTDDEGNRLSHEDIREEVDTFMFEGHDTTAAAINWSLYLLGSNPE
VQKKVDHELDDVFGKSDRPATVEDLKKLRYLECVIKETLRLFPSVPLFARSVSEDCEVAGYRVLKGTEAV
IIPYALHRDPRYFPNPEEFQPERFFPENAQGRHPYAYVPFSAGPRNCIGOKFAVMEEKTILSCILRHFWI
ESNOKREELGLEGQLILRPSNGIWIKLKRRNADER (functional variant of human CYP4V2 protein; 525 aa)
                                                           SEQ ID NO: 5
MAGLWLGLVWQKLLLWGAASALSLAGASLVLSLLQRVASYARKWQQMRPIPTVARAYPLVGHALLMKPDG
REFFQQIIEYTEEYRHMPLLKLWVGPVPMVALYNAENVEVILTSSKQIDKSSMYKFLEPWLGLGLLTSTG
NKWRSRRKMLTPTFHFTILEDFLDIMNEQANILVKKLEKHINQEAFNCFFYITLCALDIICETAMGKNIG
AQSNDDSEYVRAVYRMSEMIFRRIKMPWLWLDLWYLMFKEGWEHKKSLKILHTFTNSVIAERANEMNANE
DCRGDGRGSAPSKNKRRAFLDLLLSVTDDEGNRLSHEDIREEVDTFMFEGHDTTAAAINWSLYLLGSNPE
VQKKVDHELDDVFGKSDRPATVEDLKKLRYLECVIKETLRLFPSVPLFARSVSEDCEVAGYRVLKGTEAV
IIPYALHRDPRYFPNPEEFQPERFFPENAQGRHPYAYVPFSAGPRNCIGOKFAVMEEKTILSCILRHFWI
ESNQKREELGLEGQLILRPSNGIWIKLKRRNADER (functional fragment of CYP4V2 (lacking transmembrane domain;
490 aa)
                                                           SEQ ID NO: 6
RVASYARKWQQMRPIPTVARAYPLVGHALLMKPDGREFFQQIIEYTEEYRHMPLLKLWVGPVPMVALYNA
ENVEVILTSSKQIDKSSMYKFLEPWLGLGLLTSTGNKWRSRRKMLTPTFHFTILEDFLDIMNEQANILVK
KLEKHINQEAFNCFFYITLCALDIICETAMGKNIGAQSNDDSEYVRAVYRMSEMIFRRIKMPWLWLDLWY
LMFKEGWEHKKSLQILHTFTNSVIAERANEMNANEDCRGDGRGSAPSKNKRRAFLDLLLSVTDDEGNRLS
HEDIREEVDTFMFEGHDTTAAAINWSLYLLGSNPEVQKKVDHELDDVFGKSDRPATVEDLKKLRYLECVI
KETLRLFPSVPLFARSVSEDCEVAGYRVLKGTEAVIIPYALHRDPRYFPNPEEFQPERFFPENAQGRHPY
AYVPFSAGPRNCIGOKFAVMEEKTILSCILRHFWIESNQKREELGLEGQLILRPSNGIWIKLKRRNADER (CYP46A1, NP_006659, 500 aa)
                                                           SEQ ID NO: 7
MSPGLLLLGSAVLLAFGLCCTFVHRARSRYEHIPGPPRPSFLLGHLPCFWKKDEVGGRVLQDVFLDWAKK
YGPVVRVNVFHKTSVIVTSPESVKKFLMSTKYNKDSKMYRALQTVFGERLFGQGLVSECNYERWHKORRV
IDLAFSRSSLVSLMETFNEKAEQLVEILEAKADGQTPVSMQDMLTYTAMDILAKAAFGMETSMLLGAQKP
```

-continued

```
LSQAVKLMLEGITASRNTLAKFLPGKRKQLREVRESIRFLRQVGRDWVQRRREALKRGEEVPADILTQIL
KAEEGAQDDEGLLDNFVTFFIAGHETSANHLAFTVMELSRQPEIVARLQAEVDEVIGSKRYLDFEDLGRL
QYLSQVLKESLRLYPPAWGTFRLLEEETLIDGVRVPGNTPLLFSTYVMGRMDTYFEDPLTFNPDRFGPGA
PKPRFTYFPFSLGHRSCIGQQFAQMEVKVVMAKLLORLEFRLVPGQRFGLQEQATLKPLDPVLCTLRPRG
WQPAPPPPPC
```

(CYP4A11, NP_000769, 519 aa)

SEQ ID NO: 8

```
msvsvlspsr  llgdvsgilq  aasllillll  likavqlylh  rqwllkalqq  fpcppshwlf
ghiqelqqdq  elqriqkwve  tfpsacphwl  wggkvrvqly  dpdymkvilg  rsdpkshgsy
rflapwigyg  lllngqtwf   qhrrmitpaf  hydilkpyvg  lmadsvrvml  dkweellgqd
splevfqhvs  lmtldtimkc  afshqgsiqv  drnsqsyiqa  isdlnnlvfs  rvrnafhqnd
tiysltsagr  wthracqlah  qhtdqviqlr  kaqlqkegel  ekikrkrhld  fldilllakm
engsilsdkd  lraevdtfmf  eghdttasgi  swilyalath  pkhqercree  ihsllgdgas
itwnhldqmp  yttmcikeal  rlyppvpgig  relstpvtfp  dgrslpkgim  vllsiyglhh
npkvwpnpev  fdpfrfapgs  aqhshaflpf  sggsrncigk  qfamnelkva  taltllrfel
lpdptripip  iarlvlkskn  gihlrlrrlp  npcedkdql
```

(CYP4A22, NP_001010969, 519 aa)

SEQ ID NO: 9

```
msvsvlspsr  rlggvsgilq  vtsllillll  likaaqlylh  rqwllkalqq  fpcppshwlf
ghiqefqhdq  elqrigervk  tfpsacpywi  wggkvrvqly  dpdymkvilg  rsdpkshgsy
kflaprigyg  lllingqtwf   qhrrmltpaf  hndilkpyvg  lmadsvrvml  dkweellgqd
splevfqhvs  lmtldtimks  afshqgsiqv  drnsqsyiqa  isdinslvfc  cmrnafhend
tiysltsagr  wthracqlah  qhtdqviqlr  kaqlqkegel  ekikrkrhld  fldilllakm
engsilsdkd  lraevdtfmf  eghdttasgi  swilyalath  pkhqercree  ihgllgdgas
itwnhldqmp  yttmcikeal  rlyppvpgig  relstpvtfp  dgrslpkgim  vllsiyglhh
npkvwpnlev  fdpsrfapgs  aqhshaflpf  sggsrncigk  qfamnqlkva  raltllrfel
lpdptripip  marlvlkskn  gihlrlrrlp  npcedkdql
```

(CYP4B1, NP_000770, 511 aa)

SEQ ID NO: 10

```
mvpsflslsf  sslglwasgl  ilvlgflkli  hlllrrqtla  kamdkfpgpp  thwlfghale
iqetgsldkv  vswahqfpya  hplwfgqfig  flniyepdya  kavysrgdpk  apdvydfflq
wigrgllvle  gpkwlqhrkl  ltpgfhydvl  kpyvavftes  trimldkwee  karegksfdi
fcdvghmaln  tlmkctfgrg  dtglghrdss  yylavsdltl  lmqqrlvsfq  yhndfiywlt
phgrrflrac  qvahdhtdqv  irerkaalqd  ekvrkkiqnr  rhldfldill  gardeddikl
sdadlraevd  tfmfeghdtt  tsgiswflyc  malypehqhr  creevreilg  dqdffqwddl
gkmtyltmci  kesfrlyppv  pqvyrqlskp  vtfvdgrslp  agslismhiy  alhrnsavwp
dpevfdslrf  stenaskrhp  fafmpfsagp  rncigqqfam  semkvvtamc  llrfefsldp
srlpikmpql  vlrskngfhl  hlkplgpgsg  k
```

(CYP4F2, NP_001073, 520 aa)

SEQ ID NO: 11

```
msqlslswlg  lwpvaaspwl  llllvgaswl  lahvlawtya  fydncrrlrc  fpqpprrnwf
wghqgmvnpt  eegmrvltql  vatypqgfkv  wmgpisplls  lchpdiirsv  inasaaiapk
dkffysflep  wlgdglllsa  gdkwsrhrrm  ltpafhfnil  kpymkifnes  vnimhakwql
lasegsacld  mfehislmtl  dslqkcvfsf  dshcqekpse  yiaailelsa  lvskrhheil
lhidflyylt  pdgqrfrrac  rlvhdftdav  iqerrrtips  qgvddflqak  aksktldfid
vlllskdedg  kklsdedira  eadtfmfegh  dttasglswv  lyhlakhpey  qercrqevqe
llkdrepkei  ewddlahlpf  ltmomkeslr  lhppvpvisr  hvtqdivlpd  grvipkgiic
lisvfgthhn  pavwpdpevy  dpfrfdpeni  kersplafip  fsagprncig  qtfamaemkv
vlaltllrfr  vlpdhteprr  kpelvlraeg  glwlrvepls
```

(CYP4F3, NP_000887, 520 aa)

SEQ ID NO: 12

```
mpqlslsslg  lwpmaaspwl  llllvgaswl  larilawtyt  fydnccrlrc  fpqppkrnwf
lghlglihss  eegllytqsl  actfgdmccw  wvgpwhaivr  ifhptyikpv  lfapaaivpk
dkvfysflkp  wlgdglllsa  gekwsrhrrm  ltpafhfnil  kpymkifnes  vnimhakwql
lasegsarld  mfehislmtl  dslqkcvfsf  dshcqekpse  yiaailelsa  lvtkrhqqil
lyidflyylt  pdgqrfrrac  rlvhdftdav  iqerrrtlps  qgvddflqak  aksktldfid
vlllskdedg  kklsdedira  eadtfmfegh  dttasglswv  lyhlakhpey  qercrqevqe
llkdrepkei  ewddlaqlpf  ltmcikeslr  lhppvpavsr  cctqdivlpd  grvipkgiic
lisvfgthhn  pavwpdpevy  dpfrfdpkni  kersplafip  fsagprncig  qafamaemkv
vlgltllrfr  vlpdhteprr  kpelvlraeg  glwlrvepls
```

(CYP4F8, NP_009184, 520 aa)

SEQ ID NO: 13

```
msllslswlg  lrpvaaspwl  lllvvgaswl  larilawtya  fyhngrrlrc  fpqprkqnwf
lghlglvtpt  eeglrvltql  vatypqgfvr  wlgpitpiin  lchpdivrsv  intsdaitdk
divfyktlkp  wlgdglllsv  gdkwrhhrrl  ltpafhfnil  kpyikifsks  animhakwqr
lamegstold  vfehislmtl  dslqkcifsf  dsncqekpse  yitaimelsa  lvvkrnnqff
rykdflyflt  pcgrrfhrac  rlvhdftdav  iqerrrtlts  qgvddflqak  aksktldfid
vlllsedkng  kelsdedira  eadtfmfggh  dttasglswv  lynlarhpey  qererqevqe
llkdrepkei  ewddlaqlpf  ltmclkeslr  lhppiptfar  gctqdvvlpd  srvipkgnvc
ninifaihhn  psvwpdpevy  dpfrfdpena  qkrspmafip  fsagprncig  qkfamaemkv
vlaltllrfr  ilpdhreprr  tpeivlraed  glwlrveplg
```

-continued

```
(CYP4F11, NP_067010, 524 aa)
                                              SEQ ID NO: 14 mpqlslswlg lgpvaaspwl llllvggswl larvlawtyt fydncrrlqc fpqppkqnwf
wghqglvtpt eegmktltql vttypqgfkl wlgptfplli lchpdiirpi tsasaavapk
dmifygflkp wlgdglllsg gdkwsrhrrm ltpafhfnil kpymkifnks vnimhdkwqr
lasegsarld mfehislmtl dslqkcvfsf esncqekpse yiaailelsa fvekrnqqil
lhtdflyylt pdgqrfrrac hlvhdftdav igerrctlpt qgiddflknk aksktldfid
vlllskdedg kelsdedira eadtfmfegh dttasglswv lyhlakhpey qeqcrqevqe
llkdrepiei ewddlaqlpf ltmcikeslr lhppvpvisr cctqdfvlpd grvipkgivc
liniigihyn ptvwpdpevy dpfrfdqeni kersplafip fsagprncig qafamaemkv
vlaltllhfr ilpthteprr kpelilraeg glwlrveplg ansq (CYP4F12, NP_076433, 524 aa)
                                              SEQ ID NO: 15 msllslpwlg lrpvatspwl llllvvgswl larilawtya fynncrrlqc fpqppkrnwf
wghlglitpt eeglknstqm satysqgftv wlgpiipfiv lchpdtirsi tnasaaiapk
dnlfirflkp wlgegillsg gdkwsrhrrm ltpafhfnil ksyitifnks animldkwqh
lasegssrld mfehislmtl dslqkcifsf dshcqerpse yiatilelsa lvekrsqhil
qhmdflyyls hdgrrfhrac rlvhdftdav irerrrtlpt qgiddffkdk aksktldfid
vlllskdedg kalsdedira eadtfmfggh dttasglswv lynlarhpey qererqevqe
llkdrdpkei ewddlaqlpf ltmcvkeslr lhppapfisr cctqdivlpd grvipkgitc
lidiigvhhn ptvwpdpevy dpfrfdpens kgrsplafip fsagprncig qafamaemkv
vlalmllhfr flpdhteprr klelimraeg glwlrvepln vslq (CYP4F22, NP_775754, 531 aa)
                                              SEQ ID NO: 16 mlpitdrllh llglektafr iyavstlllf llfflfrlll rflrlersfy itcrrlrcfp
qpprrnwllg hlgmylpnea glqdekkvld nmhhvllvwm gpvlpllvlv hpdyikpllg
asaaiapkdd lfygflkpwl gdglllskgd kwsrhrrllt pafhfdilkp ymkifnqsad
imhakwrhla egsavsldmf ehislmtlds lqkcvfsyns ncqekmsdyi saiielsals
vrrqyrlhhy ldfiyyrsad grrfrqacdm vhhftteviq errralrqqg aeawlkakqg
ktldfidvll lardedgkel sdediraead tfmfeghdtt ssgiswmlfn lakypeyqek
creeiqevmk greleelewd dltqlpfttm cikeslrqyp pvtlvsrqct ediklpdgri
ipkgiiclvs iygthhnptv wpdskvynpy rfdpdnpqqr splayvpfsa gprncigqsf
amaelrvvva ltllrfrlsv drtrkvrrkp elilrtengl wlkveplppr a (CYP4X1, NP_828847, 509 aa)
                                              SEQ ID NO: 17 mefswletrw arpfylafvf clalgllqai klylrrqrll rdlrpfpapp thwflghqkf
iqddnmekle eiiekypraf pfwigpfqaf fciydpdyak tllsrtdpks qylqkfsppl
lgkglaaldg pkwfqhrrll tpgfhfnilk ayievmahsv kmmldkweki cstqdtsvev
yehinsmsld iimkcafske tncqtnsthd pyakaifels kiifhrlysl lyhsdiifkl
spqgyrfqkl srvlnqytdt iigerkkslq agvkqdntpk rkyqdfldiv lsakdesgss
fsdidvhsev stfllaghdt laasiswily clalnpehqe rcreevrgil gdgssitwdq
lgemsyttmc iketcrlipa vpsisrdlsk pltfpdgctl pagitvvlsi wglhhnpavw
knpkvfdplr fsqensdqrh pyaylpfsag srncigqefa mielkvtial illhfrvtpd
ptrpltfpnh filkpkngmy lhlkklsec (CYP4Z1, NP_835235, 505 aa)
                                              SEQ ID NO: 18 mepswlqelm ahpflllill cmslllfqvi rlyqrrrwmi ralhlfpapp ahwfyghkef
ypvkefevyh klmekypcav plwvgpftmf fsvhdpdyak illkrqdpks avshkilesw
vgrglvtldg skwkkhrqiv kpgfnisilk ifitmmsesv rmmlnkweeh iaqnsrlelf
qhvslmtlds imkcafshqg siqldstlds ylkavfnlsk isnqrmnnfl hhndlvfkfs
sqgqifskfn qelhqftekv iqdrkeslkd klkqdttqkr rwdfldills aksentkdfs
eadlqaevkt fmfaghdtts saiswilycl akypehqqrc rdeirellgd gssitwehls
qmpyttmcik eclrlyapvv nisrlldkpi tfpdgrslpa gitvfiniwa lhhnpyfwed
pqvfnplrfs rensekihpy afipfsaglr ncigqhfaii eckvavaltl lrfklapdhs
rppqpvrqvv lskngihvf akkvc (cytochrome P450 4V2 isoform X1 [Pan troglodytes chimpanzee)],
XP_001165629.1, 525 aa)
                                              SEQ ID NO: 19 maglwlglvw qkllllwgaas avslagaslv lsllqrvaty arkwqqmrpi ptvaraypl v
ghallmkpdg reffqqiiey teeyrhmpll klwvgpvpmv alynaenvev iltsskqidk
ssmykflepw lglglltstg nkwrsrrkml tptfhftile dfldimneqa ntlvkklekh
inqeafncff yitlcaldii cetamgknig aqsnddseyv ravyrmsemi frrikmpwlw
ldlwylmfke gwehkkslki lhtftnsvia eranemnane dcrgdgrgsa psknkrrafl
dlllsvtdde gnrlshedir eevdtfmfeg hdttaaainw slyllgsnpe vqkkvdheld
dvfgksdrpa tvedlkklry lecviketlr lfpsvplfar svsedcevag yrvlkgteav
iipyalhrdp ryfpnpeefq perffpknaq grhpyayvpf sagprncigq kfavmeekti
lscilrhfwi esnqkreelg legglilrps ngiwiklkrr nader (cytochrome P450 4V2 [Macaca mulatta (Rhesus Macaque,
Rhesus Monkey)], NP_001180767.1, 525 aa)
                                              SEQ ID NO: 20 magiwlglvw qklll1wgaas avslagaslv lsllqrvasy vrkwqqmrpi ptvaraypl v
ghallmkrdg reffqqiiey teeyrhmpll klwvgpvpmv alynaenvev iltsskqidk
ssmykflepw lglglltstg nkwrsrrkml tptfhftile dfldimneqa nilvkklekh
vnqeafncfv yitlcaldii cetamgknig aqsnddseyv ravyrmsemi frrikmpwlw
```

```
                              -continued
ldlwylmfke gwehkkslki lhaftnnvia eranemnvde dcrgdgrdsa psknkrrafl
dlllsvtdde gnrlshedir eevdtfmfeg hdttaaamnw slyllgsnpe vqkkvdheld
dvfgrsdrpa tvedlkklry lecviketlr lfpsvplfar svsedcevag yrvlkgteav
iipyalhrdp ryfpnpeefr perffpenaq grhpyayvpf sagprncigq kfavmeekti
lscilrhfwi esnqkreelg legqlilrpt ngiwiklkrr nadep (cytochrome P450 4V2 [Canis lupus familiaris (dog)],
XP_013975571.1, 539 aa)
                                                           SEQ ID NO: 21 mlkvkwkenv fregdkdsnm ldavqlpsik vesalsdaea ggspggrrpv ltvergrlaq
gsmssllknp kdttrnslki kyflpeffqq vilyseesrh lpllklwlgp ipivaiysae
nveviltssr qidksyvykf lepwlglgll tstgnkwrsr rkmltptfhf tiledfldvm
nehanilvnk lekhvnqeaf ncffyitlca ldiicetamg knigaqnned seyvraiyrm
sdtihrrmkm pwlwldflfl mfkegrehkr nleilhnftn nviterasel krdeehgsad
kdcspsknkr rafldlllnv tddegnklrh edvreevdtf mfeghdttaa ainwslyllg
sypevqkqvd seledvfgks drpatledlk klkylecvik eslrlfpsvp lfarnlnedc
vvagykvvkg sqaiiipyal hrdpryfpnp eefqperffp enlqgrhpya yipfsagprn
cigqrfaime ektvlscvlr hfwvesnqkr eelglageli lrptngiwik lkrrnades (cytochrome P450 4V2 [Bos taurus (cattle)],
NP_001029545, 527 aa)
                                                           SEQ ID NO: 22 mlapwllsvg pklllwsglc avslagatlt lnllkmvasy arkwrqmrpv ptigdpyplv
ghalmmkpda rdffqqiidf teecrhlpll klwlgpvplv alynaetvev ilssskhiek
symykflepw lglglltstg nkwrsrrkml tptfhftile dfldvmnega nilvtklekh
vnqeafncff yvtlctldii cetamgknig aqrnddseyv ravyrmsdsi hqrmkmpwlw
ldlifymfkn grehrrslki vhdftnnvit eranemkrhe egtsndkekd fpprktkcra
fldlllnvtd dqgnklshed ireevdtfmf eghdttaaai nwslyllgwy pevqqrvdte
leevfgksdr pvtledlkkl kyldcvikes lrlfpsvpff arnltedcev aghkivqgcq
viivpyalhr dpkyfpdpee fkperffpen lkgrhtyayv pfsagprnci gqkfaimeek
tilscilrhf wvesnqkree lglagelilr psngiwiklk rrntdes (Cyp4v3, cytochrome P450 4V2 [Mus musculus (house
mouse)], NP_598730.1, 525 aa)
                                                           SEQ ID NO: 23 mlwlwlglsg qklllwgaas avslagatil isifpmlvsy arkwqqmrsi psvarayplv
ghalymkpnn aeffqqliyy teefrhlpii klwigpvplv alykaenvev iltsskqidk
sflykflqpw lglglltstg skwrtrrkml tptfhftile nfldvmnega nilvnklekh
vnqeafncff yitlcaldii cetamgknig aqsnndseyv rtvyrmsdmi yrrmkmpwlw
fdlwylvfke grdhkrglkc lhtftnnvia ervkerkaee dwtgagrgpi psknkrkafl
dlllsvtdee gnrlsqedir eevdtfmfeg hdttaaainw slyllgtnpe vqrkvdgeld
evfgrshrpv tledlkklky ldcviketlr vfpsvplfar slsedcevgg ykvtkgteai
iipyalhrdp ryfpdpeefr perffpensq grhpyayvpf sagprncigq kfavmeekti
lacilrqfwv esnqkreelg lagdlilrpn ngiwiklkrr heddp (Cyp4v3, cytochrome P450 4V2 [Rattus norvegicus (Norway
rat)], NP_001129072, 525 aa)
                                                           SEQ ID NO: 24 mlwlwlglsg qklllwgaas avsvagatvl lnilqmlvsy arkwqqmrpi psvarayplv
ghalfmkpnn teffqqiiqy teefrhlpii klwigpvplv alykaenvev iltsskqidk
sfmykflqpw lglglltstg skwrarrkml tpsfhftile dfldvmneqa nilvnklekh
vnqeafncff pitlcaldii cetamgknig aqsngdseyv rtvyrmsdmi yrrmkmpwfw
fdlwylmfke grdhkkglks lhtftnnvia ervnarkaeq dcigagrgpl psktkrkafl
dlllsvtdee gnklshedir eevdtfmfeg hdttaaainw slyllgsnpe vqrkvdkeld
dvfgrshrpv tledlkklky ldcviketlr vfpsvplfar slsedcevag ykiskgteav
iipyalhrdp ryfpdpeefq perffpensq grhpyayvpf sagprncigq kfavmeekti
lacilrefwi esnqkreelg lagdlilrpn ngiwiklkrr heddp (cytochrome P450 4V2 [Gallus gallus (chicken)],
NP_001001879, 530 aa)
                                                           SEQ ID NO: 25 mameitlgsm egtqllpwva gaitllltvv tvhflpslln ywwwwvmkp ipgirpcypf
vgnalllern gegffkqlqq yadefrkmpm fklwlgplpv tvlfhpdsve vilssskhik
ksflytflhp wlgtglltst gdkwrsrrkm itptfhfail ndflevmneq ggvlleklek
hvdkepfnif tditlcaldi icetamgknl gaqdnkdsey vravyrmsdl iqqrqkspwl
whdlmyllfk egrehernlk ilhgftdtvi aekvaelent kltkhdtdvn teeesgskkr
eafldmllna tddegkklsy kdireevdtf mfeghdttaa amnwvlyllg hhpeaqkkvh
qeldevfgnt erpvtvddlk klrylecvvk ealrlfpsvp mfarslqedc yisgyklpkg
tnvlvltyvl hrdpeifpep defrperffp enskgrhpya yvpfsagprn cigqrfaqme
ektllalilr rfwvdcsqkp eelglsgeli lrpnngiwvq lkrrpktvte (cytochrome P450 family 4 subfamily V member 2 [Xenopus
tropicalis (tropical clawed frog)], NP_001072667.1, 523 aa)
                                                           SEQ ID NO: 26 melggevhll vwvaaavvll tllalsilpa lqdyvrkrri lkpipgpgpn ypligdalfl
knnggdfflq iceytesyrl qpllkvwigt ipfivvyhad tvepvlsssk hmdkaflykf
lhpwlgkgll tstgekwrsr rkmitptfhf ailseflevm neqskilvek lqthvdgesf
dcfmdvtlca ldiisetamg rkiqaqsnrd seyvqaiykm sdiiqrrqkm pwlwldflya
hlrdgkehdk nlkilhsftd kaileraeel kkmgeqkkeh cdsdpesdkp kkrsafldml
lmatddagnk msymdireev dtfmfeghdt taaalnwslf llgshpeaqr qvhkeldevf
gksdrpvtmd dlkklrylea vikeslriyp svplfgrtvt edcsirgfhv pkgvnvviip
```

-continued

```
yalhrdpeyf pepeefrper ffpenasgrn pyayipfsag lrncigqrfa lmeekvvlss
ilrnywveas qkreelcllg elilrpqdgm wiklknreta pta
```

(cytochrome P450 4V2 [Equus caballus (horse)],
XP_014592182.1, 469 aa)

SEQ ID NO: 27

```
mfvliefkik yslsdffqql iyyteenrhl pllklwlgpv pvvifynaen veviltssrq
idksymykfl kpwlglgllt stgnkwrsrr kmltptfhft nledfldvmn eqanilvnkl
ekhvnqeafn cflyitlcal diicetamgk nigaqrnnds eyvravyrms dmihrrmkmp
wlwldifflm fkegrehrrl lkilhnftnn viverasemk kdeersrsdd ggsapsknkr
rafldllinv tddegnklsh edirqevdtf mfeghdttaa ainwslyllg cypevqkkvd
seleevigks drpatledlk klkylecvmk etlrlfpsvp lfarnlnedc evagykivkg
sqaiivsyal hrdsryfpnp eefkperffp ensqgrhpya yvpfsagprn cigqkfavme
ekiilscilr hfwvesnqkr eelglageli lrpsngiwik lkrrntees
```

(cytochrome P450 4V2 [Oryctolagus cuniculus (rabbit)],
XP_002709379.1, 524 aa)

SEQ ID NO: 28

```
mwlwlglvgq kllfwgaasa vslagaslfl nllqmvasya rkwqqmrpip tigrpyplvg
halymkpsgk effqqliqyt eeyrhlpllk lwlgplpiva lynaenvevi lnsskqinks
smyqflepwl glglltstgy kwrsrrkmlt ptfhftiled fldimneqan ilvhklekhv
dqeafncffy itlcaldiic etamgkniga qsnedseyvr avyrmsdvif rrmkmpwlwl
dlwylmfkeg wehkrclkil hrftnnviae rvsemktdee hrdadsncap stmkrkafld
llltvtdeeg nklshedire evdtfmfegh dttaaainws lyllgshpev qrkvddelde
vfgksdrpat sedlkklkyl ecviketlrl fpsvplfars lsddcevagf rvvkgtqavi
vpyalhrdpk yfpnpeefrp erffpenaqg rhpyayvpfs agprncigqk faimeektil
scilrklwve snqkmeelgl agelilrptn giwiklkrrn adka
```

(cytochrome P450-4c3 [Drosophila melanogaster (fruit fly)],
NP_524598, 535 aa)

SEQ ID: 29

```
msskvitslm aesillskvg qvisgyspit vfllgsilif lvvynkrrsr lvkyiekipg
paampflgna iemnvdhdel fnrvigmqkl wgtriginrv wqgtaprvll fepetvepil
nsqkfvnksh dydylhpwlg eglltstdrk whsrrkiltp afhfkilddf idvfneqsav
larklavevg seafnlfpyv tlctldivce tamgrriyaq snseseyvka vygigsivqs
rqakiwlqsd fifsltaeyk lhqsyintlh gfsnmvirer kaelailgen nnnnnnnapd
ayddvgkkkr lafldllida skegtvlsne direevdtfm feghdttsaa iswtlfllgc
hpeyqervve eldsifgddk etpatmknlm dmryleccik dslrlfpsvp mmarmvgedv
niggkivpag tqaiimtyal hrnprvfpkp eqfnpdnflp encagrhpfa yipfsagprn
cigqkfaile ekavistvlr kykieavdrr edltllgeli lrpkdglrvk itprd
```

SEQ ID NO: 30 (P450 signature element, "x" denotes any amino acid) FxxGxxxCxG

SEQ ID NO: 31 (P450 signature element, "x" denotes any amino acid) ExxR (CAG promoter, 1715 bp)

SEQ ID NO: 32

```
GACATTGATTATTGACTAGTTATTAATAGTAATCAATTACGGGGTCATTAGTTCATAGCCCATATATGGA
GTTCCGCGTTACATAACTTACGGTAAATGGCCCGCCTGGCTGACCGCCCAACGACCCCCGCCCATTGACG
TCAATAATGACGTATGTTCCCATAGTAACGCCAATAGGGACTTTCCATTGACGTCAATGGGTGGACTATT
TACGGTAAACTGCCCACTTGGCAGTACATCAAGTGTATCATATGCCAAGTACGCCCCCTATTGACGTCAA
TGACGGTAAATGGCCCGCCTGGCATTATGCCCAGTACATGACCTTATGGGACTTTCCTACTTGGCAGTAC
ATCTACGTATTAGTCATCGCTATTACCATGGGTCGAGGTGAGCCCCACGTTCTGCTTCACTCTCCCCATC
TCCCCCCCCTCCCCACCCCCAATTTTGTATTTATTTATTTTTTAATTATTTTTGTGCAGCGATGGGGGCGG
GGGGGGGGGGGCGCGCGCCAGGCGGGGCGGGGGGGGGCGAGGGGGGGGGCGGGGCGAGGCGGAGAGGTG
CGGCGGCAGCCAATCAGAGCGGCGCGCTCCGAAAGTTTCCTTTTATGGCGAGGCGGCGGCGGCGGCGGCC
CTATAAAAAGCGAAGCGCGCGGCGGGCGGGAGTCGCTGCGTTGCCTTCGCCCCGTGCCCCGCTCCGCGCC
GCCTCGCGCCGCCCGCCCGGCTCTGACTGACCGCGTTACTCCCACAGGTGAGCGGGCGGGACGGCCCTT
CTCCTCCGGGCTGTAATTAGCGCTTGGTTTAATGACGAGTCGTTTCTTTTCTGTGGCTGCGTGAAAGCCT
TAAAGGGCTCCGGGAGGGCCCTTTGTGCGGGGGGAGCGGCTCGGGGGGTGCGTGCGTGTGTGTGCGT
GGGGAGCGCCGCGTGCGGCCCGCGCTGCCCGGCGGCTGTGAGCGCTGCGGGCGCGGCGCGGGGCTTTGTG
CGCTCCGCGTGTGCGCGAGGGGAGCGCGGCCGGGGGCGGTGCCCCGCGGTGCGGGAGGCGTGCGAGGGGA
ACAAAGGCTGCGTGCGGGGTGTGTGCGTGGGGGGGTGAGCAGGGGGTGTGGGCGCGGCGGTCGGGCTGTA
ACCCCCCCCTGCACCCCCCTCCCCGAGTTGCTGAGCACGGCCCGGCTTCGGGTGCGGGGCTCCGTGCGGG
GCGTGGCGCGGGGCTCGCCGTGCCGGGCGGGGGGTGGCGGCAGGTGGGGGTGCCGGGCGGGGCGGGGCCG
CCTCGGGCCGGGGAGGGCTCGGGGGAGGGGCGCGGCGGCCCCGGAGCGCCGGCGGCTGTCGAGGCGCGGC
GAGCCGCAGCCATTGCCTTTTATGGTAATCGTGCGAGAGGGCGCAGGGACTTCCTTTGTCCCAAATCTGG
CGGAGCCGAAATCTGGGAGGCGCCGCCGCACCCCCTCTAGCGGGCGCGGGCGAAGCGGTGCGGCGCCGGC
AGGAAGGAAATGGGCGGGGAGGGCCTTCGTGCGTCGCCGCGCCGCCGTCCCCTTCTCCATCTCCAGCCTC
GGGGCTGCCGCAGGGGGACGGCTGCCTTCGGGGGGGACGGGGCAGGGCGGGGTTCGGCTTCTGGCGTGTG
ACCGGCGGCTCTAGAGCCTCTGCTAACCATGTTCATGCCTTCTTCTTTTTTCCTACAGCTCCTGGGCAACG
TGCTGGTTATTGTGCTGTCTCATCATTTTGGCAAA
```

(WPRE enhancer, 589 bp)

SEQ ID NO: 33

```
AATCAACCTCTGGATTACAAAATTTGTGAAAGATTGACTGGTATTCTTAACTATGTTGCTCCTTTTACGC
TATGTGGATACGCTGCTTTAATGCCTTTGTATCATGCTATTGCTTCCCGTATGGCTTTCATTTTCTCCTC
```

-continued

CTTGTATAAATCCTGGTTGCTGTCTCTTTATGAGGAGTTGTGGCCCGTTGTCAGGCAACGTGGCGTGGTG
TGCACTGTGTTTGCTGACGCAACCCCCACTGGTTGGGGCATTGCCACCACCTGTCAGCTCCTTTCCGGGA
CTTTCGCTTTCCCCCTCCCTATTGCCACGGCGGAACTCATCGCCGCCTGCCTTGCCCGCTGCTGGACAGG
GGCTCGGCTGTTGGGCACTGACAATTCCGTGGTGTTGTCGGGGAAATCATCGTCCTTTCCTTGGCTGCTC
GCCTGTGTTGCCACCTGGATTCTGCGCGGGACGTCCTTCTGCTACGTCCCTTCGGCCCTCAATCCAGCGG
ACCTTCCTTCCCGCGGCCTGCTGCCGGCTCTGCGGCCTCTTCCGCGTCTTCGCCTTCGCCCTCAGACGAG
TCGGATCTCCCTTTGGGCCGCCTCCCCGC (bGH polyA, 225 bp)

SEQ ID NO: 34

CTGTGCCTTCTAGTTGCCAGCCATCTGTTGTTTGCCCCTCCCCCGTGCCTTCCTTGACCCTGGAAGGTGC
CACTCCCACTGTCCTTTCCTAATAAAATGAGGAAATTGCATCGCATTGTCTGAGTAGGTGTCATTCTATT
CTGGGGGGTGGGGTGGGGCAGGACAGCAAGGGGGAGGATTGGGAAGACAATAGCAGGCATGCTGGGGATG
CGGTGGGCTCTATGG (EFS promoter, 235 bp)

SEQ ID NO: 35 g attggctccg gtgcccgtca gtgggcagag cgcacatcgc ccacagtccc cgagaagttg
gggggagggg tcggcaattg aaccggtgcc tagagaaggt ggcgcggggt aaactgggaa
agtgatgtcg tgtactggct ccgccttttt cccgagggtg ggggagaacc gtatataagt
gcagtagtcg ccgtgaacgt tcttttttcgc aacgggtttg ccgccagaac acag (SPA, 54 bp)

SEQ ID NO: 36

GATCCAATAAAAGATCTTTATTTTCATTAGATCTGTGTGTTGGTTTTTTGTGTG (Kozak sequence, 6 bp)

SEQ ID NO: 37

GCCACC (Kozak sequence, 5 bp)

SEQ ID NO: 38

CCACC (SV40 late PolyA, 120 bp)

SEQ ID NO: 39

TTGTTTATTGCAGCTTATAATGGTTACAAATAAAGCAATAGCATCACAAATTTCACAAATAAAGCATTTT
TTTCACTGCATTCTAGTTGTGGTTTGTCCAAACTCATCAATGTATCTTAT (CMV promoter, 576 bp)

SEQ ID NO: 40

TAGTAATCAATTACGGGGTCATTAGTTCATAGCCCATATATGGAGTTCCGCGTTACATAACTTACGGTAA
ATGGCCCGCCTGGCTGACCGCCCAACGACCCCCGCCCATTGACGTCAATAATGACGTATGTTCCCATAGT
AACGCCAATAGGGACTTTCCATTGACGTCAATGGGTGGAGTATTTACGGTAAACTGCCCACTTGGCAGTA
CATCAAGTGTATCATATGCCAAGTACGCCCCCTATTGACGTCAATGACGGTAAATGGCCCGCCTGGCATT
ATGCCCAGTACATGACCTTATGGGACTTTCCTACTTGGCAGTACATCTACGTATTAGTCATCGCTATTAC
CATGGTGATGCGGTTTTGGCAGTACATCAATGGGCGTGGATAGCGGTTTGACTCACGGGGATTTCCAAGT
CTCCACCCCATTGACGTCAATGGGAGTTTGTTTTGGCACCAAAATCAACGGGACTTTCCAAAATGTCGTA
ACAACTCCGCCCCATTGACGCAAATGGGCGGTAGGCGTGTACGGTGGGAGGTCTATATAAGCAGAGCTGG
TTTAGTGAACCGTCAG (EF-1 alpha promoter, 1184 bp)

SEQ ID NO: 41 cgtgaggctccggtgcccgtcagtgggcagagcgcacatcgcccacagtccccgagaagttggggggagg
ggtcggcaattgaaccggtgcctagagaaggtggcgcggggtaaactgggaaagtgatgtcgtgtactgg
ctccgccttttttcccgagggtggggagaaccgtatataagtgcagtagtcgccgtgaacgttcttttttc
gcaacgggtttgccgccagaacacaggtaagtgccgtgtgtggttcccgcgggcctggcctctttacggg
ttatggcccttgcgtgccttgaattacttccacctggctgcagtacgtgattcttgatcccgagcttcgg
gttggaagtgggtgggagagttcgaggccttgcgcttaaggagccccttcgcctcgtgcttgagttgagg
cctggcctgggcgctggggccgccgcgtgcgaatctggtggcaccttcgcgcctgtctcgctgctttcga
taagtctctagccatttaaaattttttgatgacctgctgcgacgctttttttctggcaagatagtcttgta
aatgcgggccaagatctgcacactggtatttcggtttttggggccgcgggcggcgacggggcccgtgcgt
cccagcgcacatgttcggcgaggcggggcctgcgagcgcggccaccgagaatcggacggggggtagtctca
agctggccggcctgctctggtgcctggcctcgcgccgccgtgtatcgccccgccctgctgcagggagctcaaaat
ggaggacgcggcgctcgggagagcgggcgggtgagtcacccacacaaaggaaaagggccttttccgtcctc
agccgtcgcttcatgtgactccacggagtaccgggcgccgtccaggcacctcgattagttctcgagctttt
tggagtacgtcgtctttaggttggggggaggggtttttatgcgatggagtttccccacactgagtgggtgg
agactgaagttaggccagcttggcacttgatgtaattctccttggaatttgccctttttgagtttggatc
ttggttcattctcaagcctcagacagtggttcaaagtttttttcttccatttcaggtgtcgtga (AAV2 5' Left-ITR, 141 bp)

SEQ ID NO: 42 cctgcaggca gctgcgcgct cgctcgctca ctgaggccgc ccgggcaaag cccgggcgtc
gggcgacctt tggtcgcccg gcctcagtga gcgagcgagc gcgcagagag ggagtggcca
actccatcac tagggggttcc t -continued (AAV2 3' Right-ITR, 141 bp)
                  SEQ ID NO: 43
ag gaacccctag tgatggagtt ggccactccc tctctgcgcg ctcgctcgct cactgaggcc
gggcgaccaa aggtcgcccg acgcccgggc tttgcccggg cggcctcagt gagcgagcga
gcgcgcagct gcctgcagg (mutant AAV2 5' ITR in scAAV construct, 117 bp)
                  SEQ ID NO: 44
cctgcaggca gctgcgcgct cgctcgctca ctgaggccgc ccgggcaaag cccgggcgtc
gggcgacctt tggtcgcccg gcctcagtga gcgagcgagc gcgcagagag ggagtgg (AAV2 3' ITR in scAAV construct, 141 bp)
                  SEQ ID NO: 45
aggaaccc ctagtgatgg agttggccac tccctctctg cgcgctcgct cgctcactga
ggccgggcga ccaaaggtcg cccgacgccc gggctttgcc cggcggcct cagtgagcga
gcgagcgcgc agctgcctgc agg (region of human CYP4V2 gene containing c.802-8_810del17insGC mutation)
                  SEQ ID NO: 46
CAAACAGAAGCATGTGATTATCATTCAAAGCGAACGGGCCAATGAAATGAACGCCAATGA (region of wild-type human CYP4V2 gene without the
c. 802-8 810del17insGC mutation)
                  SEQ ID NO: 47
CAAACAGAAGCATGTGATTATCATTCAAATCATACAGGTCATCGCTGAACGGGCCAATGAAATGAACGCC
AATGA (g1 protospacer element, RNA sequence, 20 nt)
                  SEQ ID NO: 48
UGAUUAUCAUUCAAAGCGAA (g2 protospacer element, RNA sequence, 20 nt)
                  SEQ ID NO: 49
GAUUAUCAUUCAAAGCGAAC (g3 protospacer element, RNA sequence, 20 nt)
                  SEQ ID NO: 50
GAUAAUCACAUGCUUCUGUU (g4 protospacer element, RNA sequence, 20 nt)
                  SEQ ID NO: 51
UUCAUUGGCGUUCAUUUCAU (g5 protospacer element, RNA sequence, 20 nt)
                  SEQ ID NO: 52
CACAUGCUUCUGUUUGGACU (crRNA exemplary sequence (excluding the 5' protospacer
element sequence, 16 nt)
                  SEQ ID NO: 53
GUUUUAGAGCUAUGCU (tracrRNA exemplary sequence, 67 nt)
                  SEQ ID NO: 54
AGCAUAGCAAGUUAAAAUAAGGCUAGUCCGUUAUCAACUUGAAAAAGUGGCACCGAGUCGGUGCUUU (sgRNA exemplary sequence, excluding 5' protospacer
element sequence and the optional "G" before the protospacer element.
Sequence shown in DNA format as in a plasmid construct. For sequence
in RNA format, use "U" to replace "T", 82 nt)
                  SEQ ID NO: 55
gttttagagctagaaatagcaagttaaaataaggctagtccgttatcaacttgaaaaagtggcaccgagt
cggtgctttttt (CYP4V2 donor template 1 sequence, 200 bases)
                  SEQ ID NO: 56
AGA AAA ATA AAT GAA AGA AAC TAG CAT ATT TTA TAA GAA AAT GTG TTA ACT
AGG GTG CAT CCA AGT CCA AAC AGA AGC ATG TGA TTA TCA TTC AAA TCA TAC
AGG TCA TCG CTG AAC GGG CCA ATG AAA TGA ACG CCA ATG AAG ACT GTA GAG
GTG ATG GCA GGG GCT CTG CCC CCT CCA AAA ATA AAC GCA GGG CCT TT (CYP4V2 donor template 2 sequence, the reverse
complement of CYP4V2 donor template 1 sequence, 200 bases)
                  SEQ ID NO: 57
AA AGG CCC TGC GTT TAT TTT TGG AGG GGG CAG AGC CCC TGC CAT CAC CTC TAC
AGT CTT CAT TGG CGT TCA TTT CAT TGG CCC GTT CAG CGA TGA CCT GTA TGA
TTT GAA TGA TAA TCA CAT GCT TCT GTT TGG ACT TGG ATG CAC CCT AGT TAA
CAC ATT TTC TTA TAA AAT ATG CTA GTT CTT TCA TTT ATT TTT TCT -continued (SpCas9 exemplary amino acid sequence (1368 aa) )

SEQ ID NO: 58

```
MDKKYSIGLDIGTNSVGWAVITDEYKVPSKKFKVLGNTDRHSIKKNLIGALLFDSGETAEATRLKRTARR
RYTRRKNRICYLQEIFSNEMAKVDDSFFHRLEESFLVEEDKKHERHPIFGNIVDEVAYHEKYPTIYHLRK
KLVDSTDKADLRLIYLALAHMIKFRGHFLIEGDLNPDNSDVDKLFIQLVQTYNQLFEENPINASGVDAKA
ILSARLSKSRRLENLIAQLPGEKKNGLFGNLIALSLGLTPNFKSNFDLAEDAKLQLSKDTYDDDLDNLLA
QIGDQYADLFLAAKNLSDAILLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLRKQRTFDNGSIPHQIHLGELH
AILRRQEDFYPFLKDNREKIEKILTFRIPYYVGPLARGNSRFAWMTRKSEETITPWNFEEVVDKGASAQS
FIERMTNFDKNLPNEKVLPKHSLLYEYFTVYNELTKVKYVTEGMRKPAFLSGEQKKAIVDLLFKTNRKVT
VKQLKEDYFKKIECFDSVEISGVEDRFNASLGTYHDLLKIIKDKDFLDNEENEDILEDIVLTLTLFEDRE
MIEERLKTYAHLFDDKVMKQLKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKVMGRHKPENIVIEMARENQTT
QKGQKNSRERMKRIEEGIKELGSQILKEHPVENTQLQNEKLYLYYLQNGRDMYVDQELDINRLSDYDVDH
IVPQSFLKDDSIDNKVLTRSDKNRGKSDNVPSEEVVKKMKNYWRQLLNAKLITQRKFDNLTKAERGGLSE
LDKAGFIKRQLVETRQITKHVAQILDSRMNTKYDENDKLIREVKVITLKSKLVSDFRKDFQFYKVREINN
YHHAHDAYLNAVVGTALIKKYPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEVQTGGFSKESILPKRNSDKLI
ARKKDWDPKKYGGFDSPTVAYSVLVVAKVEKGKSKKLKSVKELLGITIMERSSFEKNPIDFLEAKGYKEV
KKDLIIKLPKYSLFELENGRKRMLASAGELQKGNELALPSKYVNFLYLASHYEKLKGSPEDNEQKQLFVE
QHKHYLDEIIEQISEFSKRVILADANLDKVLSAYNKHRDKPIREQAENIIHLFTLTNLGAPAAFKYFDTT
IDRKRYTSTKEVLDATLIHQSITGLYETRIDLSQLGGD
```

SEQ ID NO: 59 (additional nucleotide inserted immediately after the U6 promoter sequence and before the protospacer element sequence in a plasmid construct and in an IVT sgRNA, 1 nt) G SEQ ID NO: 60—Sequence of CYP4V2 expression cassette in AAV2.CYP4V2op, AAV2tri (Y-F). CYP4V2op, and AAV5.CYP4V2op.:

Left-ITR: 1-141
CAG promoter: 237-1951
CYP4V2op cDNA: 2002-3579
WPRE enhancer: 3736-4324
bGH polyA: 4350-4574
Right-ITR 4659-4799

```
   1 CCTGCAGGCA GCTGCGCGCT CGCTCGCTCA CTGAGGCCGC CCGGGCAAAG
  51 CCCGGGCGTC GGGCGACCTT TGGTCGCCCG GCCTCAGTGA GCGAGCGAGC
 101 GCGCAGAGAG GGAGTGGCCA ACTCCATCAC TAGGGGTTCC TGCGGCCAAT
 151 TCAGTCGATA ACTATAACGG TCCTAAGGTA GCGATTTAAA TACGCGCTCT
 201 CTTAAGGTAG CCCCGGGACG CGTCAATTGA GATCTCGACA TTGATTATTG
 251 ACTAGTTATT AATAGTAATC AATTACGGGG TCATTAGTTC ATAGCCCATA
 301 TATGGAGTTC CGCGTTACAT AACTTACGGT AAATGGCCCG CCTGGCTGAC
 351 CGCCCAACGA CCCCCGCCCA TTGACGTCAA TAATGACGTA TGTTCCCATA
 401 GTAACGCCAA TAGGGACTTT CCATTGACGT CAATGGGTGG ACTATTTACG
 451 GTAAACTGCC CACTTGGCAG TACATCAAGT GTATCATATG CCAAGTACGC
 501 CCCCTATTGA CGTCAATGAC GGTAAATGGC CCGCCTGGCA TTATGCCCAG
 551 TACATGACCT TATGGGACTT TCCTACTTGG CAGTACATCT ACGTATTAGT
 601 CATCGCTATT ACCATGGGTC GAGGTGAGCC CCACGTTCTG CTTCACTCTC
 651 CCCATCTCCC CCCCCTCCCC ACCCCCAATT TTGTATTTAT TTATTTTTTA
 701 ATTATTTTGT GCAGCGATGG GGGCGGGGGG GGGGGGGGGC CGCGCCAGGC
 751 GGGGCGGGGC GGGGCGAGGG GCGGGGGGGG GCGAGGCGGA GAGGTGCGGC
 801 GGCAGCCAAT CAGAGCGGCG CGCTCCGAAA GTTTCCTTTT ATGGCGAGGC
 851 GGCGGCGGCG GCGGCCCTAT AAAAAGCGAA GCGCGCGGCG GGCGGGAGTC
 901 GCTGCGTTGC CTTCGCCCCG TGCCCCGCTC CGCGCCGCCT CGCGCCGCCC
 951 GCCCCGGCTC TGACTGACCG CGTTACTCCC ACAGGTGAGC GGGCGGGACG
1001 GCCCTTCTCC TCCGGGCTGT AATTAGCGCT TGGTTTAATG ACGGCTCGTT
1051 TCTTTTCTGT GGCTGCGTGA AAGCCTTAAA GGGCTCCGGG AGGGCCCTTT
1101 GTGCGGGGGG GAGCGGCTCG GGGGGTGCGT GCGTGTGTGT GTGCGTGGGG
1151 AGCGCCGCGT GCGGCCCGCG CTGCCCGGCG GCTGTGAGCG CTGCGGGCGC
1201 GGCGCGGGGC TTTGTGCGCT CCGCGTGTGC GCGAGGGGAG CGCGGCCGGG
1251 GGCGGTGCCC CGCGGTGCGG GGGGGCTGCG AGGGGAACAA AGGCTGCGTG
1301 CGGGGTGTGT GCGTGGGGGG GTGAGCAGGG GGTGTGGGCG CGGCGGTCGG
1351 GCTGTAACCC CCCCCTGCAC CCCCCTCCCC GAGTTGCTGA GCACGGCCCG
1401 GCTTCGGGTG CGGGGCTCCG TGCGGGGCGT GGCGCGGGGC TCGCCGTGCC
1451 GGGCGGGGGG TGGCGGCAGG TGGGGGTGCC GGGGGGGGCG GGGCCGCCTC
1501 GGGCCGGGGA GGGCTCGGGG GAGGGGCGCG GCGGCCCCGG AGCGCCGGCG
1551 GCTGTCGAGG CGCGGCGAGC CGCAGCCATT GCCTTTTATG GTAATCGTGC
1601 GAGAGGGCGC AGGGACTTCC TTTGTCCCAA ATCTGGCGGA GCCGAAATCT
1651 GGGAGGCGCC GCCGCACCCC CTCTAGCGGG CGCGGGCGAA GCGGTGCGGC
1701 GCCGGCAGGA AGGAAATGGG CGGGGAGGGC CTTCGTGCGT CGCCGCGCCG
1751 CCGTCCCCTT CTCCATCTCC AGCCTCGGGG CTGCCGCAGG GGGACGGCTG
1801 CCTTCGGGGG GGACGGGGCA GGGCGGGGTT CGGCTTCTGG CGTGTGACCG
1851 GCGGCTCTAG AGCCTCTGCT AACCATGTTC ATGCCTTCTT CTTTTTCCTA
1901 CAGCTCCTGG GCAACGTGCT GGTTATTGTG CTGTCTCATC ATTTTGGCAA
1951 AGAATTCTAA TACGACTCAC TATAGGGAGA CCCAAGCTGG CTAGAGCCAC
2001 CATGGCTGGA CTGTGGCTGG GACTGGTGTG GCAGAAACTG CTGCTGTGGG
2051 GGGCCGCTTC CGCACTGTCA CTGGCTGGGG CTTCACTGGT GCTGAGCCTG
2101 CTGCAGAGGG TGGCCTCCTA CGCCAGAAAG TGGCAGCAGA TGAGGCCCAT
2151 CCCTACCGTG GCCAGAGCCT ATCCACTGGT GGGACACGCA CTGCTGATGA
2201 AGCCTGACGG CAGAGAGTTC TTTCAGCAGA TCATCGAGTA CACAGAGGAG
```

-continued

```
2251 TATAGGCACA TGCCACTGCT GAAGCTGTGG GTGGGACCCG TGCCTATGGT
2301 GGCCCTGTAC AACGCCGAGA ATGTGGAAGT GATCCTGACC AGCAGCAAGC
2351 AGATCGATAA GTCTAGCATG TATAAGTTCC TGGAGCCTTG GCTGGGCCTG
2401 GGCCTGCTGA CCTCTACAGG CAACAAGTGG AGGAGCCGGA GAAAGATGCT
2451 GACCCCAACA TTCCACTTTA CAATCCTGGA GGACTTCCTG GACATCATGA
2501 ACGAGCAGGC CAATATCCTG GTGAAGAAGC TGGAGAAGCA CATCAACCAG
2551 GAGGCCTTTA ATTGCTTCTT TTACATCACC CTGTGCGCCC TGGACATCAT
2601 CTGTGAGACA GCTATGGGCA AGAACATCGG CGCCCAGTCT AATGACGATA
2651 GCGAGTACGT GCGGGCCGTG TATAGAATGA GCGAGATGAT CTTTAGGCGC
2701 ATCAAGATGC CCTGGCTGTG GCTGGATCTG TGGTATCTGA TGTTCAAGGA
2751 GGGCTGGGAG CACAAGAAGT CCCTGCAGAT CCTGCACACC TTTACAAACT
2801 CTGTGATCGC CGAGAGAGCC AATGAGATGA ACGCCAATGA GGACTGTAGG
2851 GGCGATGGAA GGGGCAGCGC CCCTTCCAAG AACAAGCGGA GAGCCTTCCT
2901 GGACCTGCTG CTGAGCGTGA CCGACGATGA GGGCAATCGC CTGTCCCACG
2951 AGGACATCCG GGAGGAGGTG GATACATTCA TGTTTGAGGG ACACGACACC
3001 ACAGCCGCCG CCATCAACTG GTCCCTGTAC CTGCTGGGCT CTAATCCAGA
3051 GGTGCAGAAG AAGGTGGATC ACGAGCTGGA CGACGTGTTC GGCAAGTCCG
3101 ACAGGCCAGC AACCGTGGAG GATCTGAAGA AGCTGAGATA CCTGGAGTGC
3151 GTGATCAAGG AGACACTGCG CCTGTTCCCC TCTGTGCCTC TGTTTGCCCG
3201 GTCCGTGTCT GAGGACTGTG AGGTGGCCGG CTATCGCGTG CTGAAGGGCA
3251 CCGAGGCCGT GATCATCCCT TACGCCCTGC ACCGGGACCC CAGGTATTTC
3301 CCTAACCCAG AGGAGTTTCA GCCAGAGAGA TTCTTTCCCG AGAATGCCCA
3351 GGGCAGGCAC CCTTACGCCT ATGTGCCATT CTCCGCCGGA CCAAGGAACT
3401 GCATCGGACA GAAGTTTGCC GTGATGGAGG AGAAAACCAT CCTGTCTTGT
3451 ATCCTGAGAC ACTTCTGGAT CGAGAGCAAT CAGAAGAGGG AGGAGCTGGG
3501 CCTGGAGGGA CAGCTGATCC TGCGGCCAAG CAACGGCATC TGGATCAAAC
3551 TGAAAAGAAG GAACGCTGAC GAGAGGTAAA AGCTTGGTAC CGATATCGCG
3601 GCCGCCCTAG GGAGCTCCTC GAGGCGGCCC GCTCGAGTCT AGAGGGCCCT
3651 TCGAAGGTAA GCCTATCCCT AACCCTCTCC TCGGTCTCGA TTCTACGCGT
3701 ACCGGTCATC ATCACCATCA CCATTGAGTT TCGATAATCA ACCTCTGGAT
3751 TACAAAATTT GTGAAAGATT GACTGGTATT CTTAACTATG TTGCTCCTTT
3801 TACGCTATGT GGATACGCTG CTTTAATGCC TTTGTATCAT GCTATTGCTT
3851 CCCGTATGGC TTTCATTTTC TCCTCCTTGT ATAAATCCTG GTTGCTGTCT
3901 CTTTATGAGG AGTTGTGGCC CGTTGTCAGG CAACGTGGCG TGGTGTGCAC
3951 TGTGTTTGCT GACGCAACCC CCACTGGTTG GGGCATTGCC ACCACCTGTC
4001 AGCTCCTTTC CGGGACTTTC GCTTTCCCCC TCCCTATTGC CACGGCGGAA
4051 CTCATCGCCG CCTGCCTTGC CCGCTGCTGG ACAGGGGCTC GGCTGTTGGG
4101 CACTGACAAT TCCGTGGTGT TGTCGGGGAA ATCATCGTCC TTTCCTTGGC
4151 TGCTCGCCTG TGTTGCCACC TGGATTCTGC GCGGGACGTC CTTCTGCTAC
4201 GTCCCTTCGG CCCTCAATCC AGCGGACCTT CCTTCCCGCG GCCTGCTGCC
4251 GGCTCTGCGG CCTCTTCCGC GTCTTCGCCT TCGCCCTCAG ACGAGTCGGA
4301 TCTCCCTTTG GGCCGCCTCC CCGCATCGAA ACCCGCTGAT CAGCCTCGAC
4351 TGTGCCTTCT AGTTGCCAGC CATCTGTTGT TTGCCCCTCC CCGTGCCTT
4401 CCTTGACCCT GGAAGGTGCC ACTCCCACTG TCCTTTCCTA ATAAAATGAG
4451 GAAATTGCAT CGCATTGTCT GAGTAGGTGT CATTCTATTC TGGGGGGTGG
4501 GGTGGGGCAG GACAGCAAGG GGGAGGATTG GGAAGACAAT AGCAGGCATG
4551 CTGGGGATGC GGTGGGCTCT ATGGCTTCTG AGGCGGAAAG AACCAGATCC
4601 TCTCTTAAGG TAGCATCGAG ATTTAAATTA GGGATAACAG GGTAATGGCG
4651 CGGGCCGCAG GAACCCCTAG TGATGGAGTT GGCCACTCCC TCTCTGCGCG
4701 CTCGCTCGCT CACTGAGGCC GGGCGACCAA AGGTCGCCCG ACGCCCGGGC
4751 TTTGCCCGGG CGGCCTCAGT GAGCGAGCGA GCGCGCAGCT GCCTGCAGG
```

SEQ ID NO: 61—Sequence of CYP4V2 expression cassette in AAV5. CYP4V2st. AAV5. CYP4V2st has the same promoter (CAG), enhancer (WPRE) and polyA (bGH-polyA) as AAV2.CYP4V2op, AAV2tri (Y-F). CYP4V2op and AAV5.CYP4V2op (SEQ ID NO: 60) but different CYP4V2 cDNA and junction/linker sequences:

Left-ITR: 1-141
CAG promoter: 166-1880
CYP4V2st cDNA: 1938-3515
WPRE enhancer: 3551-4139
bGH polyA: 4163-4387
Right-ITR: 4399-4539

```
   1 CCTGCAGGCA GCTGCGCGCT CGCTCGCTCA CTGAGGCCGC CCGGGCAAAG
  51 CCCGGGCGTC GGGCGACCTT TGGTCGCCCG GCCTCAGTGA GCGAGCGAGC
 101 GCGCAGAGAG GGAGTGGCCA ACTCCATCAC TAGGGGTTCC TGCGGCCTAA
 151 GGCAATTGAG ATCTCGACAT TGATTATTGA CTAGTTATTA ATAGTAATCA
 201 ATTACGGGGT CATTAGTTCA TAGCCCATAT ATGGAGTTCC GCGTTACATA
 251 ACTTACGGTA AATGGCCCGC CTGGCTGACC GCCCAACGAC CCCCGCCCAT
 301 TGACGTCAAT AATGACGTAT GTTCCCATAG TAACGCCAAT AGGGACTTTC
 351 CATTGACGTC AATGGGTGGA CTATTTACGG TAAACTGCCC ACTTGGCAGT
 401 ACATCAAGTG TATCATATGC CAAGTACGCC CCCTATTGAC GTCAATGACG
 451 GTAAATGGCC CGCCTGGCAT TATGCCCAGT ACATGACCTT ATGGGACTTT
 501 CCTACTTGGC AGTACATCTA CGTATTAGTC ATCGCTATTA CCATGGGTCG
 551 AGGTGAGCCC CACGTTCTGC TTCACTCTCC CCATCTCCCC CCCCTCCCCA
 601 CCCCCAATTT TGTATTTATT TATTTTTTAA TTATTTTGTG CAGCGATGGG
 651 GGCGGGGGGG GGGGGGGCGC GCGCCAGGCG GGGGGGGGCG GGGCGAGGGG
 701 CGGGGCGGGG CGAGGCGGAG AGGTGCGGCG GCAGCCAATC AGAGCGGCGC
 751 GCTCCGAAAG TTTCCTTTTA TGGCGAGGCG GCGGCGGCGG CGGCCCTATA
 801 AAAAGCGAAG CGCGCGGCGG GCGGGAGTCG CTGCGTTGCC TTCGCCCCGT
 851 GCCCCGCTCC GCGCCGCCTC GCGCCGCCCG CCCCGGCTCT GACTGACCGC
```

-continued

```
 901 GTTACTCCCA CAGGTGAGCG GGCGGGACGG CCCTTCTCCT CCGGGCTGTA
 951 ATTAGCGCTT GGTTTAATGA CGGCTCGTTT CTTTTCTGTG GCTGCGTGAA
1001 AGCCTTAAAG GGCTCCGGGA GGGCCCTTTG TGCGGGGGGG AGCGGCTCGG
1051 GGGGTGCGTG CGTGTGTGTG TGCGTGGGGA GCGCCGCGTG CGGCCCGCGC
1101 TGCCCGGCGG CTGTGAGCGC TGCGGGCGCG GCGCGGGGCT TTGTGCGCTC
1151 CGCGTGTGCG CGAGGGGAGC GCGGCCGGGG GCGGTGCCCC GCGGTGCGGG
1201 GGGGCTGCGA GGGGAACAAA GGCTGCGTGC GGGGTGTGTG CGTGGGGGGG
1251 TGAGCAGGGG GTGTGGGCGC GGCGGTCGGG CTGTAACCCC CCCCTGCACC
1301 CCCCTCCCCG AGTTGCTGAG CACGGCCCGG CTTCGGGTGC GGGGCTCCGT
1351 GCGGGGCGTG GCGCGGGGCT CGCCGTGCCG GGCGGGGGGT GGCGGCAGGT
1401 GGGGGTGCCG GGCGGGGCGG GGCCGCCTCG GGCCGGGGAG GGCTCGGGGG
1451 AGGGGCGCGG CGGCCCCGGA GCGCCGGCGG CTGTCGAGGC GCGGCGAGCC
1501 GCAGCCATTG CCTTTTATGG TAATCGTGCG AGAGGGCGCA GGGACTTCCT
1551 TTGTCCCAAA TCTGGCGGAG CCGAAATCTG GGAGGCGCCG CCGCACCCCC
1601 TCTAGCGGGC GCGGGCGAAG CGGTGCGGCG CCGGCAGGAA GGAAATGGGC
1651 GGGGAGGGCC TTCGTGCGTC GCCGCGCCGC CGTCCCCTTC TCCATCTCCA
1701 GCCTCGGGGC TGCCGCAGGG GGACGGCTGC CTTCGGGGGG GACGGGGCAG
1751 GGCGGGGTTC GGCTTCTGGC GTGTGACCGG CGGCTCTAGA GCCTCTGCTA
1801 ACCATGTTCA TGCCTTCTTC TTTTTCCTAC AGCTCCTGGG CAACGTGCTG
1851 GTTATTGTGC TGTCTCATCA TTTTGGCAAA GAATTCTAAT ACGACTCACT
1901 ATAGGGAGAC CCAAGCTGGC TAGCCAAAGC TTCCACCATG GCGGGGCTCT
1951 GGCTGGGGCT CGTGTGGCAG AAGCTGCTGC TGTGGGGCGC GGCGAGTGCC
2001 CTTTCCCTGG CCGGCGCCAG TCTGGTCCTG AGCCTGCTGC AGAGGGTGGC
2051 GAGCTACGCG CGGAAATGGC AGCAGATGCG GCCCATCCCC ACGGTGGCCC
2101 GCGCCTACCC ACTGGTGGGC CACGCGCTGC TGATGAAGCC GGACGGGCGA
2151 GAATTTTTTC AGCAGATCAT TGAGTACACA GAGGAATACC GCCACATGCC
2201 GCTGCTGAAG CTCTGGGTCG GGCCAGTGCC CATGGTGGCC CTTTATAATG
2251 CAGAAAATGT GGAGGTAATT TTAACTAGTT CAAAGCAAAT TGACAAATCC
2301 TCTATGTACA AGTTTTTAGA ACCATGGCTT GGCCTAGGAC TTCTTACAAG
2351 TACTGGAAAC AAATGGCGCT CCAGGAGAAA GATGTTAACA CCCACTTTCC
2401 ATTTTACCAT TCTGGAAGAT TTCTTAGATA TCATGAATGA ACAAGCAAAT
2451 ATATTGGTTA AGAAACTTGA AAAACACATT AACCAAGAAG CATTTAACTG
2501 CTTTTTTTAC ATCACTCTTT GTGCCTTAGA TATCATCTGT GAAACAGCTA
2551 TGGGGAAGAA TATTGGTGCT CAAAGTAATG ATGATTCCGA GTATGTCCGT
2601 GCAGTTTATA GAATGAGTGA GATGATATTT CGAAGAATAA AGATGCCCTG
2651 GCTTTGGCTT GATCTCTGGT ACCTTATGTT TAAAGAAGGA TGGGAACACA
2701 AAAAGAGCCT TCAGATCCTA CATACTTTTA CCAACAGTGT CATCGCTGAA
2751 CGGGCCAATG AAATGAACGC CAATGAAGAC TGTAGAGGTG ATGGCAGGGG
2801 CTCTGCCCCC TCCAAAAATA AACGCAGGGC CTTTCTTGAC TTGCTTTTAA
2851 GTGTGACTGA TGACGAAGGG AACAGGCTAA GTCATGAAGA TATTCGAGAA
2901 GAAGTTGACA CCTTCATGTT TGAGGGGCAC GATACAACTG CAGCTGCAAT
2951 AAACTGGTCC TTATACCTGT TGGGTTCTAA CCCAGAAGTC CAGAAAAAAG
3001 TGGATCATGA ATTGGATGAC GTGTTTGGGA AGTCTGACCG TCCCGCTACA
3051 GTAGAAGACC TGAAGAAACT TCGGTATCTG GAATGTGTTA TTAAGGAGAC
3101 CCTTCGCCTT TTTCCTTCTG TTCCTTTATT TGCCCGTAGT GTTAGTGAAG
3151 ATTGTGAAGT GGCAGGTTAC AGAGTTCTAA AAGGCACTGA AGCCGTCATC
3201 ATTCCCTATG CATTGCACAG AGATCCGAGA TACTTCCCCA ACCCCGAGGA
3251 GTTCCAGCCT GAGCGGGTTC T TCCCCGAGAA TGCACAAGGG CGCCATCCAT
3301 ATGCCTACGT GCCCTTCTCT GCTGGCCCCA GGAACTGTAT AGGTCAAAAG
3351 TTTGCTGTGA TGGAAGAAAA GACCATTCTT TCGTGCATCC TGAGGCACTT
3401 TTGGATAGAA TCCAACCAGA AAAGAGAAGA GCTTGGTCTA GAAGGACAGT
3451 TGATTCTTCG TCCAAGTAAT GGCATCTGGA TCAAGTTGAA GAGGAGAAAT
3501 GCAGATGAAC GCTAAGCGGC CGCAACTCGA GACTCTAGAG GTTAATCGAT
3551 AATCAACCTC TGGATTACAA AATTTGTGAA AGATTGACTG GTATTCTTAA
3601 CTATGTTGCT CCTTTTACGC TATGTGGATA CGCTGCTTTA ATGCCTTTGT
3651 ATCATGCTAT TGCTTCCCGT ATGGCTTTCA TTTTCTCCTC CTTGTATAAA
3701 TCCTGGTTGC TGTCTCTTTA TGAGGAGTTG TGGCCCGTTG TCAGGCAACG
3751 TGGCGTGGTG TGCACTGTGT TTGCTGACGC AACCCCCACT GGTTGGGGCA
3801 TTGCCACCAC CTGTCAGCTC CTTTCCGGGA CTTTCGCTTT CCCCCTCCCT
3851 ATTGCCACGG CGGAACTCAT CGCCGCCTGC CTTGCCCGCT GCTGGACAGG
3901 GGCTCGGCTG TTGGGCACTG ACAATTCCGT GGTGTTGTCG GGGAAATCAT
3951 CGTCCTTTCC TTGGCTGCTC GCCTGTGTTG CCACCTGGAT TCTGCGCGGG
4001 ACGTCCTTCT GCTACGTCCC TTCGGCCCTC AATCCAGCGG ACCTTCCTTC
4051 CCGCGGCCTG CTGCCGGCTC TGCGGCCTCT TCCGCGTCTT CGCCTTCGCC
4101 CTCAGACGAG TCGGATCTCC CTTTGGGCCG CCTCCCCGCA TCGAAACCCG
4151 CTGACTAGAC GACTGTGCCT TCTAGTTGCC AGCCATCTGT TGTTTGCCCC
4201 TCCCCCGTGC CTTCCTTGAC CCTGGAAGGT GCCACTCCCA CTGTCCTTTC
4251 CTAATAAAAT GAGGAAATTG CATCGCATTG TCTGAGTAGG TGTCATTCTA
4301 TTCTGGGGGG TGGGGTGGGG CAGGACAGCA AGGGGGAGGA TTGGGAAGAC
4351 AATAGCAGGC ATGCTGGGGA TGCGGTGGGC TCTATGGCCG CGGGCCGCAG
4401 GAACCCCTAG TGATGGAGTT GGCCACTCCC TCTCTGCGCG CTCGCTCGCT
4451 CACTGAGGCC GGGCGACCAA AGGTCGCCCG ACGCCCGGGC TTTGCCCGGG
4501 CGGCCTCAGT GAGCGAGCGA GCGCGCAGCT GCCTGCAGG
```

SEQ ID NO: 62—Sequence of CYP4V2 expression cassette in AAV8.CYP4V2fv. AAV8.CYP4V2fv has the same promoter (CAG), enhancer (WPRE) and polyA (bGH-polyA) and junction/linker sequences as AAV5.CYP4V2st (SEQ ID NO: 61) and differs only in CYP4V2 cDNA sequence:

Left-ITR: 1-141
CAG promoter: 166-1880
CYP4V2fv cDNA: 1938-3515
WPRE enhancer: 3551-4139
bGH polyA: 4163-4387
Right-ITR: 4399-4539

```
   1 CCTGCAGGCA GCTGCGCGCT CGCTCGCTCA CTGAGGCCGC CCGGGCAAAG
  51 CCCGGGCGTC GGGCGACCTT TGGTCGCCCG GCCTCAGTGA GCGAGCGAGC
 101 GCGCAGAGAG GGAGTGGCCA ACTCCATCAC TAGGGGTTCC TGCGGCCTAA
 151 GGCAATTGAG ATCTCGACAT TGATTATTGA CTAGTTATTA ATAGTAATCA
 201 ATTACGGGGT CATTAGTTCA TAGCCCATAT ATGGAGTTCC GCGTTACATA
 251 ACTTACGGTA AATGGCCCGC CTGGCTGACC GCCCAACGAC CCCCGCCCAT
 301 TGACGTCAAT AATGACGTAT GTTCCCATAG TAACGCCAAT AGGGACTTTC
 351 CATTGACGTC AATGGGTGGA CTATTTACGG TAAACTGCCC ACTTGGCAGT
 401 ACATCAAGTG TATCATATGC CAAGTACGCC CCCTATTGAC GTCAATGACG
 451 GTAAATGGCC CGCCTGGCAT TATGCCCAGT ACATGACCTT ATGGGACTTT
 501 CCTACTTGGC AGTACATCTA CGTATTAGTC ATCGCTATTA CCATGGGTCG
 551 AGGTGAGCCC CACGTTCTGC TTCACTCTCC CCATCTCCCC CCCCTCCCCA
 601 CCCCCAATTT TGTATTTATT TATTTTTTAA TTATTTTGTG CAGCGATGGG
 651 GGCGGGGGGG GGGGGGGCGC GCGCCAGGCG GGGCGGGGCG GGGCGAGGGG
 701 CGGGGCGGGG CGAGGCGGAG AGGTGCGGCG GCAGCCAATC AGAGCGGCGC
 751 GCTCCGAAAG TTTCCTTTTA TGGCGAGGCG GCGGCGGCGG CGGCCCTATA
 801 AAAAGCGAAG CGCGCGGCGG GCGGGAGTCG CTGCGTTGCC TTCGCCCCGT
 851 GCCCCGCTCC GCGCCGCCTC GCGCCGCCCG CCCCGGCTCT GACTGACCGC
 901 GTTACTCCCA CAGGTGAGCG GGCGGGACGG CCCTTCTCCT CCGGGCTGTA
 951 ATTAGCGCTT GGTTTAATGA CGGCTCGTTT CTTTTCTGTG GCTGCGTGAA
1001 AGCCTTAAAG GGCTCCGGGA GGGCCCTTTG TGCGGGGGGG AGCGGCTCGG
1051 GGGGTGCGTG CGTGTGTGTG TGCGTGGGGA GCGCCGCGTG CGGCCCGCGC
1101 TGCCCGGCGG CTGTGAGCGC TGCGGGCGCG GCGCGGGGCT TTGTGCGCTC
1151 CGCGTGTGCG CGAGGGGAGC GCGGCCGGGG GCGGTGCCCC GCGGTGCGGG
1201 GGGGCTGCGA GGGGAACAAA GGCTGCGTGC GGGGTGTGTG CGTGGGGGGG
1251 TGAGCAGGGG GTGTGGGCGC GGCGGTCGGG CTGTAACCCC CCCCTGCACC
1301 CCCCTCCCCG AGTTGCTGAG CACGGCCCGG CTTCGGGTGC GGGGCTCCGT
1351 GCGGGGCGTG GCGCGGGGCT CGCCGTGCCG GGCGGGGGGT GGCGGCAGGT
1401 GGGGGTGCCG GGCGGGGCGG GGCCGCCTCG GGCCGGGGAG GGCTCGGGGG
1451 AGGGGCGCGG CGGCCCCGGA GCGCCGGCGG CTGTCGAGGC GCGGCGAGCC
1501 GCAGCCATTG CCTTTTATGG TAATCGTGCG AGAGGGCGCA GGGACTTCCT
1551 TTGTCCCAAA TCTGGCGGAG CCGAAATCTG GGAGGCGCCG CCGCACCCCC
1601 TCTAGCGGGC GCGGGCGAAG CGGTGCGGCG CCGGCAGGAA GGAAATGGGC
1651 GGGGAGGGCC TTCGTGCGTC GCCGCGCCGC CGTCCCCTTC TCCATCTCCA
1701 GCCTCGGGGC TGCCGCAGGG GGACGGCTGC CTTCGGGGGG GACGGGGCAG
1751 GGCGGGGGTTC GGCTTCTGGC GTGTGACCGG CGGCTCTAGA GCCTCTGCTA
1801 ACCATGTTCA TGCCTTCTTC TTTTTCCTAC AGCTCCTGGG CAACGTGCTG
1851 GTTATTGTGC TGTCTCATCA TTTTGGCAAA GAATTCTAAT ACGACTCACT
1901 ATAGGGAGAC CCAAGCTGGC TAGCCAAAGC TTCCACCATG GCGGGGCTCT
1951 GGCTGGGGCT CGTGTGGCAG AAGCTGCTGC TGTGGGGCGC GGCGAGTGCC
2001 CTTTCCCTGG CCGGCGCCAG TCTGGTCCTG AGCCTGCTGC AGAGGGTGGC
2051 GAGCTACGCG CGGAAATGGC AGCAGATGCG GCCCATCCCC ACGGTGGCCC
2101 GCGCCTACCC ACTGGTGGGC CACGCGCTGC TGATGAAGCC GGACGGGGCA
2151 GAATTTTTTC AGCAGATCAT TGAGTACACA GAGGAATACC GCCACATGCC
2201 GCTGCTGAAG CTCTGGGTCG GGCCAGTGCC CATGGTGGCC CTTTATAATG
2251 CAGAAAATGT GGAGGTAATT TTAACTAGTT CAAAGCAAAT TGACAAATCC
2301 TCTATGTACA AGTTTTTAGA ACCATGGCTT GGCCTAGGAC TTCTTACAAG
2351 TACTGGAAAC AAATGGCGCT CCAGGAGAAA GATGTTAACA CCCACTTTCC
2401 ATTTTACCAT TCTGGAAGAT TTCTTAGATA TCATGAATGA ACAAGCAAAT
2451 ATATTGGTTA AGAAACTTGA AAAACACATT AACCAAGAAG CATTTAACTG
2501 CTTTTTTTAC ATCACTCTTT GTGCCTTAGA TATCATCTGT GAAACAGCTA
2551 TGGGGAAGAA TATTGGTGCT CAAAGTAATG ATGATTCCGA GTATGTCCGT
2601 GCAGTTTATA GAATGAGTGA GATGATATTT CGAAGAATAA AGATGCCCTG
2651 GCTTTGGCTT GATCTCTGGT ACCTTATGTT TAAAGAAGGA TGGGAACACA
2701 AAAAGAGCCT TAAGATCCTA CATACTTTTA CCAACAGTGT CATCGCGGAA
2751 CGGGCCAATG AAATGAACGC CAATGAAGAC TGTAGAGGTG ATGGCAGGGG
2801 CTCTGCCCCC TCCAAAAATA AACGCAGGGC CTTTCTTGAC TTGCTTTTAA
2851 GTGTGACTGA TGACGAAGGG AACAGGCTAA GTCATGAAGA TATTCGAGAA
2901 GAAGTTGACA CCTTCATGTT TGAGGGGCAC GATACAACTG CAGCTGCAAT
2951 AAACTGGTCC TTATACCTGT TGGGTTCTAA CCCAGAAGTC CAGAAAAAAG
3001 TGGATCATGA ATTGGATGAC GTGTTTGGGA AGTCTGACCG TCCCGCTACA
3051 GTAGAAGACC TGAAGAAACT TCGGTATCTG GAATGTGTTA TTAAGGAGAC
3101 CCTTCGCCTT TTTCCTTCTG TTCCTTTATT TGCCCGTAGT GTTAGTGAAG
3151 ATTGTGAAGT GGCAGGTTAC AGAGTTCTAA AAGGCACTGA AGCCGTCATC
3201 ATTCCCTATG CATTGCACAG AGATCCGAGA TACTTCCCCA ACCCCGAGGA
3251 GTTCCAGCCT GAGCGGTTCT TCCCCGAGAA TGCACAAGGG CGCCATCCAT
3301 ATGCCTACGT GCCCTTCTCT GCTGGCCCCA GGAACTGTAT AGGTCAAAAG
3351 TTTGCTGTGA TGGAAGAAAA GACCATTCTT TCGTGCATCC TGAGGCACTT
3401 TTGGATAGAA TCCAACCAGA AAAGAGAAGA GCTTGGTCTA GAAGGACAGT
3451 TGATTCTTCG TCCAAGTAAT GGCATCTGGA TCAAGTTGAA GAGGAGAAAT
3501 GCAGATGAAC GCTAAGCGGC CGCAACTCGA GACTCTAGAG GTTAATCGAT
3551 AATCAACCTC TGGATTACAA AATTTGTGAA AGATTGACTG GTATTCTTAA
3601 CTATGTTGCT CCTTTTACGC TATGTGGATA CGCTGCTTTA ATGCCTTTGT
3651 ATCATGCTAT TGCTTCCCGT ATGGCTTTCA TTTTCTCCTC CTTGTATAAA
3701 TCCTGGTTGC TGTCTCTTTA TGAGGAGTTG TGGCCCGTTG TCAGGCAACG
3751 TGGCGTGGTG TGCACTGTGT TTGCTGACGC AACCCCCACT GGTTGGGGCA
3801 TTGCCACCAC CTGTCAGCTC CTTTCCGGGA CTTTCGCTTT CCCCCTCCCT
3851 ATTGCCACGG CGGAACTCAT CGCCGCCTGC CTTGCCCGCT GCTGGACAGG
3901 GGCTCGGCTG TTGGGCACTG ACAATTCCGT GGTGTTGTCG GGGAAATCAT
3951 CGTCCTTTCC TTGGCTGCTC GCCTGTGTTG CCACCTGGAT TCTGCGCGGG
4001 ACGTCCTTCT GCTACGTCCC TTCGGCCCTC AATCCAGCGG ACCTTCCTTC
```

-continued

```
4051 CCGCGGCCTG CTGCCGGCTC TGCGGCCTCT TCCGCGTCTT CGCCTTCGCC
4101 CTCAGACGAG TCGGATCTCC CTTTGGGCCG CCTCCCCGCA TCGAAACCCG
4151 CTGACTAGAC GACTGTGCCT TCTAGTTGCC AGCCATCTGT TGTTTGCCCC
4201 TCCCCCGTGC CTTCCTTGAC CCTGGAAGGT GCCACTCCCA CTGTCCTTTC
4251 CTAATAAAAT GAGGAAATTG CATCGCATTG TCTGAGTAGG TGTCATTCTA
4301 TTCTGGGGGG TGGGGTGGGG CAGGACAGCA AGGGGGAGGA TTGGGAAGAC
4351 AATAGCAGGC ATGCTGGGGA TGCGGTGGGC TCTATGGCCG CGGGCCGCAG
4401 GAACCCCTAG TGATGGAGTT GGCCACTCCC TCTCTGCGCG CTCGCTCGCT
4451 CACTGAGGCC GGGCGACCAA AGGTCGCCCG ACGCCCGGGC TTTGCCCGGG
4501 CGGCCTCAGT GAGCGAGCGA GCGCGCAGCT GCCTGCAGG
```

SEQ ID NO: 63-Sequence of CYP4V2 expression cassette in AAV5.CYP4V2op (new). AAV5. CYP4V2op (new) has the same promoter (CAG), enhancer (WPRE) and polyA (bGH-polyA) and the same junction/linker sequences as AAV5.CYP4V2st (SEQ ID NO: 61) and AAV8. CYP4V2fv (SEQ ID NO: 62) but different CYP4V2 cDNA sequences:

Left-ITR: 1-141
CAG promoter: 166-1880
CYP4V2op cDNA: 1938-3515
WPRE enhancer: 3551-4139
bGH polyA: 4163-4387
Right-ITR: 4399-4539

```
CCTGCAGGCA GCTGCGCGCT CGCTCGCTCA CTGAGGCCGC CCGGGCAAAG
CCCGGGCGTC GGGCGACCTT TGGTCGCCCG GCCTCAGTGA GCGAGCGAGC
GCGCAGAGAG GGAGTGGCCA ACTCCATCAC TAGGGGTTCC TGCGGCCTAA
GGCAATTGAG ATCTCGACAT TGATTATTGA CTAGTTATTA ATAGTAATCA
ATTACGGGGT CATTAGTTCA TAGCCCATAT ATGGAGTTCC GCGTTACATA
ACTTACGGTA AATGGCCCGC CTGGCTGACC GCCCAACGAC CCCCGCCCAT
TGACGTCAAT AATGACGTAT GTTCCCATAG TAACGCCAAT AGGGACTTTC
CATTGACGTC AATGGGTGGA CTATTTACGG TAAACTGCCC ACTTGGCAGT
ACATCAAGTG TATCATATGC CAAGTACGCC CCCTATTGAC GTCAATGACG
GTAAATGGCC CGCCTGGCAT TATGCCCAGT ACATGACCTT ATGGGACTTT
CCTACTTGGC AGTACATCTA CGTATTAGTC ATCGCTATTA CCATGGGTCG
AGGTGAGCCC CACGTTCTGC TTCACTCTCC CCATCTCCCC CCCCTCCCCA
CCCCCAATTT TGTATTTATT TATTTTTTAA TTATTTTGTG CAGCGATGGG
GGCGGGGGGG GGGGGGGCGC GCGCCAGGCG GGGGGGGCG GGGCGAGGGG
CGGGGCGGGG CGAGGCGGAG AGGTGCGGCG GCAGCCAATC AGAGCGGCGC
GCTCCGAAAG TTTCCTTTTA TGGCGAGGCG GCGGCGGCGG CGGCCCTATA
AAAAGCGAAG CGCGCGGCGG GCGGGAGTCG CTGCGTTGCC TTCGCCCCGT
GCCCCGCTCC GCGCCGCCTC GCGCCGCCCG CCCCGGCTCT GACTGACCGC
GTTACTCCCA CAGGTGAGCG GGCGGGACGG CCCTTCTCCT CCGGGCTGTA
ATTAGCGCTT GGTTTAATGA CGGCTCGTTT CTTTTCTGTG GCTGCGTGAA
AGCCTTAAAG GGCTCCGGGA GGGCCCTTTG TGCGGGGGGG AGCGGCTCGG
GGGGTGCGTG CGTGTGTGTG TGCGTGGGGA GCGCCGCGTG CGGCCCGCGC
TGCCCGGCGG CTGTGAGCGC TGCGGGCGCG GCGCGGGGCT TTGTGCGCTC
CGCGTGTGCG CGAGGGGAGC GCGGCCGGGG GCGGTGCCCC GCGGTGCGGG
GGGGCTGCGA GGGGAACAAA GGCTGCGTGC GGGGTGTGTG CGTGGGGGGG
TGAGCAGGGG GTGTGGGCGC GGCGGTCGGG CTGTAACCCC CCCCTGCACC
CCCCTCCCCG AGTTGCTGAG CACGGCCCGG CTTCGGGTGC GGGGCTCCGT
GCGGGGCGTG GCGCGGGGCT CGCCGTGCCG GGCGGGGGGT GGCGGCAGGT
GGGGGTGCCG GGCGGGGCGG GGCCGCCTCG GGCCGGGGAG GGCTCGGGGG
AGGGGCGCGG CGGCCCCGGA GCGCCGGCGG CTGTCGAGGC GCGGCGAGCC
GCAGCCATTG CCTTTTATGG TAATCGTGCG AGAGGGCGCA GGGACTTCCT
TTGTCCCAAA TCTGGCGGAG CCGAAATCTG GGAGGCGCCG CCGCACCCCC
TCTAGCGGGC GCGGGCGAAG CGGTGCGGCG CCGGCAGGAA GGAAATGGGC
GGGGAGGGCC TTCGTGCGTC GCCGCGCCGC CGTCCCCTTC TCCATCTCCA
GCCTCGGGGC TGCCGCAGGG GGACGGCTGC CTTCGGGGGG GACGGGGCAG
GGCGGGGTTC GGCTTCTGGC GTGTGACCGG CGGCTCTAGA GCCTCTGCTA
ACCATGTTCA TGCCTTCTTC TTTTTCCTAC AGCTCCTGGG CAACGTGCTG
GTTATTGTGC TGTCTCATCA TTTTGGCAAA GAATTCTAAT ACGACTCACT
ATAGGGAGAC CCAAGCTGGC TAGCCAAAGC TTCCACC
ATGGCTGGACTGTGGCTGGGACTGGTGTGGCAGAAACTGCTGCTGTGGGGGCCGCTTCCGCACTGTCAC
TGGCTGGGGCTTCACTGGTGCTGAGCCTGCTGCAGAGGGTGGCCTCCTACGCCAGAAAGTGGCAGCAGAT
GAGGCCCATCCCTACCGTGGCCAGAGCCTATCCACTGGTGGGACACGCACTGCTGATGAAGCCTGACGGC
AGAGAGTTCTTTCAGCAGATCATCGAGTACACAGAGGAGTATAGGCACATGCCACTGCTGAAGCTGTGGG
TGGGACCCGTGCCTATGGTGGCCCTGTACAACGCCGAGAATGTGGAAGTGATCCTGACCAGCAGCAAGCA
GATCGATAAGCTCTAGCATGTATAAGTTCCTGGAGCCTTGGCTGGGCCTGGGCCTGCTGACCTCTACAGGC
AACAAGTGGAGGAGCCGGAGAAAGATGCTGACCCCAACATTCCACTTTACAATCCTGGAGGACTTCCTGG
ACATCATGAACGAGCAGGCCAATATCCTGGTGAAGAAGCTGGAGAAGCACATCAACCAGGAGGCCTTTAA
TTGCTTCTTTTACATCACCCTGTGCGCCCTGGACATCATCTGTGAGACAGCTATGGGCAAGAACATCGGC
GCCCAGTCTAATGACGATAGCGAGTACGTGCGGGCCGTGTATAGAATGAGCGAGATGATCTTTAGGCGCA
TCAAGATGCCCTGGCTGTGGCTGGATCTGTGGTATCTGATGTTCAAGGAGGGCTGGGAGCACAAGAAGTC
CCTGCAGATCCTGCACACCTTTACAAACTCTGTGATCGCCGAGAGAGCCAATGAGATGAACGCCAATGAG
GACTGTAGGGGCGATGGAAGGGGCAGCGCCCCTTCCAAGAACAAGCGGAGAGCCTTCCTGGACCTGCTGC
TGAGCGTGACCGACGATGAGGGCAATCGCCTGTCCCACGAGGACATCGGGGAGGAGGTGGATACATTCAT
GTTTGAGGGACACGACACCACAGCCGCCGCCATCAACTGGTCCCTGTACCTGCTGGGCTCTAATCCAGAG
GTGCAGAAGAAGGTGGATCACGAGCTGGACGACGTGTTCGGCAAGTCCGACAGGCCAGCAACCGTGGAGG
ATCTGAAGAAGCTGAGATACCTGGAGTGCGTGATCAAGGAGACACTGCGCCTGTTCCCCTCTGTGCCTCT
GTTTGCCCGGTCCGTGTCTGAGGACTGTGAGGTGGCCGGCTATCGCGTGCTGAAGGGCACCGAGGCCGTG
ATCATCCCTTACGCCCTGCACCGGGACCCCAGGTATTTCCCTAACCCAGAGGAGTTTCAGCCAGAGAGAT
TCTTTCCCGAGAATGCCCAGGGCAGGCACCCCTTACGCCTATGTGCCATTCTCCGCCGGACCAAGGAACTG
```

```
                              -continued
CATCGGACAGAAGTTTGCCGTGATGGAGGAGAAAACCATCCTGTCTTGTATCCTGAGACACTTCTGGATC
GAGAGCAATCAGAAGAGGGAGGAGCTGGGCCTGGAGGGACAGCTGATCCTGCGGCCAAGCAACGGCATCT
GGATCAAACTGAAAAGAAGGAACGCTGACGAGAGGTAAGCGGC CGCAACTCGA GACTCTAGAG
GTTAATCGAT
AATCAACCTC TGGATTACAA AATTTGTGAA AGATTGACTG GTATTCTTAA
CTATGTTGCT CCTTTTACGC TATGTGGATA CGCTGCTTTA ATGCCTTTGT
ATCATGCTAT TGCTTCCCGT ATGGCTTTCA TTTTCTCCTC CTTGTATAAA
TCCTGGTTGC TGTCTCTTTA TGAGGAGTTG TGGCCCGTTG TCAGGCAACG
TGGCGTGGTG TGCACTGTGT TTGCTGACGC AACCCCCACT GGTTGGGGCA
TTGCCACCAC CTGTCAGCTC CTTTCCGGGA CTTTCGCTTT CCCCCTCCCT
ATTGCCACGG CGGAACTCAT CGCCGCCTGC CTTGCCCGCT GCTGGACAGG
GGCTCGGCTG TTGGGCACTG ACAATTCCGT GGTGTTGTCG GGGAAATCAT
CGTCCTTTCC TTGGCTGCTC GCCTGTGTTG CCACCTGGAT TCTGCGCGGG
ACGTCCTTCT GCTACGTCCC TTCGGCCCTC AATCCAGCGG ACCTTCCTTC
CCGCGGCCTG CTGCCGGCTC TGCGGCCTCT TCCGCGTCTT CGCCTTCGCC
CTCAGACGAG TCGGATCTCC CTTTGGGCCG CCTCCCCGCA TCGAAACCCG
CTGACTAGAC GACTGTGCCT TCTAGTTGCC AGCCATCTGT TGTTTGCCCC
TCCCCCGTGC CTTCCTTGAC CCTGGAAGGT GCCACTCCCA CTGTCCTTTC
CTAATAAAAT GAGGAAATTG CATCGCATTG TCTGAGTAGG TGTCATTCTA
TTCTGGGGGG TGGGGTGGGG CAGGACAGCA AGGGGGAGGA TTGGGAAGAC
AATAGCAGGC ATGCTGGGGA TGCGGTGGGC TCTATGGCCG CGGGCCGCAG
GAACCCCTAG TGATGGAGTT GGCCACTCCC TCTCTGCGCG CTCGCTCGCT
CACTGAGGCC GGGCGACCAA AGGTCGCCCG ACGCCCGGGC TTTGCCCGGG
CGGCCTCAGT GAGCGAGCGA GCGCGCAGCT GCCTGCAGG
```

SEQ ID NO: 64—Sequence of CYP4V2 expression cassette in SCAAV1.CYP4V2op, scAAV5.CYP4V2op, and scAAV9.CYP4V2op.

Left-ITR (truncated): 1-117
EFS promoter: 130-364
CYP4V2op cDNA: 520-2097
SPA: 2116-2169
Right-ITR: 2263-2403

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

```
   1 cctgcaggca gctgcgcgct cgctcgctca ctgaggccgc ccgggcaaag cccgggcgtc
  61 gggcgacctt tggtcgcccg gcctcagtga gcgagcgagc gcgcagagag ggagtggacg
 121 cgtaggcctg attggctccg gtgcccgtca gtgggcagag cgcacatcgc ccacagtccc
 181 cgagaagttg ggggggagggg tcggcaattg aaccggtgcc tagagaaggt ggcgcggggt
 241 aaactgggaa agtgatgtcg tgtactggct ccgccttttt cccgagggtg ggggagaacc
 301 gtatataagt gcagtagtcg ccgtgaacgt tcttttttcgc aacgggtttg ccgccagaac
 361 acaggtgtcg tgacgcgacc aggtatgcat ctgcagctct aaggtaaata taaaattttt
 421 aagtgtataa tgtgttaaac tactgattct aattgtttct ctcttttaga ttccaacctt
 481 tggaactgac tgcagggatc caagetttct agagccacca tggctggact gtggctggga
 541 ctggtgtggc agaaactgct gctgtggggg gccgcttccg cactgtcact ggctggggct
 601 tcactggtgc tgagcctgct gcagagggtg gcctcctacg ccagaaagtg gcagcagatg
 661 aggcccatcc ctaccgtggc cagagcctat ccactggtgg gacacgcact gctgatgaag
 721 cctgacggca gagagttctt tcagcagatc atcgagtaca cagaggagta taggcacatg
 781 ccactgctga agctgtgggt gggacccgtg cctatggtgg ccctgtacaa cgccgagaat
 841 gtggaagtga tcctgaccag cagcaagcag atcgataagt ctagcatgta taagttcctg
 901 gagccttggc tgggcctggg cctgctgacc tctacaggca acaagtggag gagccggaga
 961 aagatgctga ccccaacatt ccactttaca atcctggagg acttcctgga catcatgaac
1021 gagcaggcca atatcctggt gaagaagctg gagaagcaca tcaaccagga ggcctttaat
1081 tgcttctttt acatcaccct gtgcgccctg gacatcatct gtgagacagc tatgggcaag
1141 aacatcggcg cccagtctaa tgacgatagc gagtacgtgc gggccgtgta tagaatgagc
1201 gagatgatct ttaggcgcat caagatgccc tggctgtggc tggatctgtg gtatctgatg
1261 ttcaaggagg gctgggagca caagaagtcc ctgcagatcc tgcacacctt tacaaactct
1321 gtgatcgccg agagagccaa tgagatgaac gccaatgagg actgtagggg cgatggaagg
1381 ggcagcgccc cttccaagaa caagcggaga gccttcctgg acctgctgct gagcgtgacc
1441 gacgatgagg gcaatcgcct gtcccacgag gacatccggg aggaggtgga tacattcatg
1501 tttgagggac acgacaccac agccgccgcc atcaactggt ccctgtacct gctgggctct
1561 aatccagagg tgcagaagaa ggtggatcac gagctggacg acgtgttcgg caagtccgac
1621 aggccagcaa ccgtggagga tctgaagaag ctgagatacc tggagtgcgt gatcaaggag
1681 acactgcgcc tgttcccctc tgtgcctctg tttgcccggt ccgtgtctga ggactgtgag
1741 gtggccggct atcgcgtgct gaagggcacc gaggccgtga tcatccctta cgccctgcac
1801 cgggacccca ggtatttccc taacccagag gagtttcagc cagagagatt ctttcccgag
1861 aatgcccagg gcaggcacc ttacgcctat gtgccattct ccgccggacc aaggaactgc
1921 atcggacaga agtttgccgt gatggaggag aaaaccatcc tgtcttgtat cctgagacac
1981 ttctggatcg agagcaatca gaagagggag gagctgggcc tggagggaca gctgatcctg
2041 cggccaagca acggcatctg gatcaaactg aaaagaagga acgctgacga gaggtaaaag
2101 cttgaattcc tcgaggatcc aataaaagat ctttattttc attagatctg tgtgttggtt
2161 ttttgtgtgt ctagttgcca gccatctgtt gtttgcccct cccccgtgcc ttccttgacc
2221 ctggaaggtg ccactcccag tttaaactta attaagggcc gcaggaaccc ctagtgatgg
2281 agttggccac tccctctctg cgcgctcgct cgctcactga ggccgggcga ccaaaggtcg
2341 cccgacgccc gggctttgcc cgggcggcct cagtgagcga gcgagcgcgc agctgcctgc
2401 agg
```

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

---

What is claimed is:

1. A vector comprising a nucleic acid molecule comprising a sequence encoding a non-mutant or functional cytochrome P450, family 4, subfamily V, polypeptide 2 (CYP4V2) protein or a functional variant thereof having at least 99% sequence identity with the amino acid sequence of SEQ ID NO: 4 operably linked to at least one regulatory sequence, wherein the vector is a recombinant adeno-associated virus (rAAV) vector, wherein any part of the vector shares at least 60% sequence identity with the entirety of any one of the following sequences: SEQ ID NO:60; SEQ ID NO:61; SEQ ID NO:62; SEQ ID NO:63; SEQ ID NO:64; nucleotide (nt) 237-nt 3579 of SEQ ID NO 60; nt 166-nt 3515 of SEQ ID NO 61; nt 166-nt 3515 of SEQ ID NO 62; nt 166-nt 3515 of SEQ ID NO 63; or nt 130-nt 2097 of SEQ ID NO 64.

2. The vector of claim 1, wherein the rAAV vector comprises a VP1, VP2, or VP3 capsid protein selected from any serotype of AAV1, AAV2, AAV3, AAV4, AAV5, AAV6, AAV7, AAV8, AAV9, AAV10, AAV11, AAV12, or another naturally derived serotype or isolate or clade of AAV, or hybrids, variants or derivatives thereof.

3. The vector of claim 1, wherein the rAAV vector comprises a 5' AAV inverted terminal repeat (ITR) or a 3' AAV ITR selected from any one of AAV1, AAV2, AAV3, AAV4, AAV5, AAV6, AAV7, AAV8, AAV9, AAV10, AAV11, AAV12, or another naturally derived serotype or isolate or clade of AAV, or mutations, chimeras, variants or fusions thereof.

4. The vector of claim 1, wherein the rAAV vector is a chimeric AAV, a shuffled AAV, or a capsid-modified AAV.

5. The vector of claim 1, wherein the rAAV vector is a pseudotyped AAV.

6. The vector of claim 1, wherein the rAAV vector is a hybrid AAV.

7. The vector of claim 1, wherein the rAAV vector comprises one or more modifications to one or more naturally derived AAV capsid proteins.

8. The rAAV vector of claim 7, wherein the modifications to the AAV capsid protein comprises one or more amino acid residue Y-F, K-R, T-A, S-A or T-V substitutions.

9. The vector of claim 1, wherein the rAAV vector is selected from the group consisting of AAV2/5, AAV2/8, AAV2/2, AAV2 (Y444F+Y500F+Y730F), AAV2/1, AAV2/

9, AAV2/8 (Y733F), AAV2/6, AAV2/4, AAV2/7, AAV5, AAV2, AAV8, AAV1, AAV9, AAV6, AAV10, AAV3, AAV4, AAV7, AAV11, AAV12, Anc80, AAV 7m8, AAV-DJ, ShH10, AAV-PHP.B, rh10, and a hybrid, a derivative or variant thereof.

10. The vector of claim 1, wherein the rAAV vector is a single-stranded AAV vector or a self-complementary AAV (scAAV) vector.

11. The vector of claim 1, wherein the sequence encoding the non-mutant or functional CYP4V2 protein or a functional variant thereof has at least 76% sequence identity with the nucleic acid sequence of SEQ ID NO: 1 or 2.

12. The vector of claim 1, wherein the at least one regulatory sequence comprises a promoter.

13. The vector of claim 12, wherein the promoter is a retinal pigment epithelium (RPE) cell-specific promoter, a photoreceptor-specific promoter, a retinal cell-specific promoter, a corneal cell-specific promoter, an ocular cell-specific promoter, a cell-specific promoter, a tissue-specific promoter, a constitutive promoter, a ubiquitous promoter, a regulated promoter, an inducible promoter, or a derivative, hybrid or combination thereof.

14. The vector of claim 12, wherein the promoter is selected from the group consisting of a CAG promoter (also known as CAGGS promoter, CB promoter or CBA promoter), a chicken beta actin promoter, a small CBA (smCBA) promoter, a CB$^{SB}$ promoter, a CBh promoter, a beta-actin promoter, a human beta actin promoter, or an elongation factor 1 alpha short (EFS) promoter, an elongation factor 1 alpha (EF-1 alpha or EF-1a) promoter, a cytomegalovirus (CMV) promoter, a PGK promoter, a UBC promoter, a GUSB promoter, a UCOE promoter, a VMD2 (vitelliform macular dystrophy 2; also known as BEST1) promoter, an RPE65 promoter, a GRK1 promoter, a human interphotoreceptor retinoid-binding protein proximal (IRBP) promoter, a 235 nt fragment of the hIRBP promoter, an RPGR proximal promoter, the red opsin promoter, a red-green opsin promoter, the blue opsin promoter, the mouse opsin promoter, a rhodopsin (Rho) promoter, a beta phosphodiesterase (PDE) promoter, a retinitis pigmentosa (RP1) promoter, the NXNL2/NXNL1 promoter, a retinal degeneration slow/peripherin 2 (Rds/perphZ) promoter, a IRBP/GNAT2 promoter (hIRBP enhancer fused to cone transducin alpha promoter), an Rds (retinal degeneration slow) promoter, an hPDE6b promoter, a VEcad promoter (VE-cadherin/Cadherin 5 (CDH5)/CD144 promoter), a calcium-sensitive promoter, an NFAT promoter, a zinc-inducible sheep metalioihionine (MX) promoter, a dexamethasone (Dex)-inducible mouse mammary tumor virus (MMTV) promoter, a T7 polymerase promoter system, and an ecdysone insect promoter.

15. The vector of claim 1, wherein the at least one regulatory sequence comprises a Kozak sequence or a variant thereof.

16. The vector of claim 1, wherein the at least one regulatory sequence comprises an enhancer.

17. The vector of claim 16, wherein the enhancer comprises a post-transcriptional regulatory element (PRE), an internal ribosome entry site (IRES), an intron regulatory sequence, a mini-intron splice donor/splice acceptor (SD-SA) or a constitutive transport element (CTE).

18. The vector of claim 16, wherein the enhancer is selected from the group consisting of a woodchuck hepatitis virus post-transcriptional regulatory element (WPRE) enhancer, an Hepatitis B Virus post-transcriptional regulatory element (HPRE or HBVPRE) enhancer, an IRBP enhancer, a Mason-Pfizer Monkey Virus CTE enhancer, a cytomegalovirus (CMV) immediate early enhancer, an SV40 enhancer, and an Avian Leukemia Virus CTE enhancer.

19. The vector of claim 1, wherein the at least one regulatory sequence comprises a polyadenylation (polyA) signal.

20. The vector of claim 19, wherein the polyA signal is selected from the group consisting of a bovine growth hormone polyadenylation signal (bGH polyA), a small polyA signal (SPA), a human growth hormone polyadenylation signal (hGH polyA), an SV40 polyA signal, an SV40 early polyA signal, and an SV40 late polyA signal.

21. The vector of claim 1, wherein the at least one regulatory sequence comprises an upstream enhancer (USE) operably linked to a polyA signal.

22. The vector of claim 21, wherein the USE is selected from the group consisting of SV40 late 2xUSE, HIV-1 (Human immunodeficiency virus 1) USE, GHV (Ground squirrel hepatitis virus) USE, Adenovirus (L3) USE, hTHGB (Human prothrombin) USE, an hC2 (Human C2 complement gene) USE, and a derivative, variant and hybrid thereof.

23. The vector of claim 1, wherein the at least one regulatory sequence comprises an intron sequence, a UTR sequence, a splice site sequence, an upstream regulatory domain sequence, a response element sequence, an inducible element sequence, an origin of replication sequence, an internal ribosome entry sites (IRES) sequence, a transcription initiation sequence, a termination sequence, an RNA processing sequence, a junction sequence, a linker sequence, a derivative, hybrid or variant thereof.

24. The vector of claim 1, wherein the at least one regulatory sequence is heterologous or homologous relative to the CYP4V2 coding sequence whose expression said regulatory sequence regulates.

25. The vector of claim 1, wherein the at least one regulatory sequence comprises an organ-specific, tissue-specific or cell-specific microRNA (miRNA) target sequence.

26. The vector of claim 1, comprised within a pharmaceutically acceptable carrier and additional components suitable for a specific route of administration or delivery device.

27. A cell comprising the vector of claim 1, wherein the cell is a retinal pigment epithelial (RPE) cell, a photoreceptor cell, a photoreceptor progenitor cell, a choroidal cell, a retinal cell, an induced pluripotent stem (iPS) cell, or a stem cell, of or derived from a human subject suffering from Bietti's Crystalline Dystrophy (BCD, a/k/a Bietti Crystalline Corneoretinal Dystrophy, Bietti Crystalline Retinopathy, Bietti's Retinal Dystrophy), or retinitis pigmentosa (RP) or inherited retinal degeneration (IRD) with bi-allelic CYP4V2 mutations.

28. A method of treating, arresting or preventing Bietti's Crystalline Dystrophy (BCD, a/k/a Bietti Crystalline Corneoretinal Dystrophy, Bietti Crystalline Retinopathy, Bietti's Retinal Dystrophy), or retinitis pigmentosa (RP) or inherited retinal degeneration (IRD) with bi-allelic CYP4V2 mutations in a human subject in need thereof, the method comprising delivering, to the human subject's retina, a therapeutically effective amount of the cell of claim 27.

29. A method of treating, arresting or slowing progression of, rescuing or ameliorating the dysfunction, function loss, dystrophy, disorder, degeneration, atrophy or preventing the death of an ocular cell of a human subject who has Bietti's Crystalline Dystrophy (BCD, a/k/a Bietti Crystalline Corneoretinal Dystrophy, Bietti Crystalline Retinopathy, Bietti's Retinal Dystrophy), or retinitis pigmentosa (RP) or inherited retinal degeneration (IRD) with bi-allelic CYP4V2 mutations, the method comprising transducing the ocular cell with a therapeutically effective amount of the vector of claim 1.

30. The method of claim 29, wherein the ocular cell is a retina cell, a retinal pigment epithelial (RPE) cell, a photoreceptor cell (rod or cone), a choroidal epithelial cell, a corneal epithelium cell, a choroidal cell, a corneal cell, a retina bipolar cell, a photoreceptor progenitor cell, a ganglion cell, or an optic-nerve cell.

31. A method of treating, arresting or preventing Bietti's Crystalline Dystrophy (BCD, a/k/a Bietti Crystalline Corneoretinal Dystrophy, Bietti Crystalline Retinopathy, Bietti's Retinal Dystrophy), or retinitis pigmentosa (RP) or inherited retinal degeneration (IRD) with bi-allelic CYP4V2 mutations in a human subject in need thereof, the method comprising: delivering to the human subject's retina a therapeutically effective amount of the vector of claim 1, wherein one or more retinal pigment epithelial (RPE) cells, one or more choroidal cells, or one or more photoreceptor cells of the human subject is transduced with the vector, whereby said disease is treated, arrested or prevented in the human subject.

32. A method of treating, arresting, or preventing a human subject's disease which is associated with the atrophy, dystrophy, dysfunction, degeneration or death of the retinal pigment epithelial (RPE) cell, the method comprising: delivering to the human subject's retina a therapeutically effective amount of the vector of claim 1, wherein one or more RPE cells of the human subject is transduced with the vector, whereby said disease is treated, arrested or prevented in the human subject.

33. A method of treating, arresting or preventing a human subject's disease which is associated with the atrophy, dystrophy, dysfunction, degeneration or death of the retinal pigment epithelial (RPE) cell, the method comprising delivering, to the human subject's retina, a therapeutically effective amount of the RPE cell or stem cell, wherein said RPE cell or stem cell comprises the vector of claim 1.

34. A vector comprising a nucleic acid molecule comprising a sequence encoding a non-mutant or functional cytochrome P450, family 4, subfamily V, polypeptide 2 (CYP4V2) protein or a functional variant thereof having at least 99% sequence identity with the amino acid sequence of SEQ ID NO:4 operably linked to at least one regulatory sequence, wherein the vector is a recombinant adeno-associated virus (rAAV) vector, wherein the sequence encoding the non-mutant or functional CYP4V2 protein or a functional variant thereof shares at least 80% sequence identity with SEQ ID NO:2.

\* \* \* \* \*